(12) United States Patent
McAlpine et al.

(10) Patent No.: US 7,300,921 B2
(45) Date of Patent: Nov. 27, 2007

(54) POLYENE POLYKETIDES AND METHODS OF PRODUCTION

(75) Inventors: James B. McAlpine, Montreal (CA); Chris M. Farnet, Outremont (CA); Emmanuel Zazopoulos, Montreal (CA); Dan Sorensen, Montreal (CA)

(73) Assignee: Ecopia Biosciences, Inc., Saint Laurent (CA)

( * ) Notice: Subject to any disclaimer, the term of this patent is extended or adjusted under 35 U.S.C. 154(b) by 212 days.

(21) Appl. No.: 10/937,379

(22) Filed: Sep. 10, 2004

(65) Prior Publication Data

US 2005/0176653 A1   Aug. 11, 2005

Related U.S. Application Data

(60) Provisional application No. 60/581,707, filed on Jun. 23, 2004, provisional application No. 60/574,922, filed on May 28, 2004, provisional application No. 60/501,821, filed on Sep. 11, 2003.

(51) Int. Cl.
*A61K 31/70* (2006.01)
*C07H 15/00* (2006.01)
*C07D 237/00* (2006.01)
*C12P 19/60* (2006.01)

(52) U.S. Cl. .......................... 514/25; 435/75; 435/821; 536/4.1; 544/224

(58) Field of Classification Search ................. 536/4.1; 514/25; 435/75, 821; 544/224
See application file for complete search history.

(56) References Cited

U.S. PATENT DOCUMENTS

| 3,854,480 | A | | 12/1974 | Zaffaroni |
| 4,452,775 | A | | 6/1984 | Kent |
| 4,920,215 | A | * | 4/1990 | Holdom et al. ............. 536/16.8 |
| 5,039,660 | A | | 8/1991 | Leonard et al. |
| 5,286,649 | A | * | 2/1994 | Konishi et al. .......... 435/252.1 |
| 5,523,288 | A | | 6/1996 | Cohen et al. |
| 5,783,561 | A | | 7/1998 | Horwitz et al. |
| 5,917,084 | A | * | 6/1999 | Jiang .......................... 560/174 |
| 6,140,306 | A | | 10/2000 | Lambert et al. |
| 6,953,679 | B2 | * | 10/2005 | Salvati et al. ................ 435/121 |

FOREIGN PATENT DOCUMENTS

| CA | 2352451 | 4/2003 |
| WO | WO 01/34816 | 5/2001 |
| WO | 03/062458 A2 | 7/2003 |

OTHER PUBLICATIONS

Igarashi Y. et al. The Journal of Antibiotics (2003) vol. 56, No. 8, pp. 705-708 "Clethramycin, a New Inhibitor of Pollen Tube Growth with Antifungal—Activity from *Streptomyces hygroscopicus* TP-A0623".

Zazoupoulos E. et al., Database GenBank AF546140 "*Amycolatopsis prientalis* UnbL, UnbV and UnbU genes, complete cds; *Amycolatopsis orientalis* Pkse and TebC gemnes, complete cds."

Hutchinson R. et al., Current Opinion in investigational Drugs, Pharmapress US, vol. 2, No. 12, pp. 1681-1690 "Combinatorial Biosyntesis in microorganisms as a route to new antimicrobial, antitumor and neuroregenarative drugs."

Shah, J. Antibiotics, (2000) vol. 53, No. 5, pp. 502-508 "Cloning, characterization and heterologous expression of a polyketide synthase and P-450 oxidase involved in the biosynthesis of the antibiotic oleandomycin".

Rangaswamy V. et al., Proc. Natl. Acad. Sci. (1998) vol. 95, pp. 15469-15474 "Biosynthesis of the Pseudomonas polyketide coronafacic acid requires monofunctional and multifunctional polyketide synthase proteins".

Kakavas S. et al., J. Bacteriol. (1997) vol. 179, No. 23, pp. 7515-7522 "Identification and characterization of the Niddamycin polyketide synthase genes from *Streptomycetes caelestis*".

Brautaset T. et al., Chem. Biol., (2000) vol. 7, No. 6, pp. 395-403 "Biosynthesis of the polyene antifungal antibiotic nystatin in *Streptomyces noursel* ATCC 11455: analysis of the gene cluster and deduction of the biosynthetic pathway".

Fisher M. et al., Structure, (2000) vol. 8, No. 4, pp. 339-347 "The X-ray structure of *Brassica napus* beta-keto acyl carrier protein reductase and its implications for substrate bindingand catalysis".

Berge SM et al., Journal of Pharmaceutical Sciences (1977), vol. 66, No. 1, pp. 1-19 "Pharmaceutical salts".

Goodfellow Bergey's Manual of Systematic Bacteriology, vol. 4, Williams and Wilkins, Baltimore, (1989) vol. 4, pp. 2322-2339 "Supragenic classification of actinomycetes".

Embley and Stakebrandt, Annu. Rev. Microbiol., (1994) vol. 48, pp. 257-289 "The molecular phylogeny and systematics of the actinomycetes".

Gluzman Y., Cell. (1981) vol. 23, No. 1 pp. 175-182 "SV40-transformed simian cells support the replication of early SV40 mutants".

Leung D.W. et al., Technique (1989) vol. 1, pp. 11-15 "A method for random mutagenesis of a defined DNA segment using a modified polymerase chain reaction".

Caldwell R.C. and Joyce G.F., PCR Methods Applic. (1992) vol. 2, pp. 28-33 "Randomization of genes by PCR mutagenesis".

Reidhaar-Olson J.F. et al., Science (1988) vol. 241 (4861), pp. 53-57 "Combinatorial cassette mutagenesis as a probe of the informational content of protein sequences".

McDaniel R. et al., Proc Natl Acad Sci USA (1999)vol. 96, pp. 1846-1851 "Multiple genetic modifications of the erythromycin polyketide synthase to produce a library of novel "unatural" natural products".

(Continued)

*Primary Examiner*—Elli Peselev

(57) ABSTRACT

Novel polyene polyketides, their pharmaceutically acceptable salts, prodrugs and derivatives have been found to have antibiotic activity. One method for obtaining the compounds is by cultivation of *Amycolatopsis orientalis* ATCC™ 43491 or a mutant or variant such as the strain IDAC-220604-1. Another method for obtaining the compounds is post-biosynthesis chemical modification of the compounds obtained by cultivation. Novel polynucleotide sequences and encoded proteins for the biosynthesis of the polyene polyketides are also presented.

26 Claims, 27 Drawing Sheets

OTHER PUBLICATIONS

Zazopoulos E. et al., Nature Biotechnol. (2003) vol. 21, pp. 187-190 "A genomic-guided approach for discovering and expressing cryptic metabolic pathways".

Stryer Biochemistry 3rd edition (1998) W.H. Freeman and Co., New York, pp. 752-754.

Altschul S. et al., J. Mol. Biol. (1990) vol. 215, pp. 403-410 "Basic local alignment search tool".

Hopwood D., Chem Rev., (1997) vol. 97, No. 7, pp. 2465-2497 "Genetic contributions to understanding polyketide synthases".

Zahn J. et al., Applied and Environmental Microbiology (2001) vol. 67, No. 1, pp. 377-386 "Use of direct-infusion electrospray mass spectrometry to guide empirical development of improved conditions for expression of secondary metabolites from actinomycetes".

Kanzaki H. et al., Biosci Biotechnol Biochem (1998) vol. 62, pp. 438-442 "Novel bioactive oxazolomycin isomers produced by *Streptomyces albus* JA 3453".

Blanco et al., Mol. Gen. Genet. (2000) vol. 262, No. 6, pp. 991-1000 "Characterization of two glycosyltransferases involved in early glycosylation steps during biosynthesis of the antitumor polyketide mithramycin by *Streptomyces argillaceaus*".

Chen et al., Gene (2001) vol. 263, No. 1-2, pp. 255-264 "The *Streptomyces venezuelae* pikA V gene contains a transcription unit essential for expression of enzymes involved in glycosylation of narbonolide and 10-deoxymethynolide".

Oh SH and Chater J., Journal of Bacteriology (1997)vol. 179, No. 1, pp. 122-127 "Denaturation of circular or linear DNA facilitates targeted integrative transformation of *Streptomycetes coelicolor* A3(2): possible relevance to other organisms".

Hussain and Ward, Appl. Environ. Microbiol. (2003) vol. 69, No. 1, pp. 373-382 "Enhanced heterologous expression of two *Streptomyces griseolus* cytochrome P450's and *Streptomyces coelicolor* ferredoxin reductase as potentially efficient hydroxylation catalysts".

Bartzatt et al., Biotechnol. Appl. Biochem (2002) vol. 36, pp. 89-93 "Amalysis of an ampicillin propyl ester prodrug which inhibits the growth of *Escherichia coli*".

Dhingra et al., J. Ind. Microbiol. Biotechnol. (2003) vol. 30, pp. 195-204 "Development of cloning vectors and transformation methods for amycolatopsys".

Sakuda S. et al., Tetrahedron Letters (1995) vol. 36 No. 16, pp. 2777-2780 "Linearmycin A, a novel linear polyene antibiotic".

Sakuda S. et al., J. Chem Soc., Perkin Trans. (1996) vol. 1 pp. 2315-2319 "Novel linear polyene antibiotics: linearmycins".

Goodfellow, Bergey's Manual of Systematic Bacteriology (1989), vol. 4, Williams and Wilkins, Baltimore, pp. 2322-2339.

Argoudelis et al., J. of Antibiotics, vol. XL, No. 6, Jun. 1987, pp. 750-760 "Arginomycin: production, isolation, characterization and structure".

Vaara M. Microbiological review (1992) vol. 56, No. 3, pp. 395-411 "Agents that increase the permeability of the outer membrane".

Tsubery H. et al., Med. Chem. (2000) vol. 43 (16) pp. 3085-3092 "Structure-function studies of polymyxin B nonapeptide: implications to sensitization of gram-negative bacteria".

Hutchinson, C. R., et al. Combinatorial biosynthesis in microorganisms as a route to new antimicrobial, antitumor and neuroregenerative drugs, Current Opinion in Investigational Drugs, Dec. 2001, pp. 1681-1690, vol. 2, No. 12, PharmaPress Ltd.

Zazopoulos, E.,et al. A genomics-guided approach for discovering and expressing cryptic metabolic pathways, XP-002356578; GenBank Accession No. AF546140.

Igarashi, Yasuhiro,et al. "Clethramycin, a New Inhibitor of Pollen Tube Growth with Antifungal Activity from *Streptomyces hygroscopicus* TP-A0623 II, Physico-chemical Properties and Structure Determination," The Journal of Antibiotics, Aug. 2003, pp. 705-708, vol. 56 No. 8, Japan Research Association, Tokyo, Japan.

* cited by examiner

Compound 1 ¹H NMR Spectrum
Solvent = CD₃OD
Observe Transmitter Frequency = 499.752 MHz
Number of Transients = 64
Temperature = 25°C Compound 3 ¹H NMR Spectrum
Solvent = CD₃OD
Observe Transmitter Frequency = 499.572 MHz
Number of Transients = 64
Temperature = 25°C Compound 5 $^1$H NMR Spectrum
Solvent = CD$_3$OD
Observe Transmitter Frequency = 499.572 MHz
Number of Transients = 64
Temperature = 25°C

Figure 12a

```
ORF 22_KS02    PIAIIGMACRYPGGVTSPEELWDLVAAGRDGVSEFPVNRGW--EDVYDAD
ORF 22_KS03    PIAIVGMACRFPGGVRSPEDLWRLVSEGRDGITPFPADRGWDVEGLYDPE
ORF 19_KS01    PIAIIGMACRYPGGVRSPEELWDLVAGERTGLTGFPVDRGWDLDGLYDPE
ORF 18_KS02    PIAIIGMACRYPGGVSTPDDLWRLVADGNDGITRFPENRGWDTDGVYHPD
ORF 19_KS02    PIAIIGMACRYPGGVASPEDLWRLVAEGRDGISLFPADRGWDVDGLYDPD
ORF 23_KS01    PIAIVGMACRYPGGVASPEDLWRMVETGGDGISGFPVDRGWDLEALYDPD
ORF 20_KS01    PIAVVGMSCRFPGGVRSPEQLWDLVASGTDALSEFPGDRGWDLGGLFDPD
ORF 21_KS01    PIAIIGMACRYPGGVRGPEQLWDLVAAGTDAVGGFPADRGWDVEALYDPD
ORF 22_KS01    PIAIIGMACRFPGGVRSPEDLWELVAEGRDGISGFPADRGWDLSALYDPT
ORF 19_KS03    PIAIVAMSCRFPGHADTPERLWALLAEGRDALGEFPADRGWDLERLFDTD
ORF 18_KS01    PIAIVGMACRYPGGIGSPEDLWRLVTEGGDATSDFPADRGWDVESLYDPD
ORF 21_KS02    PIAIVAMSCRFPGGITDPEKFWDFVADGGDAMAAFPGDRGWDLDALYDPD
               ***::.*:**:**   *:.* ::   .   **.:***    ::..

ORF 22_KS02    PGKVGKSYAREGGFLHDAGEFDAAFFGISPREALAMDPQQRLLLETSWEV
ORF 22_KS03    ASRPGTSCTRYGGFLHDAGDFDPGFFGISPREALAMDPQQRLLLETSWEA
ORF 19_KS01    QGKPGKSYVREGGFLHDAARFDPAFFGISPREALAMDPQQRLLLEISWEA
ORF 18_KS02    ADHRGTTYVREGGFLHDAGQFDPGFFGISPREALAMDPQQRLLLEISHEA
ORF 19_KS02    PGKAGKSYVREGGFLHEAGDFDAGFFGISPREALGMDPQQRLLLEVSWEA
ORF 23_KS01    PDKQGTSYVSQGGFLHDVAEFDPAFFGISPREALAMDPQQRLLLETSWEA
ORF 20_KS01    PDTPGKTYVSEGGFLYEAGDFDAAFFGISPREAQAMDPQQRLLLEAAWEV
ORF 21_KS01    PARHGKTYTREGGFLYDAHEFDAAFFGISPREALTVDPQQRLLLETAWEA
ORF 22_KS01    GEKPGTSYCREGGFLDGAGEFDPAFFGISPREALAMDPQQRLLLEISWET
ORF 19_KS03    PDRRGTSYTRQGAFLETAGDFDAGFFGISPREALAMDPQQRLLLETSWEA
ORF 18_KS01    PGVPGKTYTRRGGFLDGAGDFDAGFFGISPREALAMDPQQRLLLETSWEA
ORF 21_KS02    PAHLGTTYAREGGFLDDAGGFDAAFFGISPREALAMDPQQRLLLETSWEA
                *.:    *.**  . **..********.:********* ; *.

ORF 22_KS02    FERAGIDPHAVRGSKTGVFAGVMYHDYAARLNSVPEDV---EGYLGTGNS
ORF 22_KS03    FERAGIDPATLRGSATGVFAGAMYHDYVSRLTEIPADL---EGYLGTGNS
ORF 19_KS01    IERAGIAPDSLRGSGTGVFAGVIHNEYSAIAGTPPADL---EPYLGNGSF
ORF 18_KS02    VERAGIDPKSLRGSGTGVFAGVMYHDYATGLNRVPDDV---EGYLGNGTS
ORF 19_KS02    FERAGIDPGTLRGSDTGVFAGQMYHDYLTGATVVPDDV---EGYLGTGNS
ORF 23_KS01    IERAGIDPGSLKGSRTGVFAGLMYHDYVSGLTEIPDEV---GGYLGTGNS
ORF 20_KS01    LERAGIDPATLRGSRTGVFAGVIHNDYTGVLTDIPPEL---EPYLGNGNF
ORF 21_KS01    FERAGIDPLSVRGSRTGVFAGVMYNDYGSRLDPRAEELREFEGYLGNGSA
ORF 22_KS01    FERAGIDPGSLRGSRTGVFAGVMYHDYVSRLAAIPEEL---EGYLGTGNS
ORF 19_KS03    FERAGIDPATLRGSRTGVFAGVMDNEYVSGSAEVPDGV---EGYLATGTS
ORF 18_KS01    FERAGIDPATLRGSATGVFVGAETQEYGPRLGGAEEGL---EGYLLTGNA
ORF 21_KS02    FERAGIDPATLRGSATGVFVGASFQNYGLDAVDAPEGT---EGYFLTGTA
               .**** * :::** ****.*   ::*             *:  .*.

ORF 22_KS02    GSVISGRLAYTFGLEGPAVSIDTACSSSLVAMHLAGQALRQGECSLAVAG
ORF 22_KS03    GSVISGRLAYAFGLEGPAVSIDTACSSSLVAMHLAAQALRQGECGLALAG
ORF 19_KS01    ASIASGRVSYTFGLEGPAVTVDTACSSSLVALHLAAQALRQGECSLALAG
ORF 18_KS02    ASIHSGRVAYTFGLEGPAVTIDTACSSSLVALHLAAQALRRGECSMALAG
ORF 19_KS02    GSVLSGRVSYTFGLEGPAVTVDTACSSSLVALHLAAQALRRGECSLALAG
ORF 23_KS01    GSIASGRVSYTFGFEGPALTVDTACSSSLVTLHLAAQALRRGECDLALSG
ORF 20_KS01    SSVASGRIAYTLGLEGPAVSVDTACSSSLVALHLAAQSLRREECTLALVG
ORF 21_KS01    GSVASGRVAYTFGLEGPAVTIDTACSSSLVALHLAAESLRRGESTLALAG
ORF 22_KS01    GSVVSGRVAYTFGLEGPAVTIDTACSSSLVALHLAAQALRQGECSMALAG
ORF 19_KS03    ASVASGRVSYTFGLEGPAVTVDTACSSSLVALHLAAQALRQGECSLALAG
ORF 18_KS01    ASVASGRVSYAFGFEGPTVTVDTACSSSLVALHLAGQALRLGECPIAVAG
ORF 21_KS02    TAVVSGRLSYTFGLEGPAVTIDTACSSSLVALHLAAQALRRGECSLALAG
               :: ***::*::***:::***.*****::**.::**  *. :*:  *
```

Figure 12b

```
ORF 22_KS02    GVTVMATPNTFIEFSRQRGMATDGRCKSFAEAADGTGWGEGVGMLLLERL
ORF 22_KS03    GVAVMSTPDTFIEFSRQRGMAPDGRIKAFSETADGTAWGEGVGMLLLERL
ORF 19_KS01    GVTVMANPAAFVDFSRQRGLAADGRIKAFAEAADGTAWGEGAGMLLVERL
ORF 18_KS02    GVTVMATPEVFVDFSRQRGLAPDGRCKSFSDEADGTVWSEGVGMLLVERL
ORF 19_KS02    GVTVMATPETFVDFSRQRGLAPDGRSKSFSDGADGTSWSEGVGMLLVERL
ORF 23_KS01    GVTVMFTPGTFVEFSRQRGMAPDGRCKPFAEEADGTGWSEGVGMLLVERL
ORF 20_KS01    GVNVMTHPAAFVDFSRQRGLAADGRCKAFADAADGTGWGEGVGMLLVERL
ORF 21_KS01    GVTVMASPETFVEFSRQRGMAPDGRCKPFADAADGTWAEGAGILLLERL
ORF 22_KS01    GVAVMSTPDTFVDFSRQRGLAADGRCKSYSDGADGTSWAEGVGMLLVEKL
ORF 19_KS03    GVTVMATPGTFVEFSRQRGLAADGRCKAFADGADGTGWGEGAGMLLVERL
ORF 18_KS01    GVAVMSSPGGFLAFSRQRGLAPDGRCKPFSAAADGTGWSEGVGMLVLERL
ORF 21_KS02    GVTVMANPAAFVEFSRQRGLAPDGRCKAFADAADGTAWSEGAGILLVERL
               ** **   *  *: ****** *.*** *.::  **** *.**.*:*::*:*

ORF 22_KS02    SDARRNGHRVLAVVRGSAVNQDGASNGLTAPNGPSQQRVIRQALAQAGLR
ORF 22_KS03    SDARRNGHRVLAVLRGTAVNQDGASNGLTAPNGPSQQRVIRQALAQAGLR
ORF 19_KS01    SDARRNGHRVLAVVRGSAVNQDGASNGLTAPNGLSQQRVIRQALANARLA
ORF 18_KS02    SDARRNGHRVLAIVRGSAVNQDGASNGLTAPSGPSQQRVIRRALADAGLK
ORF 19_KS02    SDAERNGHRILAVVRGSAVNQDGASNGLTAPNGPSQQRVIRRALADARLE
ORF 23_KS01    SDARRNGHPVLAVLRGSAVNQDGASNGLTAPNGPSQQRVIREALADARLT
ORF 20_KS01    SDAQRNGHQVLAVLRGSAINQDGASNGLTAPNGPAQQRVIRQALADARLS
ORF 21_KS01    SDARRHGHPVLAVVRGTAVNQDGASSGLTAPNGPSQQRVIRQALDSAGLA
ORF 22_KS01    SDARRLGHEVLAVVSGSAVNQDGASSGLSVPNGPSQQRVIRQALENARLS
ORF 19_KS03    SDARRNGHPVLAVLRGSAVNQDGASNGLTAPNGPSQQRVIRQALANARLE
ORF 18_KS01    SDARRNGHRVLAVVRGTAINSDGASNGLTAPNGAAQQRVIRRALANAGLA
ORF 21_KS02    SDARRLGHPVLALVRGSAVNQDGASNGLSAPNGPSQQRVIRQALANAGFA
               ***.* ** :**:: *:*:*.****.**:.*.*  :******.** .* :

ORF 22_KS02    PSDVDAVEAHGTGTTLGDPIEAQALLATYGQDR--EEPLWLGSVKSNLGH
ORF 22_KS03    PSDVDAVEAHGTGTTLGDPIEAQALLATYGQDR--EEPLWLGSVKSNLGH
ORF 19_KS01    PSDVDAMEAHGTGTRLGDPIEAQALLATYGQDR--TTPLWLGSVKSNIGH
ORF 18_KS02    PSEVDAVEAHGTGTPLGDPIEAQAMLATYGQDR--DRPLWLGSLKSNLGH
ORF 19_KS02    PSEVDAVEAHGTGTTLGDPIEAQALLATYGQRE--DAALWLGSIKSNIGH
ORF 23_KS01    TADVDVVEAHGTGTTLGDPIEAQALLATYGKGRPSDRPLWLGSIKSNLGH
ORF 20_KS01    PGQVDVVEGHGTGTTLGDPIEAQALLATYGQDR--ERPLLLGSLKSNIGH
ORF 21_KS01    PHQVDVVEAHGTGTTLGDPIEAQALLAAYGQER--VRPLWLGSLKSNVGH
ORF 22_KS01    AGQIDVVEGHGTGTTLGDPIEAQALLATYGREKSADRPLWLGSLKSNIGH
ORF 19_KS03    PSEVDAVEAHGTGTTLGDPIEAQALLATYGQDR--ERPLLGSVKSNIGH
ORF 18_KS01    PSEVDAVEAHGTGTVLGDPIEAQALLATYGRDR--ERPLLLGSVKSNIGH
ORF 21_KS02    PSDVDAVEAHGTGTSLGDPIEAQALLAAYGGER--EHPLWLGSVKSNLGH
               . ::*.:*.H**** ********:**:**   :    .* ***:***:*H

ORF 22_KS02    TQAAAGVAGVIKMVEAMRHGVLPRTLHVDEPSSHVDWTGGAVSLVTESRE
ORF 22_KS03    TQAAAGVASVIKMVEAMRHGVLPRTLHVDEPSSHVDWTEGAVSLLTETRD
ORF 19_KS01    SQAAAGVASIIKLVEAMRHGVLPKTLHVDAPTSHVDWSEGAVSLLTEAEP
ORF 18_KS02    TQAAAGVGGIIKMVQAMHHGVLPRTLNLGTPTTKVDWTSGNVSLLSEPVA
ORF 19_KS02    SQAAAGVAGVIKMVEAMRRGVLPKTLHVTEPSSHVDWTAGAVSLLTEARL
ORF 23_KS01    TQAAAGVAGIIKMVQALRSGILPRSLHAETPSSHVDWSAGAVSLLAEARP
ORF 20_KS01    TQAAAGVGGVIKMVQAIRHGIAPRTLHVDAPSSHVDWSAGEVSLLTGEQP
ORF 21_KS01    SQAAAGVGGVIKMVQAIRHGIAPMTLHVDTPTSKVDWEAGSVELLTEARP
ORF 22_KS01    SQSAAGVGGVIKMVQAIRHGILPRTLHAEDPSSKVDWSAGAVELLTEARG
ORF 19_KS03    TQAAAGVAGVIKMVLAMRHGTLPRTLHVDTPTSRVDWAAGRIELATEPTQ
ORF 18_KS01    TQSAAGVAGVIKMVQAMRHGVLPKTLHADEPTPKVAWSSGAVELLNETVA
ORF 21_KS02    TQSASGVAGVIKMVQAIRHGVLPRTLHVDAPTTEVDWTAGDVRLLTEPVD
               :*:*:**..:**:* *::   *   *  :*:      *:...* *  * : *

ORF 22_KS02    WPDTGRPRRAGVSSFGISGTNAHTIIEAV
ORF 22_KS03    WPDTGRPRRAGVSSFGISGTNAHVVLEAD
ORF 19_KS01    WPKTDRPRRAAVSSFGISGTNAHVVLEQP
ORF 18_KS02    WPETGGPRRAAVSSFGISGTNAHVVLEQA
ORF 19_KS02    WPDAGRPRRAAVSSFGISGTNAHVVLEQG
ORF 23_KS01    WPELDRPRRAAVSSFGISGTNAHVVLEAA
ORF 20_KS01    WPETGEPRRAGVSSFGISGTNAHVILEQA
ORF 21_KS01    WPETGEPRRAGISSFGVSGTNAHVIVEQA
ORF 22_KS01    WPETGQPRRAGVSSFGVSGTNAHTIIEQA
ORF 19_KS03    WPETGGPRRAAVSSFGMSGTNAHVVLEQA
ORF 18_KS01    WPENGAPRRAAVSSFGMSGTNAHAVLEQA
ORF 21_KS02    WPDTGRPRRAGVSSFGVSGTNVHTLIEEV
               ** . .****.:****:****.*.::*
```

Figure 13a

```
ORF_19_AT01        GPVPFVLSGKTEAALHEQVARVR-ELARDSDVTAADLAFSLATTRTALDH
ORF_22_AT01        GAVPAVLSGKTAEALRDQVVRLRSHILARPELSVADVAASLATTRVLHEH
ORF_19_AT02        GPAAFVLSAGSEAALHDQASRLR-DFLAETPAALADVAFSLATTRAALEH
ORF_22_AT02        DVPPWPLSGKTEEALRAQASRLHDHLLATPEVTAADVALSLT-ARADLEH
ORF_21_AT02        TWVPWVLSAKTEEALRSQASRLHAQLEEHP-GDDSDIAYTLATARAGLEI
AAF71776_ATMA03|NYST  GVVPLPLSGKSPEALRDQAARLLAGLAERPALRPLDLGYSLATTRSAFDH
ORF_22_AT03        DVLAFPLSAKTQDALREQAARLRARLLTGHAPELADVAQTLA-TRGLFEH
ORF_18_AT01        PTWLFPVSGRDEKALRRQAARLR---EALPDSDLPAIAAALATTRSALEW
ORF_20_AT01        -VLPFVLSGRSEEALAAQASKLAAYLTGEP--APKAIARALAETRSALPH
ORF_23_AT01        -ATPWLLSARTPEALRARAAQLRSFVDLPG--AAATLA-----ARPLFGH
ORF_18_AT02        -VLPFVLSGKTSAALAAQADRLAGHLAGDV--SLPAVARALAVTRSALDH
ORF_19_AT03        -VVAWPLSAKEPEAVAAQAARLKSFLTGE---RPADVAYSLATARTTLEH
ORF_21_AT01        -VTPLVLSARSAEALRAQSARLREHLRQTE--SLTDTAFSLATSRAALEH
AAF71775_ATMM01|NYST  -ALPWIVSGHSPQALRDQAAALAARVETDPALRPQDIGHTLHTARALLER
                      :*.   *:    :    :             .       :*

ORF_19_AT01        RAALVGT-LDDLLT----------ATLVEGRA-TDGGTAFLFTGQGSQR
ORF_22_AT01        RGAIVAADRDQLLAGLDILAAGATTAGVSQGVA-TDGRTAFLFTGQGSQR
ORF_19_AT02        RAAVVAADRETLLAALEN-------LTVTGRA-TEGRTAFLFTGQGSQR
ORF_22_AT02        RAVLVAGDRDGLLATLDALAHGETTEGIVRGTARHTGRTAFLFTGQGSQR
ORF_21_AT02        RAAVTGPDRLRELALLAEG----TPSAAVLRGALTAGAPGFLFTGQGSQK
AAF71776_ATMA03|NYST  RAVVLATDRADAVRALTALAAADADLSAVVGDT-RTGRHAVLFSGQGSQR
ORF_22_AT03        RAVVTAGDRDGLLDALAALAGG-EPGDFVTGLAKPGGKLAFLFTGQGSQR
ORF_18_AT01        RAVVTVADRAGLLAGLDALATGEALPSLVHGTA----RIGIVFSGQGSQR
ORF_20_AT01        RAVVLAEDLGELLGGLRSLAEGEPAARVLTGTAEA-GKAVFVFPGQGSQW
ORF_23_AT01        RAAIVGDPR----AALDALATGKPSNLLIEGTAQS-GKAVFVFPGQGSQW
ORF_18_AT02        RAVVVAGDRAGLTAGLRALADAVPAPHVVDGVAEN-GKAVFVFPGQGSQW
ORF_19_AT03        RAVVVGEDP---IAGLAALAAGEPSGSVVTGTATS-GKAVFVFPGQGSQW
ORF_21_AT01        RAVVVAEAD----ASLDALAAGAPAAGLVEGIALPPGKVAFVFPGQGSQW
AAF71775_ATMM01|NYST  RAVVVAPDRAELLAATHELAAGRSANAVVEGLADVEGRTVFVFPGQGSQW
                   *..:                    :             .:*.**:***

ORF_19_AT01        LGMGRELAERFPVFAQAFDDVSSRFERPI---------AELSAEE--LN
ORF_22_AT01        RGMGRELAERFPVFAEAFDDVCARFERPI---------KELSTEE--LN
ORF_19_AT02        LGMGLQLAERFPVFAAAYDEVCSRFEQPL---------RDLTAEE--LN
ORF_22_AT02        LGMGRELAERFPVFAEVYDEVCSRFEQPL---------RDLSAEE--LN
ORF_21_AT02        PGMGAELAARPVFAAAFDEVCAHLDPRLGLSL-----REVLETER--VH
AAF71776_ATMA03|NYST  LGMGRELYERFPVFAEALDVAIDHLDAALPAQASLREVMWGDDVEL--LD
ORF_22_AT03        AGMADELSAAFPVFARTFGEICARFDTLLDRPLR-----EALAGDL--VD
ORF_18_AT01        AGMGRELHRRFPVFAAAFDDACGHLDLQLDRPLAEIVFADEGTEEAGLLH
ORF_20_AT01        VGMAEELLLSAPVFAESMAECERALSSFVDWKLS---DVLS---DAAALE
ORF_23_AT01        VGMAEELLLSAPVFAESMAECEQALSSFVDWKLS---DVLS---DAAALE
ORF_18_AT02        TGMAVDLLGSSAVFAEAMADCEAALLSHLDWKLT---HVLS---DAAALE
ORF_19_AT03        AGMAVELLASAPVFAESMAEDCEAALLSYVDWKLT---EVLS---DATALE
ORF_21_AT01        AGMALELKDSSPVFRAALLDCERALSSFVDWKLT---DVLG---DATALE
AAF71775_ATMM01|NYST  VGMGAQLLDESAVFAERIAECAAALAEFTDWSLV---DVLRGVVGAPSLE
                   **. :*    .**                :                :.

M1              M2              M3
                              -----           --------        -----
ORF_19_AT01        QTANTQCALFAFEVALFRLVENWGLRPDFLAGHSVGEIAAAHVADVLSLD
ORF_22_AT01        QTANTQCALFAFEVALFRLVESWGVRPDFLAGHSIGEIAAAHVAGVFNLD
ORF_19_AT02        QTANTQCALFALEVALFRLVESWGVRPDFLAGHSVGEIAAAHVAGVLSLD
ORF_22_AT02        QTANTQCALFALEVALFRLVESWGVRPDFLAGHSVGEIAAAHVAGVLSLD
ORF_21_AT02        ETAFAQCALFAVEVALFRLLESWGVRPALLLGHSVGEIAAAHVAGVLSLA
AAF71776_ATMA03|NYST  ETGWTQPALFAVEVALFRLVESWGVRPDFVAGHSIGEIAAAHVVGVFSLE
ORF_22_AT03        RTEYTQCAMFAVEVALFRLVESRGVRPDFLAGHSIGELAAAHVAGVWSLE
ORF_18_AT01        RTEYAQCALFAVEVALFRLYEHWGLRPDYVAGHSIGELAAAHVSGMLSLS
ORF_20_AT01        RVDVVQPVLFAVMVSLARLWRACGVEPAAVVGHSQGEIAAACVAGALSLD
ORF_23_AT01        RVDVVQPVLFAVMVSLARLWRACGVEPAAVVGHSQGEIAAACVAGALSLD
ORF_18_AT02        RVDVVQPVLFAVMVSLARLWRACGIEPAAVVGHSQGEIAAACVAGALSLE
ORF_19_AT03        RVDVVQPALFAVMVSLARLWRASGIEPAAVVGHSQGEIAAACVAGALSLD
ORF_21_AT01        RVDVVQPALFAVMVSLARLWRACGVEPDAVTGHSQGEIAAAYVSGALSLA
AAF71775_ATMM01|NYST  RVDVVQPASFAVMVSLAALWGSRGVLPDAVVGHSQGEIAAAVVSGALSLR
                   .. .*  .**. *:.   *    *: *   :**  **:*** *  .*
```

Figure 13b

```
ORF_19_AT01           DAVTLVSARGRLM-QALPTGGAMVALQATEAEVAPLLTDR---VSLAAIN
ORF_22_AT01           DAVKLVAARGRLM-QALPTGGAMVALQATEAEVFPLLTDR---VSLAAIN
ORF_19_AT02           DAVTLVSARGRLM-QALPTGGAMVALQATEAEVTPLLTER---VSLAAIN
ORF_22_AT02           DAVTLVSARGRLM-QALPTGGAMVALRATEAEVTPLLTER---VSIAAIN
ORF_21_AT02           DAATMVEARGRLM-GALPSRGVMIALQANEDEVTPLPTER---VSIAAVN
AAF71776_ATMA03|NYST  DACRLVAARATLM-QALPTGGAMIAIQAAEDEVTQHLTDD---VSIAAVN
ORF_22_AT03           DACTVVAARGRLM-QALPSGGAMIAVQATEEEVRPLIDDET--VSIAAIN
ORF_18_AT01           DAAALVAARGRLM-QDTREGGAMLAVQATEDEVLPLLDER---LAIAAVN
ORF_20_AT01           DAARLVCLRSKAI-LALSGRGGMVSVAASEDRVRELLPAG---VSVAAVN
ORF_23_AT01           DAARVVCLRSKAI-LALSGLGGMVSVAASEDRVRELLPAG---VSVAAVN
ORF_18_AT02           DAARVVCLRSKAI-LALSGLGGMVSVAASEDRVRELLPDG---VSVAVVN
ORF_19_AT03           DAARVVCLRSKAI-TALSGRGGMVSVAAPEAQVREILPEG---VSLAAVN
ORF_21_AT01           DAAKVVALRAKAI-LALSGAGGMVAVALGRDDVLPRLTEWGDRIAVAAVN
AAF71775_ATMM01|NYST  DGARVVALRSQAIGRALAGRGGMMSVALSVDVLEPRLVEFEGRVSVAAVN
                      *.  :*  *.  :        * *:::    :           :::*.:*

M4
                                                              ----
ORF_19_AT01           GPESVVVSGDEEAVAAVVSHF--EGRKSKRLTVSHAFHSPLMEPMLDDFR
ORF_22_AT01           GPESVVLSGDEDAVAAVVSRF--EGRKHKRLAVSHAFHSPLMEPMLDDFR
ORF_19_AT02           GPESVVVSGEEDAVAAVVSQF--EGRKSKRLTVSHAFHSPLMEPMLDEFR
ORF_22_AT02           GPESVVVSGDEDAVAAVV-----EGRKHKRLTVSHAFHSPLMEPMLDEFR
ORF_21_AT02           GPEAVVLSGDEDAVTAVVDRF--ADRKSKRLVVSHAFHSPLMEPMLADFR
AAF71776_ATMA03|NYST  GPTSVVVSGAESAARTVADRLAENGRKTTRLRVSHAFHSPLMDPMLAEFR
ORF_22_AT03           GPVSVVVSGEEAAVTALAAGFAERGRKTKRLTVSHAFHSPLMDGMLGEFR
ORF_18_AT01           GPRSVVVSGDEAAVEEVAAAF--ARRKTKRLKVSHAFHSHHMDGMLDEFR
ORF_20_AT01           GPSAVVVSGDVAGLEALLKRCELLDVRAKRIPVDYASHSAHVDAIEQEVL
ORF_23_AT01           GPSAVVVSGDVAGLEALLKRCELLDVRAKRIPVDYASHSAHVDAIEQEVL
ORF_18_AT02           GPASVVVSGDVAGLEALLKRCELLDVRAKRVPVDYASHSAHVDAIEQQVV
ORF_19_AT03           GPASVVVSGDVAGLDALMTACEASGLRAKRIPVDYASHSAHVDAIEQDVL
ORF_21_AT01           GPASVVVSGDPEALDGLVSACEADGVRARRIPVDYASHSPQVDVLREELL
AAF71775_ATMM01|NYST  GPRSVVVAGEPEALDALHARLTADDIRARRIAVDYASHSHQVEDLHEELL
                      **  :**::*    .    :      :  *:  *.:*  H*   ::  :  :.

ORF_19_AT01           AVVEGLTFAEPRIPIVS------GGLAEVSTSDYWVRHVRDAVRFHDSVE
ORF_22_AT01           AVADSLSYAAPRIPIVS------GGLADVSTSDYWVRHVRDAVRFHDSVK
ORF_19_AT02           VVADSLSYAAPRIPIVS------GGLAEVSTSDYWVRHVRDAVRFHDSVK
ORF_22_AT02           TVVEGLTFAAPRIPIVS------GGLAEVSTSDYWVRHVRDAVRFHDSVK
ORF_21_AT02           RVVSGLSFSEPRIPIVSTVT--GRSDPEIASPGYWVRHVREAVRFHDAIR
AAF71776_AT03|NYST    AVAEGLSYATPTLPVVSNLTGRLATADDLCSAEYWARHVREAVRFADGVS
ORF_22_AT03           AVLDGIAAADPRIPLVSTLTGDPLTGDQARSSEYWVRHVRDAVRFCDAIR
ORF_18_AT01           RFAEILTFRKPVIPLVSTVSG--ELLTEATAPEYWVEHVRRPVRFADGVR
ORF_20_AT01           SALAGISPQAPVIPFYSTVTD-EPLE---LDAAYWFRNLRGTVRFAATVD
ORF_23_AT01           SALAGISPQAPVIPFYSTVTD-EPLE---LDAAYWFRNLRGTVRFAATVD
ORF_18_AT02           TALSGIMPREAELPMYSTVTG-EPIDTTTLDAAYWFRNLRATVRFDQAVR
ORF_19_AT03           AALDGIEPRAPEIPFYSTVAG-EPLDP-VVDAAYWFRNLRGTVHFGQAVR
ORF_21_AT01           GLLDGVEHHASTVPFYSAVTG-EPLDTAGLTPEYWFRNLRATVRFDRSVR
AAF71775_AT01|NYST    EVLAELAPRTSEVPFFSTVTG-DWLDTARMDAGYWFRNLRGRVRFADAVA
                        :*. *          . ** .::*  *:*   :

ORF_19_AT01           F--LKAEGVTRFLEIGPDAVLTAM-----AKESAE----DAVVLPASRRD
ORF_22_AT01           F--LETEGVTRFLEIGPDAVLTAM-----AQESTE----GAVVVAASRRN
ORF_19_AT02           F--LEAEGVTRFLEIGPDGVLTAM-----AKETAE----DAVVVPALRRD
ORF_22_AT02           F--LEAEGVTRFLEIGPDGVLTAM-----AQDSLE----DAVVVPALRRD
ORF_21_AT02           FAEAEAEGVRAFVELGPEGVLSAM-----AKDFLE----DTVLIPTLRGE
AAF71776_AT03|NYST    T--LENEGVTTFLELGPDGVLSAM-----AQQSLTG---DAATVPALRKD
ORF_22_AT03           T--LEAQGVRRYLELGPDAPLTALGEHCVTNESTVD---AQLFVPSLRAG
ORF_18_AT01           R--LDELGVDVLLELGPDAVLTPM-----AAEVLDGE--GAALVPSLRGS
ORF_20_AT01           R--LLEDGFRFFVEASPHPVLVPG-----ISE-------EAIALGSLRRG
ORF_23_AT01           R--LLEDGFRFFVETSPHPVLVPG-----ISE-------DAVALGSLRRG
ORF_18_AT02           R--LIADGFRFFVETSPHPVLVAG-----LTELVEEAAVPAVALASLRRD
ORF_19_AT03           R--LLDDGFRFFVEASPHPVLVTG-----IADTAEDAGERAVAVGSLRRD
ORF_21_AT01           R--LLDDGHRFFVEASAHPVLTGS-----VTETIEERGAHAVALGSLRRD
AAF71775_AT01|NYST    D--LLAAEYRAFVEVSSHPVLTMA-----VLDLIEEAGVTAVATGTLRRD
                        :*  ...    *              :             : *
```

Figure 13c

```
ORF_19_AT01              RPEVTTLLTAVAGLHVHGAEVDWAPLFDG--ARRVDLPTYPFQYEHFWL-
ORF_22_AT01              RAEDVTLLAAVSTLHVHGASVDWTPLLAG--ARRVDLPTYAFQHRRFWL-
ORF_19_AT02              RPEVETLLTAVAGLHVHGVGVDLTALLGG--GSPVDLPTYAFQHRRFWL-
ORF_22_AT02              KPEVTTLLTAVAGLHVHGAGVDWSPLSAG--ARRVDLPTYAFQRTEFWL-
ORF_21_AT02              RPEVAALATTLGRLHVHGVGIDWAGVFDGVQASRVTLPTYPFEHRHFWL-
AAF71776_AT03|NYST       RDEETSALTALAHLHTAGLRVDWAAFFAGSGATRVDLPTYAFQHATYWP-
ORF_22_AT03              RSDVESFVTALARLHVDGVRVDWAKALPG---RKIDLPTYAFQHERFWL-
ORF_18_AT01              RPEAEALAASLAELWVRGAELGWPQVFGA--HPRADLPTYAFERQRYWL-
ORF_20_AT01              EGGAERFVASLAEAHTQGLSPSWSAVLPP--AERVDLPTYAFQHKRFWLE
ORF_23_AT01              EGGAERFVASLAEAHVHGLSPAWSSILPT--ADWVDLPTYPFQRKRFWLE
ORF_18_AT02              EGGPTRFVTSLAEAHVHGLSPDWAALLPE--AGWVDLPPYAFQHQEFWLT
ORF_19_AT03              EGGPLRFLTSLAEAHVHGLSPDWAALAP---GTRVDLPTYAFQHEHYWLR
ORF_21_AT01              EGGPRRFLTSLAEAHVRGLRPDWAALWPT--ATRVDLPTYAFQRVPYWLD
AAF71775_AT01|NYST       QGGAGRFLLSAAEVFVRGVDVDWAGAFEGTGAARVDLPTYAFQRERYWNT
                            *  *.**  .    .  *    *.**  .   .   *.*:   :*
```

Figure 14

```
ORF 22_DH02    AGLSDAGHPLLGGAVTLPDSGGTVFTGRLSLAAQPWLADHAVGETVLLPG
ORF 22_DH03    LGQSPAGHPLLGAAVEAPDSGAVLFTGRLSVQEQPWLADHVVAGTTLLPG
ORF 20_DH01    FGQTVVDHPLLGAALPLADGDGLVLTGRISPDTQPWLVDHTVLDTVLLPG
ORF 23_DH01    FGQTVVDHPLLGAVVAVPGTGGLLYTGRISLETHPWLADHAVSGTVLVPG
ORF 18_DH02    FGLGATGHPLLTAATALPGSGGLLLTGRISTAAQPWLADHAVQGVVLLPG
ORF 19_DH03    AGLDDGGHPLLGAVVPLAGSDGLVATGRISARNQTWLPDHAVGGALLLPG
ORF 21_DH02    FGLGEAGHALLGAAVPVPGGSGISFTGRLSLRAQPWLAEHVVLGTALLPG
ORF 19_DH02    AGLGTTDHPLLGAAAALPGDGGFLLTGRLSGHAQPWLAEHRVGGVVLLPG
ORF 22_DH01    LGLGATDHPLLGAVVTMADAHGVLLTGRLSLAAQPWLAGHVVAGHVLLPG
ORF 19_DH01    AGLDASPHALLAAAVRPAGEDEILLTGRISLSTLPWLADHVVGGNVLLPG
ORF 18_DH01    YGLGDTGHPLLRASVTTAEDGALLLSGRLSPLTQPWLADHVVGGDVVLPG
                 *    *.**  .       .    :**:*    .**  *    :: *

ORF 22_DH02    TAFVDLALAAGRRHGRVVLDELTLESPLVLPEHGGVDLRVWVREPDDTGA
ORF 22_DH03    TAFVELALRAGELTGCAAVDELTLEAPLVLPDHGGTALRIVAAAPDETGR
ORF 20_DH01    TAFVELVLRAGREAGCDGVDELTLEAPLVLDG--PVALQVVLGEPDERGR
ORF 23_DH01    TAFVELALAAGTQVDCALLDELTLEAPLVLEEGTDVRLSVELGDADVDGR
ORF 18_DH02    TAFVELALQAGTHAGCGRIDELTLEAPLPLPEQGGVRVQVVLG-SEVNGR
ORF 19_DH03    AALVDLALTVGERTGCGRIAELTIEAPLVLGESGSARLQVTVGASADDGT
ORF 21_DH02    TAFVDLALHAGDRAGCGTVAELTLEAPLALPESGDVRLHVTVGEPGEDGG
ORF 19_DH02    TAFVEIALRAGDEAGCGHLEDLTLEAPLVLPERGATQLSVLVGAADDTGR
ORF 22_DH01    TAFVDLVLHAGDKVDCGIVEELTLREPLVLPEHDALSLQLVVGAPDETGR
ORF 19_DH01    TAFAELALAAADEAGCEAVEELNLEAPLVLPEKGGVQLQVAVGAADDQGR
ORF 18_DH01    TALLELALRAAELAGAGGVEELTLEVPMVLSEA-GVQVQVSVRDSG----
                :*:  ::.*  ..    .    :  :*.:. *: *         :  :     .

ORF 22_DH02    CAVSVHS
ORF 22_DH03    RALDVYS
ORF 20_DH01    RAVSVHS
ORF 23_DH01    REVGVYS
ORF 18_DH02    REVTVHS
ORF 19_DH03    REVAVYS
ORF 21_DH02    RTIEIHS
ORF 19_DH02    RTIEIHS
ORF 22_DH01    RTVGVHS
ORF 19_DH01    RSVTVHA
ORF 18_DH01    --LLIFF
                  :  :.
```

Figure 15

```
ORF 18_ER02              QLAWRDGELLVPRLAKVSTDGTLTPPEGP--WVLDAPRRGTLEELALVPA
ORF 19_ER03              QLALRAGTVLGARLVKASADTALVPPPGSRAWTVDTLGGGTLENLVLRDR
ORF 19_ER02              QIALRDGRALAPRLATTASSTELTPPEGA--WRLDTTGRGTLENLTLVPS
AAF71767_ER01|NYST       QAVVREGTVRVGRLARLDSGRGLVPPPGT-PWRLGSRAKGSLDGLALLPH
AAF71776_ER03|NYST       QLALRDGGVLAARLARFDTAAALTPPADR-AWRLDSTAKGSLNGLALTPY
                          *.**       **.   :  *.**  .    *  :.:   *:*: *.*

ORF 18_ER02              PTAARPLADGEVRIQVRAAGINFRDVLITLDMYPE-DKAVMGSEGAGIVT
ORF 19_ER03              PDLLAPLADGQVRIAVRSAGLNFRDVVVALGLVP--GQEGIGGEGAGVVT
ORF 19_ER02              PEAVAPLAEGEVRIAVRAAGLNFRDVLIALGMYP--GAATLGSEGAGVVT
AAF71767_ER01|NYST       PEARRPLTGHEVRVGIRAAGLNFRDVLNALGMYPG-DAGLFGSEAAGVVV
AAF71776_ER03|NYST       PAALAPLTGHEVRVEVRAAGLNFRDVLNALGMYPGDDVGSFGSEAAGVVV
                         *    **:  :**: :*:**:*****: :*.: *    .:*.*.**:*.

ORF 18_ER02              EIGSGVTGLKPGDRVFGLFDGAFGPVAIADRRTVTEMPVDWTFAEAAALP
ORF 19_ER03              ETGPGVTDLAPGDRVLGMFDASFGPIAVADRKLIAPVPDDWSFTEAASAP
ORF 19_ER02              EIGPGVTGLDVGDRVFGLMSNGFGPQVVTDHRTLAKMPEDWSFATAASVP
AAF71767_ER01|NYST       EVGPEVTGLAPGDRVMGMLFGGFGPLGIADARLLTPVPADWSWETGASVP
AAF71776_ER03|NYST       EVGPEVTGLAPGDQVMGMITGSFGSLAVDDARRLARLPEDWSWETGASVP
                         * *. **.*  **:*:*::      .**   :  *  :: :* **:: .*: *

ORF 18_ER02              VVFLTAYYGLVDLGGLRPGEKVLIHGATGGVGMAAVQLARHLGAEVFATA
ORF 19_ER03              VAFLTAYVGLADLGELRPGQTVLIHAAAGGVGMAAVQLARHFGAEIYVTA
ORF 19_ER02              IVFLTAYYGLFDLARLEAGESILVHAAAGGVGMAATQLARHAGAEVFGTA
AAF71767_ER01|NYST       LVFLTAYYALKELGGLRAGEKVLVHAGAGGVGMAAIQIARHVGAEVFATA
AAF71776_ER03|NYST       LVFLTAYYALKELGGLRAGEKVLVHAGAGGVGMAAIQIARHVGAEVFATA
                         :..*****  .*  :*.  *..*:.:**:**..:*****  *:** ***::**

ORF 18_ER02              SPGKWEVLRGLGFDDEHIASSRTLDFEDRF-----GR-MDVVLDSLAKEF
ORF 19_ER03              SPAKWDTLRAMGFDDDHIASSRTLDFEDKIREATGGRGVDLVLDSLAREF
ORF 19_ER02              GPGKWDTLRANGFDDTHLSSSRDLGFEEKFRDATGGRGVDVVLNSLAGDY
AAF71767_ER01|NYST       SEGKWDVLRSLGVADDHIASSRTLDFEAAFAEVAGDRGLDVVLNALSGEF
AAF71776_ER03|NYST       SEGKWDVLRSLGVADDHIASSRTLDFEAAFAEVAGDRGLDVVLNSLAGDF
                          .**: **. *. * *::*** *.**         .* :*:**:.:  ::

ORF 18_ER02              VDASLRLLGEGGRFVEMGKTDIRDADEVAAAHPGVTYRAFDLLDAGRPRI
ORF 19_ER03              VDASLRLVREGGRFVEMGKTDIRDADEVAAAHPGVTYRAFDLIDSGHDRI
ORF 19_ER02              VDASLRLLAPGGRFAEMGKTDIREPGE-----TGVEYHPFDVIDAGPERI
AAF71767_ER01|NYST       VDASMRLLGDGGRFLEMGKTDIRAADSVP---DGLSYHSFDLGMVDPEHI
AAF71776_ER03|NYST       VDASMRLLGDGGRFLEMGKTDIRAADSVP---DGLSYQSFDLAWVVPETI
                         ****:**:  ****  ********  ...       *: *:..**:        *

ORF 18_ER02              GEILAELLDLFGAGSLTVPRPTVWDARRAPEVFRFMSQAKHIGKNVLTIP
ORF 19_ER03              QEILGELLALADKDVVRPLPTTAWDVRRAPEAFRFLSQAKHTGKIVLEPP
ORF 19_ER02              HEMLAALLELFAAGALTPLPVTGWDVRRGPDAFRFLSQAKHVGKNVLTMP
AAF71767_ER01|NYST       QRMLLDLVELFDRGALAALPVRSWDVRRAGEAFRFMSLAQHIGKIVLTVP
AAF71776_ER03|NYST       GTMLAELMDLFRTGALRPLPVRTWDVRHAKDAFRFMSMAKHIGKIVLTLP
                          : * :: *     .        : **.*::  .***:* ***:*  **  *
```

Figure 16

```
ORF18_KR01    TGGTVLITGGTGGLAGLLARHLVERHEVRSLLLVSRRG----AAGPLVDD
ORF19_KR03    PEGTVLITGGTGVLGGLFARHLVTAHGVRRLLLTSRRGLDAEGARELVAD
ORF18_KR02    GNGTVLITGATGTLGALVARHLVTVRGVRHLLLVGRRGRAAAGMAELEAE
ORF19_KR02    PDGTVLVTGGTGALGALFARHLVRERGVRRLLLASRRGHDAPGVPELVAE
ORF21_KR02    PGKTVLVTGGTGALGALVARHLVTARGVTRLLLVSRRGLEAEGAKDLVAD
ORF22_KR01    -DGTVLVTGGTGALGADLARHLVRSRGVRRLLLTSRRGAAAPGADTLTRE
ORF22_KR02    PEGTVLLTGATGALGRSLASHLVSGHGVRHLLLVSRSGAAAHGAKDLLAE
ORF20_KR01    PDDVVLITGGTGRLGQALARHLAVRHGVRGLVLTGRTGG---GAEDLVAD
ORF23_KR01    -DDVVLITGGTGLLGAAVAKHLVVTHGVRSLVLLSRSGASAPGAAALADE
ORF22_KR03    TDGAVLITGGTGALGAALARHLVTAHGKTRLVLAGRRGPDAPGAGELADE
ORF19_KR01    PEGTVLITGGTGALATELARHLVTRRGVRNLILAGRRGPAAEGASELAAE
ORF21_KR01    PRGTVLVTGGTGAVAAHVARWLAG-NGAGHLVLTSRRGAAAEGAAELSDE
              .**:**   **.:. .*   *.   *:* .*  *   . * .   :

ORF18_KR01    LTALGADVTVAACDIADRESVAALL----AEHPVSAVVHAAGVLDDATIT
ORF19_KR03    LTGLGATVTVVACDVADRAAVAGLLGSVPPEHPLTAVVHTAGVLDDGLIP
ORF18_KR02    LTAAGASVTIAACDAADRAALAALLATVPAEHPLAGVVHAAGVLDDGLVA
ORF19_KR02    LTEAGASVTVEACDAADRGALAAVLAGIPAAHPLTGVVHTAGVLDDGLVG
ORF21_KR02    LTAAGADVTVEACDVADRAALEAALAG----HELTAVVHTAGVLDDGLVD
ORF22_KR01    LTALGAEVRIEACDAADRDALAALLA----DQPITLAVHAAGVLDDGLIG
ORF22_KR02    LTGLGASVVLESCDVADREALAGLLAGIDPGHPLTGVVHAAGVLDDGLID
ORF20_KR01    LAELGTQVTVAACDVADPDAVRALLA----AHPVTAVVHAAAVLDDGLVD
ORF23_KR01    LTGMGAEVRILACDAADREALRQVLA----AHPVTGVVHAAGVLDDGLIT
ORF22_KR03    LRGLGAEVAVIACDAADREALRRLLA----EHPVTGVVHAAGVLDDVVLD
ORF19_KR01    LADLGAQARIVACDVADRDQLTALLDG----VPLTAVVHAAGVLDDGLLA
ORF21_KR01    LAGLGARVTFAACDVADRDALAAVLA----EYPPNAVVHTAGVGATASLA
                 *: . . :** **    :    *       .**:*.*    :

ORF18_KR01    TLDHERLAAVLRPKVTGALVLDELTRDLDLSAFVLFSSSAATFDGAGQAN
ORF19_KR03    ALTPDRLGTVFRPKVDAAVHLHELTRDLGLAAVNLFSSSAATFGAAGQGN
ORF18_KR02    TLTPERLAKVLRPKVDAAVNLHELTRDAHLAEFVLFSSAAGAFGDAGQGN
ORF19_KR02    SLTPERLAKVLRPKVDAALNLHELTSGADLAEFVVFSSAAGVFGNAGQAN
ORF21_KR02    SLTPERLAKVLRPKVDAALNLHELAG--DVEEFVLFSSASATFGNPGQAN
ORF22_KR01    DLSAERLTAVLRSKVDAAVHLHELLG--DT-ELVLFSSAAGVFGNEGQAN
ORF22_KR02    SLTPERFDAVLRPKADAALNLHELAG--DVDEFVLFSSAAGTFGNAGQAN
ORF20_KR01    GLTPDRLGTVLAPKADGARVLHELAG--PVRREVTFSSAAGVFGNPQAG
ORF23_KR01    AQTPERLDRVLAPKVDAAVNLHELLP--DAAPFVMFSSAAGVFGNPGQSG
ORF22_KR03    GLTPDRLDAVLRPKVDAAVNLHELAG--DVDEFVLFSSAAGTFGNPGQAN
ORF19_KR01    DLTRDRFETVLRSKVDGAILLDELAG---DAHLVFFSSAAGVLGSAGQAN
ORF21_KR01    ETGPAELADALAAKAGGAAHLDELLEGAELDAFVLFSSNAGVWGGAGQGA
               .:   .: .*,. .*   *.**       :* ***  :... . **.

ORF18_KR01    YAAANAFLEALALRRRAEGRPGVALGWGLWATG--MGARLDEAGLRRIER
ORF19_KR03    YAAANAFLDALAQHRRAEGLAGQALAWGFWAERSAMTGHLDEADVARMKR
ORF18_KR02    YAAANSFLDSLARHRRAQGLPAVSLAWGFWAELSGMTGHLGEADLARLKR
ORF19_KR02    YAAANGFLDALSVRRAAHGLPARSLAWGLWAETGGMGGTLGEAELARMAQ
ORF21_KR02    YAAANAFLDALARHRHAQGLPATSLAWGLWATDGGMTGELSDTDLARMGR
ORF22_KR01    YAAANAFLDALARHRQANGLPGTALAWGMWAS--GMG-DALTA------R
ORF22_KR02    YAAANAFLDALAQHRQANGLPARSLAWGLWDTDDGMDASAAVA------R
ORF20_KR01    YAAANAYADALMLRRRAEGLPGVSLAWGFWAERSKLTGDLDDTDVRRMAR
ORF23_KR01    YAAANAFVDALVERRRADGAAAASLAWGLWATTSAMTG---SADVDRMAR
ORF22_KR03    YAAANAFLDALARHRHAHGLPATSLAWGLWAG-DGMAGGMSGRDLDRMSA
ORF19_KR01    YAAANAALDAVAARRRERGLPATSLAWGLWETGDGMGAGALAGTDRARMAG
ORF21_KR01    YGAANAALDALAERRRARGLPATSVAWGLWGGGSGLAG---QDDVDRLRR
              *.**:.  :::  :*   *  ..  ::.**:*        :

ORF18_KR01    SGQRALSEVDGLALFDA
ORF19_KR03    SGVSPLSSVDGLALFDA
ORF18_KR02    SGMSPLSTEDGLLLMDA
ORF19_KR02    SGTAALSTQDGLELFDA
ORF21_KR02    TGIAALTPEAGLALFDA
ORF22_KR01    PGFPALSTEDGMALFDA
ORF22_KR02    LTGSGLTTEEGLHLFDT
ORF20_KR01    AGVTALSTEEGLALFDA
ORF23_KR01    AGLTGLSTEEGLDLLDA
ORF22_KR03    SGAGALSTEEGLALFDL
ORF19_KR01    SGLLPLPVGDALTLFDF
ORF21_KR01    LGLAAMDPALAVSALVQ
                      :   .:  :
```

Figure 17

```
ORF 22_AC02    AAVLGYSGPEDVPSDRAFTELGFDSLTSVDLRNRLNSATGLRLPATLVFD
ORF 22_AC03    AGVLGHAGPEQVDPDKAFTELGFDSLAAVELRNRVNEATGLRLPATLVFD
ORF 18_AC02    AAVLGFGSPEQVGVRQAFRELGFDSLSAVELRNRLNAATGLRLPATVVFD
ORF 19_AC03    AAALGHASVAKVGPELAFRDLGFDSLTAVELRNRLGAATGLRLPSTLVFD
ORF 21_AC01    AAVLGHGGAAAVEPDRAFRDLGFDSLTAVEVRDRLAAATGLRLPATLVFD
ORF 19_AC01    AEVLGHRDAGAVEPARPFRELGFDSLTAVELRNGLNAASGLRLPATAVFD
ORF 18_AC01    AAVLGHPDAHAIDPDRAFTEVGFDSLAAVELRNRLIAATGLKIAPTLVFD
ORF 20_AC01    AAVLGHESADAIAGDRGFLELGFDSLTAVELRNRLAEATGLRLPPTLVFD
ORF 22_AC01    AIVLGHLGSEAIDAGKPFQELGFDSLAAVELRNRLTEVTGLRLAATLVFD
ORF 23_AC01    AAVLGHDGADAIDAGVAFLELGFDSLTAVDLRNRLAASTGLRLPPSLVFD
ORF 19_AC02    ATVLGHTAADAVEATRSFQEIGFDSLTAVELRNRLTAATGLRLPATLIFD
ORF 21_AC02    AAALGHAGAGAIDPGKGFVELGMDSLSAVELRNQLCALSGLKLSTTVVFD
ORF 18_AC00    AVLEAKPGAGTAAPGTPFAELGFDSLAAVELHRRISAATALELPVTLVFD
                *    ::*:* *::*:::   :    :.*.:.  :  :**

ORF 22_AC02    HPNSDAVVARLR
ORF 22_AC03    HPTTTAVAELVG
ORF 18_AC02    HPTPTALAETLG
ORF 19_AC03    QPSPAALARHLL
ORF 21_AC01    HPSASALAGHLV
ORF 19_AC01    HPTPKALADLLA
ORF 18_AC01    HPNPRAVAAFLA
ORF 20_AC01    RPNAGALAAYLA
ORF 22_AC01    YPTPLVLAEHLL
ORF 23_AC01    HPTPLAVAERIS
ORF 19_AC02    YPTPEALAAHIG
ORF 21_AC02    HPNPAALAGHLA
ORF 18_AC00    HPTPSALAGHLR
                *..  .:.  :
```

Figure 18

```
ORF 23_TE01          KGPSGPELVCVPSLLAGSGAHEYARFAASFRDVQDVSVVPVPGFGHGQPL
AAF71768_TE01|NYST   -GPGRPRLIFVSAPGATGGVHQYARIAAHFRGSRHVSALPLMGFAPGELL
                     **. *.*: *.:   * .*.*:***:** **. :.**.:*: **. *: *

ORF 23_TE01          PDSIEAVLHAQADAILREG-GDPVVLVAHSSGGPLAHALARHLEEAG-SA
AAF71768_TE01|NYST   PATSEAAARIVAESVLMASEGEPFVMVGHSTGGSLAYLAAGVLEDTWDVR
                     * : **. :  *::.*   .*:*.*:*.**:** .**:   *  **::

ORF 23_TE01          PRALVLIDVY-----PQDEHALDGIRDRLSGGLG------DDTRLTAMGA
AAF71768_TE01|NYST   PEAVVLLDTASIRYNPGEGNDLDRTTRFYLADIDSPSVTLNSARMSAMAH
                     * .*:**:*       *  : **      ..:.        :.:*::**.

ORF 23_TE01          YLRLFADYVPAPTGVPTLLVRASEPLEAWRDRTEWRSGWALPHDTVDVEG
AAF71768_TE01|NYST   WFMAMTDIQAPAPTAPTLLVRAARALDGFRLDTSSVP----ADEVRDIDA
                     ::   ::*  .... .******:...*:..:*   *.  .   ..:. *::*

ORF 23_TE01          DHFTMLERHAGTTAEAVREWLGRLG
AAF71768_TE01|NYST   DHLSLAKEHSALTAQAIEGWLAEL-
                     **::: :.**:. **:*:. **..*
```

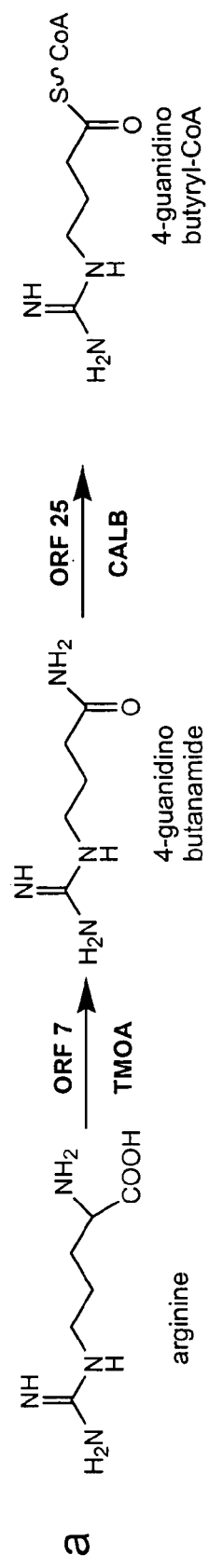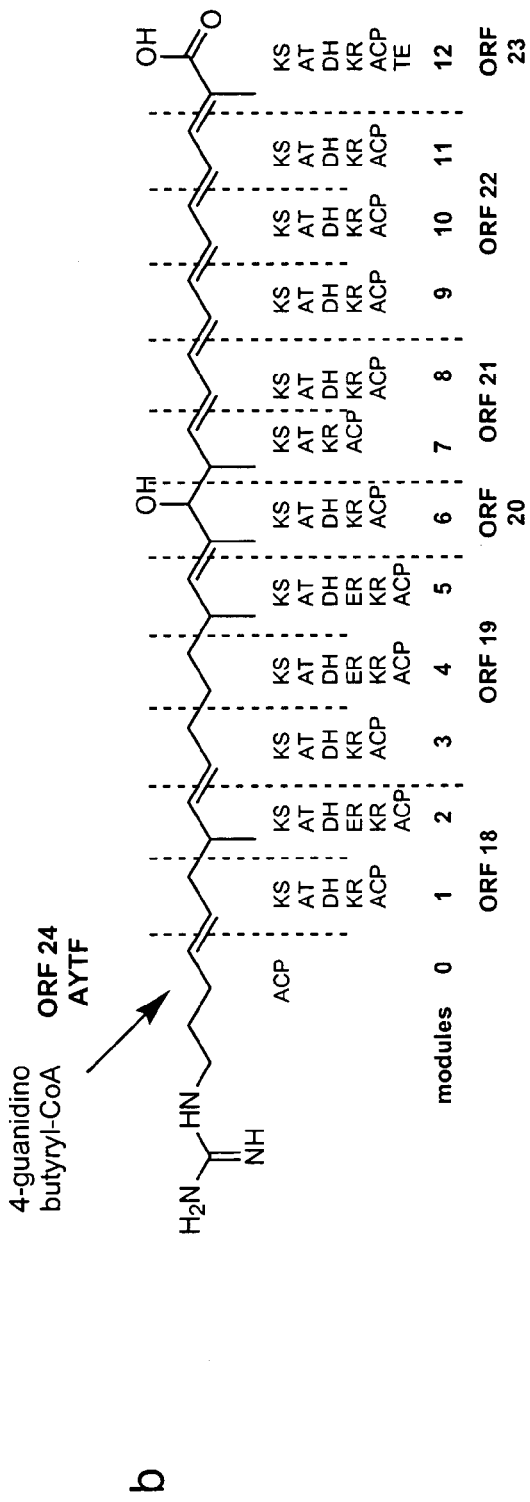
Figure 20

SEQUENCE LISTING

```
<160> NUMBER OF SEQ ID NOS: 57

<210> SEQ ID NO 1
<211> LENGTH: 12647
<212> TYPE: DNA
<213> ORGANISM: Amycolatopsis orientalis

<400> SEQUENCE: 1 atgccgaac  tctgccgccg  catcggggaa  agccgaggtc  ggccgatcaa  actcgtcgcg    60
ttcccgatgg  aggttccgg   cccgtgtgga  gcgtggctga  gcgcgtcttc  cggcgactac   120
atcgtcttcc  agtcggagac  cacccggata  caccaagagc  acatcatcgc  gcatgagctg   180
gggcatatcc  tctccggaca  tcgggcggaa  ccggacgaag  aggaaatatg  gtcccggttc   240
atgcccgacc  tcgatccggg  ggtaattcgg  aggctgttga  aaagaacgca  gtacgactcg   300
gtccgggagc  gggaggccga  gacgatcgcc  accctcctgc  tcgaacgttc  cctggtcgtc   360
cggctgctcg  acgagccggg  ttcgtcgcgg  accaggcgga  tgcggcacgt  cctcggcgag   420
gcgcggggct  ggctgtgagc  ctggccaagg  aattcgtgat  cgcggcgctg  gtgtggttct   480
cctaccggct  ggcgcgatcg  ccgcgcgacc  cggcgatctg  ggcgctggtc  ggctgcctgg   540
tgctgcggtt  gctgaccgcg  ccttcgagca  tggtggcgct  gcacgagttc  accggaggga   600
cgctcgacgt  cgacaccttc  cgcctggtcc  agacggtcgt  gctcgacgcc  agcctgttct   660
tcctgctggt  cttcttcctg  ctctccgcgg  gcggctcgcg  gcggcgggtg  gccctcgacg   720
cctggttgct  gctactggtc  tgcgcggccc  tggcggtggc  catgttcgtg  gtcccggccg   780
cgtcccgcga  gcaggccttc  ggtgtcggcg  cggcgctgcc  ggcggtcgtg  acggagccgg   840
gggtggcgct  cttcttcctg  gtcgacgcgg  cgtacggcac  ctacacgacc  gtgcaggctg   900
cgagctgggc  gctgcgtgac  gccgtggaaa  ccccgctccg  gtccgctgg   gggctgcgga   960 tcgccgcctg  cggcctgatc  acgctcgcgg  tgacctcggt  cgcgcggttc  ggcacgatcc  1020
tggtgcgctg  gtccggcggc  gacgtgccgt  cgtccctgcc  ggtcgcgacg  gccgtgctgg  1080
tccacgtggg  aatcatcctg  ttcatggccg  ggatcaccct  ggtcgggctg  ctcgccgtgc  1140
```

-continued

```
tcgccgccgt caggctgtgg ctgcggcacc ggcggcggta cgaggatctg cgaccgctgt    1200
gggggcacct gcacgacgtg ttccccggtg acgcgctgta cgccgggcag cgcggcggat    1260
ggctggagga actcgcgttc tggcggatgc atcgccggta ctggcgaagg gtcgtcgaga    1320
tccgtgacgg actggtccgg ctgagcccat acctggccga ctgcggtttc gtcgaaggca    1380
gggagcgggt ttcgcccgag gtcttccgcg aggcactggc caggttgcgg tcggggagc    1440
ggccgacctc gcgtaccgcg gtggcggtgg cgcgccccga ggggcaggac gtcgaggccg    1500
acgtcgggga gctcgtcacg ctgtcgaaga cgctgcgcgc ctgatcgtcc gttttttcct    1560
cagttgtacg gaaccgggag ggatccattc acgtcagttg atgaaaggga ggtgggcacc    1620
tatactccgg tactcggggg gacctgcacc gccatatggc agcgcggcac gggttcgtga    1680
ggaactcggc agtgttcttg ggaggcagca tgtcccggca ggacggacca ggccggagcc    1740
tggccgaaaa actcgaccat ctgttcgcgc acgtcacccg gcgcaacggc accgagttca    1800
cgtacgaaga ggtcgcgtcc gcgatcaccg ccgagggtgt gacgatctcc cagagctacg    1860
tctggcagct gcgcaaggga aagaaggaca acccgacgct caagcacctg caagggctgg    1920
cggatttctt cggtgtcccg gtcacgtact tcttcaacga ggacgtgagc gaccgggtgg    1980
accggcagct ggagtacctg cgcgcggaac aggcgcggtt gcgtgagctg gccgaaaccg    2040
acgaggtccg cctgatggcc atgcgcgcgg gcgagttgac gaccgatcgc cgcgaactgg    2100
tgaagaacct cctcgacgtg gtctggcggg atcagcaggc catgcgagag cgtgggtcca    2160
aacaggactg acgcctccgg cgacgccggt tgtgcttgtc gtgcctgggt tttcgcttcg    2220
tccacagtgg tcatccactg aggaaaacgg actaacctct catatgttct cttgggtcga    2280
cacgataggg tgacgtcctc taggctcctc ggcaagagat cctgcgtgga acggacgacg    2340
tcggtccgcc gccggactcc acattgcggg tttgccatgg gggcgacgaa gaatgcacgt    2400
gaaatcagtg atcagagtgg acggcgacgt ccgcgcgagg gcgtatcccc gcgcggagct    2460
gctggtcctg cgagacttct tgacggaatc cgaacaggga aacgccgtcg cggcggtggt    2520
caccggaacc gccgcgagcg ggaaaagtga acttctgcac gcattcgcgc aacaatgcgc    2580
tgaagcggaa gcaacggtga tgagcgcgct ttgcgtggaa gcggagaagg atctcccgtt    2640
caccgcgctg ttccagcttt tccgtggccc ggcactgtcc ggagatctgc gcgcgaaggc    2700
cgcggacctg ctgacgcggg ccgaacggac cgggctgacc gggcggccca gcacacatct    2760
catgctcgac ctgctggagc tcgtgcgcga gctcgccgcg caccgtccgg tcgtggtcct    2820
ggtcgacgac ttccaccatg tggacacccc gtcgttgcac tggctgatgt tcctcatgcg    2880
ccgcatgcgc acgatgaacg tgctcgtcgt gctgacggag tcgttgtccg ccaagcagac    2940
gttgcccttg ctgggcgccg agtacctccg gctcccgcac tgccgccgga tccggctgaa    3000
gccgctgggc cgcgacgagg tggcccggtt cgtcccgccc ggccaggacg acaccctggt    3060
gaagggcctg cacgagctca gcggcgggaa tccgttgctg gctcaggcac tcctcgaaga    3120
tctccgtgcc tcgggcgtac ccctcgcgcc cgagacccgg ccgatccccg gcgatcacta    3180
ctgccaggcg gtggcggcgt gtctccagcg cggcgaccag gacacccgga ccctcgccgg    3240
tgtcctcgcg gtgctgggta aaggggaaac ggtctgcctc gccgtccggg tgaccgggat    3300
ggaccagcgc accgccggcc gtgcgatcgc cctcctgcac caggtcggcc tgctcgacgc    3360
gggccggttc cggcatccga tgacggtgac cgcggtgctg gccgacgtcc ggtcgcgga    3420
acgcgcgcga ctgcacgagc gcgccgcggt gctcctgcat cacgacggcg ccggcgcgct    3480
```

```
cgacgtggcc cgccacctcg tcgccgccga ccgggccgac cggccgtggg cggtgcccgt    3540
gctgcgcacc gcggccgaac tggccaaagt ggacaaccgg acctcgttcg cggtccaatg    3600
cctgaaactg gcctgccggt cgtgcggcga cgaagcgctc gaggtcgaga tggtgaccca    3660
gctcgccggc ctggaatggc ggaacaaccc ggccatcggc gccgtgcaca cggaccacct    3720
ctacgagatc ttcctcgccg ggcagctccc ggtgcgggcc gccgccatcc tggtgcggtt    3780
cctgctgtgg cacggccgca ccgcggaagc gggtgaggtg ctcgacaagc tcgccgtcat    3840
ggagccttcg gccgacgatc gcaccgaggc ggaactgcgc atcacccggc tgttcattct    3900
ctgttcctat cccgttctgc gcgacaagct gcctgccccg gccgcgaagg accgcgttcc    3960
cgcgcaatcc ttcgacccca acgtgcaggc ggcgatggcg ctgagccgga tcgtcacgaa    4020 cggcccccgac gacgacgcga tcgcttcggc tgagaacgtg ctgaagagca tccagctcgg    4080
cgacacgatg gtcgaatccg tgcgcagcgc gctgttcgcg ctcatctacg ccgaccggct    4140
ggacaaggcg gtgccgtggt gcgagctgct gcagcaggag gccgccgact gcgacgcgcc    4200
cagctggcag gccgtgttcg ccgcggccag gcggaaatg gcgctgcgcc agggagatct    4260
ggtgacggcg gagaagcagg ccaaggcggc cttgacgttc atcacgccgc agagctgggg    4320
cgtggccgtc ggagtcccgc tggcgacgct gtgcctcgcc gccgtcggga tgggcaagtt    4380
cgaggaggcg gcgtcgcata tcaaccagcc ggtgccggcc tcgatgctgc aaacccggtt    4440
cggcctgcac tacctgcgcg cccgcggcag gctctacctg gagaccgacc gggtgcacgc    4500
cgcgctcggc gacttcgtcc tgtgcgggga actcagcaag agctgggatt tcgacctgcc    4560
ggtgctggtg ccctggcgcg gcgacacggc cgaggcgtac ctccggctcg gcatgccgga    4620
gaaggcgaag tccctgctgg acgagcagct cgcgaagctc gccggctcga cgtctcatgt    4680
gcggggaatc tcgttgcggc tcaaggccaa gatcgccgaa ccgcagaagc gcccggaatt    4740
gctgcgtgaa gcggtgaaga tcttccaggc gggcggtatc cgcctcgaac tcgcccgcgc    4800
gctcggcgat ctcagccgcg cgcactacac gctggccgag tcgggtcgcg cgcgcacggt    4860
ggcccggcag gcgtggcata tcgcgaaggg ttgccacgcc gacgtgatct gccgggatct    4920
gcgtctcgac gggacaggcg acgagggaaa gccggcgtcc accgcggcgg agatcgccgc    4980
gtcgggcgtc gaacgcgagc tcatcgagtc gctgagcgag gccgagcgac gggtcgccgg    5040
gctggcctcc ctcgggcaca cgaaccgggc gatcgcgagc aagctctaca tcacggtgag    5100
cacggtcgaa cagcatctca cccgcgtcta tcgcaaactg gacgtcaacc ggcgccggga    5160
tctcccgtcg tggctccagg tttcggtcgt caacagcgcc tgaccgaaag aacccggcgg    5220
gtcgcgtcgt agctctcaag tcacgcatgt cggtggtcgt gagtggcgat tcgggttaga    5280
accacccaaa tcactcacga ccctcgcgcg aagcggccaa tcgggcattt ggcgaggatc    5340
gtggtcgatc tccggctcgc gaaacgacga aggtctcctt acccggctcg ggtaaggaga    5400
ccttcgtcgt cccgtctact tgacggcggt cacggcggcc atcgtgcccg cccaccagta    5460
ggtgcagtcg gccggcggct tcaggtcccg gacgacctcc acccggaacg agctgaagtg    5520
ttcgagcagg gcgcgctggt gtgccccggct cagtgagtcg atttcgttgg tgtagtagga    5580
gaagacgcca ccgggacgaa ggtgggcggc ggcgtgctcg aagaattcgg ccgccagcac    5640
gatggccttc gggcccaggg tcctggcgaa ttcccgctcg tcggtcggat aggtgtcgta    5700
caggatcgcg tcgtactggc cgaggccgcc gagcacgtcc tgccaggcgc cgagttccag    5760
ccggatatcg cggtccggcc actgggcacg ccatttctcg aactccgcct tcacctcgga    5820
gttgatttcg atcagggtgt gcgaccggac gcccgcgtcc tggacgtagg tggccgaaat    5880
```

-continued

| | |
|---|---|
| acccatcccg aaaccgactt cgagcagatc cccgccgttc gccgcggcgt tttccgccag | 5940 |
| caccttcatc agcggccgtt cccagttctg catcacctgc tggccctgga tgagcagctg | 6000 |
| cgtcggatcg ctgtagtccg cagtgctgtc ctgccagttc cggcggatca gcggccggtg | 6060 |
| cgagccgtcg acgaattcct gctggatggt gtccagatgt tccagatcgc tggcgaactc | 6120 |
| gaacaccgcg cggccgagaa ggaggttgcg ctggccgggc ccttcgccc ggaggaagtc | 6180 |
| gtccctgacc gggtccaccg ttatcttgaa ttccttgaag ttccgttgca ttctggtata | 6240 |
| tctcctacgg tcacgcgagt cctttcaagc ccacggtatc ggtgatcttg tccggtagc | 6300 |
| cgaaatgcag ggggtgactt gaccactgaa cggcactgac gccgggaata ggggttcgga | 6360 |
| gaataggggg tgaagttctc cgcacggggg gtttccccgt gataggaact tcacatgccg | 6420 |
| ggggaaacca agaaccagga caccgacggc cgcggcgcgc gcaggcgctc cgtcgtatcg | 6480 |
| ttgatcgccg acgtcaccgt gccggtcgtc gtctactacg cgctgctcgc cttcgggtgg | 6540 |
| agcagcggct ccgccttggt ggcggccacg gtcgccatcg gggtcctcgt gctcgccgtc | 6600 |
| gcggtcaagg aacgcagggt cgacggcttc ggggtgttcg tgctcggagt ctgcgcggtg | 6660 |
| accctgctgg tctccttggt gagcggggac gaacgcctgc tgttggccaa ggatcccttc | 6720 |
| accagcggcc tggccgggat cgccttcctc ggcagcctcg tcttcgggaa accggtgacc | 6780 |
| ttcttcatct cccgccggat ccgggcgctc acccccggctc ggcgcctggg ctgggaccgg | 6840 |
| ctgtacgccg cggaacccga gttccgcaaa ctgcatcgcg tctccaccgc gggctggggc | 6900 |
| gtggtcctgg tcaccgagtc cgccgcccgg ctcgtcctga tctacctgct gcccgcgtcg | 6960 |
| gtgatggtcg gcctgtccac cgcgatcgaa ctgaccgcga tcaccggcgt ggtcgcctgg | 7020 |
| accatctggt accggcgtcg ctccgccggc cacggtctgg aaaagtcgct tcgcacggcg | 7080 |
| gatgcggcgc ccgctgctgt ctaaattgga ctaggggcga gtaggggaaa gtgaggggtt | 7140 |
| ggtccgcgcc ggaccccgtc gtacgtttcg gtcgagacag tgtggccccg atgaccaggg | 7200 |
| agatccgcca cgatgaccgc agccgatttc gcgcccccgc tgaccactct ctgccccgat | 7260 |
| ttcccgttcg cctacgacga ttggctcgcg catccgccg ggctcggtga gctgccgccg | 7320 |
| gaccgcctcg gccaggaggt cgccgtcgtc ggtggcggga tagcgggtgt ggtcgcggct | 7380 |
| tacgaactgc tgcgcctcgg cctgaaaccg gtggtctacg aagcgggcca gatcggcggg | 7440 |
| cggatgcgct ccatcccctt ggcgggcgag gacggcgcgg tcgcggagat gggcgcgatg | 7500 |
| cggttccccgc cctcggccac caccctgtac cggtacatcg acgaagtcgg cctggagacc | 7560 |
| aagccgttcg cgaacccgtt gtcccgcagc acttccacca cggtgatcaa cctcgacggg | 7620 |
| gtgacctacc gcgcgcggac cccggcggac ctcccgtcgg tgttccacga ggtcgacgac | 7680 |
| gcctggcaca aggccctgca ggaactggcc gatctgtcca ccatgcgcga cgccatccgg | 7740 |
| atgcgcgaca ccgccatggt gaaggcgatc tggaaccggc tgctgcccga actcgacgac | 7800 |
| cagtccttct atggtttcct ggcacggtcg accgctttcg cctccttccg ccatcgtgag | 7860 |
| atcttcggcc aggtcggctt cggcaccggc ggctgggaca ccgatttccc caactccgtg | 7920 |
| ctggaaatcc tccgcgtcat ctacaccggt gtcgaggagg ggccgcggca gatcatcggt | 7980 |
| ggctgccagc aacttccgcg gcggttgtgg aaccacgcac ccgcgtctgc gcgcttctgg | 8040 |
| cctgccggga catcggtcgc gtcgctgcac gacggatcgc cgcgccccgc cgtcctcggg | 8100 |
| ttgcgcccgg ccgcggacgg gttcgccgtc gaggacgcga acggtgacgt gcggacctat | 8160 |
| ccggccgtgg tcttcaccgc gcagcaccgg gtcctgctca ccaagatcgc cggagtgcgc | 8220 |

-continued

```
ccgctgctgc cgcgaacgt gtggaccgcg ctggaacgca cgcactacat gggtgcttcg      8280
aagttgttcg tcccggtcga ccggccgttc tggcacgacg tcgatcccg caccggtgag      8340 gaactgatgg ggatgaccct caccgaccgg accccgcgca gcgtctacct gttcgacgac     8400
gggccggatt cgccggccgc gctgtgcctt tcctatacct ggaacgacga ttcgctcaag     8460
ttcgcgacgc tcggcccggc ggaccggctc gaactcgcgc tcgacgcgct cgccgacatc     8520 tacccggtg tcgacatccg ctcccacatc accggcgatc cggtcaccgt cacctgggag      8580
aacgagccga acttccaagg cgcgttcaag gcgaacctgc cagggcagta ccgctatcag     8640
cgccgcctgt tcacccattt ccggcaagac gaccttcccg ccgctcagcg cggcctgttc     8700
ctcgccggtg acgacatctc gtggatgggc ggcttcgccg aaggggcggt caccagcgcg     8760 ctcaacgcg tgtgggggac gctgcgccat tcggcggg ccaccgaccc gcgtaatccc       8820
ggccccggcg acgtcttcga ccacatcgcg ccgatcgaac tgcccgagtc ctgaacgggc     8880 cgaggcccg tccgtcgact gggggtagt cggcggaccg gcaggcgag acagtgctca       8940 gctcgcgtag ctgggggttc gctgagcctg cctgagtacc ttggcccggt agacccagac     9000
cccggcggtg cggaagatga ccatcgtcag cgccatggtg acgaagaagg cggagacgcc    9060
gccggcgtcg atcccggtgt ccatcaggaa cttgccgaag tcggccgcga acgagtggct    9120
gtgttcgagg gtgtagacga agatgagccg tccgaccagg acgaacagcc acagtcccaa    9180
gtagacccag cccgccctgg tgtagacggc ggatttctcc tggtcccact cgaccttcgt    9240
gcccttcagc aatccccagc cgatcaggac gcccgccgcg atgccgacca gcccggccag    9300
tgtgttcggc gtggtcagct tgaggtcgta gaggaccgcc cagcccacca gcgcgcacgt    9360
gaagaacggc aggatcagga tgaccaggtg ggccttatgg cgaccgatgt gcgtgaacag    9420
caccagcgcc agcagtacgc cgctcaggat gagggcgttt cgcatggctt cactcatcaa    9480
aactccttcg aaagactccc catccggcag ttcgatgccg gttgtcccga aatctaaggc    9540
gagcggccgg gccgatcatc ggcgtgcggg tgggaatccg gttggagatc ggcgtccacc    9600
tcgaggtgga gtgccgtgtg gcgcggacag gtgagggcag gagatgatgc aggcatggtc    9660
gaagaagtgc ccccggtccg gatcgtgatc gccgaagacc aggcggcggt acgcgaagga    9720
ctggccctcc tggtggggac ggtcgcgggg atcaccgtgg tcggccaggc acccgacggc    9780
gaggtcgccg tgcggctggc cggggaactg cgcccggacg tcgtcctgat ggatctctcc    9840 atgcccggt gcgacggcgt cgaggcgacc cggcggatca aggaacggca tccggagatc     9900
gagatcgtcg tgctcaccac ctacgccgac gacgactggg tgctgcgcgc gttggaggcc    9960
ggggcgttgg gataccctgac gaaatcggcc aacaaacacg aaatcgggcg cgcggtacac  10020 gccgccgcg cgggccaggc cctgctcgat ccgcaggtgc agcgacgggt gctcggcgcc   10080
gccctgacgt ccgcgcccgc ttcggcgcca ccgccggagg acgacgcgaa cctcaccaag  10140
cgggaagccc atgtgctgac gctgatcgcg gcggggcaca gcaacaagga gatcgccgcg  10200
gaactgttcg tcagcgagac gacggtcaag agccatatca accggatctt cgccaagacg  10260
gggagccggg atcgcgcgca ggccgtccgt tatgcctacc aagcgggcta tgtgcgggac  10320
tgacgcggcg ctccgccgac gtcgttactg tccttcctgg gtgggctgaa ggctcccttc  10380
accacgtctg atgcggtgaa gggagccttc agcccggccg gatacgggct ctcgggcctt  10440
ggagctgatc aaccaggcat gccgcgccga cgttgcgaaa gccactttcg caacaacgcc  10500
aacgcgcttt ggggcctacc ccgggacccg ggcggtgacg tccagaacc ggccgtcggg   10560 cccggtgacc agcgtgccgt cgacgagttc gatccgttcg cgcatcccgg tcaggccgta  10620
```

-continued

```
gcccggcgtg tgcccggggt ccggcgcggc ggcgagggga ttgcggacgt gcagccggac    10680
ctcgtccggc gggtactcca gttcgacgct caccgcctcg cccgcggcgt gtttggccgc    10740
gttcgtcagc gcttcccggc agatccgcag cagcgcgatc gtctgtgccg acgggagatc    10800
gcggtgctcg cccagcatgg tgaaatccgc cggagtgtcg tgttcccggc cgaaggtccg    10860
caccagttcg gtcagcgcgt ccggcagggc gcggacgtcc tcgcgcagcg ccgccacggc    10920
gtcccggacg tcactgagcc cttggtcggc gagacttcgc gacagcgcga gcgaacgcag    10980
ggcgccttcg gtgtcgttct cctccaccag cagggtgtgc atcacctcca gctggacccg    11040
cagcgcgccg agggaatggg cgacgacgtc gtggatctcg cgggcgatgc gggtgcgctc    11100
gtccagcgtc gccgcgcgca cgccgcgggt gtgcgccagc cgttcctggt gcagcaaccg    11160
ttccgcctgc gcgaccctgg tcagatgacc gcggcgggtg aatccgacga ggaccacgat    11220
gacgaccgcg cccagtgcgc ccagccaggc ctccgaagga cggtggccga gcaggctgga    11280
aaccacgatg gcggcggcgt cgaagaccat cagcgcgatg atcgcgacgg tgcccggctc    11340
cagccgtgaa gcgaacgcgg cgagggtgat gcaggtcatg atcacggcgg tgccgtcggt    11400
ggcggcgccg gtaccgaagg cggggaccgc gctcgccgcg gcgagcggga gcagggcggc    11460
acggggggaag cgctcgctga tgccgatcca cagcagccag ctcgccgacg acaccgcgta    11520
gagcacccac agccagccgg cgccggccgg tacggtcgcg gtcatctggg tgacggccag    11580
cagcgccgtc ccggcggcgg cgcggcccca tcgccagcga cgttcctcga cctcgtcgga    11640
cactgcgtcg gtcatacgac gatcgtaggg ccacgacggt tttccgctcg cgggtgatca    11700
ttccgagggt ggaaataccg tcaccgttgg taggaggtcg ctctcgcgcg gttgtttccg    11760
caggaagcgt ccggctagtg ttcgccgagg cgaaagaaag cggtctcccg ccctccgcc    11820
gaacaattcc catcccttc ggaggaatcc tgcgatgacc gctccaagcg gcgatgccgg    11880
ggactgggtc cgtgttttcc ggcccggagg accgtcggta ccgcgtctga tctgcctgcc    11940
cgacgccggt gcggccgcga atgcgttctt cccgcttttcc gccgcgctcg cgccggggat    12000
cgaggtgcac gcggtgcaat atccgggacg ccaggatcgg gtcgcggaac cgtgcgccga    12060
agacatcggg gaattggccg accgggtcac cggggcgctc gcgctctggg aaggcgcgcc    12120
gttcgcggtg tacggccacg gaatgggcgc ggtcgtcggt ttcgaggtgg ccagacggct    12180
ggagcaggcg ctgaccggga gccggtcgc gctgatcgtg tccggctgtc ccgccccgtc    12240
ccggtccggc accgccgggc tccacctgct gccggatcag gacctcgtgg ccgagctgta    12300
ctcgcagcgc gccgccggct cgccgggcgc gcgggacgcg gagctgctca aggccacctt    12360
cccggccatc cgggccgact tccgggcgct ggccgcttac cggcccgagc ccgcgccgcc    12420
gctgcgctgc ccggtcacgg tgctcgtcgg cgacagcgat ccgacggtgt ccctcgacga    12480
ggcgcgcgac tggcacgagt acaccaccgg cccgttcgac ctccaggtct tccctggtgg    12540
gcacggttttt ccggaggcgc gtcccgagga gttcgccgag gtggtgaccg ccgcggtccg    12600
gcggcggtga accggcgcct gcgcctcaca aaagcgggtc gtgagtg               12647
```

<210> SEQ ID NO 2
<211> LENGTH: 145
<212> TYPE: PRT
<213> ORGANISM: Amycolatopsis orientalis

<400> SEQUENCE: 2

```
Met Ala Glu Leu Cys Arg Arg Ile Gly Glu Ser Arg Gly Arg Pro Ile
1               5                   10                  15
```

-continued

```
Lys Leu Val Ala Phe Pro Met Glu Val Pro Gly Pro Cys Gly Ala Trp
             20                  25                  30

Leu Ser Ala Ser Ser Gly Asp Tyr Ile Val Phe Gln Ser Glu Thr Thr
         35                  40                  45

Arg Ile His Gln Glu His Ile Ile Ala His Glu Leu Gly His Ile Leu
     50                  55                  60

Ser Gly His Arg Ala Glu Pro Asp Glu Glu Ile Trp Ser Arg Phe
 65                  70                  75                  80

Met Pro Asp Leu Asp Pro Gly Val Ile Arg Arg Leu Leu Lys Arg Thr
                 85                  90                  95

Gln Tyr Asp Ser Val Arg Glu Arg Glu Ala Glu Thr Ile Ala Thr Leu
             100                 105                 110

Leu Leu Glu Arg Ser Leu Val Val Arg Leu Leu Asp Glu Pro Gly Ser
         115                 120                 125

Ser Arg Thr Arg Arg Met Arg His Val Leu Gly Glu Ala Arg Gly Trp
     130                 135                 140

Leu
145
```

<210> SEQ ID NO 3
<211> LENGTH: 438
<212> TYPE: DNA
<213> ORGANISM: Amycolatopsis orientalis

<400> SEQUENCE: 3

| atggccgaac | tctgccgccg | catcggggaa | agccgaggtc | ggccgatcaa | actcgtcgcg | 60 |
| ttcccgatgg | aggttccggg | cccgtgtgga | gcgtggctga | gcgcgtcttc | cggcgactac | 120 |
| atcgtcttcc | agtcggagac | cacccggata | caccaagagc | acatcatcgc | gcatgagctg | 180 |
| gggcatatcc | tctccggaca | tcgggcggaa | ccggacgaag | aggaaatatg | gtcccggttc | 240 |
| atgcccgacc | tcgatccggg | ggtaattcgg | aggctgttga | aaagaacgca | gtacgactcg | 300 |
| gtccgggagc | gggaggccga | gacgatcgcc | accctcctgc | tcgaacgttc | cctggtcgtc | 360 |
| cggctgctcg | acgagccggg | ttcgtcgcgg | accaggcgga | tgcggcacgt | cctcggcgag | 420 |
| gcgcggggct | ggctgtga | | | | | 438 |

<210> SEQ ID NO 4
<211> LENGTH: 369
<212> TYPE: PRT
<213> ORGANISM: Amycolatopsis orientalis

<400> SEQUENCE: 4

```
Val Ser Leu Ala Lys Glu Phe Val Ile Ala Ala Leu Val Trp Phe Ser
 1               5                  10                  15

Tyr Arg Leu Ala Arg Ser Pro Arg Asp Pro Ala Ile Trp Ala Leu Val
             20                  25                  30

Gly Cys Leu Val Leu Arg Leu Leu Thr Ala Pro Ser Ser Met Val Ala
         35                  40                  45

Leu His Glu Phe Thr Gly Gly Thr Leu Asp Val Asp Thr Phe Arg Leu
     50                  55                  60

Val Gln Thr Val Val Leu Asp Ala Ser Leu Phe Phe Leu Val Phe
 65                  70                  75                  80

Phe Leu Leu Ser Ala Gly Gly Ser Arg Arg Arg Val Ala Leu Asp Ala
                 85                  90                  95

Trp Leu Leu Leu Leu Val Cys Ala Ala Leu Ala Val Ala Met Phe Val
```

```
                  100                 105                 110
Val Pro Ala Ala Ser Arg Glu Gln Ala Phe Gly Val Gly Ala Ala Leu
        115                 120                 125

Pro Ala Val Val Thr Glu Pro Gly Val Ala Leu Phe Phe Leu Val Asp
    130                 135                 140

Ala Ala Tyr Gly Thr Tyr Thr Thr Val Gln Ala Ser Trp Ala Leu
145                 150                 155                 160

Arg Asp Ala Val Glu Thr Pro Leu Arg Val Arg Trp Gly Leu Arg Ile
                165                 170                 175

Ala Ala Cys Gly Leu Ile Thr Leu Ala Val Thr Ser Val Ala Arg Phe
            180                 185                 190

Gly Thr Ile Leu Val Arg Trp Ser Gly Gly Asp Val Pro Ser Ser Leu
        195                 200                 205

Pro Val Ala Thr Ala Val Leu Val His Val Gly Ile Ile Leu Phe Met
    210                 215                 220

Ala Gly Ile Thr Leu Val Gly Leu Leu Ala Val Leu Ala Ala Val Arg
225                 230                 235                 240

Leu Trp Leu Arg His Arg Arg Tyr Glu Asp Leu Arg Pro Leu Trp
                245                 250                 255

Gly His Leu His Asp Val Phe Pro Gly Asp Ala Leu Tyr Ala Gly Gln
            260                 265                 270

Arg Gly Gly Trp Leu Glu Glu Leu Ala Phe Trp Arg Met His Arg Arg
        275                 280                 285

Tyr Trp Arg Arg Val Val Glu Ile Arg Asp Gly Leu Val Arg Leu Ser
    290                 295                 300

Pro Tyr Leu Ala Asp Cys Gly Phe Val Glu Gly Arg Glu Arg Val Ser
305                 310                 315                 320

Pro Glu Val Phe Arg Glu Ala Leu Ala Arg Leu Arg Ser Gly Glu Arg
                325                 330                 335

Pro Thr Ser Arg Thr Ala Val Ala Val Ala Arg Pro Glu Gly Gln Asp
            340                 345                 350

Val Glu Ala Asp Val Gly Glu Leu Val Thr Leu Ser Lys Thr Leu Arg
        355                 360                 365

Ala

<210> SEQ ID NO 5
<211> LENGTH: 1110
<212> TYPE: DNA
<213> ORGANISM: Amycolatopsis orientalis

<400> SEQUENCE: 5
gtgagcctgg ccaaggaatt cgtgatcgcg gcgctggtgt ggttctccta ccggctggcg     60
cgatcgccgc gcgacccggc gatctgggcg ctggtcggct gcctggtgct gcggttgctg    120
accgcgcctt cgagcatggt ggcgctgcac gagttcaccg agggacgct cgacgtcgac     180 accttccgcc tggtccagac ggtcgtgctc gacgccagcc tgttcttcct gctggtcttc    240
ttcctgctct ccgcgggcgg ctcgcggcgg cgggtggccc tcgacgcctg gttgctgcta    300
ctggtctgcg cggccctggc ggtggccatg ttcgtggtcc cggccgcgtc ccgcgagcag    360
gccttcggtg tcgcgcggc gctgccggcg gtcgtgacgg agccgggggt ggcgctcttc    420
ttcctggtcg acgcggcgta cggcacctac acgaccgtgc aggctgcgag ctgggcgctg    480
cgtgacgccg tggaaacccc gctccgggtc cgctgggggc tgcggatcgc cgcctgcggc    540
ctgatcacgc tcgcggtgac ctcggtcgcg cggttcggca cgatcctggt cgcgctggtcc    600
```

-continued

```
ggcggcgacg tgccgtcgtc cctgccggtc gcgacggccg tgctggtcca cgtgggaatc      660
atcctgttca tggccgggat caccctggtc gggctgctcg ccgtgctcgc cgccgtcagg      720
ctgtggctgc ggcaccggcg gcggtacgag gatctgcgac cgctgtgggg gcacctgcac      780
gacgtgttcc ccggtgacgc gctgtacgcc gggcagcgcg gcggatggct ggaggaactc      840
gcgttctggc ggatgcatcg ccggtactgg cgaagggtcg tcgagatccg tgacggactg      900
gtccggctga gcccatacct ggccgactgc ggtttcgtcg aaggcaggga gcgggtttcg      960
cccgaggtct tccgcgaggc actgccagg ttgcggtcgg gggagcggcc gacctcgcgt     1020
accgcggtgg cggtggcgcg ccccgagggg caggacgtcg aggccgacgt cggggagctc     1080
gtcacgctgt cgaagacgct gcgcgcctga                                      1110
```

<210> SEQ ID NO 6
<211> LENGTH: 171
<212> TYPE: PRT
<213> ORGANISM: Amycolatopsis orientalis

<400> SEQUENCE: 6

```
Met Ala Ala Arg His Gly Phe Val Arg Asn Ser Ala Val Phe Leu Gly
1               5                   10                  15

Gly Ser Met Ser Arg Gln Asp Gly Pro Gly Arg Ser Leu Ala Glu Lys
            20                  25                  30

Leu Asp His Leu Phe Ala His Val Thr Arg Arg Asn Gly Thr Glu Phe
        35                  40                  45

Thr Tyr Glu Glu Val Ala Ser Ala Ile Thr Ala Glu Gly Val Thr Ile
    50                  55                  60

Ser Gln Ser Tyr Val Trp Gln Leu Arg Lys Gly Lys Lys Asp Asn Pro
65                  70                  75                  80

Thr Leu Lys His Leu Gln Gly Leu Ala Asp Phe Phe Gly Val Pro Val
                85                  90                  95

Thr Tyr Phe Phe Asn Glu Asp Val Ser Asp Arg Val Asp Arg Gln Leu
            100                 105                 110

Glu Tyr Leu Arg Ala Glu Gln Ala Arg Leu Arg Glu Leu Ala Glu Thr
        115                 120                 125

Asp Glu Val Arg Leu Met Ala Met Arg Ala Gly Glu Leu Thr Thr Asp
    130                 135                 140

Arg Arg Glu Leu Val Lys Asn Leu Leu Asp Val Val Trp Arg Asp Gln
145                 150                 155                 160

Gln Ala Met Arg Glu Arg Gly Ser Lys Gln Asp
                165                 170
```

<210> SEQ ID NO 7
<211> LENGTH: 516
<212> TYPE: DNA
<213> ORGANISM: Amycolatopsis orientalis

<400> SEQUENCE: 7

```
atggcagcgc ggcacgggtt cgtgaggaac tcggcagtgt tcttgggagg cagcatgtcc       60
cggcaggacg gaccaggccg gagcctggcc gaaaaactcg accatctgtt cgcgcacgtc      120
acccggcgca acggcaccga gttcacgtac gaagaggtcg cgtccgcgat caccgccgag      180
ggtgtgacga tctcccagag ctacgtctgg cagctgcgca agggaaagaa ggacaacccg      240
acgctcaagc acctgcaagg gctggcggat ttcttcggtg tcccggtcac gtacttcttc      300
aacgaggacg tgagcgaccg ggtggaccgg cagctggagt acctgcgcgc ggaacaggcg      360
```

```
cggttgcgtg agctggccga aaccgacgag gtccgcctga tggccatgcg cgcgggcgag    420
ttgacgaccg atcgccgcga actggtgaag aacctcctcg acgtggtctg gcgggatcag    480
caggccatgc gagagcgtgg gtccaaacag gactga                              516
```

<210> SEQ ID NO 8
<211> LENGTH: 936
<212> TYPE: PRT
<213> ORGANISM: Amycolatopsis orientalis

<400> SEQUENCE: 8

```
Met His Val Lys Ser Val Ile Arg Val Asp Gly Asp Val Arg Ala Arg
1               5                   10                  15

Ala Tyr Pro Arg Ala Glu Leu Leu Val Leu Arg Asp Phe Leu Thr Glu
            20                  25                  30

Ser Glu Gln Gly Asn Ala Val Ala Val Val Thr Gly Thr Ala Ala
        35                  40                  45

Ser Gly Lys Ser Glu Leu Leu His Ala Phe Ala Gln Gln Cys Ala Glu
    50                  55                  60

Ala Glu Ala Thr Val Met Ser Ala Leu Cys Val Glu Ala Glu Lys Asp
65                  70                  75                  80

Leu Pro Phe Thr Ala Leu Phe Gln Leu Phe Arg Gly Pro Ala Leu Ser
                85                  90                  95

Gly Asp Leu Arg Ala Lys Ala Ala Asp Leu Leu Thr Arg Ala Glu Arg
            100                 105                 110

Thr Gly Leu Thr Gly Arg Pro Ser Thr His Leu Met Leu Asp Leu Leu
        115                 120                 125

Glu Leu Val Arg Glu Leu Ala Ala His Arg Pro Val Val Val Leu Val
    130                 135                 140

Asp Asp Phe His His Val Asp Thr Pro Ser Leu His Trp Leu Met Phe
145                 150                 155                 160

Leu Met Arg Arg Met Arg Thr Met Asn Val Leu Val Leu Thr Glu
                165                 170                 175

Ser Leu Ser Ala Lys Gln Thr Leu Pro Leu Leu Gly Ala Glu Tyr Leu
            180                 185                 190

Arg Leu Pro His Cys Arg Arg Ile Arg Leu Lys Pro Leu Gly Arg Asp
        195                 200                 205

Glu Val Ala Arg Phe Val Pro Pro Gly Gln Asp Asp Thr Leu Val Lys
    210                 215                 220

Gly Leu His Glu Leu Ser Gly Gly Asn Pro Leu Leu Ala Gln Ala Leu
225                 230                 235                 240

Leu Glu Asp Leu Arg Ala Ser Gly Val Pro Leu Ala Pro Glu Thr Arg
                245                 250                 255

Pro Ile Pro Gly Asp His Tyr Cys Gln Ala Val Ala Ala Cys Leu Gln
            260                 265                 270

Arg Gly Asp Gln Asp Thr Arg Thr Leu Ala Gly Val Leu Ala Val Leu
        275                 280                 285

Gly Lys Gly Glu Thr Val Cys Leu Ala Val Arg Val Thr Gly Met Asp
    290                 295                 300

Gln Arg Thr Ala Gly Arg Ala Ile Ala Leu Leu His Gln Val Gly Leu
305                 310                 315                 320

Leu Asp Ala Gly Arg Phe Arg His Pro Met Thr Val Thr Ala Val Leu
                325                 330                 335

Ala Asp Val Pro Val Ala Glu Arg Ala Arg Leu His Glu Arg Ala Ala
```

-continued

```
            340                 345                 350
Val Leu Leu His His Asp Gly Ala Gly Ala Leu Asp Val Ala Arg His
        355                 360                 365
Leu Val Ala Ala Asp Arg Ala Asp Arg Pro Trp Ala Val Pro Val Leu
    370                 375                 380
Arg Thr Ala Ala Glu Leu Ala Lys Val Asp Asn Arg Thr Ser Phe Ala
385                 390                 395                 400
Val Gln Cys Leu Lys Leu Ala Cys Arg Ser Cys Gly Asp Glu Ala Leu
                405                 410                 415
Glu Val Glu Met Val Thr Gln Leu Ala Gly Leu Glu Trp Arg Asn Asn
            420                 425                 430
Pro Ala Ile Gly Ala Val His Thr Asp His Leu Tyr Glu Ile Phe Leu
        435                 440                 445
Ala Gly Gln Leu Pro Val Arg Ala Ala Ile Leu Val Arg Phe Leu
    450                 455                 460
Leu Trp His Gly Arg Thr Ala Glu Ala Gly Glu Val Leu Asp Lys Leu
465                 470                 475                 480
Ala Val Met Glu Pro Ser Ala Asp Arg Thr Glu Ala Glu Leu Arg
                485                 490                 495
Ile Thr Arg Leu Phe Ile Leu Cys Ser Tyr Pro Val Leu Arg Asp Lys
            500                 505                 510
Leu Pro Ala Pro Ala Lys Asp Arg Val Pro Ala Gln Ser Phe Asp
        515                 520                 525
Pro Asn Val Gln Ala Ala Met Ala Leu Ser Arg Ile Val Thr Asn Gly
    530                 535                 540
Pro Asp Asp Ala Ile Ala Ser Ala Glu Asn Val Leu Lys Ser Ile
545                 550                 555                 560
Gln Leu Gly Asp Thr Met Val Glu Ser Val Arg Ser Ala Leu Phe Ala
                565                 570                 575
Leu Ile Tyr Ala Asp Arg Leu Asp Lys Ala Val Pro Trp Cys Glu Leu
            580                 585                 590
Leu Gln Gln Glu Ala Ala Asp Cys Asp Ala Pro Ser Trp Gln Ala Val
        595                 600                 605
Phe Ala Ala Arg Ala Glu Met Ala Leu Arg Gln Gly Asp Leu Val
    610                 615                 620
Thr Ala Glu Lys Gln Ala Lys Ala Ala Leu Thr Phe Ile Thr Pro Gln
625                 630                 635                 640
Ser Trp Gly Val Ala Val Gly Val Pro Leu Ala Thr Leu Cys Leu Ala
                645                 650                 655
Ala Val Gly Met Gly Lys Phe Glu Glu Ala Ala Ser His Ile Asn Gln
            660                 665                 670
Pro Val Pro Ala Ser Met Leu Gln Thr Arg Phe Gly Leu His Tyr Leu
        675                 680                 685
Arg Ala Arg Gly Arg Leu Tyr Leu Glu Thr Asp Arg Val His Ala Ala
    690                 695                 700
Leu Gly Asp Phe Val Leu Cys Gly Glu Leu Ser Lys Ser Trp Asp Phe
705                 710                 715                 720
Asp Leu Pro Val Leu Val Pro Trp Arg Gly Asp Thr Ala Glu Ala Tyr
                725                 730                 735
Leu Arg Leu Gly Met Pro Glu Lys Ala Lys Ser Leu Leu Asp Glu Gln
            740                 745                 750
Leu Ala Lys Leu Ala Gly Ser Thr Ser His Val Arg Gly Ile Ser Leu
        755                 760                 765
```

-continued

```
Arg Leu Lys Ala Lys Ile Ala Glu Pro Gln Lys Arg Pro Glu Leu Leu
        770                 775                 780

Arg Glu Ala Val Lys Ile Phe Gln Ala Gly Gly Ile Arg Leu Glu Leu
785                 790                 795                 800

Ala Arg Ala Leu Gly Asp Leu Ser Arg Ala His Tyr Thr Leu Ala Glu
                805                 810                 815

Ser Gly Arg Ala Arg Thr Val Ala Arg Gln Ala Trp His Ile Ala Lys
                820                 825                 830

Gly Cys His Ala Asp Val Ile Cys Arg Asp Leu Arg Leu Asp Gly Thr
            835                 840                 845

Gly Asp Glu Gly Lys Pro Ala Ser Thr Ala Ala Glu Ile Ala Ala Ser
    850                 855                 860

Gly Val Glu Arg Glu Leu Ile Glu Ser Leu Ser Glu Ala Glu Arg Arg
865                 870                 875                 880

Val Ala Gly Leu Ala Ser Leu Gly His Thr Asn Arg Ala Ile Ala Ser
                885                 890                 895

Lys Leu Tyr Ile Thr Val Ser Thr Val Glu Gln His Leu Thr Arg Val
                900                 905                 910

Tyr Arg Lys Leu Asp Val Asn Arg Arg Arg Asp Leu Pro Ser Trp Leu
            915                 920                 925

Gln Val Ser Val Val Asn Ser Ala
    930                 935
```

```
<210> SEQ ID NO 9
<211> LENGTH: 2811
<212> TYPE: DNA
<213> ORGANISM: Amycolatopsis orientalis

<400> SEQUENCE: 9
atgcacgtga aatcagtgat cagagtggac ggcgacgtcc gcgcgagggc gtatccccgc      60
gcggagctgc tggtcctgcg agacttcttg acggaatccg aacagggaaa cgccgtcgcg     120
gcggtggtca ccggaaccgc cgcgagcggg aaaagtgaac ttctgcacgc attcgcgcaa     180
caatgcgctg aagcggaagc aacggtgatg agcgcgcttt cgtggaagc ggagaaggat     240 ctcccgttca ccgcgctgtt ccagcttttc cgtggcccgg cactgtccgg agatctgcgc     300
gcgaaggccg cggacctgct gacgcgggcc gaacggaccg ggctgaccgg gcggcccagc     360
acacatctca tgctcgacct gctggagctc gtgcgcgagc tcgccgcgca ccgtccggtc     420
gtggtcctgg tcgacgactt ccaccatgtg gacaccccgt cgttgcactg gctgatgttc     480
ctcatgcgcc gcatgcgcac gatgaacgtg ctcgtcgtgc tgacggagtc gttgtccgcc     540
aagcagacgt tgcccttgct gggcgccgag tacctccggc tcccgcactg ccgccggatc     600
cggctgaagc cgctgggccg cgacgaggtg gcccggttcg tcccgcccgg ccaggacgac     660
accctggtga agggcctgca cgagctcagc ggcgggaatc cgttgctggc tcaggcactc     720
ctcgaagatc tccgtgcctc gggcgtaccc ctcgcgcccg agaccaggcc gatccccggc     780
gatcactact gccaggcggt ggcggcgtgt ctccagcgcg cgaccaggga cacccggacc     840
ctcgccggtg tcctcgcggt gctgggtaaa ggggaaacgg tctgcctcgc cgtccgggtg     900
accgggatgg accagcgcac cgccggccgt gcgatcgccc tcctgcacca ggtcggcctg     960
ctcgacgcgg gccggttccg gcatccgatg acggtgaccg cggtgctggc cgacgtcccg    1020
gtcgcggaac gcgcgcgact gcacgagcgc gccgcggtgc tcctgcatca cgacggcgcc    1080
ggcgcgctcg acgtggcccg ccacctcgtc gccgccgacc gggccgaccg gccgtgggcg    1140
```

-continued

```
gtgcccgtgc tgcgcaccgc ggccgaactg gccaaagtgg acaaccggac ctcgttcgcg   1200
gtccaatgcc tgaaactggc ctgccggtcg tgcggcgacg aagcgctcga ggtcgagatg   1260
gtgacccagc tcgccggcct ggaatggcgg aacaacccgg ccatcggcgc cgtgcacacg   1320
gaccacctct acgagatctt cctcgccggg cagctcccgg tgcggccgc cgccatcctg    1380
gtgcggttcc tgctgtggca cggccgcacc gcggaagcgg gtgaggtgct cgacaagctc   1440
gccgtcatgg agccttcggc cgacgatcgc accgaggcgg aactgcgcat cacccggctg   1500
ttcattctct gttcctatcc cgttctgcgc gacaagctgc ctgccccggc cgcgaaggac   1560
cgcgttcccg cgcaatcctt cgaccccaac gtgcaggcg cgatggcgct gagccggatc    1620
gtcacgaacg gccccgacga cgacgcgatc gcttcggctg agaacgtgct gaagagcatc   1680
cagctcggcg acacgatggt cgaatccgtg cgcagcgcgc tgttcgcgct catctacgcc   1740
gaccggctgg acaaggcggt gccgtggtgc gagctgctgc agcaggaggc cgccgactgc   1800
gacgcgccca gctggcaggc cgtgttcgcc gcggccaggg cggaaatggc gctgcgccag   1860
ggagatctgg tgacggcgga gaagcaggcc aaggcggcct tgacgttcat cacgccgcag   1920
agctggggcg tggccgtcgg agtcccgctg gcgacgctgt gcctcgccgc cgtcgggatg   1980
ggcaagttcg aggaggcggc gtcgcatatc aaccagccgg tgccggcctc gatgctgcaa   2040
acccggttcg gcctgcacta cctgcgcgcc cgcggcaggc tctacctgga gaccgaccgg   2100
gtgcacgccg cgctcggcga cttcgtcctg tgcggggaac tcagcaagag ctgggatttc   2160
gacctgccgg tgctggtgcc ctggcgcggc gacacgcccg aggcgtacct ccggctcggc   2220
atgccggaga aggcgaagtc cctgctggac gagcagctcg cgaagctcgc cggctcgacg   2280
tctcatgtgc ggggaatctc gttgcggctc aaggccaaga tcgccgaacc gcagaagcgc   2340
ccggaattgc tgcgtgaagc ggtgaagatc ttccaggcgg gcggtatccg cctcgaactc   2400
gcccgcgcgc tcggcgatct cagccgcgcg cactacacgc tggccgagtc gggtcgcgcg   2460
cgcacggtgg cccggcaggc gtggcatatc gcgaagggtt gccacgccga cgtgatctgc   2520
cgggatctgc gtctcgacgg gacaggcgac gagggaaagc cggcgtccac cgcggcggag   2580
atcgccgcgt cgggcgtcga acgcgagctc atcgagtcgc tgagcgaggc cgagcgacgg   2640
gtcgccgggc tggcctccct cgggcacacg aaccgggcga tcgcgagcaa gctctacatc   2700
acggtgagca cggtcgaaca gcatctcacc cgcgtctatc gcaaactgga cgtcaaccgg   2760
cgccgggatc tcccgtcgtg gctccaggtt tcggtcgtca acagcgcctg a            2811
```

<210> SEQ ID NO 10
<211> LENGTH: 271
<212> TYPE: PRT
<213> ORGANISM: Amycolatopsis orientalis

<400> SEQUENCE: 10

```
Met Gln Arg Asn Phe Lys Glu Phe Lys Ile Thr Val Asp Pro Val Arg
1               5                   10                  15

Asp Asp Phe Leu Arg Ala Lys Gly Pro Gly Gln Arg Asn Leu Leu Leu
                20                  25                  30

Gly Arg Ala Val Phe Glu Phe Ala Ser Asp Leu Glu His Leu Asp Thr
            35                  40                  45

Ile Gln Gln Glu Phe Val Asp Gly Ser His Arg Pro Leu Ile Arg Arg
        50                  55                  60

Asn Trp Gln Asp Ser Thr Ala Asp Tyr Ser Asp Pro Thr Gln Leu Leu
65                  70                  75                  80
```

```
Ile Gln Gly Gln Gln Val Met Gln Asn Trp Glu Arg Pro Leu Met Lys
                85                  90                  95
Val Leu Ala Glu Asn Ala Ala Ala Asn Gly Gly Asp Leu Leu Glu Val
            100                 105                 110
Gly Phe Gly Met Gly Ile Ser Ala Thr Tyr Val Gln Asp Ala Gly Val
            115                 120                 125
Arg Ser His Thr Leu Ile Glu Ile Asn Ser Glu Val Lys Ala Glu Phe
            130                 135                 140
Glu Lys Trp Arg Ala Gln Trp Pro Asp Arg Asp Ile Arg Leu Glu Leu
145                 150                 155                 160
Gly Ala Trp Gln Asp Val Leu Gly Gly Leu Gly Gln Tyr Asp Ala Ile
                165                 170                 175
Leu Tyr Asp Thr Tyr Pro Thr Asp Glu Arg Glu Phe Ala Arg Thr Leu
            180                 185                 190
Gly Pro Lys Ala Ile Val Leu Ala Ala Glu Phe Phe Glu His Ala Ala
            195                 200                 205
Ala His Leu Arg Pro Gly Gly Val Phe Ser Tyr Tyr Thr Asn Glu Ile
210                 215                 220
Asp Ser Leu Ser Arg Ala His Gln Arg Ala Leu Leu Glu His Phe Ser
225                 230                 235                 240
Ser Phe Arg Val Glu Val Val Arg Asp Leu Lys Pro Pro Ala Asp Cys
                245                 250                 255
Thr Tyr Trp Trp Ala Gly Thr Met Ala Ala Val Thr Ala Val Lys
                260                 265                 270

<210> SEQ ID NO 11
<211> LENGTH: 813
<212> TYPE: DNA
<213> ORGANISM: Amycolatopsis orientalis

<400> SEQUENCE: 11
cttgacggcg gtcacggcgg ccatcgtgcc cgcccaccag taggtgcagt cggccggcgg      60
cttcaggtcc cggacgacct ccacccggaa cgagctgaag tgttcgagca gggcgcgctg     120
gtgtgcccgg ctcagtgagt cgatttcgtt ggtgtagtag agaagacgc caccgggacg      180
aaggtgggcg gcggcgtgct cgaagaattc ggccgccagc acgatggcct tcgggcccag     240
ggtcctggcg aattcccgct cgtcggtcgg ataggtgtcg tacaggatcg cgtcgtactg     300
gccgaggccg ccgagcacgt cctgccaggc gccgagttcc agccggatat cgcggtccgg     360
ccactgggca cgccatttct cgaactccgc cttcacctcg gagttgattt cgatcagggt     420
gtgcgaccgg acgcccgcgt cctggacgta ggtggccgaa atacccatcc gaaaccgac     480
ttcgagcaga tccccgccgt cgccgcggc gttttccgcc agcaccttca tcagcggccg     540
ttcccagttc tgcatcacct gctggccctg atgagcagc tgcgtcggat cgctgtagtc      600
cgcagtgctg tcctgccagt tccggcggat cagcggccgg tgcgagccgt cgacgaattc     660
ctgctggatg gtgtccagat gttccagatc gctggcgaac tcgaacaccg cgcggccgag     720
aaggaggttg cgctggccgg gccccttcgc ccggaggaag tcgtccctga ccgggtccac     780
cgttatcttg aattccttga agttccgttg cat                                 813

<210> SEQ ID NO 12
<211> LENGTH: 229
<212> TYPE: PRT
<213> ORGANISM: Amycolatopsis orientalis
```

<400> SEQUENCE: 12

```
Met Pro Gly Glu Thr Lys Asn Gln Asp Thr Asp Gly Arg Gly Ala Arg
1               5                  10                  15
Arg Arg Ser Val Val Ser Leu Ile Ala Asp Val Thr Val Pro Val Val
            20                  25                  30
Val Tyr Tyr Ala Leu Leu Ala Phe Gly Trp Ser Ser Gly Ser Ala Leu
        35                  40                  45
Val Ala Ala Thr Val Ala Ile Gly Val Leu Val Leu Ala Val Ala Val
    50                  55                  60
Lys Glu Arg Arg Val Asp Gly Phe Gly Val Phe Val Leu Gly Val Cys
65                  70                  75                  80
Ala Val Thr Leu Leu Val Ser Leu Val Ser Gly Asp Glu Arg Leu Leu
                85                  90                  95
Leu Ala Lys Asp Pro Phe Thr Ser Gly Leu Ala Gly Ile Ala Phe Leu
            100                 105                 110
Gly Ser Leu Val Phe Gly Lys Pro Val Thr Phe Ile Ser Arg Arg
        115                 120                 125
Ile Arg Ala Leu Thr Pro Ala Arg Arg Leu Gly Trp Asp Arg Leu Tyr
    130                 135                 140
Ala Ala Glu Pro Glu Phe Arg Lys Leu His Arg Val Ser Thr Ala Gly
145                 150                 155                 160
Trp Gly Val Val Leu Val Thr Glu Ser Ala Ala Arg Leu Val Leu Ile
                165                 170                 175
Tyr Leu Leu Pro Ala Ser Val Met Val Gly Leu Ser Thr Ala Ile Glu
            180                 185                 190
Leu Thr Ala Ile Thr Gly Val Val Ala Trp Thr Ile Trp Tyr Arg Arg
        195                 200                 205
Arg Ser Ala Gly His Gly Leu Glu Lys Ser Leu Arg Thr Ala Asp Ala
    210                 215                 220
Ala Pro Ala Ala Val
225
```

<210> SEQ ID NO 13
<211> LENGTH: 687
<212> TYPE: DNA
<213> ORGANISM: Amycolatopsis orientalis

<400> SEQUENCE: 13

```
atgccggggg aaaccaagaa ccaggacacc gacggccgcg gcgcgcgcag gcgctccgtc      60
gtatcgttga tcgccgacgt caccgtgccg gtcgtcgtct actacgcgct gctcgccttc     120
gggtggagca gcggctccgc cttggtggcg gccacggtcg ccatcggggt cctcgtgctc     180
gccgtcgcgg tcaaggaacg cagggtcgac ggcttcgggg tgttcgtgct cggagtctgc     240
gcggtgaccc tgctggtctc cttggtgagc ggggacgaac gcctgctgtt ggccaaggat     300
cccttcacca gcggcctggc cgggatcgcc ttcctcggca gcctcgtctt cgggaaaccg     360
gtgaccttct tcatctcccg ccggatccgg gcgctcaccc cggctcggcg cctgggctgg     420
gaccggctgt acgccgcgga acccgagttc gcaaactgc atcgcgtctc caccgcgggc     480
tggggcgtgg tcctggtcac cgagtccgcc gcccggctcg tcctgatcta cctgctgccc     540
gcgtcggtga tggtcggcct gtccaccgcg atcgaactga ccgcgatcac cggcgtggtc     600
gcctggacca tctggtaccg cgtcgctcc gccggccacg gtctggaaaa gtcgcttcgc     660
acggcggatg cggcgcccgc tgctgtc                                        687
```

```
<210> SEQ ID NO 14
<211> LENGTH: 553
<212> TYPE: PRT
<213> ORGANISM: Amycolatopsis orientalis

<400> SEQUENCE: 14

Met Thr Ala Ala Asp Phe Ala Pro Pro Leu Thr Thr Leu Cys Pro Asp
1               5                   10                  15

Phe Pro Phe Ala Tyr Asp Asp Trp Leu Ala His Pro Ala Gly Leu Gly
            20                  25                  30

Glu Leu Pro Pro Asp Arg Leu Gly Gln Glu Val Ala Val Val Gly Gly
        35                  40                  45

Gly Ile Ala Gly Val Val Ala Ala Tyr Glu Leu Leu Arg Leu Gly Leu
    50                  55                  60

Lys Pro Val Val Tyr Glu Ala Gly Gln Ile Gly Gly Arg Met Arg Ser
65                  70                  75                  80

Ile Pro Leu Ala Gly Glu Asp Gly Ala Val Ala Glu Met Gly Ala Met
                85                  90                  95

Arg Phe Pro Pro Ser Ala Thr Thr Leu Tyr Arg Tyr Ile Asp Glu Val
            100                 105                 110

Gly Leu Glu Thr Lys Pro Phe Ala Asn Pro Leu Ser Arg Ser Thr Ser
        115                 120                 125

Thr Thr Val Ile Asn Leu Asp Gly Val Thr Tyr Arg Ala Arg Thr Pro
130                 135                 140

Ala Asp Leu Pro Ser Val Phe His Glu Val Asp Asp Ala Trp His Lys
145                 150                 155                 160

Ala Leu Gln Glu Leu Ala Asp Leu Ser Thr Met Arg Asp Ala Ile Arg
                165                 170                 175

Met Arg Asp Thr Ala Met Val Lys Ala Ile Trp Asn Arg Leu Leu Pro
            180                 185                 190

Glu Leu Asp Asp Gln Ser Phe Tyr Gly Phe Leu Ala Arg Ser Thr Ala
        195                 200                 205

Phe Ala Ser Phe Arg His Arg Glu Ile Phe Gly Gln Val Gly Phe Gly
210                 215                 220

Thr Gly Gly Trp Asp Thr Asp Phe Pro Asn Ser Val Leu Glu Ile Leu
225                 230                 235                 240

Arg Val Ile Tyr Thr Gly Val Glu Glu Gly Pro Arg Gln Ile Ile Gly
                245                 250                 255

Gly Cys Gln Gln Leu Pro Arg Arg Leu Trp Asn His Ala Pro Ala Ser
            260                 265                 270

Ala Arg Phe Trp Pro Ala Gly Thr Ser Val Ala Ser Leu His Asp Gly
        275                 280                 285

Ser Pro Arg Pro Ala Val Leu Gly Leu Arg Pro Ala Ala Asp Gly Phe
290                 295                 300

Ala Val Glu Asp Ala Asn Gly Asp Val Arg Thr Tyr Pro Ala Val Val
305                 310                 315                 320

Phe Thr Ala Gln His Arg Val Leu Leu Thr Lys Ile Ala Gly Val Arg
                325                 330                 335

Pro Leu Leu Pro Ala Asn Val Trp Thr Ala Leu Glu Arg Thr His Tyr
            340                 345                 350

Met Gly Ala Ser Lys Leu Phe Val Pro Val Asp Arg Pro Phe Trp His
        355                 360                 365

Asp Val Asp Pro Arg Thr Gly Glu Glu Leu Met Gly Met Thr Leu Thr
370                 375                 380
```

```
Asp Arg Thr Pro Arg Ser Val Tyr Leu Phe Asp Asp Gly Pro Asp Ser
385                 390                 395                 400

Pro Ala Ala Leu Cys Leu Ser Tyr Thr Trp Asn Asp Asp Ser Leu Lys
            405                 410                 415

Phe Ala Thr Leu Gly Pro Ala Asp Arg Leu Glu Leu Ala Leu Asp Ala
            420                 425                 430

Leu Ala Asp Ile Tyr Pro Gly Val Asp Ile Arg Ser His Ile Thr Gly
            435                 440                 445

Asp Pro Val Thr Val Thr Trp Glu Asn Glu Pro Asn Phe Gln Gly Ala
        450                 455                 460

Phe Lys Ala Asn Leu Pro Gly Gln Tyr Arg Tyr Gln Arg Arg Leu Phe
465                 470                 475                 480

Thr His Phe Arg Gln Asp Asp Leu Pro Ala Ala Gln Arg Gly Leu Phe
                485                 490                 495

Leu Ala Gly Asp Asp Ile Ser Trp Met Gly Gly Phe Ala Glu Gly Ala
            500                 505                 510

Val Thr Ser Ala Leu Asn Ala Val Trp Gly Thr Leu Arg His Leu Gly
            515                 520                 525

Gly Ala Thr Asp Pro Arg Asn Pro Gly Pro Gly Asp Val Phe Asp His
        530                 535                 540

Ile Ala Pro Ile Glu Leu Pro Glu Ser
545                 550

<210> SEQ ID NO 15
<211> LENGTH: 1659
<212> TYPE: DNA
<213> ORGANISM: Amycolatopsis orientalis

<400> SEQUENCE: 15
atgaccgcag ccgatttcgc gccccgctg accactctct gccccgattt cccgttcgcc      60
tacgacgatt ggctcgcgca tccggccggg ctcggtgagc tgccgccgga ccgcctcggc     120
caggaggtcg ccgtcgtcgg tgcgggata gcgggtgtgg tcgcggctta cgaactgctg     180
cgcctcggcc tgaaaccggt ggtctacgaa gcgggccaga tcggcgggcg gatgcgctcc     240 atcccttgg cgggcgagga cggcgcggtc gcggagatgg gcgcgatgcg gttcccgccc      300
tcggccacca ccctgtaccg gtacatcgac gaagtcggcc tggagaccaa gccgttcgcg     360
aacccgttgt cccgcagcac ttccaccacg gtgatcaacc tcgacggggt gacctaccgc     420
gcgcggaccc cggcggacct cccgtcggtg ttccacgagg tcgacgacgc ctggcacaag     480
gccctgcagg aactggccga tctgtccacc atgcgcgacg ccatccggat gcgcgacacc     540
gccatggtga aggcgatctg gaaccggctg ctgcccgaac tcgacgacca gtccttctat     600
ggtttcctgg cacggtcgac cgctttcgcc tccttccgcc atcgtgagat cttcggccag     660
gtcggcttcg gcaccggcgg ctgggacacc gatttcccca actccgtgct ggaaatcctc     720
cgcgtcatct acaccggtgt cgaggagggg ccgcggcaga tcatcggtgg ctgccagcaa     780
cttccgcggc ggttgtggaa ccacgcaccc gcgtctgcgc gcttctggcc tgccgggaca     840
tcggtcgcgt cgctgcacga cggatcgccg cgcccgccg tcctcgggtt cgcccggcc      900 gcggacgggt cgccgtcga ggacgcgaac ggtgacgtgc ggacctatcc ggccgtggtc      960
ttcaccgcgc agcaccgggt cctgctcacc aagatcgccg gagtgcgccc gctgctgccc    1020
gcgaacgtgt ggaccgcgct ggaacgcacg cactacatgg gtgcttcgaa gttgttcgtc    1080
ccggtcgacc ggccgttctg gcacgacgtc gatccccgca ccggtgagga actgatgggg    1140
```

```
atgaccctca ccgaccggac cccgcgcagc gtctacctgt tcgacgacgg gccggattcg    1200
ccggccgcgc tgtgcctttc ctatacctgg aacgacgatt cgctcaagtt cgcgacgctc    1260
ggcccggcgg accggctcga actcgcgctc gacgcgctcg ccgacatcta cccgggtgtc    1320
gacatccgct cccacatcac cggcgatccg gtcaccgtca cctgggagaa cgagccgaac    1380
ttccaaggcg cgttcaaggc gaacctgcca gggcagtacc gctatcagcg ccgcctgttc    1440
acccatttcc ggcaagacga ccttcccgcc gctcagcgcg gcctgttcct cgccggtgac    1500
gacatctcgt ggatgggcgg cttcgccgaa ggggcggtca ccagcgcgct caacgcggtg    1560
tgggggacgc tgcgccatct cggcggggcc accgacccgc gtaatcccgg ccccggcgac    1620
gtcttcgacc acatcgcgcc gatcgaactg cccgagtcc                           1659
```

<210> SEQ ID NO 16
<211> LENGTH: 179
<212> TYPE: PRT
<213> ORGANISM: Amycolatopsis orientalis

<400> SEQUENCE: 16

```
Met Ser Glu Ala Met Arg Asn Ala Leu Ile Leu Ser Gly Val Leu Leu
1               5                   10                  15

Ala Leu Val Leu Phe Thr His Ile Gly Arg His Lys Ala His Leu Val
            20                  25                  30

Ile Leu Ile Leu Pro Phe Phe Thr Cys Ala Leu Val Gly Trp Ala Val
        35                  40                  45

Leu Tyr Asp Leu Lys Leu Thr Thr Pro Asn Thr Leu Ala Gly Leu Val
    50                  55                  60

Gly Ile Ala Ala Gly Val Leu Ile Gly Trp Gly Leu Leu Lys Gly Thr
65                  70                  75                  80

Lys Val Glu Trp Asp Gln Glu Lys Ser Ala Val Tyr Thr Arg Ala Gly
                85                  90                  95

Trp Val Tyr Leu Gly Leu Trp Leu Phe Val Leu Val Gly Arg Leu Ile
            100                 105                 110

Phe Val Tyr Thr Leu Glu His Ser His Ser Phe Ala Ala Asp Phe Gly
        115                 120                 125

Lys Phe Leu Met Asp Thr Gly Ile Asp Ala Gly Val Ser Ala Phe
    130                 135                 140

Phe Val Thr Met Ala Leu Thr Met Val Ile Phe Arg Thr Ala Gly Val
145                 150                 155                 160

Trp Val Tyr Arg Ala Lys Val Leu Arg Gln Ala Gln Arg Thr Pro Ser
                165                 170                 175

Tyr Ala Ser
```

<210> SEQ ID NO 17
<211> LENGTH: 540
<212> TYPE: DNA
<213> ORGANISM: Amycolatopsis orientalis

<400> SEQUENCE: 17

```
atgagtgaag ccatgcgaaa cgccctcatc ctgagcggcg tactgctggc gctggtgctg     60
ttcacgcaca tcggtcgcca taaggcccac ctggtcatcc tgatcctgcc gttcttcacg    120
tgcgcgctgg tgggctgggc ggtcctctac gacctcaagc tgaccacgcc gaacacactg    180
gccgggctgg tcggcatcgc ggcgggcgtc ctgatcggct ggggattgct gaagggcacg    240
aaggtcgagt gggaccagga gaaatccgcc gtctacacca gggcgggctg gtctacttg    300
```

```
ggactgtggc tgttcgtcct ggtcggacgg ctcatcttcg tctacaccct cgaacacagc    360
cactcgttcg cggccgactt cggcaagttc ctgatggaca ccgggatcga cgccggcggc    420
gtctccgcct tcttcgtcac catggcgctg acgatggtca tcttccgcac cgccggggtc    480
tgggtctacc gggccaaggt actcaggcag gctcagcgaa ccccccagcta cgcgagctga   540
```

<210> SEQ ID NO 18
<211> LENGTH: 222
<212> TYPE: PRT
<213> ORGANISM: Amycolatopsis orientalis

<400> SEQUENCE: 18

```
Met Val Glu Glu Val Pro Pro Val Arg Ile Val Ile Ala Glu Asp Gln
1               5                   10                  15

Ala Ala Val Arg Glu Gly Leu Ala Leu Leu Val Gly Thr Val Ala Gly
            20                  25                  30

Ile Thr Val Val Gly Gln Ala Pro Asp Gly Glu Val Ala Val Arg Leu
        35                  40                  45

Ala Gly Glu Leu Arg Pro Asp Val Val Leu Met Asp Leu Ser Met Pro
    50                  55                  60

Arg Cys Asp Gly Val Glu Ala Thr Arg Arg Ile Lys Glu Arg His Pro
65                  70                  75                  80

Glu Ile Glu Ile Val Val Leu Thr Thr Tyr Ala Asp Asp Trp Val
                85                  90                  95

Leu Arg Ala Leu Glu Ala Gly Ala Leu Gly Tyr Leu Thr Lys Ser Ala
            100                 105                 110

Asn Lys His Glu Ile Gly Arg Ala Val His Ala Ala Ala Gly Gln
        115                 120                 125

Ala Leu Leu Asp Pro Gln Val Gln Arg Arg Val Leu Gly Ala Ala Leu
    130                 135                 140

Thr Ser Ala Pro Ala Ser Ala Pro Pro Glu Asp Asp Ala Asn Leu
145                 150                 155                 160

Thr Lys Arg Glu Ala His Val Leu Thr Leu Ile Ala Ala Gly His Ser
                165                 170                 175

Asn Lys Glu Ile Ala Ala Glu Leu Phe Val Ser Glu Thr Thr Val Lys
            180                 185                 190

Ser His Ile Asn Arg Ile Phe Ala Lys Thr Gly Ser Arg Asp Arg Ala
        195                 200                 205

Gln Ala Val Arg Tyr Ala Tyr Gln Ala Gly Tyr Val Arg Asp
    210                 215                 220
```

<210> SEQ ID NO 19
<211> LENGTH: 666
<212> TYPE: DNA
<213> ORGANISM: Amycolatopsis orientalis

<400> SEQUENCE: 19

```
atggtcgaag aagtgccccc ggtccggatc gtgatcgccg aagaccaggc ggcggtacgc    60
gaaggactgg ccctcctggt ggggacggtc gcggggatca ccgtggtcgg ccaggcaccc    120
gacggcgagg tcgccgtgcg gctggccggg gaactgcgcc cggacgtcgt cctgatggat    180
ctctccatgc cccggtgcga cggcgtcgag gcgacccggc ggatcaagga acggcatccg    240
gagatcgaga tcgtcgtgct caccacctac gccgacgacg actgggtgct gcgcgcgttg    300
gaggccgggg cgttgggata cctgacgaaa tcggccaaca acacgaaat cgggcgcgcg    360
```

-continued

```
gtacacgccg ccgcggcggg ccaggccctg ctcgatccgc aggtgcagcg acgggtgctc    420
ggcgccgccc tgacgtccgc gcccgcttcg gcgccaccgc cggaggacga cgcgaacctc    480
accaagcggg aagcccatgt gctgacgctg atcgcggcgg ggcacagcaa caaggagatc    540
gccgcggaac tgttcgtcag cgagacgacg gtcaagagcc atatcaaccg gatcttcgcc    600
aagacgggga gccgggatcg cgcgcaggcc gtccgttatg cctaccaagc gggctatgtg    660
cgggac                                                               666
```

<210> SEQ ID NO 20
<211> LENGTH: 379
<212> TYPE: PRT
<213> ORGANISM: Amycolatopsis orientalis

<400> SEQUENCE: 20

```
Met Thr Asp Ala Val Ser Asp Glu Val Glu Glu Arg Arg Trp Arg Trp
1               5                   10                  15

Ala Ala Pro Ala Ala Gly Thr Ala Leu Leu Ala Val Thr Gln Met Thr
            20                  25                  30

Ala Thr Val Pro Ala Gly Ala Gly Trp Leu Trp Val Leu Tyr Ala Val
        35                  40                  45

Ser Ser Ala Ser Trp Leu Leu Trp Ile Gly Ile Ser Glu Arg Phe Pro
    50                  55                  60

Arg Ala Ala Leu Leu Pro Leu Ala Ala Ser Ala Val Pro Ala Phe
65                  70                  75                  80

Gly Thr Gly Ala Ala Thr Asp Gly Thr Ala Val Ile Met Thr Cys Ile
                85                  90                  95

Thr Leu Ala Ala Phe Ala Ser Arg Leu Glu Pro Gly Thr Val Ala Ile
            100                 105                 110

Ile Ala Leu Met Val Phe Asp Ala Ala Ile Val Val Ser Ser Leu
        115                 120                 125

Leu Gly His Arg Pro Ser Glu Ala Trp Leu Gly Leu Gly Ala Val
    130                 135                 140

Val Ile Val Val Leu Val Gly Phe Thr Arg Arg Gly His Leu Thr Arg
145                 150                 155                 160

Val Ala Gln Ala Glu Arg Leu Leu His Gln Glu Arg Leu Ala His Thr
                165                 170                 175

Arg Gly Val Arg Ala Ala Thr Leu Asp Glu Arg Thr Arg Ile Ala Arg
            180                 185                 190

Glu Ile His Asp Val Val Ala His Ser Leu Gly Ala Leu Arg Val Gln
        195                 200                 205

Leu Glu Val Met His Thr Leu Leu Val Glu Glu Asn Asp Thr Glu Gly
    210                 215                 220

Ala Leu Arg Ser Leu Ala Leu Ser Arg Ser Leu Ala Asp Gln Gly Leu
225                 230                 235                 240

Ser Asp Val Arg Asp Ala Val Ala Ala Leu Arg Glu Asp Val Arg Ala
                245                 250                 255

Leu Pro Asp Ala Leu Thr Glu Leu Val Arg Thr Phe Gly Arg Glu His
            260                 265                 270

Asp Thr Pro Ala Asp Phe Thr Met Leu Gly Glu His Arg Asp Leu Pro
        275                 280                 285

Ser Ala Gln Thr Ile Ala Leu Leu Arg Ile Cys Arg Glu Ala Leu Thr
    290                 295                 300

Asn Ala Ala Lys His Ala Ala Gly Glu Ala Val Ser Val Glu Leu Glu
305                 310                 315                 320
```

```
Tyr Pro Pro Asp Glu Val Arg Leu His Val Arg Asn Pro Leu Ala Ala
            325                 330                 335

Ala Pro Asp Pro Gly His Thr Pro Gly Tyr Gly Leu Thr Gly Met Arg
            340                 345                 350

Glu Arg Ile Glu Leu Val Asp Gly Thr Leu Val Thr Gly Pro Asp Gly
            355                 360                 365

Arg Phe Trp Asp Val Thr Ala Arg Val Pro Gly
            370                 375
```

<210> SEQ ID NO 21
<211> LENGTH: 1140
<212> TYPE: DNA
<213> ORGANISM: Amycolatopsis orientalis

<400> SEQUENCE: 21

```
atgaccgacg cagtgtccga cgaggtcgag gaacgtcgct ggcgatgggc cgcgcccgcc      60
gccgggacgg cgctgctggc cgtcacccag atgaccgcga ccgtaccggc cggcgccggc     120
tggctgtggg tgctctacgc ggtgtcgtcg gcgagctggc tgctgtggat cggcatcagc     180
gagcgcttcc cccgtgccgc cctgctcccg ctcgccgcgg cgagcgcggt ccccgccttc     240
ggtaccggcg ccgccaccga cggcaccgcc gtgatcatga cctgcatcac cctcgccgcg     300
ttcgcttcac ggctggagcc gggcaccgtc gcgatcatcg cgctgatggt cttcgacgcc     360
gccgccatcg tggtttccag cctgctcggc caccgtcctt cggaggcctg gctgggcgca     420
ctgggcgcgg tcgtcatcgt ggtcctcgtc ggattcaccc gccgcggtca tctgaccagg     480
gtcgcgcagg cggaacggtt gctgcaccag gaacggctgg cgcacacccg cggcgtgcgc     540
gcggcgacgc tggacgagcg caccgcatc gcccgcgaga tccacgacgt cgtcgcccat     600
tccctcggcg cgctgcgggt ccagctggag gtgatgcaca ccctgctggt ggaggagaac     660
gacaccgaag cgcccctgcg ttcgctcgcg ctgtcgcgaa gtctcgccga ccaagggctc     720
agtgacgtcc gggacgccgt ggcggcgctg cgcgaggacg tccgcgccct gccggacgcg     780
ctgaccgaac tggtgcggac cttcggccgg aacacgaca ctccggcgga tttcaccatg     840
ctgggcgagc accgcgatct cccgtcggca cagacgatcg cgctgctgcg gatctgccgg     900
gaagcgctga cgaacgcggc caaacacgcc gcgggcgagg cggtgagcgt cgaactggag     960
taccccgccgg acgaggtccg gctgcacgtc cgcaatcccc tcgccgccgc gccggacccc    1020
gggcacacgc cgggctacgg cctgaccggg atgcgcgaac ggatcgaact cgtcgacggc    1080
acgctggtca ccgggcccga cggccggttc tgggacgtca ccgcccgggt cccggggtag    1140
```

<210> SEQ ID NO 22
<211> LENGTH: 251
<212> TYPE: PRT
<213> ORGANISM: Amycolatopsis orientalis

<400> SEQUENCE: 22

```
Met Thr Ala Pro Ser Gly Asp Ala Gly Asp Trp Val Arg Val Phe Arg
1               5                   10                  15

Pro Gly Gly Pro Ser Val Pro Arg Leu Ile Cys Leu Pro Asp Ala Gly
            20                  25                  30

Ala Ala Ala Asn Ala Phe Phe Pro Leu Ser Ala Ala Leu Ala Pro Gly
            35                  40                  45

Ile Glu Val His Ala Val Gln Tyr Pro Gly Arg Gln Asp Arg Val Ala
    50                  55                  60
```

Glu Pro Cys Ala Glu Asp Ile Gly Glu Leu Ala Asp Arg Val Thr Gly
65                  70                  75                  80

Ala Leu Ala Leu Trp Glu Gly Ala Pro Phe Ala Val Tyr Gly His Gly
                85                  90                  95

Met Gly Ala Val Val Gly Phe Glu Val Ala Arg Arg Leu Glu Gln Ala
            100                 105                 110

Leu Thr Gly Ser Pro Val Ala Leu Ile Val Ser Gly Cys Pro Ala Pro
        115                 120                 125

Ser Arg Ser Gly Thr Ala Gly Leu His Leu Leu Pro Asp Gln Asp Leu
    130                 135                 140

Val Ala Glu Leu Tyr Ser Gln Arg Ala Ala Gly Ser Pro Gly Ala Arg
145                 150                 155                 160

Asp Ala Glu Leu Leu Lys Ala Thr Phe Pro Ala Ile Arg Ala Asp Phe
                165                 170                 175

Arg Ala Leu Ala Ala Tyr Arg Pro Glu Pro Ala Pro Pro Leu Arg Cys
            180                 185                 190

Pro Val Thr Val Leu Val Gly Asp Ser Asp Pro Thr Val Ser Leu Asp
        195                 200                 205

Glu Ala Arg Asp Trp His Glu Tyr Thr Thr Gly Pro Phe Asp Leu Gln
    210                 215                 220

Val Phe Pro Gly Gly His Gly Phe Pro Glu Ala Arg Pro Glu Glu Phe
225                 230                 235                 240

Ala Glu Val Val Thr Ala Ala Val Arg Arg Arg
                245                 250

<210> SEQ ID NO 23
<211> LENGTH: 753
<212> TYPE: DNA
<213> ORGANISM: Amycolatopsis orientalis

<400> SEQUENCE: 23
atgaccgctc caagcggcga tgccggggac tgggtccgtg ttttccggcc cggaggaccg      60
tcggtaccgc gtctgatctg cctgcccgac gccggtgcgg ccgcgaatgc gttcttcccg     120
cttccgccg cgctcgcgcc ggggatcgag gtgcacgcgg tgcaatatcc gggacgccag     180
gatcgggtcg cggaaccgtg cgccgaagac atcggggaat tggccgaccg ggtcaccggg     240
gcgctcgcgc tctgggaagg cgcgccgttc gcggtgtacg gccacggaat gggcgcggtc     300
gtcggtttcg aggtggccag acggctggag caggcgctga ccgggagccc ggtcgcgctg     360
atcgtgtccg gctgtcccgc cccgtcccgg tccggcaccg ccgggctcca cctgctgccg     420
gatcaggacc tcgtggccga gctgtactcg cagcgcgccg ccggctcgcc gggcgcgcgg     480
gacgcggagc tgctcaaggc caccttcccg gccatccggg ccgacttccg ggcgctggcc     540
gcttaccggc ccgagcccgc cccgccgctg cgctgcccgg tcacggtgct cgtcggcgac     600
agcgatccga cggtgtccct cgacgaggcg cgcgactggc acgagtacac caccggcccg     660
ttcgacctcc aggtcttccc tggtgggcac ggttttccgg aggcgcgtcc cgaggagttc     720
gccgaggtgg tgaccgccgc ggtccggcgg cgg                                  753

<210> SEQ ID NO 24
<211> LENGTH: 73599
<212> TYPE: DNA
<213> ORGANISM: Amycolatopsis orientalis

<400> SEQUENCE: 24
tcacgacccg ctgtatcgac gcccgaatgt gtcagcgctg cgggctgccg ccggggacct      60

-continued

```
tggcgccgcc gaggcgggcg dacagcacga gcgtcatcgc catcaggttc gcgcccagcg      120
agagcaggat ggtgccgccg ccggaggtca gcgtcgcgcc ggcgaagtgc ccgatcacgc      180
cgagcacgcc gcggacgagc agcaggccca cccagacggc gaggccgacc acgccgatcc      240
gctggtagac cttgtcgccg cgccgctgca gctgcgtcat cgcgcccatc gcggcgccgc      300
cgaggagcga gaccagcagg cccaccccga ggaagacgat gtcggtcacg ctgatggtgg      360
tgtccagatg ccgcatctgg atgaccccga tggcgaccag ggtgagcggc ccgccccaga      420
tctccacgtt ctccagcggc ttccagctca tgcgctggta gatcacgtag acgacgacgg      480
cgatggcgac cgcgatgttg atcagcgtgc tggtgtccac tgcgcactct cctcggctgt      540
gggcgacctg ttcgttcggt atcgatcacg agcgtaggag ccggggcccg ccgcggcgac      600
caaccacggg ttgaggtccg ggtggaattc cccggtccac ccgaaccggg gatccggcga      660
ttaggggtgg gcaccggtcg ctaggggttg ttggtgcttc gaggccgatc ctactgtcgg      720
gttcatcggc cggaccgccg attcccggcc cgatcggctc tcgcttccga atcccctttc      780
ccggaattcg gagccggatt tcgccgactg aaaggtgtct cacgttgcat tcctaccaag      840
tggccgtcgt cggcgccgga tacgtcgggc tgaccaccgc ggcgtgtctc gcctcgctcg      900
ggcaccgggt ccgatgcacc gattccgatc gcggcaaatt ggcccggctc aaacgaggcg      960
aggtcgacat cctggaaaag ggcctgcccg gtctggtcgc cgagggaatc gccgccggac     1020
ggctcggttt cgtcgagtcg gccgcggagg ccgtcgagac cgcggaggcc gtgttcccttt    1080
gtgtacccac cccgatgggc gagggcggga tggccgatct gtcggccgtc atcgacgtcg     1140
cgaccaaggt ccgtgacgtg ctttcgccgg gttgtgtact ggtgaacaag tcgaccgtgc     1200
cggtcgggac cgcggccagg gtcgccgcgc tgctcggccg gacgacgtc gcggtggtga      1260
gcaatccgga gttcctccgc gagggcaccg ccgtccacga cttcctcaac ccggaccgga     1320
tcgtcgtcgg ttccgacacg cgcggcccgg cggaacgggt cgcggcgctc tacgcccggc     1380
tcggcgcccc gacggtgctg accgacgcgg cgagcgcgga gatggtcaag tacgccgcca     1440
actgtttcct cgcgacgaaa ctgtcctatg tgaacgccat cgccgaactg tgcgagcggc     1500
tcggcgccga catcggcgac gtcaccgaag gcatgggcta cgaccgccgg atcggcccga     1560
cgttcctctc gccggggccg ggctggggcg gttcctgcct gcccaaggac accatggcgc     1620
tcaaacaggt cgccgaggtc gcgggttttcg agttcggcct gctcgacgag gtcatctcgg    1680
gcaacgcgaa acaggcgtcc cgagtggtcg aacggatcgc cgtcgcctgt ggactcgacg     1740
cggacgcgga cctcaccggc ctgcggatcg gcctgctcgg gctgaccttc aaggcgggca     1800
ccaacgacct ccgggattcc ccggcgctca gcgtcgcccg gctgctggcc gagcgcggcg     1860
cggagctgac cggatacgac cccggtctca ccggcgccga acctccgatc cccggcgtcc     1920
gggtcgtcga cgaccgctac tacatcgcga aggacgcgca cgcgctcgtc ctgctgaccg     1980
attggccgca gttccgtgcc ctcgactggc gcgggatcgc cggtctgctc gaaggaccgg     2040
tcgtcatcga caccgcaac cacctcgacc ccgacgcgct cagccgggcc ggcatcgcct      2100
ggcgcggctt cggcaggccc ccggtcgacc cggtgcgcac gccgtccctc gaccccgttc     2160
cctgatcgtc ctcaaaggac agaaaagaaa ggtggacccc atgcgggttt tgtgcaccgt     2220
gaccggctcg cagggccacg cacgggcggt gctgcccttg gccagggcgg cggcgaaggc     2280
gggccacgaa gtgctcgtcg tgaccccgcc ggaactggcc gacgtcttcg aacccgggct     2340
gatgcggatc gaaccggtgc tcccggggat ggtcgaggcg atcgggcgga tggtccagga     2400
```

-continued

```
acgccaggag gccgaagcgg ccgggacccc gcgccgggtg ctggacacgc gcgaacagct    2460
gatcgccacc gcgagcggcc cgcacgtcac caccgcctac cagaagctct acccactggc    2520
caaggagttt cagcccgaca tcgtgctgcg cgacggcgcg gagctgtccg gcgcgctggt    2580
cgccgagcag ctcggcgtgc cctacatcag cgcgccgtcg ggtgcgggca acctgatcga    2640
cccggcgggc ctggtggagc cgctgaacga gcgccgccag gagctggggc tcgccgccga    2700
acccgacgcc gggatggtgc accgctacgg ccgtttcgac tgcctgcccg ccgacacctc    2760
gttcgccgcc ttcgatctgc cgacgccgtt cacctaccgc cagccgtcgg aggtggccac    2820
cggtgaggtc ctgccgccgg agatcgccgc attgcccgcg gaccggccgc tggtgctcgc    2880
ctcggtcggc accgcgctgc ccatgctcgg cgcgttcaag gccttcggca tcgacccgcc    2940
ggaggagatg gaagatcccg acgtcacggt gcgcgccctg atcgaaggac tgtccagtgt    3000
ggactgttcg gcggtggtgg cgacggccgg gttcccgatc ggcgacgtcg aggtcggcga    3060
caacgtgctc gtcgtcgaac ggatgccgca gccgctgctg ctcgaatgcg cgcagctgtt    3120
cctgacccac gccgggtaca acagcatccg cgaggcgctg cgtgccggag tcccgatggc    3180
cacgctgccg cagttcggcg accagccgca caacgcgcgc cgcatcgagg agctcgggtt    3240
cggcaagcag atccccgcca ccacgccgga agcggtcgcc gagacctgcc gcgcggtgct    3300
ggccgacgcc acgatcgcgg ccaccgtcgc acgggcccaa cggcggagcc tgaccatgcc    3360
gggcgtggaa tccgccgtgg cccatctcga agagctcgcc ggccgggccg cgggaacgga    3420
gtagcgcggt gcagatcgac cactacgtca gccagctgct ggacgtgctt tccacccgcc    3480
cggacgagat cgcgttgcgc tacggcgacg aagcgctgac gtcggcggaa ttcgccgcgg    3540
cgatcaccgg tgccgccgcc gcgctgcgcg accgcgggac cggcgaaggc ggggtggtgg    3600
ccctgctgac cgtggggaac agcccggcga cgctgatcgg ccggtacgcc gccaacctga    3660
tcggcgccac cgtggtgcac ctgcgcggga tcaacgccgc cgatccgctg gacgaactcc    3720
cggtcgccac gcaggtcgag atcgtcgacg acaccggcac caccgtcctg ctcaccgacg    3780
cggcgaacct cgaccgggcc aggaagatcc gcgacgccat ggcggaaccg gcggcactgg    3840
cggctttcgg ggacttcggt gacgacgtcg ccgacctcac cgggaccgcg agcgaggtcg    3900
agccgcgagc cgagggcacc gccgtgctga cctacaccag tgggaccacc ggcaggccca    3960
agggcatcgg ccgcgggttc ggcgggctgg gcgcggtggt caccaaggcc cggcacatga    4020
ccgagcgctg cacgatgctg gtcaccacgc cgctcagcca ttccgtctcg tccacagtgg    4080
acgacgcggt cgcctccggc gggatgatcg tcctgcacga ggggttcgac gccggcgccg    4140
tgctcgaagc cgtggaacgc caccgggtca accgggtcta cctggccacc ccgcagctct    4200
acgacctgct cgaccatccg gcactgggca ccaccgacca ttccagcctg cgcgagctgt    4260 actacgcgg gagcccggcc tccccggtgc ggctctcccg ggccgcggag gtgttcggcg    4320
cgaagctgat ccagatctac ggcaccaccg aaagctgggt gatcgccgcg ctttcgccgg    4380
aagagcacct gaaaccggaa ctgctcacca cggtcggcaa ggcggtcccg ttcgtccagg    4440
tcggcatccg cgaccgcat gtgcggcacg agctgcccgc cggaagacc ggggagatct    4500 gcgtccggtc gccgatgatg atggacggtt actggaagcg gcccgacctg acctcgaagg    4560
tcctcatcga cggctggctg cacaccgcg acgtcggcta cctcgacgag aacggctacc    4620
tgtacctggt cgaccggctc gccgacatga tcaagaccaa cggcatcaag gtgtatccgg    4680
ccgaggtcga gaacgcgctg ctggcccatc cggacgtcgc gcaggccgcg gtgttcgggg    4740
tcgccgacga ggacaacgtc gagtacatgc acgcgatcgc ggtgccacgc cgcggcaggg    4800
```

-continued

```
acgtggatcc cgccgacctt gccgcgcatg tcgcgcgggt gctgtcccccg agccacgtgc     4860 cggcggagat ccggctccgc gccgagcttc cgctgaccga cgcggggaag ccggacaagc     4920
tccgcctccg cgaagaggcg aaacccgcca ccaagtccag ccacgccgag ccagagagcg     4980
agttgacgtc atgaccacct acctggagtc cttccagcgc accctgcaag gcgaagtgct     5040
gcagaaacgc gacttcctgg agatcgggcg gcaggcgggc cggttcccgg cggccagccg     5100
gtacgaggag gccgaagcgg tcgccgagat caacgtctgg tgcagcaacg actacctcgg     5160
catgggccag cacccggacg tgctctccgc gatgaaggag gccgtcgagc ggttcggcgc     5220
cggggcgggc ggttcacgca acatcgcggg caccaaccac taccacgtgg cgctcgaacg     5280
cgaactggcc gaactgcacg gcaaagagga cgcgctgctc ttcacctccg gctacaccgc     5340
caacgacggt tcgctgaccg tgctggcggg ccgccccgag gactgcatcg tgttctccga     5400
cgagaagaac cacgcctcca tcatcgacgg gttgcggcac agtggtgtgg agaagaagat     5460
cttccgccac aacgacgtcg cccatctggc cgagctgctc gccgccgccc ggcggaccg      5520 gccgaagatg atcgtgttcg agtcggtcta ctcgatgaac ggcgacatcg cgccgctggc     5580
cgaattcgcc gcgttggcga agcagtacga cgccatgacc tatgtggacg aagtgcacgc     5640
cgtcggaatg tacgggcccg aaggtgccgg gatcgccgcg cgcgagggga tcgccgacga     5700
gttcaccgtc gtgatgggca cgctggccaa gggtttcggc accaccggcg gatacatcgc     5760
cgggcccgcc gcgctgatcg acgccgtgcg cacgcattcg cgatcgttca tcttcaccac     5820
cgcgctgccg cccgccgtgg ccgccggagc gctcgccgcc gtccggcacc tgcgttcgtc     5880
ggagcgggag cgcgagatcc tcgccgacaa cgcgcagctg ctgcacaaac tgctcgccga     5940
acgcggcatc cccttcctct cggacgagtc gcatatcgtg tcgatcctgg tcggcgacga     6000
cgcgctctgc aagaaggtgc acgaactcct gttgcagcgg cacgggatct acatccagtc     6060
gatcaacgcg ccgagtgtcc cgttcggaca ggagatcctg cgcacggccc cgtcggcggt     6120
gcacaccggc agcgacgtgc agaagatggt cgaggcgctg accagatct ggctggatct      6180 cggtctgccg cgcggctgag tgcgtgttgg tgaacccgtg tccgcgatcg acgtcggcag     6240
gacgccgctg gtcatccaca tcgcgatggc ggacaaggcg tcctgccacc gcgatagcgg     6300
ggccttcggc cagggtgggt tcacgcgttc gggtgcttgt cgaggtacaa cttcagcttc     6360
cgccaacagg ctctgagagg ggagaccggt gtccttgtcc ctagcggccg tcctcgccga     6420
ctcggcgggg aggcggccgg accacccgc gctcgtgttc gacggggaac cgttctccta      6480
ccgggaactc tgggccgggg cgaagaggta cgcctccgcg ctccgggacc aggggggtcgc    6540 cgccggcgac cgggtcgtgc tgctcctgcc gaacacgccg gagttcccga tggtctactt     6600
cggcgcgctg gcgctcggcg cggtcgtcgt gccggtgcac acgttgctcg tcgcggagga     6660
gatccactac atcctcaccg actgtgacgc ccgggtgctg atctgcgag ccgccctgct      6720 ggagcagggc ggcgaggccg ccgacgcggc cggtgtcgaa gtcctgacga tgctggagga    6780
ctccgacacc ggccgcgtcc gcctcgacgt cctcgccggg gacgcggccg agatcgagcg     6840
gtacgaaccg cgtgaaccct cggacctcgc gctgatcctc tacacctcgg ggaccaccgg     6900
caaacccaag ggcgcgatgc tgacccacct gagcatcgtg ctgaacgttt ccaccacgat     6960
gctgtcgccg ttcgacttcc acgccgacga cgtgctgctc ggctgcctgc cgctgttcca     7020
caccttcggc cagatctgcg ggatggcgac ctgtttccgc gccggcgcga cgatggtgct     7080
gatgtcgcgg ttcgacgcgc gagccgcgct ggaactgatg gtggagcaga actgctcgct     7140
```

```
gttcatgggc gtgccgacga tgtacgtcgc gttgctggag gccgccgagg acgagccgcg   7200
gcggcccaaa ctcgaccggg ccttctccgg tggttcgtcg ctgcccgtag cgctgctgga   7260
gcggttcgag gccgtgttcg actgcccgat ctacgaggga tacggcctca ccgagacctc   7320
gcccgtggtg gcctacaacc agcgcgcgtg gccgacccgc gcgggcaccg tcggcaaacc   7380 gatctgggc gtggacgtcg ccatcgcgcg cgccgagacc gaagaccgga tcgaacccgt    7440
gccgccgggt gaggtcggcg agatcgtcgt ccggggccac aacgtgatgg cgggctacct   7500
gaaccgtccc gaggccacgg cggccgcgat cgtggacggc tggttccgca gcggcgacct   7560
aggcttcctc gacgacgacg gctatctgtc cattgtggac cgtaagaagg acatgatcct   7620
tcgcggcggc tacaacgtgt atccgcgcga gatcgaggaa gtgctggcca ggcatcccgc   7680
gatcgcccag gtcgcggtcg tcggcgtgcc ggacgaacgg tacggcgagg agatctgcgc   7740
cgtcgtggtg gccgcttccg atcgggaacc cgggccggaa ctggcggcgg aactcgtggc   7800
gtggagcaag aagcgcgtgg cggcctacaa gtatccgcgc cgcgtggagt tcctggacgc   7860
gatgccgctc gggcccagcg ggaagatcct caagcgggag ctggcggagc tcctcgggca   7920
ctgactcctg tgcttcggcc caggcggaat cgcggcacgg tcgagtgtgg aggatttggg   7980
acgttgagtg tcccaaatcc tccacactcg aatcacctgg ccagctcaag cgttggcgtg   8040
tctggtgttg acgatgtagg aatcgggacg ttgagtgtcc cgattcctac atcgtcgggg   8100
gaccgggtct cggatcttga tcaacggagg attggggaca ctcagcgtcc caatcctcc    8160 gtcgatcaag gtcgcagccg agtggggaag atttcggaca ctggacgtcc tcaatcttcc   8220
ccgctcgccg acgttgcgaa agccactttc ccaaccttca actttgcgaa agtggctttc   8280
gcagcacacc gccgctcgcc aaccctgcc cccaccccgc gcccgaccgt gaacaggggg    8340
acgtaggggt gcgaaagggg tccgttcccg cactagcttc ggaatcccat cctcgaaccc   8400
gaaatgcgga ccatgcgaga cgaactgatt ctgcgaactc gacgtgttcg gccggactgg   8460
gccacggtgc tggccgcttt cgacgaaacc ccggacgggg agcggcggcg ggcgctcgcc   8520
gcgctggtcg tcgccgagac cgaagcggtg ctggaggcga agccgggtgc ggggaccgcc   8580
gcgcccggca cgcccttcgc cgaactcggg ttcgattccc tcgcggcggt ggaactgcac   8640
cggcggatct ccgcggccac cgcgctggag ctgccggtga cgctcgtctt cgaccacccg   8700
acaccgtcgg cgctcgccgg tcatctgcgc gatctgctcg ccggtgaggc cgtggccgag   8760
atcgaggact accaggcgat cgccgacgac gagccgatcg cgatcgtcgg catggcctgc   8820
cgttaccccg gtgggatcgg ttcgccggag gacctctggc ggctggtcac cgagggtggg   8880
gacgcgacgt cggacttccc ggccgaccgc ggctggacg tggaatcgct gtacgacccc    8940
gaccccgggg tgcccggcaa gacctacacc cggcgaggcg ggttcctcga cggcgccggg   9000
gatttcgacg cgggattctt cgggatctcg ccgcgtgagg cgctggcgat ggatccgcaa   9060
cagcggctcc tgctggagac gtcgtgggag gccttcgagc gggcgggat cgaccccgcg    9120 accttgcggg gaagcgcgac cggcgtgttc gtcggcgcgg agacccagga gtacggaccg   9180
cgtctcggtg gcgcggaaga aggtctcgaa ggttatctgc tgaccggtaa cgcggcgagt   9240
gtcgcgtcgg gccgcgtctc gtacgccttc gggttcgagg gcccgacggt caccgtggac   9300
accgcatgct cgtcgtcgct ggtggccctg cacctggcag gcaggcgct gcggctgggg    9360 gagtgcccga tcgcggtggc cggcggcgtc gcggtgatgt cgagcccgg cggtttcctc    9420 gccttcagcc gtcagcgcgg gctcgcgccg acgggcgct gcaagccgtt ctccgccgcg    9480
gcggacggca ccggctggtc cgaaggtgtc gggatgctgg tgctggaaag gctttccgac   9540
```

```
gcccggcgca acgggcaccg ggtgctcgcc gtcgtccgcg gcaccgcgat caactccgac    9600
ggcgccagca acggtctcac cgcgcccaac ggcgccgctc agcagagggt gatccggcgc    9660
gcgctggcga acgccgggct cgcaccgtcc gaagtggacg ccgtcgaagc cacacggcacc   9720
ggtaccgtcc tcggcgaccc gatcgaggcg caggcactgc tggccaccta cggccgcgac    9780
cgtgagcgcc cgttgctcct cggctcggtc aagtcgaaca tcgggcacac ccagtcggcc    9840
gccggggtgg ccggggtgat caagatggtg caggcgatgc ggcacggtgt gctgcccaag    9900
accctgcacg ccgacgagcc cacccccgaag gtcgcctggt cctccggtgc cgtcgaactg    9960
ctcaacgaga ccgttgcttg gccggagaat ggcgcgcctc gccgcgcggc ggtgtcgtcg    10020
ttcgggatga gcgggaccaa cgcgcacgcc gtcctcgaac aggcccccgc cgaggacgag    10080
cccgagccgt cgccggaagc gtggcccacc tggctgttcc ccgtcagcgg ccgcgacgag    10140
aaggccctgc gccgtcaggc cgcccggctg cgtgaagccc tgccggacag tgacctcccc    10200
gccatcgccg ccgcgctcgc caccacccgg tccgccctgg agtggcgggc cgtggtgacg    10260
gtcgccgatc gcgcgggatt gttggccggg ttggacgcgt tggccaccgg tgaagctctg    10320
ccgagcctgg tccacgggac ggcgcggatc gggatcgtct tcagcggcca gggcagccag    10380
cgcgccggga tgggccgcga actgcaccgc cggttcccgg tgttcgccgc cgccttcgac    10440
gacgcctgcg gcatctcga cctgcaactg gaccggccgc tggccgagat cgtgttcgcc    10500
gacgagggca ccgaggaagc cggcctgttg caccgcaccg aatacgcgca gtgcgcgttg    10560
ttcgccgtcg aggtcgcgct gttccggctg tacgagcatt ggggcctgcg ccccgattac    10620
gtcgccgggc actcgatcgg cgagctggcc gccgcgcacg tttcgggcat gctttcgctc    10680
tccgacgccg ccgcgctcgt cgccgcgcgg ggacgcctga tgcaggacac gcgcgagggc    10740
ggcgcgatgc tcgcggtgca ggcgacggag gacgaggtcc tgccgctgct tgacgaacgc    10800
ctcgcgatcc cggccgtcaa cggcccgcgg tcggtggtcg tctccggcga cgaggccgcg    10860
gtcgaggagg tcgccgccgc gttcgccagg cgcaagacca aacggctcaa ggtgagtcac    10920
gccttccact cgcatcacat ggacgggatg ctcgacgagt tccgccggtt cgccgagatc    10980
ctcaccttcc ggaagccggt gatcccgctg gtgtccactg tgtccggtga gctgctcacc    11040
gaggcgacgg cgccggaata ctgggtggag cacgtgcgcc gcccggtgcg gttcgccgac    11100
ggcgtgcggc ggctggacga gctcggcgtc gacgtgctcc tggaactcgg cccggacgcg    11160
gtgctgacgc cgatgccgcc cgaagtcctc gacggcgagg gagcggcgct ggtgccgagc    11220
ctgcgcgggt cgcggccgga ggcggaggcg ctcgccgcgt cgctggccga actgtgggtc    11280
cgcggcgccc aactcggctg gcctcaggtg ttcggtgcac acccgagggc cgatttgccg    11340
acttatgcct tcgaacggca gcggtactgg ctgatcgacc aggacaccgc cggggatccc    11400
ggcgcctacg gtctgggcga caccgggcat ccgctcctgc gggcgtcggt caccacggcc    11460
gaagacggtg cgctgctgct ctccggcagg ttgtccccgc tcacccagcc ctggctcgcc    11520
gaccacgtcg tcggtggcga cgtggtgctg ccgggtaccg cgctgctcga actggcgctg    11580
cgggccgcgg aactcgcggg ggccggggc gtcgaggaac tgaccctcga agtgccgatg    11640
gtgctttccg aagcgggcgt tcaggttcag gtgtcggtcc gggacagcgg gctcctgatc    11700
ttcttccgtg acaccgagga cgacgagtgg acgcgctgcg cttcgggcac gctcggcgcc    11760
gcggcgcccg ctcccggctt cggggcgtgg ccgcccgccg gtgagcccct cgacctttcc    11820
gatctctacg accggttggc cgactccggc ctcgactacg gccggcgtt ccgctgcctg    11880
```

-continued

```
cgtgccgcat ggcgctccgg tgacgacctc tacgccgagg tcgccgccgt gccggagacc    11940
cagggcgggt tcggcgtgca tccggcgctg ctggacgcgc gctgcacgt gctcgaactc     12000 ggctccgggg gcggtggagg ccccgcggcg ctgccgttcg cgtggtccgg cgtgacgttg    12060
cacgcgcgcg gcgccgacgt tctgcgcgtc aagctcgaga accacgtcgc gggtgccgaa    12120
gccgggacgt actcggtgtc cctgaaggtg gccgacggcg cgggcgaacc cgtcgcgtcg    12180
gtcgaatcct tagccctgcg acctctttcc acagctcctc gcgcgcagga cggcgcgctt    12240
tacggcgtcg actggatttc gcttcccgga acgccgggcg tcgccgagta ccggctctat    12300
ccggacctca ccgccgtcga cgacgtgcca ccggtcgtcg ccgtccgttg caccactctc    12360
gaaagcgtgc tggatctcgt ccagacgtgg ctcgccgacg accggttcgc cccggccagg    12420
ctggcgctgc tcaccgacgg cgccgtcgcc accgaaaacc ccgatcccgc cgcggccgcc    12480
atgtgggggc ttgtgcgttc gcgcaggcc gagcacccgg accggctggt attggccgac     12540
gtcacgggag aagacggcct cgccgccgga ctggcttccg gcgaacccga gttcgccgcc    12600
cgcgacggcg cggtgctggt ccccaggctg acgcgtgtgc cgagcccggc cccggcgtcg    12660
ttcaccaccg gcggcacggt gctgatcacc ggcgggaccg gcggtctcgc cgggctgctg    12720
gcccggcatc tggtcgagcg gcacgaggta cgcagcctgc ttctcgtgag ccgtcgcggt    12780 gccgcgggggc cgctcgtcga cgacctcacc gcgctggggtg ccgacgtcac cgtcgccgcc   12840
tgcgacatcg ccgaccgcga gtccgtcgcg gcactgctcg ccgagcatcc ggtgtcggcg    12900
gtcgtccacg ccgccggtgt gctcgacgac gcgaccatca ccacgctcga ccacgagcgg    12960
ctcgcggccg tcctgcggcc gaaggtcacc ggcgcgctcg tcctggacga actcacccgg    13020
gacctcgacc tgtcggcgtt cgtgctgttc tcttcgtccg cggccacctt cgacggcgcg    13080
ggtcaggcca actacgctgc ggccaatgcc ttcctcgaag cgctcgccct ccgccgccgt    13140
gcggaaggcc gccccggcgt cgcactgggc tggggcctct gggccaccgg gatgggagca    13200
cggctcgacg aggcggggct gcgccggatc gagcgctccg gccagcgtgc actatccgaa    13260
gtagacgggc tcgcgctgtt cgacgcggca ctggcggcgg accggccggt actgctgccg    13320
atgcggatgc accgtgccgc gttgcgtgcc gcgcgcctcc ccgaaggact tccggcagtc    13380
ctcggcggac tcgtccgggt cacccgcccg gcgccgtcgg ccgcaccgcg cggactggac    13440
gaggcggccc tgctcgacct cgtccggacg acggtcgccg ccgtcctggg ccacccggac    13500
gcgcacgcga tcgacccgga tcgcgcgttc accgaggtgg gtttcgactc gctcgccgcc    13560
gtggaactgc gcaaccggct gatcgcggcc accggactga agatcgcgcc gacgctggtg    13620
ttcgatcacc cgaacccgcg tgcggtcgcc gcgttcctcg ccgccggctc cgctccggtc    13680
cgggacgagc ccgccgctcc ggccgaagcc gacgagccga tcgcgatcat cggcatggcc    13740
tgccgctatc cgggcggggt gagcacaccc gacgacttgt ggcgtctggt cgccgacggg    13800
aacgacggca tcacccggtt ccccgagaac cgcggctggg acaccgacgg cgtctaccac    13860
cccgacgccg accaccgcgg cacgacctac gtgcgcgagg gcggtttcct gcacgacgcc    13920
ggacagttcg atcccggctt cttcgggatc tcgccccggg aagcgctggc gatgaccccg    13980
cagcagcggc tgctgctgga gatctcccac gaagccgtcg aacgggccgg gatcgacccg    14040
aagtccttgc gcggcagtgg aaccggcgtg ttcgccgggg tgatgtacca cgactacgcg    14100
accgggctga accgcgtccc cgacgacgtc gagggttacc tcggcaacgg gacctcggcc    14160
agcattcact ccgccgggt cgcctacacc ttcgggctgg aaggcccggc cgtcacgatc    14220
gacacggcct gttcgtcgtc gctggtggcg ctgcacctgg ccgcgcaggc gctgcggcgc    14280
```

```
ggtgagtgct cgatggcgct ggcgggcggg gtgaccgtga tggccacgcc cgaggtcttc   14340
gtggacttca gccgtcagcg cggcctcgct cccgatggcc gctgcaagtc cttttcggac   14400
gaagcagacg gcacggtgtg gagcgaaggc gtcgggatgc tcctggtgga acgcctttcc   14460
gacgcccgcc gcaacggcca tcgcgtcctc gcgatcgtgc gggggagcgc ggtcaaccag   14520
gacggcgcgt ccaacggcct caccgccccg agcggtccgt cgcagcaacg ggtgatccgc   14580
cgggccttgg cggacgccgg tctcaaaccg tccgaagtgg acgctgtgga ggcccacggc   14640
accgggacgc cgttgggtga tccgatcgag gcgcaggcga tgctcgccac ctacggccag   14700
gaccgggacc ggccgctgtg gctcgggtcg ctgaagtcga acctcggcca cacccaggcc   14760
gccgccggcg tcggcgggat catcaagatg gtgcaggcga tgcaccacgg tgtgctgccc   14820
cgcacgctca acctcggcac gccgacgacc aaggtcgact ggacatccgg gaacgtgtcc   14880
ttgctcagcg agcccgtggc ctggccgaaa accggcgggc cccggcgtgc ggctgtctcg   14940
tcgttcggga tcagcgggac caacgcgcac gtcgtcctgg agcaggcgga accggtcgaa   15000
aagtccactt cggacacatc gccgctcggt ggtgacgtgc tgccgttcgt cctgtccgga   15060
aagacgtccg ccgccctggc cgcgcaggcc gaccggctcg ccgggcacct ggccggcgac   15120
gtctccctgc ccgccgtggc ccgcgcgctc gcggtgacca ggtccgcgct ggaccaccgt   15180
gccgtggtgg tggcgggcga ccgcgccggg ttgaccgccg ggctgcgcgc gctggccgac   15240
gccgtccccg cgccccacgt ggtcgatggg gtcgccgaga acggcaaggc cgtcttcgtc   15300
tttccaggcc agggatcgca gtggaccggg atggcggtgg atctgctggg atcgtcggcg   15360
gtcttcgccg aagcgatggc cgactgcgag gccgcacttc tgtcccatct ggactggaag   15420
ctgacgcacg tcctgtccga cgcggcggcg ctggaacggg tggacgtcgt ccagccggtg   15480
ctgttcgcgg tgatggtgtc gctggcccgg ctctggcggg cgtgcggcat cgaacccgcc   15540
gccgtggtcg ggcattcgca gggtgagatc gcggccgcgt gtgtcgcggg cgcgctgtcg   15600
ctggaagacg ccgcacgcgt ggtctgcctg cgcagcaagg cgatcctggc gctgtccgga   15660
ttgggcggga tggtgtcggt cgcggcctct gaggatcgcg tccgggaact gctgcccgat   15720
ggcgtttccg tggccgtggt gaacggcccg gcttccgtcg tcgtgtccgg tgacgtcgcc   15780
gggctggagg cgctgctcaa gcgatgcgaa ctgctcgacg tgcgggcgaa gcgggtcccg   15840
gtggactacg cgtcgcactc ggctcacgtc gacgcgatcg aacagcaggt cgtgacggcg   15900
ctgagcggaa tcatgccgcg cgaagccgaa ctgccgatgt actcgaccgt caccggtgag   15960
ccgatcgaca cgaccaccct cgacgcggcc tattggttcc gcaatctccg ggccaccgtc   16020
cggttcgacc aggcggtgcg gcggctgatc gcggacgggt tccggttctt cgtcgagacg   16080
agcccgcatc cggtgctggt cgccgggctg accgaactcg tcgaagaggc cgccgtgccc   16140
gccgtcgcgc tcgcgagcct tcgccgtgac gagggtggac cgacccggtt cgtcacctcc   16200
ctggccgagg cgcacgtcca cggtctcagc cccgattggg ccgcgctgct gcccgaggcg   16260
gggtgggtgg atctgccgcc ctatgccttc cagcatcagg agttctggct caccgacgcc   16320
ggggaaccgg gtgacgccgc cggattcggt ctcggcgcca ccgggcatcc gctgctcacc   16380
gccgcgaccg cgctgccggg ctccggcggc ctgctgctca ccggccggat ctcgacggcc   16440
gcccagccgt ggctggccga ccacgcggtg cagggcgtgg tgctgctgcc gggtacggcg   16500
ttcgtggagc tggcgctgca ggccggaacc cacgcgggct gcgggcggat cgacgagctg   16560
actctcgaag cccgctgcc gcttcccgag cagggcggcg tccgcgtcca ggtcgtcctg   16620
```

-continued

```
gggtccgaag tgaacggacg ccgcgaggtc accgtgcact cccaggccga atccggtgac   16680
gacacctggg tgcggcacgc atccggcttc ctgacttcgg cggaaacccc gggagaggga   16740
ctgaccgaat ggccgcccgc cggcgcgacg agcgccgacc tcgacggctt ttacgccgac   16800
gccgaggcgc agggctacgg ctacggtccg gcgttccaag ggctgcgagc ggcctggacc   16860
ctgggttccg acgtcttcgc cgaggtcgtc ctgcccgatg ccgagggcgc ggaccggttc   16920
ggtctgcatc cggcgttgct cgacgccgcc ctccacgccc tcggtaccgt ccggtccggc   16980
gacggcgcgg aactgccgtt cgcgtggacc ggggtcaccg tgcacgccgt cggcgccacc   17040
gcgctgcggg tccggctcac cgtggggacg gacaccgtcg cggtgacggc ggccgatccg   17100
gcgggcgcgc cggtcgcgac cgtcgaaggc ctcgtcacgc ggcccgccgc cctgcccgga   17160
tcccggcggc cggactcgct gttccgcgtc gactggactc cggtctccac gccggaagcc   17220
gtcgagacgc cgaccgtcac cgtcctgtcc gacggcgacc tgaccgcgct cgccgagatc   17280
cccgacgtgt tgctggtgcc ggtgggagcc gaggccgggg acctcaccga gagcgtccat   17340
cgcacgaccg cccgggtgct cgatctgctc cggacctggc tcgacgacga gcggttcgcc   17400
gacgcgcggg tggtgctgca caccgcggcg gcggtcgcgg acgtccgcga cctgccggcc   17460
gcggcggcct ggggcctggt ccggtccgcg caggccgaga accccgaccg gatcgtcctg   17520
ctcgacagcg acaccgacct tccgccggcg ttgctcgccg aagtgctggc caccggtgag   17580
gcgcagctcg cgtggcgcga cggggaactg ctcgtgccga ggctcgccaa ggtctccacc   17640
gacggcacgc tgaccccgcc ggaaggcccc tgggtgctgg acgcgcccg ccgcggcacg   17700
ctggaagagc tcgcgctcgt cccggcgccc acggccgccc ggccgctcgc cgacggcgag   17760
gtccggatcc aggtccgggc cgccgggatc aacttccgcg acgtgctcat cacgctcgac   17820
atgtatcccg aggacaaggc ggtgatgggc agcgagggcg cgggtatcgt caccgaaatc   17880
ggttccggcg tcaccggcct gaagcccggc gaccgggtct tcggcctgtt cgacggcgcg   17940
ttcggaccgg tcgcgatcgc cgaccggcgg acggtcacgg aaatgcccgt ggactggacg   18000
ttcgccgaag cggccgctct gccggtcgtc ttcctcaccg cctactacgg gctggtcgac   18060
ctcggcgggc tccggccggg ggagaaggtg ctgatccacg gagcgaccgg cggtgtcggc   18120
atggccgcgg tccagctggc ccgccacctc ggcgccgagg tgttcgccac ggcgagcccc   18180
ggcaagtggg aagtgctgcg gggcctcggt ttcgacgacg agcacatcgc ctcctcccgc   18240
acgctggact tcgaggaccg gttcggccgg atggacgtcg tcctggactc gctcgccaag   18300
gagttcgtcg acgcgtcgct gcggctgctg ggcgagggcg gccggttcgt ggagatgggc   18360
aagaccgaca tccgtgacgc ggacgaggtc gcggccgcgc atcccggcgt cacctaccgc   18420
gcgttcgacc tgctcgacgc cggacggccg aggatcggcg agatcctggc cgaactgctg   18480
gacctgttcg gcgccgggtc gctcaccgtg ccccggccga cggtgtggga cgcgcgccgc   18540
gcacccgagg tcttccggtt catgagccag gccaagcaca tcggcaagaa cgtgctcacc   18600
atcccgtcca caatggacgg gaacgggacg gtgctgatca ccggcgccac cgggacactc   18660
ggcgcgctgg tcgcccggca tctggtcacc gtgcgcggtg tccggcacct gctgctcgtc   18720
ggccgccggg gtcgtgcggc ggccgggatg ccgaactcg aagcggaact gaccgccgcc   18780
ggggcgtccg tcaccatcgc cgcctgcgac gcggccgacc gggcggcgct ggccgccctg   18840
ctcgccaccg tcccggccga gcatccgctg gccggggtgg tgcacgccgc cggtgtcctg   18900
gacgacggcc tcgtcgccac gctgacccc gagcggctgg cgaaggtgct cgcgcccgaag   18960
gtcgacgccg cggtcaacct gcacgaactg acccgcgacg cgcatctcgc cgagttcgtc   19020
```

```
ctgttctcct cggccgccgg cgcgttcggc gacgccggac agggcaacta cgccgccgcg   19080
aacagtttcc tcgactcgct cgcccggcac cgtcgggcgc aggggttgcc cgcggtctcg   19140
ctcgcgtggg gtttctgggc cgagctgagc gggatgaccg gccacctcgg tgaagcggat   19200
ctggcccggc tcaagcggtc cgggatgagc cctctgtcca ctgaggacgg actactgttg   19260
atggacgccg cccgtgccgg gtacgaaccg gcgccgctcc cgatgcacat cgacctcgcc   19320
gccctgcggg gcgaggaagt gcacccgttg ctgcggggc tggtgaaggc accggtgcgc    19380
cgggccgccg cggccaccgg cacacagtcc gagggactag ccgaccggct ggccgggctc   19440
gccccggccg cccgcggccg ggccctgctg gacctgatcc gcgcgaacgt cgccgcggtg   19500
ctcggtttcg gctcaccgga gcaggtcggg gtccggcagg ccttccggga gctcgggttc   19560
gactcgctca gcgcggtcga actccgcaac cggctcaacg cggcgaccgg tctgcggctg   19620
cccgccacgg tcgtgttcga ccatccgacg cccaccgcgc tcgccgaaac cctcggcgac   19680
cggctggcac ccgccgaaga agccgttgac gacgaggtcg cccgtatcgg cgcggtcctc   19740
gcttcggtgc ccgccgaccg gctccgcgaa gccggcgtgc tggacctgct gaccggctg    19800 gccgaccccg gctaccgccc caccgagtcg cccgacggcg cggacatcga cgagatggac   19860
gccgaccgcc tgatcgcact cgcttttcgac gcttccgacc ccgcctgacg tgaaacaccc   19920
tggagctgcg atgtccacat ccgagaacaa ggtcgtcgag gccctgcggg cggcgctgaa   19980
ggaagccgac cgcctgcgcg gggagaaccg cgcctgacc ggcgagccca tcgcgatcat    20040
cggcatggcc tgccgttacc cgggcggggt ccgctcgccg aagagctgt gggatctggt    20100 cgccggagaa cgcaccggcc tcaccggatt cccggtcgac cgcggctggg acctcgacgg   20160
gctctacgac cccgagcagg ggaaaccggg caagagctat gtccgggaag gcggtttcct   20220
gcacgacgcc gcccggttcg acccggcgtt cttcgggatc tcgccgcgtg aggcgctggc   20280
gatgaccccg cagcagcgac tgctgctgga gatctcctgg gaggcgatcg aacgcgcggg   20340
gatcgcgccg gattccctgc ggggcagccg gaccggcgtg ttcgcgggcg tcatccacaa   20400
cgagtactcg gccatcgcgg gcacgccgcc cgcggatctc gagccgtacc tcggcaacgg   20460
gagtttcgcg agcatcgcct ccgggcgggt ttcctacacc ttcgggctcg aaggcccggc   20520
ggtcaccgtc gacacggcgt gttcgtcgtc gctggtggcg ctgcatctgg cggcacaggc   20580
gctgcggcag ggcgaatgtt cgctggcgtt ggcgggtggg gtgaccgtga tggccaaccc   20640
ggcggcgttc gtggacttca gccgtcagcg cgggctcgcg gcggacgggc ggatcaaggc   20700
gttcgccgaa gccgccgacg gcaccgcctg gggcgaaggc gcgggcatgc tgctcgtcga   20760
gcggctctcc gacgcccggc gcaacgggca ccgcgtcctc gccgtcgtgc gcggatccgc   20820
ggtgaaccag gacggcgcct cgaacgggct caccgcgccc aacggtcttt cccagcaacg   20880
ggtcatccgg caggcactcg cgaacgcgcg gctcgcaccg tccgatgtgg acgccatgga   20940
ggcgcacggc acgggcaccc ggctcggcga cccgatcgag gcacaggctt tgctggccac   21000
ctacggccag gaccggacca ccccgctctg gctcggctcg gtgaagtcca acatcggca   21060 cagccaggcc gcggccgggg tcgcgtcgat catcaaactc gtcgaggcga tgcggcacgg   21120
tgtgctgccg aagacgctgc acgtcgacgc gccgacgtcg catgtggact ggtccgaggg   21180
cgcggtctcg ttgctgaccg aggccgagcc gtggccgaag acggatcgac cccggcgggc   21240
cgcggtgtcc tcgttcggga tcagcgggac gaacgcgcac gtcgtcctcg aacagcccac   21300
cgcggaagag gaaccgccgt ccacgtttgc ggggccggtg ccgttcgtgc tgtccggcaa   21360
```

-continued

```
gaccgaagcc gccctgcacg agcaggtggc ccgcgtgcgg gaactcgcgc gggattcgga   21420
cgtcaccgcg gcggacctgg cgttctcgct ggccaccacg cggaccgcgc tggatcatcg   21480
ggccgccctg gtcggcacgc tggacgatct gctgaccgcc actttggtgg aagggcgggc   21540
gacggacggc gggacggcgt tcctgttcac gggccagggc agtcagcggc tggggatggg   21600
ccgcgagctc gccgagcgtt ccccggtgtt cgctcaagcc ttcgacgacg tctcttcgcg   21660
gttcgagcga ccgatcgcgg agctgtccgc cgaggaactg aaccagacgg cgaacacgca   21720
gtgcgcgttg ttcgccttcg aggtggcgct cttccggctg gtcgagaact ggggcctccg   21780
gccggacttc ctgccgggc attcggtcgg ggagatcgcg gcggctcatg tcgcggacgt   21840
gctctctctc gacgacgcgg tgacgttggt gtcggctcgt ggccgcctga tgcaggcgtt   21900
gccgaccggt ggggcgatgg tggcgcttca ggcgaccgag gcggaggtcg ccccgctcct   21960
gaccgaccgg gtgtcgctgg ccgcgatcaa cggcccggag tcggtggtcg tctcgggtga   22020
cgaagaagcc gtcgccgcgg tggtgtccca cttcgagggc cggaagagca agcgccttac   22080
ggtgagtcac gcgttccatt cgcccttgat ggagccgatg ctcgacgact ccgcgcggt   22140
ggtggagggg ctgaccttcg ccgaaccgcg gatcccgatc gtgtccggcg gcctggctga   22200
agtgtccact tcggactatt gggtccggca cgtccgtgac gcggtgcggt tccacgattc   22260
ggtcgaattc ctgaaggccg agggcgtcac ccggttcctg gagatcggac ccgacgccgt   22320
cctgaccgcc atggccaagg aaagcgccga ggacgcggtc gtcctcccgg cttcgcgacg   22380
ggaccgcccc gaggtgacga cgctgctgac ggcggtcgcc ggactgcacg tccatggggc   22440
cgaggtcgac tgggcgccgc tgttcgacgg tgcgcggcgc gtcgatctgc cgacgtatcc   22500
gttccagtac gagcacttct ggctcgaatc cggtgccgct caccgcgacg tgtccgccgc   22560
cgggctggac gcgtcgccgc acgccctgct cgccgccgcg gtccggccgg cgggcgagga   22620
cgagatcctc ctgacgggca ggatctcgct gagcacactg ccgtggctgg cggaccacgt   22680
cgtcggcgga aacgtccttc tgcccggtac cgcgttcgcc gaactcgcgc tcgcggccgc   22740
cgacgaggcc ggttgtgagg ccgtcgagga actgaacctg gaagcgccgc tggtgctgcc   22800
cgagaagggc ggggtccagt tgcaggtcgc ggtcggcgcg gctgacgacc agggcaggcg   22860
ctcggtcacc gtgcacgccc ggccggagga cgacggcttc tgggtgcggc acgcctccgg   22920
cgtcctcggt accgcagtgt ccacacagga cgagatgatc gagtggccgc cctcgggcgc   22980
ggagcctgtc gacctcgaag gcttctaccc gaacctggcg gccgaagggc tcggctatgg   23040
ccctgccttt cagggcgtcc gtgccgtctg gacccgcgat ggcgacgtgt tcgccgaagt   23100
ccaggtggac gacactcccg gcaccttcgg gatccacccc gcgttgttcg actccgccct   23160
gcacgccatc ggcgtcggcg agtcgcgggg gctggagatc cccttcgcct ggtcggatct   23220
ccgcctgcac gccgacggcg cgacggtgct ccgggttcgc ctcagcccg cgggcgacgg   23280
tgccgtctcc gttttcgcga ccgacccgc cggagcgccg gtgttgtcgg tcggctcgct   23340
cagcctgcgg gctccggtcg ccgcgaccgc ctcgcttccc cgtgactcgc tgttccgcgt   23400
cacctggacg ccggtgacgg tgcccgctgg tgctggggaa ccaccgtgg agtcctttgt   23460
ggacttcgat gacgtccggc aagcgacggc gcacgcccgg cagatcgccg tggagcccgg   23520
cgaggccccc gtggtgttcc tgaccagcgg cgcgttcacc gatcctgcgc aggcgtcggt   23580
ctggggactc atgcgttcgg cgcgggagga gtaccccggc cggttcgtgc tcgtcgacgc   23640
cgacgacccc gccacgctca cggccggcct gctggccgga atcgtggcct ccggcgagac   23700
cgaagccatc gtgcgtgagg gcgaggtccg tgtcccgcgg ctcacccccgg tgcgcggggg   23760
```

```
cgaaaccgga ccgggctggg acccggaagg cacggtcctg atcaccggcg gcaccggcgc   23820
gctcgccacc gaactcgccc ggcacctcgt cacacgacgc ggtgtgcgga acctgatcct   23880
cgccggacgc cgcggtcccg ccgcggaagg cgcgagcgag ctggccgccg aactggcgga   23940
cctcggcgcg caggcccgga tcgtcgcctg cgacgtcgcg gatcgcgacc agctgacggc   24000
gttgctcgac ggcgttccgc tgaccgcggt cgtccacgcc gcgggcgtcc tcgacgacgg   24060
cctgctcgcc gatctcactc gggaccgatt cgaaaccgtc ctgaggtcca aagtggacgg   24120
cgcaatcctg ctggacgaac tggccggtga cgcccacctc gtgttcttct cctccgcggc   24180
cggggtgctc ggcagcgcgg ggcaggccaa ctacgccgcc gccaacgccg ccctcgacgc   24240
ggtggccgcg cgccgccggg aacggggact acccgcgacc tcgctcgcgt gggggctctg   24300
ggagaccggc gacgggatgg cgggtgcgct cgccgggacc gatcgcgcgc ggatggcggg   24360
ctccgggctg ctgccgcttc cggtcgggga cgccttgacc ctgttcgact tcgccgtcgg   24420
agcggaggaa gtgctgttcg tgccgatgcg gctcgacgtg cccgctctgc gcgcgagcgc   24480
cacggacgtg ccgctcctgc gggccttcgc cgggaaatcc cggcggaccg cgtcggccgc   24540
ccccgccgcg cgggaactgc gtgaccggct ggcgtcgctg cccaccgagg agcggggccg   24600
ggaactgctc gcgctggtgc gcggccaggt cgccgaggta ctcggccacc gggacgccgg   24660
ggccgtcgaa ccggctcgtc cgttccggga actgggcttc gactcgctga ccgcggtgga   24720
actgcgcaac ggcctcaacg ccgcttccgg gctccggctg cccgcgaccg ccgtgttcga   24780
ccaccccacc ccgaaggcgc tcgcggacct gctcgccgcc gaactgttcg gcgcagcccc   24840
cgaagccccg gttcaggggc ccgcgatggc ggccgacgag ccgatcgcca tcatcggcat   24900
ggcatgccgg taccccggcg gggtcgcctc gccggaggac ctctggcggc tggtcgcgga   24960
gggccgcgac ggcatctcgc tcttcccggc cgaccgcggc tgggacgtgg acggcctcta   25020
cgacccggac cccggcaagg cggggaagag ctacgtgcgc gagggcggat cctccacga   25080 ggcaggcgat ttcgacgccg gtttcttcgg catctcgccg cgtgaggcac tgggcatgga   25140
cccacagcag cggctgctgc tggaggtctc gtgggaagcc ttcgaacggg ccgggatcga   25200
ccccggaacg ctgcggggca gcgacaccgg cgtcttcgcc gggcagatgt accacgacta   25260
cctcaccggc gccacggtcg ttcccgacga cgtcgagggt tacctcggca ccggcaactc   25320
cgggagtgtg ctgtccgggc gggtttccta caccttcggc ctcgaaggtc cggccgtcac   25380
cgtcgacacg gcgtgttcgt cgtcgctggt ggcgctgcat ctggcggcac aggcgttgcg   25440
gcgcggcgaa tgctcgctcg cgctggccgg cggggtgacc gtgatggcca cgccggagac   25500
gttcgtcgac ttcagccgtc agcgaggttt ggcaccggac ggccgctcga agtccttttc   25560
ggacggtgcg gatggcacgt cctggtccga aggtgtcggc atgctgctcg tcgagcggct   25620
ctccgacgcc gagcgcaacg ggcaccggat cctggccgtc gtccgggttt cggcggtgaa   25680
tcaggacggt gcgtccaacg ggctgaccgc gccgaacggt ccttcgcagc agcgggtgat   25740
ccggcgagcc ttggccgacg cgcgcctgga accgtccgaa gtggacgccg tcgaggcaca   25800
cgggaccggt accacgctgg gtgacccgat cgaggcgcaa gcgctgctgg cgacctacgg   25860
ccagggccgc gaggacgccg cgctgtggct cgggtcgatc aaatcgaaca tcgggcacag   25920
ccaggccgcc gccggggtgg cgggtgtgat caagatggtc gaggcgatgc gccgcgggt   25980 gctgccgaag acgctgcacg tcaccgaacc gtcgtctcat gtggactgga cggcgggcgc   26040
ggtctccctc ctgaccgagg cgcgactctg gccggacgcc ggacgtcccc ggcgtgcggc   26100
```

```
ggtgtcgtcg ttcgggatca gcggtaccaa cgcgcacgtc gtcctggagc agggcccccgc   26160
tccggtggag gccatcgaat ccggtgaggg accggcggcg ttcgtcctgt ccgccgggag   26220
tgaagcggcc ctgcatgacc aagcgtcgcg gttgagggac ttcctcgccg agacgcctgc   26280
tgccttggcc gacgtcgcct tctcgttggc gaccacccga gcggccctgg agcaccgggc   26340
cgccgtcgtg gccgcagacc gggaaaccct gctggccgcg ctggagaacc tcactgtcac   26400
cggccgcgcg acggagggcc ggacagcgtt cctgttcacc ggtcagggca gtcagcggct   26460
cgggatgggc cttcagctgg ccgagcgttt cccggtcttc gccgctgcct acgacgaggt   26520
gtgttcccgg ttcgagcagc cgctcaggga cctcacggcc gaggagctga accagaccgc   26580
gaacacgcag tgcgcgttgt tcgcgcttga ggtggcgctg ttccgcttgg tcgagagctg   26640
gggtgtccgc ccggacttcc tggctgggca ttcggtcggt gagatcgcgg cagctcacgt   26700
cgcgggtgtg ctttccctcg acgatgcggt gaccctggtg tcggcgcgag gccgtttgat   26760
gcaggccttg cctaccggtg gcgcgatggt ggcgttgcag gcgacggaag ccgaggtgac   26820
gccgctgctg accgagcggg tgtcgctggc ggcgatcaac ggtccggagt cggtggtcgt   26880
ttcgggtgag gaggacgccg tcgctgcggt ggtctctcag ttcgagggtc gcaagagcaa   26940
gcggctcacc gtgagtcacg cgttccactc gccgttgatg gagccgatgc tcgacgagtt   27000
ccgtgtggtc gccgacagct tgtcgtacgc ggcgccgcgg attccgatcg tgtccggtgg   27060
tctggcggag gtgtccactt cggactattg gtccgccat gtccgtgacg cggtgcgatt   27120
ccacgattcg gtgaagttcc tggaagccga ggggtcaca cggttcctgg agatcggggcc   27180
cgacggtgtc ctgaccgcga tggccaagga aactgccgag gacgcggtcg tcgttccggc   27240
actccgcgc gaccggccgg aggtggagac gctgctgacg gcggtcgcgg gcctgcacgt   27300
ccacggcgtg ggcgtcgatc tgacggcctt gctcggcggt ggaagccccg tcgacctgcc   27360
cacgtatgcc ttccagcacc gacgtttctg gctttcctcg gcgggcggcg cggcgggcga   27420
cgtcaccgca gccgggctag gcaccaccga tcacccgctg ctcggcgcgg ccgcggcact   27480
gccgggcgac ggcgggttcc tgctcaccgg ccggttgtcc gggcacgccc agccgtggct   27540
ggccgaacac cgggtcggcg gcgtggtcct gctgccgggc accgcgttcg tcgagatcgc   27600
cctgcgtgcg ggggatgagg cgggctgcgg ccacctcgaa gacctgaccc tcgaagcgcc   27660
gctcgtcctg cccgagcgcg gtgcgaccca gctgtccgtg ctggtcggcg cggccgacga   27720
caccggtcgc cggaccatcg agatccactc gcgcgaggaa ggcgaagacg gctggcagag   27780
gcacgcgacc gggctgctat cggccgccgg agccgtcgaa ccggccgggt tgacgacctg   27840
gccgccccag aacgccgaag ccgtcccggt gggtgacgtc tacgagcggc tcgccgccac   27900
cggtctcgag tacggccgg cgttccgtgg cctccgtgcg gcgtggcgag cgggtgaaga   27960
cctgttcgcg gaggtcgaac tcccggagga ccagcactcc gacgcggctc ggttcggcgt   28020
gcatccggcg ctgctcgacg ccgcgctcca caccctcggc ctcgcgggcg cggcgacgg   28080
cacccggctc ccgttcgcct ggtcgggggt gcgcctgcac gccgccggcg cgacccggct   28140
ccgtgtccgg ctgcggccgt ccggtcccga cgggttcgag gtcctggtcg ccgacggcac   28200
cggccgcccg gtcgtctcag ccgaagagtt gacgctgcgc gagatctcgg gcgacgcctt   28260
ggccgcaag gacacgact cgctctaccg gtcgcctgg cgtccggtcc cgctcccgga   28320
gaccggcgaa accctccccg cggagtcggt tttctccgtg ccgcgcggtg gcgactccgc   28380
cgagcgtgtc cacgaaacga cggccgccgt tctcgaagtc gtccagcggc ggctcgaaga   28440
cgagccgggc ggtccgcttg tcgtccacac ccggggcgga gtcgccgcgg gcgacggcga   28500
```

```
agcggtgacc gacctcgcgc acgccgcggt ctgggggctg gtgcgtgccg cgcagtcgga   28560
gaaccccggt cggttcctgt tggtcgacgc cgagaccttg cccgatggcc ggatcctggc   28620
catcgacgag cctcagatcg ctttgcgtga cggccgggca ctcgcgccgc gcctggccac   28680
caccgcctcg tccacggaac tgaccccgcc cgagggagcc tggcggctgg acaccaccgg   28740
tcgcggcacc ctggagaacc tcacgctggt gccgtcgccc gaagcagtcg cgccgttggc   28800
tgagggcgag gtccggatcg cggtgcgggc cgccgggctc aacttccgcg acgtcctgat   28860
cgcgctgggc atgtacccgg gcgcggccac cctcggcagt gaaggcgcgg gcgtggtcac   28920
cgagatcggg cccggtgtca ccggcctcga cgtcggcgac cgcgtgttcg gcctgatgtc   28980
gaacggcttc gggccccagg tcgtcaccga tcaccgacg ctggcgaaga tgcccgagga   29040
ctggtcgttc gccacggcgg cctcggtccc gatcgtgttc ctcaccgcct actacggcct   29100
gttcgacctc gcgcggctcg aagcgggaga gtcgatcctg gtgcacgcgg cggcgggcgg   29160
cgtcggtatg gccgcgaccc agctggcccg tcacgccggg gccgaggtgt tcggcaccgc   29220
cggtccgggc aaatgggaca ccttgcgtgc caacggtttc gacgacaccc acctctcgtc   29280
ctcccgtgac ctcggcttcg aggagaagtt ccgcgatgcc accggcggac gcggtgtcga   29340
cgtcgtcttg aactcgctcg ccggcgacta cgtcgacgcg tcactgcggc tgctggcccc   29400
gggcgggcgg ttcgccgaga tgggcaagac cgacatccgg gaaccggggg agaccggcgt   29460
cgagtaccac cccttcgacg tcatcgacgc cggacccgag cgcatccacg agatgctcgc   29520
cgcactgctg gagctgttcg cggccggggc gctgacgccg ttgccggtca ccggctggga   29580
cgtccggcgc ggccccgacg cgttccgttt cctcagccag gccaagcacg tcggcaagaa   29640
cgtcctgacc atgcccgccg ccctcgatcc cgacggcacc gtgctcgtca ccgggggaac   29700
gggtgccctc ggcgcgctct tcgcccggca tctggtgcgc gaacgcggcg tccggcggct   29760
gctgctggca agcaggcgcg ccacgacgc cccgggcgta cccgagctgg tcgccgaact   29820
caccgaggca ggcgcctcgg tgacggtcga ggcgtgtgac gcggcggatc gcggcgcgct   29880
cgccgccgtc ctcgccggaa tcccggccgc gcatccgctg accggcgtgg tgcacacggc   29940
gggtgtcctg gacgacggcc tcgtcggctc gctgaccccg gagcggctgg cgaaggtgtt   30000
gcggccgaag gtcgacgcgg cgctgaacct gcacgaactg accagcggcg cggatctcgc   30060
cgagttcgtc gtcttctcct cggccgccgg ggtcttcggc aacgccgggc aggcgaacta   30120
cgccgccgcc aacggtttcc tggacgcgct cagcgtccgg cgcgcggcgc acgggttgcc   30180
cgcccggtcg ctggcgtggg gtctgtgggc cgaaacgggc gggatgggcg ggacgctcgg   30240
cgaggccgag ctggccagga tggcccagag cggtaccgcc gcactgtcca cacaggacgg   30300
cctggagctc ttcgacgccg ccggcgcgct ggcggaaccg gtcctggtgc cgatgcgcct   30360
ggacgtcacc gcgatgggcg gggacggggct cccgccgttg ctgcgcggcc tcgcccgcgg   30420
cccggtacgc cgtgccgcgt ccgccggggc cgccggtgac gcggactcat tgcgagaccg   30480
gcttctcgcg gtgcccgtcg ccgaccggga cgctgctg gtcgacctcg tgcgcaccca   30540
ttccgcgacc gtgctcgggc acaccgcggc ggacgcggtc gaggccacgc ggtccttcca   30600
ggagatcggc ttcgactccc tgaccgccgt cgagctgcgc aaccggctca ccgccgccac   30660
cgggctgcgc ctgccggcga cgctgatctt cgactacccg accccggaag cgctcgccgc   30720
ccacatcggc gaaggcgtcc tgggtgcgca gggcgggccc gagaccgggc aggcggcggt   30780
gacggccgac gagccgatcg cgatcgtcgc gatgagctgc cggttccccg gccacgccga   30840
```

```
caccccgaa cggctctggg ccctgctggc cgagggccgg gacgcgctgg gcgagttccc    30900
cgccgaccgc ggctgggacc tggagcggct gttcgacacc gacccggacc gccggggcac    30960
ctcctacacc cgccaaggcg ccttcctcga aaccgccggc gatttcgacg cgggcttctt    31020
cgggatctcg ccgcgtgagg cgctggcgat ggatccgcag cagcggttgc tgctggagac    31080
gtcgtgggag gcgttcgaac gcgccgggat cgatccggcc accctgcgcg gcagccgcac    31140
cggcgtgttc gccggggtga tggacaacga atacgtatcc ggttcggcgg aggtccctga    31200
cggggtcgag ggctacctgg ccaccggcac ctcggcgagt gtcgcctcgg gccgcgtttc    31260
ctacaccttc gggctcgaag gtcccgcggt caccgtcgac acggcgtgtt cgtcgtcgct    31320
ggtcgcgctg catctcgcgg cgcaagcgct gcggcagggc gagtgctcgc tggcactggc    31380
cggtggagtg accgtgatgg ccacaccggg cacgttcgtc gagttcagcc gtcagcgcgg    31440
actggccgcc gacggccgct gcaaggcgtt cgccgacggc gccgacggga cgggctgggg    31500
cgaaggcgcc gggatgctgc tcgtggagcg gctgtccgac gcccgccgca acgggcatcc    31560
ggtgctcgcg gtgctgcggg gcagcgcggt caaccaggac ggcgcgtcga acgggctcac    31620
cgcgccgaac ggtccttcgc agcagcgggt gatccgccag gcgctggcga acgcgcggct    31680
cgaaccgtcc gaagtggacg cagtcgaagc gcacggaacc gggaccacgc tgggcgaccc    31740
gatcgaggct caggcgctgc tggcgaccta cggccaggac cgggaacggc cgttgctgct    31800
cggttcggtc aagtcgaaca tcgggcacac gcaggccgcg gcgggcgtcg ccggggtgat    31860
caagatggtg ctcgcgatgc ggcacgggac actgccgcgc acgctgcacg tcgacacgcc    31920
gacttcgcgc gtcgactggg cggcgggccg gatcgagctc gcgaccgagc cgacccagtg    31980
gccggagacc ggtggcccgc gccgggcggc ggtgtcgtcg ttcgggatga gcggtaccaa    32040
cgcgcacgtc gtcctcgaac aggccgaagc ggtcgagaca cgggatgaaa cctcgccggg    32100
gctgctcggt gacgtcgtcg cgtggccgct gtcggcgaag gaacccgagg ccgtggccgc    32160
gcaggcggca cggctgaagt ccttcctgac cggcgaacgt ccggcggacg tggcctactc    32220
gctggcgacc gcgcggacca cgctggaaca ccgggcggtc gtcgtcggcg aagacccgat    32280
cgccgggttg gccgcgctgg ccgcgggcga ccgtcgggt tcggtggtga ccgggaccgc    32340
gaccagcggg aagcggtgt tcgtcttccc cggccaggt tcgcagtggg ccgggatggc    32400
ggtcgagttg ctggcgtccg cacccgtgtt cgccgagtcg atggcggagt gcgaagcggc    32460
tctgctgtcc tatgtggact ggaagctgac cgaggtgctc tcggacgcga ccgcgctgga    32520
gcgggtcgac gtcgtgcagc ccgccttgtt cgcggtgatg gtgtcgctgg cgaggctgtg    32580
gcgtgccagt ggcatcgaac cggccgccgt ggtcggtcat cccagggcg agatcgcggc    32640 ggcgtgtgtc gccggcgcgc tgtcgctcga cgacgcggca cgggtggtct gcctgcgcag    32700
caaggcgatc acggcgcttt cgggccgggg cggcatggtc tccgtcgccg ctcccgaagc    32760
ccaggttcgc gagatcctgc ccgagggtgt gtcgctcgcc gcggtgaatg gtcccgcgtc    32820
ggtggtggtg tcgggtgacg tcgccggtct ggacgcgctc atgaccgctt gcgaggcgag    32880
cgggctgcgc gcgaagcgga tcccggtgga ctacgcgtcg cattccgcgc acgtcgatgc    32940
catcgaacaa gacgtcctgg ccgcgctcga cgggatcgag ccgcgggcgc cggagatccc    33000
gttctattcg acgtggccg gggagccgct cgatccggtg gtggacgcgg cgtactggtt    33060
ccggaacctg gcgcggaccg tccacttcgg acaagccgtc cggcggctgc tcgacgacgg    33120
gttccggttc ttcgtcgagg cgagcccgca tccggtcctg gtcaccggga tcgccgacac    33180
cgccgaggac gcgggagaac gcgccgtcgc cgtcggcagc ctgcgccggg acgagggagg    33240
```

```
gccgctgcgg ttcctcacct cgctggccga agcccacgtc cacggcctca gcccggactg    33300
ggcggcgctg gcccccggaa cccgcgtcga cctgccgacc tacgccttcc agcacgagca    33360
ctactggctg cggacgcggt cttcggccga tcccggacag gccggtctgg acgacggcgg    33420
gcatccgctg ctcggggccg tcgtcccgct ggcgggcagc gacggcctgg tggccaccgg    33480
ccggatctcg gcgcggaacc agacctggct gcccgatcac gccgtcgggg gcgcgctgct    33540
gctgcccggc gcggcgctcg tggacctggc gctcacggtg ggggagcgca ccggctgcgg    33600
ccggatcgcc gaactgacca tcgaggcgcc gctagtcctc ggggagtccg ggagcgcgcg    33660
gctgcaggtg accgtcggag cgtccgcaga cgacggcacc cgcgaggtcg ccgtgtactc    33720
ccgggacgaa accgctggca cggactggat ccggcacgcg accggcctgc tcgccgcgga    33780
cggggaaacg cccgtggcgg acctgaccca gtggccgccc gcgggagccg aaccgatctc    33840
cctcgaaggg cactacgaag gtctcgcgga actgggctac ggctacggtc cggcgttccg    33900
cgggctgcgt gccgtgtggc gccggggcga cgacgtgttc gccgaagtcg cgctcccgga    33960
agaccggatc gccgaggccg ccgcgttcgg cctgcacccc gcgctcctcg acgccgccct    34020
gcacgcgctg ggcttcggca tgctccccga cgacggacgg ctgcggcttc cgttcgcgtg    34080
gaacgaggtc tcgctgtcgg ccgtcggcgc gccgagcctg cgcgtacggc tctcccccgc    34140
cggggaggac gcggtggcgg tggacctcgc cgacaccgcc ggggcgccgg tcgcctcgat    34200
cggctccgtg gtgttccggc cggtggccga ggcacagctc gccggcgccc ggcgggatcc    34260
ggcggattcg ctgttccaga tccagtggac ggatctgtcc gcaaaggacg tcgtcgcacc    34320
ggcggtcgtc gtgctcggcg aggactgcgc ggacctcgcg gagctcgccg cggatctcga    34380
cgcgggaagg ccggcgcccg acgtggtgct cacgacctgc gcacccgtca ccggcgatat    34440
cgccgagggc gcgcacgccg ccgcgaggga cgcgctgacg ctggtccaga actggctggc    34500
cgatgagcgg ttctccggag ccaggctggt cttccgcact tcgggcgcgg tctcggtggc    34560
cgcggacgaa ccggtgtccg acccggccaa cgcgacggtc tggggcctcg tgcgcacggc    34620
gcaggaggag aatcccggcc ggttcggtct tctcgacacc gatggttccg aggccgtctt    34680
gggtgcggcg ctggcgctcg acgagcccca gctcgcgctg cgggccggaa cggtgctcgg    34740
cgcccggctg gtcaaggcgt ccgccgacac cgcgctcgtc ccgcccccgg gcagccgcgc    34800
gtggaccgtc gacacccctcg gcggcggcac cctggagaac ctggtgctac gggaccggcc    34860
cgatctgctg gccccgctcg ccgacgggca ggtccgtatc gccgtgcggt cggccgggct    34920
caacttccgg gacgtcgtgg tggccctcgg gctcgtgcca gggcaggaag gcatcggcgg    34980
ggaaggcgcg ggcgtggtca ccgagaccgg ccccggcgtc accgacctgg cgccgggcga    35040
ccgcgtgctg ggcatgttcg acgcgtcgtt cggcccgatc gccgtcgccg accggaagct    35100
gatcgcgccc gtcccggacg actggtcgtt caccgaagcc gcttcggcgc ccgtcgcgtt    35160
cctgaccgcc tacgtcggcc tggctgacct cggcgagctg cggccgggtc agaccgtgct    35220
gatccacgcc gccgccggtg gggtcggcat ggccgcggtc cagctggccc ggcacttcgg    35280
tgccgagatc tacgtgaccg cgagccccgc caagtgggac acgctgcggg cgatgggctt    35340
cgacgacgac cacatcgcgt ccagccggac cctcgatttc gaggacaaga tccgcgaagc    35400
cactggcgga cgcggggtcg acctggtgct ggactcgctg gcaagggagt tcgtcgacgc    35460
gtcgctgcgg ctggtgcgcg aaggcgggcg attcgtcgag atgggcaaga ccgacatccg    35520
cgacgcggac gaggtcgcgg ccgcccatcc cggcgtcacc taccgcgcgt tcgacctgat    35580
```

```
cgactccggg cacgaccgga tccaggagat cctgggcgaa ctcctggcgc tggcggacaa    35640
ggacgtggtg cggccgctgc cgaccacggc gtgggacgtc cggcgcgccc ccgaagcgtt    35700
ccggttcctc agccaggcca agcacacggg caagatcgtg ctggagccgc ccgccgtcct    35760
cgaccccgag ggaacggtgc tgatcaccgg tggcaccggc gtgctgggcg gcctgttcgc    35820
ccgacatctg gtgaccgcgc acggcgtccg gcggctgctg ctgaccagca ggcgcgggct    35880
cgacgccgag ggtgcgcggg aactggtcgc ggacctgacc ggcctcgggg ccacggtgac    35940
cgtcgtggcc tgcgacgtcg ccgatcgcgc cgcggtcgcc ggactgctcg gctcggtccc    36000
gcccgagcac ccgctgaccg ccgtggtgca caccgccggc gtgctcgacg acgggctgat    36060
cccggcactc acccccggacc ggctcggcac cgtgttccgc ccgaaggtcg acgccgcggt    36120
ccatctgcac gaactgaccc gcgacctcgg actggccgcg ttcgtgctgt tctcctcgtc    36180
cgcggcgacg ttcggcgccg ccggacaggg gaactacgcg gcggccaacg ccttcctcga    36240
cgcactcgcc cagcaccgcc gggccgaagg gctcgccggg caggcattgg cgtgggctt    36300 ctgggccgag cggagcgcga tgaccggcca tctcgacgag gcggacgtgg ccaggatgaa    36360
gcgatccggc gtcagtccac tgtcctctgt ggacggtctt gcgctgttcg acgcggcggc    36420
ggaacgggac gtcgcggcgc tggtgcccgt gcacctggac accgccgccc tccgagggca    36480
gaccgaagtg cccgccctgc ttcgtgttct cgcgggtgct ccggccaagc gggtcgcggg    36540
agcggccgcc acgagcggac cgtcgctcgc ccagcggctg gcggcactgc ccgccgcgga    36600
ccgggagccg ttcctgctgg atctggtgcg ctcgcacgcc gcggccgcgc tcggccacgc    36660
gtcggtcgcc aaggtcggcc cggagctggc cttccgcgac ctcggcttcg actcgctgac    36720
cgcggtcgag ctgcgcaacc ggctcggcgc ggcgaccggg ctgcggctgc cgtccacgct    36780
ggtcttcgat cagccgagcc cggccgcgct cgcccggcac ctgctggcgg aactgggcga    36840 accgccggc gccgaacccg aggtggcggt gctggcagac ctcgaccggc tggagaccgc    36900
actggccgcg gcggtcaccg acgacgagac cgcggaccgg atcaccgacc ggctgcgcgc    36960
ggtgctcgcc cggtggaccg aggcccgcgg cccggccgag gacgagggtg acggcgatct    37020
ggccgacgcc agcgccgacg agctgttcga catcttgcac aaggaattcg gaaggtcgtg    37080
acccgtgtcg ggcgatgaga aactgctgga gaacctgaag tgggcgaccg gcagctgcg    37140 gcgcgcgcgg cgcaggctgg tcgagttgga ggaggccggg cacgagccga tcgccgtcgt    37200
cgggatgagc tgccgcttcc ccggcggggt ccgctcgccc gaacagctgt gggacctggt    37260
cgcctccggg accgacgcgc tgtcggagtt ccccggtgac cggggctggg atctgggtgg    37320
gctcttcgac ccggacccg acaccccggg caagacctac gtctccgaag gcggattcct    37380
ctacgaagcc ggggatttcg acgccgcgtt cttcgggatc tcgccgcgtg aggcccaggc    37440
gatggatccg cagcagcggc tgctgctcga agcggcgtgg gaggtgctcg aacgcgccgg    37500
gatcgacccg gccaccctgc gcggcagccg gaccggcgtc ttcgccggcg tcatccacaa    37560
cgactacacc ggcgtgctca ccgacatccc gccggagctg gagccctatc tcggcaacgg    37620
gaacttcagc agcgtcgcct ccggccggat cgcctacacc ctcggcctcg agggcccgc    37680 ggtctcggtc gatacggcgt gctcgtcttc gctggtcgcg ctgcatctcg ccgcgcagtc    37740
tttacgtcgc gaggaatgca cgctcgccct cgtcggcggg gtgaacgtga tgacccatcc    37800
cgccgcgttc gtcgacttca gccgtcagcg cggactggcc gccgacggcc gctgcaaggc    37860
cttcgccgac gcggccgacg gcaccggttg gggcgaaggc gtcggaatgc tgctggtcga    37920
acggctttcc gacgcccagc gcaacggaca ccaggtcctc gcggtgctgc ggggcagcgc    37980
```

```
catcaaccag gacggcgcgt cgaacgggct caccgcgccg aacggtcccg ctcagcagcg   38040
ggtcatccgc caggcactcg ccgacgccag gctctcgccg gggcaggtgg acgtcgtcga   38100
gggacacggc accggcacca ccctcggcga cccgatcgag gcgcaggcgc tgctggcgac   38160 ctacgccag gaccgggaac gcccgctgct gctgggttcc ctcaaatcga acatcgggca   38220
tacgcaggcc gccgccgggg tcggcggggt gatcaagatg gtgcaggcca tccgcacgg   38280 gatcgcgccg cgcacgctgc acgtcgacgc tccctcgtcg catgtggact ggtcggcggg   38340
cgaggtctcg ctgctgaccg gggaacagcc gtggccggag accggggaac gcgccgagc   38400 cggggtgtcg tcgttcggga tcagcggtac caacgcgcac gtgatcctgg agcaagcgcc   38460
ggccgtcgag gtcgagtccc ttgtggacac tcgggtgctc gactccgcgg tcttgccgtt   38520
cgtgctttcc ggccgcagtg aagaggcttt ggccgcccag gcgtcgaagc tcgccgcgta   38580
tctgactggc gagcccgcgc caaggccat cgcgcgagcc ctcgccgaga cgcggtcggc   38640
gttgccgcat cgggcggtcg tgctcgccga agacctcggc gaactgctcg gcggcttgcg   38700
ttccctcgcc gagggcgaac ccgccgcgcg gtcctgacc ggtaccgccg aggcgggtaa   38760
ggccgtcttc gtgttcccgg gtcagggttc gcagtgggtg gggatggcgg aggagttgtt   38820
gttgtcggct ccggtgttcg cggagtcgat ggctgagtgt gagcgcgcgc tttcatcctt   38880
tgtggattgg aagttgtcgg atgtgttgtc ggatgcggct gcgttggagc gggttgatgt   38940
ggtgcagcct gttttgttcg cggtgatggt gtcgttggcg cggttgtggc gggcgtgtgg   39000
ggttgagcct gctgcggtgg tgggtcattc gcagggtgag atcgcggcgg cgtgtgtggc   39060
tggtgcgttg tcgttggatg atgctgcgcg gttggtgtgc ctgcggagta aggcgatttt   39120
ggcgttgtcg ggtcgtggtg gcatggtgtc ggtggctgct tcggaggatc gtgttcggga   39180
gttgctgcct gccggtgtgt cggtggcagc cgtgaacggc ccgtcggcgg tggtggtgtc   39240
cggtgatgtc gcgggcttgg aggcgttgct caagcggtgt gagctgctgg acgtgcgggc   39300
gaagcggatc ccggtggact atgcctcgca ttcggcgcat gtggatgcga tcgagcagga   39360
ggtcttgtcg gcgctggcgg gtatctcacc gcaggcgccg gtgatcccgt tttattcgac   39420
ggtgaccgat gagcctctgg aattggatgc ggcgtactgg ttccggaatc tgcggggac   39480 ggtgcggttc gcggcgacgg tggatcggtt gctggaggac ggtttccggt ttttcgtgga   39540
ggcgagtccg catccggtgc tggttccggg gatcagtgaa gaagccatcg cgttggggag   39600
tttgcgtcgg ggtgagggtg gtgcggagcg gttcgtcgcg tcgctggccg aagcccacac   39660
gcagggcctg agcccctcgt ggtccgccgt gctgccgccc gccgaacggg tcgacctgcc   39720
gacgtatgcc ttccagcaca agcggttctg gctcgaagcg ggcaccgcga gcggggacgc   39780
gtcggcgttc gggcagacgg tggtcgacca cccgctgctc ggcgccgccc tgccgctcgc   39840
ggacggcgac ggcctcgtcc tcaccggccg gatctcgccg gacacgcagc cctggctcgt   39900
cgaccacacc gtcctggaca ccgtgctcct gccggggacg gcgttcgtcg agctcgtcct   39960
gcgcgctggg cggaggcag gctgcgacgg cgtcgacgaa ctgaccttgg aagcgccgct   40020
cgtcctcgac gggcccgtgg cgctgcaggt cgtgctcggg gagcccgacg agcgcggccg   40080
tcgtgccgtg tccgtgcact cacgccgga ggattccgac gaaccctgga cccgcaacgc   40140
tcagggcacg ctgtccgcgg gcaccccatc gacggtttcg ctcgccgagt ggccgccacc   40200
cggcgccgcc gaagcgccgg agtccgatct ctacgaccgt ttcgccgagc tcggcctcgc   40260
ctacggtccg gtgttccagg gactgcgcgc ggcgtggcgc cagggcgacg acgtgttcgc   40320
```

```
cgaggtcgac ctgcccgagg aggaggaggc ggaccgcttc ggcgtgcacc ccgcccctgct   40380 cgacgcggcc ctgcacaccc tcgggctcgg ggcccaggac gagaccgtgc ggctgccgtt   40440
cacctggtcc ggtgtgaccc tccacgccac gggcgcgtcg aaactccggg tccggctcac   40500
gccgaccgcc gacggcggct cgctcaccgt ggccgacaga accggcgccc cggtgctgac   40560
cgtcggggaa ctggggctgc gcccgatctc cccggcccag ctgggccgcc accgggattc   40620
gctgttccgg ctcgactggg tccccgctcc tgtgggggccg cgccggaag agccgggggt   40680 gtggcgctgc cccgaaggcg aactgcggcc ggtcctggaa gaggtcctga agcggatcca   40740
ggccgattcg acgccacga ccgtcgtgct cacctcgggt gcggtggcga gcgcgtcgcc   40800
ggatccggtg gcggccgcgg tctggggtct cgtgcggtcg gcccaggccg agcatccggg   40860
ccggttcgtg ctgatcgacg cgcggaccga ggacgaggtc cgcaccgcgc tggcgaccgg   40920
ggaagcgcag gtcgccgtcc acgacggcaa accgctggta ccccggctcg cgcgggtggc   40980
ggccgccgac gcggggcgaac cggactggac gcccgacgac gtcgtcctga tcaccggtgg   41040
caccggacgg ctcgggcagg cgctggcccg gcacctcgcc gtccggcacg gcgtgcgcgg   41100
actggtgctg accgggcgga cgggcggggg cgcggaagac ctggtcgcgg acctggcgga   41160
actgggcacc caggtcaccg tcgcggcctg cgacgtcgcg gatccggacg cggtgcgcgc   41220
actgctggcc gcccatccgg tgaccgcggt ggtgcacgcc gcggccgtgc tcgacgacgc   41280
gctcgtcgac ggtctgaccc cggaccggct cggcaccgtg ctggccccga aggccgacgg   41340
cgcccgcgtg ctgcacgaac tcgccggacc ggtccgccgg ttcgtcacgt tctcctcggc   41400
ggccggcgtg ttcggcaacc cggggcaagc gggctacgcc gcggcgaacg cctacgccga   41460
cgctctcatg ctccggcgtc gtgccgaggg gctgcccgga gtgtccctcg cctggggatt   41520
ctgggcggaa cgcagcaagc tgaccggcga cctcgacgac accgacgtcc gccggatggc   41580
ccgcgcgggt gtcaccgcgt tgtccacgga ggaaggcctg gcgctgttcg acgccgccgt   41640
ggccggaggg gacggcctgc tcgtccccgc caagatcgac ctgaccgcct tccggggccg   41700 cccgccgcc gagatccccg ctctgctgcg cggcctggtg cgcgtccccg cgcgacggtc   41760
gggggaggcg tcgggcacgg ccgaggcact gaaacgcgac cttgccggga agccggaggc   41820
cgaacgcgtc cggctgctgg aggaggtcgt gcggatccgg gtggcggccg tgctcgggca   41880
cgagtcggcc gacgcgatcg ccggggaccg cggattcctc gaactgggct tcgactcgct   41940
gaccgcggtg gaattgcgca accggctcgc cgaggcgacc ggactgcggt tgccgcccac   42000
gctcgtcttc gaccggccca acgccggagc gctcgcggcc tacctggcgg ccgaactggc   42060
caccgagacc gccggaccgg ccctcgacgc cgaactcgac cggttcgccg ccgcgctgac   42120
cgcggccgac cccggagagg ccgaacgggc ccggctggcc gccggctgc gggcccttct   42180 cggcacgctc caaggcgggg aagacccggc cggggaaatc gacggaaaac tcgaatcggc   42240
ggacgacgag gaaatgttcg ccttcatcga caatgtgctt aagccttctt gagtggtaag   42300
aatggtttcg gcatggggtt cccgggtgtt gcgaaagcca cttcgcaac cttcaacgtt   42360 gcgaaagtgg ctttcgcaac accccccgg cggtggctcg accaacgca cgtgggctga   42420 aggctcccttt caccgcgtct gatgcggcga aggagcctt caccccggcc ggatacggtc   42480
tcgaaagcgc ccctggtcgt cgcctattcc ctaaggggac gtaggggcgg ctaggggttg   42540
tccgtctctt cgcagctcac ctagctttc ttcgagtggc atttcgtttt tcccggcgcg   42600
aagaggttgg ctactgatgc tgaacgagga gaagctgcgc gactacctca gcgggtgtc   42660 ggccgacctg catcggaccc gggcccggct gcgggaggcc gaggcgcggg agcacgagcc   42720
```

```
gatcgcgatc atcgggatgg cctgccggta cccgggcggc gtccgcggtc cggagcagtt   42780
gtgggatctc gtggccgcgg gcaccgacgc ggtcggcggt ttccccgccg accggggctg   42840
ggatgtcgag gccctctacg accccgaccc cgcgcggcac ggcaagacct acacgcgcga   42900
gggcggtttc ctctacgacg cccacgagtt cgacgccgcg ttcttcggca tcagcccgcg   42960
cgaggcgctc accgtcgacc cgcagcagcg cctcctgctg gagaccgctt gggaggcctt   43020
cgaacgcgcc gggatcgacc cgctttccgt gcgcggcagc cggaccggcg tgttcgccgg   43080
ggtgatgtac aacgactacg gctccaggct cgacccccgc gccgaggaac tgcgcgagtt   43140
cgagggatac ctcggcaacg gcagcgccgg gagcgtcgcc tccggccggg tcgcctacac   43200
cttcggcctc gaaggccggg ccgtcaccat cgacaccgcg tgttcgtctt cgctggtcgc   43260
gctacacctc gctgccgagt cgctccggcg cggggagtcc acgctcgcgc tggcgggcgg   43320
ggtgaccgtg atggcctcgc cggagaccct cgtggagttc agccgtcagc gcgggatggc   43380
gcccgacggc cgctgcaaac ccttcgccga cgcggccgac ggcaccggct gggccgaggg   43440
cgccgggatc ctgctgctcg aacggctttc cgacgcccgt cgccacgggc atcccgtcct   43500
cgccgtggtg cgcggcaccg cggtcaacca ggacggcgcg agcagcgggc tcaccgcgcc   43560
gaacggcccg tcgcagcagc gggtgatccg gcaggcgctc gacagcgccg gcctcgcgcc   43620
gcaccaggtc gacgtcgtcg aggcacacg cacgggacg accctgggcg acccgatcga   43680
ggcacaggcc ctgctcgccg cgtacggaca ggagcgcgtc cgtccactgt ggctcggttc   43740
gctgaagtcg aacgtcgggc acagccaggc tgccgccggg gtcggcggcg tgatcaagat   43800
ggtccaggcg atccggcacg ggatcgcccc gatgaccctg cacgtcgaca ccccgacgtc   43860
caaagtggac tgggaagcgg gttcggtcga actgctcacc gaagcccgcc cttggccgga   43920
gaccggggaa ccgcgccgcg ccgggatctc ttcgttcggg gtcagcggca ccaacgcgca   43980
cgtcatcgtc gaacaagcgc cggaggtcga gcccgccgaa cgcgacgcg aatcaccgct   44040 cggcgacgag gtgacgccgc tggtcctgtc cgcccggagc gccgaggctc tgcgcgcgca   44100
gtccgcccgg ctgcgtgagc accttcgcca gacggaatcc ttgaccgaca ccgccttctc   44160
gctcgcgacg tcccgtgccg cgctggagca ccgcgccgtc gtcgtggccg aagcggacgc   44220
gtcgctcgac gccttggccg ccggcgcgcc tgcggcaggg ctggtcgaag gtatcgcttt   44280
gccaccgggc aaggtcgcgt tcgtctttcc cgggcagggc tcgcaatggg ccgggatggc   44340
actggagctc aaggactcct cgccggtctt ccgggccgcg ctgctcgact gcgaacgcgc   44400
tctctcgtcc tttgtggact ggaagctcac cgacgtgctc ggcgacgcga cggcgctgga   44460
gcgcgtcgac gtcgtgcagc ccgccctctt cgcggtcaac gtgtcgctgg cggcgctgtg   44520
gcgggcgtgc ggggtcgaac ccgacgcggt gaccgggcac agtcagggtg agatcgccgc   44580
cgcgtacgtg tccggcgcgt tgtcgctggc cgacgccgcc aaggtcgtcg ccttgcgggc   44640
caaggccatc ctcgcgcttt ccggcgccgg gggcatggtc gcggtcgccc tcggccgcga   44700
cgacgtgctc cctcggctga cggagtgggg cgaccggatc gccgtggccg cggtcaacgg   44760
acccgcgtcg gtcgtggtct ccggagaccc agaggcgctc gacgggctcg tctccgcctg   44820
cgaggcggac ggcgtgcgtg cccgccggat cccggtggac tacgcctcgc attgccgcca   44880
ggtggacgtc ttgcgtgagg aactgctcgg cctgctcgac ggcgtcgagc accacgcgtc   44940
cacggtgccg ttctactcgg cggtgaccgg ggaaccctc gacacggcgg gcctgacccc   45000
ggagtactgg ttccggaacc tgcgggccac cgtccggttc gaccggtccg tccggcggct   45060
```

```
gctcgacgac ggtcaccggt tcttcgtcga agccagcgcg catccggtgc tgaccggcag    45120
cgtcaccgaa accatcgagg aacgggcgc ccacgcggtc gcgctcggtt cgcttcgccg     45180
tgacgagggc ggcccccgcc ggttcctgac gtcgctggcc gaggctcacg tacgcggcct    45240
ccgcccggat tgggccgcgt tgtggcccac tgccaccagg gtcgacctgc ccacctatgc    45300
cttccagcgg gtgccgtact ggctcgacgc cgccgtcgtc cggcagggcg cacggcggc     45360
cgaactgcgc ttctgggcgg ctgtcgacca ggccgacacc ggcgcgctcg acgccgccgt    45420
gcccgccggg gagggagcct gggacgcggt gcttcccgcg ctttcggcct ggcgccgttc    45480
cggtctcgac aagtccacag tggacaactg gcggtaccgg atcgactggg tccccgcgac    45540
cgggacggca gcggccaccc tcgacgggac gtggctgctg gtcgtcccgt ccggaccgat    45600
gccgcccgtc gcggaggcgc tcacccggct cggcgcccgt gtcttgctcg cgggccccga    45660
tgacgaactg ccgcacgagc cggtcgacgg cgtgctttcc ctgctggcac tcgacgaacg    45720
gccgcatccg gaacacccgg tggtaccgc cgggctcgcc gcgaccgcgg acctcgtccg     45780
ccagctcgcc gacctcgacg ctccactgtg gatcgtcacc tccggcgcgg tcgccgtcgg    45840
ccggtcggag accccgaacg cgcaggccgc cgtctgggt ctcggccggg cgatcggact     45900
cgaacacccc gaacgctggg gcggcctcgt cgaccttccg gaggaactcg acgaacgcgc    45960
cgcggcccgc ctcgccgggg tgctcgccac cggtcacgag gaccaggtcg ccgtccggtc    46020
gtccggggtc tatctgcggc ggctcgtgcg ggcgccgctc ggggacgccg tcgcgccgga    46080
atggcggccc cgtgggaccg tcctggtcac cggcggcacc ggtgcggtgg ccgcccacgt    46140
cgcgcggtgg ctcgccggga acggcgccgg gcatctggtg ctcaccagca ggcgcggggc    46200
ggcggccgag ggtgcggcgg aattgagtga cgaactcgcc ggtctcggtg cgcgggtgac    46260
cttcgccgcc tgcgacgtcg ccgatcgtga cgcactggcg gcggtgctgg ccgagtatcc    46320
gccgaacgcc gtcgtgcaca cggcgggggt cggggccacc gcgtcgctcg ccgagaccgg    46380
cccggcggaa ctcgccgacg cgctcgccgc caaggcgggc ggtgccgctc acctcgacga    46440
acttctcgaa ggcgccgaac tggacgcctt cgtgctcttt tcctccaacg cgggtgtctg    46500
gggcggcgcc gggcagggtg cctacggtgc cgcgaacgct gccctggacg cgctcgccga    46560
acgacgtcgt gcccgggcc tgcccgccac ctcggtggcg tgggggctgt ggggcggcgg    46620
cagcgggctg gccggccagg acgacgtcga ccgcttgcgc cgtctcggat tggccgcgat    46680
ggacccggcg ctcgccgtgt ccgcgctcgt ccaagccgtc tcgcacgacg agaccttcgt    46740
cgcggtcgcc gacgtcgact gggcgcggtt cgctcccgga ttcgccctcg cccggccccg    46800
gccgctgctc gacgcgttgc ccgaggtccg cgaggcgctg tccgccgaca ccgcgggacc    46860
gggcggctcc gaattcgccg ccggactgct ggccgccccc gaggcggacc ggacccgtat    46920
cgtgctcgac ctggttcgcg cgcaggcagc cgcggtcctc ggccacggtg gcgccgccgc    46980
cgtcgagccg gaccgcgcct tccgcgacct cggcttcgac tccctgaccg cggtcgaggt    47040
ccgcgaccgg ctggccgccg ccaccgggct gcggctgccc gcgaccctgg tcttcgacca    47100
tccgtcggcc tcgcgcttg ccgggcatct cgtcgccgaa ctcaccggcg acgtcaccgg     47160
gacacaagcc gcgccggccg tggtggtgac cgacgacgag ccgatcgcga tcgtcgcgat    47220
gagctgccgg ttccccggcg ggatcacgga tccggagaag ttctgggact tcgtcgcgga    47280
cggcgggggac gcgatggccg ccttccccgg cgaccgcggc tgggacctcg acgcgctcta    47340
cgacccggac cccgcgcacc tcggcaccac gtacgcccgt gaaggcggct tcctcgacga    47400
cgcgggcggt ttcgacgcgg cgttcttcgg gatctcgccg cgtgaggcgc tggcgatgga    47460
```

```
tccgcagcag cggttgctgc tggagacgtc gtgggaggcg ttcgaacggg ccgggatcga   47520
cccggcgacc ctgcggggga gcgcgaccgg cgtcttcgtc ggcgcatcct tccagaacta   47580
cggcctggac gccgtcgacg cgcccgaagg caccgagggc tacttcctca ccggaaccgc   47640
caccgcggtc gtctccggcc gcctctccta caccttcggg ctggaaggcc ggcggtgac   47700 gatcgacacc gcgtgctcgt cttcgctggt ggcactgcat ctcgcggcgc aggcgctgcg   47760
gcgcggcgaa tgttcgctgg cgctggcggg cggggtgacc gtgatggcca cccggccgc   47820 gttcgtggag ttcagccgtc agcgcgggct cgcgccggac gggcgttgca aggcgttcgc   47880
cgacgccgcc gacggcaccg cgtggtccga gggtgccggg atccttctgg tggaaaggct   47940
ttccgacgcg cgccgcctcg ggcacccgt cctggcgctg gtgcgcggtt cggccgtgaa   48000
ccaggacggc gcctcgaacg ggctgagcgc gccgaacggg ccgtcacagc agaggtgat   48060 ccgccaggcg ctggcgaacg ccgggttcgc accgtccgat gtggacgccg tcgaggcgca   48120
cggcaccgga accagcctcg gcgacccgat cgaggcacag gccttgctcg ccgcttacgg   48180
cggggaacgc gagcatccgc tgtggctcgg ttcggtcaag tcgaacctgg gcacacaca   48240 gtcggcgtcg ggtgtggcgg gcgtgatcaa gatggtgcag gcgatccggc acggtgtcct   48300
gccgcggacc ctgcacgtcg acgcgccgac cacggaggtg gactggacgg cgggtgatgt   48360
ccggctgctc accgaaccgg tggactggcc ggacaccgga cgtccgcgcc gggcgggcgt   48420
ctcctctttc ggggtcagcg ggaccaacgt gcacacgctg atcgaagagg tcccggagag   48480
cgctgcgcct cccgccggcg gggacacgtg ggtgccgtgg gtgctctcgg ccaagaccga   48540
ggaagcgttg cggtcccaag cttcccggct gcacgcgcaa ctggaagagc acccgggga   48600 cgactccgac atcgcgtaca cgctggcgac cgcccgtgcg ggactggaga tccgggccgc   48660
ggtgaccggg ccggatcgtc tgcgcgagct ggccctcctc gccgagggga cgccgagcgc   48720
ggcggtgctg cgcggcgcgc tcaccgccgg ggcgccgggg ttcctgttca ccggtcaggg   48780
cagccagaaa cccgggatgg gcgccgaact cgcggcccgc ttcccggtgt cgccgccgc   48840 gttcgacgag gtgtgcgccc atctggaccc gcgcctcggg ctgtcgctgc gcgaagtcct   48900
cgaaaccgag cgagtgcacg aaacggcgtt cgcccagtgt gccctgttcg ccgtcgaggt   48960
cgcgctgttc cggctgctgg agagctgggg tgtccggccc gcgctgctgc tcgggcattc   49020
ggtcggcgag atcgcggccg cgcacgtcgc cggggtcctg tcgctcgcgg acgcggccac   49080
gatggtcgag gcgcgcggaa ggctcatggg cgccctgccg tctcgcggcg tgatgatcgc   49140
cttgcaggcc aatgaagacg aggtgacccc gctgcccacc gagcgcgtgt cgatcgccgc   49200
cgtcaacggc ccggaagcgg tggtgctgtc cggggacgag gacgccgtta ccgcagtggt   49260
ggaccggttc gccgaccgca agagcaagcg gctcgtggtc agtcacgcgt tccactcgcc   49320
gctgatggaa ccgatgctcg cggacttccg ccgtgtcgtg tccgggcttt ccttcagcga   49380
gccgaggatc ccgatcgtgt cgacggtgac cggccgctcc gatcccgaaa tcgcctcacc   49440
cggctactgg gtgcggcacg tccgcgaggc ggtgcggttc cacgacgcga tccggttcgc   49500
cgaggccgag gccgagggcg tgcgcgcctt cgtcgaactc ggccccgagg gcgtcctttc   49560
cgccatggcc aaggacttcc tcgaagacac cgtgctgatc ccgaccctgc gcggggaacg   49620
tccggaggtc gccgcgctgg cgaccacact cggccgcctg cacgtccacg gtgtcggat   49680 cgactgggcg ggtgtgttcg acggcgtcca ggcgagccgg gtcacgctgc ccacgtatcc   49740
cttcgagcat cggcacttct ggctggcgag caccggcgcg accacgggcg acgcggccgc   49800
```

-continued

```
gttcgggctc ggcgaggccg ggcacgcgct gctcggcgcg ccgtcccgg tgcccggcgg    49860 gagcgggatc tcgttcaccg gaaggctctc cctgcgggct cagccgtggc tcgcggagca    49920
cgtcgtgctc ggtacggctc tgcttcccgg caccgcgttc gtcgatctcg cgttgcacgc    49980
gggtgaccgc gccggctgcg gaaccgtcgc cgagctgacc ttggaagctc cgctggcgct    50040
gccggaaagt ggtgacgtcc ggctgcacgt caccgtcggc gagccagggg aggacggcgg    50100
gcgcacgatc gagatccatt cccgtgcggg atccgccgcc gacgaggaac cgtggacgcg    50160
gcacgccacc ggcctcctgg ccaccggaac cccggccgcc agcgggaacc tggacagctg    50220
gccaccggac ggcaccgaga tcccggtcga ggacttctat gaccggctcg acggcaccgg    50280
gttcgagtac gggccgttgt tccagggcct gcgcgcggcg tggaaggccg gggacgacgt    50340
ctacgcggag gtttcgctgc ccgaggaccg ctcccgtgac gccgaaggct tcggcgtcca    50400
ccccgcgctg ctggacgccg cgctgcacgc gtcgaagctc cggctggagg gtgacagcga    50460
gggacctttc ctaccgttca cgtggaaggg tgtctcgctg gccgcgaccg gtgcgcggac    50520
gttgcgggtg cggctgtcct cgtccgctcc ggccacgatc tcgctgctgc tcgccgacgg    50580
tgaaggcgcc ccggtggcca ctgtggattc cctggtgttc cgccgggttt cgtccgagca    50640
gctcggaaac cggcagggga gcggatcgct gttccacgtc gagtggaccg acgtgcctgc    50700
cgaggaagtg tccacagagg atgtcaggat cggcgccgga gagtcctatg tggacgtcgc    50760
ggcactgctc gccgccaaga cgcccgaagt cgcgctgctg gtctgcccgt ccggggagac    50820
cgccgaggcg gtgcacgacg cgaccgtgtg ggcgctgcgc caggtgcggg actggctcgc    50880
cgacgagcgg ctggacgcgc accggctcgt cctgctgacc gacggcaccg acctggccca    50940
ggccgcggtg cggggactgt tccggtcggc ctcgtccgaa cacccggcc ggttcggcat    51000 cgccgagacc accggggatc cggtccgggt gtcggccgac gagtccgaac ttcggctgga    51060
gaacggtgtc gcgtacgcgc cgaggctggt ccgcaagatc gccgcggccg ctccggtcgc    51120
gctcgatccc ggcaagacgg tgctggtcac cggtggtacg ggcgcgctcg gcgcgctggt    51180
ggcccggcat ctggtgaccg cacgcggcgt gacccggctg ctgctggtct cccgtcgtgg    51240
gctggaggcc gaaggcgcca aggacctggt ggcggacctg acggccgcgg gcgccgacgt    51300
caccgtcgag gcctgcgacg tcgccgaccg cgctgcgctg gaagcggccc tcgccgggca    51360
cgagctgacc gccgtcgtgc acacggccgg cgtgctcgac gacggtctgg tcgattcgct    51420
gacgccggag cggctggcga aggtgctgcg gccgaaggtc gacgcggcgc tgaacctcca    51480
cgagctcgcg ggtgacgtcg aggaattcgt gctgttctcc tcggcgtcgg ccacgttcgg    51540
caatcccggg caggcgaact acgcggcggc caacgcgttc ctcgacgcgc tcgcccgcca    51600
ccgccacgca caagggcttc cggccacgtc gctcgcctgg ggactgtggg cgaccgacgg    51660
cggcatgacg ggcgaactga gcgacaccga cctggccagg atgggccgca ccggtatcgc    51720
cgcgctgacc ccggaagccg ggctcgccct gttcgacgcg cgtccggcg ccgggccggt    51780 ggtgctgccg atggcgctga cgccatcctc gctccgcgat gtggaacccg cggtgctgcc    51840
cccgttgctg cggggactgg tgcgggctcc gtccggcgc ccgcgtccg ctcccgccgg    51900 tccggcgttg caggacaggc tttcgggcct gaccggcgcc gaacgcgacg acgcggtgct    51960
ggaggtggtg cgcgagcagg tcgcggccgc gctcggtcac gcgggcgccg ggcgatcga    52020 tccgggcaag ggcttcgtcg aactcgggat ggattcgctc agcgcggtcg aactgcgcaa    52080
ccagctgtgc gcgctgagcg ggctgaaact ctcgacgacg gtggtgttcg accaccccaa    52140
cccggccgcg ctcgccgggc acctcgcggc cgaactgccc gccgaagggg tggccaccac    52200
```

-continued

```
cgcgtcggtg cacgccgggc tcgaccggct cgaagcgctg ctggccaccg ccgccccggc   52260
gaacggggat cgcgccgggg tcaccgcgcg cctgcgcacg ctgctggcga cgtggaccgg   52320
cgagcccgcc gccgaggccg acgactcgct ggagtcggcc accgcggacg aactgttcga   52380
cctgctcgat cacgaactcg gcgcgtcctg acccgcctga tactgggaga cccttccgtg   52440
gcgaacgaag acaagtacct cgactacctc aagcgcgcga ccgccgacct gcgggagacc   52500
cggcgacggc tgaaggaggc cgaggaccgc ggccacgagc cgatcgccat catcgggatg   52560
gcctgccggt tccccggcgg cgtgcggtcg ccggaggatc tgtgggagct ggtcgccgag   52620
ggccgcgacg ggatctccgg gttccccgcc gaccgcggct gggacctgtc cgcgctgtac   52680
gacccgacgg gggagaagcc cggcacctcg tactgccgcg agggcggttt cctggacggc   52740
gcgggcgaat tcgacccggc cttcttcggg atctcgccga gggaagcgct cgccatggac   52800
ccccagcagc ggctgctgct ggagatctcc tgggagacct cgagcgcgc gggcatcgac   52860 cccggctccc tgcggggcag ccggaccggg gtgttcgccg gggtgatgta ccacgactac   52920
gtctcccggc tcgccgccat cccggaggaa ctcgagggct acctcggcac cgggaactcg   52980
ggcagcgtcg tttccgggcg ggtcgcctac acgttcgggc tggaaggccc ggcggtgacg   53040
atcgacaccg cttgctcgtc ctcactcgtc gcgctgcatc tcgcagcgca ggcgctgcgg   53100
cagggcgaat gctcgatggc gctcgccggc ggtgtcgcgg tgatgtccac accggacacg   53160
ttcgtcgact tcagccgtca gcgcgggctc gccgcggacg gccgctgcaa gtcctattcg   53220
gacggagcgg acgcacgtc gtgggccgag ggcgtcggga tgctcctggt ggagaagctc   53280
tccgacgcgc ggcggctcgg ccacgaagtg ctcgcggtcg tcagcggcag cgcggtcaac   53340
caggacgggg cgagcagcgg gctcagcgtg ccgaacggcc cgtcacagca gcgggtcatc   53400
cggcaggccc tggagaacgc gcggctctcg gccggacaga tcgacgtcgt ggagggccac   53460
ggcaccggga ccaccctggg cgacccgatc gaggcgcagg cgctgctcgc cacctacggc   53520
cgggagaaat ccgcggaccg gccgttgtgg ctgggctcgc tgaagtcgaa catcgggcac   53580
tcccagtccg ccgccggggt cggcggcgtg atcaagatgg tgcaggcgat ccggcacggg   53640
atcttgccgc gtaccctgca cgcggaggac ccgtcgtcca agtggactg gtcggccggt   53700 gccgtcgaac tgctcaccga agcacgcggg tggccggaga ccgggcagcc gcgccgcgcg   53760
ggcgtgtcct cgttcggcgt cagcggcacc aacgcgcaca ccatcatcga gcaagccccc   53820
gagagcgaag agtccccggc cgtgccaccc accggcgccg tgcccgcggt gttgtctggc   53880
aagaccgccg aggcgctgcg cgaccaggtc gtgcggctgc gctcgcacat cctcgcccgg   53940
ccggagctga gcgtcgccga cgtcgccgcg tcgctcgcca ccacccgcgt cctgcacgag   54000
caccggggcg cgatcgtcgc ggccgaccgc gaccagctgc tcgcggggct ggacatcctc   54060
gccgccggcg ccacgaccgc cggggtctct caaggtgtcg ccaccgacgg ccggacggcg   54120
ttcctgttca ccggccaggg cagccagcgc cgcgggatgg ggcgggaact ggccgagcgt   54180
ttcccggtgt tcgccgaggc cttcgacgac gtctgtgccc ggttcgaacg gccgatcaag   54240
gaactgtcca ccgaggaact gaaccagacg gcgaacacgc agtgcgcgct cttcgccttc   54300
gaggtggcgc tgttccggct ggtcgaaagc tggggcgtgc ggcctgactt cctggcgggg   54360
cactcgatcg gcgagatcgc ggcagctcat gtcgcaggtg tgttcaacct cgatgacgcc   54420
gtgaagctgg tcgcgcgcg aggcggtttg atgcaggcgt tgcccaccgg cggcgcgatg   54480
gtggccttgc aggcgacgga ggccgaggtc ttcccgttgc tgacggaccg ggtgtcgctg   54540
```

```
gccgcgatca acggcccgga gtcggtggtc ctctccggcg acgaagacgc cgtcgccgct    54600
gtggtgtccc gcttcgaggg ccgtaagcac aaacggctcg ccgtgagtca cgcgttccac    54660
tcgccgctga tggagccgat gctcgacgac ttccgcgcgg tcgcggacag tctctcgtat    54720
gcggcgccac ggatcccgat cgtgtccggc ggtctggcgg atgtgtccac ttcggactac    54780
tgggtccgcc atgtccgtga cgccgtgcgg ttccacgatt cggtcaagtt cctggaaacc    54840 gaagggtca cccgcttcct ggagatcggg ccggacgccg tcctcaccgc gatgcccag     54900 gaaagcaccg agggcgcggt cgtcgtcgcg gcctcgcgcc gcaaccgcgc ggaggacgtc    54960
accctgctcg ccgcggtctc cacgctgcac gtccacgggg cgtccgtcga ctggacgccg    55020
ctgctcgccg gagcccgccg cgtcgacctg cccacgtacg ccttccagca ccgccgtttc    55080
tggctggacg gcccgctgaa cgccgagggt gacgcggcga gcctgggcct gggcgccacc    55140
gatcacccgc tgctcggcgc cgtcgtcacg atggccgacg cgcacggcgt cctgctcacc    55200
gggcggcttt ccctcgcggc gcagccgtgg ctggccgggc acgtggtcgc ggggcacgtc    55260
ctgctgccgg gcaccgcctt cgtcgacctc gtcctgcacg ccggggacaa ggtcgactgc    55320
gggatcgtgg aggaactgac cctgcgggaa cccctcgtcc tgcccgaaca cgacgccctc    55380
agcctgcaac tcgtcgtcgg cgcgccggac gagaccggca ggcgcacggt cggcgtccac    55440
tcccgccccg aggccgccga cgcagaatgg tcgtgccacg cgaccggtgt cctcgccccc    55500
ggtttccccg acaccgactt cagcctcgcc gcctggcctc ccgaaggcgc cgcgccggtc    55560
gcgatcgacg gcctctacgg cgcgctcgcg gaggtcggcc tcgactatgg gcccgccttc    55620
cagtgcgtgc gcgccgcctg gacccacgat tcggccgtct acgccgaaat cgagctggcc    55680
gacgccgaga aggccgacgc ggcccggttc ggtatccatc cggccctgct cgactcggca    55740
ctgcacgccg ccggtctcgg cgcgctggac gccaccgagg cgcgtcttcc gttctcgtgg    55800
tccggtgtga gcctgcgggc gttcggagcg acgacgatcc gcgtgcggct gaccccggcg    55860
gggccggaca cgatcgcgct ggccgtcgcg gatccggagg gacggccggt gttcgccgcc    55920 gacgcctcc tcgtccgcgc ggtccccgtcc ggtgccctca cctcgcgaaa cccggtgcgc    55980
gacgggttgt tccgggtgga ctggcagccg ctcaccatcc ccgccgaagc cgccgcggag    56040
tacgtcgtcg cctcgttcac cgggtacacc ggcgacctgc tcggcgacgc ccacgcggcc    56100
gcggtccgcg cactcgaact ggtgcatgcc gacagcggcg gcccgaaact ggtcttcctg    56160
accagcggtg ccgtcgggga cgccgtgccg cgtccggcgc aggccaccgt ctggggtctc    56220
gtccgcaccg cgcaggagga gttcccggac cggttcgtcc tcctcgacgc cgacaccgag    56280
cccacgcccg aattcatcgc ggccgccgtc gccaccggtg aacccgagct cctgctccgc    56340
gaaggtgtcc tgtccggtgc ccgtctcgtc cgcgccccgc gtgcctccgc cgagcccggc    56400
gacatcgacg ggacggtgct cgtcaccggc ggcaccggcg cgctcggcgc ggatctcgcc    56460
cggcacctcg tccggtcgcg cggtgtccgg cggctgctgc tcaccagccg tcgcggtgcg    56520
gcggcaccag cgcggacac cctcacccgt gagctgaccg cgctcggcgc cgaagtccgg    56580
atcgaagcct gcgacgccgc cgaccgcgac gctctcgccg ccctgctggc cgatcagccg    56640 atcacccctcg ccgtgcacgc cgcgggtgtc ctggacgacg gcctcatcgg tgacctgtcc    56700
gcagaacgcc tcaccgccgt cttgaggtcc aaagtggacg ccgccgtgca tctgcacgaa    56760
ctgctcggcg acaccgaact cgtcctgttc tcctccgccg ccggtgtgtt cggcaacgaa    56820
gggcaggcga actacgccgc cgcgaacgcc ttcctcgacg ccctcgcccg gcaccggcag    56880
gcgaacggcc tgcccggcac ggcactggcc tgggggatgt gggcctccgg catgggtgac    56940
```

```
gcgctcaccg ctcgcccggg ctttcccgca ctgtccacag aagacggtat ggcgctcttc   57000
gacgccgcga cggcgctcga cgacgccgca ctcgtcccga tccggctcga tctgcccgcg   57060
ttgcgagcgc ggctcggcgg tgacgtgccg cctctgttcc gcggcctgat ccggcccacc   57120
cgccgtgccg ccgtcaccgg ttcggccggc gcgctcgccg accggctggc cgcgctcgcc   57180
ccggccgaac ggagccggga actgctggag atcgtgcgga cgcacgtcgc catcgtgctg   57240
gggcacctcg gttcggaggc gatcgacgcc gggaaaccct tccaggagct cggcttcgac   57300
tcgctggcgg cggtcgaact gcgcaaccgg ctgaccgagg tcaccggcct gcggctggcc   57360
gcgaccctcg tcttcgacta cccgaccccg ctcgtgctcg ccgaacacct gctggaaggg   57420
ctcgccgggg gcggactcgc cgagacgccg gacgcgccgg tgcgcaccgg tccggtcgac   57480
gagccgatcg cgatcatcgg catggcttgc cgctacccgg gcggtgtcac ttctccggaa   57540
gagctgtggg acctggtcgc cgccggccgg gacggggttt cggagttccc ggtcaaccgg   57600
ggctgggaag acgtctacga cgccgacccc ggcaaggtgg gcaagagtta cgcccgcgag   57660
ggcggcttcc tgcacgacgc gggcgaattc gacgcggcgt tcttcgggat ctcgcccgt    57720 gaggcgctgg cgatggatcc gcagcagcgt ctgctgctgg agacgtcgtg ggaggtcttc   57780
gaacgcgccg ggatcgatcc gcacgcggtg cggggcagca agaccggcgt cttcgccggc   57840
gtgatgtacc acgactacgc ggcacggctg aactccgtac cggaggacgt cgagggctac   57900
ctcggcacgg ggaactcggg cagtgtgatc tcggggcggc tggcctacac gttcgggctg   57960
gaaggccccg cggtcagcat cgacacgccc tgttcgtcgt cgctggtcgc gatgcacctc   58020
gccggacagg cgctgcggca gggcgaatgt tcgctcgcgg tcgccggcgg cgtgaccgtg   58080
atggcgacgc cgaacaccTT catcgagttc agccgccagc gcgggatggc cactgatggc   58140
cggtgcaaat ccttcgccga ggccgcggac ggcaccggct ggggcgaggg cgtcggcatg   58200
ctcctgctgg agcggctttc ggacgcccgc cgcaacggtc accgggtgct ggccgtggtt   58260
cgcggctcgg cggtcaacca ggacggcgcg tcgaacgggc tgacggcgcc gaacgggccg   58320
tcgcagcagc gggtgatccg tcaagccttg gcgcaggcgg ggttgcgtcc gtccgatgtg   58380
gacgccgtcg aggcgcacgg tacgggaacg acactcggtg acccgatcga ggcacaggcc   58440
ttgctcgcca cctatggcca ggatcgcgag gagccgttgt ggctgggggtc ggtgaagtcg   58500 aacctcgggc acacgcaggc cgccgccggc gtcgcgggcg tgatcaagat ggtcgaggcg   58560
atgcgtcacg gcgtgctgcc tcggacgttg cacgtcgatg agccttcgtc ccatgtggac   58620
tggaccggtg gcgcggtgtc cctggtgacg gagtcgcggg agtggccgga caccggccgt   58680
ccgcgccgcg ccggggtgtc gtcgttcggg atcagcggga ccaacgcgca caccatcatc   58740
gaggccgtcg agcggaagc gcgggagccg tccggaaacc cggacgtccc gccgtggccg   58800
ctgtccggca agaccgagga agcgttgcga gcgcaggcgt cccgcctcca cgaccacctg   58860
ctggccactc ccgaggtgac cgcggcggac gtcgcgctct ccctcacggc gcgggcggac   58920
ttggagcatc gtgccgtgct cgtggccggt gaccgtgacg gtctcctcgc cacgctcgac   58980
gcgctcgcgc acggcgagac caccgagggg atcgtccggg gaacggcgcg gcacaccggc   59040 cggacgcgcgt tcctgttcac cggtcagggc agtcagcggc tcgggatggg ccgtgagctg   59100
gccgagcgtt tccggtgtt cgccgaggtc tatgacgagg tgtgttcccg gttcgagcag   59160
ccgctcaggg acttgtcggc cgaggagctg aaccagaccg cgaacacgca gtgcgcgttg   59220
ttcgcccttg aggtggccct gttccgcctg gtggagagct ggggtgtccg gccggatttc   59280
```

-continued

```
ctggccgggc actcggtcgg cgagatcgcg gccgcccacg tcgcgggtgt gctttccctc   59340
gacgatgcgg tgacgctggt gtcggcgcgc ggccgcctga tgcaggcgct gcccacgggc   59400
ggcgcgatgg tggcgctgcg ggcgaccgaa gcggaggtga ccccgctgct gacgagcgg    59460
gtgtcgatcg ccgccatcaa cggcccggag tcggtcgtcg tctcaggtga cgaagatgcc   59520
gtcgccgctg tggtcgaggg ccgcaagcac aagcgactta ccgtgagtca cgcgttccat   59580
tcgccgctga tggagccgat gctggacgag ttccgcaccg tggtggaggg cctgacgttc   59640
gcggcgccgc ggatcccgat cgtgtcgggt ggcttggcgg aggtgtccac ttcggactat   59700
tgggtccgtc atgtccgtga cgcggtgcgg ttccatgatt cggtgaagtt cctggaagcc   59760
gagggcgtca cgcggttcct ggagatcggc ccggacggtg tgctgaccgc gatggcgcag   59820
gacagcctga aggacgcggt cgtcgtcccc gccctgcggc gcgacaagcc cgaggtcacg   59880
accctgctga cggcggtcgc cggactgcac gtccacggcg ccggcgtcga ctggagcccg   59940
ctgtccgccg gggcccgccg ggtggacctg cccacgtatg ccttccagcg cacggagttc   60000
tggctcgacg cgggtgccgc ggctggcgat ctgaccgcgg cgggactgtc cgacgccgga   60060
catccgctgc tcggtggcgc ggtgaccttg ccggactccg gcgggaccgt gttcaccggg   60120
aggctgtcgc tcgcggccca gccctggctc gccgaccacg ccgtcgggga gaccgtgctc   60180
ctgcccggta ccgcgttcgt cgatctggcg ctcgccgccg gacgacggca cggccgcgtc   60240
gtcctcgacg aactcaccct ggagagcccg ctggtcctgc cggagcacgg cggtgtcgat   60300
ctgcgcgtgt gggtccgcga accggacgac accggcgcgt gcgcggtcag cgtgcattcc   60360
cgtgccgacg acgagccctg gatccgccac gcggtcggaa cgctgaccga ggacaccggc   60420
gccacgcccg ccgacctcac gtcatggccg ccgccgcgg aggagaccga cgtcgacggg   60480
ctgtacgacg cgctcgccga cgcgggcctg aactacggcc cggtcttcca aggcgtccgc   60540
gcggcctggc tcgacggcac caccgtgtac gccgagatcg acctgacga acgccatcac   60600
ggcgacgccg cccggttcgg cctgcacccg gcgctgctgg acgcggccct gcacaccgcc   60660
ggactcggcg cgctgagcac cgaaggcggg gcacggctgc ccttcctgtg gtcgggcgtc   60720
tcgctcaccg gcctcggcgc cacgagcctg cgcgtccggc tcaccgggtc gggcgacacg   60780
ctctccctgg cgatcgcgga cgggacgggt gcgccggtgg cgaccgtcgc cgggctgacc   60840
gtccgtcagg tcgaccccgc cgcgttcggt ggtggcggcg actcgctgtt ccgggtggag   60900
tgggtcccgg tccgcgcccg tgccgcggac accgcgcccg ccgtccggtc cgaagtggac   60960
agtctggtga acgtgcgcga agcgaccgcg caaacgcttg cggcgctcca atcctggctc   61020
gccgacgaaa gcaacgccga cacccactg gtcgtgctga ccagcggcgc ggtgtcggtg   61080
gcgggggagg acacgcgtga tctcgcccgc gccgccgtct gggggctggt gcggtcggcg   61140
cagtccgagc acccgggccg gttcgtgctc atcgacaccg ataccgaacc agcggacctg   61200
gccggagccg tcgccaccgg cgaggcacag cttgccatcc gcgacgggaa gctgtgggcg   61260
ccgcgtctgg tgaagagcgc accctccagt gccacaccgc gtttcgaccc ggaaggcacc   61320
gtgctgctca ccggggcgac cggtgcgctg gccgatcgc tggccagtca cctggtctcc   61380
ggacacgggg tcggcatct gctgctggtc agccgcagcg gcgcggccgc acacggtgcc   61440
aaggacctgc tggcggaact gaccgggctc ggcgcctccg tggtcctgga gtcctgcgac   61500
gtcgccgacc gggaagccct cgcggggctg ctggccggga tcgacccgg gcatccgctc   61560
accgggtcg tgcacgcggc cggcgtcctc gacgacggcc tgatcgacag cctgactccc   61620
gaacggttcg acgccgtgct gcggcccaag gccgacgcgg cgctgaacct gcacgagctg   61680
```

```
gcgggcgacg tcgacgagtt cgtcctgttc tcctcggcgg cgggcacgtt cggcaacgcc    61740
ggacaggcga actacgccgc ggcgaacgcc ttcctggacg cgttggcaca gcaccgccag    61800
gccaacggcc ttccgcccg gtccctggcc tggggtctgt gggacaccga cgacgggatg     61860
gacgcttccg ccgccgtcgc caggctcacc gggtccggcc tcaccaccga agaagggctg    61920
cacctgttcg acaccgcggg tgacggtgtc gtcctgccga tgaagctcga cctcgccgcg    61980
ctccgcgccg aactcggttc cgacgtgccg tcgctgctgc gcggtctgat caaggcgccc    62040
gcgcggcgtt ccgcgggagc gtcggcgtgg aagcggcagc tcgcgggact gtccgaagag    62100
gaccgtgacg cacgcctgct cgaactcgtg cgggcacagg tcgccgcggt gctgggctac    62160
tccggcccgg aggacgtgcc gtcggaccgg gcgttcaccg aactcggctt cgattcgctc    62220
acgtcggtgg atctgcggaa ccggctgaac tccgcgaccg gcctgcgcct gcccgccacc    62280
ctcgtgttcg accacccgaa ctccgacgcg gtcgtcgccc ggctgcggga ggaactgtcc    62340
ggcaccgtgg tcgcggccgc cgtcgtcacc acggcgccgg tggacgaacc gatcgccatc    62400
gtcggcatgg cctgccggtt ccccggcggg gtccgctcgc cggaagacct ctggcggctg    62460
gtcagcgaag gccgcgacgg catcaccccg ttccccgcgg accggggatg ggacgtcgaa    62520
ggcctgtacg accccgaggc ctcccggccc ggcacctcct gcacccgcta cggcggattc    62580
ctgcacgacg ccggggactt cgaccccggc ttcttcggga tctcgccgcg ggaggcgctg    62640
gcgatggacc cgcagcagcg gttgctgctg gagacgtcct gggaagcctt cgaacgcgcc    62700
gggatcgacc cggccaccct gcgcggctcc gcgaccggcg ttttcgccgg ggcgatgtac    62760
cacgactacg tttcgcggct caccgagatc ccggcggatc tggagggcta cctcggcacg    62820
gggaactcgg gcagcgtgat ctcggggcgc ctcgcctacg ccttcgggct ggaggggccg    62880
gcggtcagca tcgacacggc gtgctcgtct tcgctggtcg cgatgcatct cgcggcgcag    62940
gcgctgcggc agggcgaatg cggcctggcg ctggccggcg gcgtcgcggt gatgtccact    63000
ccggacactt tcatcgagtt cagccgccag cgcgggatgg cgccggacgg ccggatcaag    63060
gcgttctccg agaccgccga cggcacggcc tggggcgagg gcgtcggcat gctgctgctg    63120
gagcgccttt cggacgcccg ccgcaacgga caccgggtgc tggccgtcct gcgtggcacg    63180
gcggtgaacc aggacggcgc gtcgaacggg ttgacggcgc cgaacgggcc gtcgcagcag    63240
cgggtgatcc ggcaggcttt ggcgcaggcc ggtttgcgac catccgatgt ggacgctgtc    63300
gaggcgcacg gaaccgggac cacgctcggc gatccgatcg aggcgcaggc tctgctcgcc    63360
acctacgggc aggaccgtga agagccgttg tggctcggtt cggtgaagtc gaacctgggc    63420
cacacgcagg ccgccgccgg ggtggcgagc gtgatcaaga tggtcgaggc gatgcgtcac    63480
ggcgtcctgc ccaggacact gcacgtcgac gagccgtcgt cccatgtgga ctggacggaa    63540
ggcgccgtct ccctgctcac cgaaacgcgg gactggccgg acaccggacg cccacgcgt     63600
gccggggtgt cgtcgttcgg gatcagcggg accaacgcgc acgtcgtcct cgaagcggac    63660
ggcgccggcg acgcggcacc gcccggacag ccggatgtac ttgccttccc gttgtccgcc    63720
aagacccagg acgctctgcg cgagcaggcc gccaggttgc gtgcccggtt gctgaccgga    63780
cacgcacccg agctcgccga cgtcgcgcaa acgcttgcca cacggggggct tttcgagcac    63840
cgggcggtgg tcaccgcggg cgaccgcgac ggactgctcg acgcgctcgc cgcgctggcc    63900
gggggagaac cggcgacttc gtcaccggt ctcgcgaaac cgggcgggaa actcgcgttc     63960
ctcttcaccg gtcagggcag ccagcgcgcc gggatggccg acgaactctc cgccgccttc    64020
```

-continued

```
ccggtgttcg ctcgaacctt cggcgagatc tgcgcgcgtt tcgatacect gctggaccgt    64080 ccgctgcgcg aggcgctcgc cggtgacctg gtcgaccgca ccgaatacac ccagtgcgcg    64140
atgttcgccg tcgaggtcgc gctgttccgg ctcgtcgaga gccggggcgt gcggccggac    64200
ttcctggccg ggcactcgat cggggaactg gcggcggccc acgtcgccgg ggtctggtcg    64260
ctggaggacg cctgcaccgt ggtcgccgcg cgcggcaggc tcatgcaggc gctgccgtcg    64320
ggcggcgcga tgatcgcggt ccaggccacc gaagaggagg tccggccgct gatcgacgac    64380
gagaccgtgt cgatcgccgc gatcaacggc ccggtgtcgg tcgtcgtctc cggcgaagaa    64440
gccgccgtga ccgcgctggc cgccgggttc gccgaacgtg gccgcaagac caagcggctc    64500
accgtgagcc acgcgttcca ctcgccgctc atggacggga tgctcggcga attccgcgcc    64560
gtgctcgacg ggatcgccgc ggccgaccca cggatcccgc tggtgtccac gctgaccggt    64620
gacccgctga ccggcgatca ggcgcgatcg agcgagtact gggtccggca cgtgcgggac    64680
gcggtccggt tctgcgacgc gatccggacc ctggaggcgc agggtgtccg gcgttacctg    64740
gagctcggcc cggacgcgcc gctgaccgcc ctcggcgagc actgcgtcac gaacgagtcc    64800
acagtggacg ctcagctgtt cgtgccgtcg ctgcgggccg gtcgatccga cgtcgagtcg    64860
ttcgtcaccg cgctagcgcg gttgcacgtc gacggcgtcc gggtcgactg ggcgaaggca    64920
ctccccggcc ggaagatcga tctgcccacc tacgccttcc agcacgagcg gttctggctg    64980
cggcccgccg cgcccgcggt gggagacgtc accgggctgg ggcagtcgcc cgccgggcat    65040
ccgctgctcg gcgcggcggt cgaggcgccg gacagcggcg cggtgctgtt caccggcagg    65100
ctgtcggtgc aggagcagcc gtggctggcc gaccacgtcg tcgccgggac gacccttctc    65160
ccgggcacgg cgttcgtcga gctcgcgttg cgggccgggg agctgaccgg ctgcgcggcc    65220
gtcgacgaac tgaccctgga agcaccgctg gtgctgccgg accacggtgg cacggcactg    65280
cggatcgtcg ccgccgcgcc ggacgagacc ggcaggcgcg cgctggacgt ctactcccgc    65340
cccgacgacg gcgactggat ccgtcacgcc accgggaccg tgtcgcccct ggcggcgggc    65400
gcaccgttcg atctgtcggc ctgggcggcc gccgatgccg agaccgtcga aaccgacggc    65460
ctctacgacg gattggccgc cgccgggctc gagtacggtc cggtcttcca gggacttcgc    65520
tccgcccggc ggcgagggga cgacatctgg gccgaggtcg acctccccga ggacaccacg    65580
accgagggct tcggcctgca tccggccttg ctcgacgccg ccttgcacgc cctgggcttc    65640
gccgaagggg gtgagcagga ggccgacgtg gcggccgggc gggtgcgcct gcccttcgcc    65700
tggtccggtg tccggctcca cgcctccggt gcgcgtgccc tgcgggtccg gctgtcgccg    65760 gcggggggaga acgcggtctc cctggccgcg gcggacgaga ccggcaggct ggtggccaca    65820
gtggacgctc tgacgctgcg cccggtctcg ctggagcaac tcggcgggcg gcagggcagc    65880
cacgagtcgc tgttcggtct ggagtgggcg ccggttccgc tctacccac cgccgccgtg    65940 gccgcgagct gggcggtcgt cggtgtcgac gactacaaac tcgacgccgc gctcaccgcc    66000
gccggctatc gcggccaggc ttacgccgat ctcgccgcgc tggccgaggc gatggatcgc    66060
gcgccagagc tggtcttcgt gtcctgcgcg ccggaccacc gccaagggct ggcagccgcc    66120
gcgcacaccg ccgcccaccg cgcgctagag ctggtccgtg cgtggctggc cgaggaccgg    66180
ttcgccggtt cccggctggt gctggtcacc ggcggcgccg tcgcgaaacc ggcgcaggcg    66240
gtgatctggg gcctgatccg ctcggcgcag tccgagcacc ccggccggtt cgtgctggtg    66300
gacctcgacg aacaggacgc gtcgtaccgt gtgctgttgc ccgcgctcgc ctccggcgaa    66360
ccgcagctgg agttgcgcga gggaacggtg aaggcgccgc ggctggtcaa accggccgtg    66420
```

```
                                                         -continued
acggccgccg aaggcaaggc tcggaccgac ggcgccgtgc tgatcaccgg cggcaccggc  66480
gcgctcggcg cggcactggc ccggcatctg gtcaccgcgc acgggaagac ccggctggtg  66540
ctcgccggtc gccgcggccc ggacgcgccg ggcgcgggcg aactggccga cgaactgcgg  66600
ggtctgggcg ccgaggtcgc tgtgatcgct tgcgacgcgg ccgatcgtga agcgctgcga  66660
cgccttctgg ccgagcaccc ggtgaccggg gtggtgcacg ccgccggtgt tctcgacgac  66720
gtcgtcctcg acggcctcac cccggaccgg ctcgacgccg tcctgcggcc gaaggtcgac  66780
gccgcggtga acctgcacga actggcggga gacgtcgacg agttcgtgct gttctcctcg  66840
gcggcgggca ccttcggcaa tccggggcag gcgaattacg cggcggccaa cgccttcctc  66900
gacgcgctcg cccggcatcg tcacgcacac gggctgcccg cgacctcgct cgcctgggga  66960
ctctgggccg gtgacgggat ggcgggcggt atgtccgggc gcgatctgga ccggatgtcc  67020
gcctccggcg cgggcgcact gtccacagag gagggtctgg cgttgttcga cctcgcggtg  67080
acggcggccg aaccggtgct gttgccgatg cggctggacc tcgccaccgt gcgggcgggc  67140
ctcggcaccg acgtcccgcc cctgctgcgc ggcctgatcc gcggtaccag aaaacgcgcc  67200
gagaccgccg gttcaccgac cggggacgcg ctcaaggcgg agctggccgg gatgaccggc  67260
gaggaacgcg ccgcggcact gctgaacctc gtcgccacgc acgtcgccgg tgtcctcggg  67320
cacgccggtc ccgagcaggt cgatccggac aaggcgttca cggaactcgg gttcgactcg  67380
ctcgccgcgg tcgaactgcg caaccgggtc aacgaggcca ccggtctccg gctgcccgcc  67440
acgctggtct tcgaccatcc gaccaccacc gcggtggcgg aactggtcgg cgcggagatc  67500
gtcgtggagg acgcgccacc gccgctgggg gtgctggcgg aactcgaccg gctggaggcc  67560
gcgttcgccg ggggaagccc ggacgacgcg atccgcggca aggtcaagga ccggctgcgc  67620
gccctgctcg cggcctgcga tccgggcgag ggcaccgaat ccgtggcgga tcggctcgaa  67680
gacgcctcgg acgacgaaat gttcgaattc atcggcaagg aactcgggat ctcctgactt  67740 ggggcggaa atgaaagaca ccgaggacaa actccggtac ttcctcaagc aggtcaccgc  67800
ggatcttcac gaaacccgga aacgcctgaa ggagaccgaa gccgcgggca gcgaaccgat  67860
cgccatcgtc gggatggcct gccgctatcc cggcggggtg gcctcgcccg aggatctgtg  67920
gcggatggtc gaaaccggcg cgacgggat cagcggattc ccggtcgacc gcggctggga  67980
cctcgaagcg ctgtacgacc cggatccgga caagcagggc acgagctacg tttcgcaggg  68040
tggtttcctc cacgacgtcg ccgagttcga cccggcgttc ttcgggatct cgccgcgtga  68100
ggcgctggcg atggatccgc agcagcggct cctgctggag acgtcgtggg aggccatcga  68160
gcgggcgggt atcgatccgg gctcgctgaa gggcagccgg accggggtgt tcgccgggtt  68220
gatgtaccac gactacgtct ccgggctgac cgagatcccc gacgaggtcg gcggctacct  68280
cggcaccggg aactccggca gcatcgcctc cggccgggtg tcctacacct tcgggttcga  68340
aggccccgcg ctcaccgtgg acaccgcgtg ctcgtcgtcg ctggtgaccc tccacctcgc  68400
cgcgcaggcg ctgcggcggg gcgagtgcga cctcgccctg tccggcgggg tgacggtgat  68460 gttcacccc gggacgttcg tggagttcag ccgccagcgc gggatggcgc cggacggccg  68520
ctgcaaaccg ttcgccgaag aggcggacgg caccggctgg tccagagggtg tcgggatgct  68580 gctggtggaa cggctttccg acgcgcggcg caacggccat ccggtgctgg cggtcctgcg  68640
cgggtcggcg gtgaaccagg acggcgcgtc gaacggcctg accgccccga acggcccgtc  68700
ccagcagcgg gtgatccgcg aggcgctcgc cgacgcccgg ctgacgacgg cggacgtcga  68760
```

```
cgtcgtcgag gcgcacggaa ccggcaccac cctgggcgac ccgatcgagg cgcaggcgct   68820
gctcgcgacc tacggcaagg gcaggccgtc ggaccggccg ctgtggctcg ggtcgatcaa   68880
gtcgaacctc gggcacaccc aggccgccgc cggagtcgcc gggatcatca agatggtgca   68940
ggcgctgcga agcgggatcc tgccccggag cctgcacgcg gagacccccgt cgtcgcatgt   69000 ggactggagc gcgggcgcgg tctcgttgct ggccgaggcg cggccgtggc cggagctcga   69060
ccgtcctcgc cgggccgcgg tgtcgtcgtt cggcatcagc gggaccaacg cgcacgtcgt   69120
cctcgaagcg gccccggctg ccgaggtcga gccccggcag ccggtggtga ccggtgcgac   69180
gccgtggctg ttgtcggcgc ggacgccgga ggccttgcgt gccagggctg cacagcttcg   69240
gtcctttgtg gaccttccag gcgccgctgc cacactggcc gcgcggccgc tgttcgggca   69300
ccgggcggcc atcgtcggtg atccgcgtgc cgcgctggac gcgctcgcca ccggaaagcc   69360
ctcgaacctg ctgatcgagg gcaccgcgca gtcgggtaag gctgttttcg tgttcccggg   69420
tcagggttcg cagtgggtgg ggatggcgga ggagttgttg ttgtcggctc cggtgttcgc   69480
ggagtcgatg gctgagtgtg agcaggcgct ttcgtccttt gtggattgga agttgtccga   69540
tgtgttgtcg gatgcggctg cgttggagcg ggttgatgtg gtgcagcctg ttttgttcgc   69600
ggtgatggtt tctctggcgc ggttgtggcg ggcgtgtggg gttgagcctg ctgcggtggt   69660
tggtcattcg cagggtgaga tcgcggcggc gtgtgtggcg ggtgcgttgt cgttggatga   69720
cgctgcgcgc gtggtgtgcc tacggagtaa ggcgattctg gcgttgtcgg ggctcggtgg   69780
catggtgtcg gtggctgcct cggaggaccg ggtgcgggag ctattgcctg ccggtgtgtc   69840
ggtggcagca gtgaacggcc cgtcggcggt ggtggtgtcc ggtgatgtcg cgggcttgga   69900
ggcgttgctc aagcggtgtg agttgctgga tgtgcgggcg aagcggatcc cggtggacta   69960
tgcctcgcat tcggcgcatg tggatgcgat cgagcaggag gtcttgtcgg cgctggcggg   70020
tatctcaccg caggcgccgg tgatcccgtt ttattcgacg gtgaccgatg agcctctgga   70080
attggatgct gggtattggt tccggaatct gcggggggacg gtgcggttcg cggcgacggt   70140
ggatcggttg ctggaggacg gtttccggtt cttcgtggag acgagtccgc atccggttct   70200
ggtcccggga atcagcgaag acgctgtcgc tctggggagt ttgcgtcggg gtgagggtgg   70260
tgcggagcgg ttcgtcgcgt cactggccga agcccatgtg cacggcctga gcccggcgtg   70320
gtcttcgatc ctgccgacgg cggactgggt cgatctgccg acgtatccgt tccagcgcaa   70380
gcggttctgg ctggaagccg ggaccgccgc cggggacgcg tcggcgttcg ggcagacggt   70440
ggtggaccac ccgctgctcg gcgccgtcgt cgcggtcccc gggaccggcg ggctgctgta   70500
caccggccgg atctcgctgg agacgcatcc ctggctcgcc gatcacgccg tgtccgggac   70560
ggtactggtg cccggtaccg cttcgtgga actcgcgctg gccgccggca ctcaggtgga   70620
ctgcgcgctg ctcgacgaat tgaccctcga agcaccgctc gtgctcgaag aaggcacgga   70680
cgtccggctc tcggtcgaac tcggtgacgc ggacgtcgac ggccgtcgcg aggtcggcgt   70740
gtactcccgc cgcggcgacg aaccctggac ccggcacggc aacggtgtcc tgctgcccga   70800 aacgacggg gtgcccacgc cgctcgcgga gtggccgccc gccggggcgg aacgcgtcgg   70860
cgtcgaggcg ctgtacgacg agctcgcgaa cgcgggcctc gaatacggcc cggcgttcca   70920
aggactccgc gccgcatggc gtcgcgagaa cgaggtcttc gccgagatcg acctgcccga   70980
agcccagacc ggcgaggctc cggccttcgg cctgcatccc gcgttgctgg acggcgcgct   71040
ccacgggatc gcgctgggtg tgcttcccga cgacggggag ggactccggc ttccgttcgc   71100
gttctccggg gtccggctgt ggtcgcgggg cgcgacggca ctgcgagtgc ggctgcgacc   71160
```

```
ggcggcggac ggggtcgcgc tgaccgtcgc cgacggtgag ggcctaccgg tcgccgacgt    71220
ggacggtctg ctgctgcggc cggtgtccgt gtccggcctc ggtgggtatc gagagtccct    71280
gttcggcctg gattgggtgc ccgcgggcgc gaccgaaccg cacgacgcga cggtgtggca    71340
ctgcgaatcc ggggatctcc gcaccgtgct gggtgcggcg ctcgaacgcg tccggacgtg    71400
gctcgacgag cctggggacg gtccgctcgt ggtggccacg cgaggcggga tcgcgaccga    71460
acgcccggat ccggtgacgg ccgcggtatg ggggctcgtg cgctcggcgc agtcggagca    71520
ccccggacgg ttcgtgctcg tggacggcga cgtcccggcg gcgctgcccg ccggggaatc    71580
gcaggtcgtg gtccgtgacg gggtcggctt cgtcccgagg ctcgtccggg tcccggaacc    71640
cggcccggcc cggccgtgga gcgacgatga tgtcgtgctg atcaccggag gcaccggcct    71700
cctcggtgcg gccgtcgcga aacacctggt ggtgacgcac ggcgtccgtt cgctggtgct    71760
gctgagccgt tccggtgctt ccgcgcccgg tgcggcggca ctggcggacg aactcaccgg    71820
gatgggtgcc gaggtccgga tcctcgcgtg cgacgcggcc gaccgggagg cgctgcgcca    71880
ggtgctggcc gcgcatccgg tgaccggtgt cgtgcacgcc gccggtgtcc tcgacgacgg    71940
gctgatcacc gcgcagaccc ccgaacggct cgaccgggtg ctcgcgccga aggtggacgc    72000
cgcggtgaac ctgcacgaac tcttgcccga tgccgcgccg ttcgtgatgt tctcctcggc    72060
ggccggggtc ttcgggaatc cggggcagtc cggttacgcc gcagccaacg ctttcgtgga    72120
cgccctggtg gaacgccgcc gcgcggacgg cgccgccgcg gcgtcactgg cgtggggcct    72180
gtgggcgacc accagcgcca tgaccggttc cgccgacgtg gaccggatgg cgagggcggg    72240
actcaccgga ctgtccacag aggagggtct cgacctgctc gacgccgcgc tcgccaccgg    72300
gcggacgctg accgtcccca tggggctcga cctcgccgcg ctccgcgccg aggaggtgcc    72360
gccgttgctg cgcgggctcg tccgcgctcg tgcccggcgc gcgcccgacg gcggcggcgc    72420
gttccgcgcc cggctcgccg gactcgacgc ggacggccgc gacgcggaga tcctggaact    72480
ggtgcgcggt caggtcgcgg ccgtcctcgg ccacgacggt gccgacgcga tcgacgccgg    72540
tgtcgcgttc ctcgaactcg gcttcgactc gctcaccgcc gtcgacctgc gtaaccggct    72600
ggcggcctcg accggcctgc ggctcccgcc gtcgctggtg ttcgaccacc cgacgccgct    72660
cgccgtcgcg gaacggatct ccggtgactt cgcggttccc gaccaggccg agccggtgcc    72720
agcggccacc gacgtcttcg gcgcgatgtt cgcccgcgcg atcgaactcg acgaggtcgc    72780
gcagttcgtc gcgctagccg cgcaggcttc gcgctaccgg ccgtcgttca ccgtcgaaac    72840
cgcgcgggaa cagaacctgc aacccgtccg gctcgcgaag ggcccgtccg gccccgaact    72900
ggtctgcgtc ccctccctgc tggccggctc ggggcgcac gaatacgcgc ggttcgcggc    72960
gtcgttccgg gacgtgcagg acgtttccgt cgttccggtg cccggtttcg gccacgggca    73020
gccgctgccg gactcgatcg aggcggtcct ccacgcgcag gcggacgcga tcctccgcga    73080
aggcggtgac ccggtggtcc tggtggccca ctcctctggc ggcccgctcg cccacgcgct    73140
ggctcggcac ctggaggaag cgggctccgg gccgcgcgcg ctcgtgctga tcgacgtcta    73200
cccgcaggac gagcacgcgc tggacggcat ccgtgaccgg ctcagcggcg gcctcggcga    73260
cgacacgcgg ctcaccgcca tgggcgccta cctgcgcttg ttcgccgact atgtgcccgc    73320
gccgaccggt gtgccgactc tgctcgtgcg ggcgtcggag cccctggaag cgtggcgtga    73380
ccggaccgaa tggcggtccg gctgggcctt gccgcacgac acggtggacg tcgagggcga    73440
tcacttcacg atgctggagc ggcatgccgg gacgaccgcc gaggccgtcc gggagtggct    73500
```

-continued

```
gggcggctg gggtaacggc tgcgcgtgaa ccggtcgtgg gctgaaggct cccttcgccg    73560
cgtcttaagc ggtgaaagga gccttcgccc gcggcacag                          73599
```

<210> SEQ ID NO 25
<211> LENGTH: 162
<212> TYPE: PRT
<213> ORGANISM: Amycolatopsis orientalis

<400> SEQUENCE: 25

```
Val Asp Thr Ser Thr Leu Ile Asn Ile Ala Val Ala Ile Ala Val Val
1               5                   10                  15

Val Tyr Val Ile Tyr Gln Arg Met Ser Trp Lys Pro Leu Glu Asn Val
            20                  25                  30

Glu Ile Trp Gly Gly Pro Leu Thr Leu Val Ala Ile Gly Val Ile Gln
        35                  40                  45

Met Arg His Leu Asp Thr Thr Ile Ser Val Thr Asp Ile Val Phe Leu
    50                  55                  60

Gly Val Gly Leu Leu Val Ser Leu Leu Gly Gly Ala Ala Met Gly Ala
65                  70                  75                  80

Met Thr Gln Leu Gln Arg Arg Gly Asp Lys Val Tyr Gln Arg Ile Gly
                85                  90                  95

Val Val Gly Leu Ala Val Trp Val Gly Leu Leu Val Arg Gly Val
            100                 105                 110

Leu Gly Val Ile Gly His Phe Ala Gly Ala Thr Leu Thr Ser Gly Gly
        115                 120                 125

Gly Thr Ile Leu Leu Ser Leu Gly Ala Asn Leu Met Ala Met Thr Leu
    130                 135                 140

Val Leu Ser Ala Arg Leu Gly Gly Ala Lys Val Pro Gly Gly Ser Pro
145                 150                 155                 160

Gln Arg
```

<210> SEQ ID NO 26
<211> LENGTH: 486
<212> TYPE: DNA
<213> ORGANISM: Amycolatopsis orientalis

<400> SEQUENCE: 26

```
gcgctgcggg ctgccgccgg ggaccttggc gccgccgagg cgggcggaca gcacgagcgt    60
catcgccatc aggttcgcgc ccagcgagag caggatggtg ccgccgccgg aggtcagcgt   120
cgcgccggcg aagtgcccga tcacgccgag cacgccgcgg acgagcagca ggcccaccca   180
gacggcgagg ccgaccacgc cgatccgctg gtagacctttg tcgccgcgcc gctgcagctg   240
cgtcatcgcg cccatcgcgg cgccgccgag gagcgagacc agcaggccca ccccgaggaa   300
gacgatgtcg gtcacgctga tggtggtgtc cagatgccgc atctggatga ccccgatggc   360
gaccagggtg agcggcccgc cccagatctc cacgttctcc agcggcttcc agctcatgcg   420
ctggtagatc acgtagacga cgacggcgat ggcgaccgcg atgttgatca gcgtgctggt   480
gtccac                                                              486
```

<210> SEQ ID NO 27
<211> LENGTH: 441
<212> TYPE: PRT
<213> ORGANISM: Amycolatopsis orientalis

<400> SEQUENCE: 27

Val Ala Val Val Gly Ala Gly Tyr Val Gly Leu Thr Thr Ala Ala Cys

-continued

```
1               5                   10                  15
Leu Ala Ser Leu Gly His Arg Val Arg Cys Thr Asp Ser Asp Arg Gly
                20                  25                  30

Lys Leu Ala Arg Leu Lys Arg Gly Glu Val Asp Ile Leu Glu Lys Gly
                35                  40                  45

Leu Pro Gly Leu Val Ala Glu Gly Ile Ala Ala Gly Arg Leu Gly Phe
 50                  55                  60

Val Glu Ser Ala Ala Glu Ala Val Glu Thr Ala Glu Ala Val Phe Leu
 65                  70                  75                  80

Cys Val Pro Thr Pro Met Gly Glu Gly Met Ala Asp Leu Ser Ala
                85                  90                  95

Val Ile Asp Val Ala Thr Lys Val Arg Asp Val Leu Ser Pro Gly Cys
                100                 105                 110

Val Leu Val Asn Lys Ser Thr Val Pro Val Gly Thr Ala Ala Arg Val
                115                 120                 125

Ala Ala Leu Leu Gly Arg Asp Asp Val Ala Val Ser Asn Pro Glu
 130                 135                 140

Phe Leu Arg Glu Gly Thr Ala Val His Asp Phe Leu Asn Pro Asp Arg
 145                 150                 155                 160

Ile Val Val Gly Ser Asp Thr Arg Gly Pro Ala Glu Arg Val Ala Ala
                165                 170                 175

Leu Tyr Ala Arg Leu Gly Ala Pro Thr Val Leu Thr Asp Ala Ala Ser
                180                 185                 190

Ala Glu Met Val Lys Tyr Ala Ala Asn Cys Phe Leu Ala Thr Lys Leu
                195                 200                 205

Ser Tyr Val Asn Ala Ile Ala Glu Leu Cys Glu Arg Leu Gly Ala Asp
 210                 215                 220

Ile Gly Asp Val Thr Glu Gly Met Gly Tyr Asp Arg Arg Ile Gly Pro
 225                 230                 235                 240

Thr Phe Leu Ser Pro Gly Pro Gly Trp Gly Ser Cys Leu Pro Lys
                245                 250                 255

Asp Thr Met Ala Leu Lys Gln Val Ala Glu Val Ala Gly Phe Glu Phe
                260                 265                 270

Gly Leu Leu Asp Glu Val Ile Ser Gly Asn Ala Lys Gln Ala Ser Arg
                275                 280                 285

Val Val Glu Arg Ile Ala Val Ala Cys Gly Leu Asp Ala Asp Ala Asp
 290                 295                 300

Leu Thr Gly Leu Arg Ile Gly Leu Leu Gly Leu Thr Phe Lys Ala Gly
 305                 310                 315                 320

Thr Asn Asp Leu Arg Asp Ser Pro Ala Leu Ser Val Ala Arg Leu Leu
                325                 330                 335

Ala Glu Arg Gly Ala Glu Leu Thr Gly Tyr Asp Pro Gly Leu Thr Gly
                340                 345                 350

Ala Glu Pro Pro Ile Pro Gly Val Arg Val Asp Pro Tyr Tyr
                355                 360                 365

Ile Ala Lys Asp Ala His Ala Leu Val Leu Thr Asp Trp Pro Gln
 370                 375                 380

Phe Arg Ala Leu Asp Trp Pro Arg Ile Ala Gly Leu Glu Gly Pro
 385                 390                 395                 400

Val Val Ile Asp Thr Arg Asn His Leu Asp Pro Asp Ala Leu Ser Arg
                405                 410                 415

Ala Gly Ile Ala Trp Arg Gly Phe Gly Arg Pro Pro Val Asp Pro Val
                420                 425                 430
```

-continued

Arg Thr Pro Ser Leu Asp Pro Val Pro
        435                 440

<210> SEQ ID NO 28
<211> LENGTH: 1326
<212> TYPE: DNA
<213> ORGANISM: Amycolatopsis orientalis

<400> SEQUENCE: 28

```
gtggccgtcg tcggcgccgg atacgtcggg ctgaccaccg cggcgtgtct cgcctcgctc    60
gggcaccggg tccgatgcac cgattccgat cgcggcaaat ggcccggct caaacgaggc    120
gaggtcgaca tcctggaaaa gggcctgccc ggtctggtcg ccgagggaat cgccgccgga   180
cggctcggtt tcgtcgagtc ggccgcggag gccgtcgaga ccgcggaggc cgtgttcctt   240
tgtgtaccca ccccgatggg cgagggcggg atggccgatc tgtcggccgt catcgacgtc   300
gcgaccaagg tccgtgacgt gctttcgccg ggttgtgtac tggtgaacaa gtcgaccgtg   360
ccggtcggga ccgcggccag gtcgccgcg ctgctcggcc gggacgacgt cgcggtggtg   420
agcaatccgg agttcctccg cgagggcacc gccgtccacg acttcctcaa cccggaccgg   480
atcgtcgtcg gttccgacac gcgcggcccg gcggaacggg tcgcggcgct ctacgcccgg   540
ctcggcgccc cgacggtgct gaccgacgcg gcgagcgcgg agatggtcaa gtacgccgcc   600
aactgtttcc tcgcgacgaa actgtcctat gtgaacgcca tcgccgaact gtgcgagcgg   660
ctcggcgccc acatcggcga cgtcaccgaa ggcatgggct acgaccgccg gatcggcccg   720
acgttcctct cgccggggcc gggctggggc ggttcctgcc tgcccaagga caccatggcg   780
ctcaaacagg tcgccgaggt cgcgggtttc gagttcggcc tgctcgacga ggtcatctcg   840
ggcaacgcga acaggcgtc ccgagtggtc gaacggatcg ccgtcgcctg tggactcgac   900
gcggacgcgg acctcaccgg cctgcggatc ggcctgctcg gctgaccttc aaggcgggc   960
accaacgacc tccgggattc cccggcgctc agcgtcgccc ggctgctggc cgagcgcggc  1020
gcggagctga ccggatacga ccccggtctc accggcgccg aacctccgat ccccggcgtc  1080
cgggtcgtcg acgaccccta ctacatcgcg aaggacgcgc acgcgctcgt cctgctgacc  1140
gattggccgc agttccgtgc cctcgactgg ccgcggatcg ccggtctgct cgaaggaccg  1200
gtcgtcatcg acacccgcaa ccacctcgac cccgacgcgc tcagccgggc cggcatcgcc  1260
tggcgcgggct tcggcaggcc cccggtcgac ccggtgcgca cgccgtccct cgaccccgtt  1320
ccctga                                                              1326
```

<210> SEQ ID NO 29
<211> LENGTH: 407
<212> TYPE: PRT
<213> ORGANISM: Amycolatopsis orientalis

<400> SEQUENCE: 29

Met Arg Val Leu Cys Thr Val Thr Gly Ser Gln Gly His Ala Arg Ala
1               5                   10                  15

Val Leu Pro Leu Ala Arg Ala Ala Lys Ala Gly His Glu Val Leu
            20                  25                  30

Val Val Thr Pro Pro Glu Leu Ala Asp Val Phe Glu Pro Gly Leu Met
        35                  40                  45

Arg Ile Glu Pro Val Leu Pro Gly Met Val Glu Ala Ile Gly Arg Met
    50                  55                  60

Val Gln Glu Arg Gln Glu Ala Glu Ala Ala Gly Thr Pro Arg Arg Val

```
                65                  70                  75                  80
Leu Asp Thr Arg Glu Gln Leu Ile Ala Thr Ala Ser Gly Pro His Val
                            85                  90                  95
Thr Thr Ala Tyr Gln Lys Leu Tyr Pro Leu Ala Lys Glu Phe Gln Pro
                100                 105                 110
Asp Ile Val Leu Arg Asp Gly Ala Glu Leu Ser Gly Ala Leu Val Ala
                115                 120                 125
Glu Gln Leu Gly Val Pro Tyr Ile Ser Ala Pro Ser Gly Ala Gly Asn
            130                 135                 140
Leu Ile Asp Pro Ala Gly Leu Val Glu Pro Leu Asn Glu Arg Arg Gln
145                 150                 155                 160
Glu Leu Gly Leu Ala Ala Glu Pro Asp Ala Gly Met Val His Arg Tyr
                165                 170                 175
Gly Arg Phe Asp Cys Leu Pro Ala Asp Thr Ser Phe Ala Ala Phe Asp
                180                 185                 190
Leu Pro Thr Pro Phe Thr Tyr Arg Gln Pro Ser Glu Val Ala Thr Gly
                195                 200                 205
Glu Val Leu Pro Pro Glu Ile Ala Ala Leu Pro Ala Asp Arg Pro Leu
            210                 215                 220
Val Leu Ala Ser Val Gly Thr Ala Leu Pro Met Leu Gly Ala Phe Lys
225                 230                 235                 240
Ala Phe Gly Ile Asp Pro Pro Glu Glu Met Glu Asp Pro Asp Val Thr
                245                 250                 255
Val Arg Ala Leu Ile Glu Gly Leu Ser Ser Val Asp Cys Ser Ala Val
                260                 265                 270
Val Ala Thr Ala Gly Phe Pro Ile Gly Asp Val Glu Val Gly Asp Asn
                275                 280                 285
Val Leu Val Val Glu Arg Met Pro Gln Pro Leu Leu Leu Glu Cys Ala
            290                 295                 300
Gln Leu Phe Leu Thr His Ala Gly Tyr Asn Ser Ile Arg Glu Ala Leu
305                 310                 315                 320
Arg Ala Gly Val Pro Met Ala Thr Leu Pro Gln Phe Gly Asp Gln Pro
                325                 330                 335
His Asn Ala Arg Arg Ile Glu Glu Leu Gly Phe Gly Lys Gln Ile Pro
                340                 345                 350
Ala Thr Thr Pro Glu Ala Val Ala Glu Thr Cys Arg Ala Val Leu Ala
                355                 360                 365
Asp Ala Thr Ile Ala Ala Thr Val Ala Arg Ala Gln Arg Arg Ser Leu
            370                 375                 380
Thr Met Pro Gly Val Glu Ser Ala Val Ala His Leu Glu Glu Leu Ala
385                 390                 395                 400
Gly Arg Ala Ala Gly Thr Glu
                    405

<210> SEQ ID NO 30
<211> LENGTH: 1224
<212> TYPE: DNA
<213> ORGANISM: Amycolatopsis orientalis

<400> SEQUENCE: 30
atgcgggttt tgtgcaccgt gaccggctcg cagggccacg cacgggcggt gctgcccttg     60
gccagggcgg cggcgaaggc gggccacgaa gtgctcgtcg tgaccccgcc ggaactggcc    120
gacgtcttcg aacccgggct gatgcggatc gaaccggtgc tcccggggat ggtcgaggcg    180
```

-continued

```
atcgggcgga tggtccagga acgccaggag gccgaagcgg ccgggacccc gcgccgggtg    240
ctggacacgc gcgaacagct gatcgccacc gcgagcggcc cgcacgtcac caccgcctac    300
cagaagctct acccactggc caaggagttt cagcccgaca tcgtgctgcg cgacggcgcg    360
gagctgtccg gcgcgctggt cgccgagcag ctcggcgtgc cctacatcag cgcgccgtcg    420
ggtgcgggca acctgatcga cccggcgggc ctggtggagc cgctgaacga gcgccgccag    480
gagctggggc tcgccgccga acccgacgcc gggatggtgc accgctacgg ccgtttcgac    540
tgcctgcccg ccgacacctc gttcgccgcc ttcgatctgc cgacgccgtt cacctaccgc    600
cagccgtcgg aggtggccac cggtgaggtc ctgccgccgg agatcgccgc attgcccgcg    660
gaccggccgc tggtgctcgc ctcggtcggc accgcgctgc ccatgctcgg cgcgttcaag    720
gccttcggca tcgacccgcc ggaggagatg gaagatcccg acgtcacggt gcgcgccctg    780
atcgaaggac tgtccagtgt ggactgttcg gcggtggtgg cgacggccgg gttcccgatc    840
ggcgacgtcg aggtcggcga caacgtgctc gtcgtcgaac ggatgccgca gccgctgctg    900
ctcgaatgcg cgcagctgtt cctgacccac gccgggtaca acagcatccg cgaggcgctg    960
cgtgccggag tcccgatggc cacgctgccg cagttcggcg accagccgca caacgcgcgc   1020
cgcatcgagg agctcgggtt cggcaagcag atccccgcca ccacgccgga agcggtcgcc   1080
gagacctgcc gcgcggtgct ggccgacgcc acgatcgcgg ccaccgtcgc acgggcccaa   1140
cggcggagcc tgaccatgcc gggcgtggaa tccgccgtgg cccatctcga agagctcgcc   1200
ggccgggccg cgggaacgga gtag                                         1224
```

<210> SEQ ID NO 31
<211> LENGTH: 521
<212> TYPE: PRT
<213> ORGANISM: Amycolatopsis orientalis

<400> SEQUENCE: 31

```
Val Gln Ile Asp His Tyr Val Ser Gln Leu Leu Asp Val Leu Ser Thr
 1               5                  10                  15

Arg Pro Asp Glu Ile Ala Leu Arg Tyr Gly Asp Glu Ala Leu Thr Ser
            20                  25                  30

Ala Glu Phe Ala Ala Ala Ile Thr Gly Ala Ala Ala Leu Arg Asp
        35                  40                  45

Arg Gly Thr Gly Glu Gly Gly Val Ala Leu Leu Thr Val Gly Asn
    50                  55                  60

Ser Pro Ala Thr Leu Ile Gly Arg Tyr Ala Ala Asn Leu Ile Gly Ala
65                  70                  75                  80

Thr Val Val His Leu Arg Gly Ile Asn Ala Ala Asp Pro Leu Asp Glu
                85                  90                  95

Leu Pro Val Ala Thr Gln Val Glu Ile Val Asp Asp Thr Gly Thr Thr
            100                 105                 110

Val Leu Leu Thr Asp Ala Ala Asn Leu Asp Arg Ala Arg Lys Ile Arg
        115                 120                 125

Asp Ala Met Ala Glu Pro Ala Ala Leu Ala Ala Phe Gly Asp Phe Gly
    130                 135                 140

Asp Asp Val Ala Asp Leu Thr Gly Thr Ala Ser Glu Val Glu Pro Arg
145                 150                 155                 160

Ala Glu Gly Thr Ala Val Leu Thr Tyr Thr Ser Gly Thr Thr Gly Arg
                165                 170                 175

Pro Lys Gly Ile Gly Arg Gly Phe Gly Gly Leu Gly Ala Val Val Thr
            180                 185                 190
```

```
Lys Ala Arg His Met Thr Glu Arg Cys Thr Met Leu Val Thr Thr Pro
            195                 200                 205
Leu Ser His Ser Val Ser Ser Thr Val Asp Asp Ala Val Ala Ser Gly
        210                 215                 220
Gly Met Ile Val Leu His Glu Gly Phe Asp Ala Gly Ala Val Leu Glu
225                 230                 235                 240
Ala Val Glu Arg His Arg Val Asn Arg Val Tyr Leu Ala Thr Pro Gln
                245                 250                 255
Leu Tyr Asp Leu Leu Asp His Pro Ala Leu Gly Thr Thr Asp His Ser
            260                 265                 270
Ser Leu Arg Glu Leu Tyr Tyr Gly Gly Ser Pro Ala Ser Pro Val Arg
        275                 280                 285
Leu Ser Arg Ala Ala Glu Val Phe Gly Ala Lys Leu Ile Gln Ile Tyr
        290                 295                 300
Gly Thr Thr Glu Ser Trp Val Ile Ala Ala Leu Ser Pro Glu Glu His
305                 310                 315                 320
Leu Lys Pro Glu Leu Leu Thr Thr Val Gly Lys Ala Val Pro Phe Val
                325                 330                 335
Gln Val Gly Ile Arg Asp Pro His Val Arg His Glu Leu Pro Ala Gly
            340                 345                 350
Lys Thr Gly Glu Ile Cys Val Arg Ser Pro Met Met Met Asp Gly Tyr
        355                 360                 365
Trp Lys Arg Pro Asp Leu Thr Ser Lys Val Leu Ile Asp Gly Trp Leu
    370                 375                 380
His Thr Gly Asp Val Gly Tyr Leu Asp Glu Asn Gly Tyr Leu Tyr Leu
385                 390                 395                 400
Val Asp Arg Leu Ala Asp Met Ile Lys Thr Asn Gly Ile Lys Val Tyr
                405                 410                 415
Pro Ala Glu Val Glu Asn Ala Leu Leu Ala His Pro Asp Val Ala Gln
            420                 425                 430
Ala Ala Val Phe Gly Val Ala Asp Glu Asp Asn Val Glu Tyr Met His
        435                 440                 445
Ala Ile Ala Val Pro Arg Arg Gly Arg Asp Val Asp Pro Ala Asp Leu
450                 455                 460
Ala Ala His Val Ala Arg Val Leu Ser Pro Ser His Val Pro Ala Glu
465                 470                 475                 480
Ile Arg Leu Arg Ala Glu Leu Pro Leu Thr Asp Ala Gly Lys Pro Asp
                485                 490                 495
Lys Leu Arg Leu Arg Glu Glu Ala Lys Pro Ala Thr Lys Ser Ser His
            500                 505                 510
Ala Glu Pro Glu Ser Glu Leu Thr Ser
        515                 520
```

<210> SEQ ID NO 32
<211> LENGTH: 1563
<212> TYPE: DNA
<213> ORGANISM: Amycolatopsis orientalis

<400> SEQUENCE: 32

| | | | | | |
|---|---|---|---|---|---|
| gtgcagatcg | accactacgt | cagccagctg | ctggacgtgc | tttccacccg | cccggacgag | 60 |
| atcgcgttgc | gctacggcga | cgaagcgctg | acgtcggcgg | aattcgccgc | ggcgatcacc | 120 |
| ggtgccgccg | ccgcgctgcg | cgaccgcggg | accggcgaag | gcggggtggt | ggccctgctg | 180 |
| accgtgggga | acagcccggc | gacgctgatc | ggccggtacg | ccgccaacct | gatcggcgcc | 240 |

```
accgtggtgc acctgcgcgg gatcaacgcc gccgatccgc tggacgaact cccggtcgcc    300
acgcaggtcg agatcgtcga cgacaccggc accaccgtcc tgctcaccga cgcggcgaac    360
ctcgaccggg ccaggaagat ccgcgacgcc atggcggaac cggcggcact ggcggctttc    420
ggggacttcg gtgacgacgt cgccgacctc accgggaccg cgagcgaggt cgagccgcga    480
gccgagggca ccgccgtgct gacctacacc agtgggacca ccggcaggcc caagggcatc    540
ggccgcgggt tcggcgggct gggcgcggtg gtcaccaagg cccggcacat gaccgagcgc    600
tgcacgatgc tggtcaccac gccgctcagc cattccgtct cgtccacagt ggacgacgcg    660
gtcgcctccg gcgggatgat cgtcctgcac gagggggttcg acgccggcgc cgtgctcgaa    720
gccgtggaac gccaccgggt caaccgggtc tacctggcca ccccgcagct ctacgacctg    780
ctcgaccatc cggcactggg caccaccgac cattccagcc tgcgcgagct gtactacggc    840
gggagcccgg cctccccggt gcggctctcc cgggccgcgg aggtgttcgg cgcgaagctg    900
atccagatct acggcaccac cgaaagctgg gtgatcgccg cgctttcgcc ggaagagcac    960
ctgaaaccgg aactgctcac cacggtcggc aaggcggtcc cgttcgtcca ggtcggcatc   1020
cgcgacccgc atgtgcggca cgagctgccc gccgggaaga ccggggagat ctgcgtccgg   1080
tcgccgatga tgatggacgg ttactggaag cggcccgacc tgacctcgaa ggtcctcatc   1140
gacggctggc tgcacaccgg cgacgtcggc tacctcgacg agaacggcta cctgtacctg   1200
gtcgaccggc tcgccgacat gatcaagacc aacggcatca aggtgtatcc ggccgaggtc   1260
gagaacgcgc tgctggccca tccggacgtc gcgcaggccg cggtgttcgg ggtcgccgac   1320
gaggacaacg tcgagtacat gcacgcgatc gcggtgccac gccgcggcag ggacgtggat   1380
cccgccgacc ttgccgcgca tgtcgcgcgg gtgctgtccc cgagccacgt gccggcggag   1440
atccggctcc gcgccgagct tccgctgacc gacgcgggga agccggacaa gctccgcctc   1500
cgcgaagagg cgaaacccgc caccaagtcc agccacgccg agccagagag cgagttgacg   1560
tca                                                                 1563
```

<210> SEQ ID NO 33
<211> LENGTH: 402
<212> TYPE: PRT
<213> ORGANISM: Amycolatopsis orientalis

<400> SEQUENCE: 33

```
Met Thr Thr Tyr Leu Glu Ser Phe Gln Arg Thr Leu Gln Gly Glu Val
1               5                   10                  15

Leu Gln Lys Arg Asp Phe Leu Glu Ile Gly Arg Gln Ala Gly Arg Phe
            20                  25                  30

Pro Ala Ala Ser Arg Tyr Glu Glu Ala Glu Ala Val Ala Glu Ile Asn
        35                  40                  45

Val Trp Cys Ser Asn Asp Tyr Leu Gly Met Gly Gln His Pro Asp Val
    50                  55                  60

Leu Ser Ala Met Lys Glu Ala Val Glu Arg Phe Gly Ala Gly Ala Gly
65                  70                  75                  80

Gly Ser Arg Asn Ile Ala Gly Thr Asn His Tyr Val Ala Leu Glu
                85                  90                  95

Arg Glu Leu Ala Glu Leu His Gly Lys Glu Asp Ala Leu Leu Phe Thr
                100                 105                 110

Ser Gly Tyr Thr Ala Asn Asp Gly Ser Leu Thr Val Leu Ala Gly Arg
            115                 120                 125
```

-continued

```
Pro Glu Asp Cys Ile Val Phe Ser Asp Glu Lys Asn His Ala Ser Ile
    130                 135                 140
Ile Asp Gly Leu Arg His Ser Gly Val Glu Lys Lys Ile Phe Arg His
145                 150                 155                 160
Asn Asp Val Ala His Leu Ala Glu Leu Leu Ala Ala Pro Ala Asp
                165                 170                 175
Arg Pro Lys Met Ile Val Phe Glu Ser Val Tyr Ser Met Asn Gly Asp
            180                 185                 190
Ile Ala Pro Leu Ala Glu Phe Ala Leu Ala Lys Gln Tyr Asp Ala
        195                 200                 205
Met Thr Tyr Val Asp Glu Val His Ala Val Gly Met Tyr Gly Pro Glu
    210                 215                 220
Gly Ala Gly Ile Ala Ala Arg Glu Gly Ile Ala Asp Glu Phe Thr Val
225                 230                 235                 240
Val Met Gly Thr Leu Ala Lys Gly Phe Gly Thr Thr Gly Gly Tyr Ile
                245                 250                 255
Ala Gly Pro Ala Ala Leu Ile Asp Ala Val Arg Thr His Ser Arg Ser
            260                 265                 270
Phe Ile Phe Thr Thr Ala Leu Pro Pro Ala Val Ala Gly Ala Leu
        275                 280                 285
Ala Ala Val Arg His Leu Arg Ser Ser Glu Arg Glu Arg Glu Ile Leu
    290                 295                 300
Ala Asp Asn Ala Gln Leu Leu His Lys Leu Leu Ala Glu Arg Gly Ile
305                 310                 315                 320
Pro Phe Leu Ser Asp Glu Ser His Ile Val Ser Ile Leu Val Gly Asp
                325                 330                 335
Asp Ala Leu Cys Lys Lys Val His Glu Leu Leu Gln Arg His Gly
            340                 345                 350
Ile Tyr Ile Gln Ser Ile Asn Ala Pro Ser Val Pro Phe Gly Gln Glu
        355                 360                 365
Ile Leu Arg Thr Ala Pro Ser Ala Val His Thr Gly Ser Asp Val Gln
    370                 375                 380
Lys Met Val Glu Ala Leu Asp Gln Ile Trp Leu Asp Leu Gly Leu Pro
385                 390                 395                 400
Arg Gly
```

<210> SEQ ID NO 34
<211> LENGTH: 1206
<212> TYPE: DNA
<213> ORGANISM: Amycolatopsis orientalis

<400> SEQUENCE: 34

| | | |
|---|---|---|
| atgaccacct acctggagtc cttccagcgc accctgcaag gcgaagtgct gcagaaacgc | 60 |
| gacttcctgg agatcgggcg gcaggcgggc cggttcccgg cggccagccg gtacgaggag | 120 |
| gccgaagcgg tcgccgagat caacgtctgg tgcagcaacg actacctcgg catgggccag | 180 |
| cacccggacg tgctctccgc gatgaaggag gccgtcgagc ggttcggcgc cggggcgggc | 240 |
| ggttcacgca acatcgcggg caccaaccac taccacgtgg cgctcgaacg cgaactggcc | 300 |
| gaactgcacg gcaaagagga cgcgctgctc ttcacctccg ctacaccgc caacgacggt | 360 |
| tcgctgaccg tgctggcggg ccgccccgag gactgcatcg tgttctccga cgagaagaac | 420 |
| cacgcctcca tcatcgacgg gttgcggcac agtggtgtgg agaagaagat cttccgccac | 480 |
| aacgacgtcg cccatctggc cgagctgctc gccgccgccc cggcggaccg gccgaagatg | 540 |

-continued

```
atcgtgttcg agtcggtcta ctcgatgaac ggcgacatcg cgccgctggc cgaattcgcc    600
gcgttggcga agcagtacga cgccatgacc tatgtggacg aagtgcacgc cgtcggaatg    660
tacgggcccg aaggtgccgg gatcgccgcg cgcgagggga tcgccgacga gttcaccgtc    720
gtgatgggca cgctggccaa gggtttcggc accaccggcg atacatcgc cgggcccgcc    780
gcgctgatcg acgccgtgcg cacgcattcg cgatcgttca tcttcaccac cgcgctgccg    840
cccgccgtgg ccgccggagc gctcgccgcc gtccggcacc tgcgttcgtc ggagcgggag    900
cgcgagatcc tcgccgacaa cgcgcagctg ctgcacaaac tgctcgccga acgcggcatc    960
cccttcctct cggacgagtc gcatatcgtg tcgatcctgg tcggcgacga cgcgctctgc   1020
aagaaggtgc acgaactcct gttgcagcgg cacgggatct acatccagtc gatcaacgcg   1080
ccgagtgtcc cgttcggaca ggagatcctg cgcacggccc gtcggcggt gcacaccggc   1140
agcgacgtgc agaagatggt cgaggcgctg gaccagatct ggctggatct cggtctgccg   1200
cgcggc                                                               1206
```

<210> SEQ ID NO 35
<211> LENGTH: 511
<212> TYPE: PRT
<213> ORGANISM: Amycolatopsis orientalis

<400> SEQUENCE: 35

```
Val Ser Leu Ser Leu Ala Ala Val Leu Ala Asp Ser Ala Gly Arg Arg
 1               5                  10                  15
Pro Asp His Pro Ala Leu Val Phe Asp Gly Glu Pro Phe Ser Tyr Arg
            20                  25                  30
Glu Leu Trp Ala Gly Ala Lys Arg Tyr Ala Ser Ala Leu Arg Asp Gln
        35                  40                  45
Gly Val Ala Ala Gly Asp Arg Val Leu Leu Leu Pro Asn Thr Pro
    50                  55                  60
Glu Phe Pro Met Val Tyr Phe Gly Ala Leu Ala Leu Gly Ala Val Val
65                  70                  75                  80
Val Pro Val His Thr Leu Leu Val Ala Glu Glu Ile His Tyr Ile Leu
                85                  90                  95
Thr Asp Cys Asp Ala Arg Val Leu Ile Cys Gly Ala Ala Leu Leu Glu
            100                 105                 110
Gln Gly Gly Glu Ala Ala Asp Ala Ala Gly Val Glu Val Leu Thr Met
        115                 120                 125
Leu Glu Asp Ser Asp Thr Gly Arg Val Arg Leu Asp Val Leu Ala Gly
    130                 135                 140
Asp Ala Ala Glu Ile Glu Arg Tyr Glu Pro Arg Glu Pro Ser Asp Leu
145                 150                 155                 160
Ala Leu Ile Leu Tyr Thr Ser Gly Thr Thr Gly Lys Pro Lys Gly Ala
                165                 170                 175
Met Leu Thr His Leu Ser Ile Val Leu Asn Val Ser Thr Thr Met Leu
            180                 185                 190
Ser Pro Phe Asp Phe His Ala Asp Asp Val Leu Leu Gly Cys Leu Pro
        195                 200                 205
Leu Phe His Thr Phe Gly Gln Ile Cys Gly Met Ala Thr Cys Phe Arg
    210                 215                 220
Ala Gly Ala Thr Met Val Leu Met Ser Arg Phe Asp Ala Arg Ala Ala
225                 230                 235                 240
Leu Glu Leu Met Val Glu Gln Asn Cys Ser Leu Phe Met Gly Val Pro
                245                 250                 255
```

-continued

```
Thr Met Tyr Val Ala Leu Leu Glu Ala Ala Glu Asp Glu Pro Arg Arg
            260                 265                 270
Pro Lys Leu Asp Arg Ala Phe Ser Gly Gly Ser Leu Pro Val Ala
        275                 280                 285
Leu Leu Glu Arg Phe Glu Ala Val Phe Asp Cys Pro Ile Tyr Glu Gly
        290                 295                 300
Tyr Gly Leu Thr Glu Thr Ser Pro Val Val Ala Tyr Asn Gln Arg Ala
305                 310                 315                 320
Trp Pro Thr Arg Ala Gly Thr Val Gly Lys Pro Ile Trp Gly Val Asp
                325                 330                 335
Val Ala Ile Ala Arg Ala Glu Thr Glu Asp Arg Ile Glu Pro Val Pro
            340                 345                 350
Pro Gly Glu Val Gly Glu Ile Val Val Arg Gly His Asn Val Met Ala
        355                 360                 365
Gly Tyr Leu Asn Arg Pro Glu Ala Thr Ala Ala Ile Val Asp Gly
        370                 375                 380
Trp Phe Arg Ser Gly Asp Leu Gly Phe Leu Asp Asp Gly Tyr Leu
385                 390                 395                 400
Ser Ile Val Asp Arg Lys Lys Asp Met Ile Leu Arg Gly Gly Tyr Asn
                405                 410                 415
Val Tyr Pro Arg Glu Ile Glu Glu Val Leu Ala Arg His Pro Ala Ile
            420                 425                 430
Ala Gln Val Ala Val Gly Val Pro Asp Glu Arg Tyr Gly Glu Glu
        435                 440                 445
Ile Cys Ala Val Val Ala Ala Ser Asp Arg Glu Pro Gly Pro Glu
    450                 455                 460
Leu Ala Ala Glu Leu Val Ala Trp Ser Lys Lys Arg Val Ala Ala Tyr
465                 470                 475                 480
Lys Tyr Pro Arg Arg Val Glu Phe Leu Asp Ala Met Pro Leu Gly Pro
                485                 490                 495
Ser Gly Lys Ile Leu Lys Arg Glu Leu Ala Glu Leu Leu Gly His
                500                 505                 510
```

<210> SEQ ID NO 36
<211> LENGTH: 1533
<212> TYPE: DNA
<213> ORGANISM: Amycolatopsis orientalis

<400> SEQUENCE: 36

| | | | | | |
|---|---|---|---|---|---|
| gtgtccttgt | ccctagcggc | cgtcctcgcc | gactcggcgg | gcaggcggcc | ggaccacccc | 60 |
| gcgctcgtgt | tcgacgggga | accgttctcc | taccgggaac | tctgggccgg | ggcgaagagg | 120 |
| tacgcctccg | cgctccggga | ccagggggtc | gccgccggcg | accgggtcgt | gctgctcctg | 180 |
| ccgaacacgc | cggagttccc | gatggtctac | ttcggcgcgc | tggcgctcgg | cgcggtcgtc | 240 |
| gtgccggtgc | acacgttgct | cgtcgcggag | gagatccact | acatcctcac | cgactgtgac | 300 |
| gcccgggtgc | tgatctgcgg | agccgccctg | ctggagcagg | cggcgaggc | cgccgacgcg | 360 |
| gccggtgtcg | aagtcctgac | gatgctggag | gactccgaca | ccggccgcgt | ccgcctcgac | 420 |
| gtcctcgccg | gggacgcggc | cgagatcgag | cggtacgaac | gcgtgaacc | ctcgacctc | 480 |
| gcgctgatcc | tctacacctc | ggggaccacc | ggcaaaccca | agggcgcgat | gctgacccac | 540 |
| ctgagcatcg | tgctgaacgt | tccaccacg | atgctgtcgc | cgttcgactt | ccacgccgac | 600 |
| gacgtgctgc | tcggctgcct | gccgctgttc | cacaccttcg | ccagatctg | cgggatggcg | 660 |

-continued

```
acctgtttcc gcgccggcgc gacgatggtg ctgatgtcgc ggttcgacgc gcgagccgcg      720
ctggaactga tggtggagca gaactgctcg ctgttcatgg gcgtgccgac gatgtacgtc      780
gcgttgctgg aggccgccga ggacgagccg cggcggccca aactcgaccg ggccttctcc      840
ggtggttcgt cgctgcccgt agcgctgctg gagcggttcg aggccgtgtt cgactgcccg      900
atctacgagg gatacggcct caccgagacc tcgcccgtgg tggcctacaa ccagcgcgcg      960
tggccgaccc gcgcgggcac cgtcggcaaa ccgatctggg gcgtggacgt cgccatcgcg     1020
cgcgccgaga ccgaagaccg gatcgaaccc gtgccgccgg gtgaggtcgg cgagatcgtc     1080
gtccggggcc acaacgtgat ggcgggctac ctgaaccgtc ccgaggccac ggcggccgcg     1140
atcgtggacg gctggttccg cagcggcgac ctaggcttcc tcgacgacga cggctatctg     1200
tccattgtgg accgtaagaa ggacatgatc cttcgcggcg gctacaacgt gtatccgcgc     1260
gagatcgagg aagtgctggc caggcatccc gcgatcgccc aggtcgcggt cgtcggcgtg     1320
ccggacgaac ggtacggcga ggagatctgc gccgtcgtgg tggccgcttc cgatcgggaa     1380
cccgggccgg aactggcggc ggaactcgtg gcgtggagca agaagcgcgt ggcggcctac     1440
aagtatccgc gccgcgtgga gttcctggac gcgatgccgc tcgggcccag cgggaagatc     1500
ctcaagcggg agctggcgga gctcctcggg cac                                  1533
```

<210> SEQ ID NO 37
<211> LENGTH: 3834
<212> TYPE: PRT
<213> ORGANISM: Amycolatopsis orientalis

<400> SEQUENCE: 37

```
Met Arg Thr Met Arg Asp Glu Leu Ile Leu Arg Thr Arg Arg Val Arg
1               5                  10                  15

Pro Asp Trp Ala Thr Val Leu Ala Ala Phe Asp Glu Thr Pro Asp Gly
            20                  25                  30

Glu Arg Arg Arg Ala Leu Ala Ala Leu Val Val Ala Glu Thr Glu Ala
        35                  40                  45

Val Leu Glu Ala Lys Pro Gly Ala Gly Thr Ala Ala Pro Gly Thr Pro
    50                  55                  60

Phe Ala Glu Leu Gly Phe Asp Ser Leu Ala Ala Val Glu Leu His Arg
65                  70                  75                  80

Arg Ile Ser Ala Ala Thr Ala Leu Glu Leu Pro Val Thr Leu Val Phe
                85                  90                  95

Asp His Pro Thr Pro Ser Ala Leu Ala Gly His Leu Arg Asp Leu Leu
            100                 105                 110

Ala Gly Glu Ala Val Ala Glu Ile Glu Asp Tyr Gln Ala Ile Ala Asp
        115                 120                 125

Asp Glu Pro Ile Ala Ile Val Gly Met Ala Cys Arg Tyr Pro Gly Gly
    130                 135                 140

Ile Gly Ser Pro Glu Asp Leu Trp Arg Leu Val Thr Glu Gly Gly Asp
145                 150                 155                 160

Ala Thr Ser Asp Phe Pro Ala Asp Arg Gly Trp Asp Val Glu Ser Leu
                165                 170                 175

Tyr Asp Pro Asp Pro Gly Val Pro Gly Lys Thr Tyr Thr Arg Arg Gly
            180                 185                 190

Gly Phe Leu Asp Gly Ala Gly Asp Phe Asp Ala Gly Phe Phe Gly Ile
        195                 200                 205

Ser Pro Arg Glu Ala Leu Ala Met Asp Pro Gln Gln Arg Leu Leu Leu
    210                 215                 220
```

-continued

```
Glu Thr Ser Trp Glu Ala Phe Glu Arg Ala Gly Ile Asp Pro Ala Thr
225                 230                 235                 240

Leu Arg Gly Ser Ala Thr Gly Val Phe Val Gly Ala Glu Thr Gln Glu
            245                 250                 255

Tyr Gly Pro Arg Leu Gly Gly Ala Glu Gly Leu Glu Gly Tyr Leu
        260                 265                 270

Leu Thr Gly Asn Ala Ala Ser Val Ala Ser Gly Arg Val Ser Tyr Ala
            275                 280                 285

Phe Gly Phe Glu Gly Pro Thr Val Thr Val Asp Thr Ala Cys Ser Ser
290                 295                 300

Ser Leu Val Ala Leu His Leu Ala Gly Gln Ala Leu Arg Leu Gly Glu
305                 310                 315                 320

Cys Pro Ile Ala Val Ala Gly Gly Val Ala Val Met Ser Ser Pro Gly
            325                 330                 335

Gly Phe Leu Ala Phe Ser Arg Gln Arg Gly Leu Ala Pro Asp Gly Arg
            340                 345                 350

Cys Lys Pro Phe Ser Ala Ala Asp Gly Thr Gly Trp Ser Glu Gly
        355                 360                 365

Val Gly Met Leu Val Leu Glu Arg Leu Ser Asp Ala Arg Asn Gly
    370                 375                 380

His Arg Val Leu Ala Val Val Arg Gly Thr Ala Ile Asn Ser Asp Gly
385                 390                 395                 400

Ala Ser Asn Gly Leu Thr Ala Pro Asn Gly Ala Ala Gln Gln Arg Val
            405                 410                 415

Ile Arg Arg Ala Leu Ala Asn Ala Gly Leu Ala Pro Ser Glu Val Asp
            420                 425                 430

Ala Val Glu Ala His Gly Thr Gly Thr Val Leu Gly Asp Pro Ile Glu
            435                 440                 445

Ala Gln Ala Leu Leu Ala Thr Tyr Gly Arg Asp Arg Glu Arg Pro Leu
    450                 455                 460

Leu Leu Gly Ser Val Lys Ser Asn Ile Gly His Thr Gln Ser Ala Ala
465                 470                 475                 480

Gly Val Ala Gly Val Ile Lys Met Val Gln Ala Met Arg His Gly Val
            485                 490                 495

Leu Pro Lys Thr Leu His Ala Asp Glu Pro Thr Pro Lys Val Ala Trp
        500                 505                 510

Ser Ser Gly Ala Val Glu Leu Leu Asn Glu Thr Val Ala Trp Pro Glu
        515                 520                 525

Asn Gly Ala Pro Arg Arg Ala Val Ser Ser Phe Gly Met Ser Gly
530                 535                 540

Thr Asn Ala His Ala Val Leu Glu Gln Ala Pro Ala Glu Asp Glu Pro
545                 550                 555                 560

Glu Pro Ser Pro Glu Ala Trp Pro Thr Trp Leu Phe Pro Val Ser Gly
            565                 570                 575

Arg Asp Glu Lys Ala Leu Arg Arg Gln Ala Ala Arg Leu Arg Glu Ala
        580                 585                 590

Leu Pro Asp Ser Asp Leu Pro Ala Ile Ala Ala Ala Leu Ala Thr Thr
        595                 600                 605

Arg Ser Ala Leu Glu Trp Arg Ala Val Val Thr Val Ala Asp Arg Ala
    610                 615                 620

Gly Leu Leu Ala Gly Leu Asp Ala Leu Ala Thr Gly Glu Ala Leu Pro
625                 630                 635                 640
```

```
Ser Leu Val His Gly Thr Ala Arg Ile Gly Ile Val Phe Ser Gly Gln
            645                 650                 655

Gly Ser Gln Arg Ala Gly Met Gly Arg Glu Leu His Arg Arg Phe Pro
            660                 665                 670

Val Phe Ala Ala Ala Phe Asp Asp Ala Cys Gly His Leu Asp Leu Gln
            675                 680                 685

Leu Asp Arg Pro Leu Ala Glu Ile Val Phe Ala Asp Glu Gly Thr Glu
            690                 695                 700

Glu Ala Gly Leu Leu His Arg Thr Glu Tyr Ala Gln Cys Ala Leu Phe
705                 710                 715                 720

Ala Val Glu Val Ala Leu Phe Arg Leu Tyr Glu His Trp Gly Leu Arg
                725                 730                 735

Pro Asp Tyr Val Ala Gly His Ser Ile Gly Glu Leu Ala Ala Ala His
            740                 745                 750

Val Ser Gly Met Leu Ser Leu Ser Asp Ala Ala Leu Val Ala Ala
            755                 760                 765

Arg Gly Arg Leu Met Gln Asp Thr Arg Glu Gly Gly Ala Met Leu Ala
            770                 775                 780

Val Gln Ala Thr Glu Asp Glu Val Leu Pro Leu Leu Asp Glu Arg Leu
785                 790                 795                 800

Ala Ile Ala Ala Val Asn Gly Pro Arg Ser Val Val Ser Gly Asp
                805                 810                 815

Glu Ala Ala Val Glu Glu Val Ala Ala Phe Ala Arg Arg Lys Thr
            820                 825                 830

Lys Arg Leu Lys Val Ser His Ala Phe His Ser His His Met Asp Gly
            835                 840                 845

Met Leu Asp Glu Phe Arg Arg Phe Ala Glu Ile Leu Thr Phe Arg Lys
            850                 855                 860

Pro Val Ile Pro Leu Val Ser Thr Val Ser Gly Glu Leu Leu Thr Glu
865                 870                 875                 880

Ala Thr Ala Pro Glu Tyr Trp Val Glu His Val Arg Arg Pro Val Arg
                885                 890                 895

Phe Ala Asp Gly Val Arg Arg Leu Asp Glu Leu Gly Val Asp Val Leu
            900                 905                 910

Leu Glu Leu Gly Pro Asp Ala Val Leu Thr Pro Met Ala Ala Glu Val
            915                 920                 925

Leu Asp Gly Glu Gly Ala Ala Leu Val Pro Ser Leu Arg Gly Ser Arg
            930                 935                 940

Pro Glu Ala Glu Ala Leu Ala Ala Ser Leu Ala Glu Leu Trp Val Arg
945                 950                 955                 960

Gly Ala Glu Leu Gly Trp Pro Gln Val Phe Gly Ala His Pro Arg Ala
                965                 970                 975

Asp Leu Pro Thr Tyr Ala Phe Gln Arg Gln Arg Tyr Trp Leu Ile Asp
            980                 985                 990

Gln Asp Thr Ala Gly Asp Pro Gly  Ala Tyr Gly Leu Gly  Asp Thr Gly
            995                 1000                1005

His Pro  Leu Leu Arg Ala Ser  Val Thr Thr Ala Glu  Asp Gly Ala
            1010                1015                1020

Leu Leu Leu Ser Gly Arg Leu  Ser Pro Leu Thr Gln  Pro Trp Leu
            1025                1030                1035

Ala Asp  His Val Val Gly Gly  Asp Val Val Leu Pro  Gly Thr Ala
            1040                1045                1050

Leu Leu  Glu Leu Ala Leu Arg  Ala Ala Glu Leu Ala  Gly Ala Gly
```

```
                    1055                1060                1065
Gly Val Glu Glu Leu Thr Leu Glu Val Pro Met Val Leu Ser Glu
    1070                1075                1080
Ala Gly Val Gln Val Gln Val Ser Val Arg Asp Ser Gly Leu Leu
    1085                1090                1095
Ile Phe Phe Arg Asp Thr Glu Asp Asp Glu Trp Thr Arg Cys Ala
    1100                1105                1110
Ser Gly Thr Leu Gly Ala Ala Ala Pro Ala Pro Gly Phe Gly Ala
    1115                1120                1125
Trp Pro Pro Ala Gly Glu Pro Leu Asp Leu Ser Asp Leu Tyr Asp
    1130                1135                1140
Arg Leu Ala Asp Ser Gly Leu Asp Tyr Gly Pro Ala Phe Arg Cys
    1145                1150                1155
Leu Arg Ala Ala Trp Arg Ser Gly Asp Asp Leu Tyr Ala Glu Val
    1160                1165                1170
Ala Ala Val Pro Glu Thr Gln Gly Gly Phe Gly Val His Pro Ala
    1175                1180                1185
Leu Leu Asp Ala Ala Leu His Val Leu Glu Leu Gly Ser Gly Gly
    1190                1195                1200
Gly Gly Gly Pro Ala Ala Leu Pro Phe Ala Trp Ser Gly Val Thr
    1205                1210                1215
Leu His Ala Arg Gly Ala Asp Val Leu Arg Val Lys Leu Glu Asn
    1220                1225                1230
His Val Ala Gly Ala Glu Ala Gly Thr Tyr Ser Val Ser Leu Lys
    1235                1240                1245
Val Ala Asp Gly Ala Gly Glu Pro Val Ala Ser Val Glu Ser Leu
    1250                1255                1260
Ala Leu Arg Pro Leu Ser Thr Ala Pro Arg Ala Gln Asp Gly Ala
    1265                1270                1275
Leu Tyr Gly Val Asp Trp Ile Ser Leu Pro Gly Thr Pro Gly Val
    1280                1285                1290
Ala Glu Tyr Arg Leu Tyr Pro Asp Leu Thr Ala Val Asp Asp Val
    1295                1300                1305
Pro Pro Val Val Ala Val Arg Cys Thr Thr Leu Glu Ser Val Leu
    1310                1315                1320
Asp Leu Val Gln Thr Trp Leu Ala Asp Asp Arg Phe Ala Pro Ala
    1325                1330                1335
Arg Leu Ala Leu Leu Thr Asp Gly Ala Val Ala Thr Glu Asn Pro
    1340                1345                1350
Asp Pro Ala Ala Ala Ala Met Trp Gly Leu Val Arg Ser Ala Gln
    1355                1360                1365
Ala Glu His Pro Asp Arg Leu Val Leu Ala Asp Val Thr Gly Glu
    1370                1375                1380
Asp Gly Leu Ala Ala Gly Leu Ala Ser Gly Glu Pro Glu Phe Ala
    1385                1390                1395
Ala Arg Asp Gly Ala Val Leu Val Pro Arg Leu Thr Arg Val Pro
    1400                1405                1410
Ser Pro Ala Pro Ala Ser Phe Thr Thr Gly Gly Thr Val Leu Ile
    1415                1420                1425
Thr Gly Gly Thr Gly Gly Leu Ala Gly Leu Leu Ala Arg His Leu
    1430                1435                1440
Val Glu Arg His Glu Val Arg Ser Leu Leu Leu Val Ser Arg Arg
    1445                1450                1455
```

-continued

```
Gly Ala Ala Gly Pro Leu Val Asp Asp Leu Thr Ala Leu Gly Ala
    1460            1465                1470
Asp Val Thr Val Ala Ala Cys Asp Ile Ala Asp Arg Glu Ser Val
    1475            1480                1485
Ala Ala Leu Leu Ala Glu His Pro Val Ser Ala Val Val His Ala
    1490            1495                1500
Ala Gly Val Leu Asp Asp Ala Thr Ile Thr Thr Leu Asp His Glu
    1505            1510                1515
Arg Leu Ala Ala Val Leu Arg Pro Lys Val Thr Gly Ala Leu Val
    1520            1525                1530
Leu Asp Glu Leu Thr Arg Asp Leu Asp Leu Ser Ala Phe Val Leu
    1535            1540                1545
Phe Ser Ser Ser Ala Ala Thr Phe Asp Gly Ala Gly Gln Ala Asn
    1550            1555                1560
Tyr Ala Ala Ala Asn Ala Phe Leu Glu Ala Leu Ala Leu Arg Arg
    1565            1570                1575
Arg Ala Glu Gly Arg Pro Gly Val Ala Leu Gly Trp Gly Leu Trp
    1580            1585                1590
Ala Thr Gly Met Gly Ala Arg Leu Asp Glu Ala Gly Leu Arg Arg
    1595            1600                1605
Ile Glu Arg Ser Gly Gln Arg Ala Leu Ser Glu Val Asp Gly Leu
    1610            1615                1620
Ala Leu Phe Asp Ala Ala Leu Ala Ala Asp Arg Pro Val Leu Leu
    1625            1630                1635
Pro Met Arg Met His Arg Ala Ala Leu Arg Ala Arg Ala Ser Ala
    1640            1645                1650
Glu Gly Leu Pro Ala Val Leu Gly Gly Leu Val Arg Val Thr Arg
    1655            1660                1665
Pro Ala Pro Ser Ala Ala Pro Arg Gly Leu Asp Glu Ala Ala Leu
    1670            1675                1680
Leu Asp Leu Val Arg Thr Thr Val Ala Ala Val Leu Gly His Pro
    1685            1690                1695
Asp Ala His Ala Ile Asp Pro Asp Arg Ala Phe Thr Glu Val Gly
    1700            1705                1710
Phe Asp Ser Leu Ala Ala Val Glu Leu Arg Asn Arg Leu Ile Ala
    1715            1720                1725
Ala Thr Gly Leu Lys Ile Ala Pro Thr Leu Val Phe Asp His Pro
    1730            1735                1740
Asn Pro Arg Ala Val Ala Ala Phe Leu Ala Ala Gly Ser Ala Pro
    1745            1750                1755
Val Arg Asp Glu Pro Ala Ala Pro Ala Glu Ala Asp Glu Pro Ile
    1760            1765                1770
Ala Ile Ile Gly Met Ala Cys Arg Tyr Pro Gly Gly Val Ser Thr
    1775            1780                1785
Pro Asp Asp Leu Trp Arg Leu Val Ala Asp Gly Asn Asp Gly Ile
    1790            1795                1800
Thr Arg Phe Pro Glu Asn Arg Gly Trp Asp Thr Asp Gly Val Tyr
    1805            1810                1815
His Pro Asp Ala Asp His Arg Gly Thr Thr Tyr Val Arg Glu Gly
    1820            1825                1830
Gly Phe Leu His Asp Ala Gly Gln Phe Asp Pro Gly Phe Phe Gly
    1835            1840                1845
```

-continued

```
Ile Ser Pro Arg Glu Ala Leu Ala Met Asp Pro Gln Gln Arg Leu
1850            1855                1860

Leu Leu Glu Ile Ser His Glu Ala Val Glu Arg Ala Gly Ile Asp
1865            1870                1875

Pro Lys Ser Leu Arg Gly Ser Gly Thr Gly Val Phe Ala Gly Val
1880            1885                1890

Met Tyr His Asp Tyr Ala Thr Gly Leu Asn Arg Val Pro Asp Asp
1895            1900                1905

Val Glu Gly Tyr Leu Gly Asn Gly Thr Ser Ala Ser Ile His Ser
1910            1915                1920

Gly Arg Val Ala Tyr Thr Phe Gly Leu Glu Gly Pro Ala Val Thr
1925            1930                1935

Ile Asp Thr Ala Cys Ser Ser Ser Leu Val Ala Leu His Leu Ala
1940            1945                1950

Ala Gln Ala Leu Arg Arg Gly Glu Cys Ser Met Ala Leu Ala Gly
1955            1960                1965

Gly Val Thr Val Met Ala Thr Pro Glu Val Phe Val Asp Phe Ser
1970            1975                1980

Arg Gln Arg Gly Leu Ala Pro Asp Gly Arg Cys Lys Ser Phe Ser
1985            1990                1995

Asp Glu Ala Asp Gly Thr Val Trp Ser Glu Gly Val Gly Met Leu
2000            2005                2010

Leu Val Glu Arg Leu Ser Asp Ala Arg Arg Asn Gly His Arg Val
2015            2020                2025

Leu Ala Ile Val Arg Gly Ser Ala Val Asn Gln Asp Gly Ala Ser
2030            2035                2040

Asn Gly Leu Thr Ala Pro Ser Gly Pro Ser Gln Gln Arg Val Ile
2045            2050                2055

Arg Arg Ala Leu Ala Asp Ala Gly Leu Lys Pro Ser Glu Val Asp
2060            2065                2070

Ala Val Glu Ala His Gly Thr Gly Thr Pro Leu Gly Asp Pro Ile
2075            2080                2085

Glu Ala Gln Ala Met Leu Ala Thr Tyr Gly Gln Asp Arg Asp Arg
2090            2095                2100

Pro Leu Trp Leu Gly Ser Leu Lys Ser Asn Leu Gly His Thr Gln
2105            2110                2115

Ala Ala Ala Gly Val Gly Gly Ile Ile Lys Met Val Gln Ala Met
2120            2125                2130

His His Gly Val Leu Pro Arg Thr Leu Asn Leu Gly Thr Pro Thr
2135            2140                2145

Thr Lys Val Asp Trp Thr Ser Gly Asn Val Ser Leu Leu Ser Glu
2150            2155                2160

Pro Val Ala Trp Pro Glu Thr Gly Gly Pro Arg Arg Ala Ala Val
2165            2170                2175

Ser Ser Phe Gly Ile Ser Gly Thr Asn Ala His Val Val Leu Glu
2180            2185                2190

Gln Ala Glu Pro Val Glu Lys Ser Thr Ser Asp Thr Ser Pro Leu
2195            2200                2205

Gly Gly Asp Val Leu Pro Phe Val Leu Ser Gly Lys Thr Ser Ala
2210            2215                2220

Ala Leu Ala Ala Gln Ala Asp Arg Leu Ala Gly His Leu Ala Gly
2225            2230                2235

Asp Val Ser Leu Pro Ala Val Ala Arg Ala Leu Ala Val Thr Arg
```

-continued

```
            2240                2245                2250
    Ser Ala Leu Asp His Arg Ala Val Val Ala Gly Asp Arg Ala
        2255                2260                2265

Gly Leu Thr Ala Gly Leu Arg Ala Leu Ala Asp Ala Val Pro Ala
        2270                2275                2280

Pro His Val Val Asp Gly Val Ala Glu Asn Gly Lys Ala Val Phe
        2285                2290                2295

Val Phe Pro Gly Gln Gly Ser Gln Trp Thr Gly Met Ala Val Asp
        2300                2305                2310

Leu Leu Gly Ser Ser Ala Val Phe Ala Glu Ala Met Ala Asp Cys
        2315                2320                2325

Glu Ala Ala Leu Leu Ser His Leu Asp Trp Lys Leu Thr His Val
        2330                2335                2340

Leu Ser Asp Ala Ala Ala Leu Glu Arg Val Asp Val Val Gln Pro
        2345                2350                2355

Val Leu Phe Ala Val Met Val Ser Leu Ala Arg Leu Trp Arg Ala
        2360                2365                2370

Cys Gly Ile Glu Pro Ala Ala Val Val Gly His Ser Gln Gly Glu
        2375                2380                2385

Ile Ala Ala Ala Cys Val Ala Gly Ala Leu Ser Leu Glu Asp Ala
        2390                2395                2400

Ala Arg Val Val Cys Leu Arg Ser Lys Ala Ile Leu Ala Leu Ser
        2405                2410                2415

Gly Leu Gly Gly Met Val Ser Val Ala Ala Ser Glu Asp Arg Val
        2420                2425                2430

Arg Glu Leu Leu Pro Asp Gly Val Ser Val Ala Val Val Asn Gly
        2435                2440                2445

Pro Ala Ser Val Val Val Ser Gly Asp Val Ala Gly Leu Glu Ala
        2450                2455                2460

Leu Leu Lys Arg Cys Glu Leu Leu Asp Val Arg Ala Lys Arg Val
        2465                2470                2475

Pro Val Asp Tyr Ala Ser His Ser Ala His Val Asp Ala Ile Glu
        2480                2485                2490

Gln Gln Val Val Thr Ala Leu Ser Gly Ile Met Pro Arg Glu Ala
        2495                2500                2505

Glu Leu Pro Met Tyr Ser Thr Val Thr Gly Glu Pro Ile Asp Thr
        2510                2515                2520

Thr Thr Leu Asp Ala Ala Tyr Trp Phe Arg Asn Leu Arg Ala Thr
        2525                2530                2535

Val Arg Phe Asp Gln Ala Val Arg Arg Leu Ile Ala Asp Gly Phe
        2540                2545                2550

Arg Phe Phe Val Glu Thr Ser Pro His Pro Val Leu Val Ala Gly
        2555                2560                2565

Leu Thr Glu Leu Val Glu Glu Ala Ala Val Pro Ala Val Ala Leu
        2570                2575                2580

Ala Ser Leu Arg Arg Asp Glu Gly Gly Pro Thr Arg Phe Val Thr
        2585                2590                2595

Ser Leu Ala Glu Ala His Val His Gly Leu Ser Pro Asp Trp Ala
        2600                2605                2610

Ala Leu Leu Pro Glu Ala Gly Trp Val Asp Leu Pro Pro Tyr Ala
        2615                2620                2625

Phe Gln His Gln Glu Phe Trp Leu Thr Asp Ala Gly Glu Pro Gly
        2630                2635                2640
```

-continued

Asp Ala Ala Gly Phe Gly Leu Gly Ala Thr Gly His Pro Leu Leu
2645                2650                2655

Thr Ala Ala Thr Ala Leu Pro Gly Ser Gly Gly Leu Leu Leu Thr
2660                2665                2670

Gly Arg Ile Ser Thr Ala Ala Gln Pro Trp Leu Ala Asp His Ala
2675                2680                2685

Val Gln Gly Val Val Leu Leu Pro Gly Thr Ala Phe Val Glu Leu
2690                2695                2700

Ala Leu Gln Ala Gly Thr His Ala Gly Cys Gly Arg Ile Asp Glu
2705                2710                2715

Leu Thr Leu Glu Ala Pro Leu Pro Leu Pro Glu Gln Gly Gly Val
2720                2725                2730

Arg Val Gln Val Val Leu Gly Ser Glu Val Asn Gly Arg Arg Glu
2735                2740                2745

Val Thr Val His Ser Gln Ala Glu Ser Gly Asp Asp Thr Trp Val
2750                2755                2760

Arg His Ala Ser Gly Phe Leu Thr Ser Ala Glu Thr Pro Gly Glu
2765                2770                2775

Gly Leu Thr Glu Trp Pro Pro Ala Gly Ala Thr Ser Ala Asp Leu
2780                2785                2790

Asp Gly Phe Tyr Ala Asp Ala Glu Ala Gln Gly Tyr Gly Tyr Gly
2795                2800                2805

Pro Ala Phe Gln Gly Leu Arg Ala Ala Trp Thr Leu Gly Ser Asp
2810                2815                2820

Val Phe Ala Glu Val Val Leu Pro Asp Ala Glu Gly Ala Asp Arg
2825                2830                2835

Phe Gly Leu His Pro Ala Leu Leu Asp Ala Ala Leu His Ala Leu
2840                2845                2850

Gly Thr Val Arg Ser Gly Asp Gly Ala Glu Leu Pro Phe Ala Trp
2855                2860                2865

Thr Gly Val Thr Val His Ala Val Gly Ala Thr Ala Leu Arg Val
2870                2875                2880

Arg Leu Thr Val Gly Thr Asp Thr Val Ala Val Thr Ala Ala Asp
2885                2890                2895

Pro Ala Gly Ala Pro Val Ala Thr Val Glu Gly Leu Val Thr Arg
2900                2905                2910

Pro Ala Ala Leu Pro Gly Ser Arg Arg Pro Asp Ser Leu Phe Arg
2915                2920                2925

Val Asp Trp Thr Pro Val Ser Thr Pro Glu Ala Val Glu Thr Pro
2930                2935                2940

Thr Val Thr Val Leu Ser Asp Gly Asp Leu Thr Ala Leu Ala Glu
2945                2950                2955

Ile Pro Asp Val Val Leu Val Pro Val Gly Ala Glu Ala Gly Asp
2960                2965                2970

Leu Thr Glu Ser Val His Arg Thr Thr Ala Arg Val Leu Asp Leu
2975                2980                2985

Leu Arg Thr Trp Leu Asp Asp Glu Arg Phe Ala Asp Ala Arg Leu
2990                2995                3000

Val Leu His Thr Arg Gly Ala Val Ala Asp Val Arg Asp Leu Pro
3005                3010                3015

Ala Ala Ala Ala Trp Gly Leu Val Arg Ser Ala Gln Ala Glu Asn
3020                3025                3030

-continued

```
Pro Asp Arg Ile Val Leu Leu Asp Ser Asp Thr Asp Leu Pro Pro
3035                3040                3045

Ala Leu Leu Ala Glu Val Leu Ala Thr Gly Glu Ala Gln Leu Ala
3050                3055                3060

Trp Arg Asp Gly Glu Leu Leu Val Pro Arg Leu Ala Lys Val Ser
3065                3070                3075

Thr Asp Gly Thr Leu Thr Pro Pro Glu Gly Pro Trp Val Leu Asp
3080                3085                3090

Ala Pro Arg Arg Gly Thr Leu Glu Glu Leu Ala Leu Val Pro Ala
3095                3100                3105

Pro Thr Ala Ala Arg Pro Leu Ala Asp Gly Glu Val Arg Ile Gln
3110                3115                3120

Val Arg Ala Ala Gly Ile Asn Phe Arg Asp Val Leu Ile Thr Leu
3125                3130                3135

Asp Met Tyr Pro Glu Asp Lys Ala Val Met Gly Ser Glu Gly Ala
3140                3145                3150

Gly Ile Val Thr Glu Ile Gly Ser Gly Val Thr Gly Leu Lys Pro
3155                3160                3165

Gly Asp Arg Val Phe Gly Leu Phe Asp Gly Ala Phe Gly Pro Val
3170                3175                3180

Ala Ile Ala Asp Arg Arg Thr Val Thr Glu Met Pro Val Asp Trp
3185                3190                3195

Thr Phe Ala Glu Ala Ala Ala Leu Pro Val Val Phe Leu Thr Ala
3200                3205                3210

Tyr Tyr Gly Leu Val Asp Leu Gly Gly Leu Arg Pro Gly Glu Lys
3215                3220                3225

Val Leu Ile His Gly Ala Thr Gly Gly Val Gly Met Ala Ala Val
3230                3235                3240

Gln Leu Ala Arg His Leu Gly Ala Glu Val Phe Ala Thr Ala Ser
3245                3250                3255

Pro Gly Lys Trp Glu Val Leu Arg Gly Leu Gly Phe Asp Asp Glu
3260                3265                3270

His Ile Ala Ser Ser Arg Thr Leu Asp Phe Glu Asp Arg Phe Gly
3275                3280                3285

Arg Met Asp Val Val Leu Asp Ser Leu Ala Lys Glu Phe Val Asp
3290                3295                3300

Ala Ser Leu Arg Leu Leu Gly Glu Gly Gly Arg Phe Val Glu Met
3305                3310                3315

Gly Lys Thr Asp Ile Arg Asp Ala Asp Glu Val Ala Ala Ala His
3320                3325                3330

Pro Gly Val Thr Tyr Arg Ala Phe Asp Leu Leu Asp Ala Gly Arg
3335                3340                3345

Pro Arg Ile Gly Glu Ile Leu Ala Glu Leu Leu Asp Leu Phe Gly
3350                3355                3360

Ala Gly Ser Leu Thr Val Pro Arg Pro Thr Val Trp Asp Ala Arg
3365                3370                3375

Arg Ala Pro Glu Val Phe Arg Phe Met Ser Gln Ala Lys His Ile
3380                3385                3390

Gly Lys Asn Val Leu Thr Ile Pro Ser Thr Met Asp Gly Asn Gly
3395                3400                3405

Thr Val Leu Ile Thr Gly Ala Thr Gly Thr Leu Gly Ala Leu Val
3410                3415                3420

Ala Arg His Leu Val Thr Val Arg Gly Val Arg His Leu Leu Leu
```

-continued

```
            3425                3430                3435
Val Gly Arg Arg Gly Arg Ala Ala Ala Gly Met Ala Glu Leu Glu
        3440                3445                3450
Ala Glu Leu Thr Ala Ala Gly Ala Ser Val Thr Ile Ala Ala Cys
        3455                3460                3465
Asp Ala Ala Asp Arg Ala Ala Leu Ala Ala Leu Leu Ala Thr Val
        3470                3475                3480
Pro Ala Glu His Pro Leu Ala Gly Val Val His Ala Ala Gly Val
        3485                3490                3495
Leu Asp Asp Gly Leu Val Ala Thr Leu Thr Pro Glu Arg Leu Ala
        3500                3505                3510
Lys Val Leu Arg Pro Lys Val Asp Ala Ala Val Asn Leu His Glu
        3515                3520                3525
Leu Thr Arg Asp Ala His Leu Ala Glu Phe Val Leu Phe Ser Ser
        3530                3535                3540
Ala Ala Gly Ala Phe Gly Asp Ala Gly Gln Gly Asn Tyr Ala Ala
        3545                3550                3555
Ala Asn Ser Phe Leu Asp Ser Leu Ala Arg His Arg Arg Ala Gln
        3560                3565                3570
Gly Leu Pro Ala Val Ser Leu Ala Trp Gly Phe Trp Ala Glu Leu
        3575                3580                3585
Ser Gly Met Thr Gly His Leu Gly Glu Ala Asp Leu Ala Arg Leu
        3590                3595                3600
Lys Arg Ser Gly Met Ser Pro Leu Ser Thr Glu Asp Gly Leu Leu
        3605                3610                3615
Leu Met Asp Ala Ala Arg Ala Gly Tyr Glu Pro Ala Pro Leu Pro
        3620                3625                3630
Met His Ile Asp Leu Ala Ala Leu Arg Gly Glu Glu Val His Pro
        3635                3640                3645
Leu Leu Arg Gly Leu Val Lys Ala Pro Val Arg Arg Ala Ala Ala
        3650                3655                3660
Ala Thr Gly Thr Gln Ser Glu Gly Leu Ala Asp Arg Leu Ala Gly
        3665                3670                3675
Leu Ala Pro Ala Ala Arg Gly Arg Ala Leu Leu Asp Leu Ile Arg
        3680                3685                3690
Ala Asn Val Ala Ala Val Leu Gly Phe Gly Ser Pro Glu Gln Val
        3695                3700                3705
Gly Val Arg Gln Ala Phe Arg Glu Leu Gly Phe Asp Ser Leu Ser
        3710                3715                3720
Ala Val Glu Leu Arg Asn Arg Leu Asn Ala Ala Thr Gly Leu Arg
        3725                3730                3735
Leu Pro Ala Thr Val Val Phe Asp His Pro Thr Pro Thr Ala Leu
        3740                3745                3750
Ala Glu Thr Leu Gly Asp Arg Leu Ala Pro Ala Glu Glu Ala Val
        3755                3760                3765
Asp Asp Glu Val Ala Arg Ile Gly Ala Val Leu Ala Ser Val Pro
        3770                3775                3780
Ala Asp Arg Leu Arg Glu Ala Gly Val Leu Asp Leu Leu Thr Arg
        3785                3790                3795
Leu Ala Asp Pro Gly Tyr Arg Pro Thr Glu Ser Pro Asp Gly Ala
        3800                3805                3810
Asp Ile Asp Glu Met Asp Ala Asp Arg Leu Ile Ala Leu Ala Phe
        3815                3820                3825
```

-continued

Asp Ala  Ser Asp Pro Ala
    3830

<210> SEQ ID NO 38
<211> LENGTH: 11505
<212> TYPE: DNA
<213> ORGANISM: Amycolatopsis orientalis

<400> SEQUENCE: 38

| | | | | | |
|---|---|---|---|---|---|
| atgcggacca | tgcgagacga | actgattctg | cgaactcgac | gtgttcggcc | ggactgggcc | 60 |
| acggtgctgg | ccgctttcga | cgaaacccccg | gacggggagc | ggcggcgggc | gctcgccgcg | 120 |
| ctggtcgtcg | ccgagaccga | agcggtgctg | gaggcgaagc | cgggtgcggg | gaccgccgcg | 180 |
| cccggcacgc | ccttcgccga | actcgggttc | gattccctcg | cggcggtgga | actgcaccgg | 240 |
| cggatctccg | cggccaccgc | gctggagctg | ccggtgacgc | tcgtcttcga | ccacccgaca | 300 |
| ccgtcggcgc | tcgccggtca | tctgcgcgat | ctgctcgccg | gtgaggccgt | ggccgagatc | 360 |
| gaggactacc | aggcgatcgc | cgacgacgag | ccgatcgcga | tcgtcggcat | ggcctgccgt | 420 |
| taccccggtg | ggatcggttc | gccggaggac | ctctggcggc | tggtcaccga | gggtggggac | 480 |
| gcgacgtcgg | acttcccggc | cgaccgcggc | tgggacgtgg | aatcgctgta | cgaccccgac | 540 |
| cccggggtgc | ccggcaagac | ctacacccgg | cgaggcgggt | tcctcgacgg | cgccggggat | 600 |
| ttcgacgcgg | gattcttcgg | gatctcgccg | cgtgaggcgc | tggcgatgga | tccgcaacag | 660 |
| cggctcctgc | tggagacgtc | gtgggaggcc | ttcgagcggg | cggggatcga | ccccgcgacc | 720 |
| ttgcggggaa | gcgcgaccgg | cgtgttcgtc | ggcgcggaga | cccaggagta | cggaccgcgt | 780 |
| ctcggtggcg | cggaagaagg | tctcgaaggt | tatctgctga | ccggtaacgc | ggcgagtgtc | 840 |
| gcgtcgggcc | gcgtctcgta | cgccttcggg | ttcgagggcc | cgacggtcac | cgtggacacc | 900 |
| gcatgctcgt | cgtcgctggt | ggccctgcac | ctggcagggc | aggcgctgcg | gctggggagg | 960 |
| tgcccgatcg | cggtggccgg | cggcgtcgcg | gtgatgtcga | gcccggcgg | tttcctcgcc | 1020 |
| ttcagccgtc | agcgcgggct | cgcgccggac | gggcgctgca | agccgttctc | cgccgcggcg | 1080 |
| gacggcaccg | gctggtccga | aggtgtcggg | atgctggtgc | tggaaaggct | ttccgacgcc | 1140 |
| cggcgcaacg | ggcaccgggt | gctcgccgtc | gtccgcggca | ccgcgatcaa | ctccgacggc | 1200 |
| gccagcaacg | gtctcaccgc | gcccaacggc | gccgctcagc | agagggtgat | ccggcgcgcg | 1260 |
| ctggcgaacg | ccgggctcgc | accgtccgaa | gtggacgccg | tcgaagcaca | cggcaccggt | 1320 |
| accgtcctcg | gcgacccgat | cgaggcgcag | gcactgctgg | ccacctacgg | ccgcgaccgt | 1380 |
| gagcgcccgt | tgctcctcgg | ctcggtcaag | tcgaacatcg | gcacaccca | gtcggccgcc | 1440 |
| ggggtggccg | gggtgatcaa | gatggtgcag | gcgatgcggc | acggtgtgct | gcccaagacc | 1500 |
| ctgcacgccg | acgagcccac | cccgaaggtc | gcctggtcct | ccggtgccgt | cgaactgctc | 1560 |
| aacgagaccg | ttgcttggcc | ggagaatggc | gcgcctcgcc | gcgcggcggt | gtcgtcgttc | 1620 |
| gggatgagcg | ggaccaacgc | gcacgccgtc | ctcgaacagg | ccccgccga | ggacgagccc | 1680 |
| gagccgtcgc | cggaagcgtg | gcccacctgg | ctgttcccccg | tcagcggccg | cgacgagaag | 1740 |
| gccctgcgcc | gtcaggccgc | ccggctgcgt | gaagccctgc | cggacagtga | cctccccgcc | 1800 |
| atcgccgccc | gctcgccac | caccggtcc | gccctggagt | ggcgggccgt | ggtgacggtc | 1860 |
| gccgatcgcg | cgggattgtt | ggcgggttg | gacgcgttgg | ccaccggtga | agctctgccg | 1920 |
| agcctggtcc | acgggacggc | gcggatcggg | atcgtcttca | gcggccaggg | cagccagcgc | 1980 |
| gccgggatgg | gccgcgaact | gcaccgccgg | ttcccggtgt | cgccgccgc | cttcgacgac | 2040 |

```
gcctgcgggc atctcgacct gcaactggac cggccgctgg ccgagatcgt gttcgccgac    2100
gagggcaccg aggaagccgg cctgttgcac cgcaccgaat acgcgcagtg cgcgttgttc    2160
gccgtcgagg tcgcgctgtt ccggctgtac gagcattggg gcctgcgccc cgattacgtc    2220
gccgggcact cgatcggcga gctggccgcc gcgcacgttt cgggcatgct ttcgctctcc    2280
gacgccgccg cgctcgtcgc cgcgcgggga cgcctgatgc aggacacgcg cgagggcggc    2340
gcgatgctcg cggtgcaggc gacggaggac gaggtcctgc cgctgcttga cgaacgcctc    2400
gcgatcgcgg ccgtcaacgg cccgcggtcg gtggtcgtct ccggcgacga ggccgcggtc    2460
gaggaggtcg ccgccgcgtt cgccaggcgc aagaccaaac ggctcaaggt gagtcacgcc    2520
ttccactcgc atcacatgga cgggatgctc gacgagttcc gccggttcgc cgagatcctc    2580
accttccgga agccggtgat cccgctggtg tccactgtgt ccggtgagct gctcaccgag    2640
gcgacggcgc cggaatactg ggtggagcac gtgcgccgcc cggtgcggtt cgccgacggc    2700
gtgcggcggc tggacgagct cggcgtcgac gtgctcctgg aactcggccc ggacgcggtg    2760
ctgacgccga tggccgccga agtcctcgac ggcgagggag cggcgctggt gccgagcctg    2820
cgcgggtcgc ggccggaggc ggaggcgctc gccgcgtcgc tggccgaact gtgggtccgc    2880
ggcgccgaac tcggctggcc tcaggtgttc ggtgcacacc cgagggccga tttgccgact    2940
tatgccttcg aacggcagcg gtactggctg atcgaccagg acaccgccgg gatcccggc    3000 gcctacggtc tggcgacac cgggcatccg ctcctgcggg cgtcggtcac cacgccgaa     3060 gacggtgcgc tgctgctctc cggcaggttg tccccgctca cccagccctg gctcgccgac    3120
cacgtcgtcg gtggcgacgt ggtgctgccg ggtaccgcgc tgctcgaact ggcgctgcgg    3180
gccgcggaac tcgcggggc cggggcgtc gaggaactga ccctcgaagt gccgatggtg    3240
ctttccgaag cgggcgttca ggttcaggtg tcggtccggg acagcgggct cctgatcttc    3300
ttccgtgaca ccgaggacga cgagtggacg cgctgcgctt cgggcacgct cggcgccgcg    3360
gcgcccgctc ccggcttcgg ggcgtggccg ccgccggtg agccctcga ccttccgat     3420 ctctacgacc ggttggccga ctccggcctc gactacgggc cggcgttccg ctgcctgcgt    3480
gccgcatggc gctccggtga cgacctctac gccgaggtcg ccgccgtgcc ggagacccag    3540
ggcgggttcg cgctgcatcc ggcgctgctg gacgcggcgc tgcacgtgct cgaactcggc    3600
tccgggggcg gtggaggccc cgcggcgctg ccgttcgcgt ggtccggcgt gacgttgcac    3660
gcgcgcggcg ccgacgttct cgcgtcaag ctcgagaacc acgtcgcggg tgccgaagcc    3720
gggacgtact cggtgtccct gaaggtggcc gacggcgcgg gcgaacccgt cgcgtcggtc    3780
gaatccttag ccctgcgacc tctttccaca gctcctcgcg cgcaggacgg cgcgcttta    3840 ggcgtcgact ggatttcgct tcccggaacg ccgggcgtcg ccgagtaccg gctctatccg    3900
gacctcaccg ccgtcgacga cgtgccaccg gtcgtcgccg tccgttgcac cactctcgaa    3960
agcgtgctgg atctcgtcca gacgtggctc gccgacgacc ggttcgcccc ggccaggctg    4020
gcgctgctca ccgacggcgc cgtcgccacc gaaaacccg atcccgccgc ggccgccatg    4080
tgggggcttg tgcgttccgc gcaggccgag cacccggacc ggctggtatt ggccgacgtc    4140 acggagaag acggcctcgc cgccggactg gcttccggcg aacccgagtt cgccgcccgc    4200
gacggcgcgg tgctggtccc caggctgacg cgtgtgccga gccggcccc ggcgtcgttc    4260 accaccggcg gcacggtgct gatcaccggc gggaccggcg gtctcgccgg gctgctggcc    4320
cggcatctgg tcgagcggca cgaggtacgc agcctgcttc tcgtgagccg tcgcggtgcc    4380
```

-continued

```
gcggggccgc tcgtcgacga cctcaccgcg ctgggtgccg acgtcaccgt cgccgcctgc    4440
gacatcgccg accgcgagtc cgtcgcggca ctgctcgccg agcatccggt gtcggcggtc    4500
gtccacgccg ccggtgtgct cgacgacgcg accatcacca cgctcgacca cgagcggctc    4560
gcggccgtcc tgcggccgaa ggtcaccggc gcgctcgtcc tggacgaact caccgggac    4620 ctcgacctgt cggcgttcgt gctgttctct tcgtccgcgg ccaccttcga cggcgcgggt    4680
caggccaact acgctgcggc caatgccttc ctcgaagcgc tcgccctccg ccgccgtgcg    4740
gaaggccgcc ccggcgtcgc actgggctgg ggcctctggg ccaccgggat gggagcacgg    4800
ctcgacgagg cggggctgcg ccggatcgag cgctccggcc agcgtgcact atccgaagta    4860
gacgggctcg cgctgttcga cgcggcactg gcggcggacc ggccggtact gctgccgatg    4920
cggatgcacc gtgccgcgtt gcgtgcccgc gcctccgccg aaggacttcc ggcagtcctc    4980
ggcggactcg tccgggtcac ccgcccggcg ccgtcggccg caccgcgcgg actggacgag    5040
gcggccctgc tcgacctcgt ccggacgacg gtcgccgccg tcctgggcca cccgacgcg    5100 cacgcgatcg acccggatcg cgcgttcacc gaggtgggtt tcgactcgct cgccgccgtg    5160
gaactgcgca accggctgat cgcggccacc ggactgaaga tcgcgccgac gctggtgttc    5220
gatcacccga accgcgtgc ggtcgccgcg ttcctcgccg ccggctccgc tccggtccgg    5280
gacgagcccg ccgctccggc cgaagccgac gagccgatcg cgatcatcgg catggcctgc    5340
cgctatccgg gcggggtgag cacacccgac gacttgtggc gtctggtcgc cgacgggaac    5400
gacggcatca cccggttccc cgagaaccgc ggctgggaca ccgacggcgt ctaccacccc    5460
gacgccgacc accgcggcac gacctacgtg cgcgagggcg gtttcctgca cgacgccgga    5520
cagttcgatc ccggcttctt cgggatctcg ccccgggaag cgctggcgat ggacccgcag    5580
cagcggctgc tgctggagat ctcccacgaa gccgtcgaac gggccgggat cgacccgaag    5640
tccttgcgcg gcagtggaac cggcgtgttc gccggggtga tgtaccacga ctacgcgacc    5700
gggctgaacc gcgtccccga cgacgtcgag ggttacctcg gcaacgggac ctcggccagc    5760
attcactccg gccgggtcgc ctacaccttc gggctggaag gcccggccgt cacgatcgac    5820
acggcctgtt cgtcgtcgct ggtggcgctg cacctggccg cgcaggcgct gcggcgcggt    5880
gagtgctcga tggcgctggc gggcggggtg accgtgatgg ccacgcccga ggtcttcgtg    5940
gacttcagcc gtcagcgcgg cctcgctccc gatggccgct gcaagtcctt ttcggacgaa    6000
gcagacggca cggtgtggag cgaaggcgtc gggatgctcc tggtggaacg cctttccgac    6060
gcccgccgca acgccatcg cgtcctcgcg atcgtgcggg ggagcgcggt caaccaggac    6120
ggcgcgtcca acggcctcac cgccccgagc ggtccgtcgc agcaacgggt gatccgccgg    6180
gccttggcgg acgccggtct caaaccgtcc gaagtggacg ctgtggaggc ccacggcacc    6240
gggacgccgt tgggtgatcc gatcgaggcg caggcgatgc tcgccaccta cggccaggac    6300
cgggaccggc cgctgtggct cggtcgctg aagtcgaacc tcggccacac ccaggccgcc    6360
gccggcgtcg cgggatcat caagatggtg caggcgatgc accacggtgt gctgccccgc    6420
acgctcaacc tcggcacgcc gacgaccaag gtcgactgga catccgggaa cgtgtccttg    6480
ctcagcgagc ccgtggcctg ccggaaaacc ggcgggcccc ggcgtgcggc tgtctcgtcg    6540
ttcgggatca gcgggaccaa cgcgcacgtc gtcctggagc aggcggaacc ggtcgaaaag    6600
tccacttcgg acacatcgcc gctcggtggt gacgtgctgc cgttcgtcct gtccggaaag    6660
acgtccgccg ccctgccgc gcaggccgac cggctcgccg ggcacctggc cggcgacgtc    6720
tccctgcccg ccgtggcccg cgcgctcgcg gtgaccaggt ccgcgctgga ccaccgtgcc    6780
```

```
gtggtggtgg cgggcgaccg cgccggggttg accgccgggc tgcgcgcgct ggccgacgcc    6840
gtccccgcgc cccacgtggt cgatggggtc gccgagaacg gcaaggccgt cttcgtcttt    6900
ccaggccagg gatcgcagtg gaccgggatg gcggtggatc tgctgggatc gtcggcggtc    6960
ttcgccgaag cgatggccga ctgcgaggcc gcacttctgt cccatctgga ctggaagctg    7020
acgcacgtcc tgtccgacgc ggcggcgctg aacgggtgg acgtcgtcca gccggtgctg     7080
ttcgcggtga tggtgtcgct ggcccggctc tggcgggcgt gcggcatcga acccgccgcc    7140
gtggtcgggc attcgcaggg tgagatcgcg gccgcgtgtg tcgcgggcgc gctgtcgctg    7200
gaagacgccg cacgcgtggt ctgcctgcgc agcaaggcga tcctggcgct gtccggattg    7260
ggcgggatgg tgtcggtcgc ggcctctgag gatcgcgtcc gggaactgct gcccgatggc    7320
gtttccgtgg ccgtggtgaa cggcccggct tccgtcgtcg tgtccggtga cgtcgccggg    7380
ctggaggcgc tgctcaagcg atgcgaactg ctcgacgtgc gggcgaagcg ggtcccggtg    7440
gactacgcgt cgcactcggc tcacgtcgac gcgatcgaac agcaggtcgt gacggcgctg    7500
agcggaatca tgccgcgcga agccgaactg ccgatgtact cgaccgtcac cggtgagccg    7560
atcgacacga ccaccctcga cgcggcctat tggttccgca atctccgggc caccgtccgg    7620
ttcgaccagg cggtgcggcg gctgatcgcg gacgggttcc ggttcttcgt cgagacgagc    7680
ccgcatccgg tgctggtcgc cgggctgacc gaactcgtcg aagaggccgc cgtgcccgcc    7740
gtcgcgctcg cgagccttcg ccgtgacgag ggtggaccga cccggttcgt cacctccctg    7800
gccgaggcgc acgtccacgg tctcagcccc gattgggccg cgctgctgcc cgaggcgggg    7860
tgggtggatc tgccgcccta tgccttccag catcaggagt tctggctcac cgacgccggg    7920
gaaccgggtg acgccgccgg attcggtctc ggcgccaccg gcatccgct gctcaccgcc      7980 gcgaccgcgc tgccgggctc cggcggcctg ctgctcaccg gccggatctc gacggccgcc    8040
cagccgtggc tggccgacca cgcggtgcag ggcgtggtgc tgctgccggg tacgcgttc     8100 gtggagctgg cgctgcaggc cggaacccac gcgggctgcg gcggatcga cgagctgact     8160 ctcgaagccc cgctgccgct tcccgagcag ggcggcgtcc gcgtccaggt cgtcctgggg    8220
tccgaagtga acggacgccg cgaggtcacc gtgcactccc aggccgaatc cggtgacgac    8280
acctgggtgc ggcacgcatc cggcttcctg acttcggcgg aaaccccggg agagggactg    8340
accgaatggc cgcccgccgg cgcgacgagc gccgacctcg acggctttta cgccgacgcc    8400
gaggcgcagg gctacggcta cggtccggcg ttccaagggc tgcgagcggc ctggaccctg    8460
ggttccgacg tcttcgccga ggtcgtcctg cccgatgccg agggcgcgga ccggttcggt    8520
ctgcatccgg cgttgctcga cgccgccctc cacgccctcg gtaccgtccg gtccggcgac    8580
ggcgcggaac tgccgttcgc gtggaccggg gtcaccgtgc acgccgtcgg cgccaccgcg    8640
ctgcgggtcc ggctcaccgt ggggacggac accgtcgcgg tgacggcggc cgatccggcg    8700
ggcgcgccgg tcgcgaccgt cgaaggcctc gtcacgcggc ccgccgccct gcccggatcc    8760
cggcggccgg actcgctgtt ccgcgtcgac tggactccgg tctccacgcc ggaagccgtc    8820
gagacgccga ccgtcaccgt cctgtccgac ggcgacctga ccgcgctcgc cgagatcccc    8880
gacgtggtgc tggtgccggt gggagccgag gccggggacc tcaccgagag cgtccatcgc    8940
acgaccgccc gggtgctcga tctgctccgg acctggctcg acgacgagcg gttcgccgac    9000
gcgcggctgg tgctgcacac ccgcggcgcg gtcgcggacg tccgcgacct gccggccgcg    9060
gcggcctggg gcctggtccg gtccgcgcag gccgagaacc ccgaccggat cgtcctgctc    9120
```

-continued

```
gacagcgaca ccgaccttcc gccggcgttg ctcgccgaag tgctggccac cggtgaggcg   9180
cagctcgcgt ggcgcgacgg ggaactgctc gtgccgaggc tcgccaaggt ctccaccgac   9240
ggcacgctga ccccgccgga aggcccctgg gtgctggacg cgccccgccg cggcacgctg   9300
gaagagctcg cgctcgtccc ggcgcccacg gccgcccggc cgctcgccga cggcgaggtc   9360
cggatccagg tccgggccgc cgggatcaac ttccgcgacg tgctcatcac gctcgacatg   9420
tatcccgagg acaaggcggt gatgggcagc gagggcgcgg gtatcgtcac cgaaatcggt   9480
tccggcgtca ccggcctgaa gcccggcgac cgggtcttcg gcctgttcga cggcgcgttc   9540
ggaccggtcg cgatcgccga ccggcggacg gtcacgaaaa tgcccgtgga ctggacgttc   9600
gccgaagcgg ccgctctgcc ggtcgtcttc ctcaccgcct actacgggct ggtcgacctc   9660
ggcgggctcc ggccggggga gaaggtgctg atccacggag cgaccggcgg tgtcggcatg   9720
gccgcggtcc agctggcccg ccacctcggc gccgaggtgt cgccacggc gagccccggc    9780 aagtgggaag tgctgcgggg cctcggtttc gacgacgagc acatcgcctc ctcccgcacg   9840
ctggacttcg aggaccggtt cggccggatg gacgtcgtcc tggactcgct cgccaaggag   9900
ttcgtcgacg cgtcgctgcg gctgctgggc gagggcggcc ggttcgtgga gatgggcaag   9960
accgacatcc gtgacgcgga cgaggtcgcg gccgcgcatc ccggcgtcac ctaccgcgcg  10020
ttcgacctgc tcgacgccgg acggccgagg atcggcgaga tcctggccga actgctggac  10080
ctgttcggcg ccgggtcgct caccgtgccc cggccgacgg tgtgggacgc gcgccgcgca  10140
cccgaggtct tccggttcat gagccaggcc aagcacatcg caagaacgt gctcaccatc    10200 ccgtccacaa tggacgggaa cgggacggtg ctgatcaccg gcgccaccgg gacactcggc  10260
gcgctggtcg cccggcatct ggtcaccgtg cgcggtgtcc ggcacctgct gctcgtcggc  10320
cgccggggtc gtgcggcggc cgggatggcc gaactcgaag cggaactgac cgccgccggg  10380
gcgtccgtca ccatcgccgc ctgcgacgcg ccgaccggg cggcgctggc cgccctgctc    10440
gccaccgtcc cggccgagca tccgctggcc ggggtggtgc acgccgccgg tgtcctggac  10500
gacggcctcg tcgccacgct gaccccgag cggctggcga aggtgctgcg cccgaaggtc    10560
gacgccgcgg tcaacctgca cgaactgacc cgcgacgcgc atctcgccga gttcgtcctg  10620
ttctcctcgg ccgccggcgc gttcggcgac gccggacagg gcaactacgc cgccgcgaac  10680
agtttcctcg actcgctcgc ccggcaccgt cgggcgcagg ggttgcccgc ggtctcgctc  10740
gcgtggggtt tctgggccga gctgagcggg atgaccggcc acctcggtga agcggatctg  10800
gcccggctca agcggtccgg gatgagccct ctgtccactg aggacggact actgttgatg  10860
gacgccgccc gtgccgggta cgaaccggcc ccgctcccga tgcacatcga cctcgccgcc  10920
ctgcggggcg aggaagtgca cccgttgctg cggggctgg tgaaggcacc ggtgcgccgg   10980
gccgccgcgg ccaccggcac acagtccgag ggactagccg accggctggc cgggctcgcc  11040
ccggccgccc gcgccgggc cctgctggac ctgatccgcg cgaacgtcgc cgcggtgctc    11100
ggtttcggct caccggagca ggtcgggtc cggcaggcct tccgggagct cgggttcgac    11160
tcgctcagcg cggtcgaact ccgcaaccgg ctcaacgcgg cgaccggtct gcggctgccc  11220
gccacggtcg tgttcgacca tccgacgccc accgcgctcg ccgaaaccct cggcgaccgg  11280
ctggcacccg ccgaagaagc cgttgacgac gaggtcgccc gtatcggcgc ggtcctcgct  11340
tcggtgcccg ccgaccggct ccgcgaagcc ggcgtgctgg acctgctgac ccggctggcc  11400
gaccccggct accgcccac cgagtcgccc gacggcgcgg acatcgacga gatggacgcc  11460
gaccgcctga tcgcactcgc tttcgacgct tccgaccccg cctga                   11505
```

-continued

<210> SEQ ID NO 39
<211> LENGTH: 5723
<212> TYPE: PRT
<213> ORGANISM: Amycolatopsis orientalis

<400> SEQUENCE: 39

```
Val Lys His Pro Gly Ala Ala Met Ser Thr Ser Glu Asn Lys Val Val
  1               5                  10                  15

Glu Ala Leu Arg Ala Ala Leu Lys Glu Ala Asp Arg Leu Arg Gly Glu
             20                  25                  30

Asn Arg Arg Leu Thr Gly Glu Pro Ile Ala Ile Gly Met Ala Cys
         35                  40                  45

Arg Tyr Pro Gly Gly Val Arg Ser Pro Glu Glu Leu Trp Asp Leu Val
     50                  55                  60

Ala Gly Glu Arg Thr Gly Leu Thr Gly Phe Pro Val Asp Arg Gly Trp
 65                  70                  75                  80

Asp Leu Asp Gly Leu Tyr Asp Pro Glu Gln Gly Lys Pro Gly Lys Ser
                 85                  90                  95

Tyr Val Arg Glu Gly Gly Phe Leu His Asp Ala Arg Phe Asp Pro
            100                 105                 110

Ala Phe Phe Gly Ile Ser Pro Arg Glu Ala Leu Ala Met Asp Pro Gln
            115                 120                 125

Gln Arg Leu Leu Leu Glu Ile Ser Trp Glu Ala Ile Glu Arg Ala Gly
130                 135                 140

Ile Ala Pro Asp Ser Leu Arg Gly Ser Arg Thr Gly Val Phe Ala Gly
145                 150                 155                 160

Val Ile His Asn Glu Tyr Ser Ala Ile Ala Gly Thr Pro Pro Ala Asp
                165                 170                 175

Leu Glu Pro Tyr Leu Gly Asn Gly Ser Phe Ala Ser Ile Ala Ser Gly
            180                 185                 190

Arg Val Ser Tyr Thr Phe Gly Leu Glu Gly Pro Ala Val Thr Val Asp
        195                 200                 205

Thr Ala Cys Ser Ser Ser Leu Val Ala Leu His Leu Ala Ala Gln Ala
    210                 215                 220

Leu Arg Gln Gly Glu Cys Ser Leu Ala Leu Ala Gly Gly Val Thr Val
225                 230                 235                 240

Met Ala Asn Pro Ala Ala Phe Val Asp Phe Ser Arg Gln Arg Gly Leu
                245                 250                 255

Ala Ala Asp Gly Arg Ile Lys Ala Phe Ala Glu Ala Ala Asp Gly Thr
            260                 265                 270

Ala Trp Gly Glu Gly Ala Gly Met Leu Leu Val Glu Arg Leu Ser Asp
        275                 280                 285

Ala Arg Arg Asn Gly His Arg Val Leu Ala Val Arg Gly Ser Ala
    290                 295                 300

Val Asn Gln Asp Gly Ala Ser Asn Gly Leu Thr Ala Pro Asn Gly Leu
305                 310                 315                 320

Ser Gln Gln Arg Val Ile Arg Gln Ala Leu Ala Asn Ala Arg Leu Ala
                325                 330                 335

Pro Ser Asp Val Asp Ala Met Glu Ala His Gly Thr Gly Thr Arg Leu
            340                 345                 350

Gly Asp Pro Ile Glu Ala Gln Ala Leu Leu Ala Thr Tyr Gly Gln Asp
        355                 360                 365

Arg Thr Thr Pro Leu Trp Leu Gly Ser Val Lys Ser Asn Ile Gly His
```

```
              370                 375                 380
  Ser Gln Ala Ala Ala Gly Val Ala Ser Ile Ile Lys Leu Val Glu Ala
  385                 390                 395                 400

Met Arg His Gly Val Leu Pro Lys Thr Leu His Val Asp Ala Pro Thr
                  405                 410                 415

Ser His Val Asp Trp Ser Glu Gly Ala Val Ser Leu Leu Thr Glu Ala
                  420                 425                 430

Glu Pro Trp Pro Lys Thr Asp Arg Pro Arg Ala Ala Val Ser Ser
                  435                 440                 445

Phe Gly Ile Ser Gly Thr Asn Ala His Val Val Leu Glu Gln Pro Thr
                  450                 455                 460

Ala Glu Glu Pro Pro Ser Thr Phe Ala Gly Pro Val Pro Phe Val
  465                 470                 475                 480

Leu Ser Gly Lys Thr Glu Ala Ala Leu His Glu Gln Val Ala Arg Val
                  485                 490                 495

Arg Glu Leu Ala Arg Asp Ser Asp Val Thr Ala Ala Asp Leu Ala Phe
                  500                 505                 510

Ser Leu Ala Thr Thr Arg Thr Ala Leu Asp His Arg Ala Ala Leu Val
                  515                 520                 525

Gly Thr Leu Asp Asp Leu Leu Thr Ala Thr Leu Val Glu Gly Arg Ala
                  530                 535                 540

Thr Asp Gly Gly Thr Ala Phe Leu Phe Thr Gly Gln Gly Ser Gln Arg
  545                 550                 555                 560

Leu Gly Met Gly Arg Glu Leu Ala Glu Arg Phe Pro Val Phe Ala Gln
                  565                 570                 575

Ala Phe Asp Asp Val Ser Ser Arg Phe Glu Arg Pro Ile Ala Glu Leu
                  580                 585                 590

Ser Ala Glu Glu Leu Asn Gln Thr Ala Asn Thr Gln Cys Ala Leu Phe
                  595                 600                 605

Ala Phe Glu Val Ala Leu Phe Arg Leu Val Glu Asn Trp Gly Leu Arg
                  610                 615                 620

Pro Asp Phe Leu Ala Gly His Ser Val Gly Glu Ile Ala Ala Ala His
  625                 630                 635                 640

Val Ala Asp Val Leu Ser Leu Asp Asp Ala Val Thr Leu Val Ser Ala
                  645                 650                 655

Arg Gly Arg Leu Met Gln Ala Leu Pro Thr Gly Gly Ala Met Val Ala
                  660                 665                 670

Leu Gln Ala Thr Glu Ala Glu Val Ala Pro Leu Leu Thr Asp Arg Val
                  675                 680                 685

Ser Leu Ala Ala Ile Asn Gly Pro Glu Ser Val Val Ser Gly Asp
                  690                 695                 700

Glu Glu Ala Val Ala Ala Val Ser His Phe Glu Gly Arg Lys Ser
  705                 710                 715                 720

Lys Arg Leu Thr Val Ser His Ala Phe His Ser Pro Leu Met Glu Pro
                  725                 730                 735

Met Leu Asp Asp Phe Arg Ala Val Val Glu Gly Leu Thr Phe Ala Glu
                  740                 745                 750

Pro Arg Ile Pro Ile Val Ser Gly Gly Leu Ala Glu Val Ser Thr Ser
                  755                 760                 765

Asp Tyr Trp Val Arg His Val Arg Asp Ala Val Arg Phe His Asp Ser
                  770                 775                 780

Val Glu Phe Leu Lys Ala Glu Gly Val Thr Arg Phe Leu Glu Ile Gly
  785                 790                 795                 800
```

```
Pro Asp Ala Val Leu Thr Ala Met Ala Lys Glu Ser Ala Glu Asp Ala
            805                 810                 815

Val Val Leu Pro Ala Ser Arg Arg Asp Arg Pro Glu Val Thr Thr Leu
            820                 825                 830

Leu Thr Ala Val Ala Gly Leu His Val His Gly Ala Glu Val Asp Trp
            835                 840                 845

Ala Pro Leu Phe Asp Gly Ala Arg Arg Val Asp Leu Pro Thr Tyr Pro
            850                 855                 860

Phe Gln Tyr Glu His Phe Trp Leu Glu Ser Gly Ala Ala His Arg Asp
865                 870                 875                 880

Val Ser Ala Ala Gly Leu Asp Ala Ser Pro His Ala Leu Leu Ala Ala
            885                 890                 895

Ala Val Arg Pro Ala Gly Glu Asp Glu Ile Leu Leu Thr Gly Arg Ile
            900                 905                 910

Ser Leu Ser Thr Leu Pro Trp Leu Ala Asp His Val Val Gly Gly Asn
            915                 920                 925

Val Leu Leu Pro Gly Thr Ala Phe Ala Glu Leu Ala Leu Ala Ala Ala
            930                 935                 940

Asp Glu Ala Gly Cys Glu Ala Val Glu Glu Leu Asn Leu Glu Ala Pro
945                 950                 955                 960

Leu Val Leu Pro Glu Lys Gly Val Gln Leu Gln Val Ala Val Gly
            965                 970                 975

Ala Ala Asp Asp Gln Gly Arg Arg Ser Val Thr Val His Ala Arg Pro
            980                 985                 990

Glu Asp Asp Gly Phe Trp Val Arg His Ala Ser Gly Val Leu Gly Thr
            995                 1000                1005

Ala Val  Ser Thr Gln Asp Glu  Met Ile Glu Trp Pro  Pro Ser Gly
            1010                1015                1020

Ala Glu  Pro Val Asp Leu Glu  Gly Phe Tyr Pro Asn  Leu Ala Ala
            1025                1030                1035

Glu Gly  Leu Gly Tyr Gly Pro  Ala Phe Gln Gly Val  Arg Ala Val
            1040                1045                1050

Trp Thr  Arg Asp Gly Asp Val  Phe Ala Glu Val Gln  Val Asp Asp
            1055                1060                1065

Thr Pro  Gly Thr Phe Gly Ile  His Pro Ala Leu Phe  Asp Ser Ala
            1070                1075                1080

Leu His  Ala Ile Gly Val Gly  Glu Ser Arg Gly Leu  Glu Ile Pro
            1085                1090                1095

Phe Ala  Trp Ser Asp Leu Arg  Leu His Ala Asp Gly  Ala Thr Val
            1100                1105                1110

Leu Arg  Val Arg Leu Ser Pro  Ala Gly Asp Gly Ala  Val Ser Val
            1115                1120                1125

Phe Ala  Thr Asp Pro Ala Gly  Ala Pro Val Leu Ser  Val Gly Ser
            1130                1135                1140

Leu Ser  Leu Arg Ala Pro Val  Ala Ala Thr Ala Ser  Leu Pro Arg
            1145                1150                1155

Asp Ser  Leu Phe Arg Val Thr  Trp Thr Pro Val Thr  Val Pro Ala
            1160                1165                1170

Gly Ala  Gly Glu Pro Thr Val  Glu Ser Phe Val Asp  Phe Asp Asp
            1175                1180                1185

Val Arg  Gln Ala Thr Ala His  Ala Arg Gln Ile Ala  Val Glu Pro
            1190                1195                1200
```

-continued

Gly Glu Ala Pro Val Val Phe Leu Thr Ser Gly Ala Phe Thr Asp
1205                1210                1215

Pro Ala Gln Ala Ser Val Trp Gly Leu Met Arg Ser Ala Arg Glu
1220                1225                1230

Glu Tyr Pro Gly Arg Phe Val Leu Val Asp Ala Asp Asp Pro Ala
1235                1240                1245

Thr Leu Thr Ala Gly Leu Leu Ala Gly Ile Val Ala Ser Gly Glu
1250                1255                1260

Thr Glu Ala Ile Val Arg Glu Gly Glu Val Arg Val Pro Arg Leu
1265                1270                1275

Thr Pro Val Arg Gly Gly Glu Thr Gly Pro Gly Trp Asp Pro Glu
1280                1285                1290

Gly Thr Val Leu Ile Thr Gly Gly Thr Gly Ala Leu Ala Thr Glu
1295                1300                1305

Leu Ala Arg His Leu Val Thr Arg Arg Gly Val Arg Asn Leu Ile
1310                1315                1320

Leu Ala Gly Arg Arg Gly Pro Ala Ala Glu Gly Ala Ser Glu Leu
1325                1330                1335

Ala Ala Glu Leu Ala Asp Leu Gly Ala Gln Ala Arg Ile Val Ala
1340                1345                1350

Cys Asp Val Ala Asp Arg Asp Gln Leu Thr Ala Leu Leu Asp Gly
1355                1360                1365

Val Pro Leu Thr Ala Val Val His Ala Ala Gly Val Leu Asp Asp
1370                1375                1380

Gly Leu Leu Ala Asp Leu Thr Arg Asp Arg Phe Glu Thr Val Leu
1385                1390                1395

Arg Ser Lys Val Asp Gly Ala Ile Leu Leu Asp Glu Leu Ala Gly
1400                1405                1410

Asp Ala His Leu Val Phe Phe Ser Ser Ala Ala Gly Val Leu Gly
1415                1420                1425

Ser Ala Gly Gln Ala Asn Tyr Ala Ala Ala Asn Ala Ala Leu Asp
1430                1435                1440

Ala Val Ala Ala Arg Arg Arg Glu Arg Gly Leu Pro Ala Thr Ser
1445                1450                1455

Leu Ala Trp Gly Leu Trp Glu Thr Gly Asp Gly Met Ala Gly Ala
1460                1465                1470

Leu Ala Gly Thr Asp Arg Ala Arg Met Ala Gly Ser Gly Leu Leu
1475                1480                1485

Pro Leu Pro Val Gly Asp Ala Leu Thr Leu Phe Asp Phe Ala Val
1490                1495                1500

Gly Ala Glu Glu Val Leu Phe Val Pro Met Arg Leu Asp Val Pro
1505                1510                1515

Ala Leu Arg Ala Ser Ala Thr Asp Val Pro Leu Leu Arg Ala Phe
1520                1525                1530

Ala Gly Lys Ser Arg Arg Thr Ala Ser Ala Ala Pro Ala Ala Arg
1535                1540                1545

Glu Leu Arg Asp Arg Leu Ala Ser Leu Pro Thr Glu Glu Arg Gly
1550                1555                1560

Arg Glu Leu Leu Ala Leu Val Arg Gly Gln Val Ala Glu Val Leu
1565                1570                1575

Gly His Arg Asp Ala Gly Ala Val Glu Pro Ala Arg Pro Phe Arg
1580                1585                1590

Glu Leu Gly Phe Asp Ser Leu Thr Ala Val Glu Leu Arg Asn Gly

-continued

```
                1595                1600                1605

Leu Asn Ala Ala Ser Gly Leu Arg Leu Pro Ala Thr Ala Val Phe
    1610                1615                1620

Asp His Pro Thr Pro Lys Ala Leu Ala Asp Leu Leu Ala Ala Glu
    1625                1630                1635

Leu Phe Gly Ala Ala Pro Glu Ala Pro Val Gln Gly Pro Ala Met
    1640                1645                1650

Ala Ala Asp Glu Pro Ile Ala Ile Ile Gly Met Ala Cys Arg Tyr
    1655                1660                1665

Pro Gly Gly Val Ala Ser Pro Glu Asp Leu Trp Arg Leu Val Ala
    1670                1675                1680

Glu Gly Arg Asp Gly Ile Ser Leu Phe Pro Ala Asp Arg Gly Trp
    1685                1690                1695

Asp Val Asp Gly Leu Tyr Asp Pro Asp Pro Gly Lys Ala Gly Lys
    1700                1705                1710

Ser Tyr Val Arg Glu Gly Gly Phe Leu His Glu Ala Gly Asp Phe
    1715                1720                1725

Asp Ala Gly Phe Phe Gly Ile Ser Pro Arg Glu Ala Leu Gly Met
    1730                1735                1740

Asp Pro Gln Gln Arg Leu Leu Leu Glu Val Ser Trp Glu Ala Phe
    1745                1750                1755

Glu Arg Ala Gly Ile Asp Pro Gly Thr Leu Arg Gly Ser Asp Thr
    1760                1765                1770

Gly Val Phe Ala Gly Gln Met Tyr His Asp Tyr Leu Thr Gly Ala
    1775                1780                1785

Thr Val Val Pro Asp Asp Val Glu Gly Tyr Leu Gly Thr Gly Asn
    1790                1795                1800

Ser Gly Ser Val Leu Ser Gly Arg Val Ser Tyr Thr Phe Gly Leu
    1805                1810                1815

Glu Gly Pro Ala Val Thr Val Asp Thr Ala Cys Ser Ser Ser Leu
    1820                1825                1830

Val Ala Leu His Leu Ala Ala Gln Ala Leu Arg Arg Gly Glu Cys
    1835                1840                1845

Ser Leu Ala Leu Ala Gly Gly Val Thr Val Met Ala Thr Pro Glu
    1850                1855                1860

Thr Phe Val Asp Phe Ser Arg Gln Arg Gly Leu Ala Pro Asp Gly
    1865                1870                1875

Arg Ser Lys Ser Phe Ser Asp Gly Ala Asp Gly Thr Ser Trp Ser
    1880                1885                1890

Glu Gly Val Gly Met Leu Leu Val Glu Arg Leu Ser Asp Ala Glu
    1895                1900                1905

Arg Asn Gly His Arg Ile Leu Ala Val Val Arg Gly Ser Ala Val
    1910                1915                1920

Asn Gln Asp Gly Ala Ser Asn Gly Leu Thr Ala Pro Asn Gly Pro
    1925                1930                1935

Ser Gln Gln Arg Val Ile Arg Arg Ala Leu Ala Asp Ala Arg Leu
    1940                1945                1950

Glu Pro Ser Glu Val Asp Ala Val Glu Ala His Gly Thr Gly Thr
    1955                1960                1965

Thr Leu Gly Asp Pro Ile Glu Ala Gln Ala Leu Leu Ala Thr Tyr
    1970                1975                1980

Gly Gln Gly Arg Glu Asp Ala Ala Leu Trp Leu Gly Ser Ile Lys
    1985                1990                1995
```

-continued

```
Ser Asn Ile Gly His Ser Gln Ala Ala Ala Gly Val Ala Gly Val
2000                2005                2010

Ile Lys Met Val Glu Ala Met Arg Arg Gly Val Leu Pro Lys Thr
2015                2020                2025

Leu His Val Thr Glu Pro Ser Ser His Val Asp Trp Thr Ala Gly
2030                2035                2040

Ala Val Ser Leu Leu Thr Glu Ala Arg Leu Trp Pro Asp Ala Gly
2045                2050                2055

Arg Pro Arg Arg Ala Ala Val Ser Ser Phe Gly Ile Ser Gly Thr
2060                2065                2070

Asn Ala His Val Val Leu Glu Gln Gly Pro Ala Pro Val Glu Ala
2075                2080                2085

Ile Glu Ser Gly Glu Gly Pro Ala Ala Phe Val Leu Ser Ala Gly
2090                2095                2100

Ser Glu Ala Ala Leu His Asp Gln Ala Ser Arg Leu Arg Asp Phe
2105                2110                2115

Leu Ala Glu Thr Pro Ala Ala Leu Ala Asp Val Ala Phe Ser Leu
2120                2125                2130

Ala Thr Thr Arg Ala Ala Leu Glu His Arg Ala Ala Val Val Ala
2135                2140                2145

Ala Asp Arg Glu Thr Leu Leu Ala Ala Leu Glu Asn Leu Thr Val
2150                2155                2160

Thr Gly Arg Ala Thr Glu Gly Arg Thr Ala Phe Leu Phe Thr Gly
2165                2170                2175

Gln Gly Ser Gln Arg Leu Gly Met Gly Leu Gln Leu Ala Glu Arg
2180                2185                2190

Phe Pro Val Phe Ala Ala Ala Tyr Asp Glu Val Cys Ser Arg Phe
2195                2200                2205

Glu Gln Pro Leu Arg Asp Leu Thr Ala Glu Glu Leu Asn Gln Thr
2210                2215                2220

Ala Asn Thr Gln Cys Ala Leu Phe Ala Leu Glu Val Ala Leu Phe
2225                2230                2235

Arg Leu Val Glu Ser Trp Gly Val Arg Pro Asp Phe Leu Ala Gly
2240                2245                2250

His Ser Val Gly Glu Ile Ala Ala Ala His Val Ala Gly Val Leu
2255                2260                2265

Ser Leu Asp Asp Ala Val Thr Leu Val Ser Ala Arg Gly Arg Leu
2270                2275                2280

Met Gln Ala Leu Pro Thr Gly Gly Ala Met Val Ala Leu Gln Ala
2285                2290                2295

Thr Glu Ala Glu Val Thr Pro Leu Leu Thr Glu Arg Val Ser Leu
2300                2305                2310

Ala Ala Ile Asn Gly Pro Glu Ser Val Val Ser Gly Glu Glu
2315                2320                2325

Asp Ala Val Ala Ala Val Ser Gln Phe Glu Gly Arg Lys Ser
2330                2335                2340

Lys Arg Leu Thr Val Ser His Ala Phe His Ser Pro Leu Met Glu
2345                2350                2355

Pro Met Leu Asp Glu Phe Arg Val Val Ala Asp Ser Leu Ser Tyr
2360                2365                2370

Ala Ala Pro Arg Ile Pro Ile Val Ser Gly Gly Leu Ala Glu Val
2375                2380                2385
```

```
Ser Thr Ser Asp Tyr Trp Val Arg His Val Arg Asp Ala Val Arg
    2390            2395            2400

Phe His Asp Ser Val Lys Phe Leu Glu Ala Glu Gly Val Thr Arg
    2405            2410            2415

Phe Leu Glu Ile Gly Pro Asp Gly Val Leu Thr Ala Met Ala Lys
    2420            2425            2430

Glu Thr Ala Glu Asp Ala Val Val Pro Ala Leu Arg Arg Asp
    2435            2440            2445

Arg Pro Glu Val Glu Thr Leu Leu Thr Ala Val Ala Gly Leu His
    2450            2455            2460

Val His Gly Val Gly Val Asp Leu Thr Ala Leu Leu Gly Gly Gly
    2465            2470            2475

Ser Pro Val Asp Leu Pro Thr Tyr Ala Phe Gln His Arg Arg Phe
    2480            2485            2490

Trp Leu Ser Ser Ala Gly Gly Ala Ala Gly Asp Val Thr Ala Ala
    2495            2500            2505

Gly Leu Gly Thr Thr Asp His Pro Leu Leu Gly Ala Ala Ala Ala
    2510            2515            2520

Leu Pro Gly Asp Gly Gly Phe Leu Leu Thr Gly Arg Leu Ser Gly
    2525            2530            2535

His Ala Gln Pro Trp Leu Ala Glu His Arg Val Gly Gly Val Val
    2540            2545            2550

Leu Leu Pro Gly Thr Ala Phe Val Glu Ile Ala Leu Arg Ala Gly
    2555            2560            2565

Asp Glu Ala Gly Cys Gly His Leu Glu Asp Leu Thr Leu Glu Ala
    2570            2575            2580

Pro Leu Val Leu Pro Glu Arg Gly Ala Thr Gln Leu Ser Val Leu
    2585            2590            2595

Val Gly Ala Ala Asp Asp Thr Gly Arg Arg Thr Ile Glu Ile His
    2600            2605            2610

Ser Arg Glu Glu Gly Glu Asp Gly Trp Gln Arg His Ala Thr Gly
    2615            2620            2625

Leu Leu Ser Ala Ala Gly Ala Val Glu Pro Ala Gly Leu Thr Thr
    2630            2635            2640

Trp Pro Pro Gln Asn Ala Glu Ala Val Pro Val Gly Asp Val Tyr
    2645            2650            2655

Glu Arg Leu Ala Ala Thr Gly Leu Glu Tyr Gly Pro Ala Phe Arg
    2660            2665            2670

Gly Leu Arg Ala Ala Trp Arg Ala Gly Glu Asp Leu Phe Ala Glu
    2675            2680            2685

Val Glu Leu Pro Glu Asp Gln His Ser Asp Ala Ala Arg Phe Gly
    2690            2695            2700

Val His Pro Ala Leu Leu Asp Ala Ala Leu His Thr Leu Gly Leu
    2705            2710            2715

Ala Gly Gly Gly Asp Gly Thr Arg Leu Pro Phe Ala Trp Ser Gly
    2720            2725            2730

Val Arg Leu His Ala Ala Gly Ala Thr Arg Leu Arg Val Arg Leu
    2735            2740            2745

Arg Pro Ser Gly Pro Asp Gly Phe Glu Val Leu Val Ala Asp Gly
    2750            2755            2760

Thr Gly Arg Pro Val Val Ser Ala Glu Glu Leu Thr Leu Arg Glu
    2765            2770            2775

Ile Ser Gly Asp Ala Leu Ala Arg Lys Gly His Asp Ser Leu Tyr
```

```
                      2780              2785              2790
 Arg  Val  Ala  Trp  Arg  Pro  Val  Pro  Leu  Pro  Glu  Thr  Gly  Glu  Thr
           2795                2800                2805

Leu  Pro  Ala  Glu  Ser  Val  Phe  Ser  Val  Pro  Arg  Gly  Gly  Asp  Ser
           2810                2815                2820

Ala  Glu  Arg  Val  His  Glu  Thr  Thr  Ala  Ala  Val  Leu  Glu  Val  Val
           2825                2830                2835

Gln  Arg  Arg  Leu  Glu  Asp  Glu  Pro  Gly  Gly  Pro  Leu  Val  Val  His
           2840                2845                2850

Thr  Arg  Gly  Gly  Val  Ala  Ala  Gly  Asp  Gly  Glu  Ala  Val  Thr  Asp
           2855                2860                2865

Leu  Ala  His  Ala  Ala  Val  Trp  Gly  Leu  Val  Arg  Ala  Ala  Gln  Ser
           2870                2875                2880

Glu  Asn  Pro  Gly  Arg  Phe  Leu  Leu  Val  Asp  Ala  Glu  Thr  Leu  Pro
           2885                2890                2895

Asp  Gly  Arg  Ile  Leu  Ala  Ile  Asp  Glu  Pro  Gln  Ile  Ala  Leu  Arg
           2900                2905                2910

Asp  Gly  Arg  Ala  Leu  Ala  Pro  Arg  Leu  Ala  Thr  Thr  Ala  Ser  Ser
           2915                2920                2925

Thr  Glu  Leu  Thr  Pro  Pro  Glu  Gly  Ala  Trp  Arg  Leu  Asp  Thr  Thr
           2930                2935                2940

Gly  Arg  Gly  Thr  Leu  Glu  Asn  Leu  Thr  Leu  Val  Pro  Ser  Pro  Glu
           2945                2950                2955

Ala  Val  Ala  Pro  Leu  Ala  Glu  Gly  Glu  Val  Arg  Ile  Ala  Val  Arg
           2960                2965                2970

Ala  Ala  Gly  Leu  Asn  Phe  Arg  Asp  Val  Leu  Ile  Ala  Leu  Gly  Met
           2975                2980                2985

Tyr  Pro  Gly  Ala  Ala  Thr  Leu  Gly  Ser  Glu  Gly  Ala  Gly  Val  Val
           2990                2995                3000

Thr  Glu  Ile  Gly  Pro  Gly  Val  Thr  Gly  Leu  Asp  Val  Gly  Asp  Arg
           3005                3010                3015

Val  Phe  Gly  Leu  Met  Ser  Asn  Gly  Phe  Gly  Pro  Gln  Val  Val  Thr
           3020                3025                3030

Asp  His  Arg  Thr  Leu  Ala  Lys  Met  Pro  Glu  Asp  Trp  Ser  Phe  Ala
           3035                3040                3045

Thr  Ala  Ala  Ser  Val  Pro  Ile  Val  Phe  Leu  Thr  Ala  Tyr  Tyr  Gly
           3050                3055                3060

Leu  Phe  Asp  Leu  Ala  Arg  Leu  Glu  Ala  Gly  Glu  Ser  Ile  Leu  Val
           3065                3070                3075

His  Ala  Ala  Gly  Gly  Val  Gly  Met  Ala  Ala  Thr  Gln  Leu  Ala
           3080                3085                3090

Arg  His  Ala  Gly  Ala  Glu  Val  Phe  Gly  Thr  Ala  Gly  Pro  Gly  Lys
           3095                3100                3105

Trp  Asp  Thr  Leu  Arg  Ala  Asn  Gly  Phe  Asp  Asp  Thr  His  Leu  Ser
           3110                3115                3120

Ser  Ser  Arg  Asp  Leu  Gly  Phe  Glu  Glu  Lys  Phe  Arg  Asp  Ala  Thr
           3125                3130                3135

Gly  Gly  Arg  Gly  Val  Asp  Val  Val  Leu  Asn  Ser  Leu  Ala  Gly  Asp
           3140                3145                3150

Tyr  Val  Asp  Ala  Ser  Leu  Arg  Leu  Leu  Ala  Pro  Gly  Gly  Arg  Phe
           3155                3160                3165

Ala  Glu  Met  Gly  Lys  Thr  Asp  Ile  Arg  Glu  Pro  Gly  Glu  Thr  Gly
           3170                3175                3180
```

```
Val Glu Tyr His Pro Phe Asp Val Ile Asp Ala Gly Pro Glu Arg
3185             3190                 3195

Ile His Glu Met Leu Ala Ala Leu Leu Glu Leu Phe Ala Ala Gly
3200             3205                 3210

Ala Leu Thr Pro Leu Pro Val Thr Gly Trp Asp Val Arg Arg Gly
3215             3220                 3225

Pro Asp Ala Phe Arg Phe Leu Ser Gln Ala Lys His Val Gly Lys
3230             3235                 3240

Asn Val Leu Thr Met Pro Ala Ala Leu Asp Pro Asp Gly Thr Val
3245             3250                 3255

Leu Val Thr Gly Gly Thr Gly Ala Leu Gly Ala Leu Phe Ala Arg
3260             3265                 3270

His Leu Val Arg Glu Arg Gly Val Arg Arg Leu Leu Leu Ala Ser
3275             3280                 3285

Arg Arg Gly His Asp Ala Pro Gly Val Pro Glu Leu Val Ala Glu
3290             3295                 3300

Leu Thr Glu Ala Gly Ala Ser Val Thr Val Glu Ala Cys Asp Ala
3305             3310                 3315

Ala Asp Arg Gly Ala Leu Ala Ala Val Leu Ala Gly Ile Pro Ala
3320             3325                 3330

Ala His Pro Leu Thr Gly Val Val His Thr Ala Gly Val Leu Asp
3335             3340                 3345

Asp Gly Leu Val Gly Ser Leu Thr Pro Glu Arg Leu Ala Lys Val
3350             3355                 3360

Leu Arg Pro Lys Val Asp Ala Ala Leu Asn Leu His Glu Leu Thr
3365             3370                 3375

Ser Gly Ala Asp Leu Ala Glu Phe Val Val Phe Ser Ser Ala Ala
3380             3385                 3390

Gly Val Phe Gly Asn Ala Gly Gln Ala Asn Tyr Ala Ala Ala Asn
3395             3400                 3405

Gly Phe Leu Asp Ala Leu Ser Val Arg Arg Ala Ala His Gly Leu
3410             3415                 3420

Pro Ala Arg Ser Leu Ala Trp Gly Leu Trp Ala Glu Thr Gly Gly
3425             3430                 3435

Met Gly Gly Thr Leu Gly Glu Ala Glu Leu Ala Arg Met Ala Gln
3440             3445                 3450

Ser Gly Thr Ala Ala Leu Ser Thr Gln Asp Gly Leu Glu Leu Phe
3455             3460                 3465

Asp Ala Ala Gly Ala Leu Ala Glu Pro Val Leu Val Pro Met Arg
3470             3475                 3480

Leu Asp Val Thr Ala Met Gly Gly Asp Gly Leu Pro Pro Leu Leu
3485             3490                 3495

Arg Gly Leu Ala Arg Gly Pro Val Arg Arg Ala Ala Ser Ala Gly
3500             3505                 3510

Ala Ala Gly Asp Ala Asp Ser Leu Arg Asp Arg Leu Leu Ala Val
3515             3520                 3525

Pro Val Ala Asp Arg Glu Thr Leu Leu Val Asp Leu Val Arg Thr
3530             3535                 3540

His Ser Ala Thr Val Leu Gly His Thr Ala Ala Asp Ala Val Glu
3545             3550                 3555

Ala Thr Arg Ser Phe Gln Glu Ile Gly Phe Asp Ser Leu Thr Ala
3560             3565                 3570
```

-continued

```
Val Glu Leu Arg Asn Arg Leu Thr Ala Ala Thr Gly Leu Arg Leu
    3575                3580                3585

Pro Ala Thr Leu Ile Phe Asp Tyr Pro Thr Pro Glu Ala Leu Ala
    3590                3595                3600

Ala His Ile Gly Glu Gly Val Leu Gly Ala Gln Gly Gly Pro Glu
    3605                3610                3615

Thr Gly Gln Ala Ala Val Thr Ala Asp Glu Pro Ile Ala Ile Val
    3620                3625                3630

Ala Met Ser Cys Arg Phe Pro Gly His Ala Asp Thr Pro Glu Arg
    3635                3640                3645

Leu Trp Ala Leu Leu Ala Glu Gly Arg Asp Ala Leu Gly Glu Phe
    3650                3655                3660

Pro Ala Asp Arg Gly Trp Asp Leu Glu Arg Leu Phe Asp Thr Asp
    3665                3670                3675

Pro Asp Arg Arg Gly Thr Ser Tyr Thr Arg Gln Gly Ala Phe Leu
    3680                3685                3690

Glu Thr Ala Gly Asp Phe Asp Ala Gly Phe Phe Gly Ile Ser Pro
    3695                3700                3705

Arg Glu Ala Leu Ala Met Asp Pro Gln Gln Arg Leu Leu Leu Glu
    3710                3715                3720

Thr Ser Trp Glu Ala Phe Glu Arg Ala Gly Ile Asp Pro Ala Thr
    3725                3730                3735

Leu Arg Gly Ser Arg Thr Gly Val Phe Ala Gly Val Met Asp Asn
    3740                3745                3750

Glu Tyr Val Ser Gly Ser Ala Glu Val Pro Asp Gly Val Glu Gly
    3755                3760                3765

Tyr Leu Ala Thr Gly Thr Ser Ala Ser Val Ala Ser Gly Arg Val
    3770                3775                3780

Ser Tyr Thr Phe Gly Leu Glu Gly Pro Ala Val Thr Val Asp Thr
    3785                3790                3795

Ala Cys Ser Ser Ser Leu Val Ala Leu His Leu Ala Ala Gln Ala
    3800                3805                3810

Leu Arg Gln Gly Glu Cys Ser Leu Ala Leu Ala Gly Gly Val Thr
    3815                3820                3825

Val Met Ala Thr Pro Gly Thr Phe Val Glu Phe Ser Arg Gln Arg
    3830                3835                3840

Gly Leu Ala Ala Asp Gly Arg Cys Lys Ala Phe Ala Asp Gly Ala
    3845                3850                3855

Asp Gly Thr Gly Trp Gly Glu Gly Ala Gly Met Leu Leu Val Glu
    3860                3865                3870

Arg Leu Ser Asp Ala Arg Arg Asn Gly His Pro Val Leu Ala Val
    3875                3880                3885

Leu Arg Gly Ser Ala Val Asn Gln Asp Gly Ala Ser Asn Gly Leu
    3890                3895                3900

Thr Ala Pro Asn Gly Pro Ser Gln Gln Arg Val Ile Arg Gln Ala
    3905                3910                3915

Leu Ala Asn Ala Arg Leu Glu Pro Ser Glu Val Asp Ala Val Glu
    3920                3925                3930

Ala His Gly Thr Gly Thr Thr Leu Gly Asp Pro Ile Glu Ala Gln
    3935                3940                3945

Ala Leu Leu Ala Thr Tyr Gly Gln Asp Arg Glu Arg Pro Leu Leu
    3950                3955                3960

Leu Gly Ser Val Lys Ser Asn Ile Gly His Thr Gln Ala Ala Ala
```

-continued

|  | 3965 |  |  |  | 3970 |  |  |  | 3975 |  |  |
|---|---|---|---|---|---|---|---|---|---|---|---|
| Gly | Val | Ala | Gly | Val | Ile | Lys | Met | Val | Leu | Ala | Met | Arg | His | Gly |
|  | 3980 |  |  |  | 3985 |  |  |  | 3990 |  |  |

Gly Val Ala Gly Val Ile Lys Met Val Leu Ala Met Arg His Gly
     3980                3985                3990

Thr Leu Pro Arg Thr Leu His Val Asp Thr Pro Thr Ser Arg Val
     3995                4000                4005

Asp Trp Ala Ala Gly Arg Ile Glu Leu Ala Thr Glu Pro Thr Gln
     4010                4015                4020

Trp Pro Glu Thr Gly Gly Pro Arg Arg Ala Ala Val Ser Ser Phe
     4025                4030                4035

Gly Met Ser Gly Thr Asn Ala His Val Val Leu Glu Gln Ala Glu
     4040                4045                4050

Ala Val Glu Thr Arg Asp Glu Thr Ser Pro Gly Leu Leu Gly Asp
     4055                4060                4065

Val Val Ala Trp Pro Leu Ser Ala Lys Glu Pro Glu Ala Val Ala
     4070                4075                4080

Ala Gln Ala Ala Arg Leu Lys Ser Phe Leu Thr Gly Glu Arg Pro
     4085                4090                4095

Ala Asp Val Ala Tyr Ser Leu Ala Thr Ala Arg Thr Thr Leu Glu
     4100                4105                4110

His Arg Ala Val Val Gly Glu Asp Pro Ile Ala Gly Leu Ala
     4115                4120                4125

Ala Leu Ala Ala Gly Glu Pro Ser Gly Ser Val Thr Gly Thr
     4130                4135                4140

Ala Thr Ser Gly Lys Ala Val Phe Val Phe Pro Gly Gln Gly Ser
     4145                4150                4155

Gln Trp Ala Gly Met Ala Val Glu Leu Leu Ala Ser Ala Pro Val
     4160                4165                4170

Phe Ala Glu Ser Met Ala Glu Cys Glu Ala Ala Leu Leu Ser Tyr
     4175                4180                4185

Val Asp Trp Lys Leu Thr Glu Val Leu Ser Asp Ala Thr Ala Leu
     4190                4195                4200

Glu Arg Val Asp Val Val Gln Pro Ala Leu Phe Ala Val Met Val
     4205                4210                4215

Ser Leu Ala Arg Leu Trp Arg Ala Ser Gly Ile Glu Pro Ala Ala
     4220                4225                4230

Val Val Gly His Ser Gln Gly Glu Ile Ala Ala Ala Cys Val Ala
     4235                4240                4245

Gly Ala Leu Ser Leu Asp Asp Ala Ala Arg Val Val Cys Leu Arg
     4250                4255                4260

Ser Lys Ala Ile Thr Ala Leu Ser Gly Arg Gly Gly Met Val Ser
     4265                4270                4275

Val Ala Ala Pro Glu Ala Gln Val Arg Glu Ile Leu Pro Glu Gly
     4280                4285                4290

Val Ser Leu Ala Ala Val Asn Gly Pro Ala Ser Val Val Val Ser
     4295                4300                4305

Gly Asp Val Ala Gly Leu Asp Ala Leu Met Thr Ala Cys Glu Ala
     4310                4315                4320

Ser Gly Leu Arg Ala Lys Arg Ile Pro Val Asp Tyr Ala Ser His
     4325                4330                4335

Ser Ala His Val Asp Ala Ile Glu Gln Asp Val Leu Ala Ala Leu
     4340                4345                4350

Asp Gly Ile Glu Pro Arg Ala Pro Glu Ile Pro Phe Tyr Ser Thr
     4355                4360                4365

-continued

```
Val Ala Gly Glu Pro Leu Asp Pro Val Val Asp Ala Ala Tyr Trp
    4370                4375                4380

Phe Arg Asn Leu Arg Gly Thr Val His Phe Gly Gln Ala Val Arg
    4385                4390                4395

Arg Leu Leu Asp Asp Gly Phe Arg Phe Val Glu Ala Ser Pro
    4400                4405                4410

His Pro Val Leu Val Thr Gly Ile Ala Asp Thr Ala Glu Asp Ala
    4415                4420                4425

Gly Glu Arg Ala Val Ala Val Gly Ser Leu Arg Arg Asp Glu Gly
    4430                4435                4440

Gly Pro Leu Arg Phe Leu Thr Ser Leu Ala Glu Ala His Val His
    4445                4450                4455

Gly Leu Ser Pro Asp Trp Ala Ala Leu Ala Pro Gly Thr Arg Val
    4460                4465                4470

Asp Leu Pro Thr Tyr Ala Phe Gln His Glu His Tyr Trp Leu Arg
    4475                4480                4485

Thr Arg Ser Ser Ala Asp Pro Gly Gln Ala Gly Leu Asp Asp Gly
    4490                4495                4500

Gly His Pro Leu Leu Gly Ala Val Val Pro Leu Ala Gly Ser Asp
    4505                4510                4515

Gly Leu Val Ala Thr Gly Arg Ile Ser Ala Arg Asn Gln Thr Trp
    4520                4525                4530

Leu Pro Asp His Ala Val Gly Gly Ala Leu Leu Leu Pro Gly Ala
    4535                4540                4545

Ala Leu Val Asp Leu Ala Leu Thr Val Gly Glu Arg Thr Gly Cys
    4550                4555                4560

Gly Arg Ile Ala Glu Leu Thr Ile Glu Ala Pro Leu Val Leu Gly
    4565                4570                4575

Glu Ser Gly Ser Ala Arg Leu Gln Val Thr Val Gly Ala Ser Ala
    4580                4585                4590

Asp Asp Gly Thr Arg Glu Val Ala Val Tyr Ser Arg Asp Glu Thr
    4595                4600                4605

Ala Gly Thr Asp Trp Ile Arg His Ala Thr Gly Leu Leu Ala Ala
    4610                4615                4620

Asp Gly Glu Thr Pro Val Ala Asp Leu Thr Gln Trp Pro Pro Ala
    4625                4630                4635

Gly Ala Glu Pro Ile Ser Leu Glu Gly His Tyr Glu Gly Leu Ala
    4640                4645                4650

Glu Leu Gly Tyr Gly Tyr Gly Pro Ala Phe Arg Gly Leu Arg Ala
    4655                4660                4665

Val Trp Arg Arg Gly Asp Asp Val Phe Ala Glu Val Ala Leu Pro
    4670                4675                4680

Glu Asp Arg Ile Ala Glu Ala Ala Ala Phe Gly Leu His Pro Ala
    4685                4690                4695

Leu Leu Asp Ala Ala Leu His Ala Leu Gly Phe Gly Met Leu Pro
    4700                4705                4710

Asp Asp Gly Arg Leu Arg Leu Pro Phe Ala Trp Asn Glu Val Ser
    4715                4720                4725

Leu Ser Ala Val Gly Ala Pro Ser Leu Arg Val Arg Leu Ser Pro
    4730                4735                4740

Ala Gly Glu Asp Ala Val Ala Val Asp Leu Ala Asp Thr Ala Gly
    4745                4750                4755
```

-continued

```
Ala Pro Val Ala Ser Ile Gly Ser Val Val Phe Arg Pro Val Ala
    4760                4765                4770

Glu Ala Gln Leu Ala Gly Ala Arg Arg Asp Pro Ala Asp Ser Leu
    4775                4780                4785

Phe Gln Ile Gln Trp Thr Asp Leu Ser Ala Lys Asp Val Val Ala
    4790                4795                4800

Pro Ala Val Val Leu Gly Glu Asp Cys Ala Asp Leu Ala Glu
    4805                4810                4815

Leu Ala Ala Asp Leu Asp Ala Gly Arg Pro Ala Pro Asp Val Val
    4820                4825                4830

Leu Thr Thr Cys Ala Pro Val Thr Gly Asp Ile Ala Glu Gly Ala
    4835                4840                4845

His Ala Ala Ala Arg Asp Ala Leu Thr Leu Val Gln Asn Trp Leu
    4850                4855                4860

Ala Asp Glu Arg Phe Ser Gly Ala Arg Leu Val Phe Arg Thr Ser
    4865                4870                4875

Gly Ala Val Ser Val Ala Ala Asp Glu Pro Val Ser Asp Pro Ala
    4880                4885                4890

Asn Ala Thr Val Trp Gly Leu Val Arg Thr Ala Gln Glu Glu Asn
    4895                4900                4905

Pro Gly Arg Phe Gly Leu Leu Asp Thr Asp Gly Ser Glu Ala Val
    4910                4915                4920

Leu Gly Ala Ala Leu Ala Leu Asp Glu Pro Gln Leu Ala Leu Arg
    4925                4930                4935

Ala Gly Thr Val Leu Gly Ala Arg Leu Val Lys Ala Ser Ala Asp
    4940                4945                4950

Thr Ala Leu Val Pro Pro Gly Ser Arg Ala Trp Thr Val Asp
    4955                4960                4965

Thr Leu Gly Gly Gly Thr Leu Glu Asn Leu Val Leu Arg Asp Arg
    4970                4975                4980

Pro Asp Leu Leu Ala Pro Leu Ala Asp Gly Gln Val Arg Ile Ala
    4985                4990                4995

Val Arg Ser Ala Gly Leu Asn Phe Arg Asp Val Val Val Ala Leu
    5000                5005                5010

Gly Leu Val Pro Gly Gln Glu Gly Ile Gly Gly Glu Gly Ala Gly
    5015                5020                5025

Val Val Thr Glu Thr Gly Pro Gly Val Thr Asp Leu Ala Pro Gly
    5030                5035                5040

Asp Arg Val Leu Gly Met Phe Asp Ala Ser Phe Gly Pro Ile Ala
    5045                5050                5055

Val Ala Asp Arg Lys Leu Ile Ala Pro Val Pro Asp Asp Trp Ser
    5060                5065                5070

Phe Thr Glu Ala Ala Ser Ala Pro Val Ala Phe Leu Thr Ala Tyr
    5075                5080                5085

Val Gly Leu Ala Asp Leu Gly Glu Leu Arg Pro Gly Gln Thr Val
    5090                5095                5100

Leu Ile His Ala Ala Ala Gly Gly Val Gly Met Ala Ala Val Gln
    5105                5110                5115

Leu Ala Arg His Phe Gly Ala Glu Ile Tyr Val Thr Ala Ser Pro
    5120                5125                5130

Ala Lys Trp Asp Thr Leu Arg Ala Met Gly Phe Asp Asp Asp His
    5135                5140                5145

Ile Ala Ser Ser Arg Thr Leu Asp Phe Glu Asp Lys Ile Arg Glu
```

-continued

```
            5150                5155                5160
Ala Thr Gly Gly Arg Gly Val Asp Leu Val Leu Asp  Ser Leu Ala
    5165                5170                5175
Arg Glu Phe Val Asp Ala Ser Leu Arg Leu Val Arg  Glu Gly Gly
    5180                5185                5190
Arg Phe Val Glu Met Gly Lys Thr Asp Ile Arg Asp  Ala Asp Glu
    5195                5200                5205
Val Ala Ala Ala His Pro Gly Val Thr Tyr Arg Ala  Phe Asp Leu
    5210                5215                5220
Ile Asp Ser Gly His Asp Arg Ile Gln Glu Ile Leu  Gly Glu Leu
    5225                5230                5235
Leu Ala Leu Ala Asp Lys Asp Val Val Arg Pro Leu  Pro Thr Thr
    5240                5245                5250
Ala Trp Asp Val Arg Arg Ala Pro Glu Ala Phe Arg  Phe Leu Ser
    5255                5260                5265
Gln Ala Lys His Thr Gly Lys Ile Val Leu Glu Pro  Pro Ala Val
    5270                5275                5280
Leu Asp Pro Glu Gly Thr Val Leu Ile Thr Gly Gly  Thr Gly Val
    5285                5290                5295
Leu Gly Gly Leu Phe Ala Arg His Leu Val Thr Ala  His Gly Val
    5300                5305                5310
Arg Arg Leu Leu Leu Thr Ser Arg Arg Gly Leu Asp  Ala Glu Gly
    5315                5320                5325
Ala Arg Glu Leu Val Ala Asp Leu Thr Gly Leu Gly  Ala Thr Val
    5330                5335                5340
Thr Val Val Ala Cys Asp Val Ala Asp Arg Ala Ala  Val Ala Gly
    5345                5350                5355
Leu Leu Gly Ser Val Pro Pro Glu His Pro Leu Thr  Ala Val Val
    5360                5365                5370
His Thr Ala Gly Val Leu Asp Asp Gly Leu Ile Pro  Ala Leu Thr
    5375                5380                5385
Pro Asp Arg Leu Gly Thr Val Phe Arg Pro Lys Val  Asp Ala Ala
    5390                5395                5400
Val His Leu His Glu Leu Thr Arg Asp Leu Gly Leu  Ala Ala Phe
    5405                5410                5415
Val Leu Phe Ser Ser Ser Ala Ala Thr Phe Gly Ala  Ala Gly Gln
    5420                5425                5430
Gly Asn Tyr Ala Ala Ala Asn Ala Phe Leu Asp Ala  Leu Ala Gln
    5435                5440                5445
His Arg Arg Ala Glu Gly Leu Ala Gly Gln Ala Leu  Ala Trp Gly
    5450                5455                5460
Phe Trp Ala Glu Arg Ser Ala Met Thr Gly His Leu  Asp Glu Ala
    5465                5470                5475
Asp Val Ala Arg Met Lys Arg Ser Gly Val Ser Pro  Leu Ser Ser
    5480                5485                5490
Val Asp Gly Leu Ala Leu Phe Asp Ala Ala Ala Glu  Arg Asp Val
    5495                5500                5505
Ala Ala Leu Val Pro Val His Leu Asp Thr Ala Ala  Leu Arg Gly
    5510                5515                5520
Gln Thr Glu Val Pro Ala Leu Leu Arg Val Leu Ala  Gly Ala Pro
    5525                5530                5535
Ala Lys Arg Val Ala Gly Ala Ala Ala Thr Ser Gly  Pro Ser Leu
    5540                5545                5550
```

```
Ala Gln Arg Leu Ala Ala Leu Pro Ala Ala Asp Arg Glu Pro Phe
    5555                5560                5565
Leu Leu Asp Leu Val Arg Ser His Ala Ala Ala Leu Gly His
    5570                5575                5580
Ala Ser Val Ala Lys Val Gly Pro Glu Leu Ala Phe Arg Asp Leu
    5585                5590                5595
Gly Phe Asp Ser Leu Thr Ala Val Glu Leu Arg Asn Arg Leu Gly
    5600                5605                5610
Ala Ala Thr Gly Leu Arg Leu Pro Ser Thr Leu Val Phe Asp Gln
    5615                5620                5625
Pro Ser Pro Ala Ala Leu Ala Arg His Leu Leu Ala Glu Leu Gly
    5630                5635                5640
Glu Pro Ala Gly Ala Glu Pro Glu Val Ala Val Leu Ala Asp Leu
    5645                5650                5655
Asp Arg Leu Glu Thr Ala Leu Ala Ala Ala Val Thr Asp Asp Glu
    5660                5665                5670
Thr Ala Asp Arg Ile Thr Asp Arg Leu Arg Ala Val Leu Ala Arg
    5675                5680                5685
Trp Thr Glu Ala Arg Gly Pro Ala Glu Asp Glu Gly Asp Gly Asp
    5690                5695                5700
Leu Ala Asp Ala Ser Ala Asp Glu Leu Phe Asp Ile Leu His Lys
    5705                5710                5715
Glu Phe Gly Arg Ser
    5720

<210> SEQ ID NO 40
<211> LENGTH: 17172
<212> TYPE: DNA
<213> ORGANISM: Amycolatopsis orientalis

<400> SEQUENCE: 40
```

| | | | | | |
|---|---|---|---|---|---|
| gtgaaacacc | ctggagctgc | gatgtccaca | tccgagaaca | aggtcgtcga | ggccctgcgg | 60 |
| gcggcgctga | aggaagccga | ccgcctgcgc | ggggagaacc | ggcgcctgac | cggcgagccc | 120 |
| atcgcgatca | tcggcatggc | ctgccgttac | ccgggcgggg | tccgctcgcc | ggaagagctg | 180 |
| tgggatctgg | tcgccggaga | acgcaccggc | ctcaccggat | tccgggtcga | ccgcggctgg | 240 |
| gacctcgacg | ggctctacga | ccccgagcag | gggaaaccgg | gcaagagcta | tgtccgggaa | 300 |
| ggcggttttcc | tgcacgacgc | cgcccggttc | gacccggcgt | tcttcgggat | ctcgccgcgt | 360 |
| gaggcgctgg | cgatggaccc | gcagcagcga | ctgctgctgg | agatctcctg | ggaggcgatc | 420 |
| gaacgcgcgg | ggatcgcgcc | ggattccctg | cggggcagcc | ggaccggcgt | gttcgcgggc | 480 |
| gtcatccaca | acgagtactc | ggccatcgcg | ggcacgccgc | ccgcggatct | cgagccgtac | 540 |
| ctcggcaacg | ggagtttcgc | gagcatcgcc | tccgggcggg | tttcctacac | cttcgggctc | 600 |
| gaaggcccgg | cggtcaccgt | cgacacggcg | tgttcgtcgt | cgctggtggc | gctgcatctg | 660 |
| gcggcacagg | cgctgcggca | gggcgaatgt | tcgctggcgt | tggcgggtgg | ggtgaccgtg | 720 |
| atggccaacc | cggcggcgtt | cgtggacttc | agccgtcagc | gcgggctcgc | ggcggacggg | 780 |
| cggatcaagg | cgttcgccga | agccgccgac | ggcaccgcct | ggggcgaagg | cgcgggcatg | 840 |
| ctgctcgtcg | agcggctctc | cgacgcccgg | cgcaacgggc | accgcgtcct | cgccgtcgtg | 900 |
| cgcggatccg | cggtgaacca | ggacggcgcc | tcgaacgggc | tcaccgcgcc | caacggtctt | 960 |
| tcccagcaac | gggtcatccg | gcaggcactc | gcgaacgcgc | ggctcgcacc | gtccgatgtg | 1020 |

```
gacgccatgg aggcgcacgg cacgggcacc cggctcggcg acccgatcga ggcacaggct    1080
ttgctggcca cctacggcca ggaccggacc acccgctct ggctcggctc ggtgaagtcc    1140
aacatcgggc acagccaggc cgcggccggg gtcgcgtcga tcatcaaact cgtcgaggcg    1200
atgcggcacg gtgtgctgcc gaagacgctg cacgtcgacg cgccgacgtc gcatgtggac    1260
tggtccgagg gcgcggtctc gttgctgacc gaggccgagc cgtggccgaa gacggatcga    1320
ccccggcggg ccgcggtgtc ctcgttcggg atcagcggga cgaacgcgca cgtcgtcctc    1380
gaacagccca ccgcggaaga ggaaccgccg tccacgtttg cggggccggt gccgttcgtg    1440
ctgtccggca agaccgaagc cgccctgcac gagcaggtgg cccgcgtgcg ggaactcgcg    1500
cgggattcgg acgtcaccgc ggcggacctg gcgttctcgc tggccaccac gcggaccgcg    1560
ctggatcatc gggccgccct ggtcggcacg ctggacgatc tgctgaccgc cactttggtg    1620
gaagggcggg cgacggacgg cgggacggcg ttcctgttca cgggccaggg cagtcagcgg    1680
ctggggatgg gccgcgagct cgccgagcgt ttcccggtgt tcgctcaagc cttcgacgac    1740
gtctcttcgc ggttcgagcg accgatcgcg gagctgtccg ccgaggaact gaaccagacg    1800
gcgaacacgc agtgcgcgtt gttcgccttc gaggtggcgc tcttccggct ggtcgagaac    1860
tggggcctcc ggccggactt cctggccggg cattcggtcg gggagatcgc ggcggctcat    1920
gtcgcggacg tgctctctct cgacgacgcg gtgacgttgg tgtcggctcg tggccgcctg    1980
atgcaggcgt tgccgaccgg tggggcgatg gtggcgcttc aggcgaccga ggcggaggtc    2040
gccccgctcc tgaccgaccg ggtgtcgctg gccgcgatca acggcccgga gtcggtggtc    2100
gtctcgggtg acgaagaagc cgtcgccgcg gtggtgtccc acttcgaggg ccggaagagc    2160
aagcgcctta cggtgagtca cgcgttccat tcgcccttga tggagccgat gctcgacgac    2220
ttccgcgcgg tggtggaggg gctgaccttc gccgaaccgc ggatcccgat cgtgtccggc    2280
ggcctggctc aagtgtccac ttcggactat tgggtccggc acgtccgtga cgcggtgcgg    2340
ttccacgatt cggtcgaatt cctgaaggcc gagggcgtca cccggttcct ggagatcgga    2400
cccgacgccg tcctgaccgc catggccaag gaaagcgccg aggacgcggt cgtcctcccg    2460
gcttcgcgac gggaccgccc cgaggtgacg acgctgctga cggcggtcgc cggactgcac    2520
gtccatgggg ccgaggtcga ctgggcgccg ctgttcgacg tgcgcggcg cgtcgatctg    2580 ccgacgtatc cgttccagta cgagcacttc tggctcgaat ccggtgccgc tcaccgcgac    2640
gtgtccgccg ccgggctgga cgcgtcgccg cacgccctgc tcgccgccgc ggtccggccg    2700
gcgggcgagg acgagatcct cctgacgggc aggatctcgc tgagcacact gccgtggctg    2760
gcggaccacg tcgtcggcgg aaacgtcctt ctgcccggta ccgcgttcgc cgaactcgcg    2820
ctcgcggccg ccgacgaggc cggttgtgag gccgtcgagg aactgaacct ggaagcgccg    2880
ctggtgctgc ccgagaaggg cggggtccag ttgcaggtcg cggtcggcgc ggctgacgac    2940
cagggcaggc gctcggtcac cgtgcacgcc cggccggagg acgacggctt ctgggtgcgg    3000
cacgcctccg gcgtcctcgg taccgcagtg tccacacagg acgagatgat cgagtggccg    3060
ccctcgggcg cggagcctgt cgacctcgaa ggcttctacc cgaacctggc ggccgaaggg    3120
ctcggctatg gcctgccctt tcagggcgtc cgtgccgtct ggaccgcgca tggcgacgtg    3180
ttcgccgaag tccaggtgga cgacactccc ggcaccttcg ggatccaccc cgcgttgttc    3240
gactccgccc tgcacgccat cggcgtcggc gagtcgcggg ggctggagat cccttcgcc    3300 tggtcggatc tccgcctgca cgccgacggc gcgacggtgc tccgggttcg cctcagcccc    3360
gcgggcgacg gtgccgtctc cgttttcgcg accgaccccg ccggagcgcc ggtgttgtcg    3420
```

-continued

```
gtcggctcgc tcagcctgcg ggctccggtc gccgcgaccg cctcgcttcc ccgtgactcg    3480
ctgttccgcg tcacctggac gccggtgacg gtgcccgctg gtgctgggga acccaccgtg    3540
gagtcctttg tggacttcga tgacgtccgc aagcgacgg cgcacgcccg gcagatcgcc     3600
gtggagcccg gcgaggcccc cgtggtgttc ctgaccagcg gcgcgttcac cgatcctgcg    3660
caggcgtcgg tctggggact catgcgttcg gcgcgggagg agtacccgg ccggttcgtg     3720 ctcgtcgacg ccgacgaccc cgccacgctc acggccggcc tgctggccgg catcgtggcc    3780
tccggcgaga ccgaagccat cgtgcgtgag ggcgaggtcc gtgtcccgcg gctcaccccg    3840
gtgcgcgggg gcgaaaccgg accgggctgg gacccggaag gcacggtcct gatcaccggc    3900
ggcaccggcg cgctcgccac cgaactcgcc cggcacctcg tcacgacg cggtgtgcgg      3960 aacctgatcc tcgccggacg ccgcggtccc gccgcggaag gcgcgagcga gctggccgcc    4020
gaactggcgg acctcggcgc gcaggcccgg atcgtcgcct gcgacgtcgc ggatcgcgac    4080
cagctgacgg cgttgctcga cggcgttccg ctgaccgcgg tcgtccacgc cgcgggcgtc    4140
ctcgacgacg gcctgctcgc cgatctcact cgggaccgat tcgaaaccgt cctgaggtcc    4200
aaagtggacg gcgcaatcct gctggacgaa ctggccggtg acgccacct cgtgttcttc     4260 tcctccgcgg ccgggtgct cggcagcgcg gggcaggcca actacgccgc cgccaacgcc     4320
gccctcgacg cggtggccgc gcgccgccgg gaacgggac tacccgcgac ctcgctcgcg     4380
tgggggctct gggagaccgg cgacgggatg gcgggtgcgc tcgccgggac cgatcgcgcg    4440
cggatggcgg gctccgggct gctgccgctt ccggtcgggg acgccttgac cctgttcgac    4500
ttcgccgtcg gagcggagga agtgctgttc gtgccgatgc ggctcgacgt gcccgctctg    4560
cgcgcgagcg ccacggacgt gccgctcctg cgggccttcg ccgggaaatc ccggcggacc    4620
gcgtcggccg cccccgccgc gcgggaactg cgtgaccggc tggcgtcgct gcccaccgag    4680
gagcggggcc gggaactgct cgcgctggtg cgcggccagg tcgccgaggt actcggccac    4740
cgggacgccg gggccgtcga accggctcgt ccgttccggg aactgggctt cgactcgctg    4800
accgcggtgg aactgcgcaa cggcctcaac gccgcttccg ggctccggct gcccgcgacc    4860
gccgtgttcg accaccccac cccgaaggcg ctcgcggacc tgctcgccgc cgaactgttc    4920
ggcgcagccc ccgaagcccc ggttcagggg ccgcgatgg cggccgacga gccgatcgcc     4980
atcatcggca tggcatgccg gtaccccggc ggggtcgcct cgccggagga cctctggcgg    5040
ctggtcgcga agggccgcga cggcatctcg ctcttcccgg ccgaccgcgg ctgggacgtg    5100
gacggcctct acgacccgga ccccggcaag gcggggaaga gctacgtgcg cgagggcgga    5160
ttcctccacg aggcaggcga tttcgacgcc ggtttcttcg gcatctcgcc gcgtgaggca    5220
ctgggcatgg acccacagca gcggctgctg ctggaggtct cgtgggaagc cttcgaacgg    5280
gccgggatcg accccggaac gctgcgggc agcgacaccg gcgtcttcgc cgggcagatg    5340
taccacgact acctcaccgg cgccacggtc gttcccgacg acgtcgaggg ttacctcggc    5400
accggcaact ccgggagtgt gctgtccggg cgggtttcct acaccttcgg cctcgaaggt    5460
ccggccgtca ccgtcgacac ggcgtgttcg tcgtcgctgg tggcgctgca tctggcggca    5520
caggcgttgc ggcgcggcga atgctcgctc gcgctggccg gcgggtgac cgtgatggcc     5580 acgccggaga cgttcgtcga cttcagccgt cagcgaggtt tggcaccgga cggccgctcg    5640
aagtcctttt cggacggtgc ggatggcacg tcctggtccg aaggtgtcgg catgctgctc    5700
gtcgagcggc tctccgacgc cgagcgcaac gggcaccgga tcctggccgt cgtccggggt    5760
```

```
tcggcggtga atcaggacgg tgcgtccaac gggctgaccg cgccgaacgg tccttcgcag    5820
cagcgggtga tccggcgagc cttggccgac gcgcgcctgg aaccgtccga agtggacgcc    5880
gtcgaggcac acgggaccgg taccacgctg ggtgacccga tcgaggcgca agcgctgctg    5940
gcgacctacg gccagggccg cgaggacgcc gcgctgtggc tcggtcgat caaatcgaac     6000
atcgggcaca gccaggccgc cgccggggtg gcgggtgtga tcaagatggt cgaggcgatg    6060
cgccgcgggg tgctgccgaa gacgctgcac gtcaccgaac cgtcgtctca tgtggactgg    6120
acggcgggcg cggtctcccct cctgaccgag gcgcgactct ggccggacgc cggacgtccc   6180
cggcgtgcgg cggtgtcgtc gttcgggatc agcggtacca acgcgcacgt cgtcctggag    6240
cagggcccg ctccggtgga ggccatcgaa tccggtgagg accggcggc gttcgtcctg      6300
tccgccggga gtgaagcggc cctgcatgac caagcgtcgc ggttgaggga cttcctcgcc    6360
gagacgcctg ctgccttggc cgacgtcgcc ttctcgttgg cgaccacccg agcggccctg    6420
gagcaccggg ccgccgtcgt ggccgcagac cgggaaaccc tgctggccgc gctggagaac    6480
ctcactgtca ccggccgcgc gacggagggc cggacagcgt tcctgttcac cggtcagggc    6540
agtcagcggc tcgggatggg ccttcagctg gccgagcgtt tccgggtctt cgccgctgcc    6600
tacgacgagg tgtgttcccg gttcgagcag ccgctcaggg acctcacggc cgaggagctg    6660
aaccagaccg cgaacacgca gtgcgcgttg ttcgcgcttg aggtgcgct gttccgcttg     6720
gtcgagagct ggggtgtccg cccggacttc ctggctgggc attcggtcgg tgagatcgcg    6780
gcagctcacg tcgcgggtgt gctttccctc gacgatgcgg tgaccctggt gtcggcgcga    6840
ggccgtttga tgcaggcctt gcctaccggt ggcgcgatgg tggcgttgca ggcgacggaa    6900
gccgaggtga cgccgctgct gaccgagcgg gtgtcgctgg cggcgatcaa cggtccggag    6960
tcggtggtcg tttcgggtga ggaggacgcc gtcgctgcgg tggtctctca gttcgagggt    7020
cgcaagagca agcggctcac cgtgagtcac gcgttccact cgccgttgat ggagccgatg    7080
ctcgacgagt tccgtgtggt cgccgacagc ttgtcgtacg cggcgccgcg gattccgatc    7140
gtgtccggtg gtctggcgga ggtgtccact tcggactatt gggtccgcca tgtccgtgac    7200
gcggtgcgat tccacgattc ggtgaagttc ctggaagccg aggggtcac acggttcctg     7260
gagatcgggc ccgacggtgt cctgaccgcg atggccaagg aaactgccga ggacgcggtc    7320
gtcgttccgg cactccggcg cgaccggccg gaggtggaga cgctgctgac ggcggtcgcg    7380
ggcctgcacg tccacggcgt gggcgtcgat ctgacggcct tgctcggcgg tggaagcccc    7440
gtcgacctgc ccacgtatgc cttccagcac cgacgtttct ggctttcctc ggcgggcggc    7500
gcggcgggcg acgtcaccgc agccgggcta ggcaccaccg atcacccgct gctcggcgcg    7560
gccgcggcac tgccgggcga cggcgggttc ctgctcaccg gccggttgtc cgggcacgcc    7620
cagccgtggc tggccgaaca ccgggtcggc ggcgtggtcc tgctgccggg caccgcgttc    7680
gtcgagatcg ccctgcgtgc gggggatgag gcgggctgcg gccacctcga agacctgacc    7740
ctcgaagcgc cgctcgtcct gcccgagcgc ggtgcgaccc agctgtccgt gctggtcggc    7800
gcggccgacg acaccggtcg ccggaccatc gagatccact cgcgcgagga aggcgaagac    7860
ggctggcaga ggcacgcgac cgggctgcta tcggccgccg gagccgtcga accggccggg    7920
ttgacgacct ggccgcccca gaacgccgaa gccgtcccgg tgggtgacgt ctacgagcgg    7980
ctcgccgcca ccggtctcga gtacggcccg gcgttccgtg gcctccgtgc ggcgtggcga    8040
gcgggtgaag acctgttcgc ggaggtcgaa ctcccggagg accagcactc cgacgcggct    8100
cggttcggcg tgcatccggc gctgctcgac gccgcgctcc acaccctcgg cctcgcgggc    8160
```

```
ggcggcgacg gcacccggct cccgttcgcc tggtcggggg tgcgcctgca cgccgccggc    8220 gcgaccggc  tccgtgtccg gctgcggccg tccggtcccg acgggttcga ggtcctggtc    8280
gccgacggca ccggccgccc ggtcgtctca gccgaagagt tgacgctgcg cgagatctcg    8340
ggcgacgcct tggcccgcaa gggacacgac tcgctctacc gggtcgcctg gcgtccggtc    8400
ccgctcccgg agaccggcga aaccctcccc gcggagtcgg ttttctccgt gccgcgcggt    8460
ggcgactccg ccgagcgtgt ccacgaaacg acggccgccg ttctcgaagt cgtccagcgg    8520
cggctcgaag acgagccggg cggtccgctt gtcgtccaca cccggggcgg agtcgccgcg    8580
ggcgacggcg aagcggtgac cgacctcgcg cacgccgcgg tctgggggct ggtgcgtgcc    8640
gcgcagtcgg agaaccccgg tcggttcctg ttggtcgacg ccgagacctt gcccgatggc    8700
cggatcctgg ccatcgacga gcctcagatc gctttgcgtg acggccgggc actcgcgccg    8760
cgcctggcca ccaccgcctc gtccacggaa ctgaccccgc cgagggagc  ctggcggctg    8820 gacaccaccg gtcgcggcac cctggagaac ctcacgctgg tgccgtcgcc cgaagcagtc    8880
gcgccgttgg ctgagggcga ggtccggatc gcggtgcggg ccgccgggct caacttccgc    8940
gacgtcctga tcgcgctggg catgtacccg ggcgcggcca ccctcggcag tgaaggcgcg    9000
ggcgtggtca ccgagatcgg gcccggtgtc accggcctcg acgtcggcga ccgcgtgttc    9060
ggcctgatgt cgaacggctt cgggcccag  gtcgtcaccg atcaccggac gctggcgaag    9120
atgcccgagg actggtcgtt cgccacggcg gcctcggtcc cgatcgtgtt cctcaccgcc    9180
tactacggcc tgttcgacct cgcgcggctc gaagcgggag agtcgatcct ggtgcacgcg    9240
gcggcgggcg gcgtcggtat ggccgcgacc cagctggccc gtcacgccgg ggccgaggtg    9300
ttcggcaccg ccggtccggg caaatgggac accttgcgtg ccaacggttt cgacgacacc    9360
cacctctcgt cctcccgtga cctcggcttc gaggagaagt tccgcgatgc caccggcgga    9420
cgcggtgtcg acgtcgtctt gaactcgctc gccggcgact acgtcgacgc gtcactgcgg    9480
ctgctggccc cgggcgggcg gttcgccgag atgggcaaga ccgacatccg ggaaccgggg    9540
gagaccggcg tcgagtacca ccccttcgac gtcatcgacg ccggacccga gcgcatccac    9600
gagatgctcg ccgcactgct ggagctgttc gcggccgggg cgctgacgcc gttgccggtc    9660
accggctggg acgtccggcg cggccccgac gcgttccgtt tcctcagcca ggccaagcac    9720
gtcggcaaga acgtcctgac catgcccgcc gccctcgatc ccgacggcac cgtgctcgtc    9780
accgggggaa cgggtgccct cggcgcgctc ttcgcccggc atctggtgcg cgaacgcggc    9840
gtccggcggc tgctgctggc cagcaggcgc ggccacgacg ccccgggcgt acccgagctg    9900
gtcgccgaac tcaccgaggc aggcgcctcg gtgacggtcg aggcgtgtga cgcggcggat    9960
cgcggcgcgc tcgccgccgt cctcgccgga atcccggccg cgcatccgct gaccggcgtg   10020
gtgcacacgg cgggtgtcct ggacgacggc ctcgtcggct cgctgacccc ggagcggctg   10080
gcgaaggtgt tgcggccgaa ggtcgacgcg gcgctgaacc tgcacgaact gaccagcggc   10140
gcggatctcg ccgagttcgt cgtcttctcc tcggccgccg ggtcttcgg  caacgccggg   10200 caggcgaact acgccgccgc caacggtttc ctggacgcgc tcagcgtccg gcgcgcggcg   10260
cacgggttgc ccgccggtc  gctggcgtgg ggtctgtggg ccgaaacggg cgggatgggc   10320
gggacgctcg gcgaggccga gctggccagg atggcccaga gcgtaccgc  cgcactgtcc   10380 acacaggacg gcctgagct  cttcgacgcc gccggcgcgc tggcggaacc ggtcctggtg   10440
ccgatgcgcc tggacgtcac cgcgatgggc ggggacgggc tcccgccgtt gctgcgcggc   10500
```

```
ctcgcccgcg gcccggtacg ccgtgccgcg tccgccgggg ccgccggtga cgcggactca   10560
ttgcgagacc ggcttctcgc ggtgcccgtc gccgaccggg agacgctgct ggtcgacctc   10620
gtgcgcaccc attccgcgac cgtgctcggg cacaccgcgg cggacgcggt cgaggccacg   10680
cggtccttcc aggagatcgg cttcgactcc ctgaccgccg tcgagctgcg caaccggctc   10740
accgccgcca ccgggctgcg gctgccggcg acgctgatct tcgactaccc gaccccggaa   10800
gcgctcgccg cccacatcgg cgaaggcgtc ctgggtgcgc agggcgggcc cgagaccggg   10860
caggcggcgg tgacggccga cgagccgatc gcgatcgtcg cgatgagctg ccggttcccc   10920
ggccacgccg acaccccga acggctctgg gccctgctgg ccgagggccg ggacgcgctg   10980
ggcgagttcc ccgccgaccg cggctggac ctggagcggc tgttcgacac cgacccggac   11040
cgccggggca cctcctacac ccgccaaggc gccttcctcg aaaccgccgg cgatttcgac   11100
gcgggcttct tcgggatctc gccgcgtgag gcgctggcga tggatccgca gcagcggttg   11160
ctgctggaga cgtcgtggga ggcgttcgaa cgcgccggga tcgatccggc caccctgcgc   11220
ggcagccgca ccggcgtgtt cgccggggtg atggacaacg aatacgtatc cggttcggcg   11280
gaggtccctg acggggtcga gggctacctg gccaccggca cctcggcgag tgtcgcctcg   11340
ggccgcgttt cctacacctt cgggctcgaa ggtcccgcgg tcaccgtcga cacggcgtgt   11400
tcgtcgtcgc tggtcgcgct gcatctcgcg gcgcaagcgc tgcggcaggg cgagtgctcg   11460
ctggcactgg ccggtggagt gaccgtgatg gccacaccgg gcacgttcgt cgagttcagc   11520
cgtcagcgcg gactggccgc cgacggccgc tgcaaggcgt tcgccgacgg cgccgacggg   11580
acgggctggg gcgaaggcgc cgggatgctg ctcgtggagc ggctgtccga cgcccgccgc   11640
aacgggcatc cggtgctcgc ggtgctgcgg ggcagcgcgg tcaaccagga cggcgcgtcg   11700
aacgggctca ccgcgccgaa cggtccttcg cagcagcggg tgatccgcca ggcgctggcg   11760
aacgcgcggc tcgaaccgtc cgaagtggac gcagtcgaag cgcacggaac cgggaccacg   11820
ctgggcgacc cgatcgaggc tcaggcgctg ctggcgacct acggccagga ccgggaacgg   11880
ccgttgctgc tcggttcggt caagtcgaac atcgggcaca cgcaggccgc ggcgggcgtc   11940
gccggggtga tcaagatggt gctcgcgatg cggcacggga cactgccgcg cacgctgcac   12000
gtcgacacgc cgacttcgcg cgtcgactgg gcggcgggcc ggatcgagct cgcgaccgag   12060
ccgacccagt ggccggagac cggtggcccg cgccgggcgg cggtgtcgtc gttcgggatg   12120
agcggtacca acgcgcacgt cgtcctcgaa caggccgaag cggtcgagac acgggatgaa   12180
acctcgccgg ggctgctcgg tgacgtcgtc gcgtggccgc tgtcggcgaa ggaacccgag   12240
gccgtggccg cgcaggcggc acggctgaag tccttcctga ccggcgaacg tccggcggac   12300
gtggcctact cgctggcgac cgcgcggacc acgctggaac accgggcggt cgtcgtcggc   12360
gaagacccga tcgccgggtt ggccgcgctg gccgcgggcg agccgtcggg ttcggtggtg   12420
accgggaccg cgaccagcgg gaaggcgtg ttcgtcttcc ccggccaggg ttcgcagtgg   12480
gccgggatgg cggtcgagtt gctggcgtcc gcacccgtgt tcgccgagtc gatggcggag   12540 tgcgaagcg ctctgctgtc ctatgtggac tggaagctga ccgaggtgct ctcggacgcg   12600
accgcgctgg agcgggtcga cgtcgtgcag cccgccttgt tcgcggtgat ggtgtcgctg   12660
gcgaggctgt ggcgtgccag tggcatcgaa ccggccgccg tggtcggtca ttcccagggc   12720
gagatcgcgg cggcgtgtgt cgccggcgcg ctgtcgctcg acgacgcggc acgggtggtc   12780
tgcctgcgca gcaaggcgat cacgcgcgtt tcgggccggg cggcatggt ctccgtcgcc   12840 gctcccgaag cccaggttcg cgagatcctg cccgagggtg tgtcgctcgc cgcggtgaat   12900
```

```
ggtcccgcgt cggtggtggt gtcgggtgac gtcgccggtc tggacgcgct catgaccgct   12960
tgcgaggcga gcgggctgcg cgcgaagcgg atcccggtgg actacgcgtc gcattccgcg   13020
cacgtcgatg ccatcgaaca agacgtcctg gccgcgctcg acgggatcga gccgcgggcc   13080
ccggagatcc cgttctattc gacggtggcc ggggagccgc tcgatccggt ggtggacgcg   13140
gcgtactggt tccggaacct gccgcgggacc gtccacttcg acaagccgt ccggcggctg   13200 ctcgacgacg ggttccggtt cttcgtcgag gcgagcccgc atccggtcct ggtcaccggg   13260
atcgccgaca ccgccgagga cgcggggagaa cgcgccgtcg ccgtcggcag cctgcgccgg   13320
gacgagggag ggccgctgcg gttcctcacc tcgctggccg aagcccacgt ccacggcctc   13380
agcccggact gggcggcgct ggccccggga accgcgtcg acctgccgac ctacgccttc   13440
cagcacgagc actactggct gcggacgcgg tcttcggccg atcccggaca ggccggtctg   13500
gacgacggcg ggcatccgct gctcggggcc gtcgtcccgc tggcgggcag cgacggcctg   13560
gtggccaccg gccggatctc ggcgcggaac cagacctggc tgcccgatca cgccgtcggg   13620
ggcgcgctgc tgctgcccgg cgcggcgctc gtggacctgg cgctcacggt ggggagcgc   13680 accggctgcg gccggatcgc cgaactgacc atcgaggcgc cgctagtcct cggggagtcc   13740
gggagcgcgc ggctgcaggt gaccgtcgga gcgtccgcag acgacggcac ccgcgaggtc   13800
gccgtgtact cccgggacga aaccgctggc acggactgga tccggcacgc gaccggcctg   13860
ctcgccgcgg acgggaaac gcccgtggcg gacctgaccc agtggccgcc cgcgggagcc   13920
gaaccgatct ccctcgaagg gcactacgaa ggtctcgcgg aactgggcta cggctacggt   13980
ccggcgttcc gcgggctgcg tgccgtgtgg cgccggggcg acgacgtgtt cgccgaagtc   14040
gcgctcccgg aagaccggat cgccgaggcc gccgcgttcg gcctgcaccc cgcgctcctc   14100
gacgccgccc tgcacgcgct gggcttcggc atgctccccg acgacggacg gctgcggctt   14160
ccgttcgcgt ggaacgaggt ctcgctgtcg gccgtcggcg cgccgagcct gcgcgtacgg   14220
ctctcccccg ccggggagga cgcggtggcg gtggacctcg ccgacaccgc cggggcgccg   14280
gtcgcctcga tcggctccgt ggtgttccgg ccggtggccg aggcacagct cgccggcgcc   14340
cggcgggatc cggcggattc gctgttccag atccagtgga cggatctgtc cgcaaaggac   14400
gtcgtcgcac cggcggtcgt cgtgctcggc gaggactgcg cggacctcgc ggagctcgcc   14460
gcggatctcg acgcgggaag gccggcgccc gacgtggtgc tcacgacctg cgcacccgtc   14520
accggcgata tcgccgaggg cgcgcacgcc gccgcgaggg acgcgctgac gctggtccag   14580
aactggctgg ccgatgagcg gttctccgga gccaggctgg tcttccgcac ttcgggcgcg   14640
gtctcggtgg ccgcggacga accggtgtcc gacccgccca acgcgacggt ctggggcctc   14700
gtgcgcacgg cgcaggagga gaatcccggc cggttcggtc ttctcgacac cgatggttcc   14760
gaggccgtct tgggtgcggc gctggcgctc gacgagcccc agctcgcgct gcgggccgga   14820
acggtgctcg gcgcccggct ggtcaaggcg tccgccgaca ccgcgctcgt cccgccccg   14880 ggcagccgcg cgtggaccgt cgacaccctc ggcggcggca ccctggagaa cctggtgcta   14940
cgggaccggc ccgatctgct ggccccgctc gccgacgggc aggtccgtat cgccgtgcgg   15000
tcggccgggc tcaacttccg ggacgtcgtg gtgggccctcg ggctcgtgcc agggcaggaa   15060
ggcatcggcc gggaaggcgc gggcgtggtc accgagaccg gccccggcgt caccgacctg   15120
gcgccgggcg accgcgtgct gggcatgttc gacgcgtcgt tcggcccgat cgccgtcgcc   15180
gaccggaagc tgatcgcgcc cgtcccggac gactggtcgt tcaccgaagc cgcttcggcg   15240
```

-continued

```
cccgtcgcgt tcctgaccgc ctacgtcggc ctggctgacc tcggcgagct gcggccgggt    15300
cagaccgtgc tgatccacgc cgccgccggt ggggtcggca tggccgcggt ccagctggcc    15360
cggcacttcg gtgccgagat ctacgtgacc gcgagcccg ccaagtggga cacgctgcgg     15420
gcgatgggct cgacgacga ccacatcgcg tccagccgga ccctcgattt cgaggacaag     15480
atccgcgaag ccactggcgg acgcgggtc gacctggtgc tggactcgct ggcaagggag     15540
ttcgtcgacg cgtcgctgcg gctggtgcgc gaaggcgggc gattcgtcga gatgggcaag    15600
accgacatcc gcgacgcgga cgaggtcgcg gccgcccatc ccggcgtcac ctaccgcgcg    15660
ttcgacctga tcgactccgg gcacgaccgg atccaggaga tcctgggcga actcctgggc    15720
ctggcggaca aggacgtggt gcggccgctg ccgaccacgg cgtgggacgt ccggcgcgcc    15780
cccgaagcgt tccggttcct cagccaggcc aagcacacgg gcaagatcgt gctggagccg    15840
cccgccgtcc tcgaccccga gggaacggtg ctgatcaccg gtggcaccgg cgtgctgggc    15900
ggcctgttcg cccgacatct ggtgaccgcg cacggcgtcc ggcggctgct gctgaccagc    15960
aggcgcgggc tcgacgccga gggtgcgcgg gaactggtcg cggacctgac cggcctcggg    16020
gccacggtga ccgtcgtggc ctgcgacgtc gccgatcgcg ccgcggtcgc cggactgctc    16080
ggctcggtcc cgcccgagca cccgctgacc gccgtggtgc acaccgccgg cgtgctcgac    16140
gacgggctga tcccggcact cacccccgac cggctcggca ccgtgttccg cccgaaggtc    16200
gacgccgcgg tccatctgca cgaactgacc cgcgacctcg actggccgc gttcgtgctg     16260 ttctcctcgt ccgcggcgac gttcggcgcc gccggacagg ggaactacgc ggcggccaac    16320
gccttcctcg acgcactcgc ccagcaccgc cgggccgaag ggctcgccgg gcaggcattg    16380
gcgtggggct tctgggccga gcggagcgcg atgaccggcc atctcgacga ggcggacgtg    16440
gccaggatga agcgatccgg cgtcagtcca ctgtcctctg tggacggtct tgcgctgttc    16500
gacgcggcgg cggaacggga cgtcgcggcg ctggtgcccg tgcacctgga caccgccgcc    16560
ctccgagggc agaccgaagt gcccgccctg cttcgtgttc tcgcgggtgc tccggccaag    16620
cgggtcgcgg gagcggccgc cacgagcgga ccgtcgctcg cccagcggct ggcggcactg    16680
cccgccgcgg accgggagcc gttcctgctg gatctggtgc gctcgcacgc cgcggccgcg    16740
ctcggccacg cgtcggtcgc caaggtcggc ccggagctgg ccttccgcga cctcggcttc    16800
gactcgctga ccgcggtcga gctgcgcaac cggctcggcg cggcgaccgg gctgcggctg    16860
ccgtccacgc tggtcttcga tcagccgagc ccggccgcgc tcgcccggca cctgctggcg    16920
gaactgggcg aaccggccgg cgccgaaccc gaggtggcg tgctggcaga cctcgaccgg     16980
ctggagaccg cactggccgc ggcggtcacc gacgacgaga ccgcggaccg gatcaccgac    17040
cggctgcgcg cggtgctcgc ccggtggacc gaggcccgcg gccggccga ggacgagggt     17100 gacggcgatc tggccgacgc cagcgccgac gagctgttcg acatcttgca caaggaattc    17160
ggaaggtcgt ga                                                        17172
```

<210> SEQ ID NO 41
<211> LENGTH: 1735
<212> TYPE: PRT
<213> ORGANISM: Amycolatopsis orientalis

<400> SEQUENCE: 41

```
Val Ser Gly Asp Glu Lys Leu Leu Glu Asn Leu Lys Trp Ala Thr Gly
1               5                   10                  15

Glu Leu Arg Arg Ala Arg Arg Arg Leu Val Glu Leu Glu Glu Ala Gly
            20                  25                  30
```

```
His Glu Pro Ile Ala Val Val Gly Met Ser Cys Arg Phe Pro Gly Gly
         35                  40                  45

Val Arg Ser Pro Glu Gln Leu Trp Asp Leu Val Ala Ser Gly Thr Asp
     50                  55                  60

Ala Leu Ser Glu Phe Pro Gly Asp Arg Gly Trp Asp Leu Gly Gly Leu
 65                  70                  75                  80

Phe Asp Pro Asp Pro Asp Thr Pro Gly Lys Thr Tyr Val Ser Glu Gly
                 85                  90                  95

Gly Phe Leu Tyr Glu Ala Gly Asp Phe Asp Ala Ala Phe Phe Gly Ile
             100                 105                 110

Ser Pro Arg Glu Ala Gln Ala Met Asp Pro Gln Gln Arg Leu Leu Leu
         115                 120                 125

Glu Ala Ala Trp Glu Val Leu Glu Arg Ala Gly Ile Asp Pro Ala Thr
         130                 135                 140

Leu Arg Gly Ser Arg Thr Gly Val Phe Ala Gly Val Ile His Asn Asp
145                 150                 155                 160

Tyr Thr Gly Val Leu Thr Asp Ile Pro Pro Glu Leu Glu Pro Tyr Leu
                 165                 170                 175

Gly Asn Gly Asn Phe Ser Ser Val Ala Ser Gly Arg Ile Ala Tyr Thr
             180                 185                 190

Leu Gly Leu Glu Gly Pro Ala Val Ser Val Asp Thr Ala Cys Ser Ser
         195                 200                 205

Ser Leu Val Ala Leu His Leu Ala Ala Gln Ser Leu Arg Arg Glu Glu
     210                 215                 220

Cys Thr Leu Ala Leu Val Gly Gly Val Asn Val Met Thr His Pro Ala
225                 230                 235                 240

Ala Phe Val Asp Phe Ser Arg Gln Arg Gly Leu Ala Ala Asp Gly Arg
                 245                 250                 255

Cys Lys Ala Phe Ala Asp Ala Ala Asp Gly Thr Gly Trp Gly Glu Gly
             260                 265                 270

Val Gly Met Leu Leu Val Glu Arg Leu Ser Asp Ala Gln Arg Asn Gly
         275                 280                 285

His Gln Val Leu Ala Val Leu Arg Gly Ser Ala Ile Asn Gln Asp Gly
         290                 295                 300

Ala Ser Asn Gly Leu Thr Ala Pro Asn Gly Pro Ala Gln Gln Arg Val
305                 310                 315                 320

Ile Arg Gln Ala Leu Ala Asp Ala Arg Leu Ser Pro Gly Gln Val Asp
                 325                 330                 335

Val Val Glu Gly His Gly Thr Gly Thr Thr Leu Gly Asp Pro Ile Glu
             340                 345                 350

Ala Gln Ala Leu Leu Ala Thr Tyr Gly Gln Asp Arg Glu Arg Pro Leu
         355                 360                 365

Leu Leu Gly Ser Leu Lys Ser Asn Ile Gly His Thr Gln Ala Ala Ala
         370                 375                 380

Gly Val Gly Gly Val Ile Lys Met Val Gln Ala Ile Arg His Gly Ile
385                 390                 395                 400

Ala Pro Arg Thr Leu His Val Asp Ala Pro Ser Ser His Val Asp Trp
                 405                 410                 415

Ser Ala Gly Glu Val Ser Leu Leu Thr Gly Glu Gln Pro Trp Pro Glu
             420                 425                 430

Thr Gly Glu Pro Arg Arg Ala Gly Val Ser Ser Phe Gly Ile Ser Gly
         435                 440                 445
```

```
Thr Asn Ala His Val Ile Leu Glu Gln Ala Pro Ala Val Glu Val Glu
450                 455                 460

Ser Leu Val Asp Thr Arg Val Leu Asp Ser Ala Val Leu Pro Phe Val
465                 470                 475                 480

Leu Ser Gly Arg Ser Glu Glu Ala Leu Ala Ala Gln Ala Ser Lys Leu
                485                 490                 495

Ala Ala Tyr Leu Thr Gly Glu Pro Ala Pro Lys Ala Ile Ala Arg Ala
            500                 505                 510

Leu Ala Glu Thr Arg Ser Ala Leu Pro His Arg Ala Val Val Leu Ala
            515                 520                 525

Glu Asp Leu Gly Glu Leu Leu Gly Gly Leu Arg Ser Leu Ala Glu Gly
        530                 535                 540

Glu Pro Ala Ala Arg Val Leu Thr Gly Thr Ala Glu Ala Gly Lys Ala
545                 550                 555                 560

Val Phe Val Phe Pro Gly Gln Gly Ser Gln Trp Val Gly Met Ala Glu
                565                 570                 575

Glu Leu Leu Ser Ala Pro Val Phe Ala Glu Ser Met Ala Glu Cys
            580                 585                 590

Glu Arg Ala Leu Ser Ser Phe Val Asp Trp Lys Leu Ser Asp Val Leu
            595                 600                 605

Ser Asp Ala Ala Leu Glu Arg Val Asp Val Gln Pro Val Leu
            610                 615                 620

Phe Ala Val Met Val Ser Leu Ala Arg Leu Trp Arg Ala Cys Gly Val
625                 630                 635                 640

Glu Pro Ala Ala Val Val Gly His Ser Gln Gly Glu Ile Ala Ala Ala
                645                 650                 655

Cys Val Ala Gly Ala Leu Ser Leu Asp Asp Ala Ala Arg Leu Val Cys
            660                 665                 670

Leu Arg Ser Lys Ala Ile Leu Ala Leu Ser Gly Arg Gly Met Val
        675                 680                 685

Ser Val Ala Ala Ser Glu Asp Arg Val Arg Glu Leu Leu Pro Ala Gly
690                 695                 700

Val Ser Val Ala Ala Val Asn Gly Pro Ser Ala Val Val Ser Gly
705                 710                 715                 720

Asp Val Ala Gly Leu Glu Ala Leu Leu Lys Arg Cys Glu Leu Leu Asp
                725                 730                 735

Val Arg Ala Lys Arg Ile Pro Val Asp Tyr Ala Ser His Ser Ala His
            740                 745                 750

Val Asp Ala Ile Glu Gln Val Leu Ser Ala Leu Ala Gly Ile Ser
        755                 760                 765

Pro Gln Ala Pro Val Ile Pro Phe Tyr Ser Thr Val Thr Asp Glu Pro
770                 775                 780

Leu Glu Leu Asp Ala Ala Tyr Trp Phe Arg Asn Leu Arg Gly Thr Val
785                 790                 795                 800

Arg Phe Ala Ala Thr Val Asp Arg Leu Leu Glu Asp Gly Phe Arg Phe
                805                 810                 815

Phe Val Glu Ala Ser Pro His Pro Leu Val Pro Gly Ile Ser Glu
            820                 825                 830

Glu Ala Ile Ala Leu Gly Ser Leu Arg Arg Gly Glu Gly Ala Glu
        835                 840                 845

Arg Phe Val Ala Ser Leu Ala Glu Ala His Thr Gln Gly Leu Ser Pro
850                 855                 860

Ser Trp Ser Ala Val Leu Pro Pro Ala Glu Arg Val Asp Leu Pro Thr
```

-continued

```
            865                 870                 875                 880
Tyr Ala Phe Gln His Lys Arg Phe Trp Leu Glu Ala Gly Thr Ala Ser
                    885                 890                 895
Gly Asp Ala Ser Ala Phe Gly Gln Thr Val Val Asp His Pro Leu Leu
            900                 905                 910
Gly Ala Ala Leu Pro Leu Ala Asp Gly Asp Gly Leu Val Leu Thr Gly
            915                 920                 925
Arg Ile Ser Pro Asp Thr Gln Pro Trp Leu Val Asp His Thr Val Leu
    930                 935                 940
Asp Thr Val Leu Leu Pro Gly Thr Ala Phe Val Glu Leu Val Leu Arg
945                 950                 955                 960
Ala Gly Arg Glu Ala Gly Cys Asp Gly Val Asp Glu Leu Thr Leu Glu
            965                 970                 975
Ala Pro Leu Val Leu Asp Gly Pro Val Ala Leu Gln Val Val Leu Gly
            980                 985                 990
Glu Pro Asp Glu Arg Gly Arg Arg  Ala Val Ser Val His  Ser Arg Pro
            995                 1000                1005
Glu Asp  Ser Asp Glu Pro Trp  Thr Arg Asn Ala Gln  Gly Thr Leu
    1010                1015                1020
Ser Ala  Gly Thr Pro Ser Thr  Val Ser Leu Ala Glu  Trp Pro Pro
    1025                1030                1035
Pro Gly  Ala Ala Glu Ala Pro  Glu Ser Asp Leu Tyr  Asp Arg Phe
    1040                1045                1050
Ala Glu  Leu Gly Leu Ala Tyr  Gly Pro Val Phe Gln  Gly Leu Arg
    1055                1060                1065
Ala Ala  Trp Arg Gln Gly Asp  Asp Val Phe Ala Glu  Val Asp Leu
    1070                1075                1080
Pro Glu  Glu Glu Glu Ala Asp  Arg Phe Gly Val His  Pro Ala Leu
    1085                1090                1095
Leu Asp  Ala Ala Leu His Thr  Leu Gly Leu Gly Ala  Gln Asp Glu
    1100                1105                1110
Thr Val  Arg Leu Pro Phe Thr  Trp Ser Gly Val Thr  Leu His Ala
    1115                1120                1125
Thr Gly  Ala Ser Lys Leu Arg  Val Arg Leu Thr Pro  Thr Ala Asp
    1130                1135                1140
Gly Gly  Ser Leu Thr Val Ala  Asp Glu Thr Gly Ala  Pro Val Leu
    1145                1150                1155
Thr Val  Gly Glu Leu Gly Leu  Arg Pro Ile Ser Pro  Ala Gln Leu
    1160                1165                1170
Gly Arg  His Arg Asp Ser Leu  Phe Arg Leu Asp Trp  Val Pro Ala
    1175                1180                1185
Pro Val  Gly Pro Ala Pro Glu  Glu Pro Gly Val Trp  Arg Cys Pro
    1190                1195                1200
Glu Gly  Glu Leu Arg Pro Val  Leu Glu Glu Val Leu  Lys Arg Ile
    1205                1210                1215
Gln Ala  Asp Ser Thr Ala Thr  Thr Val Val Leu Thr  Ser Gly Ala
    1220                1225                1230
Val Ala  Ser Ala Ser Pro Asp  Pro Val Ala Ala Ala  Val Trp Gly
    1235                1240                1245
Leu Val  Arg Ser Ala Gln Ala  Glu His Pro Gly Arg  Phe Val Leu
    1250                1255                1260
Ile Asp  Ala Arg Thr Glu Asp  Glu Val Arg Thr Ala  Leu Ala Thr
    1265                1270                1275
```

-continued

```
Gly Glu Ala Gln Val Ala Val His Asp Gly Lys Pro Leu Val Pro
    1280                1285                1290

Arg Leu Ala Arg Val Ala Ala Ala Asp Ala Gly Glu Pro Asp Trp
    1295                1300                1305

Thr Pro Asp Asp Val Val Leu Ile Thr Gly Gly Thr Gly Arg Leu
    1310                1315                1320

Gly Gln Ala Leu Ala Arg His Leu Ala Val Arg His Gly Val Arg
    1325                1330                1335

Gly Leu Val Leu Thr Gly Arg Thr Gly Gly Ala Glu Asp Leu
    1340                1345                1350

Val Ala Asp Leu Ala Glu Leu Gly Thr Gln Val Thr Val Ala Ala
    1355                1360                1365

Cys Asp Val Ala Asp Pro Asp Ala Val Arg Ala Leu Leu Ala Ala
    1370                1375                1380

His Pro Val Thr Ala Val Val His Ala Ala Ala Val Leu Asp Asp
    1385                1390                1395

Gly Leu Val Asp Gly Leu Thr Pro Asp Arg Leu Gly Thr Val Leu
    1400                1405                1410

Ala Pro Lys Ala Asp Gly Ala Arg Val Leu His Glu Leu Ala Gly
    1415                1420                1425

Pro Val Arg Arg Phe Val Thr Phe Ser Ser Ala Ala Gly Val Phe
    1430                1435                1440

Gly Asn Pro Gly Gln Ala Gly Tyr Ala Ala Ala Asn Ala Tyr Ala
    1445                1450                1455

Asp Ala Leu Met Leu Arg Arg Arg Ala Glu Gly Leu Pro Gly Val
    1460                1465                1470

Ser Leu Ala Trp Gly Phe Trp Ala Glu Arg Ser Lys Leu Thr Gly
    1475                1480                1485

Asp Leu Asp Asp Thr Asp Val Arg Arg Met Ala Arg Ala Gly Val
    1490                1495                1500

Thr Ala Leu Ser Thr Glu Glu Gly Leu Ala Leu Phe Asp Ala Ala
    1505                1510                1515

Val Ala Gly Gly Asp Gly Leu Leu Val Pro Ala Lys Ile Asp Leu
    1520                1525                1530

Thr Ala Phe Arg Gly Arg Pro Ala Ala Glu Ile Pro Ala Leu Leu
    1535                1540                1545

Arg Gly Leu Val Arg Val Pro Ala Arg Arg Ser Gly Glu Ala Ser
    1550                1555                1560

Gly Thr Ala Glu Ala Leu Lys Arg Asp Leu Ala Gly Lys Pro Glu
    1565                1570                1575

Ala Glu Arg Val Arg Leu Leu Glu Glu Val Val Arg Ile Arg Val
    1580                1585                1590

Ala Ala Val Leu Gly His Glu Ser Ala Asp Ala Ile Ala Gly Asp
    1595                1600                1605

Arg Gly Phe Leu Glu Leu Gly Phe Asp Ser Leu Thr Ala Val Glu
    1610                1615                1620

Leu Arg Asn Arg Leu Ala Glu Ala Thr Gly Leu Arg Leu Pro Pro
    1625                1630                1635

Thr Leu Val Phe Asp Arg Pro Asn Ala Gly Ala Leu Ala Ala Tyr
    1640                1645                1650

Leu Ala Ala Glu Leu Ala Thr Glu Thr Ala Gly Pro Ala Leu Asp
    1655                1660                1665
```

-continued

Ala Glu Leu Asp Arg Phe Ala Ala Ala Leu Thr Ala Ala Asp Pro
    1670            1675                1680

Gly Glu Ala Glu Arg Ala Arg Leu Ala Ala Arg Leu Arg Ala Leu
1685                1690                1695

Leu Gly Thr Leu Gln Gly Gly Glu Asp Pro Ala Gly Glu Ile Asp
1700                1705                1710

Gly Lys Leu Glu Ser Ala Asp Asp Glu Glu Met Phe Ala Phe Ile
1715                1720                1725

Asp Asn Val Leu Lys Pro Ser
1730                1735

<210> SEQ ID NO 42
<211> LENGTH: 5208
<212> TYPE: DNA
<213> ORGANISM: Amycolatopsis orientalis

<400> SEQUENCE: 42

| | | | | | |
|---|---|---|---|---|---|
| gtgtcgggcg | atgagaaact | gctggagaac | ctgaagtggg | cgaccggcga | gctgcggcgc | 60 |
| gcgcggcgca | ggctggtcga | gttggaggag | gccgggcacg | agccgatcgc | cgtcgtcggg | 120 |
| atgagctgcc | gcttccccgg | cggggtccgc | tcgcccgaac | agctgtggga | cctggtcgcc | 180 |
| tccgggaccg | acgcgctgtc | ggagttcccc | ggtgaccggg | gctgggatct | gggtgggctc | 240 |
| ttcgacccgg | accccgacac | cccgggcaag | acctacgtct | ccgaaggcgg | attcctctac | 300 |
| gaagccgggg | atttcgacgc | cgcgttcttc | gggatctcgc | cgcgtgaggc | ccaggcgatg | 360 |
| gatccgcagc | agcggctgct | gctcgaagcg | gcgtgggagt | gctcgaacg | cgccgggatc | 420 |
| gacccggcca | ccctgcgcgg | cagccggacc | ggcgtcttcg | ccggcgtcat | ccacaacgac | 480 |
| tacaccggcg | tgctcaccga | catcccgccg | gagctggagc | cctatctcgg | caacgggaac | 540 |
| ttcagcagcg | tcgcctccgg | ccggatcgcc | tacaccctcg | gcctcgaggg | ccccgcggtc | 600 |
| tcggtcgata | cggcgtgctc | gtcttcgctg | gtcgcgctgc | atctcgccgc | gcagtcttta | 660 |
| cgtcgcgagg | aatgcacgct | cgccctcgtc | ggcggggtga | acgtgatgac | ccatcccgcc | 720 |
| gcgttcgtcg | acttcagccg | tcagcgcgga | ctggccgccg | acggccgctg | caaggccttc | 780 |
| gccgacgcgg | ccgacggcac | cggttgggcc | gaaggcgtcg | gaatgctgct | ggtcgaacgg | 840 |
| cttccgacg | cccagcgcaa | cggacaccag | gtcctcgcgg | tgctgcgggg | cagcgccatc | 900 |
| aaccaggacg | gcgcgtcgaa | cgggctcacc | gcgccgaacg | gtcccgctca | gcagcgggtc | 960 |
| atccgccagg | cactcgccga | cgccaggctc | tcgccggggc | aggtggacgt | cgtcgaggga | 1020 |
| cacggcaccg | gcaccaccct | cggcgacccg | atcgaggcgc | aggcgctgct | ggcgacctac | 1080 |
| ggccaggacc | gggaacgccc | gctgctgctg | ggttccctca | aatcgaacat | cgggcatacg | 1140 |
| caggccgccg | ccggggtcgg | cggggtgatc | aagatggtgc | aggccatccg | gcacgggatc | 1200 |
| gcgccgcgca | cgctgcacgt | cgacgctccc | tcgtcgcatg | tggactggtc | ggcgggcgag | 1260 |
| gtctcgctgc | tgaccgggga | acagccgtgg | ccggagaccg | gggaaccgcg | ccgagccggg | 1320 |
| gtgtcgtcgt | tcgggatcag | cggtaccaac | gcgcacgtga | tcctggagca | agcgccggcc | 1380 |
| gtcgaggtcg | agtcccttgt | ggacactcgg | gtgctcgact | ccgcggtctt | gccgttcgtg | 1440 |
| ctttccggcc | gcagtgaaga | ggcttttggcc | gcccaggcgt | cgaagctcgc | cgcgtatctg | 1500 |
| actggcgagc | ccgcgcccaa | ggccatcgcg | cgagccctcg | ccgagacgcg | gtcggcgttg | 1560 |
| ccgcatcggg | cggtcgtgct | cgccgaagac | ctcggcgaac | tgctcggcgg | cttgcgttcc | 1620 |
| ctcgccgagg | gcgaacccgc | cgcgcgggtc | ctgaccggta | ccgccgaggc | gggtaaggcc | 1680 |

-continued

```
gtcttcgtgt tcccgggtca gggttcgcag tgggtgggga tggcggagga gttgttgttg   1740
tcggctccgg tgttcgcgga gtcgatggct gagtgtgagc gcgcgctttc atcctttgtg   1800
gattggaagt tgtcggatgt gttgtcggat gcggctgcgt tggagcgggt tgatgtggtg   1860
cagcctgttt tgttcgcggt gatggtgtcg ttggcgcggt tgtggcgggc gtgtgggatt   1920
gagcctgctg cggtggtggg tcattcgcag ggtgagatcg cggcggcgtg tgtggctggt   1980
gcgttgtcgt tggatgatgc tgcgcggttg gtgtgcctgc ggagtaaggc gattttggcg   2040
ttgtcgggtc gtggtggcat ggtgtcggtg gctgcttcgg aggatcgtgt tcgggagttg   2100
ctgcctgccg gtgtgtcggt ggcagccgtg aacggcccgt cggcggtggt ggtgtccggt   2160
gatgtcgcgg gcttggaggc gttgctcaag cggtgtgagc tgctggacgt gcgggcgaag   2220
cggatcccgg tggactatgc ctcgcattcg gcgcatgtgg atgcgatcga gcaggaggtc   2280
ttgtcggcgc tggcgggtat ctcaccgcag gcgccggtga tcccgtttta ttcgacggtg   2340
accgatgagc ctctggaatt ggatgcggcg tactggttcc ggaatctgcg ggggacggtg   2400
cggttcgcgg cgacggtgga tcggttgctg gaggacggtt tccggttttt cgtggaggcg   2460
agtccgcatc cggtgctggt tccggggatc agtgaagaag ccatcgcgtt ggggagtttg   2520
cgtcggggtg agggtggtgc ggagcggttc gtcgcgtcgc tggccgaagc ccacacgcag   2580
ggcctgagcc cctcgtggtc cgccgtgctg ccgcccgccg aacgggtcga cctgccgacg   2640
tatgccttcc agcacaagcg gttctggctc gaagcgggca ccgcgagcgg ggacgcgtcg   2700
gcgttcgggc agacggtggt cgaccacccg ctgctcggcg ccgccctgcc gctcgcggac   2760
ggcgacggcc tcgtcctcac cggccggatc tcgccggaca cgcagccctg gctcgtcgac   2820
cacaccgtcc tggacaccgt gctcctgccg gggacggcgt tcgtcgagct cgtcctgcgc   2880
gctgggcggg aggcaggctg cgacggcgtc gacgaactga ccttggaagc gccgctcgtc   2940
ctcgacgggc ccgtggcgct gcaggtcgtg ctcggggagc ccgacgagcg cggccgtcgt   3000
gccgtgtccg tgcactcacg gccggaggat tccgacgaac cctggacccg caacgctcag   3060
ggcacgctgt ccgcgggcac cccatcgacg gtttcgctcg ccgagtggcc gccacccggc   3120
gccgccgaag cgccggagtc cgatctctac gaccgtttcg ccgagctcgg cctcgcctac   3180
ggtccggtgt tccagggact gcgcgcggcg tggcgccagg gcgacgacgt gttcgccgag   3240
gtcgacctgc ccgaggagga ggaggcggac cgcttcggcg tgcaccccgc cctgctcgac   3300
gcggccctgc acaccctcgg gctcggggcc caggacgaga ccgtgcggct gccgttcacc   3360
tggtccggtg tgaccctcca cgccacgggc gcgtcgaaac tccgggtccg gctcacgccg   3420
accgccgacg gcggctcgct caccgtggcc gacgagaccg gcgccccggt gctgaccgtc   3480
ggggaactgg ggctgcgccc gatctccccg gcccagctgg gccgccaccg ggattcgctg   3540
ttccggctcg actgggtccc cgctcctgtg gggccggcgc cggaagagcc ggggtgtgg    3600 cgctgccccg aaggcgaact gcggccggtc ctggaagagg tcctgaagcg gatccaggcc   3660
gattcgacgg ccacgaccgt cgtgctcacc tcgggtgcgg tggcgagcgc gtcgccggat   3720
ccggtggcgg ccgcggtctg gggtctcgtg cggtcggccc aggccgagca tccgggccgg   3780
ttcgtgctga tcgacgcgcg gaccgaggac gaggtccgca ccgcgctggc gaccggggaa   3840
gcgcaggtcg ccgtccacga cggcaaaccg ctggtacccc ggctcgcgcg ggtggcggcc   3900
gccgacgcgg gcgaaccgga ctggacgccc gacgacgtcg tcctgatcac cggtggcacc   3960
ggacggctcg ggcaggcgct ggcccggcac ctcgccgtcc ggcacggcgt gcgcggactg   4020
gtgctgaccg ggcggacggg cggggcgcg gaagacctgg tcgcggacct gcggaactg    4080
```

-continued

```
ggcacccagg tcaccgtcgc ggcctgcgac gtcgcggatc cggacgcggt gcgcgcactg    4140
ctggccgccc atccggtgac cgcggtggtg cacgccgcgg ccgtgctcga cgacgggctc    4200
gtcgacggtc tgaccccgga ccggctcggc accgtgctgg ccccgaaggc cgacggcgcc    4260
cgcgtgctgc acgaactcgc cggaccggtc cgccggttcg tcacgttctc ctcggcggcc    4320
ggcgtgttcg gcaacccggg gcaagcgggc tacgccgcgg cgaacgccta cgccgacgct    4380
ctcatgctcc ggcgtcgtgc cgaggggctg cccggagtgt ccctcgcctg ggattctgg     4440 gcggaacgca gcaagctgac cggcgacctc gacgacaccg acgtccgccg gatggcccgc    4500
gcgggtgtca ccgcgttgtc cacggaggaa ggcctggcgc tgttcgacgc cgccgtggcc    4560
ggaggggacg gcctgctcgt ccccgccaag atcgacctga ccgccttccg gggccgcccg    4620
gccgccgaga tccccgctct gctgcgcggc ctggtgcgcg tccccgcgcg acggtcgggg    4680
gaggcgtcgg gcacggccga ggcactgaaa cgcgaccttg ccgggaagcc ggaggccgaa    4740
cgcgtccggc tgctggagga ggtcgtgcgg atccgggtgg cggccgtgct cgggcacgag    4800
tcggccgacg cgatcgccgg ggaccgcgga ttcctcgaac tgggcttcga ctcgctgacc    4860
gcggtggaat tgcgcaaccg gctcgccgag gcgaccggac tgcggttgcc gcccacgctc    4920
gtcttcgacc ggcccaacgc cggagcgctc gcggcctacc tggcggccga actggccacc    4980
gagaccgccg gaccggccct cgacgccgaa ctcgaccggt tcgccgccgc gctgaccgcg    5040
gccgaccccg gagaggccga acgggcccgg ctggccgccc ggctgcgggc ccttctcggc    5100
acgctccaag gcggggaaga cccggccggg gaaatcgacg gaaaactcga atcggcggac    5160
gacgaggaaa tgttcgcctt catcgacaat gtgcttaagc cttcttga                5208
```

<210> SEQ ID NO 43
<211> LENGTH: 3264
<212> TYPE: PRT
<213> ORGANISM: Amycolatopsis orientalis

<400> SEQUENCE: 43

```
Met Leu Asn Glu Glu Lys Leu Arg Asp Tyr Leu Lys Arg Val Ser Ala
1               5                   10                  15

Asp Leu His Arg Thr Arg Ala Arg Leu Arg Glu Ala Glu Ala Arg Glu
            20                  25                  30

His Glu Pro Ile Ala Ile Ile Gly Met Ala Cys Arg Tyr Pro Gly Gly
        35                  40                  45

Val Arg Gly Pro Glu Gln Leu Trp Asp Leu Val Ala Ala Gly Thr Asp
    50                  55                  60

Ala Val Gly Gly Phe Pro Ala Asp Arg Gly Trp Asp Val Glu Ala Leu
65                  70                  75                  80

Tyr Asp Pro Asp Pro Ala Arg His Gly Lys Thr Tyr Thr Arg Glu Gly
                85                  90                  95

Gly Phe Leu Tyr Asp Ala His Glu Phe Asp Ala Ala Phe Gly Ile
            100                 105                 110

Ser Pro Arg Glu Ala Leu Thr Val Asp Pro Gln Gln Arg Leu Leu Leu
        115                 120                 125

Glu Thr Ala Trp Glu Ala Phe Glu Arg Ala Gly Ile Asp Pro Leu Ser
    130                 135                 140

Val Arg Gly Ser Arg Thr Gly Val Phe Ala Gly Val Met Tyr Asn Asp
145                 150                 155                 160

Tyr Gly Ser Arg Leu Asp Pro Arg Ala Glu Glu Leu Arg Glu Phe Glu
                165                 170                 175
```

-continued

```
Gly Tyr Leu Gly Asn Gly Ser Ala Gly Ser Val Ala Ser Gly Arg Val
            180                 185                 190

Ala Tyr Thr Phe Gly Leu Glu Gly Pro Ala Val Thr Ile Asp Thr Ala
            195                 200                 205

Cys Ser Ser Ser Leu Val Ala Leu His Leu Ala Ala Glu Ser Leu Arg
            210                 215                 220

Arg Gly Glu Ser Thr Leu Ala Leu Ala Gly Gly Val Thr Val Met Ala
225                 230                 235                 240

Ser Pro Glu Thr Phe Val Glu Phe Ser Arg Gln Arg Gly Met Ala Pro
                245                 250                 255

Asp Gly Arg Cys Lys Pro Phe Ala Asp Ala Ala Asp Gly Thr Gly Trp
                260                 265                 270

Ala Glu Gly Ala Gly Ile Leu Leu Leu Glu Arg Leu Ser Asp Ala Arg
            275                 280                 285

Arg His Gly His Pro Val Leu Ala Val Val Arg Gly Thr Ala Val Asn
            290                 295                 300

Gln Asp Gly Ala Ser Ser Gly Leu Thr Ala Pro Asn Gly Pro Ser Gln
305                 310                 315                 320

Gln Arg Val Ile Arg Gln Ala Leu Asp Ser Ala Gly Leu Ala Pro His
                325                 330                 335

Gln Val Asp Val Val Glu Ala His Gly Thr Gly Thr Thr Leu Gly Asp
                340                 345                 350

Pro Ile Glu Ala Gln Ala Leu Leu Ala Ala Tyr Gly Gln Glu Arg Val
            355                 360                 365

Arg Pro Leu Trp Leu Gly Ser Leu Lys Ser Asn Val Gly His Ser Gln
            370                 375                 380

Ala Ala Ala Gly Val Gly Gly Val Ile Lys Met Val Gln Ala Ile Arg
385                 390                 395                 400

His Gly Ile Ala Pro Met Thr Leu His Val Asp Thr Pro Thr Ser Lys
                405                 410                 415

Val Asp Trp Glu Ala Gly Ser Val Glu Leu Leu Thr Glu Ala Arg Pro
            420                 425                 430

Trp Pro Glu Thr Gly Glu Pro Arg Arg Ala Gly Ile Ser Ser Phe Gly
            435                 440                 445

Val Ser Gly Thr Asn Ala His Val Ile Val Glu Gln Ala Pro Glu Val
            450                 455                 460

Glu Pro Ala Glu Arg Asp Gly Glu Ser Pro Leu Gly Asp Glu Val Thr
465                 470                 475                 480

Pro Leu Val Leu Ser Ala Arg Ser Ala Glu Ala Leu Arg Ala Gln Ser
                485                 490                 495

Ala Arg Leu Arg Glu His Leu Arg Gln Thr Glu Ser Leu Thr Asp Thr
            500                 505                 510

Ala Phe Ser Leu Ala Thr Ser Arg Ala Ala Leu Glu His Arg Ala Val
            515                 520                 525

Val Val Ala Glu Ala Asp Ala Ser Leu Asp Ala Leu Ala Ala Gly Ala
            530                 535                 540

Pro Ala Ala Gly Leu Val Gly Ile Ala Leu Pro Pro Gly Lys Val
545                 550                 555                 560

Ala Phe Val Phe Pro Gly Gln Gly Ser Gln Trp Ala Gly Met Ala Leu
                565                 570                 575

Glu Leu Lys Asp Ser Ser Pro Val Phe Arg Ala Ala Leu Leu Asp Cys
            580                 585                 590
```

-continued

```
Glu Arg Ala Leu Ser Ser Phe Val Asp Trp Lys Leu Thr Asp Val Leu
            595                 600                 605
Gly Asp Ala Thr Ala Leu Glu Arg Val Asp Val Val Gln Pro Ala Leu
    610                 615                 620
Phe Ala Val Asn Val Ser Leu Ala Ala Leu Trp Arg Ala Cys Gly Val
625                 630                 635                 640
Glu Pro Asp Ala Val Thr Gly His Ser Gln Gly Glu Ile Ala Ala Ala
                645                 650                 655
Tyr Val Ser Gly Ala Leu Ser Leu Ala Asp Ala Lys Val Val Ala
            660                 665                 670
Leu Arg Ala Lys Ala Ile Leu Ala Leu Ser Gly Ala Gly Gly Met Val
    675                 680                 685
Ala Val Ala Leu Gly Arg Asp Asp Val Leu Pro Arg Leu Thr Glu Trp
690                 695                 700
Gly Asp Arg Ile Ala Val Ala Ala Val Asn Gly Pro Ala Ser Val Val
705                 710                 715                 720
Val Ser Gly Asp Pro Glu Ala Leu Asp Gly Leu Val Ser Ala Cys Glu
                725                 730                 735
Ala Asp Gly Val Arg Ala Arg Ile Pro Val Asp Tyr Ala Ser His
            740                 745                 750
Ser Pro Gln Val Asp Val Leu Arg Glu Glu Leu Leu Gly Leu Leu Asp
            755                 760                 765
Gly Val Glu His His Ala Ser Thr Val Pro Phe Tyr Ser Ala Val Thr
770                 775                 780
Gly Glu Pro Leu Asp Thr Ala Gly Leu Thr Pro Glu Tyr Trp Phe Arg
785                 790                 795                 800
Asn Leu Arg Ala Thr Val Arg Phe Asp Arg Ser Val Arg Arg Leu Leu
                805                 810                 815
Asp Asp Gly His Arg Phe Phe Val Glu Ala Ser Ala His Pro Val Leu
            820                 825                 830
Thr Gly Ser Val Thr Glu Thr Ile Glu Glu Arg Gly Ala His Ala Val
            835                 840                 845
Ala Leu Gly Ser Leu Arg Arg Asp Glu Gly Pro Arg Arg Phe Leu
    850                 855                 860
Thr Ser Leu Ala Glu Ala His Val Arg Gly Leu Arg Pro Asp Trp Ala
865                 870                 875                 880
Ala Leu Trp Pro Thr Ala Thr Arg Val Asp Leu Pro Thr Tyr Ala Phe
                885                 890                 895
Gln Arg Val Pro Tyr Trp Leu Asp Ala Ala Val Val Arg Gln Gly Gly
            900                 905                 910
Thr Ala Ala Glu Leu Arg Phe Trp Ala Ala Val Asp Gln Ala Asp Thr
    915                 920                 925
Gly Ala Leu Asp Ala Ala Val Pro Ala Gly Glu Gly Ala Trp Asp Ala
930                 935                 940
Val Leu Pro Ala Leu Ser Ala Trp Arg Arg Ser Gly Leu Asp Lys Ser
945                 950                 955                 960
Thr Val Asp Asn Trp Arg Tyr Arg Ile Asp Trp Val Pro Ala Thr Gly
                965                 970                 975
Thr Ala Ala Ala Thr Leu Asp Gly Thr Trp Leu Leu Val Pro Ser
            980                 985                 990
Gly Pro Met Pro Pro Val Ala Glu Ala Leu Thr Arg Leu Gly Ala Arg
        995                 1000                1005
Val Leu Leu Ala Gly Pro Asp Asp Glu Leu Pro His Glu Pro Val
```

-continued

```
                   1010                1015                1020

Asp Gly Val Leu Ser Leu Leu Ala Leu Asp Glu Arg Pro His Pro
        1025                1030                1035

Glu His Pro Val Val Pro Ala Gly Leu Ala Ala Thr Ala Asp Leu
        1040                1045                1050

Val Arg Gln Leu Ala Asp Leu Asp Ala Pro Leu Trp Ile Val Thr
        1055                1060                1065

Ser Gly Ala Val Ala Val Gly Arg Ser Glu Thr Pro Asn Ala Gln
        1070                1075                1080

Ala Ala Val Trp Gly Leu Gly Arg Ala Ile Gly Leu Glu His Pro
        1085                1090                1095

Glu Arg Trp Gly Gly Leu Val Asp Leu Pro Glu Leu Asp Glu
        1100                1105                1110

Arg Ala Ala Ala Arg Leu Ala Gly Val Leu Ala Thr Gly His Glu
        1115                1120                1125

Asp Gln Val Ala Val Arg Ser Ser Gly Val Tyr Leu Arg Arg Leu
        1130                1135                1140

Val Arg Ala Pro Leu Gly Asp Ala Val Ala Pro Glu Trp Arg Pro
        1145                1150                1155

Arg Gly Thr Val Leu Val Thr Gly Gly Thr Gly Ala Val Ala Ala
        1160                1165                1170

His Val Ala Arg Trp Leu Ala Gly Asn Gly Ala Gly His Leu Val
        1175                1180                1185

Leu Thr Ser Arg Arg Gly Ala Ala Ala Glu Gly Ala Ala Glu Leu
        1190                1195                1200

Ser Asp Glu Leu Ala Gly Leu Gly Ala Arg Val Thr Phe Ala Ala
        1205                1210                1215

Cys Asp Val Ala Asp Arg Asp Ala Leu Ala Ala Val Leu Ala Glu
        1220                1225                1230

Tyr Pro Pro Asn Ala Val Val His Thr Ala Gly Val Gly Ala Thr
        1235                1240                1245

Ala Ser Leu Ala Glu Thr Gly Pro Ala Glu Leu Ala Asp Ala Leu
        1250                1255                1260

Ala Ala Lys Ala Gly Gly Ala Ala His Leu Asp Glu Leu Leu Glu
        1265                1270                1275

Gly Ala Glu Leu Asp Ala Phe Val Leu Phe Ser Ser Asn Ala Gly
        1280                1285                1290

Val Trp Gly Gly Ala Gly Gln Gly Ala Tyr Gly Ala Ala Asn Ala
        1295                1300                1305

Ala Leu Asp Ala Leu Ala Glu Arg Arg Arg Ala Arg Gly Leu Pro
        1310                1315                1320

Ala Thr Ser Val Ala Trp Gly Leu Trp Gly Gly Gly Ser Gly Leu
        1325                1330                1335

Ala Gly Gln Asp Asp Val Asp Arg Leu Arg Arg Leu Gly Leu Ala
        1340                1345                1350

Ala Met Asp Pro Ala Leu Ala Val Ser Ala Leu Val Gln Ala Val
        1355                1360                1365

Ser His Asp Glu Thr Phe Val Ala Val Ala Asp Val Asp Trp Ala
        1370                1375                1380

Arg Phe Ala Pro Gly Phe Ala Leu Ala Arg Pro Arg Pro Leu Leu
        1385                1390                1395

Asp Ala Leu Pro Glu Val Arg Glu Ala Leu Ser Ala Asp Thr Ala
        1400                1405                1410
```

-continued

```
Gly Pro Gly Gly Ser Glu Phe Ala Ala Gly Leu Leu Ala Ala Pro
    1415                1420                1425

Glu Ala Asp Arg Thr Arg Ile Val Leu Asp Leu Val Arg Ala Gln
    1430                1435                1440

Ala Ala Ala Val Leu Gly His Gly Gly Ala Ala Ala Val Glu Pro
    1445                1450                1455

Asp Arg Ala Phe Arg Asp Leu Gly Phe Asp Ser Leu Thr Ala Val
    1460                1465                1470

Glu Val Arg Asp Arg Leu Ala Ala Ala Thr Gly Leu Arg Leu Pro
    1475                1480                1485

Ala Thr Leu Val Phe Asp His Pro Ser Ala Ser Ala Leu Ala Gly
    1490                1495                1500

His Leu Val Ala Glu Leu Thr Gly Asp Val Thr Gly Thr Gln Ala
    1505                1510                1515

Ala Pro Ala Val Val Val Thr Asp Asp Glu Pro Ile Ala Ile Val
    1520                1525                1530

Ala Met Ser Cys Arg Phe Pro Gly Gly Ile Thr Asp Pro Glu Lys
    1535                1540                1545

Phe Trp Asp Phe Val Ala Asp Gly Gly Asp Ala Met Ala Ala Phe
    1550                1555                1560

Pro Gly Asp Arg Gly Trp Asp Leu Asp Ala Leu Tyr Asp Pro Asp
    1565                1570                1575

Pro Ala His Leu Gly Thr Thr Tyr Ala Arg Glu Gly Gly Phe Leu
    1580                1585                1590

Asp Asp Ala Gly Gly Phe Asp Ala Ala Phe Phe Gly Ile Ser Pro
    1595                1600                1605

Arg Glu Ala Leu Ala Met Asp Pro Gln Gln Arg Leu Leu Leu Glu
    1610                1615                1620

Thr Ser Trp Glu Ala Phe Glu Arg Ala Gly Ile Asp Pro Ala Thr
    1625                1630                1635

Leu Arg Gly Ser Ala Thr Gly Val Phe Val Gly Ala Ser Phe Gln
    1640                1645                1650

Asn Tyr Gly Leu Asp Ala Val Asp Ala Pro Glu Gly Thr Glu Gly
    1655                1660                1665

Tyr Phe Leu Thr Gly Thr Ala Thr Ala Val Val Ser Gly Arg Leu
    1670                1675                1680

Ser Tyr Thr Phe Gly Leu Glu Gly Pro Ala Val Thr Ile Asp Thr
    1685                1690                1695

Ala Cys Ser Ser Ser Leu Val Ala Leu His Leu Ala Ala Gln Ala
    1700                1705                1710

Leu Arg Arg Gly Glu Cys Ser Leu Ala Leu Ala Gly Gly Val Thr
    1715                1720                1725

Val Met Ala Asn Pro Ala Ala Phe Val Glu Phe Ser Arg Gln Arg
    1730                1735                1740

Gly Leu Ala Pro Asp Gly Arg Cys Lys Ala Phe Ala Asp Ala Ala
    1745                1750                1755

Asp Gly Thr Ala Trp Ser Glu Gly Ala Gly Ile Leu Leu Val Glu
    1760                1765                1770

Arg Leu Ser Asp Ala Arg Arg Leu Gly His Pro Val Leu Ala Leu
    1775                1780                1785

Val Arg Gly Ser Ala Val Asn Gln Asp Gly Ala Ser Asn Gly Leu
    1790                1795                1800
```

-continued

```
Ser Ala Pro Asn Gly Pro Ser Gln Gln Arg Val Ile Arg Gln Ala
1805                1810                1815

Leu Ala Asn Ala Gly Phe Ala Pro Ser Asp Val Asp Ala Val Glu
1820                1825                1830

Ala His Gly Thr Gly Thr Ser Leu Gly Asp Pro Ile Glu Ala Gln
1835                1840                1845

Ala Leu Leu Ala Ala Tyr Gly Gly Glu Arg Glu His Pro Leu Trp
1850                1855                1860

Leu Gly Ser Val Lys Ser Asn Leu Gly His Thr Gln Ser Ala Ser
1865                1870                1875

Gly Val Ala Gly Val Ile Lys Met Val Gln Ala Ile Arg His Gly
1880                1885                1890

Val Leu Pro Arg Thr Leu His Val Asp Ala Pro Thr Thr Glu Val
1895                1900                1905

Asp Trp Thr Ala Gly Asp Val Arg Leu Leu Thr Glu Pro Val Asp
1910                1915                1920

Trp Pro Asp Thr Gly Arg Pro Arg Arg Ala Gly Val Ser Ser Phe
1925                1930                1935

Gly Val Ser Gly Thr Asn Val His Thr Leu Ile Glu Glu Val Pro
1940                1945                1950

Glu Ser Ala Ala Pro Pro Ala Gly Gly Asp Thr Trp Val Pro Trp
1955                1960                1965

Val Leu Ser Ala Lys Thr Glu Glu Ala Leu Arg Ser Gln Ala Ser
1970                1975                1980

Arg Leu His Ala Gln Leu Glu Glu His Pro Gly Asp Asp Ser Asp
1985                1990                1995

Ile Ala Tyr Thr Leu Ala Thr Ala Arg Ala Gly Leu Glu Ile Arg
2000                2005                2010

Ala Ala Val Thr Gly Pro Asp Arg Leu Arg Glu Leu Ala Leu Leu
2015                2020                2025

Ala Glu Gly Thr Pro Ser Ala Ala Val Leu Arg Gly Ala Leu Thr
2030                2035                2040

Ala Gly Ala Pro Gly Phe Leu Phe Thr Gly Gln Gly Ser Gln Lys
2045                2050                2055

Pro Gly Met Gly Ala Glu Leu Ala Ala Arg Phe Pro Val Phe Ala
2060                2065                2070

Ala Ala Phe Asp Glu Val Cys Ala His Leu Asp Pro Arg Leu Gly
2075                2080                2085

Leu Ser Leu Arg Glu Val Leu Glu Thr Glu Arg Val His Glu Thr
2090                2095                2100

Ala Phe Ala Gln Cys Ala Leu Phe Ala Val Glu Val Ala Leu Phe
2105                2110                2115

Arg Leu Leu Glu Ser Trp Gly Val Arg Pro Ala Leu Leu Leu Gly
2120                2125                2130

His Ser Val Gly Glu Ile Ala Ala Ala His Val Ala Gly Val Leu
2135                2140                2145

Ser Leu Ala Asp Ala Ala Thr Met Val Glu Ala Arg Gly Arg Leu
2150                2155                2160

Met Gly Ala Leu Pro Ser Arg Gly Val Met Ile Ala Leu Gln Ala
2165                2170                2175

Asn Glu Asp Glu Val Thr Pro Leu Pro Thr Glu Arg Val Ser Ile
2180                2185                2190

Ala Ala Val Asn Gly Pro Glu Ala Val Val Leu Ser Gly Asp Glu
```

-continued

```
            2195                2200                2205

Asp Ala Val Thr Ala Val Val Asp Arg Phe Ala Asp Arg Lys Ser
    2210                2215                2220

Lys Arg Leu Val Val Ser His Ala Phe His Ser Pro Leu Met Glu
    2225                2230                2235

Pro Met Leu Ala Asp Phe Arg Arg Val Val Ser Gly Leu Ser Phe
    2240                2245                2250

Ser Glu Pro Arg Ile Pro Ile Val Ser Thr Val Thr Gly Arg Ser
    2255                2260                2265

Asp Pro Glu Ile Ala Ser Pro Gly Tyr Trp Val Arg His Val Arg
    2270                2275                2280

Glu Ala Val Arg Phe His Asp Ala Ile Arg Phe Ala Glu Ala Glu
    2285                2290                2295

Ala Glu Gly Val Arg Ala Phe Val Glu Leu Gly Pro Glu Gly Val
    2300                2305                2310

Leu Ser Ala Met Ala Lys Asp Phe Leu Glu Asp Thr Val Leu Ile
    2315                2320                2325

Pro Thr Leu Arg Gly Glu Arg Pro Glu Val Ala Ala Leu Ala Thr
    2330                2335                2340

Thr Leu Gly Arg Leu His Val His Gly Val Gly Ile Asp Trp Ala
    2345                2350                2355

Gly Val Phe Asp Gly Val Gln Ala Ser Arg Val Thr Leu Pro Thr
    2360                2365                2370

Tyr Pro Phe Glu His Arg His Phe Trp Leu Ala Ser Thr Gly Ala
    2375                2380                2385

Thr Thr Gly Asp Ala Ala Ala Phe Gly Leu Gly Glu Ala Gly His
    2390                2395                2400

Ala Leu Leu Gly Ala Ala Val Pro Val Pro Gly Gly Ser Gly Ile
    2405                2410                2415

Ser Phe Thr Gly Arg Leu Ser Leu Arg Ala Gln Pro Trp Leu Ala
    2420                2425                2430

Glu His Val Val Leu Gly Thr Ala Leu Leu Pro Gly Thr Ala Phe
    2435                2440                2445

Val Asp Leu Ala Leu His Ala Gly Asp Arg Ala Gly Cys Gly Thr
    2450                2455                2460

Val Ala Glu Leu Thr Leu Glu Ala Pro Leu Ala Leu Pro Glu Ser
    2465                2470                2475

Gly Asp Val Arg Leu His Val Thr Val Gly Glu Pro Gly Glu Asp
    2480                2485                2490

Gly Gly Arg Thr Ile Glu Ile His Ser Arg Ala Gly Ser Ala Ala
    2495                2500                2505

Asp Glu Glu Pro Trp Thr Arg His Ala Thr Gly Leu Leu Ala Thr
    2510                2515                2520

Gly Thr Pro Ala Ala Ser Gly Asn Leu Asp Ser Trp Pro Pro Asp
    2525                2530                2535

Gly Thr Glu Ile Pro Val Glu Asp Phe Tyr Asp Arg Leu Asp Gly
    2540                2545                2550

Thr Gly Phe Glu Tyr Gly Pro Leu Phe Gln Gly Leu Arg Ala Ala
    2555                2560                2565

Trp Lys Ala Gly Asp Asp Val Tyr Ala Glu Val Ser Leu Pro Glu
    2570                2575                2580

Asp Arg Ser Arg Asp Ala Glu Gly Phe Gly Val His Pro Ala Leu
    2585                2590                2595
```

-continued

```
Leu Asp Ala Ala Leu His Ala Ser Lys Leu Arg Leu Glu Gly Asp
2600                 2605                 2610

Ser Glu Gly Pro Phe Leu Pro Phe Thr Trp Lys Gly Val Ser Leu
2615                 2620                 2625

Ala Ala Thr Gly Ala Arg Thr Leu Arg Val Arg Leu Ser Ser Ser
2630                 2635                 2640

Ala Pro Ala Thr Ile Ser Leu Leu Leu Ala Asp Gly Glu Gly Ala
2645                 2650                 2655

Pro Val Ala Thr Val Asp Ser Leu Val Phe Arg Arg Val Ser Ser
2660                 2665                 2670

Glu Gln Leu Gly Asn Arg Gln Gly Ser Gly Ser Leu Phe His Val
2675                 2680                 2685

Glu Trp Thr Asp Val Pro Ala Glu Glu Val Ser Thr Glu Asp Val
2690                 2695                 2700

Arg Ile Gly Ala Gly Glu Ser Tyr Val Asp Val Ala Ala Leu Leu
2705                 2710                 2715

Ala Ala Lys Thr Pro Glu Val Ala Leu Leu Val Cys Pro Ser Gly
2720                 2725                 2730

Glu Thr Ala Glu Ala Val His Asp Ala Thr Val Trp Ala Leu Arg
2735                 2740                 2745

Gln Val Arg Asp Trp Leu Ala Asp Glu Arg Leu Asp Ala His Arg
2750                 2755                 2760

Leu Val Leu Leu Thr Asp Gly Thr Asp Leu Ala Gln Ala Ala Val
2765                 2770                 2775

Arg Gly Leu Phe Arg Ser Ala Ser Ser Glu His Pro Gly Arg Phe
2780                 2785                 2790

Gly Ile Ala Glu Thr Thr Gly Asp Pro Val Arg Val Ser Ala Asp
2795                 2800                 2805

Glu Ser Glu Leu Arg Leu Glu Asn Gly Val Ala Tyr Ala Pro Arg
2810                 2815                 2820

Leu Val Arg Lys Ile Ala Ala Ala Pro Val Ala Leu Asp Pro
2825                 2830                 2835

Gly Lys Thr Val Leu Val Thr Gly Gly Thr Gly Ala Leu Gly Ala
2840                 2845                 2850

Leu Val Ala Arg His Leu Val Thr Ala Arg Gly Val Thr Arg Leu
2855                 2860                 2865

Leu Leu Val Ser Arg Arg Gly Leu Glu Ala Glu Gly Ala Lys Asp
2870                 2875                 2880

Leu Val Ala Asp Leu Thr Ala Ala Gly Ala Asp Val Thr Val Glu
2885                 2890                 2895

Ala Cys Asp Val Ala Asp Arg Ala Ala Leu Glu Ala Ala Leu Ala
2900                 2905                 2910

Gly His Glu Leu Thr Ala Val His Thr Ala Gly Val Leu Asp
2915                 2920                 2925

Asp Gly Leu Val Asp Ser Leu Thr Pro Glu Arg Leu Ala Lys Val
2930                 2935                 2940

Leu Arg Pro Lys Val Asp Ala Ala Leu Asn Leu His Glu Leu Ala
2945                 2950                 2955

Gly Asp Val Glu Glu Phe Val Leu Phe Ser Ser Ala Ser Ala Thr
2960                 2965                 2970

Phe Gly Asn Pro Gly Gln Ala Asn Tyr Ala Ala Ala Asn Ala Phe
2975                 2980                 2985
```

-continued

```
Leu Asp Ala Leu Ala Arg His Arg His Ala Gln Gly Leu Pro Ala
    2990                2995                3000

Thr Ser Leu Ala Trp Gly Leu Trp Ala Thr Asp Gly Gly Met Thr
    3005                3010                3015

Gly Glu Leu Ser Asp Thr Asp Leu Ala Arg Met Gly Arg Thr Gly
    3020                3025                3030

Ile Ala Ala Leu Thr Pro Glu Ala Gly Leu Ala Leu Phe Asp Ala
    3035                3040                3045

Ala Ser Gly Ala Gly Pro Val Val Leu Pro Met Ala Leu Thr Pro
    3050                3055                3060

Ser Ser Leu Arg Asp Val Glu Pro Ala Val Leu Pro Pro Leu Leu
    3065                3070                3075

Arg Gly Leu Val Arg Ala Pro Ser Arg Arg Ala Ala Ser Ala Pro
    3080                3085                3090

Ala Gly Pro Ala Leu Gln Asp Arg Leu Ser Gly Leu Thr Gly Ala
    3095                3100                3105

Glu Arg Asp Asp Ala Val Leu Glu Val Val Arg Glu Gln Val Ala
    3110                3115                3120

Ala Ala Leu Gly His Ala Gly Ala Gly Ala Ile Asp Pro Gly Lys
    3125                3130                3135

Gly Phe Val Glu Leu Gly Met Asp Ser Leu Ser Ala Val Glu Leu
    3140                3145                3150

Arg Asn Gln Leu Cys Ala Leu Ser Gly Leu Lys Leu Ser Thr Thr
    3155                3160                3165

Val Val Phe Asp His Pro Asn Pro Ala Ala Leu Ala Gly His Leu
    3170                3175                3180

Ala Ala Glu Leu Pro Ala Glu Gly Val Ala Thr Thr Ala Ser Val
    3185                3190                3195

His Ala Gly Leu Asp Arg Leu Glu Ala Leu Leu Ala Thr Ala Ala
    3200                3205                3210

Pro Ala Asn Gly Asp Arg Ala Gly Val Thr Ala Arg Leu Arg Thr
    3215                3220                3225

Leu Leu Ala Thr Trp Thr Gly Glu Pro Ala Ala Glu Ala Asp Asp
    3230                3235                3240

Ser Leu Glu Ser Ala Thr Ala Asp Glu Leu Phe Asp Leu Leu Asp
    3245                3250                3255

His Glu Leu Gly Ala Ser
    3260

<210> SEQ ID NO 44
<211> LENGTH: 9795
<212> TYPE: DNA
<213> ORGANISM: Amycolatopsis orientalis

<400> SEQUENCE: 44
atgctgaacg aggagaagct gcgcgactac ctcaagcggg tgtcggccga cctgcatcgg     60
acccgggccc ggctgcggga ggccgaggcg cgggagcacg agccgatcgc gatcatcggg    120
atggcctgcc ggtacccggg cggcgtccgc ggtccggagc agttgtggga tctcgtggcc    180
gcgggcaccg acgcggtcgg cggtttcccc gccgaccggg gctgggatgt cgaggccctc    240 tacgacccg  accccgcgcg gcacggcaag acctacacgc gcgagggcgg tttcctctac    300
gacgcccacg agttcgacgc cgcgttcttc ggcatcagcc cgcgcgaggc gctcaccgtc    360
gacccgcagc agcgcctcct gctggagacc gcttgggagg ccttcgaacg cgccgggatc    420
```

-continued

| | |
|---|---|
| gacccgcttt ccgtgcgcgg cagccggacc ggcgtgttcg ccggggtgat gtacaacgac | 480 |
| tacggctcca ggctcgaccc ccgcgccgag gaactgcgcg agttcgaggg atacctcggc | 540 |
| aacggcagcg ccgggagcgt cgcctccggc cgggtcgcct acaccttcgg cctcgaaggc | 600 |
| ccggccgtca ccatcgacac cgcgtgttcg tcttcgctgg tcgcgctaca cctcgctgcc | 660 |
| gagtcgctcc ggcgcgggga gtccacgctc cgcgctggcg gcggggtgac cgtgatggcc | 720 |
| tcgccggaga ccttcgtgga gttcagccgt cagcgcggga tggcgcccga cggccgctgc | 780 |
| aaacccttcg ccgacgcggc cgacggcacc ggctgggccg agggcgccgg gatcctgctg | 840 |
| ctcgaacggc tttccgacgc ccgtcgccac gggcatcccg tcctcgccgt ggtgcgcggc | 900 |
| accgcggtca accaggacgg cgcgagcagc gggctcaccg cgccgaacgg cccgtcgcag | 960 |
| cagcgggtga tccggcaggc gctcgacagc gccggcctcg cgccgcacca ggtcgacgtc | 1020 |
| gtcgaggcac acggcacggg gacgaccctg ggcgacccga tcgaggcaca ggccctgctc | 1080 |
| gccgcgtacg gacaggagcg cgtccgtcca ctgtggctcg gttcgctgaa gtcgaacgtc | 1140 |
| gggcacagcc aggctgccgc cggggtcggc ggcgtgatca agatggtcca ggcgatccgg | 1200 |
| cacgggatcg ccccgatgac cctgcacgtc gacaccccga cgtccaaagt ggactgggaa | 1260 |
| gcgggttcgg tcgaactgct caccgaagcc cgcccttggc cggagaccgg ggaaccgcgc | 1320 |
| cgcgccggga tctcttcgtt cggggtcagc ggcaccaacg cgcacgtcat cgtcgaacaa | 1380 |
| gcgccggagg tcgagcccgc cgaacgcgac ggcgaatcac cgctcggcga cgaggtgacg | 1440 |
| ccgctggtcc tgtccgcccg gagcgccgag gctctgcgcg cgcagtccgc ccggctgcgt | 1500 |
| gagcaccttc gccagacgga atccttgacc gacaccgcct tctcgctcgc gacgtcccgt | 1560 |
| gccgcgctgg agcaccgcgc cgtcgtcgtg gccgaagcgg acgcgtcgct cgacgccttg | 1620 |
| gccgccggcg cgcctgcggc agggctggtc gaaggtatcg ctttgccacc gggcaaggtc | 1680 |
| gcgttcgtct ttcccgggca gggctcgcaa tgggccggga tggcactgga gctcaaggac | 1740 |
| tcctcgccgg tcttccgggc cgcgctgctc gactgcgaac gcgctctctc gtcctttgtg | 1800 |
| gactggaagc tcaccgacgt gctcggcgac gcgacggcgc tggagcgcgt cgacgtcgtg | 1860 |
| cagcccgccc tcttcgcggt caacgtgtcg ctggcggcgc tgtggcgggc gtgcggggtc | 1920 |
| gaacccgacg cggtgaccgg gcacagtcag ggtgagatcg ccgccgcgta cgtgtccggc | 1980 |
| gcgttgtcgc tggccgacgc cgccaaggtc gtcgccttgc gggccaaggc catcctcgcg | 2040 |
| ctttccggcg ccgggggcat ggtcgcggtc gccctcggcc gcgacgacgt gctccctcgg | 2100 |
| ctgacggagt ggggcgaccg gatcgccgtg gccgcggtca acggacccgc gtcggtcgtg | 2160 |
| gtctccggag acccagaggc gctcgacggg ctcgtctccg cctgcgaggc ggacggcgtg | 2220 |
| cgtgcccgcc ggatcccggt ggactacgcc tcgcattcgc cgcaggtgga cgtcttgcgt | 2280 |
| gaggaactgc tcggcctgct cgacggcgtc gagcaccacg cgtccacggt gccgttctac | 2340 |
| tcggcggtga ccggggaacc cctcgacacg gcgggcctga cccgagta ctggttccgg | 2400 |
| aacctgcggg ccaccgtccg gttcgaccgg tccgtccggc ggctgctcga cgacggtcac | 2460 |
| cggttcttcg tcgaagccag cgcgcatccg gtgctgaccg cagcgtcac cgaaaccatc | 2520 |
| gaggaacggg gcgcccacgc ggtcgcgctc ggttcgcttc gccgtgacga gggcggcccc | 2580 |
| cgccggttcc tgacgtcgct ggccgaggct cacgtacgcg gcctccgccc ggattgggcc | 2640 |
| gcgttgtggc ccactgccac cagggtcgac ctgcccacct atgccttcca gcgggtgccg | 2700 |
| tactggctcg acgccgccgt cgtccggcag ggcggcacgg cggccgaact gcgcttctgg | 2760 |
| gcggctgtcg accaggccga caccggcgcg ctcgacgccg ccgtgcccgc cggggaggga | 2820 |

```
gcctgggacg cggtgcttcc cgcgctttcg gcctggcgcc gttccggtct cgacaagtcc    2880
acagtggaca actggcggta ccggatcgac tgggtccccg cgaccgggac ggcagcggcc    2940
accctcgacg ggacgtggct gctggtcgtc ccgtccggac cgatgccgcc cgtcgcggag    3000
gcgctcaccc ggctcggcgc ccgtgtcttg ctcgcgggcc ccgatgacga actgccgcac    3060
gagccggtcg acggcgtgct ttccctgctg gcactcgacg aacggccgca tccggaacac    3120
ccggtggtac ccgccgggct cgccgcgacc gcggacctcg tccgccagct cgccgacctc    3180
gacgctccac tgtggatcgt cacctccggc gcggtcgccg tcggccggtc ggagaccccg    3240
aacgcgcagg ccgccgtctg gggtctcggc cgggcgatcg gactcgaaca ccccgaacgc    3300
tggggcggcc tcgtcgacct tccggaggaa ctcgacgaac gcgccgcggc ccggctcgcc    3360
ggggtgctcg ccaccggtca cgaggaccag gtcgccgtcc ggtcgtccgg ggtctatctg    3420
cggcggctcg tgcgggcgcc gctcggggac gccgtcgcgc cggaatggcg gccccgtggg    3480
accgtcctgg tcaccggcgg caccggtgcg gtggccgccc acgtcgcgcg gtggctcgcc    3540
gggaacggcg ccgggcatct ggtgctcacc agcaggcgcg gggcggcggc cgagggtgcg    3600
gcggaattga gtgacgaact cgccggtctc ggtgcgcggg tgaccttcgc cgcctgcgac    3660
gtcgccgatc gtgacgcact ggcggcggtg ctggccgagt atccgccgaa cgccgtcgtg    3720
cacacggcgg gggtcggggc caccgcgtcg ctcgccgaga ccggcccggc ggaactcgcc    3780
gacgcgctcg ccgccaaggc gggcggtgcc gctcacctcg acgaacttct cgaaggcgcc    3840
gaactggacg ccttcgtgct cttttcctcc aacgcgggtg tctggggcgg cgccgggcag    3900
ggtgcctacg gtgccgcgaa cgctgccctg gacgcgctcg ccgaacgacg tcgtgcccgg    3960
ggcctgcccg ccacctcggt ggcgtggggg ctgtggggcg gcggcagcgg gctggccggc    4020
caggacgacg tcgaccgctt gcgccgtctc ggattggccg cgatggaccc ggcgctcgcc    4080
gtgtccgcgc tcgtccaagc cgtctcgcac gacgagacct tcgtcgcggt cgccgacgtc    4140
gactgggcgc ggttcgctcc cggattcgcc ctcgcccggc cccggccgct gctcgacgcg    4200
ttgcccgagg tccgcgaggc gctgtccgcc gacaccgcgg gaccgggcgg ctccgaattc    4260
gccgccggac tgctggccgc ccccgaggcg gaccggaccc gtatcgtgct cgacctggtt    4320
cgcgcgcagg cagccgcggt cctcggccac ggtggcgccg ccgccgtcga gccgaccgc    4380 gccttccgcg acctcggctt cgactccctg accgcggtcg aggtccgcga ccggctggcc    4440
gccgccaccg ggctgcggct gcccgcgacc ctggtcttcg accatccgtc ggcctcggcg    4500
cttgccgggc atctcgtcgc cgaactcacc ggcgacgtca ccgggacaca agccgcgccg    4560
gccgtggtgg tgaccgacga cgagccgatc gcgatcgtcg cgatgagctg ccggttcccc    4620
ggcgggatca cggatccgga gaagttctgg gacttcgtcg cggacggcgg ggacgcgatg    4680
gccgccttcc ccgcgaccg cggctgggac ctcgacgcgc tctacaccc ggaccccgcg    4740 cacctcggca ccacgtacgc ccgtgaaggc ggcttcctcg acgacgcggg cggtttcgac    4800
gcggcgttct tcgggatctc gccgcgtgag gcgctggcga tggatccgca gcagcggttg    4860
ctgctggaga cgtcgtggga ggcgttcgaa cgggccggga tcgacccggc gaccctgcgg    4920
gggagcgcga ccggcgtctt cgtcggcgca tccttccaga actacggcct ggacgccgtc    4980
gacgcgcccg aaggcaccga gggctacttc ctcaccggaa ccgccaccgc ggtcgtctcc    5040
ggccgcctct cctacacctt cgggctggaa ggcccggcgg tgacgatcga caccgcgtgc    5100
tcgtcttcgc tggtggcact gcatctcgcg gcgcaggcgc tgcggcgcgg cgaatgttcg    5160
```

```
ctggcgctgg cgggcggggt gaccgtgatg gccaacccgg ccgcgttcgt ggagttcagc   5220
cgtcagcgcg ggctcgcgcc ggacgggcgt tgcaaggcgt cgccgacgc cgccgacggc    5280 accgcgtggt ccgagggtgc cgggatcctt ctggtggaaa ggctttccga cgcgcgccgc   5340
ctcgggcacc ccgtcctggc gctggtgcgc ggttcggccg tgaaccagga cggcgcctcg   5400
aacgggctga gcgcgccgaa cgggccgtca cagcagaggg tgatccgcca ggcgctggcg   5460
aacgccgggt tcgcaccgtc cgatgtggac gccgtcgagg cgcacggcac cggaaccagc   5520
ctcggcgacc cgatcgaggc acaggccttg ctcgccgctt acggcgggga acgcgagcat   5580
ccgctgtggc tcggttcggt caagtcgaac ctggggcaca cacagtcggc gtcgggtgtg   5640
gcgggcgtga tcaagatggt gcaggcgatc cggcacggtg tcctgccgcg gaccctgcac   5700
gtcgacgcgc cgaccacgga ggtggactgg acggcgggtg atgtccggct gctcaccgaa   5760
ccggtggact ggccggacac cggacgtccg cgccgggcgg cgtctcctc tttcggggtc    5820 agcgggacca acgtgcacac gctgatcgaa gaggtcccgg agagcgctgc gcctcccgcc   5880
ggcggggaca cgtgggtgcc gtgggtgctc tcggccaaga ccgaggaagc gttgcggtcc   5940
caagcttccc ggctgcacgc gcaactgaa gagcaccccg gggacgactc cgacatcgcg    6000
tacacgctgg cgaccgcccg tgcgggactg gagatccggg ccgcggtgac cgggccggat   6060
cgtctgcgcg agctggccct cctcgccgag gggacgccga gcgcggcggt gctgcgcggc   6120
gcgctcaccg ccggggcgcc ggggttcctg ttcaccggtc agggcagcca gaaacccggg   6180
atgggcgccg aactcgcggc ccgcttcccg gtgttcgccg ccgcgttcga cgaggtgtgc   6240
gcccatctgg acccgcgcct cgggctgtcg ctgcgcgaag tcctcgaaac cgagcgagtg   6300
cacgaaacgg cgttcgccca gtgtgccctg ttcgccgtcg aggtcgcgct gttccggctg   6360
ctggagagct ggggtgtccg gccgcgctg ctgctcgggc attcggtcgg cgagatcgcg    6420
gccgcgcacg tcgccggggt cctgtcgctc gcggacgcgg ccacgatggt cgaggcgcgc   6480
ggaaggctca tgggcgccct gccgtctcgc ggcgtgatga tcgccttgca ggccaatgaa   6540
gacgaggtga ccccgctgcc caccgagcgc gtgtcgatcg ccgccgtcaa cggcccggaa   6600
gcggtggtgc tgtccgggga cgaggacgcc gttaccgcag tggtggaccg gttcgccgac   6660
cgcaagagca agcggctcgt ggtcagtcac gcgttccact cgccgctgat ggaaccgatg   6720
ctcgcggact tccgccgtgt cgtgtccggg ctttccttca gcgagccgag gatcccgatc   6780
gtgtcgacgg tgaccggccg ctccgatccc gaaatcgcct cacccggcta ctgggtgcgg   6840
cacgtccgcg aggcggtgcg gttccacgac gcgatccggt tcgccgaggc cgaggccgag   6900
ggcgtgcgcg ccttcgtcga actcggcccc gagggcgtcc tttccgccat ggccaaggac   6960
ttcctcgaag acaccgtgct gatccgacc ctgcgcgggg aacgtccgga ggtcgccgcg    7020
ctggcgacca cactcggccg cctgcacgtc cacggtgtcg ggatcgactg ggcgggtgtg   7080
ttcgacggcg tccaggcgag ccgggtcacg ctgcccacgt atcccttcga gcatcggcac   7140
ttctggctgg cgagcaccgg cgcgaccacg ggcgacgcgg ccgcgttcgg gctcggcgag   7200
gccgggcacg cgctgctcgg cgcggccgtc ccggtgcccg cgggagcgg gatctcgttc    7260 accggaaggc tctccctgcg ggctcagccg tggctcgcgg agcacgtcgt gctcggtacg   7320
gctctgcttc ccggcaccgc gttcgtcgat ctcgcgttgc acgcgggtga ccgcgccggc   7380
tgcggaaccg tcgccgagct gaccttggaa gctccgctgg cgctgccgga aagtggtgac   7440
gtccggctgc acgtcaccgt cggcgagcca ggggaggacg gcgggcgcac gatcgagatc   7500
cattcccgtg cgggatccgc cgccgacgag gaaccgtgga cgcggcacgc caccggcctc   7560
```

-continued

```
ctggccaccg gaaccccggc cgccagcggg aacctggaca gctggccacc ggacggcacc    7620
gagatcccgg tcgaggactt ctatgaccgg ctcgacggca ccgggttcga gtacgggccg    7680
ttgttccagg gcctgcgcgc ggcgtggaag gccggggacg acgtctacgc ggaggtttcg    7740
ctgcccgagg accgctcccg tgacgccgaa ggcttcggcg tccaccccgc gctgctggac    7800
gccgcgctgc acgcgtcgaa gctccggctg gagggtgaca gcgagggacc tttcctaccg    7860
ttcacgtgga agggtgtctc gctggccgcg accggtgcgc ggacgttgcg ggtgcggctg    7920
tcctcgtccg ctccggccac gatctcgctg ctgctcgccg acggtgaagg cgccccggtg    7980
gccactgtgg attccctggt gttccgccgg gtttcgtccg agcagctcgg aaaccggcag    8040
gggagcggat cgctgttcca cgtcgagtgg accgacgtgc ctgccgagga agtgtccaca    8100
gaggatgtca ggatcggcgc cggagagtcc tatgtggacg tcgcggcact gctcgccgcc    8160
aagacgcccg aagtcgcgct gctggtctgc ccgtccgggg agaccgccga ggcggtgcac    8220
gacgcgaccg tgtgggcgct gcgccaggtg cgggactggc tcgccgacga gcggctggac    8280
gcgcaccggc tcgtcctgct gaccgacggc accgacctgg cccaggccgc ggtgcgggga    8340
ctgttccggt cggcctcgtc cgaacacccc ggccggttcg gcatcgccga gaccaccggg    8400
gatccggtcc gggtgtcggc cgacgagtcc gaacttcggc tggagaacgg tgtcgcgtac    8460
gcgccgaggc tggtccgcaa gatcgccgcg gccgctccgg tcgcgctcga tcccggcaag    8520
acggtgctgg tcaccggtgg tacgggcgcg ctcggcgcgc tggtggcccg gcatctggtg    8580
accgcacgcg gcgtgacccg gctgctgctg gtctcccgtc gtgggctgga ggccgaaggc    8640
gccaaggacc tggtggcgga cctgacggcc gcgggcgccg acgtcaccgt cgaggcctgc    8700
gacgtcgccg accgcgctgc gctggaagcg cccctcgccg ggcacgagct gaccgccgtc    8760
gtgcacacgg ccggcgtgct cgacgacggt ctggtcgatt cgctgacgcc ggagcggctg    8820
gcgaaggtgc tgcggccgaa ggtcgacgcg gcgctgaacc tccacgagct cgcgggtgac    8880
gtcgaggaat tcgtgctgtt ctcctcggcg tcggccacgt tcggcaatcc cgggcaggcg    8940
aactacgcgc cggccaacgc gttcctcgac gcgctcgccc gccaccgcca cgcacaaggg    9000
cttccggcca cgtcgctcgc ctggggactg tgggcgaccg acggcggcat gacgggcgaa    9060
ctgagcgaca ccgacctggc caggatgggc cgcaccggta tcgccgcgct gaccccggaa    9120
gccgggctcg ccctgttcga cgcggcgtcc ggcgccgggc cggtggtgct gccgatggcg    9180
ctgacgccat cctcgctccg cgatgtggaa cccgcggtgc tgccccgtt gctgcgggga    9240
ctggtgcggg ctccgtcccg gcgcgccgcg tccgctcccg ccggtccggc gttgcaggac    9300
aggctttcgg gcctgaccgg cgccgaacgc gacgacgcgg tgctggaggt ggtgcgcgag    9360
caggtcgcgg ccgcgctcgg tcacgcgggc gccggggcga tcgatccggg caagggcttc    9420
gtcgaactcg ggatggattc gctcagcgcg gtcgaactgc gcaaccagct gtgcgcgctg    9480
agcgggctga aactctcgac gacggtggtg ttcgaccacc ccaacccggc cgcgctcgcc    9540
gggcacctcg cggccgaact gcccgccgaa ggggtggcca ccaccgcgtc ggtgcacgcc    9600
gggctcgacc ggctcgaagc gctgctggcc accgccgccc ggcgaacgg ggatcgcgcc    9660
ggggtcaccg cgcgcctgcg cacgctgctg gcgacgtgga ccggcgagcc cgccgccgag    9720
gccgacgact cgctggagtc ggccaccgcg gacgaactgt tcgacctgct cgatcacgaa    9780
ctcggcgcgt cctga                                                     9795
```

<210> SEQ ID NO 45

-continued

```
<211> LENGTH: 5099
<212> TYPE: PRT
<213> ORGANISM: Amycolatopsis orientalis

<400> SEQUENCE: 45

Val Ala Asn Glu Asp Lys Tyr Leu Asp Tyr Leu Lys Arg Ala Thr Ala
1               5                   10                  15

Asp Leu Arg Glu Thr Arg Arg Leu Lys Glu Ala Glu Asp Arg Gly
            20                  25                  30

His Glu Pro Ile Ala Ile Ile Gly Met Ala Cys Arg Phe Pro Gly Gly
        35                  40                  45

Val Arg Ser Pro Glu Asp Leu Trp Glu Leu Val Ala Glu Gly Arg Asp
    50                  55                  60

Gly Ile Ser Gly Phe Pro Ala Asp Arg Gly Trp Asp Leu Ser Ala Leu
65              70                  75                  80

Tyr Asp Pro Thr Gly Glu Lys Pro Gly Thr Ser Tyr Cys Arg Glu Gly
                85                  90                  95

Gly Phe Leu Asp Gly Ala Gly Glu Phe Asp Pro Ala Phe Phe Gly Ile
            100                 105                 110

Ser Pro Arg Glu Ala Leu Ala Met Asp Pro Gln Gln Arg Leu Leu Leu
        115                 120                 125

Glu Ile Ser Trp Glu Thr Phe Glu Arg Ala Gly Ile Asp Pro Gly Ser
130                 135                 140

Leu Arg Gly Ser Arg Thr Gly Val Phe Ala Gly Val Met Tyr His Asp
145                 150                 155                 160

Tyr Val Ser Arg Leu Ala Ala Ile Pro Glu Glu Leu Glu Gly Tyr Leu
                165                 170                 175

Gly Thr Gly Asn Ser Gly Ser Val Val Ser Gly Arg Val Ala Tyr Thr
            180                 185                 190

Phe Gly Leu Glu Gly Pro Ala Val Thr Ile Asp Thr Ala Cys Ser Ser
        195                 200                 205

Ser Leu Val Ala Leu His Leu Ala Ala Gln Ala Leu Arg Gln Gly Glu
210                 215                 220

Cys Ser Met Ala Leu Ala Gly Gly Val Ala Val Met Ser Thr Pro Asp
225                 230                 235                 240

Thr Phe Val Asp Phe Ser Arg Gln Arg Gly Leu Ala Ala Asp Gly Arg
                245                 250                 255

Cys Lys Ser Tyr Ser Asp Gly Ala Asp Gly Thr Ser Trp Ala Glu Gly
            260                 265                 270

Val Gly Met Leu Leu Val Glu Lys Leu Ser Asp Ala Arg Arg Leu Gly
        275                 280                 285

His Glu Val Leu Ala Val Val Ser Gly Ser Ala Val Asn Gln Asp Gly
    290                 295                 300

Ala Ser Ser Gly Leu Ser Val Pro Asn Gly Pro Ser Gln Gln Arg Val
305                 310                 315                 320

Ile Arg Gln Ala Leu Glu Asn Ala Arg Leu Ser Ala Gly Gln Ile Asp
                325                 330                 335

Val Val Glu Gly His Gly Thr Gly Thr Thr Leu Gly Asp Pro Ile Glu
            340                 345                 350

Ala Gln Ala Leu Leu Ala Thr Tyr Gly Arg Glu Lys Ser Ala Asp Arg
        355                 360                 365

Pro Leu Trp Leu Gly Ser Leu Lys Ser Asn Ile Gly His Ser Gln Ser
    370                 375                 380

Ala Ala Gly Val Gly Gly Val Ile Lys Met Val Gln Ala Ile Arg His
```

-continued

```
             385                 390                 395                 400
Gly Ile Leu Pro Arg Thr Leu His Ala Glu Asp Pro Ser Ser Lys Val
                 405                 410                 415
Asp Trp Ser Ala Gly Ala Val Glu Leu Leu Thr Glu Ala Arg Gly Trp
                 420                 425                 430
Pro Glu Thr Gly Gln Pro Arg Arg Ala Gly Val Ser Ser Phe Gly Val
                 435                 440                 445
Ser Gly Thr Asn Ala His Thr Ile Ile Glu Gln Ala Pro Glu Ser Glu
                 450                 455                 460
Glu Ser Pro Ala Val Pro Pro Thr Gly Ala Val Pro Ala Val Leu Ser
465                 470                 475                 480
Gly Lys Thr Ala Glu Ala Leu Arg Asp Gln Val Val Arg Leu Arg Ser
                 485                 490                 495
His Ile Leu Ala Arg Pro Glu Leu Ser Val Ala Asp Val Ala Ala Ser
                 500                 505                 510
Leu Ala Thr Thr Arg Val Leu His Glu His Arg Gly Ala Ile Val Ala
                 515                 520                 525
Ala Asp Arg Asp Gln Leu Leu Ala Gly Leu Asp Ile Leu Ala Ala Gly
                 530                 535                 540
Ala Thr Thr Ala Gly Val Ser Gln Gly Val Ala Thr Asp Gly Arg Thr
545                 550                 555                 560
Ala Phe Leu Phe Thr Gly Gln Gly Ser Gln Arg Arg Gly Met Gly Arg
                 565                 570                 575
Glu Leu Ala Glu Arg Phe Pro Val Phe Ala Glu Ala Phe Asp Asp Val
                 580                 585                 590
Cys Ala Arg Phe Glu Arg Pro Ile Lys Glu Leu Ser Thr Glu Glu Leu
                 595                 600                 605
Asn Gln Thr Ala Asn Thr Gln Cys Ala Leu Phe Ala Phe Glu Val Ala
                 610                 615                 620
Leu Phe Arg Leu Val Glu Ser Trp Gly Val Arg Pro Asp Phe Leu Ala
625                 630                 635                 640
Gly His Ser Ile Gly Glu Ile Ala Ala Ala His Val Ala Gly Val Phe
                 645                 650                 655
Asn Leu Asp Asp Ala Val Lys Leu Val Ala Ala Arg Gly Arg Leu Met
                 660                 665                 670
Gln Ala Leu Pro Thr Gly Gly Ala Met Val Ala Leu Gln Ala Thr Glu
                 675                 680                 685
Ala Glu Val Phe Pro Leu Leu Thr Asp Arg Val Ser Leu Ala Ala Ile
                 690                 695                 700
Asn Gly Pro Glu Ser Val Val Leu Ser Gly Asp Glu Asp Ala Val Ala
705                 710                 715                 720
Ala Val Val Ser Arg Phe Glu Gly Arg Lys His Lys Arg Leu Ala Val
                 725                 730                 735
Ser His Ala Phe His Ser Pro Leu Met Glu Pro Met Leu Asp Asp Phe
                 740                 745                 750
Arg Ala Val Ala Asp Ser Leu Ser Tyr Ala Ala Pro Arg Ile Pro Ile
                 755                 760                 765
Val Ser Gly Gly Leu Ala Asp Val Ser Thr Ser Asp Tyr Trp Val Arg
                 770                 775                 780
His Val Arg Asp Ala Val Arg Phe His Asp Ser Val Lys Phe Leu Glu
785                 790                 795                 800
Thr Glu Gly Val Thr Arg Phe Leu Glu Ile Gly Pro Asp Ala Val Leu
                 805                 810                 815
```

-continued

Thr Ala Met Ala Gln Glu Ser Thr Glu Gly Ala Val Val Ala Ala
        820                 825                 830

Ser Arg Arg Asn Arg Ala Glu Asp Val Thr Leu Leu Ala Ala Val Ser
            835                 840                 845

Thr Leu His Val His Gly Ala Ser Val Asp Trp Thr Pro Leu Leu Ala
        850                 855                 860

Gly Ala Arg Arg Val Asp Leu Pro Thr Tyr Ala Phe Gln His Arg Arg
865                 870                 875                 880

Phe Trp Leu Asp Gly Pro Leu Asn Ala Glu Gly Asp Ala Ala Ser Leu
                885                 890                 895

Gly Leu Gly Ala Thr Asp His Pro Leu Leu Gly Ala Val Val Thr Met
            900                 905                 910

Ala Asp Ala His Gly Val Leu Leu Thr Gly Arg Leu Ser Leu Ala Ala
        915                 920                 925

Gln Pro Trp Leu Ala Gly His Val Val Ala Gly His Val Leu Leu Pro
    930                 935                 940

Gly Thr Ala Phe Val Asp Leu Val Leu His Ala Gly Asp Lys Val Asp
945                 950                 955                 960

Cys Gly Ile Val Glu Glu Leu Thr Leu Arg Glu Pro Leu Val Leu Pro
                965                 970                 975

Glu His Asp Ala Leu Ser Leu Gln Leu Val Val Gly Ala Pro Asp Glu
            980                 985                 990

Thr Gly Arg Arg Thr Val Gly Val His Ser Arg Pro Glu Ala Ala Asp
        995                 1000                1005

Ala Glu Trp Ser Cys His Ala Thr Gly Val Leu Ala Pro Gly Phe
    1010                1015                1020

Pro Asp Thr Asp Phe Ser Leu Ala Ala Trp Pro Pro Glu Gly Ala
    1025                1030                1035

Ala Pro Val Ala Ile Asp Gly Leu Tyr Gly Ala Leu Ala Glu Val
    1040                1045                1050

Gly Leu Asp Tyr Gly Pro Ala Phe Gln Cys Val Arg Ala Ala Trp
    1055                1060                1065

Thr His Asp Ser Ala Val Tyr Ala Glu Ile Glu Leu Ala Asp Ala
    1070                1075                1080

Glu Lys Ala Asp Ala Ala Arg Phe Gly Ile His Pro Ala Leu Leu
    1085                1090                1095

Asp Ser Ala Leu His Ala Ala Gly Leu Gly Ala Leu Asp Ala Thr
    1100                1105                1110

Glu Ala Arg Leu Pro Phe Ser Trp Ser Gly Val Ser Leu Arg Ala
    1115                1120                1125

Phe Gly Ala Thr Thr Ile Arg Val Arg Leu Thr Pro Ala Gly Pro
    1130                1135                1140

Asp Thr Ile Ala Leu Ala Val Ala Asp Pro Glu Gly Arg Pro Val
    1145                1150                1155

Phe Ala Ala Asp Gly Leu Leu Val Arg Ala Val Pro Ser Gly Ala
    1160                1165                1170

Leu Thr Ser Arg Asn Pro Val Arg Asp Gly Leu Phe Arg Val Asp
    1175                1180                1185

Trp Gln Pro Leu Thr Ile Pro Ala Glu Ala Ala Ala Glu Tyr Val
    1190                1195                1200

Val Ala Ser Phe Thr Gly Tyr Thr Gly Asp Leu Leu Gly Asp Ala
    1205                1210                1215

-continued

| | | | | | | | | | |
|---|---|---|---|---|---|---|---|---|---|
| His | Ala | Ala | Ala | Val | Arg | Ala | Leu | Glu | Leu | Val | His | Ala | Asp | Ser |
| 1220 | | | | 1225 | | | | 1230 | |
| Gly | Gly | Pro | Lys | Leu | Val | Phe | Leu | Thr | Ser | Gly | Ala | Val | Gly | Asp |
| 1235 | | | | 1240 | | | | 1245 | |
| Ala | Val | Pro | Arg | Pro | Ala | Gln | Ala | Thr | Val | Trp | Gly | Leu | Val | Arg |
| 1250 | | | | 1255 | | | | 1260 | |
| Thr | Ala | Gln | Glu | Glu | Phe | Pro | Asp | Arg | Phe | Val | Leu | Leu | Asp | Ala |
| 1265 | | | | 1270 | | | | 1275 | |
| Asp | Thr | Glu | Pro | Thr | Pro | Glu | Phe | Ile | Ala | Ala | Ala | Val | Ala | Thr |
| 1280 | | | | 1285 | | | | 1290 | |
| Gly | Glu | Pro | Glu | Leu | Leu | Leu | Arg | Glu | Gly | Val | Leu | Ser | Gly | Ala |
| 1295 | | | | 1300 | | | | 1305 | |
| Arg | Leu | Val | Arg | Ala | Pro | Arg | Ala | Ser | Ala | Glu | Pro | Gly | Asp | Ile |
| 1310 | | | | 1315 | | | | 1320 | |
| Asp | Gly | Thr | Val | Leu | Val | Thr | Gly | Gly | Thr | Gly | Ala | Leu | Gly | Ala |
| 1325 | | | | 1330 | | | | 1335 | |
| Asp | Leu | Ala | Arg | His | Leu | Val | Arg | Ser | Arg | Gly | Val | Arg | Arg | Leu |
| 1340 | | | | 1345 | | | | 1350 | |
| Leu | Leu | Thr | Ser | Arg | Arg | Gly | Ala | Ala | Pro | Gly | Ala | Asp | Thr |
| 1355 | | | | 1360 | | | | 1365 | |
| Leu | Thr | Arg | Glu | Leu | Thr | Ala | Leu | Gly | Ala | Glu | Val | Arg | Ile | Glu |
| 1370 | | | | 1375 | | | | 1380 | |
| Ala | Cys | Asp | Ala | Ala | Asp | Arg | Asp | Ala | Leu | Ala | Ala | Leu | Leu | Ala |
| 1385 | | | | 1390 | | | | 1395 | |
| Asp | Gln | Pro | Ile | Thr | Leu | Ala | Val | His | Ala | Ala | Gly | Val | Leu | Asp |
| 1400 | | | | 1405 | | | | 1410 | |
| Asp | Gly | Leu | Ile | Gly | Asp | Leu | Ser | Ala | Glu | Arg | Leu | Thr | Ala | Val |
| 1415 | | | | 1420 | | | | 1425 | |
| Leu | Arg | Ser | Lys | Val | Asp | Ala | Ala | Val | His | Leu | His | Glu | Leu | Leu |
| 1430 | | | | 1435 | | | | 1440 | |
| Gly | Asp | Thr | Glu | Leu | Val | Leu | Phe | Ser | Ser | Ala | Ala | Gly | Val | Phe |
| 1445 | | | | 1450 | | | | 1455 | |
| Gly | Asn | Glu | Gly | Gln | Ala | Asn | Tyr | Ala | Ala | Ala | Asn | Ala | Phe | Leu |
| 1460 | | | | 1465 | | | | 1470 | |
| Asp | Ala | Leu | Ala | Arg | His | Arg | Gln | Ala | Asn | Gly | Leu | Pro | Gly | Thr |
| 1475 | | | | 1480 | | | | 1485 | |
| Ala | Leu | Ala | Trp | Gly | Met | Trp | Ala | Ser | Gly | Met | Gly | Asp | Ala | Leu |
| 1490 | | | | 1495 | | | | 1500 | |
| Thr | Ala | Arg | Pro | Gly | Phe | Pro | Ala | Leu | Ser | Thr | Glu | Asp | Gly | Met |
| 1505 | | | | 1510 | | | | 1515 | |
| Ala | Leu | Phe | Asp | Ala | Ala | Thr | Ala | Leu | Asp | Asp | Ala | Ala | Leu | Val |
| 1520 | | | | 1525 | | | | 1530 | |
| Pro | Ile | Arg | Leu | Asp | Leu | Pro | Ala | Leu | Arg | Ala | Arg | Leu | Gly | Gly |
| 1535 | | | | 1540 | | | | 1545 | |
| Asp | Val | Pro | Pro | Leu | Phe | Arg | Gly | Leu | Ile | Arg | Pro | Thr | Arg | Arg |
| 1550 | | | | 1555 | | | | 1560 | |
| Ala | Ala | Val | Thr | Gly | Ser | Ala | Gly | Ala | Leu | Ala | Asp | Arg | Leu | Ala |
| 1565 | | | | 1570 | | | | 1575 | |
| Ala | Leu | Ala | Pro | Ala | Glu | Arg | Ser | Arg | Glu | Leu | Leu | Glu | Ile | Val |
| 1580 | | | | 1585 | | | | 1590 | |
| Arg | Thr | His | Val | Ala | Ile | Val | Leu | Gly | His | Leu | Gly | Ser | Glu | Ala |
| 1595 | | | | 1600 | | | | 1605 | |
| Ile | Asp | Ala | Gly | Lys | Pro | Phe | Gln | Glu | Leu | Gly | Phe | Asp | Ser | Leu |

-continued

|  | 1610 |  |  |  | 1615 |  |  |  | 1620 |  |  |
|---|---|---|---|---|---|---|---|---|---|---|---|
| Ala | Ala | Val | Glu | Leu | Arg | Asn | Arg | Leu | Thr | Glu | Val | Thr | Gly | Leu |
|  | 1625 |  |  |  | 1630 |  |  |  | 1635 |  |  |

Ala Ala Val Glu Leu Arg Asn Arg Leu Thr Glu Val Thr Gly Leu
                    1625                1630                1635

Arg Leu Ala Ala Thr Leu Val Phe Asp Tyr Pro Thr Pro Leu Val
        1640                1645                1650

Leu Ala Glu His Leu Leu Glu Gly Leu Ala Gly Gly Gly Leu Ala
        1655                1660                1665

Glu Thr Pro Asp Ala Pro Val Arg Thr Gly Pro Val Asp Glu Pro
        1670                1675                1680

Ile Ala Ile Ile Gly Met Ala Cys Arg Tyr Pro Gly Gly Val Thr
        1685                1690                1695

Ser Pro Glu Glu Leu Trp Asp Leu Val Ala Ala Gly Arg Asp Gly
        1700                1705                1710

Val Ser Glu Phe Pro Val Asn Arg Gly Trp Glu Asp Val Tyr Asp
        1715                1720                1725

Ala Asp Pro Gly Lys Val Gly Lys Ser Tyr Ala Arg Glu Gly Gly
        1730                1735                1740

Phe Leu His Asp Ala Gly Glu Phe Asp Ala Ala Phe Phe Gly Ile
        1745                1750                1755

Ser Pro Arg Glu Ala Leu Ala Met Asp Pro Gln Gln Arg Leu Leu
        1760                1765                1770

Leu Glu Thr Ser Trp Glu Val Phe Glu Arg Ala Gly Ile Asp Pro
        1775                1780                1785

His Ala Val Arg Gly Ser Lys Thr Gly Val Phe Ala Gly Val Met
        1790                1795                1800

Tyr His Asp Tyr Ala Ala Arg Leu Asn Ser Val Pro Glu Asp Val
        1805                1810                1815

Glu Gly Tyr Leu Gly Thr Gly Asn Ser Gly Ser Val Ile Ser Gly
        1820                1825                1830

Arg Leu Ala Tyr Thr Phe Gly Leu Glu Gly Pro Ala Val Ser Ile
        1835                1840                1845

Asp Thr Ala Cys Ser Ser Ser Leu Val Ala Met His Leu Ala Gly
        1850                1855                1860

Gln Ala Leu Arg Gln Gly Glu Cys Ser Leu Ala Val Ala Gly Gly
        1865                1870                1875

Val Thr Val Met Ala Thr Pro Asn Thr Phe Ile Glu Phe Ser Arg
        1880                1885                1890

Gln Arg Gly Met Ala Thr Asp Gly Arg Cys Lys Ser Phe Ala Glu
        1895                1900                1905

Ala Ala Asp Gly Thr Gly Trp Gly Glu Gly Val Gly Met Leu Leu
        1910                1915                1920

Leu Glu Arg Leu Ser Asp Ala Arg Arg Asn Gly His Arg Val Leu
        1925                1930                1935

Ala Val Val Arg Gly Ser Ala Val Asn Gln Asp Gly Ala Ser Asn
        1940                1945                1950

Gly Leu Thr Ala Pro Asn Gly Pro Ser Gln Gln Arg Val Ile Arg
        1955                1960                1965

Gln Ala Leu Ala Gln Ala Gly Leu Arg Pro Ser Asp Val Asp Ala
        1970                1975                1980

Val Glu Ala His Gly Thr Gly Thr Thr Leu Gly Asp Pro Ile Glu
        1985                1990                1995

Ala Gln Ala Leu Leu Ala Thr Tyr Gly Gln Asp Arg Glu Glu Pro
        2000                2005                2010

-continued

```
Leu Trp Leu Gly Ser Val Lys Ser Asn Leu Gly His Thr Gln Ala
    2015                2020                2025

Ala Ala Gly Val Ala Gly Val Ile Lys Met Val Glu Ala Met Arg
    2030                2035                2040

His Gly Val Leu Pro Arg Thr Leu His Val Asp Glu Pro Ser Ser
    2045                2050                2055

His Val Asp Trp Thr Gly Gly Ala Val Ser Leu Val Thr Glu Ser
    2060                2065                2070

Arg Glu Trp Pro Asp Thr Gly Arg Pro Arg Arg Ala Gly Val Ser
    2075                2080                2085

Ser Phe Gly Ile Ser Gly Thr Asn Ala His Thr Ile Ile Glu Ala
    2090                2095                2100

Val Glu Pro Glu Ala Ala Glu Pro Ser Gly Asn Pro Asp Val Pro
    2105                2110                2115

Pro Trp Pro Leu Ser Gly Lys Thr Glu Glu Ala Leu Arg Ala Gln
    2120                2125                2130

Ala Ser Arg Leu His Asp His Leu Leu Ala Thr Pro Glu Val Thr
    2135                2140                2145

Ala Ala Asp Val Ala Leu Ser Leu Thr Ala Arg Ala Asp Leu Glu
    2150                2155                2160

His Arg Ala Val Leu Val Ala Gly Asp Arg Asp Gly Leu Leu Ala
    2165                2170                2175

Thr Leu Asp Ala Leu Ala His Gly Glu Thr Thr Glu Gly Ile Val
    2180                2185                2190

Arg Gly Thr Ala Arg His Thr Gly Arg Thr Ala Phe Leu Phe Thr
    2195                2200                2205

Gly Gln Gly Ser Gln Arg Leu Gly Met Gly Arg Glu Leu Ala Glu
    2210                2215                2220

Arg Phe Pro Val Phe Ala Glu Val Tyr Asp Glu Val Cys Ser Arg
    2225                2230                2235

Phe Glu Gln Pro Leu Arg Asp Leu Ser Ala Glu Leu Asn Gln
    2240                2245                2250

Thr Ala Asn Thr Gln Cys Ala Leu Phe Ala Leu Glu Val Ala Leu
    2255                2260                2265

Phe Arg Leu Val Glu Ser Trp Gly Val Arg Pro Asp Phe Leu Ala
    2270                2275                2280

Gly His Ser Val Gly Glu Ile Ala Ala Ala His Val Ala Gly Val
    2285                2290                2295

Leu Ser Leu Asp Asp Ala Val Thr Leu Val Ser Ala Arg Gly Arg
    2300                2305                2310

Leu Met Gln Ala Leu Pro Thr Gly Gly Ala Met Val Ala Leu Arg
    2315                2320                2325

Ala Thr Glu Ala Glu Val Thr Pro Leu Leu Thr Glu Arg Val Ser
    2330                2335                2340

Ile Ala Ala Ile Asn Gly Pro Glu Ser Val Val Ser Gly Asp
    2345                2350                2355

Glu Asp Ala Val Ala Ala Val Val Glu Gly Arg Lys His Lys Arg
    2360                2365                2370

Leu Thr Val Ser His Ala Phe His Ser Pro Leu Met Glu Pro Met
    2375                2380                2385

Leu Asp Glu Phe Arg Thr Val Val Glu Gly Leu Thr Phe Ala Ala
    2390                2395                2400
```

-continued

```
Pro Arg Ile Pro Ile Val Ser Gly Gly Leu Ala Glu Val Ser Thr
2405                2410                2415

Ser Asp Tyr Trp Val Arg His Val Arg Asp Ala Val Arg Phe His
2420                2425                2430

Asp Ser Val Lys Phe Leu Glu Ala Glu Gly Val Thr Arg Phe Leu
2435                2440                2445

Glu Ile Gly Pro Asp Gly Val Leu Thr Ala Met Ala Gln Asp Ser
2450                2455                2460

Leu Glu Asp Ala Val Val Val Pro Ala Leu Arg Arg Asp Lys Pro
2465                2470                2475

Glu Val Thr Thr Leu Leu Thr Ala Val Ala Gly Leu His Val His
2480                2485                2490

Gly Ala Gly Val Asp Trp Ser Pro Leu Ser Ala Gly Ala Arg Arg
2495                2500                2505

Val Asp Leu Pro Thr Tyr Ala Phe Gln Arg Thr Glu Phe Trp Leu
2510                2515                2520

Asp Ala Gly Ala Ala Ala Gly Asp Leu Thr Ala Ala Gly Leu Ser
2525                2530                2535

Asp Ala Gly His Pro Leu Leu Gly Gly Ala Val Thr Leu Pro Asp
2540                2545                2550

Ser Gly Gly Thr Val Phe Thr Gly Arg Leu Ser Leu Ala Ala Gln
2555                2560                2565

Pro Trp Leu Ala Asp His Ala Val Gly Glu Thr Val Leu Leu Pro
2570                2575                2580

Gly Thr Ala Phe Val Asp Leu Ala Leu Ala Ala Gly Arg Arg His
2585                2590                2595

Gly Arg Val Val Leu Asp Glu Leu Thr Leu Glu Ser Pro Leu Val
2600                2605                2610

Leu Pro Glu His Gly Gly Val Asp Leu Arg Val Trp Val Arg Glu
2615                2620                2625

Pro Asp Asp Thr Gly Ala Cys Ala Val Ser Val His Ser Arg Ala
2630                2635                2640

Asp Asp Glu Pro Trp Ile Arg His Ala Val Gly Thr Leu Thr Glu
2645                2650                2655

Asp Thr Gly Ala Thr Pro Ala Asp Leu Thr Ser Trp Pro Pro Ala
2660                2665                2670

Ala Glu Glu Thr Asp Val Asp Gly Leu Tyr Asp Ala Leu Ala Asp
2675                2680                2685

Ala Gly Leu Asn Tyr Gly Pro Val Phe Gln Gly Val Arg Ala Ala
2690                2695                2700

Trp Leu Asp Gly Thr Thr Val Tyr Ala Glu Ile Asp Leu Asp Glu
2705                2710                2715

Arg His His Gly Asp Ala Ala Arg Phe Gly Leu His Pro Ala Leu
2720                2725                2730

Leu Asp Ala Ala Leu His Thr Ala Gly Leu Gly Ala Leu Ser Thr
2735                2740                2745

Glu Gly Gly Ala Arg Leu Pro Phe Leu Trp Ser Gly Val Ser Leu
2750                2755                2760

Thr Gly Leu Gly Ala Thr Ser Leu Arg Val Arg Leu Thr Gly Ser
2765                2770                2775

Gly Asp Thr Leu Ser Leu Ala Ile Ala Asp Gly Thr Gly Ala Pro
2780                2785                2790

Val Ala Thr Val Ala Gly Leu Thr Val Arg Gln Val Asp Pro Ala
```

-continued

```
            2795                2800                2805
Ala Phe Gly Gly Gly Asp Ser Leu Phe Arg Val Glu Trp Val
    2810                2815                2820
Pro Val Arg Ala Arg Ala Ala Asp Thr Ala Pro Ala Val Arg Ser
    2825                2830                2835
Glu Val Asp Ser Leu Val Asn Val Arg Glu Ala Thr Ala Gln Thr
    2840                2845                2850
Leu Ala Ala Leu Gln Ser Trp Leu Ala Asp Glu Ser Asn Ala Asp
    2855                2860                2865
Thr Pro Leu Val Val Leu Thr Ser Gly Ala Val Ser Val Ala Gly
    2870                2875                2880
Glu Asp Thr Arg Asp Leu Ala Arg Ala Ala Val Trp Gly Leu Val
    2885                2890                2895
Arg Ser Ala Gln Ser Glu His Pro Gly Arg Phe Val Leu Ile Asp
    2900                2905                2910
Thr Asp Thr Glu Pro Ala Asp Leu Ala Gly Ala Val Ala Thr Gly
    2915                2920                2925
Glu Ala Gln Leu Ala Ile Arg Asp Gly Lys Leu Trp Ala Pro Arg
    2930                2935                2940
Leu Val Lys Ser Ala Pro Ser Ser Ala Thr Pro Arg Phe Asp Pro
    2945                2950                2955
Glu Gly Thr Val Leu Leu Thr Gly Ala Thr Gly Ala Leu Gly Arg
    2960                2965                2970
Ser Leu Ala Ser His Leu Val Ser Gly His Gly Val Arg His Leu
    2975                2980                2985
Leu Leu Val Ser Arg Ser Gly Ala Ala Ala His Gly Ala Lys Asp
    2990                2995                3000
Leu Leu Ala Glu Leu Thr Gly Leu Gly Ala Ser Val Val Leu Glu
    3005                3010                3015
Ser Cys Asp Val Ala Asp Arg Glu Ala Leu Ala Gly Leu Leu Ala
    3020                3025                3030
Gly Ile Asp Pro Gly His Pro Leu Thr Gly Val Val His Ala Ala
    3035                3040                3045
Gly Val Leu Asp Asp Gly Leu Ile Asp Ser Leu Thr Pro Glu Arg
    3050                3055                3060
Phe Asp Ala Val Leu Arg Pro Lys Ala Asp Ala Ala Leu Asn Leu
    3065                3070                3075
His Glu Leu Ala Gly Asp Val Asp Glu Phe Val Leu Phe Ser Ser
    3080                3085                3090
Ala Ala Gly Thr Phe Gly Asn Ala Gly Gln Ala Asn Tyr Ala Ala
    3095                3100                3105
Ala Asn Ala Phe Leu Asp Ala Leu Ala Gln His Arg Gln Ala Asn
    3110                3115                3120
Gly Leu Pro Ala Arg Ser Leu Ala Trp Gly Leu Trp Asp Thr Asp
    3125                3130                3135
Asp Gly Met Asp Ala Ser Ala Ala Val Ala Arg Leu Thr Gly Ser
    3140                3145                3150
Gly Leu Thr Thr Glu Glu Gly Leu His Leu Phe Asp Thr Ala Gly
    3155                3160                3165
Asp Gly Val Val Leu Pro Met Lys Leu Asp Leu Ala Ala Leu Arg
    3170                3175                3180
Ala Glu Leu Gly Ser Asp Val Pro Ser Leu Leu Arg Gly Leu Ile
    3185                3190                3195
```

```
Lys Ala Pro Ala Arg Arg Ser Ala Gly Ala Ser Ala Trp Lys Arg
3200            3205                3210

Gln Leu Ala Gly Leu Ser Glu Glu Asp Arg Asp Ala Arg Leu Leu
3215            3220                3225

Glu Leu Val Arg Ala Gln Val Ala Ala Val Leu Gly Tyr Ser Gly
3230            3235                3240

Pro Glu Asp Val Pro Ser Asp Arg Ala Phe Thr Glu Leu Gly Phe
3245            3250                3255

Asp Ser Leu Thr Ser Val Asp Leu Arg Asn Arg Leu Asn Ser Ala
3260            3265                3270

Thr Gly Leu Arg Leu Pro Ala Thr Leu Val Phe Asp His Pro Asn
3275            3280                3285

Ser Asp Ala Val Val Ala Arg Leu Arg Glu Glu Leu Ser Gly Thr
3290            3295                3300

Val Val Ala Ala Ala Val Val Thr Thr Ala Pro Val Asp Glu Pro
3305            3310                3315

Ile Ala Ile Val Gly Met Ala Cys Arg Phe Pro Gly Gly Val Arg
3320            3325                3330

Ser Pro Glu Asp Leu Trp Arg Leu Val Ser Glu Gly Arg Asp Gly
3335            3340                3345

Ile Thr Pro Phe Pro Ala Asp Arg Gly Trp Asp Val Glu Gly Leu
3350            3355                3360

Tyr Asp Pro Glu Ala Ser Arg Pro Gly Thr Ser Cys Thr Arg Tyr
3365            3370                3375

Gly Gly Phe Leu His Asp Ala Gly Asp Phe Asp Pro Gly Phe Phe
3380            3385                3390

Gly Ile Ser Pro Arg Glu Ala Leu Ala Met Asp Pro Gln Gln Arg
3395            3400                3405

Leu Leu Leu Glu Thr Ser Trp Glu Ala Phe Glu Arg Ala Gly Ile
3410            3415                3420

Asp Pro Ala Thr Leu Arg Gly Ser Ala Thr Gly Val Phe Ala Gly
3425            3430                3435

Ala Met Tyr His Asp Tyr Val Ser Arg Leu Thr Glu Ile Pro Ala
3440            3445                3450

Asp Leu Glu Gly Tyr Leu Gly Thr Gly Asn Ser Gly Ser Val Ile
3455            3460                3465

Ser Gly Arg Leu Ala Tyr Ala Phe Gly Leu Glu Gly Pro Ala Val
3470            3475                3480

Ser Ile Asp Thr Ala Cys Ser Ser Ser Leu Val Ala Met His Leu
3485            3490                3495

Ala Ala Gln Ala Leu Arg Gln Gly Glu Cys Gly Leu Ala Leu Ala
3500            3505                3510

Gly Gly Val Ala Val Met Ser Thr Pro Asp Thr Phe Ile Glu Phe
3515            3520                3525

Ser Arg Gln Arg Gly Met Ala Pro Asp Gly Arg Ile Lys Ala Phe
3530            3535                3540

Ser Glu Thr Ala Asp Gly Thr Ala Trp Gly Glu Gly Val Gly Met
3545            3550                3555

Leu Leu Leu Glu Arg Leu Ser Asp Ala Arg Arg Asn Gly His Arg
3560            3565                3570

Val Leu Ala Val Leu Arg Gly Thr Ala Val Asn Gln Asp Gly Ala
3575            3580                3585
```

-continued

| | | | | | | | | | | |
|---|---|---|---|---|---|---|---|---|---|---|
| Ser | Asn | Gly | Leu | Thr | Ala | Pro | Asn | Gly | Pro | Ser | Gln | Gln | Arg | Val |
| | 3590 | | | | 3595 | | | | 3600 | |

Ser Asn Gly Leu Thr Ala Pro Asn Gly Pro Ser Gln Gln Arg Val
　　　3590　　　　　　　3595　　　　　　　3600

Ile Arg Gln Ala Leu Ala Gln Ala Gly Leu Arg Pro Ser Asp Val
3605　　　　　　　3610　　　　　　　3615

Asp Ala Val Glu Ala His Gly Thr Gly Thr Thr Leu Gly Asp Pro
3620　　　　　　　3625　　　　　　　3630

Ile Glu Ala Gln Ala Leu Leu Ala Thr Tyr Gly Gln Asp Arg Glu
3635　　　　　　　3640　　　　　　　3645

Glu Pro Leu Trp Leu Gly Ser Val Lys Ser Asn Leu Gly His Thr
3650　　　　　　　3655　　　　　　　3660

Gln Ala Ala Gly Val Ala Ser Val Ile Lys Met Val Glu Ala
3665　　　　　　　3670　　　　　　　3675

Met Arg His Gly Val Leu Pro Arg Thr Leu His Val Asp Glu Pro
3680　　　　　　　3685　　　　　　　3690

Ser Ser His Val Asp Trp Thr Glu Gly Ala Val Ser Leu Leu Thr
3695　　　　　　　3700　　　　　　　3705

Glu Thr Arg Asp Trp Pro Asp Thr Gly Arg Pro Arg Arg Ala Gly
3710　　　　　　　3715　　　　　　　3720

Val Ser Ser Phe Gly Ile Ser Gly Thr Asn Ala His Val Val Leu
3725　　　　　　　3730　　　　　　　3735

Glu Ala Asp Gly Ala Gly Asp Ala Ala Pro Pro Gly Gln Pro Asp
3740　　　　　　　3745　　　　　　　3750

Val Leu Ala Phe Pro Leu Ser Ala Lys Thr Gln Asp Ala Leu Arg
3755　　　　　　　3760　　　　　　　3765

Glu Gln Ala Ala Arg Leu Arg Ala Arg Leu Leu Thr Gly His Ala
3770　　　　　　　3775　　　　　　　3780

Pro Glu Leu Ala Asp Val Ala Gln Thr Leu Ala Thr Arg Gly Leu
3785　　　　　　　3790　　　　　　　3795

Phe Glu His Arg Ala Val Val Thr Ala Gly Asp Arg Asp Gly Leu
3800　　　　　　　3805　　　　　　　3810

Leu Asp Ala Leu Ala Ala Leu Ala Gly Gly Glu Pro Gly Asp Phe
3815　　　　　　　3820　　　　　　　3825

Val Thr Gly Leu Ala Lys Pro Gly Gly Lys Leu Ala Phe Leu Phe
3830　　　　　　　3835　　　　　　　3840

Thr Gly Gln Gly Ser Gln Arg Ala Gly Met Ala Asp Glu Leu Ser
3845　　　　　　　3850　　　　　　　3855

Ala Ala Phe Pro Val Phe Ala Arg Thr Phe Gly Glu Ile Cys Ala
3860　　　　　　　3865　　　　　　　3870

Arg Phe Asp Thr Leu Leu Asp Arg Pro Leu Arg Glu Ala Leu Ala
3875　　　　　　　3880　　　　　　　3885

Gly Asp Leu Val Asp Arg Thr Glu Tyr Thr Gln Cys Ala Met Phe
3890　　　　　　　3895　　　　　　　3900

Ala Val Glu Val Ala Leu Phe Arg Leu Val Glu Ser Arg Gly Val
3905　　　　　　　3910　　　　　　　3915

Arg Pro Asp Phe Leu Ala Gly His Ser Ile Gly Glu Leu Ala Ala
3920　　　　　　　3925　　　　　　　3930

Ala His Val Ala Gly Val Trp Ser Leu Glu Asp Ala Cys Thr Val
3935　　　　　　　3940　　　　　　　3945

Val Ala Ala Arg Gly Arg Leu Met Gln Ala Leu Pro Ser Gly Gly
3950　　　　　　　3955　　　　　　　3960

Ala Met Ile Ala Val Gln Ala Thr Glu Glu Glu Val Arg Pro Leu
3965　　　　　　　3970　　　　　　　3975

Ile Asp Asp Glu Thr Val Ser Ile Ala Ala Ile Asn Gly Pro Val

-continued

```
              3980              3985              3990
Ser Val Val Val Ser Gly Glu  Glu Ala Ala Val Thr  Ala Leu Ala
    3995              4000              4005

Ala Gly Phe Ala Glu Arg Gly  Arg Lys Thr Lys Arg  Leu Thr Val
    4010              4015              4020

Ser His Ala Phe His Ser Pro  Leu Met Asp Gly Met  Leu Gly Glu
    4025              4030              4035

Phe Arg Ala Val Leu Asp Gly  Ile Ala Ala Asp Pro  Arg Ile
    4040              4045              4050

Pro Leu Val Ser Thr Leu Thr  Gly Asp Pro Leu Thr  Gly Asp Gln
    4055              4060              4065

Ala Arg Ser Ser Glu Tyr Trp  Val Arg His Val Arg  Asp Ala Val
    4070              4075              4080

Arg Phe Cys Asp Ala Ile Arg  Thr Leu Glu Ala Gln  Gly Val Arg
    4085              4090              4095

Arg Tyr Leu Glu Leu Gly Pro  Asp Ala Pro Leu Thr  Ala Leu Gly
    4100              4105              4110

Glu His Cys Val Thr Asn Glu  Ser Thr Val Asp Ala  Gln Leu Phe
    4115              4120              4125

Val Pro Ser Leu Arg Ala Gly  Arg Ser Asp Val Glu  Ser Phe Val
    4130              4135              4140

Thr Ala Leu Ala Arg Leu His  Val Asp Gly Val Arg  Val Asp Trp
    4145              4150              4155

Ala Lys Ala Leu Pro Gly Arg  Lys Ile Asp Leu Pro  Thr Tyr Ala
    4160              4165              4170

Phe Gln His Glu Arg Phe Trp  Leu Arg Pro Ala Ala  Pro Ala Val
    4175              4180              4185

Gly Asp Val Thr Gly Leu Gly  Gln Ser Pro Ala Gly  His Pro Leu
    4190              4195              4200

Leu Gly Ala Ala Val Glu Ala  Pro Asp Ser Gly Ala  Val Leu Phe
    4205              4210              4215

Thr Gly Arg Leu Ser Val Gln  Glu Gln Pro Trp Leu  Ala Asp His
    4220              4225              4230

Val Val Ala Gly Thr Thr Leu  Leu Pro Gly Thr Ala  Phe Val Glu
    4235              4240              4245

Leu Ala Leu Arg Ala Gly Glu  Leu Thr Gly Cys Ala  Ala Val Asp
    4250              4255              4260

Glu Leu Thr Leu Glu Ala Pro  Leu Val Leu Pro Asp  His Gly Gly
    4265              4270              4275

Thr Ala Leu Arg Ile Val Ala  Ala Ala Pro Asp Glu  Thr Gly Arg
    4280              4285              4290

Arg Ala Leu Asp Val Tyr Ser  Arg Pro Asp Asp Gly  Asp Trp Ile
    4295              4300              4305

Arg His Ala Thr Gly Thr Val  Ser Pro Leu Ala Ala  Gly Ala Pro
    4310              4315              4320

Phe Asp Leu Ser Ala Trp Ala  Ala Ala Asp Ala Glu  Thr Val Glu
    4325              4330              4335

Thr Asp Gly Leu Tyr Asp Gly  Leu Ala Ala Ala Gly  Leu Glu Tyr
    4340              4345              4350

Gly Pro Val Phe Gln Gly Leu  Arg Ser Ala Arg Arg  Arg Gly Asp
    4355              4360              4365

Asp Ile Trp Ala Glu Val Asp  Leu Pro Glu Asp Thr  Thr Thr Glu
    4370              4375              4380
```

-continued

```
Gly Phe Gly Leu His Pro Ala Leu Leu Asp Ala Ala Leu His Ala
    4385            4390            4395

Leu Gly Phe Ala Glu Gly Gly Glu Gln Glu Ala Asp Val Ala Ala
    4400            4405            4410

Gly Arg Val Arg Leu Pro Phe Ala Trp Ser Gly Val Arg Leu His
    4415            4420            4425

Ala Ser Gly Ala Arg Ala Leu Arg Val Arg Leu Ser Pro Ala Gly
    4430            4435            4440

Glu Asn Ala Val Ser Leu Ala Ala Ala Asp Glu Thr Gly Arg Leu
    4445            4450            4455

Val Ala Thr Val Asp Ala Leu Thr Leu Arg Pro Val Ser Leu Glu
    4460            4465            4470

Gln Leu Gly Gly Arg Gln Gly Ser His Glu Ser Leu Phe Gly Leu
    4475            4480            4485

Glu Trp Ala Pro Val Pro Leu Tyr Pro Thr Ala Ala Val Ala Ala
    4490            4495            4500

Ser Trp Ala Val Val Gly Val Asp Asp Tyr Lys Leu Asp Ala Ala
    4505            4510            4515

Leu Thr Ala Ala Gly Tyr Arg Gly Gln Ala Tyr Ala Asp Leu Ala
    4520            4525            4530

Ala Leu Ala Glu Ala Met Asp Arg Ala Pro Glu Leu Val Phe Val
    4535            4540            4545

Ser Cys Ala Pro Asp His Arg Gln Gly Leu Ala Ala Ala Ala His
    4550            4555            4560

Thr Ala Ala His Arg Ala Leu Glu Leu Val Arg Ala Trp Leu Ala
    4565            4570            4575

Glu Asp Arg Phe Ala Gly Ser Arg Leu Val Leu Val Thr Gly Gly
    4580            4585            4590

Ala Val Gly Glu Pro Ala Gln Ala Val Ile Trp Gly Leu Ile Arg
    4595            4600            4605

Ser Ala Gln Ser Glu His Pro Gly Arg Phe Val Leu Val Asp Leu
    4610            4615            4620

Asp Glu Gln Asp Ala Ser Tyr Arg Val Leu Leu Pro Ala Leu Ala
    4625            4630            4635

Ser Gly Glu Pro Gln Leu Glu Leu Arg Glu Gly Thr Val Lys Ala
    4640            4645            4650

Pro Arg Leu Val Lys Pro Ala Val Thr Ala Ala Glu Gly Lys Ala
    4655            4660            4665

Arg Thr Asp Gly Ala Val Leu Ile Thr Gly Gly Thr Gly Ala Leu
    4670            4675            4680

Gly Ala Ala Leu Ala Arg His Leu Val Thr Ala His Gly Lys Thr
    4685            4690            4695

Arg Leu Val Leu Ala Gly Arg Arg Gly Pro Asp Ala Pro Gly Ala
    4700            4705            4710

Gly Glu Leu Ala Asp Glu Leu Arg Gly Leu Gly Ala Glu Val Ala
    4715            4720            4725

Val Ile Ala Cys Asp Ala Ala Asp Arg Glu Ala Leu Arg Arg Leu
    4730            4735            4740

Leu Ala Glu His Pro Val Thr Gly Val Val His Ala Ala Gly Val
    4745            4750            4755

Leu Asp Asp Val Val Leu Asp Gly Leu Thr Pro Asp Arg Leu Asp
    4760            4765            4770
```

```
Ala Val Leu Arg Pro Lys Val Asp Ala Ala Val Asn Leu His Glu
    4775            4780                4785
Leu Ala Gly Asp Val Asp Glu Phe Val Leu Phe Ser Ser Ala Ala
    4790            4795                4800
Gly Thr Phe Gly Asn Pro Gly Gln Ala Asn Tyr Ala Ala Ala Asn
    4805            4810                4815
Ala Phe Leu Asp Ala Leu Ala Arg His Arg His Ala His Gly Leu
    4820            4825                4830
Pro Ala Thr Ser Leu Ala Trp Gly Leu Trp Ala Gly Asp Gly Met
    4835            4840                4845
Ala Gly Gly Met Ser Gly Arg Asp Leu Asp Arg Met Ser Ala Ser
    4850            4855                4860
Gly Ala Gly Ala Leu Ser Thr Glu Glu Gly Leu Ala Leu Phe Asp
    4865            4870                4875
Leu Ala Val Thr Ala Ala Glu Pro Val Leu Leu Pro Met Arg Leu
    4880            4885                4890
Asp Leu Ala Thr Val Arg Ala Gly Leu Gly Thr Asp Val Pro Pro
    4895            4900                4905
Leu Leu Arg Gly Leu Ile Arg Gly Thr Arg Lys Arg Ala Glu Thr
    4910            4915                4920
Ala Gly Ser Pro Thr Gly Asp Ala Leu Lys Ala Glu Leu Ala Gly
    4925            4930                4935
Met Thr Gly Glu Glu Arg Ala Ala Ala Leu Leu Asn Leu Val Ala
    4940            4945                4950
Thr His Val Ala Gly Val Leu Gly His Ala Gly Pro Glu Gln Val
    4955            4960                4965
Asp Pro Asp Lys Ala Phe Thr Glu Leu Gly Phe Asp Ser Leu Ala
    4970            4975                4980
Ala Val Glu Leu Arg Asn Arg Val Asn Glu Ala Thr Gly Leu Arg
    4985            4990                4995
Leu Pro Ala Thr Leu Val Phe Asp His Pro Thr Thr Thr Ala Val
    5000            5005                5010
Ala Glu Leu Val Gly Ala Glu Ile Val Val Glu Asp Ala Pro Pro
    5015            5020                5025
Pro Leu Gly Val Leu Ala Glu Leu Asp Arg Leu Glu Ala Ala Phe
    5030            5035                5040
Ala Gly Gly Ser Pro Asp Asp Ala Ile Arg Gly Lys Val Lys Asp
    5045            5050                5055
Arg Leu Arg Ala Leu Leu Ala Ala Cys Asp Pro Gly Glu Gly Thr
    5060            5065                5070
Glu Ser Val Ala Asp Arg Leu Glu Asp Ala Ser Asp Asp Glu Met
    5075            5080                5085
Phe Glu Phe Ile Gly Lys Glu Leu Gly Ile Ser
    5090            5095

<210> SEQ ID NO 46
<211> LENGTH: 15300
<212> TYPE: DNA
<213> ORGANISM: Amycolatopsis orientalis

<400> SEQUENCE: 46
gtggcgaacg aagacaagta cctcgactac ctcaagcgcg cgaccgccga cctgcgggag      60
acccggcgac ggctgaagga ggccgaggac cgcggccacg agccgatcgc catcatcggg     120
atggcctgcc ggttccccgg cggcgtgcgg tcgccggagg atctgtggga gctggtcgcc     180
```

-continued

```
gagggccgcg acgggatctc cgggttcccc gccgaccgcg gctgggacct gtccgcgctg    240
tacgacccga cggggagaa gcccggcacc tcgtactgcc gcgagggcgg tttcctggac     300
ggcgcgggcg aattcgaccc ggccttcttc gggatctcgc cgagggaagc gctcgccatg    360
gacccccagc agcggctgct gctggagatc tcctgggaga ccttcgagcg cgcgggcatc    420
gaccccggct ccctgcgggg cagccggacc ggggtgttcg ccggggtgat gtaccacgac    480
tacgtctccc ggctcgccgc catcccggag gaactcgagg gctacctcgg caccgggaac    540 tcggcagcg tcgtttccgg gcgggtcgcc tacacgttcg gctggaagg cccggcggtg     600 acgatcgaca ccgcttgctc gtcctcactc gtcgcgctgc atctcgcagc gcaggcgctg    660
cggcagggcg aatgctcgat ggcgctcgcc ggcggtgtcg cggtgatgtc cacaccggac    720
acgttcgtcg acttcagccg tcagcgcggg ctcgccgcgg acggccgctg caagtcctat    780
tcggacggag cggacggcac gtcgtgggcc gagggcgtcg ggatgctcct ggtggagaag    840
ctctccgacg cgcggcggct cggccacgaa gtgctcgcgg tcgtcagcgg cagcgcggtc    900
aaccaggacg gggcgagcag cgggctcagc gtgccgaacg gcccgtcaca gcagcgggtc    960
atccggcagg ccctggagaa cgcgcggctc tcggccggac agatcgacgt cgtggagggc   1020
cacggcaccg ggaccaccct gggcgacccg atcgaggcgc aggcgctgct cgccacctac   1080
ggccgggaga atccgcgga ccggccgttg tggctgggct cgctgaagtc gaacatcggg    1140
cactcccagt ccgccgccgg ggtcggcggc gtgatcaaga tggtgcaggc gatccggcac   1200
gggatcttgc cgcgtaccct gcacgcggag gacccgtcgt ccaaagtgga ctggtcggcc   1260
ggtgccgtcg aactgctcac cgaagcacgc gggtggccgg agaccgggca gccgcgccgc   1320
gcgggcgtgt cctcgttcgg cgtcagcggc accaacgcgc acaccatcat cgagcaagcc   1380
cccgagagcg aagagtcccc ggccgtgcca cccaccggcg ccgtgcccgc ggtgttgtct   1440
ggcaagaccg ccgaggcgct gcgcgaccag gtcgtgcggc tgcgctcgca catcctcgcc   1500
cggccggagc tgagcgtcgc cgacgtcgcc gcgtcgctcg ccaccacccg cgtcctgcac   1560
gagcaccggg gcgcgatcgt cgcggccgac cgcgaccagc tgctcgcggg gctggacatc   1620
ctcgccgccg gcgccacgac cgccggggtc tctcaaggtg tcgccaccga cggccggacg   1680
gcgttcctgt tcaccggcca gggcagccag cgccgcggga tggggcggga actggccgag   1740
cgtttcccgg tgttcgccga ggccttcgac gacgtctgtg cccggttcga acggccgatc   1800
aaggaactgt ccaccgagga actgaaccag acggcgaaca cgcagtgcgc gctcttcgcc   1860
ttcgaggtgg cgctgttccg gctggtcgaa agctggggcg tgcggcctga cttcctggcg   1920
gggcactcga tcgcgagat cgcggcagct catgtcgcag gtgtgttcaa cctcgatgac   1980
gccgtgaagc tggtcgcggc gcgaggccgg ttgatgcagg cgttgcccac cggcggcgcg   2040
atggtggcct tgcaggcgac ggaggccgag gtcttcccgt tgctgacgga ccgggtgtcg   2100
ctggccgcga tcaacggccc ggagtcggtg gtcctctccg gcgacgaaga cgccgtcgcc   2160
gctgtggtgt cccgcttcga gggccgtaag cacaaacggc tcgccgtgag tcacgcgttc   2220
cactcgccgc tgatggagcc gatgctcgac gacttccgcg cggtcgcgga cagtctctcg   2280
tatgcggcgc cacggatccc gatcgtgtcc ggcggtctgg cggatgtgtc cacttcggac   2340
tactgggtcc gccatgtccg tgacgccgtg cggttccacg attcggtcaa gttcctggaa   2400
accgaagggg tcaccgcctt cctggagatc gggccggacg ccgtcctcac cgcgatggcc   2460
caggaaagca ccgagggcgc ggtcgtcgtc gcggcctcgc gccgcaaccg cgcggaggac   2520
```

-continued

```
gtcaccctgc tcgccgcggt ctccacgctg cacgtccacg gggcgtccgt cgactggacg   2580
ccgctgctcg ccggagcccg ccgcgtcgac ctgcccacgt acgccttcca gcaccgccgt   2640
ttctggctgg acggcccgct gaacgccgag ggtgacgcgg cgagcctggg cctgggcgcc   2700
accgatcacc cgctgctcgg cgccgtcgtc acgatggccg acgcgcacgg cgtcctgctc   2760
accgggcggc tttccctcgc ggcgcagccg tggctggccg ggcacgtggt cgcggggcac   2820
gtcctgctgc cgggcaccgc cttcgtcgac ctcgtcctgc acgccgggga caaggtcgac   2880
tgcgggatcg tggaggaact gaccctgcgg gaacccctcg tcctgcccga acacgacgcc   2940
ctcagcctgc aactcgtcgt cggcgcgccg gacgagaccg gcaggcgcac ggtcggcgtc   3000
cactcccgcc ccgaggccgc cgacgcagaa tggtcgtgcc acgcgaccgg tgtcctcgcc   3060
cccggtttcc ccgacaccga cttcagcctc gccgcctggc ctcccgaagg cgccgcgccg   3120
gtcgcgatcg acggcctcta cggcgcgctc gcggaggtcg gcctcgacta tgggcccgcc   3180
ttccagtgcg tgccgccgc ctggacccac gattcggccg tctacgccga aatcgagctg   3240
gccgacgccg agaaggccga cgcggcccgg ttcggtatcc atccggccct gctcgactcg   3300
gcactgcacg ccgccggtct cggcgcgctg gacgccaccg aggcgcgtct tccgttctcg   3360
tggtccggtg tgagcctgcg ggcgttcgga gcgacgacga tccgcgtgcg gctgaccccg   3420
gcggggccgg acacgatcgc gctggccgtc gcggatccgg agggacggcc ggtgttcgcc   3480
gccgacggcc tcctcgtccg cgcggtcccg tccggtgccc tcacctcgcg aaacccggtg   3540
cgcgacgggt tgttccgggt ggactggcag ccgctcacca tccccgccga agccgccgcg   3600
gagtacgtcg tcgcctcgtt caccgggtac accggcgacc tgctcggcga cgcccacgcg   3660
gccgcggtcc gcgcactcga actggtgcat gccgacagcg gcggcccgaa actggtcttc   3720
ctgaccagcg gtgccgtcgg ggacgccgtg ccgcgtccgg cgcaggccac cgtctggggt   3780
ctcgtccgca ccgcgcagga ggagttcccg gaccggttcg tcctcctcga cgccgacacc   3840
gagcccacgc ccgaattcat cgcggccgcc gtcgccaccg gtgaacccga gctcctgctc   3900
cgcgaaggtg tcctgtccgg tgcccgtctc gtccgcgccc cgcgtgcctc cgccgagccc   3960
ggcgacatcg acgggacggt gctcgtcacc ggcggcaccg gcgcgctcgg cgcggatctc   4020
gcccggcacc tcgtccggtc gcgcggtgtc cggcggctgc tgctcaccag ccgtcgcggt   4080
gcggcggcac caggcgcgga caccctcacc cgtgagctga ccgcgctcgg cgccgaagtc   4140
cggatcgaag cctgcgacgc cgccgaccgc gacgctctcg ccgccctgct ggccgatcag   4200
ccgatcaccc tcgccgtgca cgccgcgggt gtcctggacg acggcctcat cggtgacctg   4260
tccgcagaac gcctcaccgc cgtcttgagg tccaaagtgg acgccgccgt gcatctgcac   4320
gaactgctcg gcgacaccga actcgtcctg ttctcctccg ccgccggtgt gttcggcaac   4380
gaagggcagg cgaactacgc cgccgcgaac gccttcctcg acgccctcgc cggcaccgg   4440 caggcgaacg gcctgcccgg cacggcactg gcctggggga tgtgggcctc cggcatgggt   4500
gacgcgctca ccgctcgccc gggctttccc gcactgtcca cagaagacgg tatggcgctc   4560
ttcgacgccg cgacggcgct cgacgacgcc gcactcgtcc cgatccggct cgatctgccc   4620
gcgttgcgag cgcggctcgg cggtgacgtg ccgcctctgt tccgcggcct gatccggccc   4680
acccgccgtg ccgccgtcac cggttcggcc ggcgcgctcg ccgaccggct ggccgcgctc   4740
gccccggccg aacggagccg ggaactgctg gagatcgtgc ggacgcacgt cgccatcgtg   4800
ctggggcacc tcggttcgga ggcgatcgac gccgggaaac ccttccagga gctcggcttc   4860
gactcgctgg cggcggtcga actgcgcaac cggctgaccg aggtcaccgg cctgcggctg   4920
```

```
gccgcgaccc tcgtcttcga ctacccgacc ccgctcgtgc tcgccgaaca cctgctggaa    4980
gggctcgccg ggggcggact cgccgagacg ccggacgcgc cggtgcgcac cggtccggtc    5040
gacgagccga tcgcgatcat cggcatggct tgccgctacc cgggcggtgt cacttctccg    5100
gaagagctgt gggacctggt cgccgccggc cgggacgggg tttcggagtt cccggtcaac    5160
cggggctggg aagacgtcta cgacgccgac cccggcaagg tgggcaagag ttacgcccgc    5220
gagggcggct tcctgcacga cgcgggcgaa ttcgacgcgg cgttcttcgg gatctcgccc    5280
cgtgaggcgc tggcgatgga tccgcagcag cgtctgctgc tggagacgtc gtgggaggtc    5340
ttcgaacgcg ccgggatcga tccgcacgcg gtgcggggca gcaagaccgg cgtcttcgcc    5400
ggcgtgatgt accacgacta cgcggcacgg ctgaactccg taccggagga cgtcgagggc    5460
tacctcggca cggggaactc gggcagtgtg atctcggggc ggctggccta cacgttcggg    5520
ctggaaggcc ccgcgtcag catcgacacg gcctgttcgt cgtcgctggt cgcgatgcac    5580
ctcgccggac aggcgctgcg gcagggcgaa tgttcgctcg cggtcgccgg cggcgtgacc    5640
gtgatggcga cgccgaacac cttcatcgag ttcagccgcc agcgcgggat ggccactgat    5700
ggccggtgca aatccttcgc cgaggccgcg gacggcaccg gctggggcga gggcgtcggc    5760
atgctcctgc tggagcggct tcggacgcc cgccgcaacg gtcaccgggt gctggccgtg    5820
gttcgcggct cggcggtcaa ccaggacggc gcgtcgaacg ggctgacggc gccgaacggg    5880
ccgtcgcagc agcgggtgat ccgtcaagcc ttggcgcagg cggggttgcg tccgtccgat    5940
gtggacgccg tcgaggcgca cggtacggga acgacactcg gtgacccgat cgaggcacag    6000
gccttgctcg ccacctatgg ccaggatcgc gaggagccgt tgtggctggg gtcggtgaag    6060
tcgaacctcg gcacacgca ggccgccgcc ggcgtcgcgg gcgtgatcaa gatggtcgag    6120
gcgatgcgtc acggcgtgct gcctcggacg ttgcacgtcg atgagccttc gtcccatgtg    6180
gactggaccg tgcgcgcgt gtccctggtg acggagtcgc gggagtggcc ggacaccggc    6240
cgtccgcgcc gcgccggggt gtcgtcgttc gggatcagcg ggaccaacgc gcacaccatc    6300
atcgaggccg tcgagccgga agccgcggag ccgtccggaa acccgacgt cccgccgtgg    6360 ccgctgtccg gcaagaccga ggaagcgttg cgagcgcagg cgtcccgcct ccacgaccac    6420
ctgctggcca ctcccgaggt gaccgcgcg gacgtcgcgc tctccctcac ggcgcgggcg    6480
gacttggagc atcgtgccgt gctcgtggcc ggtgaccgtg acggtctcct cgccacgctc    6540
gacgcgctcg cgcacggcga gaccaccgag gggatcgtcc ggggaacggc gcggcacacc    6600
ggccggacgg cgttcctgtt caccggtcag ggcagtcagc ggctcgggat gggccgtgag    6660
ctggccgagc gtttccggt gttcgccgag gtctatgacg aggtgtgttc ccggttcgag    6720
cagccgctca gggacttgtc ggccgaggag ctgaaccaga ccgcgaacac gcagtgcgcg    6780
ttgttcgccc ttgaggtggc cctgttccgc ctggtggaga gctggggtgt ccggccggat    6840
ttcctggccg ggcactcggt cggcgagatc gcggccgccc acgtcgcggg tgtgctttcc    6900
ctcgacgatg cggtgacgct ggtgtcggcg cgcggccgcc tgatgcaggc gctgcccacg    6960
ggcggcgcga tggtggcgct gcgggcgacc gaagcggagg tgaccccgct gctgacggag    7020
ccgggtgtcg atcgccgcca tcaacggccc gagtcggtcg tcgtctcagg tgacgaagat    7080
gccgtcgccc ctgtggtcga gggccgcaag cacaagcgac ttaccgtgag tcacgcgttc    7140
cattcgccgc tgatggagcc gatgctggac gagttccgca ccgtggtgga gggcctgacg    7200
ttcgcggcgc cgcggatccc gatcgtgtcg ggtggcttgg cggaggtgtc cacttcggac    7260
```

```
tattgggtcc gtcatgtccg tgacgcggtg cggttccatg attcggtgaa gttcctggaa    7320
gccgagggcg tcacgcggtt cctggagatc ggcccggacg tgtgctgac cgcgatggcg     7380
caggacagcc tggaggacgc ggtcgtcgtc cccgccctgc ggcgcgacaa gcccgaggtc    7440
acgaccctgc tgacggcggt cgccggactg cacgtccacg cgccggcgt cgactggagc    7500
ccgctgtccg ccggggcccg ccgggtggac ctgcccacgt atgccttcca gcgcacggag    7560
ttctggctcg acgcgggtgc cgcggctggc gatctgaccg cggcgggact gtccgacgcc    7620
ggacatccgc tgctcggtgg cgcggtgacc ttgccggact ccggcgggac cgtgttcacc    7680
gggaggctgt cgctcgcggc ccagccctgg ctcgccgacc acgccgtcgg ggagaccgtg    7740
ctcctgcccg gtaccgcgtt cgtcgatctg gcgctcgccg ccggacgacg gcacggccgc    7800
gtcgtcctcg acgaactcac cctggagagc ccgctggtcc tgccggagca cggcggtgtc    7860
gatctgcgcg tgtgggtccg cgaaccggac gacaccggcg cgtgcgcggt cagcgtgcat    7920
tcccgtgccg acgacgagcc ctggatccgc cacgcggtcg gaacgctgac cgaggacacc    7980
ggcgccacgc ccgccgacct cacgtcatgg ccgcccgccg cggaggagac cgacgtcgac    8040
gggctgtacg acgcgctcgc cgacgcgggc ctgaactacg gcccggtctt ccaaggcgtc    8100
cgcgcggcct ggctcgacgg caccaccgtg tacgccgaga tcgacctcga cgaacgccat    8160
cacggcgacg ccgcccggtt cggcctgcac ccggcgctgc tggacgcggc cctgcacacc    8220
gccggactcg gcgcgctgag caccgaaggc ggggcacggc tgcccttcct gtggtcgggc    8280
gtctcgctca ccgcctcgg cgccacgagc ctgcgcgtcc ggctcaccgg tcgggcgac    8340
acgctctccc tggcgatcgc ggacgggacg ggtgcgccgg tggcgaccgt cgccgggctg    8400
accgtccgtc aggtcgaccc cgccgcgttc ggtggtggcg gcgactcgct gttccgggtg    8460
gagtgggtcc cggtccgcgc ccgtgccgcg gacaccgcgc ccgccgtccg gtccgaagtg    8520
gacagtctgg tgaacgtgcg cgaagcgacc gcgcaaacgc ttgcggcgct ccaatcctgg    8580
ctcgccgacg aaagcaacgc cgacaccca ctggtcgtgc tgaccagcgg cgcggtgtcg    8640
gtggcggggg aggacacgcg tgatctcgcc cgcgccgccg tctgggggct ggtgcggtcg    8700
gcgcagtccg agcacccggg ccggttcgtg ctcatcgaca ccgataccga accagcggac    8760
ctggccggag ccgtcgccac cggcgaggca cagcttgcca tccgcgacgg gaagctgtgg    8820
gcgccgcgtc tggtgaagag cgcacccctcc agtgccacac cgcgtttcga cccggaaggc    8880
accgtgctgc tcaccggggc gaccggtgcg ctgggccgat cgctggccag tcacctggtc    8940
tccggacacg gggtgcggca tctgctgctg gtcagccgca gcggcgcggc cgcacacggt    9000
gccaaggacc tgctggcgga actgaccggg ctcggcgcct ccgtggtcct ggagtcctgc    9060
gacgtcgccg accgggaagc cctcgcgggg ctgctggccg ggatcgaccc cgggcatccg    9120
ctcaccgggg tcgtgcacgc ggccggcgtc ctcgacgacg gcctgatcga cagcctgact    9180
cccgaacggt tcgacgccgt gctgcggccc aaggccgacg cggcgctgaa cctgcacgag    9240
ctggcgggcg acgtcgacga gttcgtcctg ttctcctcgg cggcgggcac gttcggcaac    9300
gccgacaggc gaactacgc cgcggcgaac gccttcctgg acgcgttggc acagcaccgc    9360
caggccaacg gccttccggc ccggtccctg gcctggggtc tgtgggacac cgacgacggg    9420
atggacgctt ccgccgccgt cgccaggctc accgggtccg gcctcaccac cgaagaaggg    9480
ctgcacctgt tcgacaccgc gggtgacggt gtcgtcctgc cgatgaagct cgacctcgcc    9540
gcgctccgcg ccgaactcgg ttccgacgtg ccgtcgctgc tgcgcggtct gatcaaggcg    9600
cccgcgcggc gttccgcggg agcgtcggcg tggaagcggc agctcgcggg actgtccgaa    9660
```

```
gaggaccgtg acgcacgcct gctcgaactc gtgcgggcac aggtcgccgc ggtgctgggc    9720
tactccggcc cggaggacgt gccgtcggac cgggcgttca ccgaactcgg cttcgattcg    9780
ctcacgtcgg tggatctgcg gaaccggctg aactccgcga ccggcctgcg cctgcccgcc    9840
accctcgtgt cgaccaccc gaactccgac gcggtcgtcg cccggctgcg ggaggaactg    9900
tccggcaccg tggtcgcggc cgccgtcgtc accacggcgc cggtggacga accgatcgcc    9960
atcgtcggca tggcctgccg gttccccggc ggggtccgct cgccggaaga cctctggcgg    10020
ctggtcagca aggccgcga cggcatcacc ccgttcccg cggaccgggg atgggacgtc    10080
gaaggcctgt acgaccccga ggcctcccgg cccggcacct cctgcacccg ctacggcgga    10140
ttcctgcacg acgccggga cttcgacccc ggcttcttcg ggatctcgcc gcgggaggcg    10200
ctggcgatgg acccgcagca gcggttgctg ctggagacgt cctgggaagc cttcgaacgc    10260
gccgggatcg accggccac cctgcgcggc tccgcgaccg gcgttttcgc cggggcgatg    10320
taccacgact acgtttcgcg gctcaccgag atcccggcgg atctggaggg ctacctcggc    10380
acggggaact cgggcagcgt gatctcgggg cgcctcgcct acgccttcgg gctgaggggg    10440
ccggcggtca gcatcgacac ggcgtgctcg tcttcgctgg tcgcgatgca tctcgcggcg    10500
caggcgctgc ggcagggcga atgcggcctg gcgctggccg gcggcgtcgc ggtgatgtcc    10560
actccggaca ctttcatcga gttcagccgc cagcgcggga tggcgccgga cggccggatc    10620
aaggcgttct ccgagaccgc cgacggcacg gcctggggcg agggcgtcgg catgctgctg    10680
ctggagcgcc tttcggacgc ccgccgcaac ggacaccggg tgctggccgt cctgcgtggc    10740
acggcggtga accaggacgg cgcgtcgaac gggttgacgg cgccgaacgg gccgtcgcag    10800
cagcgggtga tccggcaggc tttggcgcag gccggttttgc gaccatccga tgtggacgct    10860
gtcgaggcgc acggaaccgg gaccacgctc ggcgatccga tcgaggcgca ggctctgctc    10920
gccacctacg ggcaggaccg tgaagagccg ttgtggctcg gttcggtgaa gtcgaacctg    10980
ggccacacgc aggccgccgc cggggtggcg agcgtgatca agatggtcga ggcgatgcgt    11040 cacgcgtcc tgcccaggac actgcacgtc gacgagccgt cgtcccatgt ggactggacg    11100
gaaggcgccg tctccctgct caccgaaacg cgggactggc cggacaccgg acgcccacgg    11160
cgtgccgggg tgtcgtcgtt cgggatcagc gggaccaacg cgcacgtcgt cctcgaagcg    11220
gacggcgccg gcgacgcggc accgcccgga cagccggatg tacttgcctt cccgttgtcc    11280
gccaagaccc aggacgctct gcgcgagcag gccgccaggt tgcgtgcccg gttgctgacc    11340
ggacacgcac ccgagctcgc cgacgtcgcg caaacgcttg ccacacgggg gcttttcgag    11400 caccgggcg tggtcaccgc gggcgaccgc gacggactgc tcgacgcgct cgccgcgctg    11460 gccggggag aaccgggcga cttcgtcacc ggtctcgcga aaccgggcgg gaaactcgcg    11520
ttcctcttca ccggtcaggg cagccagcgc gccgggatgg ccgacgaact ctccgccgcc    11580
ttcccggtgt tcgctcgaac cttcggcgag atctgcgcgc gtttcgatac cctgctggac    11640
cgtccgctgc gcgaggcgct cgccggtgac ctggtcgacc gcaccgaata cacccagtgc    11700
gcgatgttcg ccgtcgaggt cgcgctgttc cggctcgtcg agagccgggg cgtgcggccg    11760
gacttcctgg ccgggcactc gatcgggaa ctggcggcgg cccacgtcgc cggggtctgg    11820
tcgctggagg acgcctgcac cgtggtcgcc gcgcgcggca ggctcatgca ggcgctgccg    11880
tcgggcggcg cgatgatcgc ggtccaggcc accgaagagg aggtccggcc gctgatcgac    11940
gacgagaccg tgtcgatcgc cgcgatcaac ggcccggtgt cggtcgtcgt ctccggcgaa    12000
```

```
gaagccgccg tgaccgcgct ggccgccggg ttcgccgaac gtggccgcaa gaccaagcgg   12060
ctcaccgtga gccacgcgtt ccactcgccg ctcatgacg gatgctcgg cgaattccgc    12120 gccgtgctcg acgggatcgc cgcggccgac ccacggatcc cgctggtgtc cacgctgacc   12180
ggtgacccgc tgaccggcga tcaggcgcga tcgagcgagt actgggtccg gcacgtgcgg   12240
gacgcggtcc ggttctgcga cgcgatccgg acccctggagg cgcagggtgt ccggcgttac   12300
ctggagctcg gcccggacgc gccgctgacc gccctcggcg agcactgcgt cacgaacgag   12360
tccacagtgg acgctcagct gttcgtgccg tcgctgcggg ccggtcgatc cgacgtcgag   12420
tcgttcgtca ccgcgctagc gcggttgcac gtcgacggcg tccgggtcga ctgggcgaag   12480
gcactccccg gccggaagat cgatctgccc acctacgcct tccagcacga gcggttctgg   12540
ctgcggcccg ccgcgcccgc ggtgggagac gtcaccgggc tggggcagtc gcccgccggg   12600
catccgctgc tcggcgcggc ggtcgaggcg ccggacagcg gcgcggtgct gttcaccggc   12660
aggctgtcgt tgcaggagca ccgtggctg gccgaccacg tcgtcgccgg gacgaccctt   12720
ctcccgggca cggcgttcgt cgagctcgcg ttgcgggccg gggagctgac cggctgcgcg   12780
gccgtcgacg aactgaccct ggaagcaccg ctggtgctgc cggaccacgg tggcacggca   12840
ctgcggatcg tcgccgccgc gccggacgag accggcaggc gcgcgctgga cgtctactcc   12900
cgccccgacg acggcgactg gatccgtcac gccaccggga ccgtgtcgcc cctggcggcg   12960
ggcgcaccgt tcgatctgtc ggcctgggcg gccgccgatg ccgagaccgt cgaaaccgac   13020
ggcctctacg acggattggc cgccgccggg ctcgagtacg gtccggtctt ccagggactt   13080
cgctccgccc ggcggcgagg ggacgacatc tgggccgagg tcgacctccc cgaggacacc   13140
acgaccgagg gcttcggcct gcatccggcc ttgctcgacg ccgccttgca cgccctgggc   13200
ttcgccgaag ggggtgagca ggaggccgac gtggcggccg ggcgggtgcg cctgcccttc   13260
gcctggtccg gtgtccggct ccacgcctcc ggtgcgcgtg ccctgcgggt ccggctgtcg   13320
ccggcggggg agaacgcggt ctccctggcc gcggcggacg agaccggcag gctggtggcc   13380
acagtggacg ctctgacgct gcgcccggtc tcgctggagc aactcggcgg gcggcagggc   13440
agccacgagt cgctgttcgg tctggagtgg gcgccggttc cgctctaccc caccgccgcc   13500
gtggccgcga gctgggcggt cgtcggtgtc gacgactaca aactcgacgc cgcgctcacc   13560
gccgccggct atcgcggcca ggcttacgcc gatctcgccg cgctggccga ggcgatggat   13620
cgcgcgccag agctggtctt cgtgtcctgc gcgccggacc accgccaagg gctggcagcc   13680
gccgcgcaca ccgccgccca ccgcgcgcta gagctggtcc gtgcgtggct ggccgaggac   13740
cggttcgccg gttccggct ggtgctggtc accggcggcg ccgtcggcga accggcgcag   13800
gcggtgatct ggggcctgat ccgctcggcg cagtccgagc accccggccg gttcgtgctg   13860
gtggacctcg acgaacagga cgcgtcgtac cgtgtgctgt tgcccgcgct cgcctccggc   13920
gaaccgcagc tggagttgcg cgagggaacg gtgaaggcgc cgcggctggt caaaccggcc   13980
gtgacggccg ccgaaggcaa ggctcggacc gacggcgccg tgctgatcac cggcggcacc   14040
ggcgcgctcg gcgcggcact ggcccggcat ctggtcaccg cgcacgggaa gacccggctg   14100
gtgctcgccg gtcgccgcgg cccggacgcg ccgggcgcgg gcgaactggc cgacgaactg   14160
cggggtctgg gcgccgaggt cgctgtgatc gcttgcgacg cggccgatcg tgaagcgctg   14220
cgacgccttc tggccgagca cccggtgacc ggggtggtgc acgccgccgg tgttctcgac   14280
gacgtcgtcc tcgacggcct caccccggac cggctcgacg ccgtcctgcg gccgaaggtc   14340
gacgccgcgg tgaacctgca cgaactggcg ggagacgtcg acgagttcgt gctgttctcc   14400
```

-continued

```
tcggcggcgg gcaccttcgg caatccgggg caggcgaatt acgcggcggc caacgccttc    14460
ctcgacgcgc tcgcccggca tcgtcacgca cacgggctgc ccgcgacctc gctcgcctgg    14520
ggactctggg ccggtgacgg gatggcgggc ggtatgtccg ggcgcgatct ggaccggatg    14580
tccgcctccg gcgcgggcgc actgtccaca gaggagggtc tggcgttgtt cgacctcgcg    14640
gtgacggcgg ccgaaccggt gctgttgccg atgcggctgg acctcgccac cgtgcgggcg    14700
ggcctcggca ccgacgtccc gcccctgctg cgcggcctga tccgcggtac cagaaaacgc    14760
gccgagaccg ccggttcacc gaccggggac gcgctcaagg cggagctggc cgggatgacc    14820
ggcgaggaac gcgccgcggc actgctgaac ctcgtcgcca cgcacgtcgc cggtgtcctc    14880
gggcacgccg gtcccgagca ggtcgatccg gacaaggcgt tcacggaact cgggttcgac    14940
tcgctcgccg cggtcgaact gcgcaaccgg gtcaacgagg ccaccggtct ccggctgccc    15000
gccacgctgg tcttcgacca tccgaccacc accgcggtgg cggaactggt cggcgcggag    15060
atcgtcgtgg aggacgcgcc accgccgctg ggggtgctgg cggaactcga ccggctggag    15120
gccgcgttcg ccgggggaag cccggacgac gcgatccgcg gcaaggtcaa ggaccggctg    15180
cgcgccctgc tcgcggcctg cgatccgggc gagggcaccg aatccgtggc ggatcggctc    15240
gaagacgcct cggacgacga aatgttcgaa ttcatcggca aggaactcgg gatctcctga    15300
```

<210> SEQ ID NO 47
<211> LENGTH: 1921
<212> TYPE: PRT
<213> ORGANISM: Amycolatopsis orientalis

<400> SEQUENCE: 47

```
Met Lys Asp Thr Glu Asp Lys Leu Arg Tyr Phe Leu Lys Gln Val Thr
1               5                   10                  15

Ala Asp Leu His Glu Thr Arg Lys Arg Leu Lys Glu Thr Glu Ala Ala
            20                  25                  30

Gly Ser Glu Pro Ile Ala Ile Val Gly Met Ala Cys Arg Tyr Pro Gly
        35                  40                  45

Gly Val Ala Ser Pro Glu Asp Leu Trp Arg Met Val Glu Thr Gly Gly
    50                  55                  60

Asp Gly Ile Ser Gly Phe Pro Val Asp Arg Gly Trp Asp Leu Glu Ala
65                  70                  75                  80

Leu Tyr Asp Pro Asp Pro Asp Lys Gln Gly Thr Ser Tyr Val Ser Gln
                85                  90                  95

Gly Gly Phe Leu His Asp Val Ala Glu Phe Asp Pro Ala Phe Phe Gly
            100                 105                 110

Ile Ser Pro Arg Glu Ala Leu Ala Met Asp Pro Gln Gln Arg Leu Leu
        115                 120                 125

Leu Glu Thr Ser Trp Glu Ala Ile Glu Arg Ala Gly Ile Asp Pro Gly
    130                 135                 140

Ser Leu Lys Gly Ser Arg Thr Gly Val Phe Ala Gly Leu Met Tyr His
145                 150                 155                 160

Asp Tyr Val Ser Gly Leu Thr Glu Ile Pro Asp Glu Val Gly Gly Tyr
                165                 170                 175

Leu Gly Thr Gly Asn Ser Gly Ser Ile Ala Ser Gly Arg Val Ser Tyr
            180                 185                 190

Thr Phe Gly Phe Glu Gly Pro Ala Leu Thr Val Asp Thr Ala Cys Ser
        195                 200                 205

Ser Ser Leu Val Thr Leu His Leu Ala Ala Gln Ala Leu Arg Arg Gly
```

```
                210                 215                 220
Glu Cys Asp Leu Ala Leu Ser Gly Gly Val Thr Val Met Phe Thr Pro
225                 230                 235                 240

Gly Thr Phe Val Glu Phe Ser Arg Gln Arg Gly Met Ala Pro Asp Gly
                245                 250                 255

Arg Cys Lys Pro Phe Ala Glu Glu Ala Asp Gly Thr Gly Trp Ser Glu
                260                 265                 270

Gly Val Gly Met Leu Leu Val Glu Arg Leu Ser Asp Ala Arg Arg Asn
                275                 280                 285

Gly His Pro Val Leu Ala Val Leu Arg Gly Ser Ala Val Asn Gln Asp
                290                 295                 300

Gly Ala Ser Asn Gly Leu Thr Ala Pro Asn Gly Pro Ser Gln Gln Arg
305                 310                 315                 320

Val Ile Arg Glu Ala Leu Ala Asp Ala Arg Leu Thr Thr Ala Asp Val
                325                 330                 335

Asp Val Val Glu Ala His Gly Thr Gly Thr Thr Leu Gly Asp Pro Ile
                340                 345                 350

Glu Ala Gln Ala Leu Leu Ala Thr Tyr Gly Lys Gly Arg Pro Ser Asp
                355                 360                 365

Arg Pro Leu Trp Leu Gly Ser Ile Lys Ser Asn Leu Gly His Thr Gln
370                 375                 380

Ala Ala Ala Gly Val Ala Gly Ile Ile Lys Met Val Gln Ala Leu Arg
385                 390                 395                 400

Ser Gly Ile Leu Pro Arg Ser Leu His Ala Glu Thr Pro Ser Ser His
                405                 410                 415

Val Asp Trp Ser Ala Gly Ala Val Ser Leu Leu Ala Glu Ala Arg Pro
                420                 425                 430

Trp Pro Glu Leu Asp Arg Pro Arg Arg Ala Ala Val Ser Ser Phe Gly
                435                 440                 445

Ile Ser Gly Thr Asn Ala His Val Val Leu Glu Ala Ala Pro Ala Ala
                450                 455                 460

Glu Val Glu Pro Arg Gln Pro Val Val Thr Gly Ala Thr Pro Trp Leu
465                 470                 475                 480

Leu Ser Ala Arg Thr Pro Glu Ala Leu Arg Ala Arg Ala Ala Gln Leu
                485                 490                 495

Arg Ser Phe Val Asp Leu Pro Gly Ala Ala Ala Thr Leu Ala Ala Arg
                500                 505                 510

Pro Leu Phe Gly His Arg Ala Ala Ile Val Gly Asp Pro Arg Ala Ala
                515                 520                 525

Leu Asp Ala Leu Ala Thr Gly Lys Pro Ser Asn Leu Leu Ile Glu Gly
530                 535                 540

Thr Ala Gln Ser Gly Lys Ala Val Phe Val Phe Pro Gly Gln Gly Ser
545                 550                 555                 560

Gln Trp Val Gly Met Ala Glu Leu Leu Leu Ser Ala Pro Val Phe
                565                 570                 575

Ala Glu Ser Met Ala Glu Cys Glu Gln Ala Leu Ser Ser Phe Val Asp
                580                 585                 590

Trp Lys Leu Ser Asp Val Leu Ser Asp Ala Ala Ala Leu Glu Arg Val
                595                 600                 605

Asp Val Val Gln Pro Val Leu Phe Ala Val Met Val Ser Leu Ala Arg
                610                 615                 620

Leu Trp Arg Ala Cys Gly Val Glu Pro Ala Ala Val Val Gly His Ser
625                 630                 635                 640
```

-continued

```
Gln Gly Glu Ile Ala Ala Ala Cys Val Ala Gly Ala Leu Ser Leu Asp
                645                 650                 655
Asp Ala Ala Arg Val Val Cys Leu Arg Ser Lys Ala Ile Leu Ala Leu
                660                 665                 670
Ser Gly Leu Gly Gly Met Val Ser Val Ala Ala Ser Glu Asp Arg Val
675                 680                 685
Arg Glu Leu Leu Pro Ala Gly Val Ser Val Ala Ala Val Asn Gly Pro
        690                 695                 700
Ser Ala Val Val Val Ser Gly Asp Val Ala Gly Leu Glu Ala Leu Leu
705                 710                 715                 720
Lys Arg Cys Glu Leu Leu Asp Val Arg Ala Lys Arg Ile Pro Val Asp
                725                 730                 735
Tyr Ala Ser His Ser Ala His Val Asp Ala Ile Glu Gln Glu Val Leu
                740                 745                 750
Ser Ala Leu Ala Gly Ile Ser Pro Gln Ala Pro Val Ile Pro Phe Tyr
            755                 760                 765
Ser Thr Val Thr Asp Glu Pro Leu Glu Leu Asp Ala Gly Tyr Trp Phe
770                 775                 780
Arg Asn Leu Arg Gly Thr Val Arg Phe Ala Ala Thr Val Asp Arg Leu
785                 790                 795                 800
Leu Glu Asp Gly Phe Arg Phe Val Glu Thr Ser Pro His Pro Val
                805                 810                 815
Leu Val Pro Gly Ile Ser Glu Asp Ala Val Ala Leu Gly Ser Leu Arg
                820                 825                 830
Arg Gly Glu Gly Gly Ala Glu Arg Phe Val Ala Ser Leu Ala Glu Ala
            835                 840                 845
His Val His Gly Leu Ser Pro Ala Trp Ser Ser Ile Leu Pro Thr Ala
850                 855                 860
Asp Trp Val Asp Leu Pro Thr Tyr Pro Phe Gln Arg Lys Arg Phe Trp
865                 870                 875                 880
Leu Glu Ala Gly Thr Ala Ala Gly Asp Ala Ser Ala Phe Gly Gln Thr
                885                 890                 895
Val Val Asp His Pro Leu Leu Gly Ala Val Ala Val Pro Gly Thr
                900                 905                 910
Gly Gly Leu Leu Tyr Thr Gly Arg Ile Ser Leu Glu Thr His Pro Trp
            915                 920                 925
Leu Ala Asp His Ala Val Ser Gly Thr Val Leu Val Pro Gly Thr Ala
        930                 935                 940
Phe Val Glu Leu Ala Leu Ala Ala Gly Thr Gln Val Asp Cys Ala Leu
945                 950                 955                 960
Leu Asp Glu Leu Thr Leu Glu Ala Pro Leu Val Leu Glu Glu Gly Thr
                965                 970                 975
Asp Val Arg Leu Ser Val Glu Leu Gly Asp Ala Asp Val Asp Gly Arg
            980                 985                 990
Arg Glu Val Gly Val Tyr Ser Arg  Arg Gly Asp Glu Pro  Trp Thr Arg
            995                 1000                1005
His Gly  Asn Gly Val Leu Leu  Pro Glu Thr Asp Gly  Val Pro Thr
    1010                1015                1020
Pro Leu  Ala Glu Trp Pro Pro  Ala Gly Ala Glu Arg  Val Gly Val
    1025                1030                1035
Glu Ala  Leu Tyr Asp Glu Leu  Ala Asn Ala Gly Leu  Glu Tyr Gly
    1040                1045                1050
```

```
Pro Ala Phe Gln Gly Leu Arg Ala Ala Trp Arg Arg Glu Asn Glu
    1055                1060                1065

Val Phe Ala Glu Ile Asp Leu Pro Glu Ala Gln Thr Gly Glu Ala
    1070                1075                1080

Pro Ala Phe Gly Leu His Pro Ala Leu Leu Asp Gly Ala Leu His
    1085                1090                1095

Gly Ile Ala Leu Gly Val Leu Pro Asp Asp Gly Glu Gly Leu Arg
    1100                1105                1110

Leu Pro Phe Ala Phe Ser Gly Val Arg Leu Trp Ser Arg Gly Ala
    1115                1120                1125

Thr Ala Leu Arg Val Arg Leu Arg Pro Ala Ala Asp Gly Val Ala
    1130                1135                1140

Leu Thr Val Ala Asp Gly Glu Gly Leu Pro Val Ala Asp Val Asp
    1145                1150                1155

Gly Leu Leu Arg Pro Val Ser Val Ser Gly Leu Gly Gly Tyr
    1160                1165                1170

Arg Glu Ser Leu Phe Gly Leu Asp Trp Val Pro Ala Gly Ala Thr
    1175                1180                1185

Glu Pro His Asp Ala Thr Val Trp His Cys Glu Ser Gly Asp Leu
    1190                1195                1200

Arg Thr Val Leu Gly Ala Ala Leu Glu Arg Val Arg Thr Trp Leu
    1205                1210                1215

Asp Glu Pro Gly Asp Gly Pro Leu Val Val Ala Thr Arg Gly Gly
    1220                1225                1230

Ile Ala Thr Glu Arg Pro Asp Pro Val Thr Ala Ala Val Trp Gly
    1235                1240                1245

Leu Val Arg Ser Ala Gln Ser Glu His Pro Gly Arg Phe Val Leu
    1250                1255                1260

Val Asp Gly Asp Val Pro Ala Ala Leu Pro Ala Gly Glu Ser Gln
    1265                1270                1275

Val Val Val Arg Asp Gly Val Gly Phe Val Pro Arg Leu Val Arg
    1280                1285                1290

Val Pro Glu Pro Gly Pro Ala Arg Pro Trp Ser Asp Asp Asp Val
    1295                1300                1305

Val Leu Ile Thr Gly Gly Thr Gly Leu Leu Gly Ala Ala Val Ala
    1310                1315                1320

Lys His Leu Val Val Thr Gly Val Arg Ser Leu Val Leu Leu
    1325                1330                1335

Ser Arg Ser Gly Ala Ser Ala Pro Gly Ala Ala Ala Leu Ala Asp
    1340                1345                1350

Glu Leu Thr Gly Met Gly Ala Glu Val Arg Ile Leu Ala Cys Asp
    1355                1360                1365

Ala Ala Asp Arg Glu Ala Leu Arg Gln Val Leu Ala Ala His Pro
    1370                1375                1380

Val Thr Gly Val Val His Ala Ala Gly Val Leu Asp Asp Gly Leu
    1385                1390                1395

Ile Thr Ala Gln Thr Pro Glu Arg Leu Asp Arg Val Leu Ala Pro
    1400                1405                1410

Lys Val Asp Ala Ala Val Asn Leu His Glu Leu Leu Pro Asp Ala
    1415                1420                1425

Ala Pro Phe Val Met Phe Ser Ser Ala Ala Gly Val Phe Gly Asn
    1430                1435                1440

Pro Gly Gln Ser Gly Tyr Ala Ala Ala Asn Ala Phe Val Asp Ala
```

-continued

```
            1445                1450                1455

Leu Val Glu Arg Arg Arg Ala Asp Gly Ala Ala Ala Ala Ser Leu
    1460                1465                1470

Ala Trp Gly Leu Trp Ala Thr Thr Ser Ala Met Thr Gly Ser Ala
    1475                1480                1485

Asp Val Asp Arg Met Ala Arg Ala Gly Leu Thr Gly Leu Ser Thr
    1490                1495                1500

Glu Glu Gly Leu Asp Leu Leu Asp Ala Ala Leu Ala Thr Gly Arg
    1505                1510                1515

Thr Leu Thr Val Pro Met Gly Leu Asp Leu Ala Ala Leu Arg Ala
    1520                1525                1530

Glu Glu Val Pro Pro Leu Leu Arg Gly Leu Val Arg Ala Arg Ala
    1535                1540                1545

Arg Arg Ala Pro Asp Gly Gly Gly Ala Phe Arg Ala Arg Leu Ala
    1550                1555                1560

Gly Leu Asp Ala Asp Gly Arg Asp Ala Glu Ile Leu Glu Leu Val
    1565                1570                1575

Arg Gly Gln Val Ala Ala Val Leu Gly His Asp Gly Ala Asp Ala
    1580                1585                1590

Ile Asp Ala Gly Val Ala Phe Leu Glu Leu Gly Phe Asp Ser Leu
    1595                1600                1605

Thr Ala Val Asp Leu Arg Asn Arg Leu Ala Ala Ser Thr Gly Leu
    1610                1615                1620

Arg Leu Pro Pro Ser Leu Val Phe Asp His Pro Thr Pro Leu Ala
    1625                1630                1635

Val Ala Glu Arg Ile Ser Gly Asp Phe Ala Val Pro Asp Gln Ala
    1640                1645                1650

Glu Pro Val Pro Ala Ala Thr Asp Val Phe Gly Ala Met Phe Ala
    1655                1660                1665

Arg Ala Ile Glu Leu Asp Glu Val Ala Gln Phe Val Ala Leu Ala
    1670                1675                1680

Ala Gln Ala Ser Arg Tyr Arg Pro Ser Phe Thr Val Glu Thr Ala
    1685                1690                1695

Arg Glu Gln Asn Leu Gln Pro Val Arg Leu Ala Lys Gly Pro Ser
    1700                1705                1710

Gly Pro Glu Leu Val Cys Val Pro Ser Leu Leu Ala Gly Ser Gly
    1715                1720                1725

Ala His Glu Tyr Ala Arg Phe Ala Ala Ser Phe Arg Asp Val Gln
    1730                1735                1740

Asp Val Ser Val Val Pro Val Pro Gly Phe Gly His Gly Gln Pro
    1745                1750                1755

Leu Pro Asp Ser Ile Glu Ala Val Leu His Ala Gln Ala Asp Ala
    1760                1765                1770

Ile Leu Arg Glu Gly Gly Asp Pro Val Val Leu Val Ala His Ser
    1775                1780                1785

Ser Gly Gly Pro Leu Ala His Ala Leu Ala Arg His Leu Glu Glu
    1790                1795                1800

Ala Gly Ser Ala Pro Arg Ala Leu Val Leu Ile Asp Val Tyr Pro
    1805                1810                1815

Gln Asp Glu His Ala Leu Asp Gly Ile Arg Asp Arg Leu Ser Gly
    1820                1825                1830

Gly Leu Gly Asp Asp Thr Arg Leu Thr Ala Met Gly Ala Tyr Leu
    1835                1840                1845
```

-continued

```
Arg Leu Phe Ala Asp Tyr Val Pro Ala Pro Thr Gly Val Pro Thr
    1850                1855                1860

Leu Leu Val Arg Ala Ser Glu Pro Leu Glu Ala Trp Arg Asp Arg
    1865                1870                1875

Thr Glu Trp Arg Ser Gly Trp Ala Leu Pro His Asp Thr Val Asp
    1880                1885                1890

Val Glu Gly Asp His Phe Thr Met Leu Glu Arg His Ala Gly Thr
    1895                1900                1905

Thr Ala Glu Ala Val Arg Glu Trp Leu Gly Arg Leu Gly
    1910                1915                1920

<210> SEQ ID NO 48
<211> LENGTH: 5766
<212> TYPE: DNA
<213> ORGANISM: Amycolatopsis orientalis

<400> SEQUENCE: 48
atgaaagaca ccgaggacaa actccggtac ttcctcaagc aggtcaccgc ggatcttcac      60
gaaacccgga aacgcctgaa ggagaccgaa gccgcgggca gcgaaccgat cgccatcgtc     120
gggatggcct gccgctatcc cggcggggtg gcctcgcccg aggatctgtg cggatggtc      180 gaaaccggcg cgacgggat cagcggattc cggtcgacc gcggctggga cctcgaagcg       240
ctgtacgacc cggatccgga caagcagggc acgagctacg tttcgcaggg tggtttcctc     300
cacgacgtcg ccgagttcga cccggcgttc ttcgggatct cgccgcgtga ggcgctggcg     360
atggatccgc agcagcggct cctgctggag acgtcgtggg aggccatcga gcgggcgggt     420
atcgatccgg gctcgctgaa gggcagccgg accggggtgt cgccgggtt gatgtaccac     480 gactacgtct ccgggctgac cgagatcccc gacgaggtcg gcggctacct cggcaccggg     540
aactccggca gcatcgcctc cggccggtgt cctacacct cgggttcga aggccccgcg      600 ctcaccgtgg acaccgcgtg ctcgtcgtcg ctggtgaccc tccacctcgc cgcgcaggcg     660
ctgcggcggg gcgagtgcga cctcgccctg tccggcgggg tgacggtgat gttcaccccc     720
gggacgttcg tggagttcag ccgccagcgc gggatggcgc cggacggccg ctgcaaaccg     780
ttcgccgaag aggcggacgg caccggctgg tccgagggtg tcgggatgct gctggtggaa     840
cggctttccg acgcgcggcg caacggccat ccggtgctgg cggtcctgcg cgggtcggcg     900
gtgaaccagg acggcgcgtc gaacggcctg accgccccga acggcccgtc ccagcagcgg     960
gtgatccgcg aggcgctcgc cgacgcccgg ctgacgacgg cggacgtcga cgtcgtcgag    1020
gcgcacggaa ccggcaccac cctgggcgac ccgatcgagg cgcaggcgct gctcgcgacc    1080
tacggcaagg gcaggccgtc ggaccggccg ctgtggctcg gtcgatcaa gtcgaacctc     1140 ggcacaccc aggccgccgc cggagtcgcc gggatcatca agatggtgca ggcgctgcga     1200
agcgggatcc tgccccggag cctgcacgcg gagacccgt cgtcgcatgt ggactggagc     1260
gcgggcgcgg tctcgttgct ggccgaggcg cggccgtggc cggagctcga ccgtcctcgc    1320
cgggccgcgg tgtcgtcgtt cggcatcagc gggaccaacg cgcacgtcgt cctcgaagcg    1380
gccccggctg ccgaggtcga gcccggcag ccggtggtga ccgtgcgac gccgtggctg       1440 ttgtcggcgc ggacgccgga ggccttgcgt gccaggctg cacagcttcg gtcctttgtg      1500
gaccttccag gcgccgctgc cacactggcc gcgcggccgc tgttcgggca ccgggcggcc    1560
atcgtcggtg atccgcgtgc cgcgctggac gcgctcgcca ccggaaagcc ctcgaacctg    1620
ctgatcgagg gcaccgcgca gtcgggtaag gctgttttcg tgttcccggg tcagggttcg    1680
```

```
cagtgggtgg ggatggcgga ggagttgttg ttgtcggctc cggtgttcgc ggagtcgatg    1740
gctgagtgtg agcaggcgct tcgtccttt gtggattgga agttgtccga tgtgttgtcg    1800
gatgcggctg cgttggagcg ggttgatgtg gtgcagcctg ttttgttcgc ggtgatggtt    1860
tctctggcgc ggttgtggcg ggcgtgtggg gttgagcctg ctgcggtggt tggtcattcg    1920
cagggtgaga tcgcgcggc gtgtgtggcg ggtgcgttgt cgttggatga cgctgcgcgc    1980
gtggtgtgcc tacggagtaa ggcgattctg gcgttgtcgg ggctcggtgg catggtgtcg    2040
gtggctgcct cggaggaccg ggtgcgggag ctattgcctg ccggtgtgtc ggtggcagca    2100
gtgaacggcc cgtcggcggt ggtggtgtcc ggtgatgtcg cgggcttgga ggcgttgctc    2160
aagcggtgtg agttgctgga tgtgcgggcg aagcggatcc cggtggacta tgcctcgcat    2220
tcggcgcatg tggatgcgat cgagcaggag gtcttgtcgg cgctggcggg tatctcaccg    2280
caggcgccgg tgatcccgtt ttattcgacg gtgaccgatg agcctctgga attggatgct    2340
gggtattggt tccggaatct gcgggggacg gtgcggttcg cggcgacggt ggatcggttg    2400
ctggaggacg gtttccggtt cttcgtggag acgagtccgc atccggttct ggtcccggga    2460
atcagcgaag acgctgtcgc tctggggagt ttgcgtcggg gtgagggtgg tgcggagcgg    2520
ttcgtcgcgt cactggccga agcccatgtg cacggcctga gcccggcgtg gtcttcgatc    2580
ctgccgacgg cggactgggt cgatctgccg acgtatccgt tccagcgcaa gcggttctgg    2640
ctggaagccg ggaccgccgc cggggacgcg tcgcgcttcg ggcagacggt ggtggaccac    2700
ccgctgctcg gcgccgtcgt cgcggtcccc gggaccggcg ggctgctgta caccggccgg    2760
atctcgctgg agacgcatcc ctggctcgcc gatcacgccg tgtccgggac ggtactggtg    2820
cccggtaccg ctttcgtgga actcgcgctg ccgccggca ctcaggtgga ctgcgcgctg    2880
ctcgacgaat tgaccctcga agcaccgctc gtgctcgaag aaggcacgga cgtccggctc    2940
tcggtcgaac tcgtgacgc ggacgtcgac ggccgtcgcg aggtcggcgt gtactcccgc    3000
cgcggcgacg aaccctggac ccggcacggc aacggtgtcc tgctgcccga acggacggc    3060 gtgcccacgc cgctcgcgga gtggccgccc gccggggcgg aacgcgtcgg cgtcgaggcg    3120
ctgtacgacg agctcgcgaa cgcgggcctc gaatacggcc cggcgttcca aggactccgc    3180
gccgcatggc gtcgcgagaa cgaggtcttc gccgagatcg acctgcccga agcccagacc    3240
ggcgaggctc cggccttcgg cctgcatccc gcgttgctgg acgcgcgct ccacgggatc    3300 gcgctgggtg tgcttcccga cgacggggag ggactccggc ttccgttcgc gttctccggg    3360
gtccggctgt ggtcgcgggg cgcgacggca ctgcgagtgc ggctgcgacc ggcggcggac    3420
ggggtcgcgc tgaccgtcgc cgacggtgag ggcctaccgg tcgccgacgt ggacggtctg    3480
ctgctgcggc cggtgtccgt gtccggcctc ggtgggtatc gagagtccct gttcggcctg    3540
gattgggtgc ccgcgggcgc gaccgaaccg cacgacgcga cggtgtggca ctgcgaatcc    3600
ggggatctcc gcaccgtgct gggtgcggcg ctcgaacgcg tccggacgtg gctcgacgag    3660 cctgggacg gtccgctcgt ggtggccacg cgaggcggga tcgcgaccga acgcccggat    3720
ccggtgacgg ccgcggtatg ggggctcgtg cgctcggcgc agtcggagca ccccggacgg    3780
ttcgtgctcg tggacggcga cgtcccggcg gcgctgcccg ccggggaatc gcaggtcgtg    3840
gtccgtgacg gggtcggctt cgtcccgagg ctcgtccggg tccggaacc cggcccggcc    3900 cggccgtgga gcgacgatga tgtcgtgctg atcaccggag gcaccggcct cctcggtgcg    3960
gccgtcgcga aacacctggt ggtgacgcac ggcgtccgtt cgctggtgct gctgagccgt    4020
```

-continued

```
tccggtgctt ccgcgcccgg tgcggcggca ctggcggacg aactcaccgg gatgggtgcc    4080
gaggtccgga tcctcgcgtg cgacgcgccc gaccgggagg cgctgcgcca ggtgctggcc    4140
gcgcatccgg tgaccggtgt cgtgcacgcc gccggtgtcc tcgacgacgg gctgatcacc    4200
gcgcagaccc ccgaacggct cgaccgggtg ctcgcgccga aggtggacgc cgcggtgaac    4260
ctgcacgaac tcttgcccga tgccgcgccc ttcgtgatgt tctcctcggc ggccggggtc    4320
ttcgggaatc cggggcagtc cggttacgcc gcagccaacc ctttcgtgga cgccctggtg    4380
gaacgccgcc gcgcggacgg cgccgccgcg gcgtcactgg cgtggggcct gtgggcgacc    4440
accagcgcca tgaccggttc cgccgacgtg gaccggatgg cgagggcggg actcaccgga    4500
ctgtccacag aggagggtct cgacctgctc gacgccgcgc tcgccaccgg gcggacgctg    4560
accgtcccca tggggctcga cctcgccgcg ctccgcgccg aggaggtgcc gccgttgctg    4620
cgcgggctcg tccgcgctcg tgcccggcgc gcgcccgacg gcggcggcgc gttccgcgcc    4680
cggctcgccg gactcgacgc ggacggccgc gacgcggaga tcctggaact ggtgcgcggt    4740
caggtcgcgg ccgtcctcgg ccacgacggt gccgacgcga tcgacgccgg tgtcgcgttc    4800
ctcgaactcg gcttcgactc gctcaccgcc gtcgacctgc gtaaccggct ggcggcctcg    4860
accggcctgc ggctcccgcc gtcgctggtg ttcgaccacc cgacgccgct cgccgtcgcg    4920
gaacggatct ccggtgactt cgcggttccc gaccaggccg agccggtgcc agcggccacc    4980
gacgtcttcg gcgcgatgtt cgcccgcgcg atcgaactcg acgaggtcgc gcagttcgtc    5040
gcgctagccg cgcaggcttc gcgctaccgg ccgtcgttca ccgtcgaaac cgcgcgggaa    5100
cagaacctgc aacccgtccg gctcgcgaag ggcccgtccg gccccgaact ggtctgcgtc    5160 ccctcccctgc tggccggctc gggggcgcac gaatacgcgc ggttcgcggc gtcgttccgg    5220
gacgtgcagg acgtttccgt cgttccggtg cccggtttcg gccacgggca gccgctgccg    5280
gactcgatcg aggcggtcct ccacgcgcag gcggacgcga tcctccgcga aggcggtgac    5340
ccggtggtcc tggtggccca ctcctctggc ggcccgctcg cccacgcgct ggctcggcac    5400
ctggaggaag cgggctccgc gccgcgcgcg ctcgtgctga tcgacgtcta cccgcaggac    5460
gagcacgcgc tggacggcat ccgtgaccgg ctcagcggcg gcctcggcga cgacacgcgg    5520
ctcaccgcca tggcgcccta cctgcgcttg ttcgccgact atgtgcccgc gccgaccggt    5580
gtgccgactc tgctcgtgcg ggcgtcggag ccccctggaag cgtggcgtga ccggaccgaa    5640
tggcggtccg gctgggcctt gccgcacgac acggtggacg tcgagggga tcacttcacg    5700 atgctggagc ggcatgccgg gacgaccgcc gaggccgtcc gggagtggct ggggcggctg    5760
gggtaa                                                              5766
```

<210> SEQ ID NO 49
<211> LENGTH: 3760
<212> TYPE: DNA
<213> ORGANISM: Amycolatopsis orientalis

<400> SEQUENCE: 49

```
ccactcacca gaacctcaag cgcggctccg cggcttcaaa gccatccccg gcgtcaccgt      60
ccgcacctcg aaattcgcca ccgtgctgtc caccccggtgg aagagattgt ccggcccggc    120
gaaacacaag gacgtcaccc cctgctcccg caaggtcgcg accatcgacg gccagtcgat    180
cggccggtcg aaggtgtcga gcagcatccg gcgcacccc gccgccgagt ccaggagcgc     240
accgtcctgg tccgcgacca ccggaagtcc ggggtcgcga agagtgaagc cggacagcac    300
ctcctcctcg gcccgccggc gcaaaccacc gaagaaggtg gagtgcacgg gcgggcgcat    360
```

-continued

```
ggtgtgcatc gagtagccgc cgatcgcccg gactcgcgcc ttcacccgct ccaaatcctt      420
ctcccgcaac gaaagcaggt agaagccctg gtcgatgacg cccgaaatgt cgtggaactc      480
gtccttcagc tcggccagga cctcggcgaa accctcctcc ggagtccgga cgaaacagtg      540
ggtcacgacg tcggaatagt cgctttcgaa gtacgacatc tcgcaccgcg agagctccgc      600
ggtgagccga acggtctcct cgaacggcag cactcccgta tacgcggtca gcgccttctg      660
gccgaaactg ggaccggcgc atatctccgg tttcacgccg agggcgtctt cggcccactc      720
cgcgagggaa agacacgtca gcatgaagac gacctgtgcg gcctcgtcgt acacatcgcc      780
gtcttcgcgg gcggggccga gcaggcgacg gccgaggacg tcctcggccg tggcgagccg      840
ttcccgtgcc ttccggttga tcatcaggaa ccggctcacg tccccgcttc tcgtgggggc      900
catacccggg aagaccaggg cggtgcgttc gtcggtcacg ttctcagccg gctttcggcg      960
aagtggtcga ttcggccagt gccagttccg tcatccgctt cttgtcgggt tttccgttgc     1020
ggttcaacgg aaacctttcg acgacccgga tgcggtccgg tcgctcgaac tccggcagca     1080
cctcggcgat gcgcgtacgc cagtgcctgc cgtcgtggcc gagcggatct tcgacgaaga     1140
acgccagctg gcagccacgc cgttcgtccg gcagcgcgat gatcttgacc gggcacagcg     1200
cttcggtgac cttgtgctcg atgatctccg ggtagagcgt gtgtcccttg cggtgcacgg     1260
cgaatttgcg gcccaccacg aacaggttgt cgttctcgtc caggtagccg aagtcgccgg     1320
tgtgccgcca gccctgctcc gccggctcca gggagccgtc cgcggcgagg tagcccgcca     1380
tcatgtcggg gcagtacatc acgatctcgc cggtctgccc ggcgggcagc ggatggcctt     1440
cgtcgtcgag gatccgcagt tcgtgcccgg ggagcgcgcg gccacagccg accgggttct     1500
ccggcgtcgc gaaggcgagg ttgcccagtt ccgtgctgcc gtagctgtcc agcaagggga     1560
ggccgaacca ggcgacgtag tcttcgctga gcgtcgaccc cagggagcg gcgccactgc     1620 agaacatccg cacgccggcc aggtcgaggc cgtagcgggg attgcgcttc acgatgttga     1680
gaatgctctg gtaggtcgac ggcgtgccgt cggtcacggt caccccgcac tggcccgcca     1740
tccgcagggc acgtcgatc cgccggtacg gcgccaccac gagcgaacag cgcaccagcc     1800
acgcgatcag caccatcgac aggccgtact ggtgggaaaa gggcagcatc ggcatcagga     1860
cgtcgcccga gtggtggccg acctggtcgg cgttgcgctg gaggttcttc aggaaccgcc     1920
cgccgttctt gaccacgccc ttgggcactc cggtcgatcc ggaggagtac atgatcagcc     1980
cgtccggcag ttcgcaccac gggcccaccc gcagctccgg atcgcgggtg gcctgtgacg     2040
ccccggcgac gagcaattcg tagagcaggg tgtgcgggcc gtcggtgacc aacggcgcgt     2100
cctcgtcgac caggctgatc ttgacccccgg cctggttgca gacccgctgg gtctcggcgg     2160
cgttctcctg ctggtcgacg aggacgatgc tcgcaccgac atgcatcagg ccagcagcg     2220 tggtcacgta ggcggccgaa ttcccggcct tcagcatcac cctggtcgag ggtgtcacgc     2280
cgcgctcccg gagggactcc gccaccccca gcgcgctgtg ttcgagctcg tcgaacgtct     2340
gcaaggaatc gagggcgaag agtctcgcgg acatgggatt ccccttttctc tcactcggcg     2400 atcttggtgc ggccagacca ccggaagacg gcgaagacct catgaccgtc cttttggaac     2460 tccccgcgt gggaaaagtg ttcgtagcct ccgtcgacgc agatcttcac gtcctgggtg     2520
aggtcttcga ccttctggta ggactccaga tccgccgacc gcgcgcggga tcccgtggga     2580
tcgattctga tgtgcaccac ggaagggctc ctttcactgg gtgatatgga ggtcggacgg     2640
ccgcaaggcg tccgagatgg cccggatcac ggccggggcg tgggtgttca ggtagaaatg     2700
```

-continued

```
cccgccggga tacgtggtca gggtgaaccg cccggacgtg tgcgcggccc agtcgcggac    2760
ctcgccgacg gtcgccttcg ggtcgttttc gccgagatgg gcgtggatcg gggcctgcaa    2820
cagaggaccc ggcgtgtatc gataggtctc cgcggcggtg tagtccgtcc ggatcgaggg    2880
cagcaccatt tccaggatcg cttcgtcctc gaagacctgg gcgtcggtgc cgccgagttc    2940
cttcaccgcg gcgacgagtc ccgcgtcgtc gcgccggtgg accgtctcgt cgcgggcgcg    3000
gctgggtgcc acgcgcccgg agacgaacaa cgcgtgcggc cgcacttcag cggcttcgag    3060
ccggcgggcg acctcgaagc cgagggtcgc gcccatgctg tgtccgaaaa ggacggccgg    3120
ccggtccagc cacggcagga gtgcctcggt gacgccgtcg gcgagttcgg cgatggtggc    3180
gagccccggt tcgtgacgcc ggtcctggcg tccggggtac tggatcgcga gtacgtcggc    3240 ggcgggctc aacgtccgtg agaccgggaa gaaatagctc gcggaacccc cggcgtgcgg    3300
gaaacagacg acgcggtagg gcgcgtcgtc cgcgggatgg aacctgcgta cccagagtcc    3360
ctcgtcgttg tccgccaccc ggccacctcc tgcgtcggcg acgggcggat cgcccgtccc    3420
accgagcgtg cgggcggccg gtccgggcgg acaacccta ccgacccggc gtggccccta    3480
tcgcgcctcg tggtcgcggc gcaccccgta gctcaggtga agcacccggt cgccccgaat    3540
cgccacgtca gggtcctcca gcaggtgctg tgcgcggacc gacccgaaga agcgcctgcc    3600
ggagccgaac acgacgggta cgacgtccat gcgcacctcg tcgaccaggc ccgcggcgag    3660
cgcctggcca ccgacgtcgc cggccgcgat ctcgacgaca cggtcgcccg cgagctcccg    3720
cgccttggcg acggccgcct cgacgccgtc gacgaagtgg                          3760
```

<210> SEQ ID NO 50
<211> LENGTH: 307
<212> TYPE: PRT
<213> ORGANISM: Amycolatopsis orientalis

<400> SEQUENCE: 50

```
Val Thr Asp Glu Arg Thr Ala Leu Val Phe Pro Gly Met Ala Pro Thr
  1               5                  10                  15

Arg Ser Gly Asp Val Ser Arg Phe Leu Met Ile Asn Arg Lys Ala Arg
             20                  25                  30

Glu Arg Leu Ala Thr Ala Glu Asp Val Leu Gly Arg Arg Leu Leu Gly
         35                  40                  45

Pro Ala Arg Glu Asp Gly Asp Val Tyr Asp Glu Ala Ala Gln Val Val
     50                  55                  60

Phe Met Leu Thr Cys Leu Ser Leu Ala Glu Trp Ala Glu Asp Ala Leu
 65                  70                  75                  80

Gly Val Lys Pro Glu Ile Cys Ala Gly Pro Ser Phe Gly Gln Lys Ala
                 85                  90                  95

Leu Thr Ala Tyr Thr Gly Val Leu Pro Phe Glu Glu Thr Val Arg Leu
            100                 105                 110

Thr Ala Glu Leu Ser Arg Cys Glu Met Ser Tyr Phe Glu Ser Asp Tyr
        115                 120                 125

Ser Asp Val Val Thr His Cys Phe Val Arg Thr Pro Glu Glu Gly Phe
    130                 135                 140

Ala Glu Val Leu Ala Glu Leu Lys Asp Glu Phe His Asp Ile Ser Gly
145                 150                 155                 160

Val Ile Asp Gln Gly Phe Tyr Leu Leu Ser Leu Arg Glu Lys Asp Leu
                165                 170                 175

Glu Arg Val Lys Ala Arg Val Arg Ala Ile Gly Gly Tyr Ser Met His
            180                 185                 190
```

```
Thr Met Arg Pro Pro Val His Ser Thr Phe Phe Gly Gly Leu Arg Arg
        195                 200                 205

Arg Ala Glu Glu Glu Val Leu Ser Gly Phe Thr Leu Arg Asp Pro Gly
        210                 215                 220

Leu Pro Val Val Ala Asp Gln Asp Gly Ala Leu Leu Asp Ser Ala Ala
225                 230                 235                 240

Gly Val Arg Arg Met Leu Leu Asp Thr Phe Asp Arg Pro Ile Asp Trp
                245                 250                 255

Pro Ser Met Val Ala Thr Leu Arg Glu Gln Gly Val Thr Ser Leu Cys
            260                 265                 270

Phe Ala Gly Pro Asp Asn Leu Phe His Arg Val Asp Ser Thr Val Ala
        275                 280                 285

Asn Phe Glu Val Arg Thr Val Thr Pro Gly Met Ala Leu Lys Pro Arg
        290                 295                 300

Ser Arg Ala
305

<210> SEQ ID NO 51
<211> LENGTH: 924
<212> TYPE: DNA
<213> ORGANISM: Amycolatopsis orientalis

<400> SEQUENCE: 51
gtgaccgacg aacgcaccgc cctggtcttc ccgggtatgg cccccacgag aagcggggac      60
gtgagccggt tcctgatgat caaccggaag gcacgggaac ggctcgccac ggccgaggac     120
gtcctcggcc gtcgcctgct cggccccgcc cgcgaagacg gcgatgtgta cgacgaggcc     180
gcacaggtcg tcttcatgct gacgtgtctt tccctcgcgg agtgggccga agacgccctc     240
ggcgtgaaac cggagatatg cgccggtccc agtttcggcc agaaggcgct gaccgcgtat     300
acgggagtgc tgccgttcga ggagaccgtc cggctcaccg cggagctctc gcggtgcgag     360
atgtcgtact cgaaagcga ctattccgac gtcgtgaccc actgtttcgt ccggactccg     420
gaggagggtt cgccgaggt cctggccgag ctgaaggacg agttccacga catttcgggc     480
gtcatcgacc agggcttcta cctgctttcg ttgcgggaga aggatttgga gcgggtgaag     540
gcgcgagtcc gggcgatcgg cggctactcg atgcacacca tgcgcccgcc cgtgcactcc     600
accttcttcg gtggtttgcg ccggcgggcc gaggaggagg tgctgtccgg cttcactctt     660
cgcgaccccg gacttccggt ggtcgcggac caggacggtg cgctcctgga ctcggcggcg     720
ggggtgcgcc ggatgctgct cgacaccttc gaccggccga tcgactggcc gtcgatggtc     780
gcgaccttgc gggagcaggg ggtgacgtcc ttgtgtttcg ccgggccgga caatctcttc     840
caccgggtgg acagcacggt ggcgaatttc gaggtgcgga cggtgacgcc ggggatggct     900
ttgaagccgc ggagccgcgc ttga                                             924

<210> SEQ ID NO 52
<211> LENGTH: 476
<212> TYPE: PRT
<213> ORGANISM: Amycolatopsis orientalis

<400> SEQUENCE: 52

Met Ser Ala Arg Leu Phe Ala Leu Asp Ser Leu Gln Thr Phe Asp Glu
1               5                   10                  15

Leu Glu His Ser Ala Leu Gly Val Ala Glu Ser Leu Arg Glu Arg Gly
            20                  25                  30
```

```
Val Thr Pro Ser Thr Arg Val Met Leu Lys Ala Gly Asn Ser Ala Ala
        35                  40                  45

Tyr Val Thr Thr Leu Leu Ala Leu Met His Val Gly Ala Ser Ile Val
    50                  55                  60

Leu Val Asp Gln Gln Glu Asn Ala Ala Glu Thr Gln Arg Val Cys Asn
65                  70                  75                  80

Gln Ala Gly Val Lys Ile Ser Leu Val Asp Glu Asp Ala Pro Leu Val
                85                  90                  95

Thr Asp Gly Pro His Thr Leu Leu Tyr Glu Leu Leu Val Ala Gly Ala
                100                 105                 110

Ser Gln Ala Thr Arg Asp Pro Glu Leu Arg Val Gly Pro Trp Cys Glu
            115                 120                 125

Leu Pro Asp Gly Leu Ile Met Tyr Ser Ser Ser Thr Gly Val Pro
    130                 135                 140

Lys Gly Val Val Lys Asn Gly Gly Arg Phe Leu Lys Asn Leu Gln Arg
145                 150                 155                 160

Asn Ala Asp Gln Val Gly His His Ser Gly Asp Val Leu Met Pro Met
                165                 170                 175

Leu Pro Phe Ser His Gln Tyr Gly Leu Ser Met Val Leu Ile Ala Trp
            180                 185                 190

Leu Val Arg Cys Ser Leu Val Val Ala Pro Tyr Arg Arg Ile Asp Arg
        195                 200                 205

Ala Leu Arg Met Ala Gly Gln Cys Gly Val Thr Val Thr Asp Gly Thr
    210                 215                 220

Pro Ser Thr Tyr Gln Ser Ile Leu Asn Ile Val Lys Arg Asn Pro Arg
225                 230                 235                 240

Tyr Gly Leu Asp Leu Ala Gly Val Arg Met Phe Cys Ser Gly Ala Ala
                245                 250                 255

Pro Leu Gly Ser Thr Leu Ser Glu Asp Tyr Val Ala Trp Phe Gly Leu
            260                 265                 270

Pro Leu Leu Asp Ser Tyr Gly Ser Thr Glu Leu Gly Asn Leu Ala Phe
        275                 280                 285

Ala Thr Pro Glu Asn Pro Val Gly Cys Gly Arg Ala Leu Pro Gly His
    290                 295                 300

Glu Leu Arg Ile Leu Asp Asp Glu Gly His Pro Leu Pro Ala Gly Gln
305                 310                 315                 320

Thr Gly Glu Ile Val Met Tyr Cys Pro Asp Met Met Ala Gly Tyr Leu
                325                 330                 335

Ala Ala Asp Gly Ser Leu Glu Pro Ala Glu Gln Gly Trp Arg His Thr
            340                 345                 350

Gly Asp Phe Gly Tyr Leu Asp Glu Asn Asp Asn Leu Phe Val Val Gly
        355                 360                 365

Arg Lys Phe Ala Val His Arg Lys Gly His Thr Leu Tyr Pro Glu Ile
370                 375                 380

Ile Glu His Lys Val Thr Glu Ala Leu Cys Pro Val Lys Ile Ile Ala
385                 390                 395                 400

Leu Pro Asp Glu Arg Arg Gly Cys Gln Leu Ala Phe Phe Val Glu Asp
                405                 410                 415

Pro Leu Gly His Asp Gly Arg His Trp Arg Thr Arg Ile Ala Glu Val
            420                 425                 430

Leu Pro Glu Phe Glu Arg Pro Asp Arg Ile Arg Val Val Glu Arg Phe
        435                 440                 445

Pro Leu Asn Arg Asn Gly Lys Pro Asp Lys Lys Arg Met Thr Glu Leu
```

```
                450                 455                 460
Ala Leu Ala Glu Ser Thr Thr Ser Pro Lys Ala Gly
465                 470                 475

<210> SEQ ID NO 53
<211> LENGTH: 1431
<212> TYPE: DNA
<213> ORGANISM: Amycolatopsis orientalis

<400> SEQUENCE: 53
atgtccgcga gactcttcgc cctcgattcc ttgcagacgt tcgacgagct cgaacacagc      60
gcgctggggg tggcggagtc cctccgggag cgcggcgtga caccctcgac caggtgatg     120 ctgaaggccg ggaattcggc cgcctacgtg accacgctgc tggccctgat gcatgtcggt     180
gcgagcatcg tcctcgtcga ccagcaggag aacgccgccg agacccagcg ggtctgcaac     240
caggccgggg tcaagatcag cctggtcgac gaggacgcgc cgttggtcac cgacggcccg     300
cacaccctgc tctacgaatt gctcgtcgcc ggggcgtcac aggccacccg cgatccggag     360
ctgcgggtgg gcccgtggtg cgaactgccg gacgggctga tcatgtactc ctccggatcg     420
accggagtgc ccaagggcgt ggtcaagaac ggcgggcggt tcctgaagaa cctccagcgc     480
aacgccgacc aggtcggcca ccactcgggc gacgtcctga tgccgatgct gccctttccc     540
caccagtacg gcctgtcgat ggtgctgatc gcgtggctgg tgcgctgttc gctcgtggtg     600
gcgccgtacc ggcggatcga ccgtgccctg cggatggcgg ccagtgcgg ggtgaccgtg     660 accgacggca cgccgtcgac ctaccagagc attctcaaca tcgtgaagcg caatccccgc     720
tacggcctcg acctgccgg cgtgcggatg ttctgcagtg gcgccgctcc cctggggtcg     780
acgctcagcg aagactacgt cgcctggttc ggcctccct tgctggacag ctacggcagc     840
acggaactgg gcaacctcgc cttcgcgacg ccggagaacc cggtcggctg tggccgcgcg     900
ctccccgggc acgaactgcg gatcctcgac gacgaaggcc atccgctgcc cgccgggcag     960
accggcgaga tcgtgatgta ctgccccgac atgatggcgg gctacctcgc cgcggacggc    1020
tccctggagc cggcggagca gggctggcgg cacaccggcg acttcggcta cctggacgag    1080
aacgacaacc tgttcgtggt gggccgcaaa ttcgccgtgc accgcaaggg acacacgctc    1140
tacccggaga tcatcgagca caaggtcacc gaagcgctgt gcccggtcaa gatcatcgcg    1200
ctgccggacg aacggcgtgg ctgccagctg gcgttcttcg tcgaagatcc gctcggccac    1260
gacggcaggc actggcgtac gcgcatcgcc gaggtgctgc cggagttcga gcgaccggac    1320
cgcatccggg tcgtcgaaag gtttccgttg aaccgcaacg gaaaacccga caagaagcgg    1380
atgacggaac tggcactggc cgaatcgacc acttcgccga aagccggctg a             1431

<210> SEQ ID NO 54
<211> LENGTH: 69
<212> TYPE: PRT
<213> ORGANISM: Amycolatopsis orientalis

<400> SEQUENCE: 54

Val Val His Ile Arg Ile Asp Pro Thr Gly Ser Arg Ala Arg Ser Ala
1               5                   10                  15

Asp Leu Glu Ser Tyr Gln Lys Val Glu Asp Leu Thr Gln Asp Val Lys
            20                  25                  30

Ile Cys Val Asp Gly Gly Tyr Glu His Phe Ser His Ala Gly Glu Phe
        35                  40                  45

Gln Lys Asp Gly His Glu Val Phe Ala Val Phe Arg Trp Ser Gly Arg
```

-continued

```
                   50                  55                  60
Thr Lys Ile Ala Glu
 65

<210> SEQ ID NO 55
<211> LENGTH: 210
<212> TYPE: DNA
<213> ORGANISM: Amycolatopsis orientalis

<400> SEQUENCE: 55
gtggtgcaca tcagaatcga tcccacggga tcccgcgcgc ggtcggcgga tctggagtcc      60
taccagaagg tcgaagacct cacccaggac gtgaagatct gcgtcgacgg aggctacgaa     120 cactttccc acgccgggga gttccaaaag gacggtcatg aggtcttcgc cgtcttccgg      180
tggtctggcc gcaccaagat cgccgagtga                                      210

<210> SEQ ID NO 56
<211> LENGTH: 254
<212> TYPE: PRT
<213> ORGANISM: Amycolatopsis orientalis

<400> SEQUENCE: 56

Val Ala Asp Asn Asp Glu Gly Leu Trp Val Arg Arg Phe His Pro Ala
 1               5                  10                  15

Asp Asp Ala Pro Tyr Arg Val Val Cys Phe Pro His Ala Gly Gly Ser
                20                  25                  30

Ala Ser Tyr Phe Phe Pro Val Ser Arg Thr Leu Ser Pro Ala Ala Asp
            35                  40                  45

Val Leu Ala Ile Gln Tyr Pro Gly Arg Gln Asp Arg Arg His Glu Pro
        50                  55                  60

Gly Leu Ala Thr Ile Ala Glu Leu Ala Asp Gly Val Thr Glu Ala Leu
 65                  70                  75                  80

Leu Pro Trp Leu Asp Arg Pro Ala Val Leu Phe Gly His Ser Met Gly
                85                  90                  95

Ala Thr Leu Gly Phe Glu Val Ala Arg Arg Leu Glu Ala Ala Glu Val
            100                 105                 110

Arg Pro His Ala Leu Phe Val Ser Gly Arg Val Ala Pro Ser Arg Ala
        115                 120                 125

Arg Asp Glu Thr Val His Arg Arg Asp Ala Gly Leu Val Ala Ala
    130                 135                 140

Val Lys Glu Leu Gly Gly Thr Asp Ala Gln Val Phe Glu Asp Glu Ala
145                 150                 155                 160

Ile Leu Glu Met Val Leu Pro Ser Ile Arg Thr Asp Tyr Thr Ala Ala
                165                 170                 175

Glu Thr Tyr Arg Tyr Thr Pro Gly Pro Leu Leu Gln Ala Pro Ile His
            180                 185                 190

Ala His Leu Gly Glu Asn Asp Pro Lys Ala Thr Val Gly Glu Val Arg
        195                 200                 205

Asp Trp Ala Ala His Thr Ser Gly Arg Phe Thr Leu Thr Thr Tyr Pro
    210                 215                 220

Gly Gly His Phe Tyr Leu Asn Thr His Ala Pro Ala Val Ile Arg Ala
225                 230                 235                 240

Ile Ser Asp Ala Leu Arg Pro Ser Asp Leu His Ile Thr Gln
                245                 250

<210> SEQ ID NO 57
```

```
<211> LENGTH: 765
<212> TYPE: DNA
<213> ORGANISM: Amycolatopsis orientalis

<400> SEQUENCE: 57
gtggcggaca acgacgaggg actctgggta cgcaggttcc atcccgcgga cgacgcgccc      60
taccgcgtcg tctgtttccc gcacgccggg ggttccgcga gctatttctt cccggtctca     120
cggacgttga gccccgccgc cgacgtactc gcgatccagt accccggacg ccaggaccgg     180
cgtcacgaac cggggctcgc caccatcgcc gaactcgccg acggcgtcac cgaggcactc     240
ctgccgtggc tggaccggcc ggccgtcctt ttcggacaca gcatgggcgc gaccctcggc     300
ttcgaggtcg cccgccggct cgaagccgct gaagtgcggc cgcacgcgtt gttcgtctcc     360
gggcgcgtgg cacccagccg cgcccgcgac gagacggtcc accggcgcga cgacgcggga     420
ctcgtcgccg cggtgaagga actcggcggc accgacgccc aggtcttcga ggacgaagcg     480
atcctggaaa tggtgctgcc ctcgatccgg acggactaca ccgccgcgga gacctatcga     540
tacacgccgg gtcctctgtt gcaggcccccg atccacgccc atctcggcga aaacgacccg     600
aaggcgaccg tcgcgaggt ccgcgactgg gccgcgcaca cgtccgggcg gttcaccctg      660
accacgtatc ccggcgggca tttctacctg aacacccacg ccccggccgt gatccgggcc     720
atctcggacg ccttgcggcc gtccgacctc catatcaccc agtga                     765
```

POLYENE POLYKETIDES AND METHODS OF PRODUCTION

RELATED APPLICATIONS

This application claims priority to U.S. provisional application No. 60/501,821 filed Sep. 11, 2003, U.S. provisional application No. 60/574,922 filed May 28, 2004 and U.S. provisional application No. 60/581,707 filed Jun. 23, 2004, the entire contents of which are incorporated herein by reference.

FIELD OF THE INVENTION

This invention relates to novel biologically active polyene polyketides, their pharmaceutically acceptable salts and derivatives, and to methods of obtaining them. One method for obtaining the compounds is by cultivation of *Amycolatopsis orientalis* ATCC™ 43491, the *Amycolatopsis orientalis* species having accession number IDAC 220604-01, or a mutant or variant of strain ATCC™ 43491 or strain IDAC 220604-1. Another method of producing these polyene polyketides involves expression of the biosynthetic gene cluster of the invention in transformed host cells. Another method of producing these polyene polyketide is by post-biosynthesis chemical modifications. The present invention further relates to *Amycolatopsis orientalis* sp. strains IDAC 220604-01, to the use of the polyene polyketides and their pharmaceutically acceptable salts and derivatives as pharmaceuticals, in particular to their use as inhibitors of bacterial cell growth and to pharmaceutical compositions comprising a polyene polyketide of the invention or a pharmaceutically acceptable salt or derivative thereof. Finally, the invention relates to novel polynucleotide sequences and their encoded proteins, which are involved in the biosynthesis of the polyene polyketides of the invention.

BACKGROUND OF THE INVENTION

Polyketides are a diverse class of naturally occurring molecules typically produced by a variety of organisms, including fungi and mycelial bacteria, in particular actinomycetes. Although polyketides have widely divergent structures, they are classified together because they all share a common general biosynthetic pathway in which the carbon backbone of these molecules are assembled by sequential, step-wise addition of two carbon or substituted two carbon units referred to as ketides. Polyene polyketides comprise a chain of ketide units that have been strung together by a series of enzymatic reactions by multimodular polyketide synthase proteins.

Polyketides are usually found in their natural environment in trace amounts. Moreover, due to their structural complexity, poyketides are notoriously difficult to synthesize chemically. Nevertheless, many polyketides have been developed into effective drugs for the treatment of conditions such as bacterial and fungal infections, cancer and high cholesterol. Adriamycin, erythromycin, zocor and nystatin are but a few examples of polyketide molecules, which have been developed into valuable pharmaceuticals. Linearmycin A, having a 60 carbon chain and a degree of unsaturation of 15, is an example of a linear polyene polyketide reported to possess antifungal and antibacterial activity (Sakuda et al., *Tetrahedron Letters*. Vol. 36, No. 16, 2777-2870 (1995); Sakuda et al., *J. Chem Soc., Perkin Trans.* 1,2315-2319 (1996)).

Although large numbers of therapeutically important polyketides have been identified, there remains a need to obtain novel polyketides that have enhanced properties or possess completely novel bioactivities. The complex polyketides produced by modular Type I polyketide synthases (PKSs) are particularly valuable, in that they include compounds with known utility as antihelminthics, insecticides, immunosuppressants, cytotoxic, antifungal or antibacterial agents.

Because of their structural complexity, such novel polyketides are not readily obtainable by total chemical synthesis. The present invention addresses this need by providing a new class of polyketide compounds with therapeutic activity, together with means for their production. The compounds of the invention are prepared by fermentation or by fermentation followed by chemical modifications. The compounds of the invention may also be produced by appropriate application of recombinant DNA technology. A wide variety of polyketides can be prepared in a variety of different host cells provided one has access to nucleic acid compounds that encode PKS proteins and polyketide modification enzymes.

PKSs are large proteins that contain multiple enzymatic activities. PKSs catalyse the biosynthesis of polyketides through repeated, decarboxylative Claisen condensations between acylthioester building blocks, such as acetyl, butyryl, isobutyryl, propionyl, malonyl, hydroxymalonyl, methylmalonyl, and ethylmalonyl CoA.

PKS enzymes are generally classified into Type I or "modular" PKSs and Type II or "iterative" PKSs according to the polyketide synthetized and by the mode of synthesis. Type I PKSs are responsible for producing a large number of 12-, 14- and 16-membered macrolide antibiotics.

Type I or modular PKS enzymes are multifunctional proteins containing catalytic sites for acyl transferases (AT), acyl carrier protein (ACP), ketosynthase (KS), dehydratase (DH), and enoyl reductase (ER) activities. Type I enzymes are formed by a set of separate catalytic active sites for each cycle of carbon chain elongation and modification in the polyketide synthesis pathway. Each active site is termed a domain. A set of active sites or domains is termed a module. The typical modular PKS complex is composed of several large PKS polypeptides that act coordinately to achieve polyketide synthesis. Each PKS polypeptide can be segregated from amino to carboxy terminus into a loading module (found only in the first PKS polypeptide of the complex), multiple extender modules, and a releasing or thioesterase (TE) domain (generally found only in the final module of the terminal PKS polypeptide of the complex).

Generally, the loading module is responsible for binding the first building block used to synthesize the polyketide and transferring it to the first extender module. The AT domain of the loading module recognizes a particular acyl-CoA (usually acetyl or propionyl but sometimes butyryl, isobutyryl or other acyl-CoA) and transfers it as a thiol ester to the ACP domain of the loading module. The loading module may not encode a KS domain, or may encode a KS(Q) domain, a KS-like domain that carries an amino acid substitution at the active site cysteine residue (typically a glutamine residue, single letter code Q). KS(Q) domains decarboxylate the acylthioester of the loading domain before proceeding with chain elongation. For example, the loader module of the oleandomycin PKS complex initiates deoxyoleandolide synthesis by loading the ACP with a malonyl unit and performing a decarboxylation to generate acetyl-ACP (Shah, (2000), *J. Antibiotics*, Vol. 53, pp. 502-508).

The AT domain on each of the extender modules recognizes a particular extender-CoA (typically malonyl or alpha-substituted malonyl, i.e. methylmalonyl, ethylmalonyl, and 2-hydroxymalonyl) and transfers it to the ACP domain of that extender module to form a thioester. Each extender module is responsible for accepting a compound from a prior module, binding a building block, attaching the building block to the compound from the prior module, optionally performing one or more additional functions, and transferring the resulting compound to the next module.

Each extender module of a modular PKS contains a KS, AT, ACP, and zero, one, two or three domains that modify the beta-carbon of the growing polyketide chain. A typical (non-loading) minimal Type I PKS extender module may contain a KS domain, an AT domain, and an ACP domain. Such domains are sufficient to activate a 2-carbon extender unit and attach it to the growing polyketide molecule. The next extender module, in turn, is responsible for attaching the next building block and transferring the growing compound to the next extender module until synthesis of the polyketide is complete.

Once the PKS is primed with acyl- and malonyl-ACPs, the acyl group of the loading module is transferred to form a thiol ester (trans-esterification) at the KS of the first extender module; at this stage, extender module one possesses an acyl-KS and a malonyl (or substituted malonyl)-ACP. The acyl group derived from the loading module is then covalently attached to the alpha-carbon of the malonyl group to form a carbon-carbon bond, driven by concomitant decarboxylation, and generating a new acyl-ACP that carries a backbone two carbons longer than the loading building block (elongation or extension) and side chains if a substituted malonyl unit is used for extension.

The polyketide chain, growing by two or more carbons with each extender module, is sequentially passed as covalently bound thiol esters from extender module to extender module, in an assembly line-like process. The carbon chain produced by this process alone would possess a ketone at every other carbon atom, producing a polyketone, from which the name polyketide arises. Most commonly, however, additional enzymatic activities modify the beta keto group of each two carbon unit just after it has been added to the growing polyketide chain but before it is transferred to the next module.

After traversing the final extender module, the polyketide encounters a releasing domain (TE) that cleaves the polyketide from the PKS and typically cyclizes the polyketide. Further, tailoring enzymes can modify the polyketide; these tailoring enzymes add carbohydrate groups, methyl groups, or make other modifications, i.e. oxidation or reduction, on the polyketide core molecule.

Type I PKSs displays a one-to-one correlation between the number and clustering of active sites in the primary sequence of the PKS and the structure of the polyketide backbone. The activities catalyzed by the domains within a type I PKS are often apparent in the structure of the growing polyketide chain; consequently, nucleotide sequence has become a predictive tool for deducing the biosynthetic route for these compounds (Rangaswamy et al, *Proc. Natl. Acad. Sci. USA*, (1998) Vol. 95, pp. 15469-15474).

In Type I PKS polypeptides, the order of catalytic domains is conserved. When all beta-keto processing domains are present in a module, the order of domains in that module from N-to-C-terminus is always KS, AT, DH, ER, KR, and ACP. Some or all of the beta-keto processing domains may be missing in particular modules, but the order of the domains present in a module remains the same. The order of domains within modules is believed to be important for proper folding of the PKS polypeptides into an active complex. Importantly, there is considerable flexibility in PKS enzymes, this flexibility provides a means for genetically engineering novel catalytic complexes. By manipulating the polynucleotide sequences encoding the PKS polypeptide, genetically engineered novel PKSs can be achieved. Genetically engineering PKS enzymes can be achieved by the modification, addition or deletion of domains, or by replacing domains with domains taken from other Type I PKS enzymes. As well, this can also be achieved by deletion, addition or replacement of entire modules with modules taken from other sources. A genetically engineered PKS complex should, of course, have the ability to catalyze the synthesis of the product predicted from the genetic alterations made. Alignment of the many available amino acid sequences for Type I PKS enzymes has approximately defined the boundaries of the various catalytic domains. Sequence alignments also have revealed linker regions between the catalytic domains and at the N- and C-termini of individual PKS polypeptides. The sequences of these linker regions are less well conserved than are those for the catalytic domains, which is in part how linker regions are identified. Linker regions can be important for proper association between domains and between the individual polypeptides that comprise the PKS complex. One can thus view the linkers and domains together as creating a scaffold on which the domains and modules are positioned in the correct orientation to be active. This organization and positioning, if retained, permits PKS domains of different or identical substrate specificities to be substituted (usually at the DNA level) between PKS enzymes by various available methodologies. In selecting the boundaries of, for example, an AT domain replacement, one can thus make the replacement so as to retain the linkers of the recipient PKS or to replace them with the linkers of the donor PKS AT domain, or, preferably, make both constructs to ensure that the correct linker regions between the KS and AT domains have been included in at least one of the engineering enzymes. Thus, there is considerable flexibility in the design of new PKS enzymes with the result that known polyketides can be produced more effectively, and novel polyketides can be made.

SUMMARY OF THE INVENTION

In one aspect of this embodiment the invention relates to novel polyene polyketides Compounds 1, 2, 3, 4, 5, 6 and 7:

Compound 1

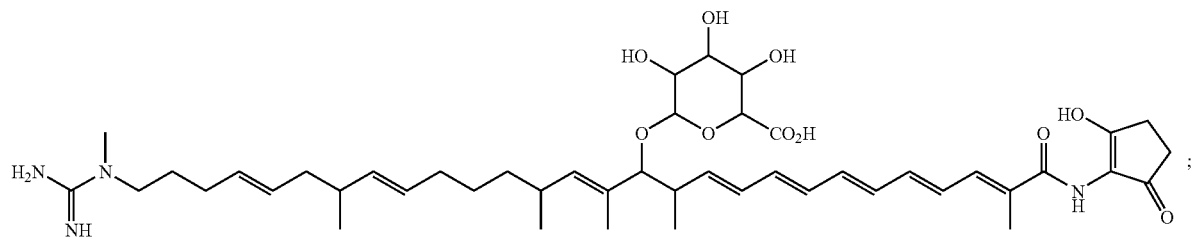

-continued

Compound 2

Compound 3

Compound 4
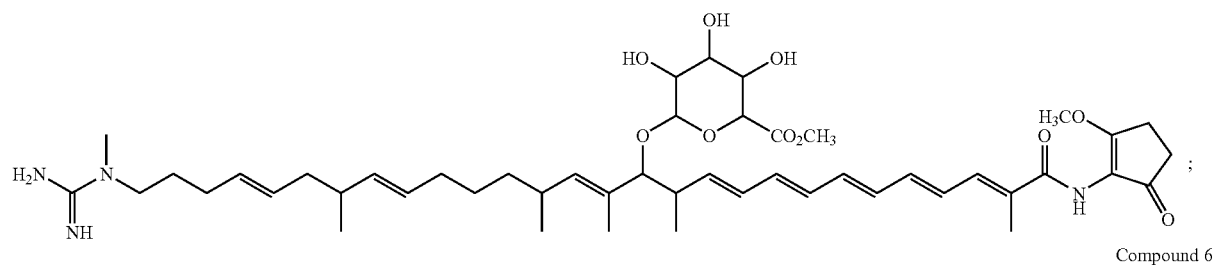
Compound 5
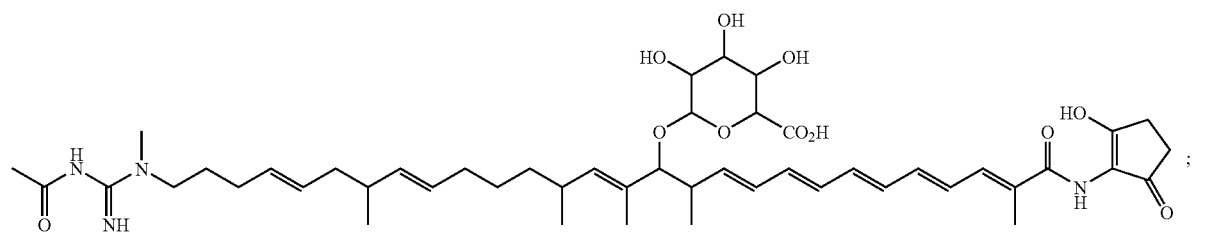
Compound 6
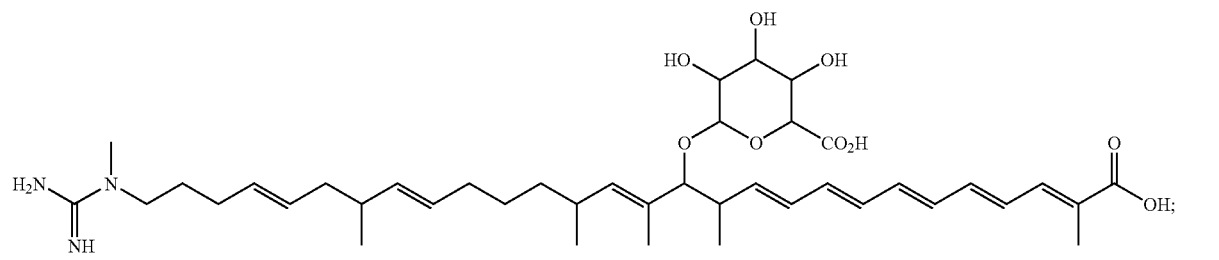
Compound 7
or a pharmaceutically acceptable salt or prodrug thereof.

In another aspect the invention provides polyene polyketides of Formula I, as illustrated below, which compounds may be derived by chemical modification of Compounds 1 to 7.

Formula I

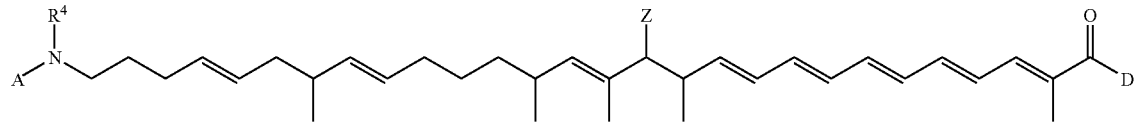

wherein,
A is selected from —C(NH)NHR$^1$, CH$_3$, H or

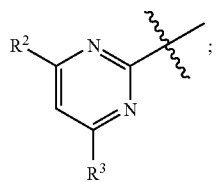

R$^1$ is selected from H, C$_{1-6}$alkyl, C$_{6-10}$aryl, C(O)C$_{1-6}$alkyl and C(O)C$_{6-10}$aryl;
R$^2$ and R$^3$ are each independently selected from H, C$_{1-6}$ alkyl, C$_{2-7}$ alkene and C$_{6-10}$ aryl;
R$^4$ is selected from H or CH$_3$;
Z is OH or O when taken with adjacent carbon atom to form a carbonyl; or
Z may be a tetrahydropyranoxy of formula:

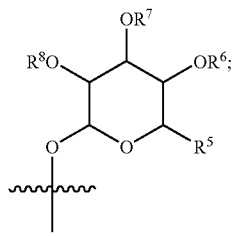

R$^5$ is selected from H, COOH, C$_{1-6}$ alkyl or C(O)OC$_{1-6}$ alkyl;
R$^6$, R$^7$ and R$^8$ are each independently selected from H, C$_{1-6}$ alkyl and C(O)C$_{1-6}$ alkyl; or
R$^6$, R$^7$ and R$^8$ may each independently be absent when the adjacent oxygen and carbon atoms are taken together to form a carbonyl; or
R$^6$, R$^7$ and R$^8$ may each independently be a bond when any of two neighboring R$^6$, R$^7$ and R$^8$ are taken together with attached oxygen and carbon atoms to form a 1,3-dioxolane ring of formula:

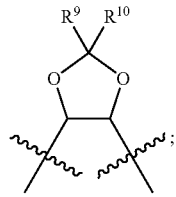

R$^9$ and R$^{10}$ are each independently selected from H, C$_{1-6}$ alkyl, C$_{2-7}$ alkene and C$_{6-10}$ aryl; or
R$^9$ and R$^{10}$ are taken together with adjacent carbon atom to form a ring having from 5 to 7 carbons;

D is selected from OH, NH$_2$, NH(C$_{1-3}$alkyl), N(C$_{1-3}$alkyl)$_2$, OC$_{1-3}$alkyl or

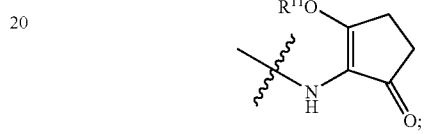

R$^{11}$ is selected from H or C$_{1-3}$ alkyl;

or a pharmaceutically acceptable salt or prodrug thereof.

In one embodiment the invention provides compounds of Formula I, wherein A is —C(NH)NH$_2$; and all other groups are as previously defined; or a pharmaceutically acceptable salt or prodrug thereof.

In a further embodiment of the invention provides compounds of Formula I, wherein A is H; and all other groups are as previously defined; or a pharmaceutically acceptable salt or prodrug thereof.

In a further embodiment the invention provides compounds of Formula I, wherein A is —C(NH)NHC(O)CH$_3$; and all other groups are as previously defined; or a pharmaceutically acceptable salt or prodrug thereof.

In a further embodiment the invention provides compounds of Formula I, wherein A is

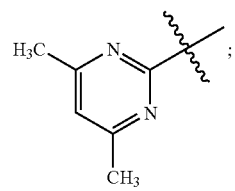

and all other groups are as previously defined; or a pharmaceutically acceptable salt or prodrug thereof.

In a further embodiment the invention provides compounds of Formula I, wherein R$^4$ is CH$_3$; and all other groups are as previously defined; or a pharmaceutically acceptable salt or prodrug thereof.

In a further embodiment the invention provides compounds of Formula I, wherein R$^4$ is H; and all other groups are as previously defined; or a pharmaceutically acceptable salt or prodrug thereof.

In a further embodiment the invention provides compounds of Formula I, wherein Z is

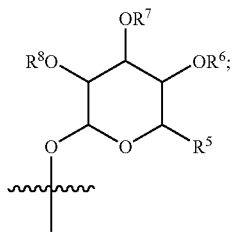

and all other groups are as previously defined; or a pharmaceutically acceptable salt or prodrug thereof. In a subclass of this embodiment $R^6$, $R^7$ and $R^8$ are each H, and $R^5$ is COOH, all other groups are as previously defined; or a pharmaceutically acceptable salt or prodrug thereof.

In a further embodiment the invention provides compounds of Formula I, wherein Z is

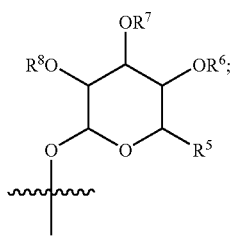

and all other groups are as previously defined; or a pharmaceutically acceptable salt or prodrug thereof. In a subclass of this embodiment $R^6$, $R^7$ and $R^8$ are each H, and $R^5$ is $CO_2CH_3$, all other groups are as previously defined; or a pharmaceutically acceptable salt or prodrug thereof.

In a further embodiment the invention provides compounds of Formula I, wherein Z is OH and all other groups are as previously defined; or a pharmaceutically acceptable salt or prodrug thereof.

In a further embodiment the invention provides compounds of Formula I, wherein D is

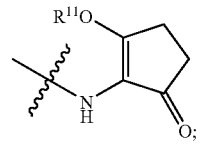

and all other groups are as previously defined; or a pharmaceutically acceptable salt or prodrug thereof. In a subclass of this embodiment $R^{11}$ is H and all other groups are as previously defined; or a pharmaceutically acceptable salt or prodrug thereof.

In a further embodiment the invention provides compounds of Formula I, wherein D is

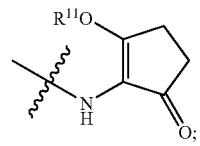

and all other groups are as previously defined; or a pharmaceutically acceptable salt or prodrug thereof. In a subclass of this embodiment $R^{11}$ is $CH_3$ and all other groups are as previously defined; or a pharmaceutically acceptable salt or prodrug thereof.

In another embodiment the invention provides compounds of Formula I, wherein D is OH; and all other groups are as previously defined; or a pharmaceutically acceptable salt or prodrug thereof.

The following are exemplary compounds of the invention:

Compound 1

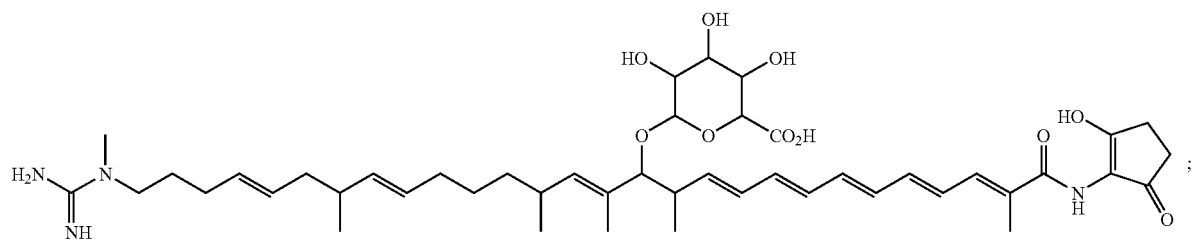

Compound 2

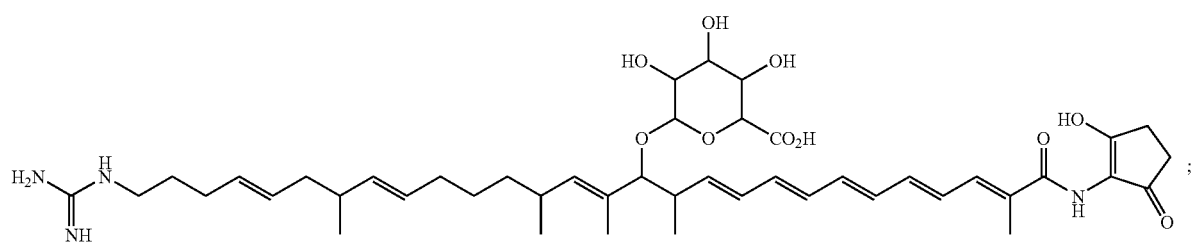

Compound 3
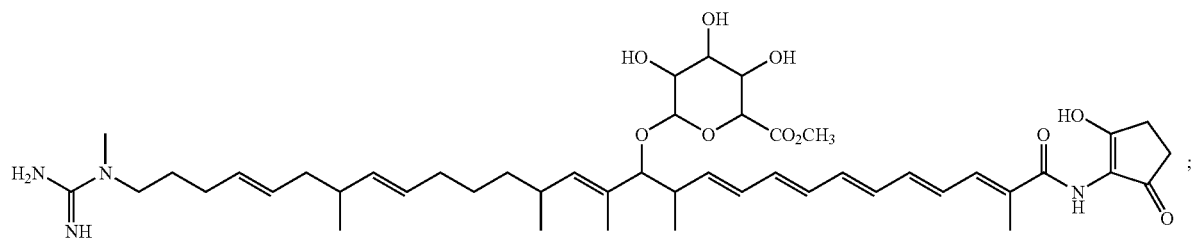
Compound 4
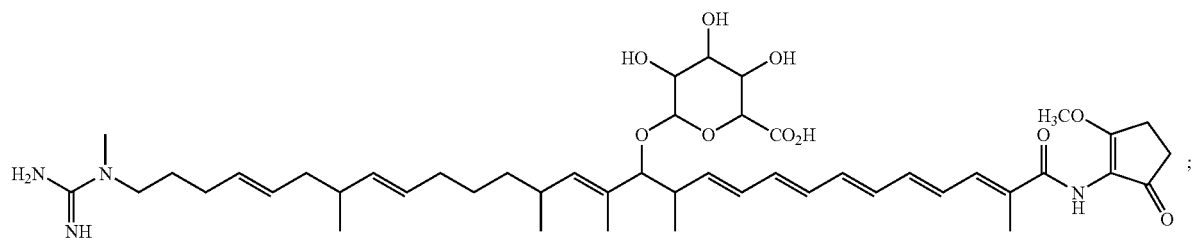
Compound 5
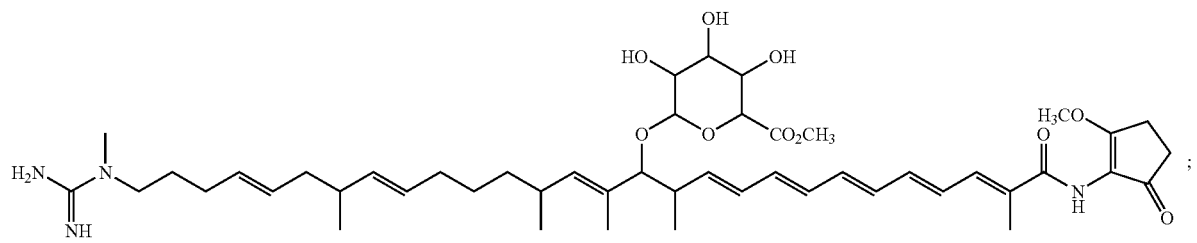
Compound 6
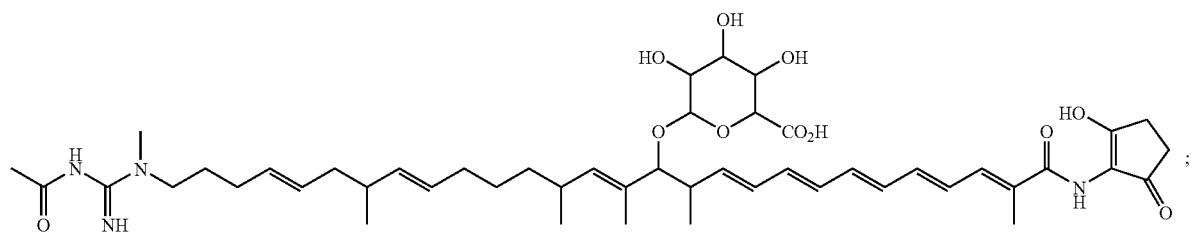
Compound 7
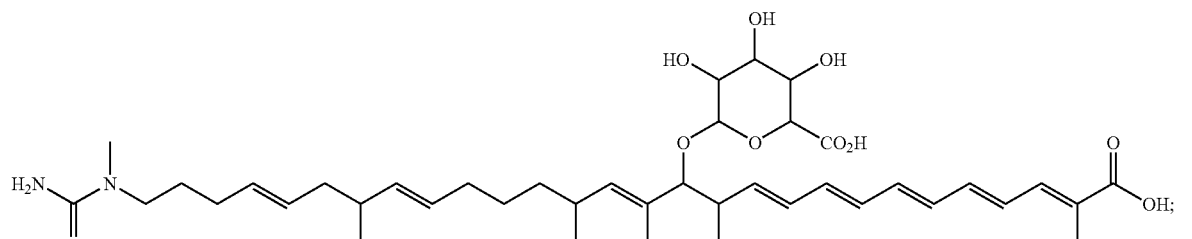
Compound 8
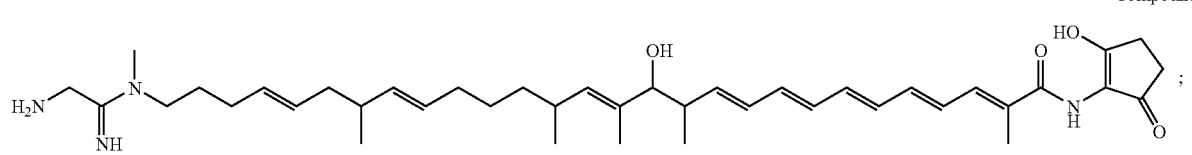

-continued
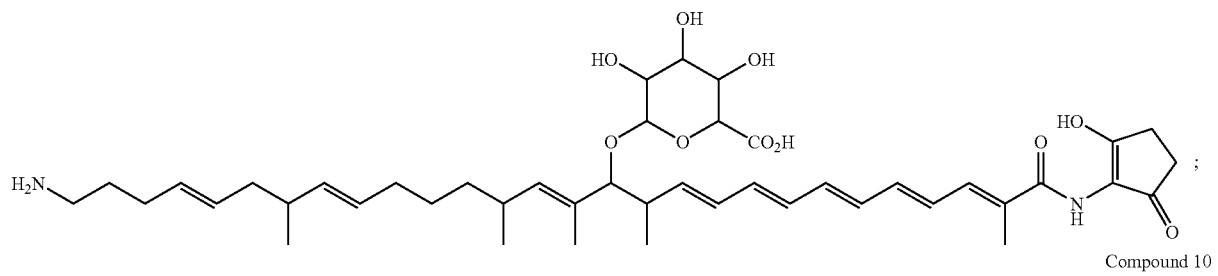
Compound 9;
Compound 10
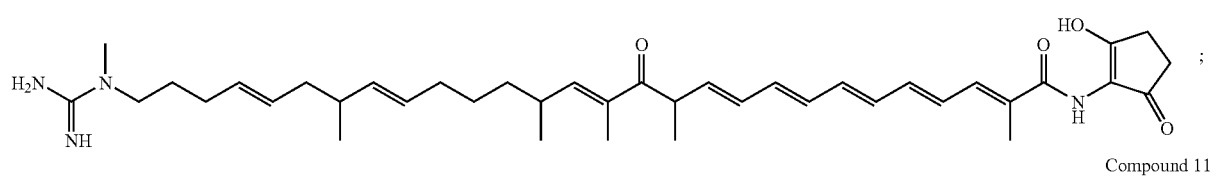
Compound 11;
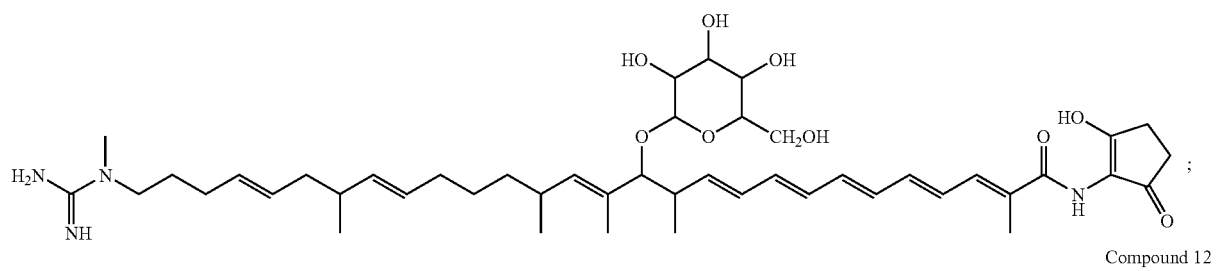
Compound 12;
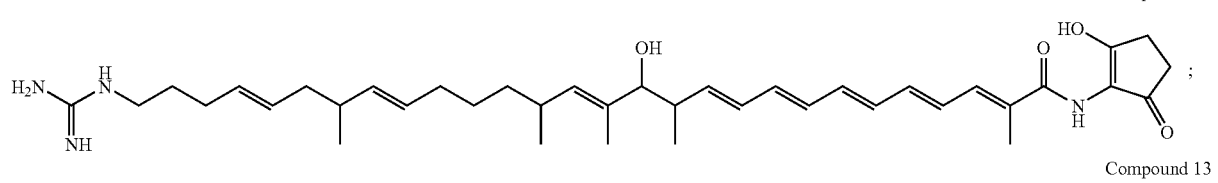
Compound 13;

Compound 14;
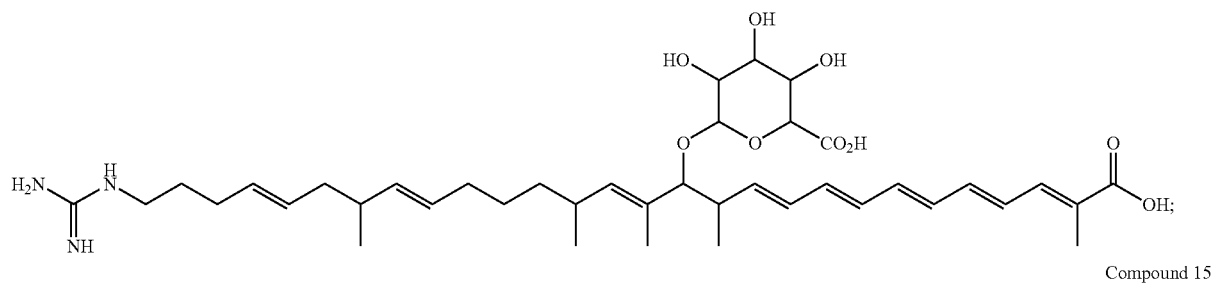
Compound 15;
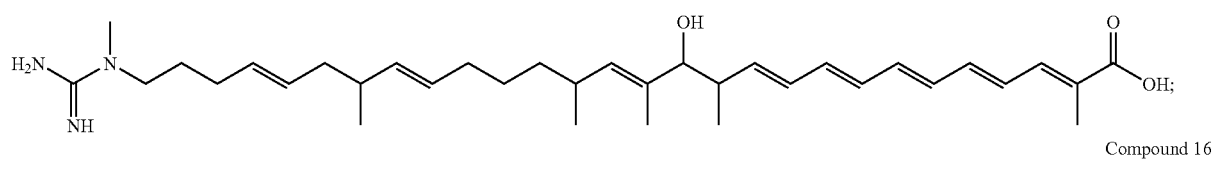
Compound 16;
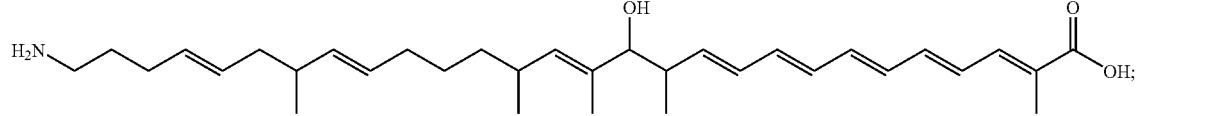

-continued
Compound 17
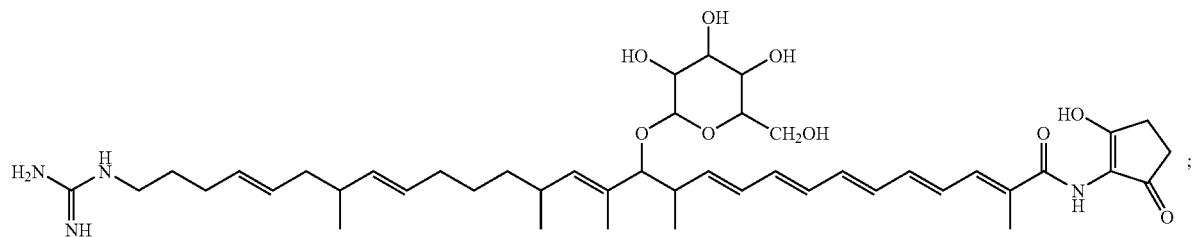
Compound 18
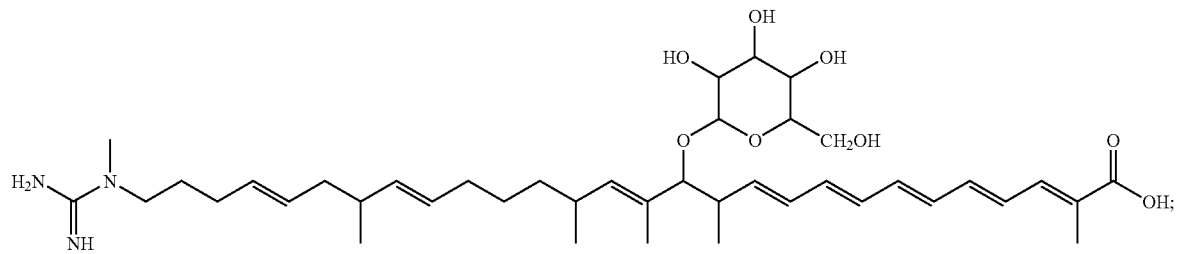
Compound 19
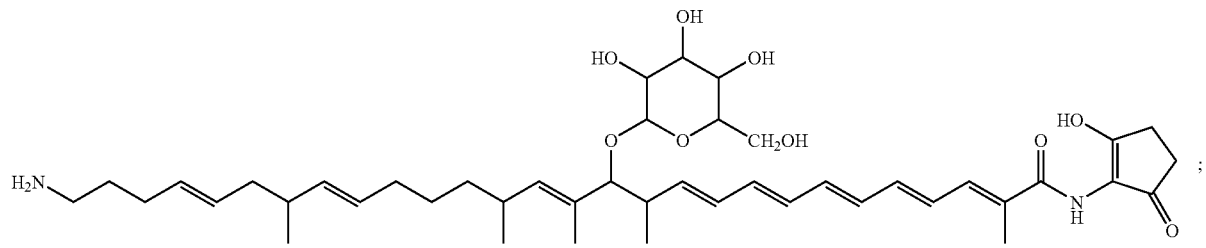
Compound 20
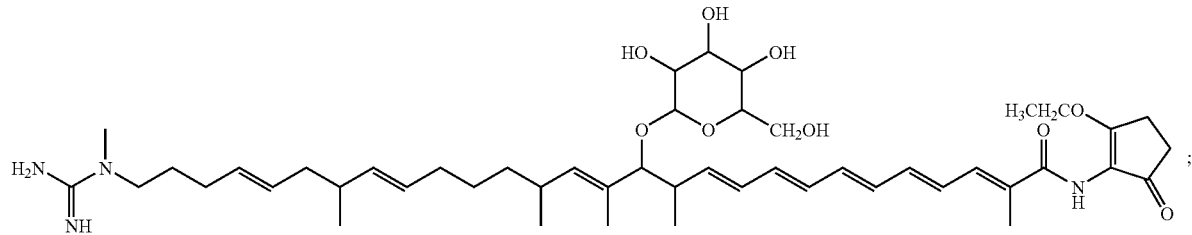
Compound 21
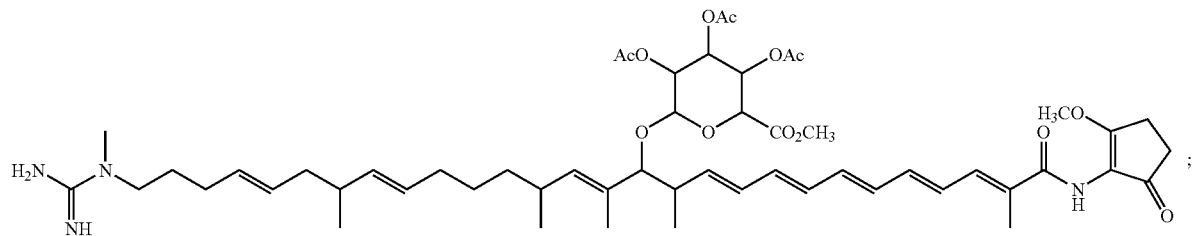

-continued
Compound 22
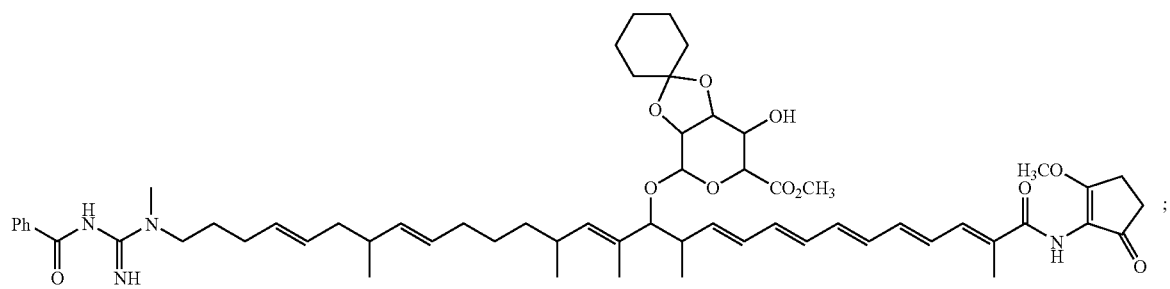
Compound 23
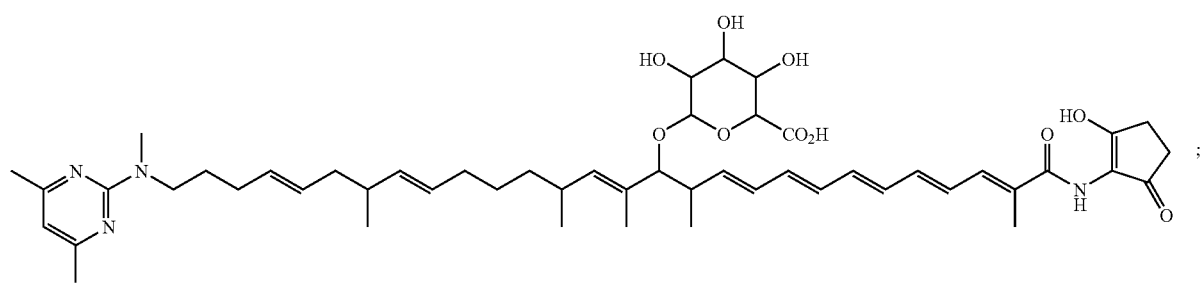
Compound 24
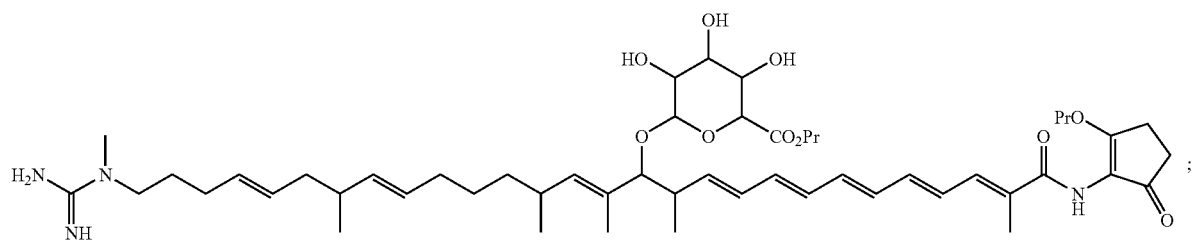
Compound 25
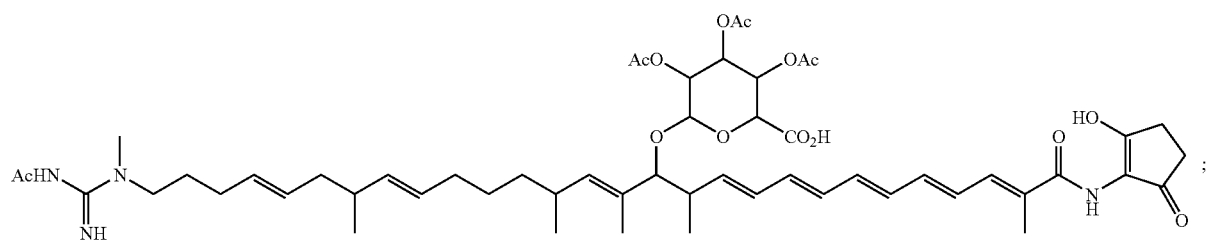
Compound 26
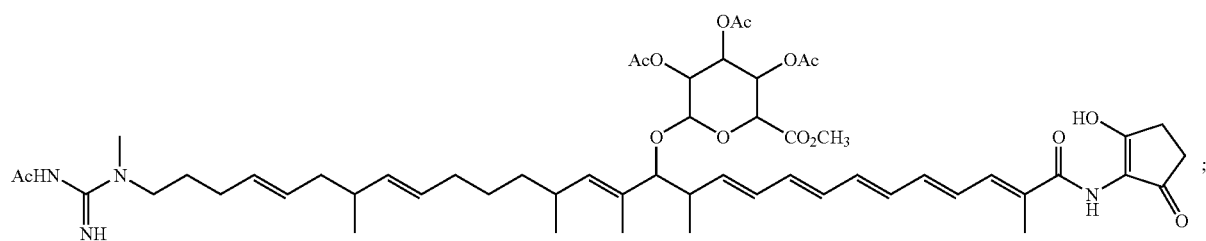

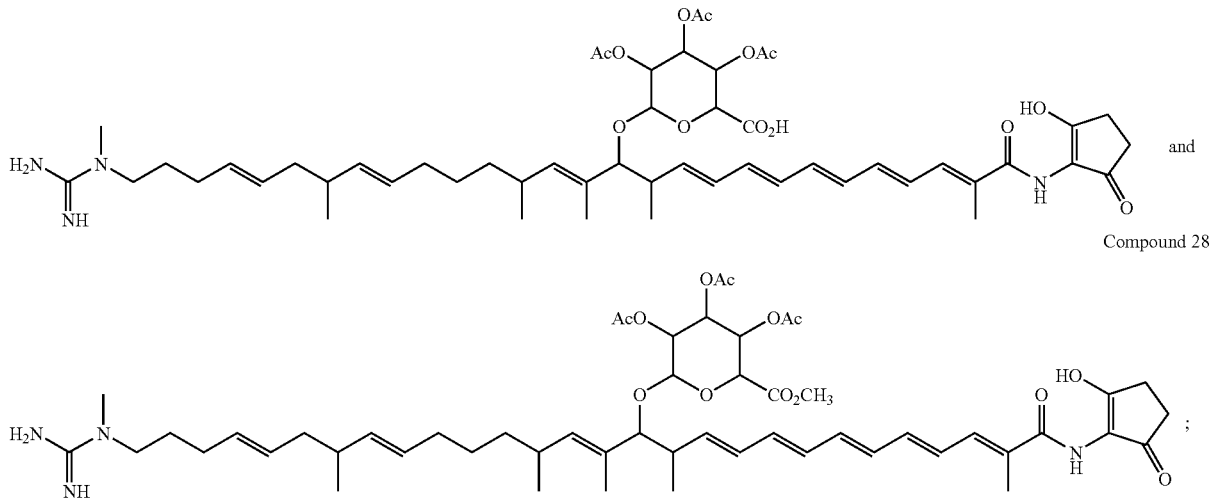

Compound 27

Compound 28 or a pharmaceutically acceptable salt or prodrug of any one of Compound 1-28.

In a further aspect, the invention relates to a pharmaceutical composition comprising of a compound of Formula I, or a pharmaceutically acceptable salt or prodrug thereof, with a pharmaceutically acceptable carrier.

In an additional embodiment the invention relates to pharmaceutical compositions of polyene polyketides of the invention, comprising a therapeutically effective amount of the compound of Formula I, or a pharmaceutically acceptable salt or prodrug thereof, and a pharmaceutically acceptable carrier.

The present invention further encompasses methods for producing the compounds of Formula I and related compounds, the method comprising: (a) cultivating *Amycolatopsis* sp. strain under aerobic conditions in a nutrient medium comprising at least one source of carbon atoms and at least one source of nitrogen atoms, (b) isolating a compound of Formula I, from the bacteria cultivated in (a). In an aspect of the invention, the *Amycolatopsis orientalis* strain useful in the methods of the invention may be ATCC™ 43491 or a mutant thereof. In another embodiment, the strain is the *Amycolatopsis orientalis* strain deposited at the International Depositary Authority of Canada (IDAC), Bureau of Microbiology, Health Canada, 1015 Arlington Street, Winnipeg, Manitoba, Canada R3E 3R2, and having accession no. 220604-01. In another aspect of the invention, the method of producing the compounds of Formula I comprises:

(a) and (b) as described above and (c) chemically modifying the compound isolated in (b). In a further embodiment, the polyene polyketide generates a ¹H NMR spectra essentially as shown in any one of FIGS. 4 to 10. In a further embodiment, the polyene polyketide is any one of Compounds 1 to 7. In a further embodiment, the nutrient medium is selected from the media of Table 1.

The invention further provides a process for producing a polyene polyketide of the invention comprising cultivation of an *Amycolatopsis* strain in a nutrient medium comprising at least one source of carbon atoms and at least one source of nitrogen atoms, and isolation and purification of the polyene polyketide. In another embodiment, the strain is an *Amycolatopsis orientalis*. In a further embodiment, the strain is *Amycolatopsis orientalis* ATCC™ 43491 or a mutant thereof. In a further embodiment, the strain is the *Amycolatopsis orientalis* strain having accession no. 220604-01 deposited at the International Depositary Authority of Canada. In one embodiment, the carbon and nitrogen atoms sources are chosen from the components of Table 1. In a further embodiment, the nutrient medium is selected from the media of Table 1. In a further embodiment, the cultivation is carried out under aerobic conditions. In another embodiment, the cultivation is carried out at a temperature ranging from about 18° C. to about 40° C. In another embodiment, the temperature range is 18° C. to 29° C. In another embodiment, the cultivation is carried out at a pH ranging from about 6 to about 9.

The invention further provides polyene polyketides of Formula I that are a derivative or structural analog of any one of Compounds 1 to 7. In one embodiment the polyene polyketides of Formula I are produced by post-biosynthesis chemical modification of any one of Compounds 1 to 7. In another embodiment, the polyene polyketides generate a ¹H NMR spectra essentially as shown in any one of FIGS. 4 to 10.

The invention further provides an *Amycolatopsis orientalis* strain having accession no. 220604-01 deposited at the International Depositary Authority of Canada.

The invention further provides Compounds 1 to 7, compounds of Formula I, or pharmaceutically acceptable salts or prodrugs thereof, for use as pharmaceuticals for the treatment of a bacterial infection in a subject. In another aspect, the invention provides the use of any one of Compounds 1 to 7, compounds of Formula I, or pharmaceutically acceptable salts or prodrugs thereof, for the manufacture of a medicament for the treatment of a bacterial infection in a subject.

The invention also provides methods of inhibiting bacterial cell growth, which comprise contacting said bacterial cell with a compound of Formula I, or a pharmaceutically acceptable salt or prodrug thereof. The invention further encompasses methods for treating a bacterial infection in a subject, comprising administering to said subject suffering from said bacterial infection, a therapeutically effective amount of a compound of Formula I, or a pharmaceutically acceptable salt or prodrug thereof. Examples of bacteria organisms that may be treated or inhibited according to the methods of the invention include: *Streptococcus pneumoniae, Streptococcus pyogenes, Enterococcus faecalis, Enterococcus faecium, Klebsiella pneumoniae, Enterobacter* spp., *Proteus* spp., *Pseudomonas aeruginosa, E. coli, Serratia marcesens, Staphylococcus aureus,* Coagulase negative *Staphylococcus, Haemophilus infuenzae, Bacillus anthracis, Mycoplasma pneumoniae,* and *Staphylococcus epidermidis.*

The present invention also provides the biosynthetic locus responsible for producing the compounds of Formula I. Thus the invention provides polynucleotides and polypeptides useful in the production and engineering of compounds of Formula I.

The present invention provides recombinant DNA vectors that encode all or part of the PKS enzymes useful for the production of polyketide compounds of Formula I. The invention also provides nucleic acid compounds that encode the specific domains of the PKS system useful for the production of polyketides of compound of Formula I. The recombinant DNA vectors, PKS enzymes, PKS systems and nucleic acid compounds encoding the domains of the PKS systems of the invention can be readily used, alone or in combination with nucleic acids encoding other PKS domains, as intermediates in the construction of recombinant vectors that encode all or part of PKS enzymes that make novel polyketides selected from the compounds of Formula I.

The invention also provides isolated nucleic acids that encode all or part of one or more modules of the PKSs of the invention, each module comprising a ketosynthase activity, an acyl transferase activity, and an acyl carrier protein activity. The invention also provides isolated nucleic acids that encode all or part of a PKS loader module comprising an acyl transferase activity and an acyl carrier protein activity. The invention provides an isolated nucleic acid that encodes one or more open reading frames of PKS genes of the invention. The invention also provides recombinant expression vectors containing these nucleic acids.

The invention provides a method of preparing polyketide compounds of Formula I, said method comprising transforming a host cell with a recombinant DNA vector that encodes at least one module of a PKS, said method comprising transforming a host cell with a recombinant DNA vector that encodes at least one module of a PKS, said module comprising at least one PKS domain of the invention, and culturing said host cell under conditions such that said PKS is produced and catalyzes synthesis of said polyketide. The invention also provides a method of preparing polyketide compounds of Formula I, said method comprising transforming a host cell with a recombinant DNA vector that encodes at least one gene of the invention, and culturing said host cell under conditions such that said polyketide is produced. In one aspect, the method is practiced with a *Streptomyces* host cell. In another aspect, the polyketide produced is a compound of Formula I. In another aspect, the polyketide produced is a polyketide related in structure to a compound described in any one of Examples 17 to 20.

The invention provides a set of genes in recombinant form sufficient for the synthesis of a compound of Formula I in a heterologous host cell. These genes and the methods of the invention enable one to create recombinant host cells with the ability to produce polyketides.

The invention provides recombinant PKS genes that produce a variety of polyketides that cannot be readily synthesized by chemical methodology alone. Moreover the present invention provides polyketides, some of which are produced only by fermentation and others of which are produced by fermentation and chemical modification. The invention allows direct manipulation of the genes and proteins for production of the compounds of Formula I via genetic engineering of the enzymes involved in the biosynthesis of a polyketide according to the invention.

The present invention provides recombinant DNA vectors that encode all or part of the PKS enzymes useful for the production of a polyketide of Formula I. The invention also provides nucleic acid compounds that encode the various domains of PKS systems useful for the production of a polyketide of Formula I. The recombinant DNA vectors, PKS enzymes, PKS systems and nucleic acid compounds encoding the domains of the PKS systems of the invention can be readily used, alone or in combination with nucleic acids encoding other PKS domains, as intermediates in the construction of recombinant vectors that encode all or part of PKS enzymes that make novel polyketides selected from the compounds of Formula I.

The invention also provides isolated nucleic acids that encode all or part of one or more modules of the PKSs of the invention, each module comprising a ketosynthase activity, an acyl transferase activity, and an acyl carrier protein activity. The invention also provides isolated nucleic acids that encode all or part of a PKS loader module comprising an acyl transferase activity and an acyl carrier protein activity. The invention provides an isolated nucleic acid that encodes one or more open reading frames of PKS genes of the invention. The invention also provides recombinant expression vectors containing these nucleic acids.

The invention provides a method of preparing a polyketide of Formula I, said method comprising transforming a host cell with a recombinant DNA vector that encodes at least one module of a PKS, said method comprising transforming a host cell with a recombinant DNA vector that encodes at least one module of a PKS, said module comprising at least one PKS domain from the PKS system of the invention, and culturing said host cell under conditions such that said PKS is produced and catalyzes synthesis of said polyketide. In one aspect, the method is practiced using an *Amycolatopsis orientalis* organism for homologous expression of the modified endogenous gene cluster. In another aspect, the method is practiced with a *Streptomyces* host cell. The invention further provides a set of genes in recombinant form sufficient for the synthesis of a compound of Formula I. In one aspect the genes reside in an *Amycolatopsis orientalis* organism for homologous expression of the endogenous gene cluster. In another aspect, a *Streptomyces* host cell is transformed with a recombinant DNA vector containing the set of genes.

Thus, the invention provides recombinant PKS genes that produce a variety of polyketides that cannot be readily synthesized by chemical methodology alone. Moreover the present invention provides polyketides, some of which are produced only by fermentation and others of which are produced by fermentation and chemical modification.

BRIEF DESCRIPTION OF THE DRAWINGS

FIGS. 12 to 18: multiple amino acid alignments comparing the domains of the polyketide synthase system of the biosynthetic locus for the production of the compounds of Formula I, wherein the asterisks (*) indicate positions which have a single, fully conserved residue, colons (:) indicate that one of the following strong groups is fully conserved: STA, NEQK, NHQK, NDEQ, QHRK, MILV, MILF, HY, and FYW, and periods (.) indicate that one of the following weaker groups is fully conserved: CSA, ATV, SAG, STNK, STPA, SGND, SNDEQK, NDEQHK, NEQHRK, FVLIM, and HFY.

FIGS. 12a and 12b: amino acid alignment comparing the twelve ketosynthase (KS) domains present in the polyketide synthase (PKS) system of ORFs 18 to 23 (SEQ ID NOS: 37, 39, 41, 43, 45 and 47). The boundaries and key residues of the KS domains were chosen as described by Kakavas et al., *J. Bacteriol.*, 179, 7515-7522 (1997) and indicated in black.

FIGS. 13a, 13b and 13c: amino acid alignment comparing the twelve acyl transferase (AT) domains present in the polyketide synthase system of ORFs 18 to 23 (SEQ ID NOS: 37, 39 41, 43, 45 and 47). The boundaries and key residues of the AT domains were chosen as described by Kakavas et al., supra and indicated in black.

FIG. 14: amino acid alignment comparing the eleven dehydratase (DH) domains present in the polyketide synthase system of ORFs 18 to 23 (SEQ ID NOS: 37, 39, 41, 43, 45 and 47). The boundaries and key residues of the DH domains were chosen as described by Kakavas et al. supra and indicated in black.

FIG. 15: amino acid alignment comparing the three enoyl reductase (ER) domains present in ORFs 18 and 19 (SEQ ID NOS: 37 and 39) with the ER domains from modules 5 and 15 of the nystatin biosynthetic locus as described by Brautaset et al., *Chem. Biol.*, 7, 395-403 (2000). The boundaries and key residues of the ER domain were chosen as described by Kakavas et al. supra and indicated in black.

FIG. 16: amino acid alignment comparing the twelve ketoreductase (KR) domains present in ORFs 18 to 23 (SEQ ID NOS: 37, 39, 41, 43, 45 and 47). The boundaries and key residues of the KR domains were chosen as described by Kakavas et al. supra, and Fisher et al. *Structure Fold Des.*, 8, 339-347 (2000) and indicated in black.

FIG. 17: amino acid alignment comparing the thirteen acyl carrier proteins (ACP) domains present in ORFs 18 to 23 (SEQ ID NOS: 37, 39, 41, 43, 45 and 47). The boundaries and key serine residues of the ACP domains were chosen as described by Kakavas et al. supra and indicated in black.

FIG. 18: amino acid alignment comparing the TE domain present in ORF 23 (SEQ ID NO: 47) with the TE domain from module 7 in the nystatin biosynthetic locus as described by Brautaset et al. supra. The boundaries and key residues of the TE domain were chosen as described by Kakavas et al. supra and indicated in black.

FIG. 20a: biosynthesis of the 4-guanidino butyryl-CoA component of compounds of Formula I from arginine and involving ORF 7 (SEQ ID NO: 14) and ORF 25 (SEQ ID NO: 52). FIG. 20b: biosynthesis of the polyketide core structure of compounds of Formula I involving the polyketide synthase system of ORFs 18 to 23 (SEQ ID NOS: 37, 39, 41, 43, 45 and 47) and incorporation of the 4-guanidino butyryl-CoA component of FIG. 20a using ORF 24 (SEQ ID NO: 50).

FIG. 22a: inactivation of the glycosyltransferase gene (SEQ ID NO: 30) disrupting the transfer of the sugar moiety onto the backbone of the polyketide core and producing the non-glycosylated Compound 8. FIG. 22b: inactivation of sugar oxidoreductase gene product of ORF 13 (SEQ ID NO: 28) followed by transfer of the glucose onto the polyketide backbone chain by the glycosyltransferase gene product of ORF 14 (SEQ ID NO: 29) producing Compound 11.

DETAILED DESCRIPTION OF THE INVENTION

Figure 1:
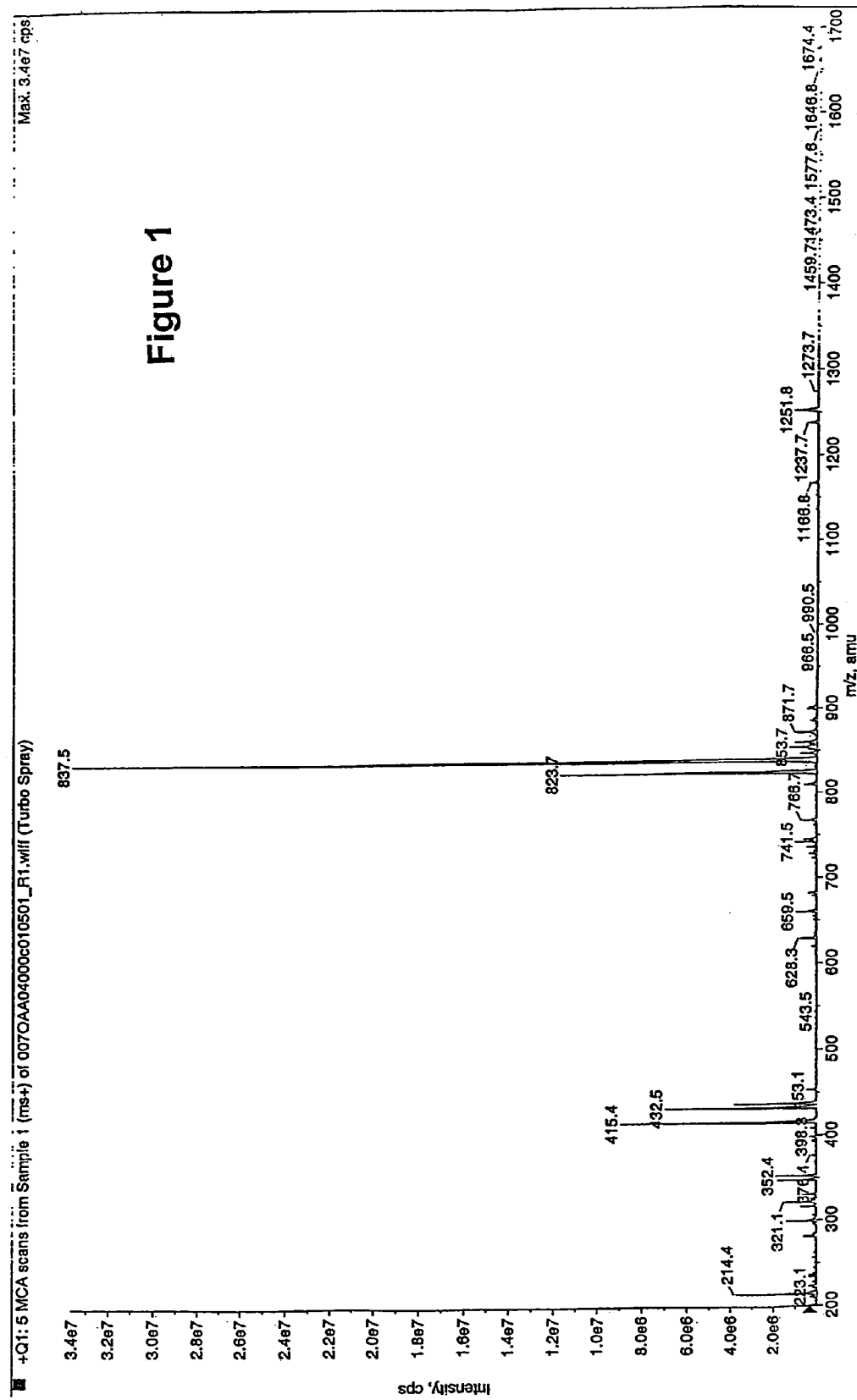
FIG. 1: Electrospray mass spectrum (Positive Ion Mode) of Compound 1.

The present invention relates to novel polyene polyketides, exemplified herein as Compound 1, Compound 2 and Compound 7, which are isolated from strains of actinomycetes, *Amycolatopsis* sp. such as *Amycolatopsis orientalis* ATCC™ 43491, or a mutant or a variant thereof.

The invention further relates to pharmaceutically acceptable salts and derivatives of Compound 1, Compound 2 and Compound 7, and to methods for obtaining such compounds. One method of obtaining the compounds is by cultivating *Amycolatopsis orientalis* ATCC™ 43491, or a mutant or a variant thereof, under suitable *Amycolatopsis* sp. culture conditions preferably using the fermentation protocol described herein below.

The invention also relates to polyene polyketides of Formula I, exemplified herein as Compounds 3, 4, 5 and 6, produced from Compound 1, Compound 2 or Compound 7 by selective chemical modification of Compound 1, Compound 2 or Compound 7 using techniques described herein and well known to those skilled in the synthesis of natural products.

The present invention also relates to pharmaceutical compositions comprising a polyene polyketide selected from any one of Compounds 1 to 7, pharmaceutically acceptable salts or prodrugs of any one of Compounds 1 to 7, and derivatives of any one of Compounds 1 to 7 as defined by Formula I. In another aspect of the invention, Compounds 1 to 7 are each useful as antibacterial agents, and for use as inhibitors of bacterial cell growth. Accordingly, in an aspect the present invention relates to pharmaceutical compositions comprising any one of Compounds 1 to 7 of the invention together with a pharmaceutically acceptable carrier and methods of using the compositions as antibacterial agents to inhibit bacterial cell growth.

The following detailed description discloses how to make and use any of Compounds 1 to 7, compounds of Formula I and compositions containing these compounds to inhibit microbial growth.

Accordingly, certain aspects of the present invention relate to pharmaceutical compositions comprising the polyene polyketide compounds of the present invention together with a pharmaceutically acceptable carrier, methods of using the compositions to inhibit bacterial growth, and methods of using the pharmaceutical compositions to treat diseases, including cancer, and chronic and acute inflammation.

The present invention also provides the biosynthetic locus from *Amycolatopsis orientalis* strain ATCC™ 43491 which biosynthetic locus is responsible for producing the compounds of Formula I. Thus the invention provides polynucleotides and polypeptides useful in the production and engineering of compounds of Formula I.

Definitions

Molecular terms, when used in this application, have their common meaning unless otherwise specified.

Abreviations, as used herein, have the following meaning: Me refers to methyl ($CH_3$), Et refers to ethyl ($CH_2CH_3$), Pr refers to n-propyl ($CH_2CH_2CH_3$) and Ac refers to acetyl ($C(O)CH_3$).

The term alkyl refers to a linear or branched hydrocarbon groups. Examples of alkyl groups include, without limitation, methyl, ethyl, n-propyl, isopropyl, n-butyl, pentyl, hexyl, heptyl, cyclopentyl, cyclohexyl, cyclohexymethyl, and the like. Alkyl may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, oxo, guanidino and formyl.

The term alkenyl refers to linear, branched or cyclic hydrocarbon groups containing at least one carbon-carbon double bond. Examples of alkenyl groups include, without limitation, vinyl, 1-propene-2-yl, 1-butene-4-yl, 2-butene-4-yl, 1-pentene-5-yl and the like. Alkenyl may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, alkoxy, aryloxy, sulfinyl, sulfonyl, formyl, oxo and guanidino. The double bond portion(s) of the unsaturated hydrocarbon chain may be either in the cis or trans configuration.

The term cycloalkyl or cycloalkyl ring refers to a saturated or partially unsaturated carbocyclic ring in a single or fused carbocyclic ring system having from three to fifteen ring members. Examples of cycloalkyl groups include, without limitation, cyclopropyl, cyclobutyl, cyclohexyl, and cycloheptyl. Cycloalkyl may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl.

The term heterocyclyl, heterocyclic or heterocyclyl ring refers to a saturated or partially unsaturated ring containing one to four hetero atoms or hetero groups selected from O, N, NH, $NR^x$, $PO_2$, S, SO or $SO_2$ in a single or fused heterocyclic ring system having from three to fifteen ring members. Examples of a heterocyclyl, heterocyclic or heterocyclyl ring include, without limitation, morpholinyl, piperidinyl, and pyrrolidinyl. Heterocyclyl, heterocyclic or heterocyclyl ring may optionally be substituted with substituents selected from acyl, amino, acylamino, acyloxy, oxo, thiocarbonyl, imino, carboalkoxy, carboxy, carboxyamido, cyano, halo, hydroxyl, nitro, thio, alkyl, alkenyl, alkynyl, cycloalkyl, heterocyclyl, aryl, alkoxy, aryloxy, sulfinyl, sulfonyl and formyl.

The term amino acid refers to any natural amino acid, all natural amino acids are well known to a person skilled in the art.

The term halo is defined as a bromine, chlorine, fluorine or iodine.

The term aryl or aryl ring refers to common aromatic groups having "4n+2" electrons, wherein n is an integer from 1 to 3, in a monocyclic or conjugated polycyclic system and having from five to fifteen ring atoms. Aryl ring may include from 1 to 3 heteroatoms such as nitrogen, oxygen and sulphur atoms. Examples of aryl include, without limitation, phenyl, naphthyl, biphenyl, terphenyl, furyl, pyrrollyl, thienyl, pyridyl, oxazolyl, imidazolyl, pyrazolyl and indolyl groups. Aryl may optionally be substituted with one or more substituent group selected from acyl, amino, acylamino, acyloxy, azido, alkythio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl.

The compounds of the present invention can possess one or more asymetric carbon atoms and can exist as optical isomers forming mixtures of racemic or non-racemic compounds. The compounds of the present invention are useful as a single isomer or as a mixture of stereochemical isomeric forms. Diastereoisomers, i.e., nonsuperimposable stereochemical isomers, can be separated by conventional means such as chromatography, distillation, crystallization or sublimation. The optical isomers can be obtained by resolution of the racemic mixtures according to conventional processes.

The invention embraces isolated compounds. An isolated compound refers to a compound which represents at least 10%, 20%, 50% and 80% of the compound of the present invention present in a mixture, provided that the mixture comprising the compound of the invention has demonstrable (i.e. statistically significant) biological activity including antimicrobial activity when tested in conventional biological assays known to a person skilled in the art.

As used herein, the term "treatment" refers to the application or administration of a therapeutic agent to a patient, or application or administration of a therapeutic agent to an isolated tissue or cell line from a patient, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease.

As used herein, a "pharmaceutical composition" comprises a pharmacologically effective amount of a compound of the invention and a pharmaceutically acceptable carrier. As used herein, "pharmacologically effective amount," "therapeutically effective amount" or simply "effective amount" refers to that amount of polyene polyketide effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

The term "pharmaceutically acceptable salts" include acid addition salts and base addition salts. The nature of the salt is not critical, provided that it is pharmaceutically-acceptable. Without being limited, examples of acid addition salts include hydrochloric, hydrobromic, hydroiodic, nitric, carbonic, sulphuric, phosphoric, formic, acetic, citric, tartaric, succinic, oxalic, malic, glutamic, propionic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactantic, galacturonic acid and the like. Suitable pharmaceutically-acceptable base addition salts of compounds of the invention include, but are not limited to, metallic salts made from aluminium, calcium, lithium, magnesium, potassium, sodium and zinc or organic salts made from N,N'-dibenzylethylenediamine, chloroprocaine, choline, diethanolamine, ethylenediamine, N-methylglucamine, lysine, procaine and the like. Additional examples of pharmaceutically acceptable salts are listed in Berge S M et al., *Journal of Pharmaceutical Sciences*, (1977) Vol. 66 no 1, pp. 1-19. All of these salts may be prepared by conventional means form the corresponding compounds of Formula I by treating with the appropriate acid or base.

The term "isolated" polynucleotide or polypeptide means that the material is removed from its original environment, e.g. the natural environment if it is naturally-occurring. For example, a naturally-occurring polynucleotide or polypeptide present in a living organism is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The term "purified" polynucleotide or polypeptide does not require absolute purity; rather, it is intended as a relative definition. Individual nucleic acids obtained from a library have been conventionally purified to electrophoretic homogeneity. The purified nucleic acids of the present invention have been purified from the remainder of the genomic DNA in the organism by at least $10^4$ to $10^6$ fold. However, the term "purified" also includes nucleic acids which have been purified from the remainder of the genomic DNA or from other sequences in a library or other environment by at least one order of magnitude, preferably two or three orders of magnitude, and more preferably four or five orders of magnitude.

"Recombinant" nucleic acid means that the nucleic acid is adjacent to "backbone" nucleic acid to which it is not adjacent in its natural environment. "Enriched" nucleic acids represent 5% or more of the number of nucleic acid inserts in a population of nucleic acid backbone molecules. "Backbone" molecules include nucleic acids such as expression vectors, self-replicating nucleic acids, viruses, integrating nucleic acids, and other vectors or nucleic acids used to maintain or manipulate a nucleic acid of interest. Preferably, the enriched nucleic acids represent 15% or more, more preferably 50% or more, and most preferably 90% or more, of the number of nucleic acid inserts in the population of recombinant backbone molecules.

"Recombinant" polypeptides or proteins refer to polypeptides or proteins produced by the reassortment of sections of DNA or RNA sequences between at least two DNA or RNA molecules that are created by recombinant DNA techniques that are well known in the art. An extensive guide to such techniques is described in Sambrook et al., (1989), Molecular Cloning: A Laboratory Manual, second edition, Cold Spring Harbor Laboratory Press. "Synthetic" polypeptides or proteins are those prepared by chemical synthesis.

A "coding sequence" or "sequence encoding" a particular polypeptide or protein, is a DNA sequence which is transcribed and translated into a polypeptide or protein when placed under the control of appropriate regulatory sequences.

Thus, as used herein, the term "polynucleotide encoding a polypeptide" encompasses a polynucleotide that includes only coding sequence for the polypeptide as well as a polynucleotide that includes additional coding and/or non-coding sequence.

The term "complement" and "complementary", refers to the ability of two single stranded nucleic acid fragments to sufficiently base pair with each other or to "hybridize" under certain stringent conditions. By way of example, and not limitation, a procedure of using high stringency is as follows: Prehybridizaion of filters containing DNA is carried out for 2 hrs. to overnight at 65° C. in buffer composed of 6×SSC, 5× Denhardt's solution and 100 μg/ml denatured salmon sperm DNA. Filters are hybridized for 12 to 48 hrs at 65° C. in prehybridization buffer mixture containing a labeled probe (e.g. 5-20×$10^6$ $^{32}$P labeled probe). Washing of the hybridized filters is conducted at 37° C. for 1 hr. in a solution of containing 2×SSC, 0.1% SDS. This is followed by a wash in 0.1×SSC, 0.1% SDS at 50° C. for 45 min. followed by autoradiography. Other conditions for stringency are described in Sambrook et al., supra.

Expression "control sequences" refers collectively to promoter sequences, ribosomal binding sites, polyadenylation signals, transcription termination sequences, regulatory regions, enhancers, and the like, which collectively provide for the transcription and translation of a coding sequence in a host cell. Not all these control sequences need always be present in a recombinant vector so long as the desired gene is capable of being transcribed or translated.

"Oligonucleotide" refers to a nucleic acid, generally of at least 10 to about 100 nucleotides, that are hybridizable to a genomic DNA molecule, a cDNA molecule, or an mRNA molecule encoding a gene or other nucleic acid of interest.

A promoter sequence is "operably linked to" a coding sequence recognized by RNA polymerase which initiates transcription at the promoter and transcribes the coding sequence into mRNA.

"Plasmids" are designated herein by a lower case p preceded or followed by capital letters and/or numbers. The starting plasmids herein are commercially available, publicly available on an unrestricted basis, or can be constructed from available plasmids in accord with published procedures. In addition, equivalent plasmids to those described herein are known in the art and will be apparent to the skilled artisan.

"Digestion" of DNA refers to enzymatic cleavage of the DNA with a restriction enzyme that acts only at certain sequences in the DNA. The various restriction enzymes used herein are commercially available and their reaction conditions, cofactors and other requirements were used as would be known to the ordinary skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular enzymes are specified by the manufacturer. Incubation times of about 1 hour at 37° C. are ordinarily used, but may vary in accordance with the supplier's instructions. After digestion the gel electrophoresis may be performed to isolate the desired fragment.

Unless otherwise indicated, all numbers expressing quantities of ingredients and properties such as molecular weight, reaction conditions, MIC and so forth used in the specification and claims are to be understood as being modified in all instances by the term "about". Accordingly, unless indicated to the contrary, the numerical parameters set forth in the present specification and attached claims are approximations. At the very least, and not as an attempt to limit the application of the doctrine of equivalents to the scope of the claims, each numerical parameter should at least be construed in light of the number of significant figures and by applying ordinary rounding techniques. Notwithstanding that the numerical ranges and parameters setting forth the broad scope of the invention are approximations, the numerical values set forth in the examples, tables and figures are reported as precisely as possible. Any numerical values may inherently contain certain errors resulting from variations in experiments, testing measurements, statistical analysis and such.

Compounds of the Invention

In one aspect of this embodiment the invention relates to novel polyene polyketides, referred to herein as Compounds 1 to Compound 7:

Compound 1

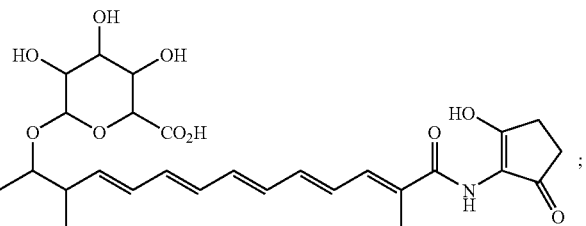

Compound 2

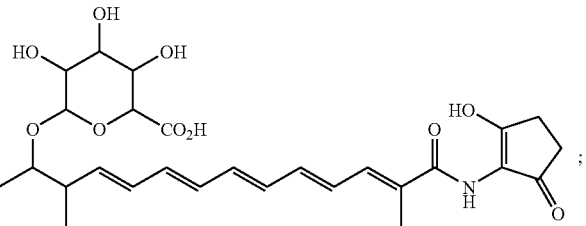

Compound 3

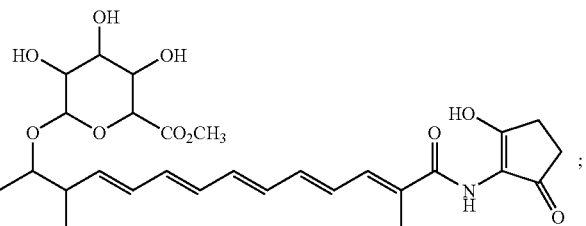

-continued

Compound 4

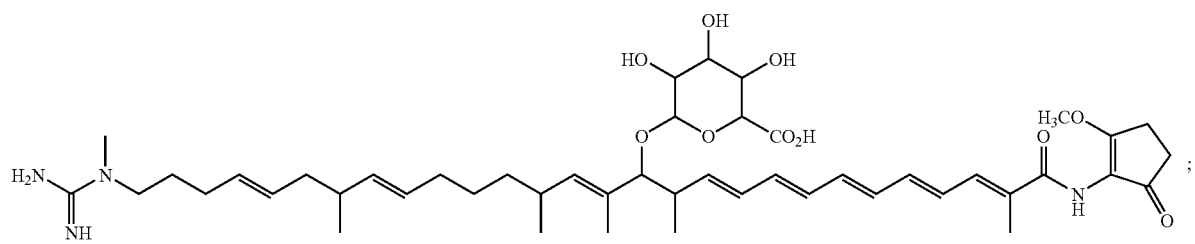

Compound 5

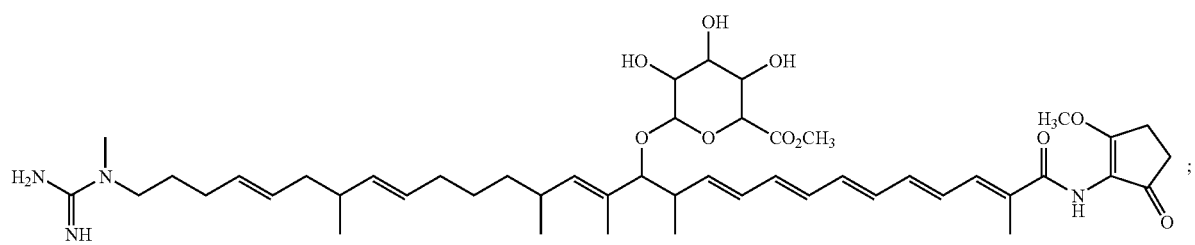

Compound 6

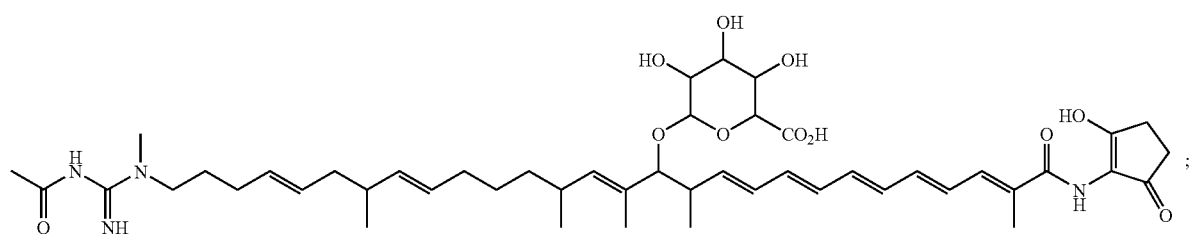

Compound 7

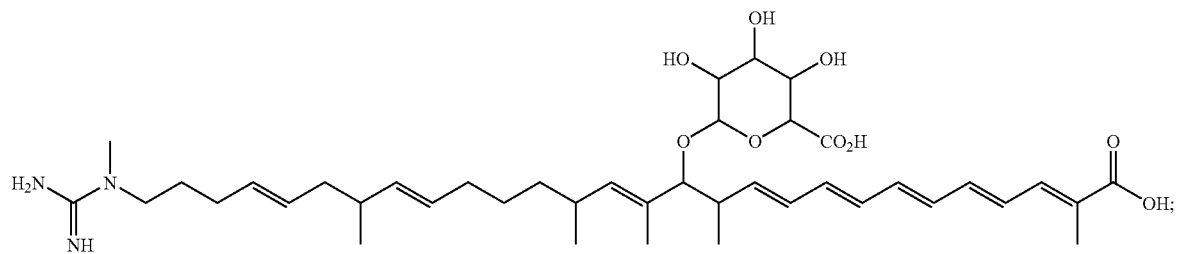

or, to a pharmaceutically acceptable salt or prodrug of any of Compounds 1 to 7. Compounds 1 to 7 may be characterized by any one or more of their physicochemical and spectral properties given below, such as mass, UV, and NMR spectroscopic data.

In another aspect the invention relates to derivatives of Compound 1 to 7, as represented by the polyene polyketides of Formula I:

Formula I

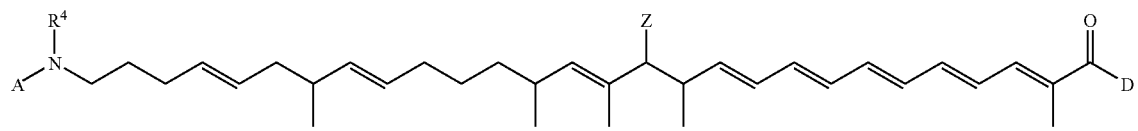

wherein,
A is selected from —C(NH)NHR$^1$, CH$_3$, H or

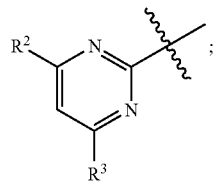

R$^1$ is selected from H, C$_{1-6}$alkyl, C$_{6-10}$aryl, C(O)C$_{1-6}$alkyl and C(O)C$_{6-10}$aryl;
R$^2$ and R$^3$ are each independently selected from H, C$_{1-6}$ alkyl, C$_{2-7}$ alkene and C$_{6-10}$ aryl;
R$^4$ is selected from H or CH$_3$;
Z is OH or O when taken with adjacent carbon atom to form a carbonyl; or
Z may be a tetrahydropyranoxy of formula:

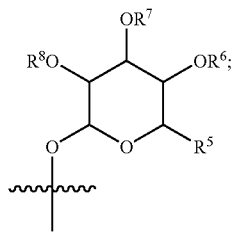

R$^5$ is selected from H, COOH, C$_{1-6}$ alkyl or C(O)OC$_{1-6}$ alkyl;
R$^6$, R$^7$ and R$^8$ are each independently selected from H, C$_{1-6}$ alkyl and C(O)C$_{1-6}$ alkyl; or
R$^6$, R$^7$ and R$^8$ may each independently be absent when the adjacent oxygen and carbon atoms are taken together to form a carbonyl; or
R$^6$, R$^7$ and R$^8$ may each independently be a bond when any of two neighboring R$^6$, R$^7$ and R$^8$ are taken together with attached oxygen and carbon atoms to form a 1,3-dioxolane ring of formula:

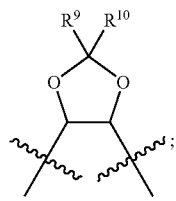

R$^9$ and R$^{10}$ are each independently selected from H, C$_{1-6}$ alkyl, C$_{2-7}$ alkene and C$_{6-10}$ aryl; or
R$^9$ and R$^{10}$ are taken together with adjacent carbon atom to form a ring having from 5 to 7 carbons;
D is selected from OH, NH$_2$, NH(C$_{1-3}$alkyl), N(C$_{1-3}$alkyl)$_2$, OC$_{1-3}$alkyl or

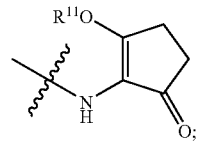

R$^{11}$ is selected from H or C$_{1-3}$ alkyl;
or a pharmaceutically acceptable salt or prodrug thereof.

In an embodiment the invention provides compounds of Formula I, wherein A is —C(NH)NH$_2$; and all other groups are as previously defined; or a pharmaceutically acceptable salt or prodrug thereof.

In a further embodiment of the invention provides compounds of Formula I, wherein A is H; and all other groups are as previously defined; or a pharmaceutically acceptable salt or prodrug thereof.

In a further embodiment the invention provides compounds of Formula I, wherein A is —C(NH)NHC(O)CH$_3$; and all other groups are as previously defined; or a pharmaceutically acceptable salt or prodrug thereof.

In a further embodiment the invention provides compounds of Formula I, wherein A is

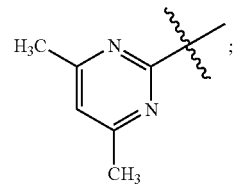

and all other groups are as previously defined; or a pharmaceutically acceptable salt or prodrug thereof.

In a further embodiment the invention provides compounds of Formula I, wherein R$^4$ is CH$_3$; and all other groups are as previously defined; or a pharmaceutically acceptable salt or prodrug thereof.

In a further embodiment the invention provides compounds of Formula I, wherein R$^4$ is H; and all other groups are as previously defined; or a pharmaceutically acceptable salt or prodrug thereof.

In a further embodiment the invention provides compounds of Formula I, wherein Z is

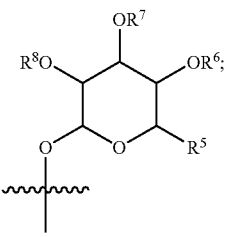

and all other groups are as previously defined; or a pharmaceutically acceptable salt or prodrug thereof. In a subclass of this embodiment R$^6$, R$^7$ and R$^8$ are each H, and R$^5$ is COOH, all other groups are as previously defined; or a pharmaceutically acceptable salt or prodrug thereof.

In a further embodiment the invention provides compounds of Formula I, wherein Z is

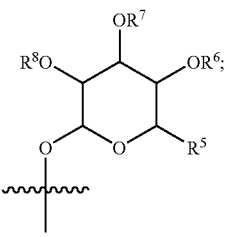

and all other groups are as previously defined; or a pharmaceutically acceptable salt or prodrug thereof. In a subclass of this embodiment $R^6$, $R^7$ and $R^8$ are each H, and $R^5$ is $CO_2CH_3$, all other groups are as previously defined; or a pharmaceutically acceptable salt or prodrug thereof.

In a further embodiment the invention provides compounds of Formula I, wherein Z is OH and all other groups are as previously defined; or a pharmaceutically acceptable salt or prodrug thereof.

In a further embodiment the invention provides compounds of Formula I, wherein D is

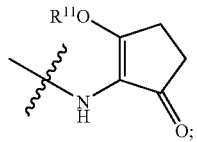

and all other groups are as previously defined; or a pharmaceutically acceptable salt or prodrug thereof. In a subclass of this embodiment $R^{11}$ is H and all other groups are as previously defined; or a pharmaceutically acceptable salt or prodrug thereof.

In a further embodiment the invention provides compounds of Formula I, wherein D is

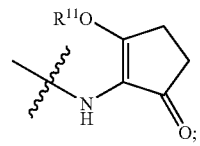

and all other groups are as previously defined; or a pharmaceutically acceptable salt or prodrug thereof. In a subclass of this embodiment $R^{11}$ is $CH_3$ and all other groups are as previously defined; or a pharmaceutically acceptable salt or prodrug thereof.

In another embodiment the invention provides compounds of Formula I, wherein D is OH; and all other groups are as previously defined; or a pharmaceutically acceptable salt or prodrug thereof.

The following are exemplary compounds of the invention:

Compound 1

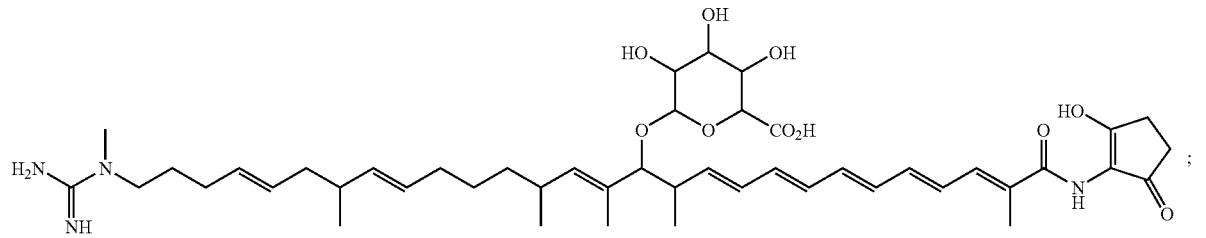

Compound 2

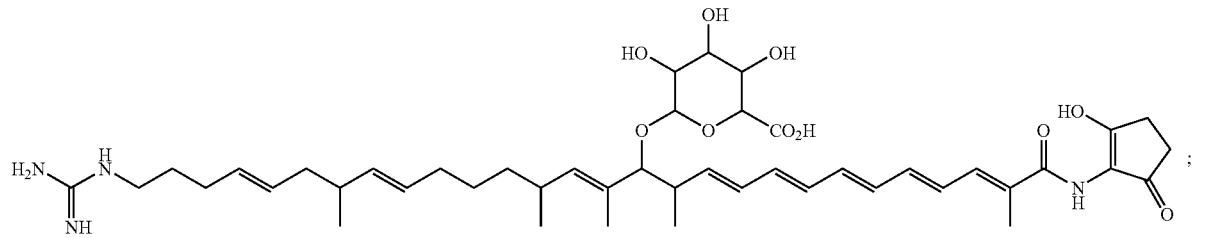

Compound 3

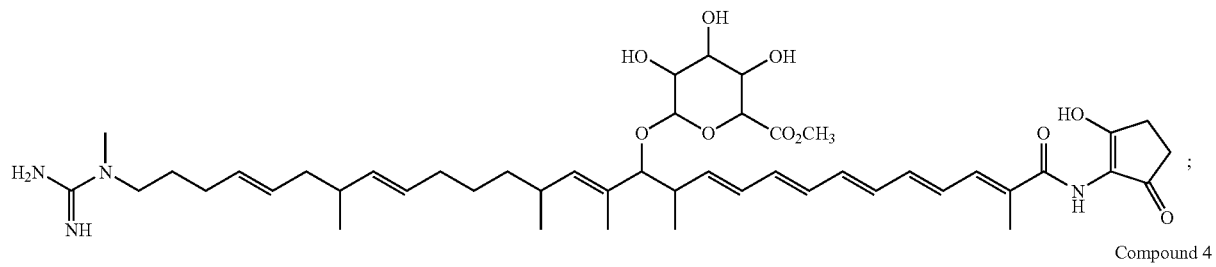

Compound 4

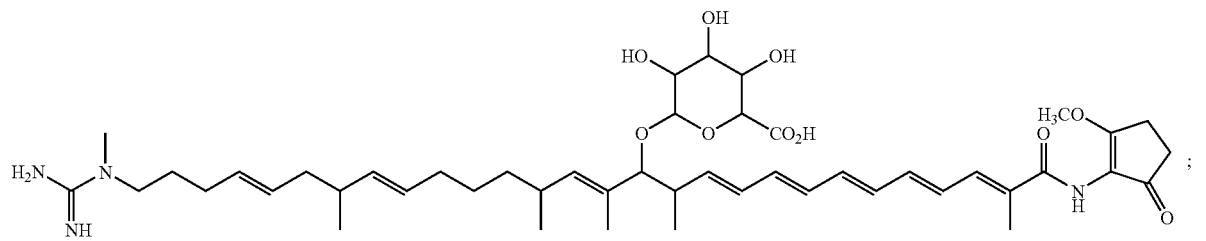

-continued
Compound 5
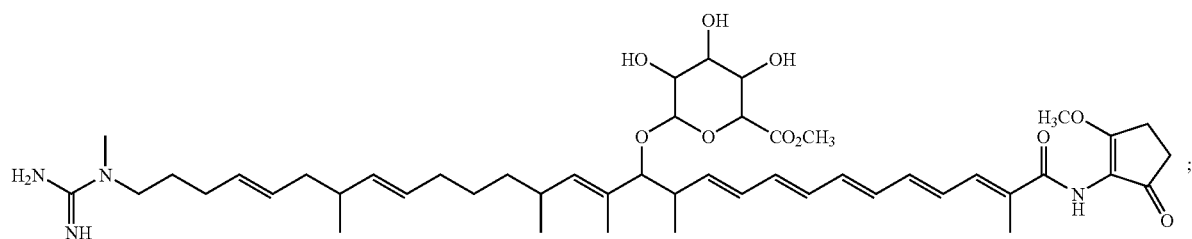
Compound 6
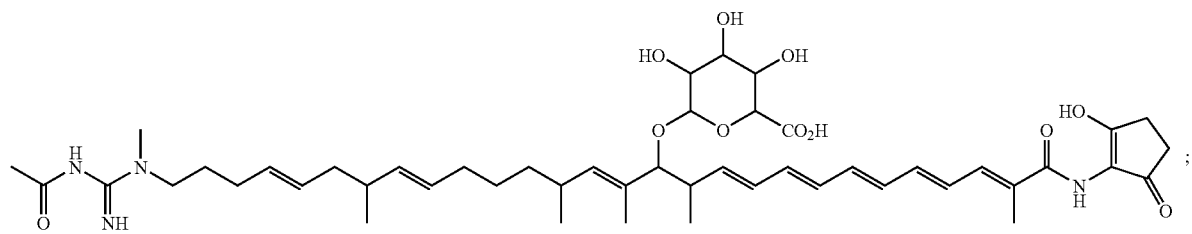
Compound 7
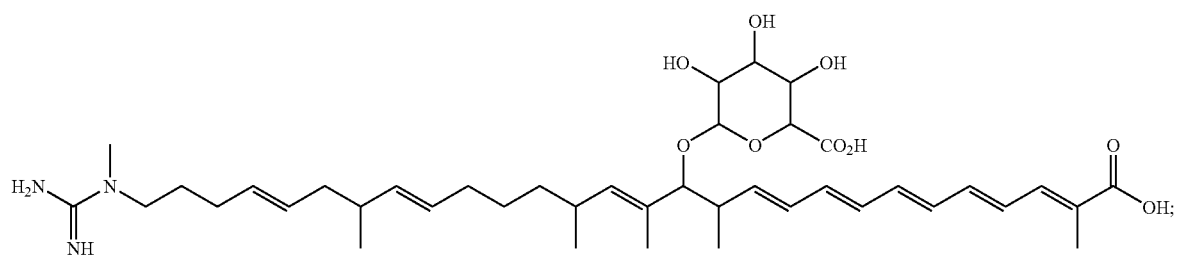
Compound 8
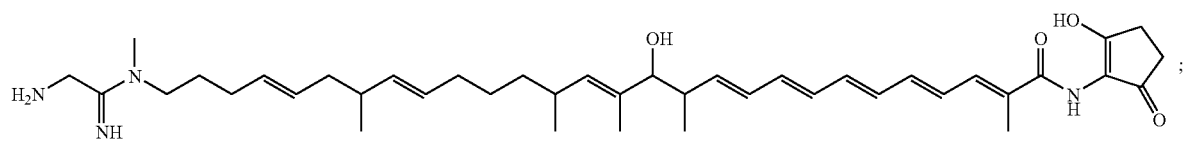
Compound 9
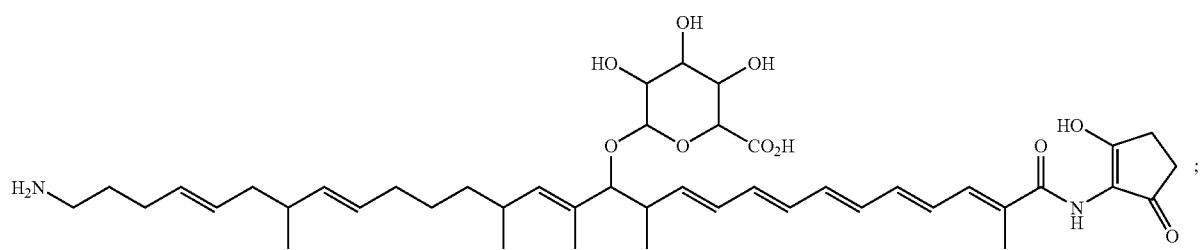
Compound 10
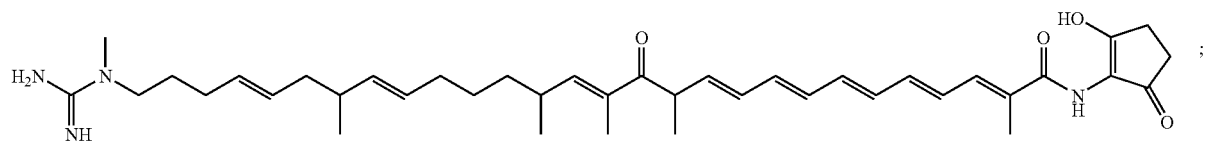

-continued
Compound 11
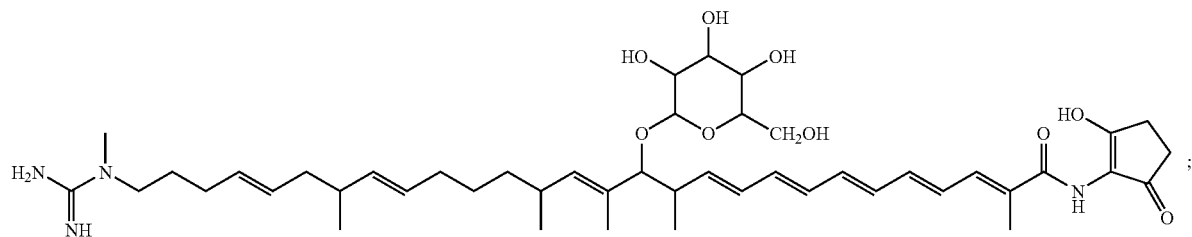
Compound 12
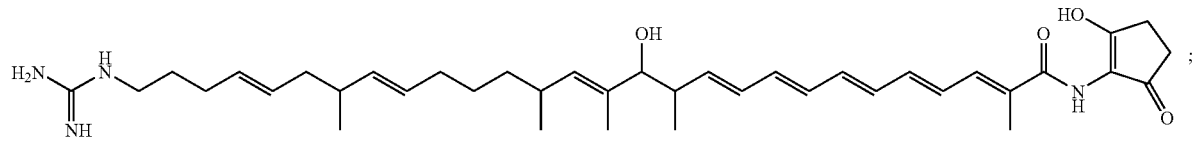
Compound 13
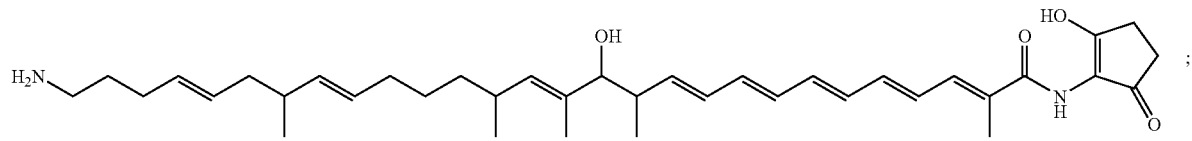
Compound 14
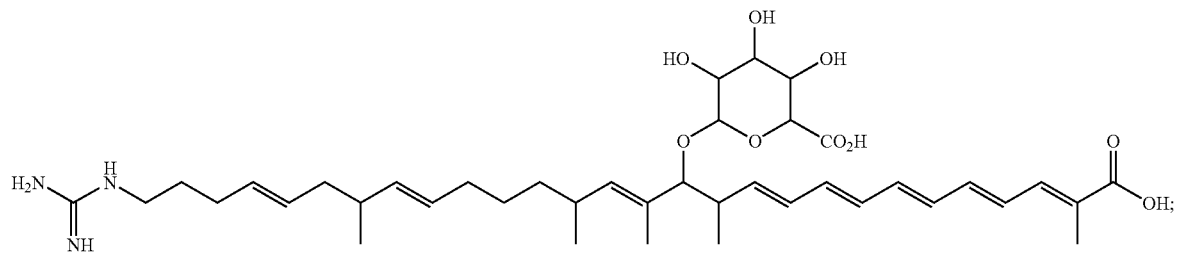
Compound 15
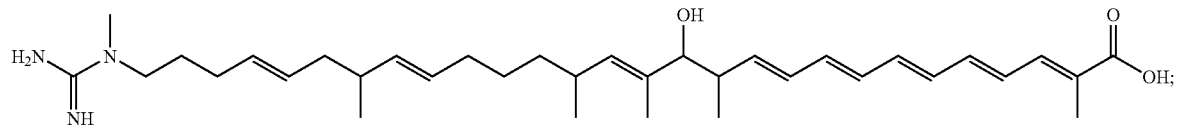
Compound 16
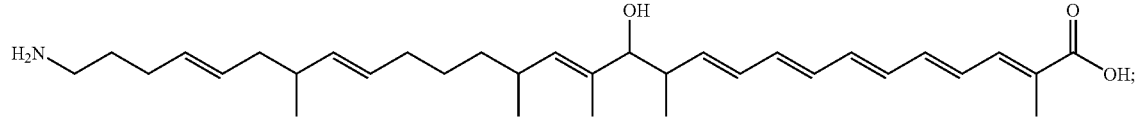
Compound 17
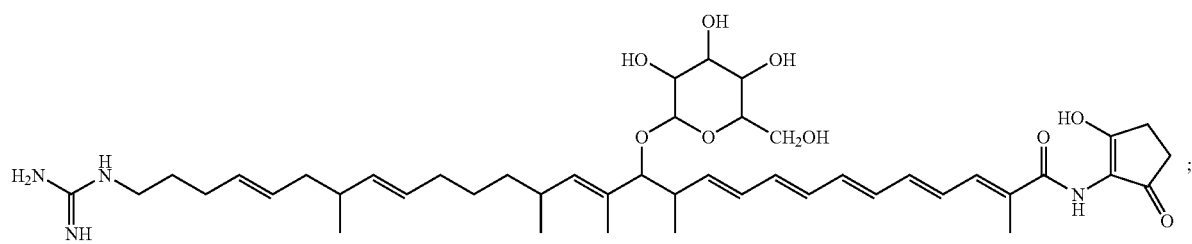

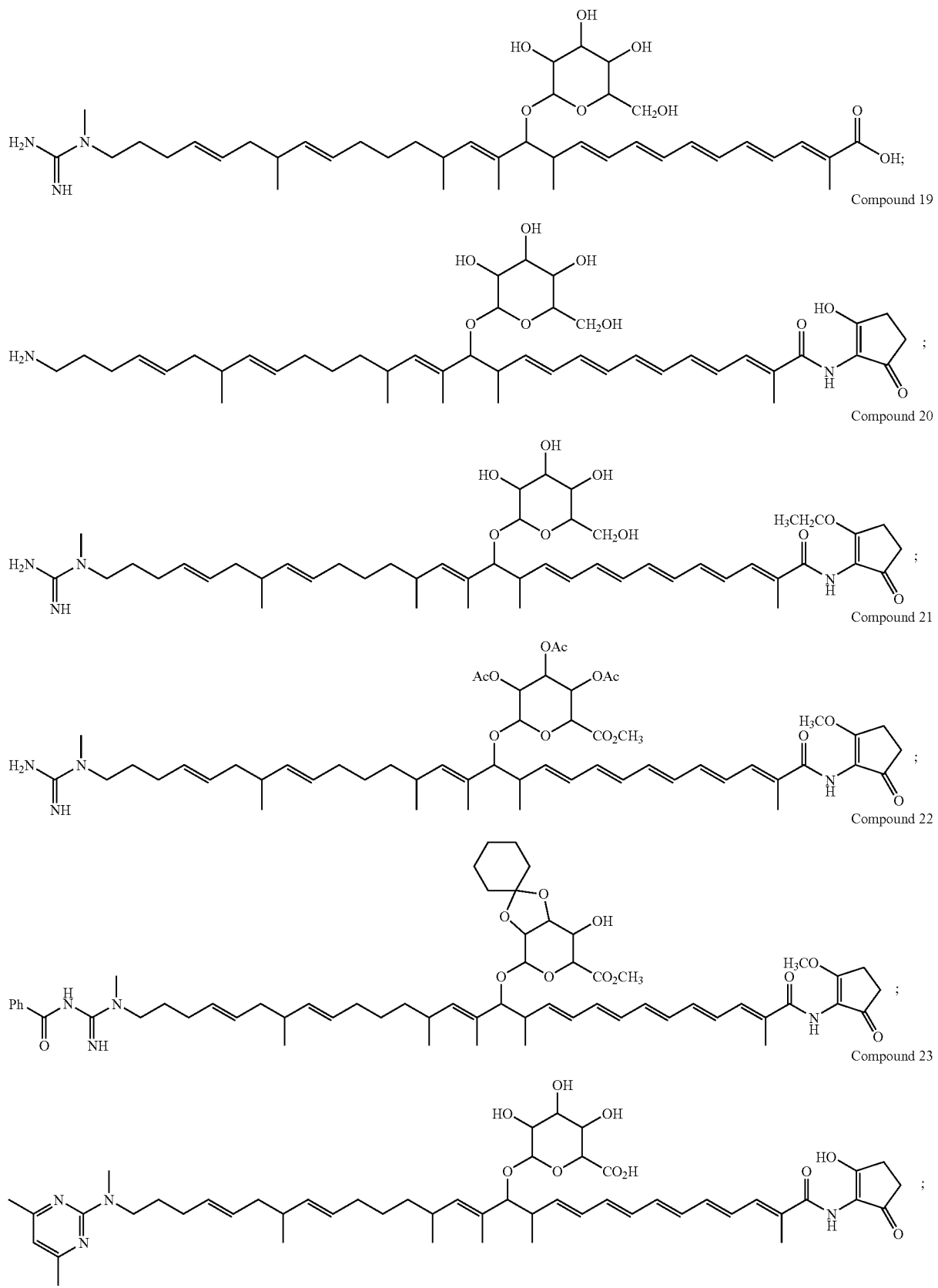

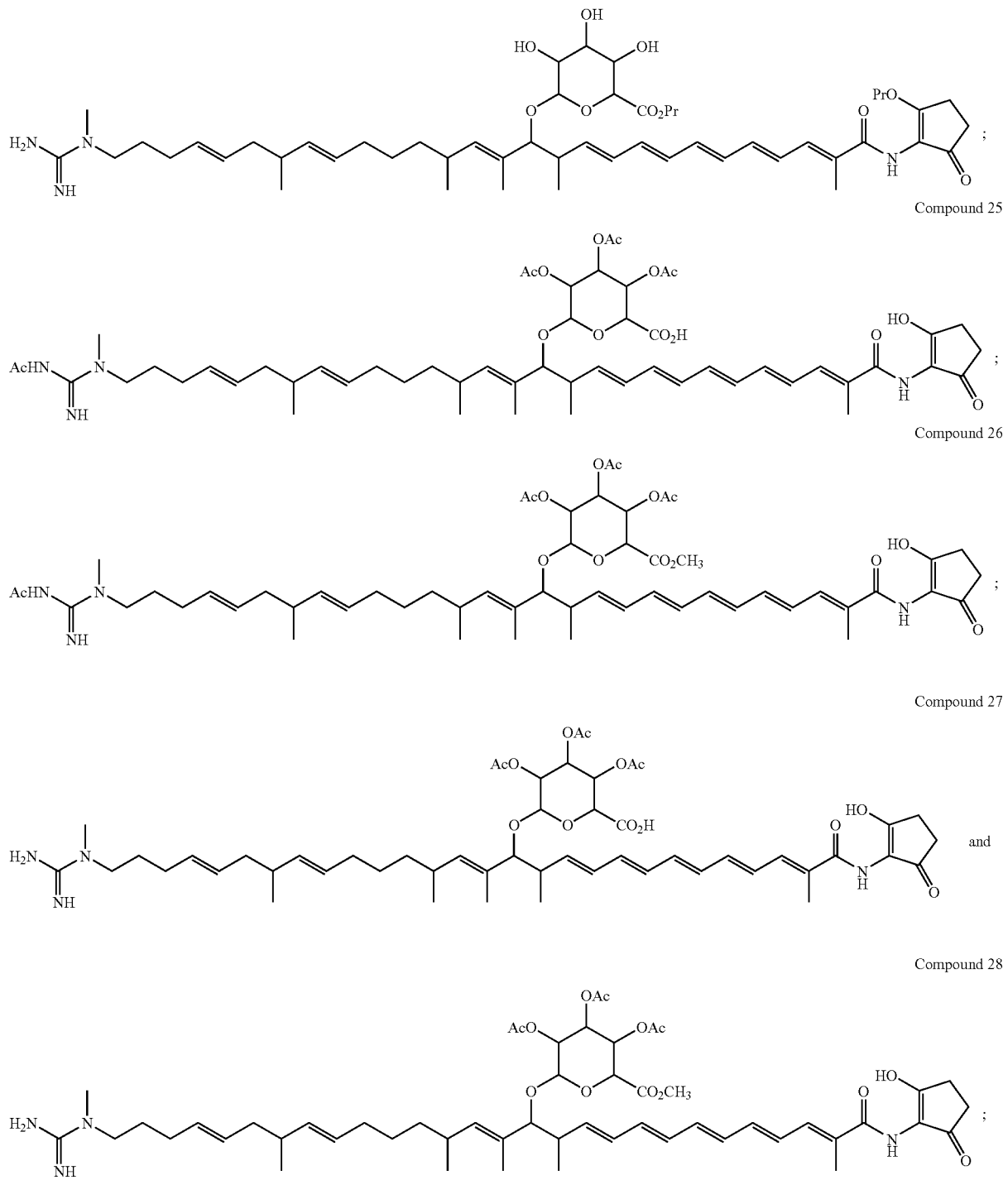

or a pharmaceutically acceptable salt or prodrug of any one of Compound 1-28. Certain embodiments may exclude one or more of the compounds of Formula I.

III. Methods for Producing the Compounds of the Invention by Fermentation

The compounds of Formula I may be biosynthesized by various microorganisms. Microorganisms that may synthesize the compounds of the present invention include but are not limited to bacteria of the order Actinomycetales, also referred to as actinomycetes. Non-limiting examples of members belonging to the genera of Actinomycetes include *Nocardia, Geodermatophilus, Actinoplanes, Micromonospora, Nocardioides, Saccharothrix, Amycolatopsis, Kutzneria, Saccharomonospora, Saccharopolyspora, Kita-*

*satospora, Streptomyces, Microbispora, Streptosporangium, Actinomadura.* The taxonomy of actinomycetes is complex and reference is made to Goodfellow (1989) Suprageneric classification of actinomycetes, *Bergey's Manual of Systematic Bacteriology*, Vol. 4, Williams and Wilkins, Baltimore, pp 2322-2339, and to Embley and Stackebrandt, (1994), and *The molecular phylogeny and systematics of the actinomycetes, Annu. Rev. Microbiol.* 48, 257-289 (1994), for genera that may synthesize the compounds of the invention, incorporated herein in its entirety by reference.

Microorganisms biosynthetically producing compounds of Formula I are cultivated in culture media containing known nutritional sources for actinomycetes having assimilable sources of carbon, nitrogen plus optional inorganic salts and other known growth factors at a pH of about 6 to about 9, non-limiting examples of growth media are provided in Table 1. Microorganisms are cultivated at incubation temperatures of about 20° C. to about 40° C. for about 3 to about 40 days. The culture media inoculated with the microorganisms, which biosynthetically produce compounds of Formula I, may be aerated by incubating the inoculated culture media with agitation, for example shaking on a rotary shaker, or a shaking water bath. Aeration may also be achieved by the injection of air, oxygen or an appropriate gaseous mixture to the inoculated culture media during incubation.

After cultivation and production of compounds of Formula I, the compounds can be extracted and isolated from the cultivated culture media by techniques known to a skilled person in the art and/or disclosed herein, including for example centrifugation, chromatography, adsorption. For example, the cultivated culture media can be mixed with a suitable organic solvent such as n-butanol, n-butyl acetate and 4-methyl-2-pentanone, the organic layer can be separated for example, by centrifugation followed by the removal of the solvent, by evaporation to dryness or by evaporation to dryness under vacuum. The resulting residue can optionally be reconstituted with for example water, ethyl ether, ethanol acetate, methanol or a mixture thereof, and re-extracted in a two-phase system with a suitable organic solvent such as hexane, carbon tetrachloride, methylene chloride or a mixture thereof. After removal of the solvent, the compound of Formula I can be further purified by the use of standard techniques such as chromatography.

TABLE 1

| Component | \multicolumn{7}{c}{Fermentation media} | | | | | | |
|---|---|---|---|---|---|---|---|
| | CA | CB | GA[a] | JA | NA | OA | RM |
| pH[b] | 7 | 7 | | 7.3 | 7 | 7 | 6.9 |
| Glucose | 10 | | 10 | | | 10 | 10 |
| Sucrose | | 20 | 103 | | | | 100 |
| Cane molasses | 15 | 5 | | | 10 | | |
| Corn starch | | | | 30 | | | |
| Potato dextrin | 40 | | | | | | |
| Corn steep liquor | | | | 15 | | 3 | |
| Yeast extract | | | 5 | | | 3 | 5 |
| Malt extract | | | | 35 | | 3 | |
| Pharmamedia ™ | | | | 15 | | | |
| Glycerol | | | | | 20 | 5 | |
| N-Z Amine A | 10 | | | | | | |
| Beef extract | | | | | | 3 | |
| Bacto-peptone | | 2 | | | 1 | | |
| Casamino acid | | | 0.1 | | 5 | | 0.1 |
| Thiamine | | | | | | 0.1 | |
| MgSO$_4$•7H$_2$O | 1 | 0.2 | | | | | |
| MgCl$_2$•6H$_2$O | | | 10.12 | | | | 10.13 |
| CaCO$_3$ | 2 | 5 | | 2 | 4 | 2 | |
| K$_2$SO$_4$ | | | 0.25 | | | | 0.25 |

TABLE 1-continued

| Component | \multicolumn{7}{c}{Fermentation media} | | | | | | |
|---|---|---|---|---|---|---|---|
| | CA | CB | GA[a] | JA | NA | OA | RM |
| FeSO$_4$•7H$_2$O | | 0.1 | | | | | |
| KI | | 0.5 | | | | | |
| MOPS | | | | | | | 21 |
| Trace Elements Solution[c] ml/L | | | 2 | | | | 2 |

Unless otherwise indicated, all the components are in gm/L
To a liter of media GA add: 10 ml KH$_2$PO$_4$ (0.5% solution); 80 ml CaCl$_2$.2H$_2$O (3.68% solution); 15 ml L-proline (20% solution); 100 ml TES buffer (5.73% solution, pH 7.2); 5 ml NaOH (1N solution).
The pH is adjusted as marked prior to the addition of CaCO$_3$.
Solution of trace elements contains: ZnCl$_2$ 40 mg; FeCl$_3$.6H$_2$O (200 mg); CuCl$_2$.2H$_2$O (10 mg); (NH$_4$)$_6$Mo$_7$O$_{24}$.4H$_2$O (10 mg) per litre.

IV. Chemical Modifications of Compounds 1 to 7

The compounds of Formula I that are biosynthesized by microorganisms may optionally be subjected to chemical modifications to form compounds that are derivatives or structural analogs of compounds of Formula I. Derivatives or structural analogs of compounds of Formula I having similar functional activities are within the scope of the present invention. Compounds of Formula I may optionally be modified using methods known in the art and described herein.

General principles of organic chemistry including functional moieties, reactivity and common protocols are described, for example, in Advanced Organic Chemistry 3rd Edition by Jerry March (1985), which is incorporated herein by reference in its entirety. In addition, it will be appreciated by one of ordinary skill in the art that the synthetic methods described herein may use a variety of protecting groups, whether or not they are explicitly described. A "protecting group" as used herein means a moiety used to block one or more functional moieties such as reactive groups including oxygen, sulfur or nitrogen, so that a reaction can be carried out selectively at another reactive site in a polyfunctional compound. General principles for the use of protective groups, their applicability to specific functional groups and their uses are described for example in T. H. Greene and P. G. M. Wuts, Protective Groups in Organic Synthesis, 3rd Edition, John Wiley & Sons, New York (1999), Scheme 1: Modifications of Acidic Functions:

Scheme 1

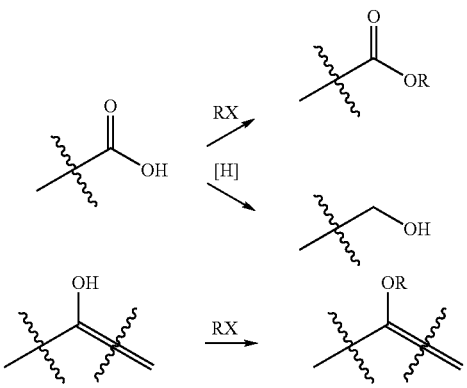

wherein R is alkyl or aryl and X is a suitable leaving group

In Scheme 1, acidic functional groups are alkylated either individually or together. Simple ester is prepared from treatment of the carboxylic acid by an RX reagent such as diazoalkanes in the appropriate solvent. In Scheme 1, hydroxycyclopentenone is converted to alkoxycyclopentenone by similar treatment with the suitable RX reagent. In Scheme 1, carboxylic acids are also converted to alcohol by a reducing agent [H] such as lithiumaluminum hydride. Scheme 1 is used to obtain Compounds 3, 4, 5, 11 and 24 from Compound 1, Compounds 17, 18, 20, 26 and 28 respectively from Compounds 2, 7, 11, 25 and 27.

Scheme 2: Modifications to Alcohol Functions:

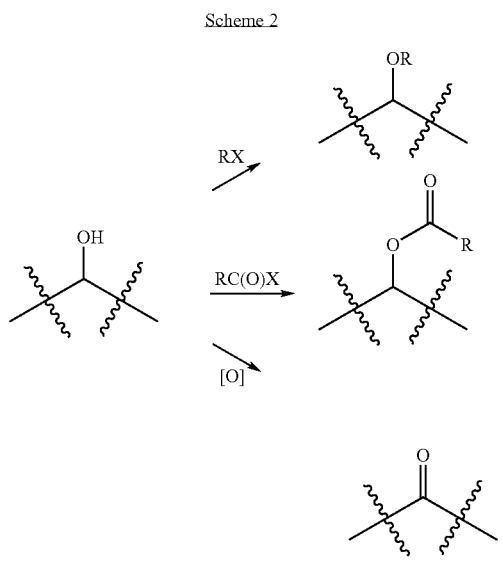

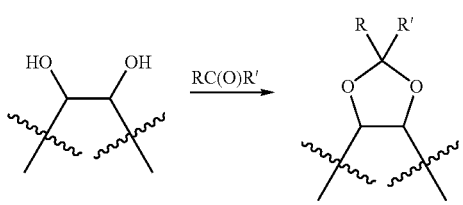

wherein R and X are as in Scheme 1 and R' is alkyl, aryl or H

In Scheme 2, an alkylating agent such as methyliodide, converts alcohol to ether in the presence of a base such as potassium tert-butoxide. In Scheme 2, ester is obtained from the reaction of the alcohol with an activated carboxylic acid such as acid halides or anhydrides and N-hydroxysuccinimide esters in the presence of a base like diisopropylethylamine. In Scheme 2, a ketone is obtained from the oxidation of the alcohol by an oxidating agent [O] such as Dess-Martin (1,1,1-triacetoxy-1,1-dihydro-1,2-benziodoxol-3(1H)one) or Swern (oxalyl chloride and methylsulfoxide) reagents. In scheme 2, a vicinal diol is converted to a 1,3-dioxolane ring by reaction with a ketone or an aldehyde (when R' is H) using an acid catalyst such as p-toluenesulfonic acid with removal of the water formed (like: Dean-Stark or molecular sieves). Scheme 2 is used to obtain Compound 10 from Compound 8, Compound 28 form Compound 3, Compounds 21 and 22 from Compound 5 and Compounds 25 and 27 from Compound 1.

Scheme 3: Modifications of Guanidine Group:

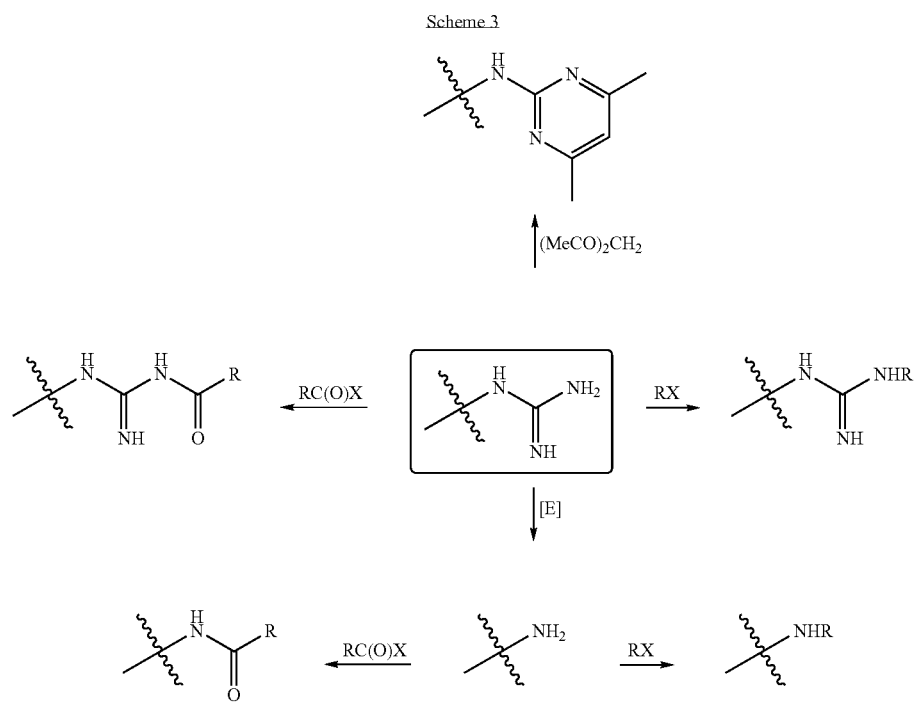

wherein R and X are as in Scheme 1

In Scheme 3, a pyrimidine ring is obtained from the condensation of the guanidine group with a diketone, such as 2,4-pentadione in a solvent like ethanol under reflux. In Scheme 3, the guanidine functional group is enzymatically [E] hydrolyzed to amine in the appropriate conditions. In Scheme 3, the guanidine group or the amine group are alkylated by a suitable RX or acylated by a suitable RC(O)X in the presence of a base. Scheme 3 is used to produce Compounds 9, 13, 19 and 22 respectively from Compounds 2, 12, 17 and 5 and Compounds 6, 23 and 25 from Compound 1. The following examples illustrate the invention but are not to be construed as limiting. Unless otherwise noted, all reagents were purchased from Sigma Chemical Co. (St. Louis, Mo.), (Aldrich).

Genes and Proteins for Producing the Compounds of the Invention

The invention also provides the genes and proteins forming the biosynthetic locus for the production of the compounds of Formula I.

Nucleic acid sequences encoding proteins involved in the biosynthesis of compounds of Formula I are provided in the accompanying sequence listing as SEQ ID NOS: 3, 5, 7, 9, 11, 13, 15, 17, 19, 21, 23, 26, 28, 30, 32, 34, 36, 38, 40, 42, 44, 46, 48, 51, 53, 55, 57. Polypeptides involved in the biosynthesis of compounds of Formula I are provided in the accompanying sequence listing as SEQ ID NOS: 2, 4, 6, 8, 10, 12, 14, 16, 18, 20, 22, 25, 27, 29, 31, 33, 35, 37, 39, 41, 43, 47, 50, 52, 54, 56.

One aspect of the present invention is an isolated, purified, or enriched nucleic acid comprising one of the sequences of SEQ ID NOS: 3, 5, 7, 9, 11, 13, 15, 17, 19, 21, 23, 26, 28, 30, 32, 34, 36, 38, 40, 42, 44, 46, 48, 51, 53, 55, 57, the sequences complementary thereto, and isolated, purified or enriched nucleic acids having at least 70%, 75%, 80%, 85%, 90%, 95%, 97% or 99% identity to the above sequences as determined by analysis with BLASTN™ version 2.0 with the default parameters.

The isolated, purified or enriched nucleic acids may comprise DNA, including cDNA, genomic DNA, and synthetic DNA. The DNA may be double stranded or single stranded, and if single stranded may be the coding (sense) or non-coding (anti-sense) strand. Alternatively, the isolated, purified or enriched nucleic acids may comprise RNA.

As discussed in more detail below, the isolated, purified or enriched nucleic acids of one of SEQ ID NOS: 3, 5, 7, 9, 11, 13, 15, 17, 19, 21, 23, 26, 28, 30, 32, 34, 36, 38, 40, 42, 44, 46, 48, 51, 53, 55, 57 may be used to prepare one of the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56 respectively or an isolated or purified polypeptide having at least 70%, 75%, 80%, 85%, 90%, 95%, 97%, or 99% homology to the polypeptide of SEQ ID NOS: 2, 4, 6, 8, 10, 12, 14, 16, 18, 20, 22, 25, 27, 29, 31, 33, 35, 37, 39, 41, 43, 47, 50, 52, 54, 56 as determined by analysis with BLASTP™ version 2.2.2 with the default parameters.

Accordingly, another aspect of the present invention is an isolated, purified or enriched nucleic acid which encodes one of the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56 or an isolated or purified polypeptide having at least 70%, 75%, 80%, 85%, 90%, 95%, 97%, or 99% homology to the polypeptide of SEQ ID NOS: 2, 4, 6, 8, 10, 12, 14, 16, 18, 20, 22, 25, 27, 29, 31, 33, 35, 37, 39, 41, 43, 47, 50, 52, 54, 56 as determined by analysis with BLASTP™ version 2.2.2 with the default parameters. The coding sequences of these nucleic acids may be identical to one of the coding sequences of one of the nucleic acids of SEQ ID NOS: 3, 5, 7, 9, 11, 13, 15, 17, 19, 21, 23, 26, 28, 30, 32, 34, 36, 38, 40, 42, 44, 46, 48, 51, 53, 55, 57 or may be different coding sequences which encode one of the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56 or fragments comprising at least 50, 75, 100, 150, 200, 300 consecutive amino acids of one of the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56 as a result of the redundancy or degeneracy of the genetic code. The genetic code is well known to those of skill in the art and can be obtained, for example, from Stryer, *Biochemistry*, 3$^{rd}$ edition, W. H. Freeman & Co., New York (1998).

The isolated, purified or enriched nucleic acid which encodes one of the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56, may include, but is not limited to: (1) only the coding sequences of one of SEQ ID NOS: 3, 5, 7, 9, 11, 13, 15, 17, 19, 21, 23, 26, 28, 30, 32, 34, 36, 38, 40, 42, 44, 46, 48, 51, 53, 55, 57; (2) the coding sequences of SEQ ID NOS: 3, 5, 7, 9, 11, 13, 15, 17, 19, 21, 23, 26, 28, 30, 32, 34, 36, 38, 40, 42, 44, 46, 48, 51, 53, 55, 57 and additional coding sequences, such as leader sequences or proprotein; and (3) the coding sequences of SEQ ID NOS: 3, 5, 7, 9, 11, 13, 15, 17, 19, 21, 23, 26, 28, 30, 32, 34, 36, 38, 40, 42, 44, 46, 48, 51, 53, 55, 57 and non-coding sequences, such as introns or non-coding sequences 5' and/or 3' of the coding sequence.

The invention relates to polynucleotides based on SEQ ID NOS: 3, 5, 7, 9, 11, 13, 15, 17, 19, 21, 23, 26, 28, 30, 32, 34, 36, 38, 40, 42, 44, 46, 48, 51, 53, 55, 57 but having polynucleotide changes that are "silent", for example changes which do not alter the amino acid sequence encoded by the polynucleotides of SEQ ID NOS: 3, 5, 7, 9, 11, 13, 15, 17, 19, 21, 23, 26, 28, 30, 32, 34, 36, 38, 40, 42, 44, 46, 48, 51, 53, 55, 57. The invention also relates to polynucleotides which have nucleotide changes which result in amino acid substitutions, additions, deletions, fusions and truncations of the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56. Such nucleotide changes may be introduced using techniques such as site directed mutagenesis, random chemical mutagenesis, exonuclease III deletion, and other recombinant DNA techniques.

The isolated, purified or enriched nucleic acids of SEQ ID NOS: 3, 5, 7, 9, 11, 13, 15, 17, 19, 21, 23, 26, 28, 30, 32, 34, 36, 38, 40, 42, 44, 46, 48, 51, 53, 55, 57, the sequences complementary thereto may be used as probes to identify and isolate DNAs encoding the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56 respectively. In such procedures, a genomic DNA library is constructed from a sample microorganism or a sample containing a microorganism capable of producing a polyketide. The genomic DNA library is then contacted with a probe comprising a coding sequence or a fragment of the coding sequence, encoding one of the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56, or a fragment thereof under conditions which permit the probe to specifically hybridize to sequences complementary thereto. In a preferred embodiment, the probe is an oligonucleotide of about 10 to about 30 nucleotides in length designed based on a nucleic acid of SEQ ID NOS: 3, 5, 7, 9, 11, 13, 15, 17, 19, 21, 23, 26, 28, 30, 32, 34, 36, 38, 40, 42, 44, 46, 48, 51, 53, 55, 57. Genomic DNA clones which hybridize to the probe are then detected and isolated. Procedures for preparing and identifying DNA clones of interest are disclosed in Ausubel et al., Current Protocols in Molecular Biology, John Wiley 503 Sons, Inc. (1997); and Sambrook et al., Molecular Cloning: A Laboratory Manual 2d Ed., Cold Spring Harbor Laboratory Press, (1989). In another embodiment, the probe is a restriction fragment or a PCR amplified nucleic acid derived from SEQ ID NOS: 3, 5, 7, 9, 11, 13, 15, 17, 19, 21, 23, 26, 28, 30, 32, 34, 36, 38, 40, 42, 44, 46, 48, 51, 53, 55, 57.

The isolated, purified or enriched nucleic acids of SEQ ID NOS: 3, 5, 7, 9, 11, 13, 15, 17, 19, 21, 23, 26, 28, 30, 32, 34, 36, 38, 40, 42, 44, 46, 48, 51, 53, 55, 57, the sequences complementary thereto may be used as probes to identify and isolate related nucleic acids. In some embodiments, the related nucleic acids may be genomic DNAs (or cDNAs) from potential polyketide producers. In such procedures, a nucleic acid sample containing nucleic acids from a potential microbial producer of a compound of Formula I is contacted with the probe under conditions that permit the probe to specifically hybridize to related sequences. The nucleic acid sample may be a genomic DNA (or cDNA) library from the potential polyketide-producer. Hybridization of the probe to nucleic acids is then detected using any of the methods described above.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10× Denhardt's, and 0.5 mg/ml polyriboadenylic acid. Approximately $2 \times 10^7$ cpm (specific activity $4-9 \times 10^8$ cpm/ug) of $^{32}P$ end-labeled oligonucleotide probe are then added to the solution. After 12-16 hours of incubation, the membrane is washed for 30 minutes at room temperature in 1×SET (150 mM NaCl, 20 mM Tris hydrochloride, pH 7.8, 1 mM $Na_2EDTA$) containing 0.5% SDS, followed by a 30 minute wash in fresh 1×SET at Tm-10° C. for the oligonucleotide probe where Tm is the melting temperature. The membrane is then exposed to autoradiographic film for detection of hybridization signals.

By varying the stringency of the hybridization conditions used to identify nucleic acids, such as genomic DNAs or cDNAs, which hybridize to the detectable probe, nucleic acids having different levels of homology to the probe can be identified and isolated. Stringency may be varied by conducting the hybridization at varying temperatures below the melting temperatures of the probes. The melting temperature of the probe may be calculated using the following formulas:

For oligonucleotide probes between 14 and 70 nucleotides in length the melting temperature (Tm) in degrees Celcius may be calculated using the formula: Tm=81.5+16.6(log [Na+])+0.41 (fraction G+C)−(600/N) where N is the length of the oligonucleotide.

If the hybridization is carried out in a solution containing formamide, the melting temperature may be calculated using the equation Tm=81.5+16.6(log [Na+])+0.41 (fraction G+C)−(0.63% formamide)−(600/N) where N is the length of the probe.

Prehybridization may be carried out in 6×SSC, 5× Denhardt's reagent, 0.5% SDS, 0.1 mg/ml denatured fragmented salmon sperm DNA or 6× SSC, 5× Denhardt's reagent, 0.5% SDS, 0.1 mg/ml denatured fragmented salmon sperm DNA, 50% formamide. The composition of the SSC and Denhardt's solutions are listed in Sambrook et al., supra.

Hybridization is conducted by adding the detectable probe to the hybridization solutions listed above. Where the probe comprises double stranded DNA, it is denatured by incubating at elevated temperatures and quickly cooling before addition to the hybridization solution. It may also be desirable to similarly denature single stranded probes to eliminate or diminish formation of secondary structures or oligomerization. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 5-10° C. below the Tm. Preferably, the hybridization is conducted in 6×SSC, for shorter probes. Preferably, the hybridization is conducted in 50% formamide containing solutions, for longer probes.

All the foregoing hybridizations would be considered to be examples of hybridization performed under conditions of high stringency.

Following hybridization, the filter is washed for at least 15 minutes in 2×SSC, 0.1% SDS at room temperature or higher, depending on the desired stringency. The filter is then washed with 0.1×SSC, 0.5% SDS at room temperature (again) for 30 minutes to 1 hour.

Nucleic acids which have hybridized to the probe are identified by conventional autoradiography and non-radioactive detection methods.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate stringency" conditions above 50° C. and "low stringency" conditions below 50° C. A specific example of "moderate stringency" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate stringency" conditions above 25% formamide and "low stringency" conditions below 25% formamide. A specific example of "moderate stringency" hybridization conditions is when the above hybridization is conducted at 30% formamide. A specific example of "low stringency" hybridization conditions is when the above hybridization is conducted at 10% formamide.

Nucleic acids which have hybridized to the probe are identified by conventional autoradiography and non-radioactive detection methods.

For example, the preceding methods may be used to isolate nucleic acids having a sequence with at least 97%, at least 95%, at least 90%, at least 85%, at least 80%, or at least 70% homology to a nucleic acid sequence selected from the group consisting of the sequences of SEQ ID NOS: 3, 5, 7, 9, 11, 13, 15, 17, 19, 21, 23, 26, 28, 30, 32, 34, 36, 38, 40, 42, 44, 46, 48, 51, 53, 55, 57, fragments comprising at least 10, 15, 20, 25, 30, 35, 40, 50, 75, 100, 150, 200, 300, 400, or 500 consecutive bases thereof, and the sequences complementary thereto. Homology may be measured using BLASTN™ version 2.0 with the default parameters. For example, the homologous polynucleotides may have a coding sequence that is a naturally occurring allelic variant of one of the coding sequences described herein. Such allelic variant may have a substitution, deletion or addition of one or more nucleotides when compared to the nucleic acids of SEQ ID NOS: 3, 5, 7, 9, 11, 13, 15, 17, 19, 21, 23, 26, 28, 30, 32, 34, 36, 38, 40, 42, 44, 46, 48, 51, 53, 55, 57, or the sequences complementary thereto.

Additionally, the above procedures may be used to isolate nucleic acids which encode polypeptides having at least 99%, 95%, at least 90%, at least 85%, at least 80%, or at least 70% homology to a polypeptide having the sequence of one of SEQ ID NOS: 2, 4, 6, 8, 10, 12, 14, 16, 18, 20, 22, 25, 27, 29, 31, 33, 35, 37, 39, 41, 43, 47, 50, 52, 54, 56, or fragments comprising at least 50, 75, 100, 150, 200, 300 consecutive amino acids thereof as determined using the BLASTP™ version 2.2.2 algorithm with default parameters.

Another aspect of the present invention is an isolated or purified polypeptide comprising the sequence of one of SEQ ID NOS: 2, 4, 6, 8, 10, 12, 14, 16, 18, 20, 22, 25, 27, 29, 31, 33, 35, 37, 39, 41, 43, 47, 50, 52, 54, 56 or fragments comprising at least 50, 75, 100, 150, 200 or 300 consecutive amino acids thereof. As discussed herein, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for modulating expression levels, an origin of replication and a selectable marker.

Promoters suitable for expressing the polypeptide or fragment thereof in bacteria include the *E. coli* lac or trp promoters, the lad promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK), and the acid phosphatase promoter. Fungal promoters include the α factor promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Mammalian expression vectors may also comprise an origin of replication, any necessary ribosome binding sites, a polyadenylation site, splice donors and acceptor sites, transcriptional termination sequences, and 5' flanking non-transcribed sequences. In some embodiments, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

In addition, the expression vectors preferably contain one or more selectable marker genes to permit selection of host cells containing the vector. Examples of selectable markers that may be used include genes encoding dihydrofolate reductase or genes conferring neomycin resistance for eukaryotic cell culture, genes conferring tetracycline or ampicillin resistance in *E. coli*, and the *S. cerevisiae* TRP1 gene.

In some embodiments, the nucleic acid encoding one of the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56, or fragments comprising at least 50, 75, 100, 150, 200 or 300 consecutive amino acids thereof is assembled in appropriate phase with a leader sequence capable of directing secretion of the translated polypeptides or fragments thereof. Optionally, the nucleic acid can encode a fusion polypeptide in which one of the polypeptide of SEQ ID NOS: 2, 4, 6, 8, 10, 12, 14, 16, 18, 20, 22, 25, 27, 29, 31, 33, 35, 37, 39, 41, 43, 47, 50, 52, 54, 56 or fragments comprising at least 5, 10, 15, 20, 25, 30, 35, 40, 50, 75, 100, or 150 consecutive amino acids thereof is fused to heterologous peptides or polypeptides, such as N-terminal identification peptides which impart desired characteristics such as increased stability or simplified purification or detection.

The appropriate DNA sequence may be inserted into the vector by a variety of procedures. In general, the DNA sequence is ligated to the desired position in the vector following digestion of the insert and the vector with appropriate restriction endonucleases. Alternatively, appropriate restriction enzyme sites can be engineered into a DNA sequence by PCR. A variety of cloning techniques are disclosed in Ausbel et al. Current Protocols in Molecular Biology, John Wiley 503 Sons, Inc. (1997) and Sambrook et al., Molecular Cloning: A Laboratory Manual 2d Ed., Cold Spring Harbour Laboratory Press, (1989). Such procedures and others are deemed to be within the scope of those skilled in the art.

The vector may be, for example, in the form of a plasmid, a viral particle, or a phage. Other vectors include derivatives of chromosomal, nonchromosomal and synthetic DNA sequences, viruses, bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by Sambrook, et al., Molecular Cloning: A Laboratory Manual, Second Edition, Cold Spring Harbor, N.Y., (1989).

Particular bacterial vectors which may be used include the commercially available plasmids comprising genetic elements of the well known cloning vector pBR322 (ATCC™ 37017), pKK223-3 (Pharmacia Fine Chemicals, Uppsala, Sweden), pGEM1 (Promega Biotec, Madison, Wis., USA) pQE70, pQE60, pQE-9 (Qiagen), pD10, phiX174, pBluescript™ II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, PBPV, pMSG, and pSVL (Pharmacia). However, any other vector may be used as long as it is replicable and stable in the host cell.

The host cell may be any of the host cells familiar to those skilled in the art, including prokaryotic cells or eukaryotic cells. As representative examples of appropriate hosts, there may be mentioned: bacteria cells, such as *E. coli, Streptomyces, Bacillus subtilis, Salmonella typhimurium* and various species within the genera *Pseudomonas, Streptomyces,* and *Staphylococcus*, fungal cells, such as yeast, insect cells such as *Drosophila* S2 and *Spodoptera* Sf9, animal cells such as CHO, COS or Bowes melanoma, and adenoviruses. The selection of an appropriate host is within the abilities of those skilled in the art.

The vector may be introduced into the host cells using any of a variety of techniques, including electroporation transformation, transfection, transduction, viral infection, gene guns, or Ti-mediated gene transfer. Where appropriate, the engineered host cells can be cultured in conventional nutrient media modified as appropriate for activating promoters, selecting transformants or amplifying the genes of the present invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, Cell, 23:175(1981)), and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptide produced by host cells containing the vector may be glycosylated or may be non-glycosylated. Polypeptides of the invention may or may not also include an initial methionine amino acid residue.

Alternatively, the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56, or fragments comprising at least 50, 75, 100, 150, 200 or 300 consecutive amino acids thereof can be synthetically produced by conventional peptide synthesizers. In other embodiments, fragments or portions of the polynucleotides may be employed for producing the corresponding full-length polypeptide by peptide synthesis; therefore, the fragments may be employed as intermediates for producing the full-length polypeptides.

Cell-free translation systems can also be employed to produce one of the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56, or fragments comprising at least 50, 75, 100, 150, 200 or 300 consecutive amino acids thereof using mRNAs transcribed from a DNA construct comprising a promoter operably linked to a nucleic acid encoding the polypeptide or fragment thereof. In some embodiments, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The present invention also relates to variants of the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56, or fragments comprising at least 50, 75, 100, 150, 200 or 300 consecutive amino acids thereof. The term "variant" includes derivatives or analogs of these polypeptides. In particular, the variants may differ in amino acid sequence from the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56, by one or more substitutions, additions, deletions, fusions and truncations, which may be present in any combination.

The variants may be naturally occurring or created in vitro. In particular, such variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures.

Other methods of making variants are also familiar to those skilled in the art. These include procedures in which nucleic acid sequences obtained from natural isolates are modified to generate nucleic acids that encode polypeptides having characteristics which enhance their value in industrial or laboratory applications. In such procedures, a large number of variant sequences having one or more nucleotide differences with respect to the sequence obtained from the natural isolate are generated and characterized. Preferably, these nucleotide differences result in amino acid changes with respect to the polypeptides encoded by the nucleic acids from the natural isolates.

For example, variants may be created using error prone PCR. In error prone PCR, DNA amplification is performed under conditions where the fidelity of the DNA polymerase is low, such that a high rate of point mutation is obtained along the entire length of the PCR product. Error prone PCR is described in Leung, D. W., et al., Technique, 1:11-15 (1989) and Caldwell, R. C. & Joyce G. F., PCR Methods Applic., 2:28-33 (1992). Variants may also be created using site directed mutagenesis to generate site-specific mutations in any cloned DNA segment of interest. Oligonucleotide mutagenesis is described in Reidhaar-Olson, J. F. & Sauer, R. T., et al., Science, 241:53-57 (1988). Variants may also be created using directed evolution strategies such as those described in U.S. Pat. Nos. 6,361,974 and 6,372,497. The variants of the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56, may be (i) variants in which one or more of the amino acid residues of the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56, are substituted with a conserved or non-conserved amino acid residue (preferably a conserved amino acid residue) and such substituted amino acid residue may or may not be one encoded by the genetic code.

Conservative substitutions are those that substitute a given amino acid in a polypeptide by another amino acid of like characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp or Glu with another acidic residue; replacement of a residue bearing an amide group, such as Asn or Gln, with another residue bearing an amide group; exchange of a basic residue such as Lys or Arg with another basic residue; and replacement of an aromatic residue such as Phe or Tyr with another aromatic residue.

Other variants are those in which one or more of the amino acid residues of the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56 includes a substituent group.

Still other variants are those in which the polypeptide is associated with another compound, such as a compound to increase the half-life of the polypeptide (for example, polyethylene glycol).

Additional variants are those in which additional amino acids are fused to the polypeptide, such as leader sequence, a secretory sequence, a proprotein sequence or a sequence which facilitates purification, enrichment, or stabilization of the polypeptide.

In some embodiments, the fragments, derivatives and analogs retain the same biological function or activity as the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56. In other embodiments, the fragment, derivative or analogue includes a fused heterologous sequence which facilitates purification, enrichment, detection, stabilization or secretion of the polypeptide that can be enzymatically cleaved, in whole or in part, away from the fragment, derivative or analogue.

Another aspect of the present invention are polypeptides or fragments thereof which have at least 70%, at least 80%, at least 85%, at least 90%, or more than 95% homology to one of the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56, or a fragment comprising at least 50, 75, 100, 150, 200 or 300 consecutive amino acids thereof. Homology may be determined using a program, such as BLASTP version 2.2.2 with the default parameters, which aligns the polypeptides or fragments being compared and determines the extent of amino acid identity or similarity between them. It will be appreciated that amino acid "homology" includes conservative substitutions such as those described above.

The polypeptides or fragments having homology to one of the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56, or a fragment thereof may be obtained by isolating the nucleic acids encoding them using the techniques described above.

Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of SEQ ID NOS: 2, 4, 6, 8, 10, 12, 14, 16, 18, 20, 22, 25, 27, 29, 31, 33, 35, 37, 39, 41, 43, 47, 50, 52, 54, 56, or a fragment thereof using a program such as BLASTP version 2.2.2 with the default parameters.

The PKS system of SEQ ID NOS: 37, 39, 41, 43, 45 and 47 may be modified to produce compounds of Formula I. Genetic modifications of PKS biosynthetic loci are well known in the art. The WO 01/34816 patent publication teaches the construction of a library of structural variants of the macrolide polyketide rapamycin derived from the genetic modification of genes in the locus that directs rapamycin synthesis. The genetic modifications taught include gene inactivations, gene insertions and gene replacements. These modifications, both individually and in combination at different positions within the rapamycin locus, resulted in alteration of polyketide starter units, chain length and hydroxyl sterospecificities in rapamycin. Similarly, McDaniel, et.al. [Proc Natl Acad Sci USA, 1999, 96:18646-51] generated a library of over 50 derivatives of the macrolide antibiotic erythromycin using a combination of genetic modifications including gene inactivations, macrolide chain length and hydroxyl sterospecificity modifications of the erythromycin biosynthesis genes. The PKS system of the invention may be genetically modified to produce compounds of Formula I. The biosynthetic locus of Example 1 is modified by deletion, mutagenesis, inactivation or replacement of one or more nucleic acid sequence that encode enzymatic activities. The modified gene locus of Example 1 produces compounds of Formula I that differ in size, degree of saturation and degree of oxidation. Compounds produced by these genetic modifications include, without limitations, Compounds 12, 14 and 16.

Pharmaceutical Composition Comprising the Compounds of the Invention

The compounds of the present invention, or pharmaceutically acceptable salts or prodrugs thereof, can be formulated for oral, intravenous, intramuscular, subcutaneous, topical or parenteral administration for the therapeutic or prophylactic treatment of diseases, particularly bacterial infections. For oral or parental administration, compounds of the present invention can be mixed with conventional pharmaceutical carriers and excipients and used in the form of tablets, capsules, elixirs, suspensions, syrups, wafers and the like. The compositions comprising a compound of this present invention will contain from about 0.1% to about 99.9%, about 5% to about 95%, about 10% to about 80% or about 15% to about 60% by weight of the active compound.

The pharmaceutical preparations disclosed herein are prepared in accordance with standard procedures and are administered at dosages that are selected to reduce, prevent, or eliminate bacterial infection (See, e.g., Remington's Pharmaceutical Sciences, Mack Publishing Company, Easton, Pa. and Goodman and Gilman's the Pharmaceutical Basis of Therapeutics, Pergamon Press, New York, N.Y., the contents of which are incorporated herein by reference, for a general description of the methods for administering various antimicrobial agents for human therapy). The compositions of the present invention can be delivered using controlled (e.g., capsules) or sustained release delivery systems (e.g., bioerodable matrices). Exemplary delayed release delivery systems for drug delivery that are suitable for administration of the compositions of the invention (preferably of Formula I) are described in U.S. Pat. No. 4,452,775 (issued to Kent), U.S. Pat. No. 5,039,660 (issued to Leonard), U.S. Pat. No. 3,854,480 (issued to Zaffaroni).

The pharmaceutically-acceptable compositions of the present invention comprise one or more compounds of the present invention in association with one or more non-toxic, pharmaceutically-acceptable carriers and/or diluents and/or adjuvants and/or excipients, collectively referred to herein as "carrier" materials, and if desired other active ingredients. The compositions may contain common carriers and excipients, such as corn starch or gelatin, lactose, sucrose, microcrystalline cellulose, kaolin, mannitol, dicalcium phosphate, sodium chloride and alginic acid. The compositions may contain crosarmellose sodium, microcrystalline cellulose, sodium starch glycolate and alginic acid.

Tablet binders that can be included are acacia, methylcellulose, sodium carboxymethylcellulose, polyvinylpyrrolidone (Providone), hydroxypropyl methylcellulose, sucrose, starch and ethylcellulose.

Lubricants that can be used include magnesium stearate or other metallic stearates, stearic acid, silicon fluid, talc, waxes, oils and colloical silica. Flavouring agents such as peppermint, oil of wintergreen, cherry flavouring or the like can also be used. It may also be desirable to add a coloring agent to make the dosage form more esthetic in appearance or to help identify the product comprising a compound of the present invention.

For oral use, solid formulations such as tablets and capsules are particularly useful. Sustained released or enterally coated preparations may also be devised. For pediatric and geriatric applications, suspension, syrups and chewable tablets are especially suitable. For oral administration, the pharmaceutical compositions are in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica or talc: disintegrants, for example, potato starch, flavoring or coloring agents, or acceptable wetting agents. Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For intravenous (IV) use, compounds of the present invention can be dissolved or suspended in any of the commonly used intravenous fluids and administered by infusion. Intravenous fluids include, without limitation, physiological saline or Ringer's solution.

Formulations for parental administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

For intramuscular preparations, a sterile formulation of compounds of the present invention or suitable soluble salts forming the compound, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g. an ester of a long chain fatty acid such as ethyl oleate.

For topical use the compounds of present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compound of the present invention can be in powder form for reconstitution in the appropriate pharmaceutically acceptable carrier at the time of delivery. In another embodiment, the unit dosage form of the compound can be a solution of the compound or a salt thereof in a suitable diluent in sterile, hermetically sealed ampoules.

The amount of the compound of the present invention in a unit dosage comprises a therapeutically-effective amount of at least one active compound of the present invention which may vary depending on the recipient subject, route and frequency of administration. A recipient subject refers to a plant, a cell culture or an animal such as an ovine or a mammal including a human.

According to this aspect of the present invention, the novel compositions disclosed herein are placed in a pharmaceutically acceptable carrier and are delivered to a recipient subject (including a human subject) in accordance with known methods of drug delivery. In general, the methods of the invention for delivering the compositions of the invention in vivo utilize art-recognized protocols for delivering the agent with the only substantial procedural modification being the substitution of the compounds of the present invention for the drugs in the art-recognized protocols.

Likewise, the methods for using the claimed composition for treating cells in culture, for example, to eliminate or reduce the level of bacterial contamination of a cell culture, utilize art-recognized protocols for treating cell cultures with antibacterial agents with the only substantial procedural modification being the substitution of the compounds of the present invention for the agents used in the art-recognized protocols.

The compounds of the present invention provide a method for treating microbial infections. As used herein the term unit dosage refers to a quantity of a therapeutically-effective amount of a compound of the present invention that elicits a desired therapeutic response. As used herein the phrase therapeutically-effective amount means an amount of a compound of the present invention that prevents the onset, alleviates the symptoms, or stops the progression of a bacterial infection. The term treating is defined as administering, to a subject, a therapeutically-effective amount of at least one compound of the present invention, both to prevent the occurrence of a bacterial infection, or to control or eliminate a bacterial infection. The term desired therapeutic response refers to treating a recipient subject with a compound of the present invention such that a bacterial infection is reversed, arrested or prevented in a recipient subject.

The compounds of the present invention can be administered as a single daily dose or in multiple doses per day. The treatment regime may require administration over extended periods of time, e.g., for several days or for from two to four weeks. The amount per administered dose or the total amount administered will depend on such factors as the nature and severity of the infection, the age and general health of the recipient subject, the tolerance of the recipient subject to the compound and the type of the bacterial infection.

A compound according to this invention may also be administered in the diet or feed of a patient or animal. The diet for animals can be normal foodstuffs to which the compound can be added or it can be added to a premix.

The compounds of the present invention may be taken in combination, together or separately with any known clinically approved antibiotic to treat a recipient subject in need of such treatment.

Method of Inhibiting Bacterial Growth

In one embodiment, the present invention relates to a method for treating bacterial infection in a mammalian subject in need thereof, comprising the step of administering to the mammal a therapeutically effective amount of a polyene polyketide of Formula I, a compound as described herein, or a pharmaceutically acceptable derivative or prodrug thereof.

In another embodiment, the present invention relates to the use of a polyene polyketide of Formula I, a compound as described herein, or a pharmaceutically acceptable salt, derivative or prodrug thereof, as a pharmaceutical for treating bacterial infection in a mammalian subject in need thereof.

According to another embodiment, the invention provides a method of decreasing bacterial quantity in a biological sample. This method comprises the step of contacting the biological sample with a polyene polyketide of Formula I, a compound as described herein, or a pharmaceutically acceptable derivative or prodrug thereof. This method is effective if the number of bacteria decreases by at least 10%, and preferably more, e.g., 25%, 50%, 75% or even 100% after contacting the biological sample with a polyene polyketide of Formula I, a compound as described herein, or a pharmaceutically acceptable derivative or prodrug thereof.

These pharmaceutical compositions effective to treat or prevent a bacterial infection which comprise any one of Compounds 1 to 7, a compound of Formula I as described herein, or a pharmaceutically acceptable derivative or prodrug thereof in an amount sufficient to measurably decrease bacterial quantity, and a pharmaceutically acceptable carrier, are another embodiment of the present invention. The term "measurably decrease bacterial quantity", as used herein means a measurable change in the number of bacteria between a sample containing the inhibitor and a sample not containing the inhibitor.

Agents which increase the susceptibility of bacterial organisms to antibiotics are known. For example, U.S. Pat. Nos. 5,523,288, 5,783,561 and 6,140,306 describe methods of using bactericidal/permeability-increasing protein (BPI) for increasing antibiotic susceptibility of gram-positive and gram-negative bacteria. Agents that increase the permeability of the outer membrane of bacterial organisms have been described by Vaara, M. in Microbiological Reviews (1992) pp. 395-411, and the sensitization of gram-negative bacteria has been described by Tsubery, H., et al, in J. Med. Chem. (2000) pp. 3085-3092.

For the method of the invention related to treatment of subjects with a bacterial infection, a typical effective unit dose of any one of Compounds 1 to 7, a compound of Formula I as described herein or a pharmaceutically acceptable derivative or prodrug thereof given orally or parenterally would be from about 5 to about 100 mg/kg of body weight of the subject with a daily dose ranging from about 15 to about 300 mg/kg of body weight of the subject.

Another preferred embodiment of this invention relates to a method, as described above, of treating a bacterial infection in a mammal in need thereof, but further comprising the step of administering to the mammal an agent which increases the susceptibility of bacterial organisms to antibiotics.

According to another preferred embodiment, the invention provides a method, as described above, of decreasing bacterial quantity in a biological sample, but further comprising the step of contacting the biological sample with an agent which increases the susceptibility of bacterial organisms to antibiotics.

Methods of decreasing bacterial quantity are effective if the number of bacteria decreases at least 10%, and preferably more, e.g., 25%, 50%, 75% or even 100% after contacting the biological sample with any one of Compounds 1 to 7, a compound of Formula I as described herein, or a pharmaceutically acceptable derivative or prodrug thereof.

The pharmaceutical compositions and methods of this invention will be useful generally for controlling bacterial infections in vivo. Examples of bacterial organisms that may be controlled by the compositions and methods of this invention include, but are not limited to the following organisms: *Streptococcus pneumoniae, Streptococcus pyogenes, Enterococcus faecalis, Enterococcus faecium, Klebsiella pneumoniae, Enterobacter* spp., *Proteus* spp., *Pseudomonas aeruginosa, Escherichia coli, Serratia marcesens, Staphylococcus aureus, Haemophilus infuenzae, Bacillus anthracis, Mycoplasma pneumoniae*, and Coagulase negative *Staphylococcus* including *Staphylococcus epidermidis*. The compositions and methods will therefore be useful for controlling, treating or reducing the advancement, severity or effects of nosocomial or non-nosocomial infections. Examples of nosocomial uses include, but are not limited to, urinary tract infections, pneumonia, surgical wound infections, bacteremia and therapy for febrile neutropenic patients. Examples of non-nosocomial uses include but are not limited to urinary tract infections, pneumonia, prostatitis, skin and soft tissue infections and intra-abdominal infections.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

EXAMPLE 1

Genes and Proteins for Producing the Compounds of the Invention

*Amycolatopsis orientalis* ATCC™ 43491 was obtained from the American Type Culture Collection (P.O. Box 1549, Manassas, Va. 20108, USA). The biosynthetic locus for the production of the compound of Formula I was identified in the genome of *Amycolatopsis orientalis* ATCC™ 43491 using the genome scanning method described in U.S. Ser. No. 10/232,370, CA 2,352,451 and Zazopoulos et. al., *Nature Biotechnol.*, 21,187-190 (2003).

Figure 11:
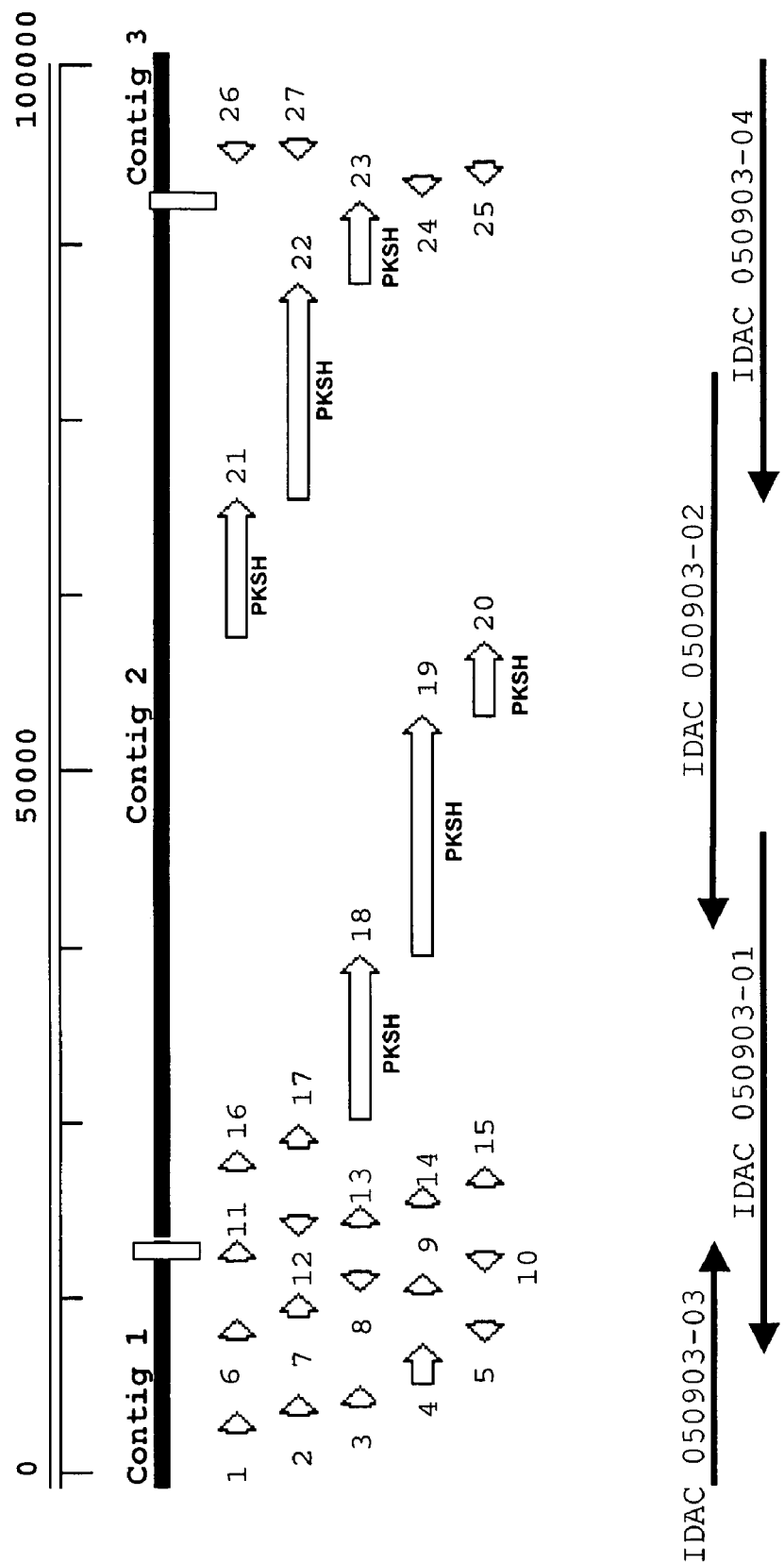
FIG. 11: biosynthetic locus producing compounds of Formula I in *Amycolatopsis orientalis*, showing a scale in base pairs units; the position of the three sequence of contiguous nucleic acids of SEQ ID NOS: 1, 24 and 49; the position and orientation of the 27 open reading frames of the biosynthetic locus identified by ORF number with the six polyketide synthase ORFs identified with PKSE designation; and the coverage of the biosynthetic locus by cosmids having deposit accession nos: IDAC 050903-01, IDAC 050903-$O_2$, IDAC 050903-03 and IDAC 050903-04.

The biosynthetic locus spans approximately 100,000 base pairs of DNA and encodes 27 proteins. More than 10 kilobases of DNA sequence were analyzed on each side of the locus and these regions were deemed to contain primary genes or genes unrelated to the synthesis of the compound of Formula I. As illustrated in FIG. 11, the locus is contained within three sequences of contiguous base pairs, namely Contig 1 having the 12,647 contiguous base pairs of SEQ ID NO: 1 and comprising ORFs 1 to 11 (SEQ ID NOS: 3, 5, 7, 9, 11, 13, 15, 17, 19, 21 and 23), Contig 2 having the 73,599 contiguous base pairs of SEQ ID NO: 24 and comprising ORFs 12 to 23 (SEQ ID NOS: 26, 28, 30, 32, 34, 36, 38, 40, 42, 44, 46 and 48), and Contig 3 having the 6,995 base pairs of SEQ ID NO: 49 and comprising ORFs 24 to 27 (SEQ ID NOS: 51, 53, 55 and 57). The order, relative position and orientation of the 27 open reading frames representing the proteins of the biosynthetic locus are illustrated schematically in FIG. 11. The top line in FIG. 11 provides a scale in base pairs. The black bars depict the three DNA contigs (SEQ ID NOS: 1, 24 and 49) that cover the locus. The empty arrows represent the 27 open reading frames of this biosynthetic locus. The black arrows represent the four deposited cosmid clones covering the locus.

The biosynthetic locus will further be understood with reference to the sequence listing which provides contiguous nucleotide sequences and deduced amino acid sequences of the locus from *Amycolatopsis orientalis* ATCC™ 43491. The contiguous nucleotide sequences are arranged such that, as found within the biosynthetic locus, Contig 1 (SEQ ID NO: 1) is adjacent to the 5' end of Contig 2 (SEQ ID NO: 24), which in turn is adjacent to Contig 3 (SEQ ID NO: 49). The ORFs illustrated in FIG. 11 and provided in the sequence listing represent open reading frames deduced from the nucleotide sequences of Contigs 1, 2 and 3 (SEQ ID NOS: 1, 24 and 49). Referring to the Sequence Listing, ORF 1 (SEQ ID NO: 3) is the polynucleotide drawn from residues 1 to 438 (sense/antisense strand) of SEQ ID NO: 1, and SEQ ID NO: 2 represents that polypeptide deduced from SEQ ID NO: 3. ORF 2 (SEQ ID NO: 5) is the polynucleotide drawn from residues 435 to 1544 of SEQ ID NO: 1, and SEQ ID NO: 4 represents the polypeptide deduced from SEQ ID NO: 5. ORF 3 (SEQ ID NO: 7) is the polynucleotide drawn from residues 1656 to 2171 of SEQ ID NO: 1, and SEQ ID NO: 6 represents the polypeptide deduced from SEQ ID NO: 7. ORF 4 (SEQ ID NO: 9) is the polynucleotide drawn from residues 2393 to 5203 of SEQ ID NO: 1, and SEQ ID NO: 8 represents the polypeptide deduced from SEQ ID NO: 9. ORF 5 (SEQ ID NO: 11) is the polynucleotide drawn from residues 6231 to 5419 of SEQ ID NO: 1, and SEQ ID NO: 10 represents the polypeptide deduced from SEQ ID NO: 11. ORF 6 (SEQ ID NO: 13) is the polynucleotide drawn from residues 6415 to 7104 of SEQ ID NO: 1, and SEQ ID NO: 12 represents the polypeptide deduced from SEQ ID NO: 13. ORF 7 (SEQ ID NO: 15) is the polynucleotide drawn from residues 7213 to 8874 of SEQ ID NO: 1, and SEQ ID NO: 14 represents the polypeptide deduced from SEQ ID NO: 15. ORF 8 (SEQ ID NO: 17) is the polynucleotide drawn from residues 9477 to 8938 of SEQ ID NO: 1, and SEQ ID NO: 16 represents the polypeptide deduced from SEQ ID NO: 17. ORF 9 (SEQ ID NO: 19) is the polynucleotide drawn from residues 9655 to 10323 of SEQ ID NO: 1, and SEQ ID NO: 18 represents the polypeptide deduced from SEQ ID NO: 19. ORF 10 (SEQ ID NO: 21) is the polynucleotide drawn from residues 11655 to 10516 of SEQ ID NO: 1, and SEQ ID NO: 20 represents the polypeptide deduced from SEQ ID NO: 21. ORF 11 (SEQ ID NO: 23) is the polynucleotide drawn from residues 11855 to 12610 of SEQ ID NO: 1, and SEQ ID NO: 22 represents the polypeptide deduced from SEQ ID NO: 23. ORF 12 (SEQ ID NO: 26) is the polynucleotide drawn from residues 520 to 32 of SEQ ID NO: 24, and SEQ ID NO: 25 represents the polypeptide deduced from SEQ ID NO: 26. ORF 13 (SEQ ID NO: 28) is the polynucleotide drawn from residues 840 to 2165 of SEQ ID NO: 24, and SEQ ID NO: 27 represents the polypeptide deduced from SEQ ID NO: 28. ORF 14 (SEQ ID NO: 30) is the polynucleotide drawn from residues 2201 to 3424 of SEQ ID NO: 24, and SEQ ID NO: 29 represents the polypeptide deduced from SEQ ID NO: 30. ORF 15 (SEQ ID NO: 32) is the polynucleotide drawn from residues 3429 to 4994 of SEQ ID NO: 24, and SEQ ID NO: 31 represents the polypeptide deduced from SEQ ID NO: 32. ORF 16 (SEQ ID NO: 34) is the polynucleotide drawn from residues 4991 to 6199 of SEQ ID NO: 24, and SEQ ID NO: 33 represents the polypeptide deduced from SEQ ID NO: 34. ORF 17 (SEQ ID NO: 36) is the polynucleotide drawn from residues 6389 to 7924 of SEQ ID NO: 24, and SEQ ID NO: 35 represents the polypeptide deduced from SEQ ID NO: 36. ORF 18 (SEQ ID NO: 38) is the polynucleotide drawn from residues 8404 to 19908 of SEQ ID NO: 24, and SEQ ID NO: 37 represents the polypeptide deduced from SEQ ID NO: 38. ORF 19 (SEQ ID NO: 40) is the polynucleotide drawn from residues 19910 to 37081 of SEQ ID NO: 24, and SEQ ID NO: 39 represents the polypeptide deduced from SEQ ID NO: 40. ORF 20 (SEQ ID NO: 42) is the polynucleotide drawn from residues 37085 to 42292 of SEQ ID NO: 24, and SEQ ID NO: 41 represents the polypeptide deduced from SEQ ID NO: 42. ORF 21 (SEQ ID NO: 44) is the polynucleotide drawn from residues 42617 to 52411 of SEQ ID NO: 24, and SEQ ID NO: 43 represents the polypeptide deduced from SEQ ID NO: 44. ORF 22 (SEQ ID NO: 46) is the polynucleotide drawn from residues 52438 to 67737 of SEQ ID NO: 24, and SEQ ID NO: 45 represents the polypeptide deduced from SEQ ID NO: 46. ORF 23 (SEQ ID NO: 48) is the polynucleotide drawn from residues 67751 to 73516 of SEQ ID NO: 24, and SEQ ID NO: 47 represents the polypeptide deduced from SEQ ID NO: 48. ORF 24 (SEQ ID NO: 51) is the polynucleotide drawn from residues 939 to 16 of SEQ ID NO: 49, and SEQ ID NO: 50 represents the polypeptide deduced from SEQ ID NO: 51. ORF 25 (SEQ ID NO: 53) is the polynucleotide drawn from residues 2374 to 944 of SEQ ID NO: 49, and SEQ ID NO: 52 represents the polypeptide deduced from SEQ ID NO: 53. ORF 26 (SEQ ID NO: 55) is the polynucleotide drawn from residues 2600 to 2391 of SEQ ID NO: 49, and SEQ ID NO: 54 represents the polypeptide deduced from SEQ ID NO: 55. ORF 27 (SEQ ID NO: 57) is the polynucleotide drawn from residues 3378 to 2614 of SEQ ID NO: 49, and SEQ ID NO: 56 represents the polypeptide deduced from SEQ ID NO: 57.

Some open reading frames provided in the Sequence Listing, namely ORF 2 (SEQ ID NO: 4), ORF 5 (SEQ ID NO: 10), ORF 12 (SEQ ID NO: 25), ORF 13 (SEQ ID NO: 27), ORF 15 (SEQ ID NO: 31), ORF 17 (SEQ ID NO: 35), ORF 19 (SEQ ID NO: 39), ORF 20 (SEQ ID NO: 41), ORF 22 (SEQ ID NO: 45), ORF 24 (SEQ ID NO: 50), ORF 26 (SEQ ID NO: 54) and ORF 27 (SEQ ID NO: 56) initiate with non-standard initiation codons (eg. GTG—Valine, or CTG—Leucine) rather than standard initiation codon ATG methionine. All ORFs are listed with the appropriate M, V or L amino acids at the amino-terminal position to indicate the specificity of the first codon of the ORF. It is expected, however, that in all cases the biosynthesized protein will contain a methionine residue, and more specifically a formylmethionine residue, at the amino terminal position, in keeping with the widely accepted principle that protein synthesis in bacteria initiates with methionine (formylmethionine) even when the encoding gene specifies a non-standard initiation codon (e.g. Stryer BioChemistry $3^{rd}$ edition, 1998, W. H. Freeman and Co., New York, pp. 752-754).

Four deposits of *E. coli* DH10B vectors, each harbouring a cosmid clone of a partial biosynthetic locus for the compound of Formula I from *Amycolatopsis orientalis* (ATCC™ 43491) and together spanning the full biosynthetic locus for production of the compound of Formula I have been deposited with the International Depositary Authority of Canada, Bureau of Microbiology, Health Canada, 1015 Arlington Street, Winnipeg, Manitoba, Canada R3E 3R2 on Sep. 5, 2003 and were assigned deposit accession numbers IDAC 050903-01, IDAC 050903-$O_2$, IDAC 050903-03 and IDAC 050903-04 respectively. The cosmid of deposit IDAC 050903-03 covers residue 1 to residue 8800 of Contig 1 (SEQ ID NO: 1). The cosmid of deposit IDAC 050903-01 covers residue 1600 of Contig 1 (SEQ ID NO: 1) to residue 19840 of Contig 2 (SEQ ID NO: 24). The cosmid of deposit IDAC 050903-02 covers the residue 14700 to residue 52230 of Contig 2 (SEQ ID NO: 24). The cosmid of deposit IDAC 050903-04 covers residue 41090 of Contig 2 (SEQ ID NO: 24) to residue 3378 of Contig 3 (SEQ ID NO: 49). The sequence of the polynucleotides comprised in the deposited strains, as well as the amino acid sequence of any polypeptide encoded thereby are controlling in the event of any conflict with any description of sequences herein.

The deposit of the deposited strains has been made under the terms of the Budapest Treaty on the International Recognition of the Deposit of Micro-organisms for Purposes of Patent Procedure. The deposited strains will be irrevocably and without restriction or condition released to the public upon the issuance of a patent. The deposited strains are provided merely as convenience to those skilled in the art and are not an admission that a deposit is required for enablement, such as that required under 35 U.S.C. §112. A license may be required to make, use or sell the deposited strains, and compounds derived therefrom, and no such license is hereby granted.

In order to identify the function of the proteins coded by the genes forming the biosynthetic locus for the production of the compounds of Formula I the gene products of ORFs 1 to 27, namely SEQ ID NOS: 2, 4, 6, 8, 10, 12, 14, 16, 18, 20, 22, 25, 27, 29, 31, 33, 35, 37, 39, 41, 43, 45, 47, 50, 52, 54 and 56, were compared, using the BLASTP version 2.2.6 algorithm with the default parameters, to sequences in the National Center for Biotechnology Information (NCBI) nonredundant protein database and the DECIPHER® database of microbial genes, pathways and natural products (Ecopia BioSciences Inc. St.-Laurent, QC, Canada).

The accession numbers of the top GenBank™ hits of this BLAST analysis are presented in Table 2 along with the corresponding E values. The E value relates the expected number of chance alignments with an alignment score at least equal to the observed alignment score. An E value of 0.00 indicates a perfect homolog. The E values are calculated as described in Altschul et al. *J. Mol. Biol.*, 215, 403-410 (1990). The E value assists in the determination of whether two sequences display sufficient similarity to justify an inference of homology.

TABLE 2

| ORF | Family | # aa | Genbank homology | probability | % identity | % similarity | proposed function of GenBank match |
|---|---|---|---|---|---|---|---|
| 1 | UNBP | 145 | CAD60535.1, 194aa | 1e−21 | 52/127 (40.94%) | 71/127 (55.91%) | Cinorf13 protein *Streptomyces cinnamoneus* |
| | | | NP_822919.1, 176aa | 1e−06 | 36/113 (31.86%) | 57/113 (50.44%) | hypothetical protein *Streptomyces avermitilis* |
| | | | NP_301329.1, 79aa | 0.014 | 20/56 (35.71%) | 29/56 (51.79%) | hypothetical protein *Mycobacterium leprae* |
| 2 | MEBA | 369 | CAB86101, 260aa | 6.00E−05 | 69/260 (26%) | 97/260 (36%) | membrane protein |
| 3 | REQB | 171 | NP_301177.1, 132aa | 4e−10 | 41/131 (31.3%) | 73/131 (55.73%) | conserved hypothetical protein *Mycobacterium leprae* pir |
| | | | NP_218366.1, 132aa | 4e−10 | 41/131 (31.3%) | 73/131 (55.73%) | hypothetical protein Rv3849 *Mycobacterium tuberculosis* |
| | | | CAD60534.1, 163aa | 2e−09 | 42/120 (35%) | 61/120 (50.83%) | Cinorf12 protein *Streptomyces cinnamoneus* |
| 4 | REGD | 936 | AAC68887.1, 928aa | 1e−149 | 345/919 (37.54%) | 476/919 (51.8%) | putative transcriptional activator PikD *Streptomyces venezuelae* |
| | | | AAM88362.1, 945aa | 1e−146 | 337/915 (36.83%) | 469/915 (51.26%) | NbmM *Streptomyces narbonensis* |
| | | | NP_824077.1, 942aa | 1e−138 | 343/933 (36.76%) | 457/933 (48.98%) | LuxR-family transcriptional regulator *Streptomyces avermitilis* |
| 5 | MTNA | 271 | AAP36564.1, 237aa | 6e−20 | 74/214 (34.58%) | 99/214 (46.26%) | *Homo sapiens* guanidinoacetate N-methyltransferase |
| | | | NP_036925.1, 236aa | 2e−20 | 72/214 (33.64%) | 100/214 (46.73%) | guanidinoacetate methyltransferase *Rattus norvegicus* |
| | | | AAP36564.1, 237aa | 6e−20 | 74/214 (34.58%) | 99/214 (46.26%) | *Homo sapiens* guanidinoacetate N-methyltransferase |

TABLE 2-continued

| ORF | Family | # aa | Genbank homology | probability | % identity | % similarity | proposed function of GenBank match |
|---|---|---|---|---|---|---|---|
| 6 | MEMO | 229 | NP_825904.1, 233aa | 5e−23 | 71/187 (37.97%) | 91/187 (48.66%) | putative membrane protein *Streptomyces avermitilis* |
|  |  |  | NP_627542.1, 238aa | 5e−19 | 64/191 (33.51%) | 93/191 (48.69%) | putative membrane protein *Streptomyces coelicolor* |
|  |  |  | AAN07910.1, 277aa | 3e−17 | 58/181 (32.04%) | 88/181 (48.62%) | AlbD *Streptomyces noursei* |
| 7 | TMOA | 553 | NP_828069.1, 565aa | 0.0 | 328/548 (59.85%) | 394/548 (71.9%) | putative amino oxidase *Streptomyces avermitilis* |
|  |  |  | NP_625735.1, 565aa | 0.0 | 325/548 (59.31%) | 394/548 (71.9%) | putative amino oxidase *Streptomyces coelicolor* |
|  |  |  | ZP_00086824.1, 560aa | 1e−172 | 290/552 (52.54%) | 371/552 (67.21%) | hypothetical protein *Pseudomonas fluorescens* |
| 8 | UNEW | 179 | ZP_00100936.1, 308aa | 0.086 | 30/98 (30.61%) | 49/98 (50%) | hypothetical protein *Desulfitobacterium hafniense* |
|  |  |  | NP_629948.1, 229aa | 6e−55 | 120/225 (53.3%) | 143/225 (63.56%) | two-component response regulator *Streptomyces* |
|  |  |  | NP_628533.1, 226aa | 1e−43 | 101/219 (46.12%) | 130/219 (59.36%) | two-component response regulator *Streptomyces* |
| 10 | SPKF | 379 | NP_629947.1, 384aa | 2e−34 | 93/216 (43.06%) | 119/216 (55.09%) | putative two-component sensor *Streptomyces coelicolor* |
|  |  |  | NP_823615.1, 384aa | 4e−34 | 93/216 (43.06%) | 122/216 (56.48%) | putative two-component sensor kinase *Streptomyces* |
|  |  |  | NP_628532.1, 403aa | 8e−29 | 87/231 (37.66%) | 115/231 (49.78%) | putative two component sensor kinase *Streptomyces* |
| 11 | TESA | 251 | AAO65810.1, 267aa | 8e−50 | 112/251 (44.62%) | 139/251 (55.38%) | thioesterase; MonAX *Streptomyces cinnamonensis* |
|  |  |  | NP_822128.1, 250aa | 1e−48 | 107/242 (44.21%) | 134/242 (55.37%) | thioesterase *Streptomyces avermitilis* |
|  |  |  | NP_851508.1, 265aa | 1e−47 | 103/225 (45.78%) | 131/225 (58.22%) | probable thioesterase *Streptomyces rochei* |
| 12 | UNIQ | 162 | No hits | No hits | No hits | No hits | No hits |
| 13 | SOXA | 441 | AAF23790.1, 437aa | 6e−88 | 176/436 (40.37%) | 256/436 (58.72%) | UDP-glucose dehydrogenase *Zymomonas mobilis* |
|  |  |  | NP_385188.1, 437aa | 1e−87 | 180/438 (41.1%) | 253/438 (57.76%) | UDP-GLUCOSE 6-DEHYDROGENASE *Sinorhizobium* |
|  |  |  | ZP_00052125.1, 439aa | 2e−87 | 182/434 (41.94%) | 248/434 (57.14%) | hypothetical protein *Magnetospirillum magnetotacticum* |
| 14 | GTFA | 407 | AAM54103.1, 402aa | 4e−67 | 165/409 (40.34%) | 207/409 (50.61%) | glycosyltransferase *Actinosynnema pretiosum* subsp. *auranticum* |
|  |  |  | AAM70336.1, 392aa | 1e−16 | 103/418 (24.64%) | 158/418 (37.8%) | CalG1 *Micromonospora echinospora* |
|  |  |  | NP_624398.1, 407aa | 1e−13 | 87/270 (32.22%) | 122/270 (45.19%) | putative glycosyl transferase *Streptomyces coelicolor* |
| 15 | ADSN | 521 | AAG34183.1, 519aa | 1e−111 | 223/515 (43.3%) | 297/515 (57.67%) | SimL *Streptomyces antibioticus* |
|  |  |  | AAG29784.1, 529aa | 2e−76 | 178/510 (34.9%) | 246/510 (48.24%) | putative ligase *Streptomyces rishiriensis* |
|  |  |  | AAN65228.1, 527aa | 4e−76 | 175/513 (34.11%) | 246/513 (47.95%) | amide synthetase *Streptomyces roseochromogenes* subsp. *oscitans* |
| 16 | AYTP | 402 | NP_387095.1, 405aa | 1e−101 | 190/382 (49%) | 237/382 (62%) | 5-aminolevulinic acid synthase *Sinorhizobium meliloti* |
|  |  |  | BAA35068.1, 403aa | 1e−101 | 191/400 (47%) | 251/400 (62%) | 5-aminolevulinate synthase *Rhodopseudomonas palustris* |
|  |  |  | ZP_00011134.1, 443aa | 1e−101 | 193/400 (48%) | 249/400 (62%) | hypothetical protein *Rhodopseudomonas palustris* |
| 17 | CALB | 511 | NP_631034.1, 511aa | 1e−125 | 240/493 (48.68%) | 298/493 (60.45%) | probable long-chain-fatty-acid-CoA ligase *Streptomyces coelicolor* |
|  |  |  | NP_822779.1, 503aa | 1e−123 | 236/491 (48.07%) | 294/491 (59.88%) | putative long-chain fatty acid: CoA ligase *Streptomyces avermitilis* |
|  |  |  | ZP_00059397.1, 557aa | 1e−117 | 224/496 (45.16%) | 291/496 (58.67%) | hypothetical protein *Thermobifida fusca* |
| 18 | PKSH | 3834 | AAF71776.1, 11096aa | 0.0 | 1806/3951 (45.71%) | 2169/3951 (54.9%) | NysC *Streptomyces noursei* |
|  |  |  | AAF71776.1, 11096aa | 0.0 | 1417/3280 (43.2%) | 1733/3280 (52.84%) | NysC *Streptomyces noursei* |
|  |  |  | AAF71776.1, 11096aa | 0.0 | 1132/2687 (42.13%) | 1387/2687 (51.62%) | NysC *Streptomyces noursei* |
| 19 | PKSH | 5723 | AAK73514.1, 10917aa | 0.0 | 2653/5231 (50.72%) | 3158/5231 (60.37%) | AmphC *Streptomyces nodosus* |
|  |  |  | AAK73514.1, 10917aa | 0.0 | 1682/3155 (53.31%) | 2014/3155 (63.84%) | AmphC *Streptomyces nodosus* |
|  |  |  | AAK73514.1, 10917aa | 0.0 | 1643/3190 (51.5%) | 1984/3190 (62.19%) | AmphC *Streptomyces nodosus* |
| 20 | PKSH | 1735 | NP_821593.1, 3564aa | 0.0 | 876/1803 (48.59%) | 1051/1803 (58.29%) | modular polyketide synthase *Streptomyces avermitilis* |
|  |  |  | NP_821593.1, 3564aa | 0.0 | 805/1750 (46%) | 988/1750 (56.46%) | modular polyketide synthase *Streptomyces avermitilis* |
|  |  |  | BAB69304.1, 3524aa | 0.0 | 876/1803 (48.59%) | 1051/1803 (58.29%) | modular polyketide synthase *Streptomyces avermitilis* |
| 21 | PKSH | 3264 | NP_824071.1, 3613aa | 0.0 | 1600/3344 (47.85%) | 1951/3344 (58.34%) | modular polyketide synthase *Streptomyces avermitilis* |
|  |  |  | T17409, 4613aa | 0.0 | 1562/3444 (45.35%) | 1898/3444 (55.11%) | polyketide synthase type I - *Streptomyces venezuelae* |
|  |  |  | T17409, 4613aa | 0.0 | 492/994 (49.5%) | 616/994 (61.97%) | polyketide synthase type I - *Streptomyces venezuelae* |

TABLE 2-continued

| ORF | Family | # aa | Genbank homology | probability | % identity | % similarity | proposed function of GenBank match |
|---|---|---|---|---|---|---|---|
| 22 | PKSH | 5099 | CAB41041.1, 6797aa | 0.0 | 2006/4012 (50%) | 2442/4012 (60.87%) | polyketide synthase *Streptomyces natalensis* |
| | | | CAB41041.1, 6797aa | 0.0 | 1105/2269 (48.7%) | 1342/2269 (59.14%) | polyketide synthase *Streptomyces natalensis* |
| | | | CAB41041.1, 6797aa | 0.0 | 541/881 (61.41%) | 637/881 (72.3%) | polyketide synthase *Streptomyces natalensis* |
| 23 | PKSH | 1921 | NP_821593.1, 3564aa | 0.0 | 888/1748 (50.8%) | 1083/1748 (61.96%) | modular polyketide synthase *Streptomyces avermitilis* |
| | | | NP_821593.1, 3564aa | 0.0 | 848/1757 (48.26%) | 1030/1757 (58.62%) | modular polyketide synthase *Streptomyces avermitilis* |
| | | | BAB69304.1, 3524aa | 0.0 | 888/1748 (50.8%) | 1083/1748 (61.96%) | modular polyketide synthase *Streptomyces avermitilis* |
| 24 | AYTF | 307 | AAK60008.1, 316aa | 7e−12 | 83/312 (26.6%) | 126/312 (40.38%) | malonyl-CoA: acyl carrier protein transacylase-like protein *Streptomyces aureofaciens* |
| | | | NP_657821.1, 314aa | 2e−07 | 64/305 (20.98%) | 118/305 (38.69%) | Acyl_transf, Acyl transferase domain *Bacillus anthracis* |
| | | | NP_228607.1, 293aa | 4e−07 | 64/294 (21.77%) | 118/294 (40.14%) | malonyl CoA-acyl carrier protein transacylase *Thermotoga maritima* |
| 25 | CALB | 476 | AAL35216.1, 540aa | 3e−34 | 142/485 (29.28%) | 224/485 (46.19%) | 4-coumarate: CoA ligase *Amorpha fruticosa* |
| | | | AAC97600.1, 547aa | 2e−33 | 132/487 (27.1%) | 223/487 (45.79%) | 4-coumarate: CoA ligase isoenzyme 2 *Glycine max* |
| | | | NP_821780.1, 518aa | 3e−33 | 132/470 (28.09%) | 201/470 (42.77%) | putative acyl-CoA synthetase, long-chain fatty acid: CoA ligase *Streptomyces avermitilis* |
| 26 | UNAC | 69 | AAC01708.1, 88aa | 7e−06 | 32/70 (45.71%) | 38/70 (54.29%) | unknown *Amycolatopsis mediterranei* |
| 27 | TESA | 254 | NP_824079.1, 252aa | 4e−80 | 149/238 (62.61%) | 172/238 (72.27%) | putative thioesterase *Streptomyces avermitilis* |
| | | | NP_822128.1, 250aa | 7e−80 | 145/237 (61.18%) | 170/237 (71.73%) | thioesterase *Streptomyces avermitilis* |
| | | | NP_821582.1, 255aa | 2e−75 | 136/243 (55.97%) | 169/243 (69.55%) | putative thioesterase *Streptomyces avermitilis* |

The ORFs encoding proteins involved in the biosynthesis of compounds of Formula I are assigned a putative function and grouped together in families based on sequence similarity to known proteins. To correlate structure and function, the protein families are given a four-letter designation used throughout the description and figures as indicated in Table 3. The meaning of the four letter designations is as follows: ADSN designates an amide synthetase; AYTF and AYTP designate acyltransferase activities; CALB designates an acylCoA ligase; GTFA designates a glycosyltransferase; MEBA and UNEW designate membrane proteins; MTNA designates a methyltransferase; PKSH designates a type I polyketide synthase system; REGD, REQB and RREB designate transcriptional regulators; SPKF designates a sensory protein kinase; TESA designates a thioesterase activity; TMOA designates an amino acid oxidase; UNIQ, UNBP and UNAC designate proteins of unknown function.

TABLE 3

| Family | Function |
|---|---|
| ADSN | adenylating/condensing synthetase, amide synthetase, enzymes able to activate substrates as acyl adenylates and subsequently transfer the acyl group to an amino group of the acceptor molecule |
| AYTP | acyltransferase; pyridoxal phosphate dependent |
| AYTF | acyltransferase; acyl CoA-acyl carrier protein transacylase); includes malonyl CoA-ACP transacylases |
| CALB | acyl CoA ligase; shows similarity to plant coumarate CoA ligases, other aryl CoA ligases, yeast CoA synthetase and aminocoumarin ligases |
| GTFA | Glycosyltransferases |
| MEBA | membrane protein; putative transporter, permease; |
| MTNA | N-methyltransferase |
| PKSH | Polyketide synthase, type I |
| REGD | transcriptional regulator |

TABLE 3-continued

| Family | Function |
|---|---|
| REBQ | Regulator |
| RREB | Response regulator |
| SOXA | sugar oxidoreductase |
| SPKF | sensory protein kinase |
| TESA | Thioesterase |
| TMOA | amino acid monooxygenase |
| UNIQ | Unknown; |
| UNBP | Unknown |
| UNAC | Unknown |
| UNEW | Similarity to membrane proteins |

Biosynthesis of the compounds of Formula I involves the action of a multimodular type I polyketide synthase system (PKS) corresponding to ORFs 18 to 23 (SEQ ID NOS: 37, 39, 41, 43, 45 and 47). Type I PKSs are large modular proteins that condense acyl thioester units in a sequential manner. PKS systems consist of one or more polyfunctional polypeptides each of which is made up of modules. Each type I PKS module contains three domains: a β-ketoacyl protein synthase (KS), an acyltransferase (AT) and an acyl carrier protein (ACP). Domains conferring additional enzymatic activities such as ketoreductase (KR), dehydratase (DH) and enoylreductase (ER) can also be found in the PKS modules. These additional domains result in various degrees of reduction of the β-keto groups of the growing polyketide chain. Each module is responsible for one round of condensation and reduction of the β-ketoacyl units. As a result, there is a direct correlation between the number of modules and the length of the polyketide chain as well as between the domain composition of the modules and the degree of reduction of the polyketide product. The final polyketide product is released from the PKS protein through the action of a thioesterase (TE) domain found in the ultimate module of the PKS system. The genetic organization of most type I PKS enzymes is colinear with the order of biochemical reactions giving rise to the polyketide chain. This feature allows prediction of polyketide core structure based on the architecture of the PKS modules found in a given biosynthetic pathway (Hopwood, *Chem. Rev.*, 97, 2465-2497 (1997)).

The PKS system in the biosynthetic locus for the production of the compounds of Formula I is composed of ORFs 18 to 23 (SEQ ID NOS: 37, 39, 41, 43, 45 and 47) and comprises a total of 12 modules as described below in Table 4. The first module contains only an ACP domain and corresponds to the loading module (module 0) whereas each of the remaining 12 modules contain domains KS, AT and ACP in various combinations with KR, DH and ER domains. The thioesterase domain present in ORF 23/module 12 indicates that this module is the ultimate one in the biosynthesis of the polyketide chain.

TABLE 4

Domain coordinates for PKS system

| ORF Nos. | Amino acid coordinates | Domain | Module No. |
|---|---|---|---|
| 18 | 47-109 | ACP | 0 |
|  | 130-554 | KS | 1 |
|  | 567-990 | AT |  |
|  | 1001-1101 | DH |  |
|  | 1421-1628 | KR |  |
|  | 1691-1753 | ACP |  |
|  | 1771-2195 | KS | 2 |
|  | 2211-2638 | AT |  |
|  | 2647-2753 | DH |  |
|  | 3060-3401 | ER |  |
|  | 3405-3622 | KR |  |
|  | 3696-3758 | ACP |  |
| 19 | 39-463 | KS | 3 |
|  | 474-872 | AT |  |
|  | 883-990 | DH |  |
|  | 1291-1501 | KR |  |
|  | 1574-1636 | ACP |  |
|  | 1657-2082 | KS | 4 |
|  | 2093-2495 | AT |  |
|  | 2507-2614 | DH |  |
|  | 2908-3249 | ER |  |
|  | 3253-3470 | KR |  |
|  | 3545-3607 | ACP |  |
|  | 3628-4052 | KS | 5 |
|  | 4068-4489 | AT |  |
|  | 4497-4604 | DH |  |
|  | 4933-5281 | ER |  |
|  | 5285-5502 | KR |  |
|  | 5577-5639 | ACP |  |
| 20 | 34-458 | KS | 6 |
|  | 475-892 | AT |  |
|  | 901-1006 | DH |  |
|  | 1309-1517 | KR |  |
|  | 1593-1655 | ACP |  |
| 21 | 34-461 | KS | 7 |
|  | 478-905 | AT |  |
|  | 1157-1366 | KR |  |
|  | 1444-1506 | ACP |  |
|  | 1528-1952 | KS | 8 |
|  | 1963-2383 | AT |  |
|  | 2395-2502 | DH |  |
|  | 2837-3048 | KR |  |
|  | 3122-3184 | ACP |  |
| 22 | 34-460 | KS | 9 |
|  | 472-883 | AT |  |
|  | 895-1002 | DH |  |
|  | 1323-1523 | KR |  |
|  | 1597-1659 | ACP |  |
|  | 1682-2104 | KS | 10 |
|  | 2115-2523 | AT |  |
|  | 2534-2641 | DH |  |
|  | 2957-3166 | KR |  |
|  | 3235-3297 | ACP |  |
|  | 3317-3741 | KS | 11 |
|  | 3752-4181 | AT |  |
|  | 4193-4300 | DH |  |
|  | 4669-4879 | KR |  |
|  | 4956-5018 | ACP |  |
| 23 | 35-461 | KS | 12 |
|  | 475-883 | AT |  |
|  | 892-999 | DH |  |
|  | 1305-1512 | KR |  |
|  | 1582-1644 | ACP |  |
|  | 1709-1921 | TE |  |

Multiple amino acid alignment of KS domains present in the PKS system, described in FIGS. 12*a* and 12*b*, shows an overall similarity of domains and conservation of amino acid residues and domain regions important for activity indicating that all KS domains are functional. Similarly, multiple amino acid alignment of AT domains (described in FIGS. 13*a*, 13*b* and 13*c*), DH domains (described in FIG. 14), ER domains (described in FIG. 15), KR domains (described in FIG. 16), ACP domains (described in FIG. 17) and TE domains (described in FIG. 18) show an overall similarity of related domains and a high conservation of protein regions and of amino acid residues important for catalytic activity. The domains that occur only once in the PKS system, namely the thioesterase (TE) domain in ORF 23 (SEQ ID NO: 47) is compared to prototypical domains from the nystatin type I polyketide system (Brautaset, supra).

Figure 19:
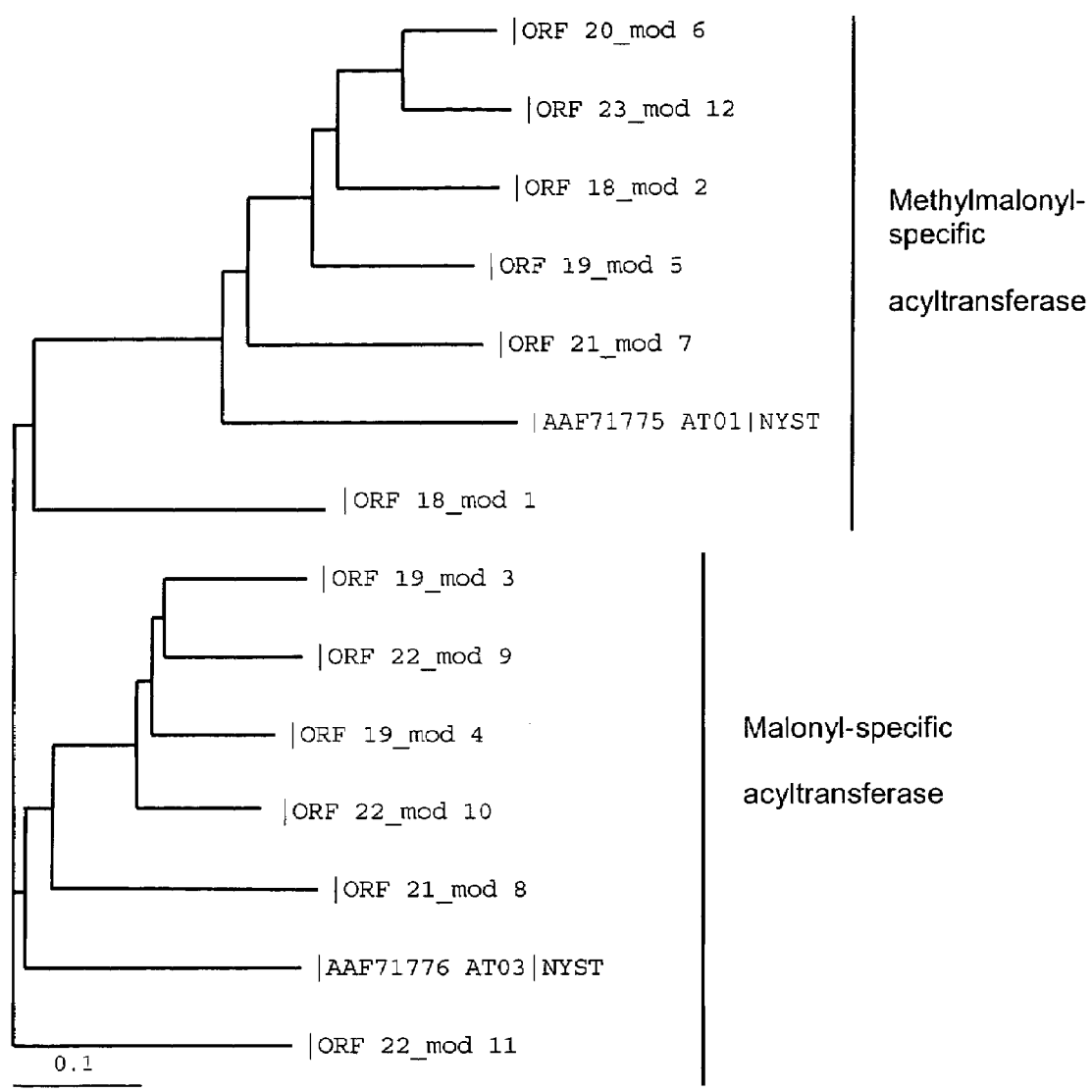
FIG. 19: phylogenetic analysis of the twelve acyl transferase (AT) domains present in ORFs 18 to 23 (SEQ ID NOS: 37, 39, 41, 43, 45 and 47) along with a malonyl-specific and a methylmalonyl-specific AT domain present in modules 3 and 11 respectively of the nystatin PKS system as described by Brautaset et al. supra.

Phylogenetic analysis of the AT domains in the PKS system was conducted to assess the nature of the β-keto acyl units that are incorporated in the growing polyketide chain. The AT domains of the PKS system were compared to two domains, AAF71779mod03 and AAF71766mod11 (National Center for Biotechnology Information (NCBI) nonredundant protein database), derived from the nystatin PKS system (Brautaset, supra) and responsible for the incorporation of malonyl-CoA and methylmalonyl-CoA respectively. FIG. 19 shows the phylogenetic relatedness of the various AT domains indicating that, in the PKS system for production of compounds of Formula I, module 2 of ORF 18 (SEQ ID NO: 37), module 5 of ORF 19 (SEQ ID NO: 39), module 6 of ORF 20 (SEQ ID NO: 41), module 7 of ORF 21 (SEQ ID NO: 43) and module 12 of ORF 23 (SEQ ID NO: 47) incorporate methylmalonate in the polyketide backbone of compounds of Formula I, whereas all remaining AT domains, namely module 1 of ORF 18 (SEQ ID NO: 37), modules 3 and 4 of ORF 19 (SEQ ID NO: 39), module 8 of ORF 21 (SEQ ID NO: 43) and modules 9, 10 and 11 of ORF 22 (SEQ ID NO: 45) incorporate malonate extender β-keto acyl units in the polyketide backbone of compounds of Formula I.

Figure 2:
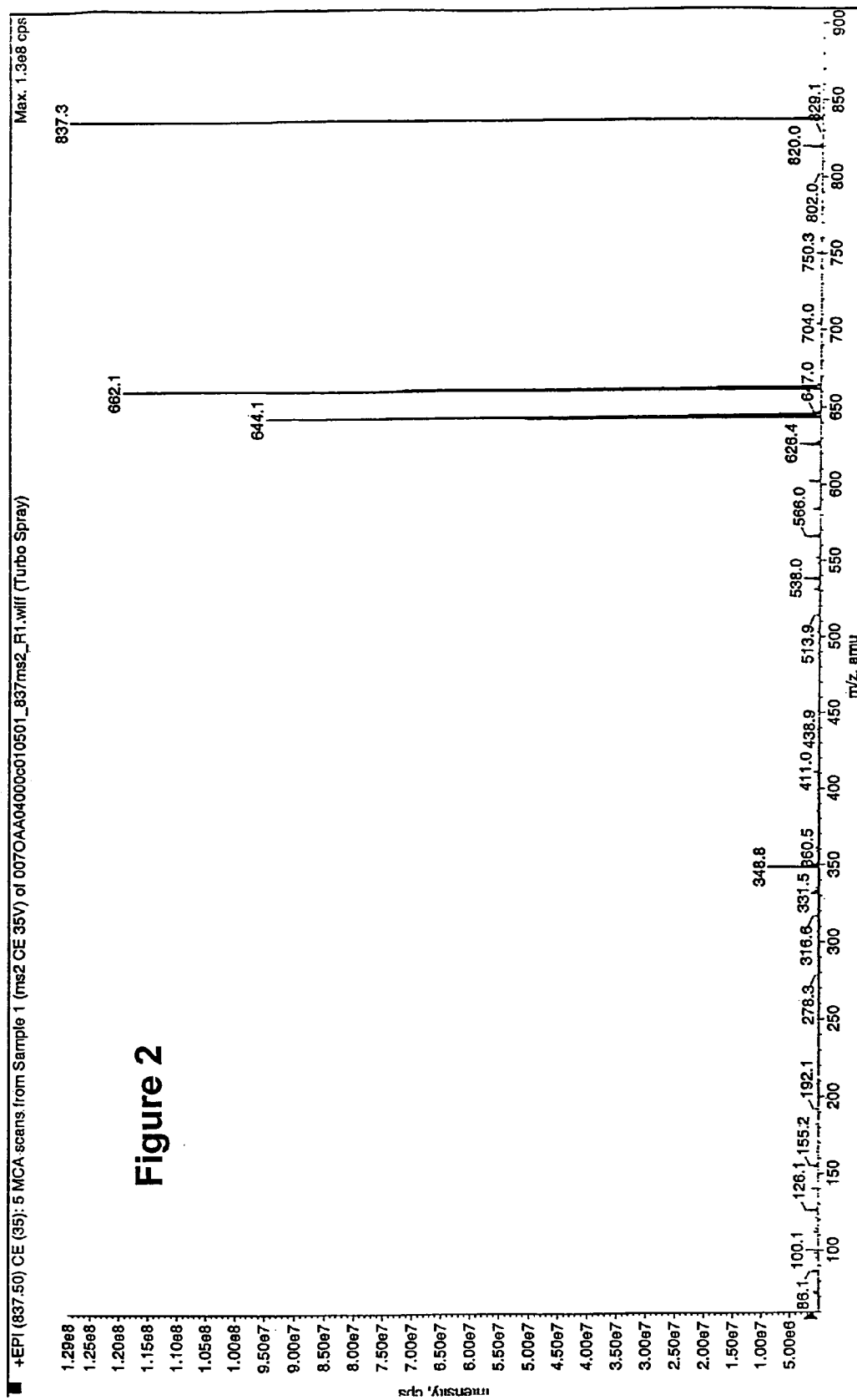
FIG. 2: Electrospray mass (ms/ms of m/z:837.50) spectrum (Positive Ion Mode) of Compound 1.
Figure 3:
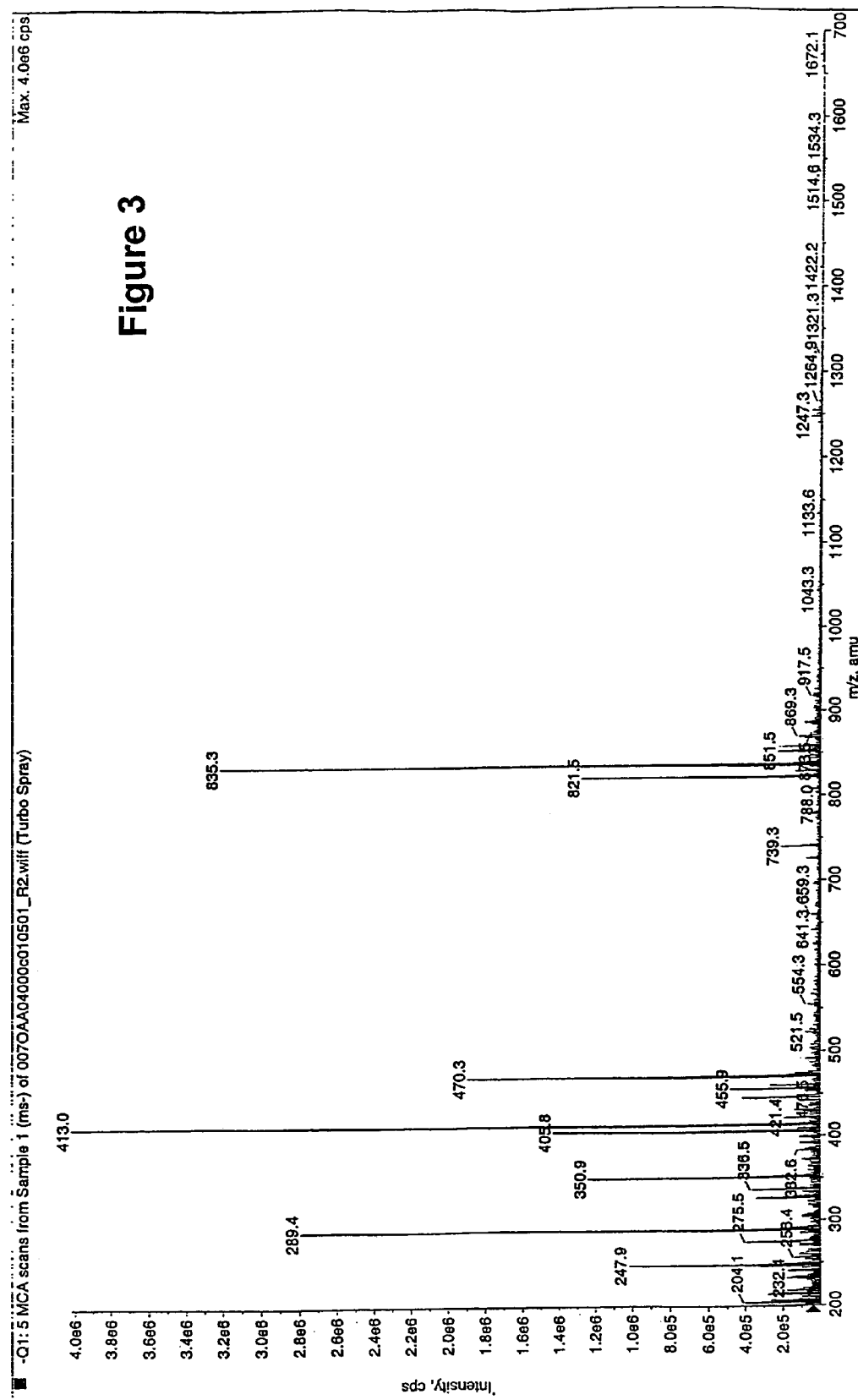
FIG. 3: Electrospray mass spectrum (Negative Ion Mode) of Compound 1.
Figure 4:
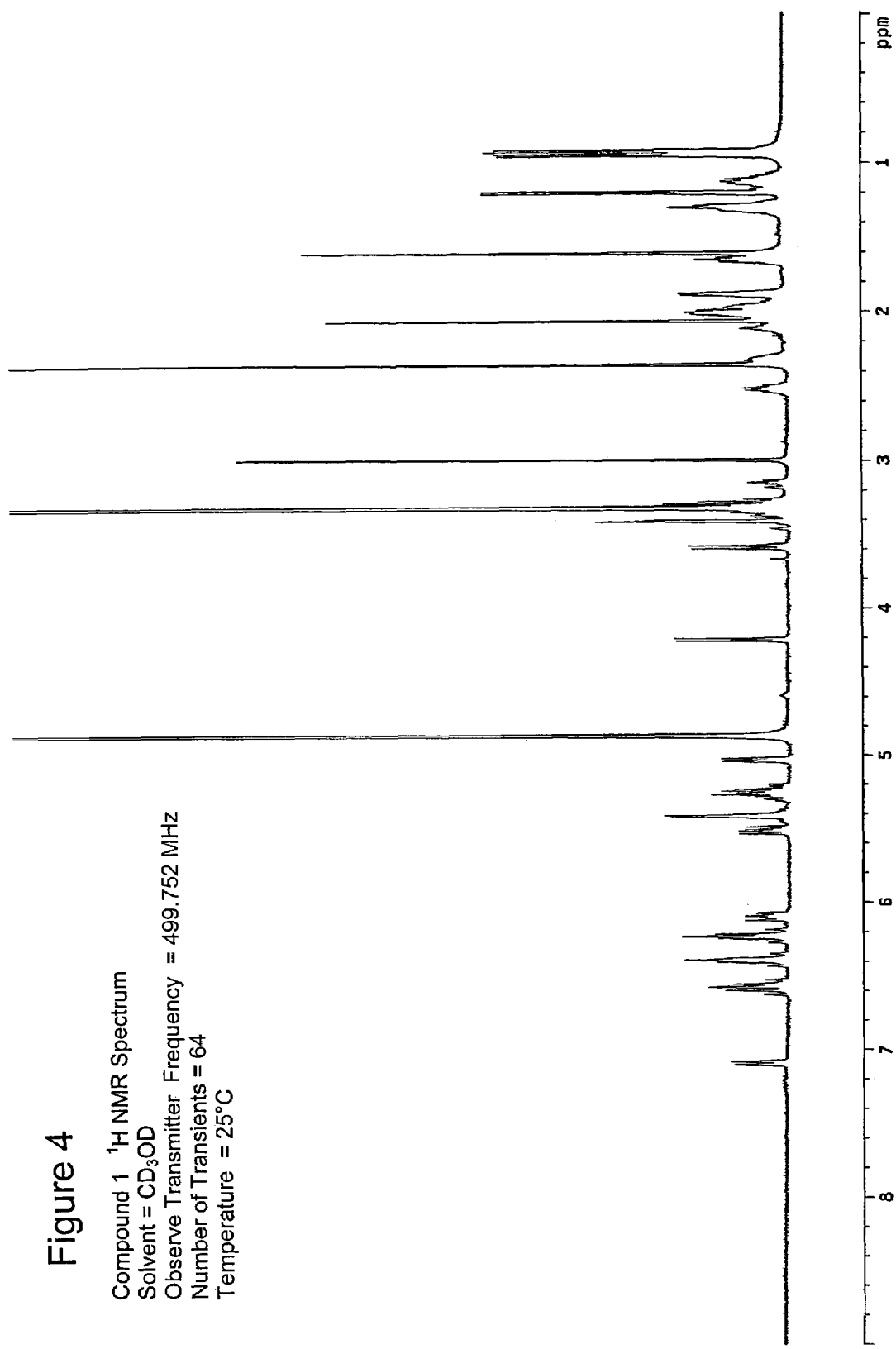
FIG. 4: 500 MHz proton nuclear magnetic resonance ($^1$H-NMR) spectrum of Compound 1 in $d_4$-MeOH.
Figure 21:
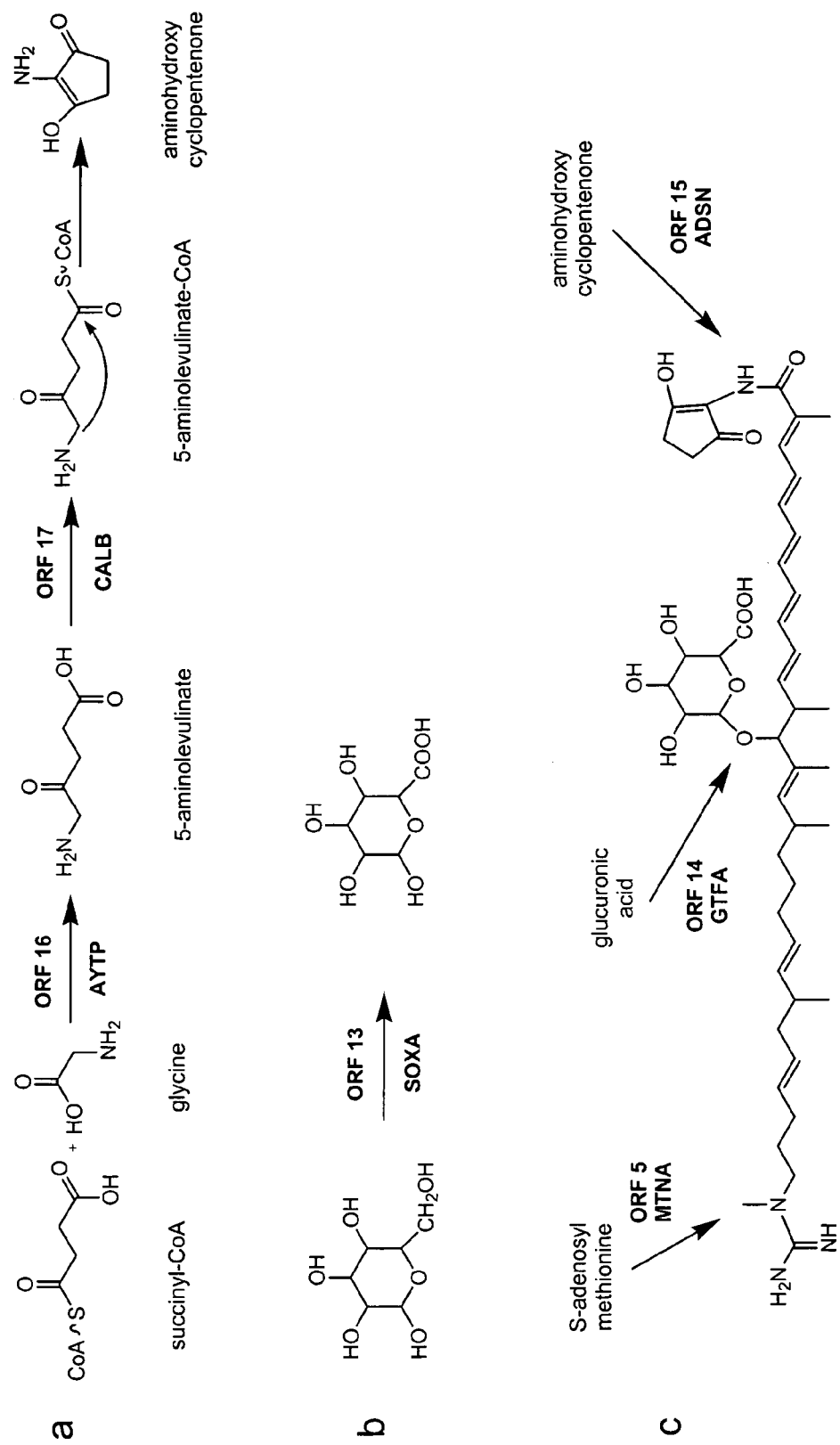
FIG. 21a: biosynthesis of the aminohydroxy-cyclopentenone moiety of compounds of Formula I using ORF 16 (SEQ ID NO: 33) and ORF 17 (SEQ ID NO: 35).
FIG. 21b: biosynthesis of the glucuronic acid component of compounds of Formula I using ORF 13 (SEQ ID NO: 27).
FIG. 21c: methylation, glycosylation and amide condensation of the polyketide core structure of compounds of Formula I using ORF 5 (SEQ ID NO: 10), ORF 14 (SEQ ID NO: 29) and ORF 15 (SEQ ID NO: 31) respectively.

Type I PKS domains and the reactions they carry out are well known to those skilled in the art and well documented in the literature (see, for example, Hopwood, supra). Those skilled in the art will readily appreciate that it is possible to determine the polyketide core structure produced by PKS system through domain analysis. The genes and proteins of the invention provide for biosynthesis of compounds of Formula I. While not intending to be limited to any particular mode of action or biosynthetic scheme, FIGS. 20 and 21 describe production of Compound 1 using the genes and proteins of the invention. FIG. 20b schematically describes a series of reactions catalyzed by the PKS system based on the correlation between the deduced domain architecture and the polyketide core of compounds of Formula I. FIG. 20a describes a biosynthetic pathway for the production of the γ-aminobutyryl-CoA starter unit. Referring to FIG. 20a, the amino acid monooxygenase of ORF 7 (SEQ ID NO: 14) catalyzes the decarboxylative oxidation of arginine forming 4-guanidinobutanamide that is further activated by the acyl CoA ligase of ORF 25 (SEQ ID NO: 52) to give 4-guanidinobutyryl-CoA. Referring to FIG. 20b, the acyltransferase of ORF 24 (SEQ ID NO: 50) loads the 4-guanidinobutyryl-CoA extender unit onto the ACP domain of the loading module (module 0) of the type I polyketide synthase of ORF 18 (SEQ ID NO: 37). The polyketide chain continues to grow by the sequential condensation of malonyl-CoA and methylmalonyl-CoA extender units that are further reduced by specific domains to various degrees. The mature polyketide chain is then released through the action of the thioesterase domain found in module 12 of the type I polyketide synthase of ORF 23 (SEQ ID NO: 47). The polyketide core structure described in FIG. 20b based on the architecture of the PKS system of the biosynthetic locus for the production of Compound 1 is entirely consistent with the polyketide portion of the chemical structure of Compound 1 as determined by MS sprectra data (FIGS. 1, 2 and 3), $^1$H NMR (FIG. 4) and $^{13}$C NMR spectra data, demonstrating that the biosynthetic locus of the invention is responsible for the biosynthesis of Compound 1.

The biosynthetic locus contains genes involved in the synthesis of two other components found in the chemical structure of compounds of Formula I. FIG. 21a describes a biosynthetic pathway for the production of the aminohydroxy-cyclopentenone moiety found in compounds of Formula I. Referring to FIG. 21a, the pyridoxal phosphate dependent acyltransferase of ORF 16 (SEQ ID NO: 33) condenses glycine with succinyl-CoA forming 5-aminolevulinate. The 5-aminolevulinate intermediate is further activated through the action of the acyl CoA ligase of ORF 17 (SEQ ID NO: 35) forming 5-aminolevulinate-CoA, which in turn, cyclizes to produce aminohydroxycyclopentenone. Referring to FIG. 21c, the aminohydroxycyclopentenone moiety is activated and condensed to the carboxy terminus of the polyketide chain through the action of the adenylating/condensing synthetase of ORF 15 (SEQ ID NO: 31). FIG. 21b describes the biosynthesis of the sugar component of compounds of Formula I. The sugar oxidoreductase of ORF 13 (SEQ ID NO: 27) oxidizes D-glucose to form D-glucuronic acid that is subsequently transferred onto a hydroxyl group of the polyketide core structure through the action of the glycosyltransferase of ORF 14 (SEQ ID NO: 29) as shown in FIG. 21c. D-glucose derives from the primary metabolism of the microorganism and is expected to be activated by the primary metabolism enzyme nucleotidyl transferase that catalyzes the formation of NDP-D-Glucose. It is expected that the sugar oxidoreductase of ORF 13 (SEQ ID NO: 27) acts on NDP-D-Glucose to generate NDP-D-Glucuronic acid that is subsequently transferred onto the polyketide core structure through the action of the glycosyltransferase of ORF 14 (SEQ ID NO: 29).

The final modification of the polyketide core structure is the methylation reaction catalyzed by the N-methyltransferase of ORF 5 (SEQ ID NO: 10). Referring to FIG. 21c, the N-methyltransferase of ORF 5 (SEQ ID NO: 10) catalyzes the transfer of a methyl group derived from S-adenosylmethionine onto the guanidine moiety or the polyketide structure. While FIG. 21c describes the reactions catalyzed by the N-methyltransferase of ORF 5 (SEQ ID NO: 10), the adenylating/condensing synthetase of ORF 15 (SEQ ID NO: 31) and the glycosyltransferase of ORF 14 (SEQ ID NO: 29), the invention does not reside in the actual timing and order of the reactions, which may be different than as described in FIG. 21c.

In regards to other ORFs forming the biosynthetic locus for production of the compounds of Formula I, the thioesterases of ORFs 11 and 27 (SEQ ID NOS: 22 and 56) are expected to have polyketide-priming editing functions; the regulator of ORF 3 (SEQ ID NO: 6), the transcriptional regulator of ORF 4 (SEQ ID NO: 8), the response regulator of ORF 9 (SEQ ID NO: 18) and the sensory protein kinase of ORF 10 (SEQ ID NO: 20) are expected to regulate synthesis of the compound of Formula I; and the membrane transporters of ORF 2 (SEQ ID NO: 4) and of ORF 8 (SEQ ID NO: 16) are expected to be involved in transmembrane transport.

The genes and proteins of the invention may be used to produce compounds of Formula I as described below in Examples 17 to 20.

EXAMPLE 2

Production of Compounds 1, 2, 7, 8 and 15 by Fermentation

*Amycolatopsis orientalis* ATCC™ 43491 was cultivated under aerobic conditions in an aqueous nutrient medium containing assimilable sources of carbon, assimilable sources of nitrogen, inorganic salts and vitamins. Preferred carbon sources are glucose, glycerol and the like. Preferred nitrogen sources are beef extract, malt extract, yeast extract, and the like. Representative media are provided in Table 1.

Compounds 1, 2, 7, 8 and 15 were produced by the following procedure: *Amycolatopsis orientalis* ATCC™ 43491 was maintained and sporulated on agar plates of ISP2 medium (Difco). The innoculum for the production phase was prepared by adding two loopfull of the spores obtained from the surface of the ISP2 agar plate to a 125-ml flask containing 25 ml of ITSB medium (Zahn et al. (2001). *Applied and Environmental Microbiology* 76, 377-386) composed of 30 g trypticase soy broth (Bacto), 3 g yeast extract, 2 g MgSO$_4$, 5 g glucose, 4 g maltose made up to one liter with distilled water. The flasks are shaken (250 rpm) for about 60 hours at 28° C. and then 10 ml of the culture is used to inoculate each 2-L flasks containing ten glass beads and 500 ml of sterile production medium OA consisting of glucose 10 g, glycerol 5 g, corn steep liquor 3 g, beef extract 3 g, malt extract 3 g, yeast extract 3 g, calcium carbonate 2 g, thiamine 0.1 g made up to one liter with distilled water (Kanzaki et al. (1998). *Biosci Biotechnol Biochem* 62; 438-442). The medium was adjusted at pH 7.0, and then 1 ml of silicon defoamer-oil (Chem Service) was added to each flask before sterilization. The fermentation batches are incubated aerobically under stirring (200 rpm) at 28° C. for a period of 4 days. A fermentation period of 7 days without defoamer-oil was also used to produce Compound 1.

Compounds 1, 2, 7, 8 and 15 could also be produced in other media including JA, GA, RM, NA, CA, and CB (Table 1). Compounds 1 and 2 were further produced as described above using a preferred strain, namely *Amycolatopsis orientalis* IDAC 220604-01.

EXAMPLE 3

Purification of Compound 1, 2 and 7

Procedure 1: (for 12×500 mL of Fermentation)

a) The whole fermentation broth at harvest was centrifuged at 3500 rpm for 20 minutes and the supernatant liquid was decanted and discarded. The residual mycelial pellet was treated with methanol (200 mL/L of original fermentation broth volume), stirred and centrifuged. The methanolic supernatant liquid was removed and the mycelial solid was extracted with acetone, the same manner as the methanol extraction. The combined methanol and acetone extracts are evaporated to dryness to a crude residue.

b) The crude residue of a) was partitioned between 100 mL(per litre of fermentation) of chloroform ($CHCl_3$) and 100 mL(per litre of fermentation) of methanol (MeOH) in water (3:2) buffered to pH 10 with ammonium hydroxide ($NH_4OH$) and at 10 mM ammonium bicarbonate ($NH_4HCO_3$) salt concentration. The two layers were separated and the methanol:water layer evaporated to dryness. The residue from the upper phase was partitioned between n-butanol (100 ml/L of fermentation) and water (100 ml/L of fermentation), buffered as above. The butanol layer was concentrated to a orange-brown residue.

The residue was further purified by HPLC (Waters Autopurification System with ACD), using a Waters Xterra MS C18 column (5%, 19×150 mm), and a gradient of 10 mM aqueous $NH_4HCO_3$, pH 10/acetonitrile 85:15 to 25:75 over 30 min at 19 mL/min, UV detector set at 261 nm. The sample was loaded as a suspension in DMSO/MeOH (3:1). The pooling of eluate gave samples of Compound 7 (<1 mg, RT: 16-17 min) and a mixture of Compounds 1 and 2 (1.04 g, non-freezedried, RT: 11.8-12.1 min).

Alternatively, the first purification (step 2) was also accomplished using a Phenomenex Max-RP C12 column (4μ, 21.2×250 mm) using the gradient buffer (as above) and acetonitrile 89.5:10.5 to 20:80 over 25 minutes, with the same flow and UV detection. Fractions were collected at a retention time of 16.5-17 minutes (mixture of Compounds 1 and 2) and at RT: 21-22 minutes (Compound 7).

The mixture of Compounds 1 and 2 is further purified by HPLC (Waters Autopurification System with ACD), using a RCM Column (Novapak C-18, 6μ, 40×200 mm), and a gradient of 10 mM aqueous ammonium acetate ($NH_4OAc$) to pH 5 with glacial acetic acid/acetonitrile 80:20 to 20:80 over 25 min at 35 mL/min. Fractions were collected and freeze-dried to give pure Compound 1 (RT: 18.5-18.8 minutes, 224.5 mg) and pure Compound 2 (RT: 17.3-17.6 minutes, 34.6 mg).

Procedure 2:

The crude residue of 1 a) (see Procedure 1) was partitioned between 100 mL(per litre of fermentation) of hexanes and 100 mL(per litre of fermentation) of methanol (MeOH) in water (3:2) buffered to pH 10 with ammonium hydroxide ($NH_4OH$) and at 10 mM ammonium bicarbonate ($NH_4HCO_3$) salt concentration. The two layers were separated and the methanol:water layer evaporated to dryness. The procedure was repeated and concentrated to dryness.

The crude residue was purified by solid phase extraction. Methanol washed Diaion® HP-20 resin (30 mL) was added to the crude residue. The mixture was added to a column made of 75 mL of methanol washed HP-20 resin and eluted with a mixture of ethanol and pH 10 buffered aqueous ammonium carbonate following the following gradient:

| Fraction | Ethanol | Aqueous | Volume |
| --- | --- | --- | --- |
| 1 | 10 | 90 | 500 |
| 2 | 20 | 80 | 200 |
| 3 | 30 | 70 | 200 |
| 4 | 40 | 60 | 200 |
| 5 | 50 | 50 | 200 |
| 6 | 60 | 40 | 200 |
| 7 | 80 | 20 | 200 |
| 8 | 100 | 0 | 200 |

Fractions 4, 5 and 6 were combined and concentrated to give a mixture of Compounds 1 and 2 and Compound 7 was found in the concentrated fraction 7.

The mixture of Compounds 1 and 2 was further purified by HPLC (Waters Autopurification System with ACD), using a Symmetry C18 column (5μ, 30×100 mm), and a gradient of 10 mM aqueous $NH_4OAc$, made to pH 5 with glacial acetic acid/acetonitrile 74:26 to 50:50 over 20 min at 39 mL/min. The collection was triggered by UV 261 nm (PDA). The sample was loaded as a suspension in DMSO:MeOH (3:1). The pooling of eluates gave pure Compound 1 (RT: 14.9-15.2 min) and pure Compound 2 (RT: 14.1-14.2 min), generally with a ratio of 5:1. Compound 7 had a retention time of 13-14 minutes using the same conditions.

EXAMPLE 4

Structure Identification of Compounds 1, 2 and 7

Compounds 1, 2 and 7 were produced by fermentation as described in Example 2 and isolated as described in Example 3.

Compound 1

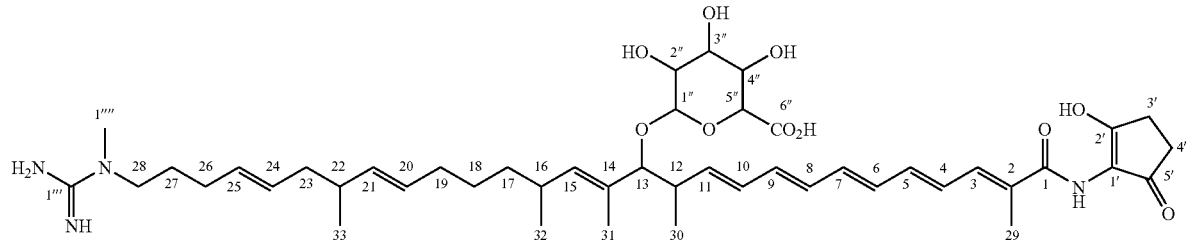

Compound 1 is named 3,4,5-trihydroxy-6-[1-[11-(2-hydroxy-5-oxocyclopent-1-enylcarbamoyl)-1-methyldodeca-2,4,6,8,10-pentaenyl]-2,4,10-trimethyl-16-(N-methylguanidino)-hexadeca-2,8,12-trienyloxy]-tetrahydropyran-2-carboxylic acid.

Compound 1 structure determination was based on mass, UV and NMR data. The NMR data detailed in Table 5 was collected at 500 MHz in $d_4$-MeOH including $^1$H-NMR spectrum of FIG. 4, and the multidimensional pulse sequences gCOSY, gDQCOSY, gHSQC, and gHMBC. The molecular formula of $C_{46}H_{68}N_4O_{10}$ and the chemical structure were established based the $^1$H-NMR data, the COSY, HSQC and HMBC measured on about 500 μg of very pure material of structure illustrated above. The carbon assignments shown in Table 5 were made by virtue of the HSQC and HMBC. The straight chain nature of Compound 1 was supported by the fact that the two protons on each of the seven methylene groups were of almost indistinguishable chemical shift.

TABLE 5

$^1$H and $^{13}$C NMR (δ, ppm) Data for Compounds 1 in MeOH-D$_4$

| Assignment | $δ_H$ (ppm) | $δ_c$ (ppm) | Group |
|---|---|---|---|
| 1 | — | 170.1 | C |
| 2 | — | 138.8 | C |
| 3 | 7.09 | 135.2 | CH |
| 4 | 6.60 | 127.9 | CH |
| 5 | 6.38 | 132.5 | CH |
| 6 | 6.38 | 135.8 | CH |
| 7 | 6.56 | 127.9 | CH |
| 8 | 6.23 | 132.5 | CH |
| 9 | 6.23 | 131.3 | CH |
| 10 | 6.08 | 130.0 | CH |
| 11 | 5.51 | 137.9 | CH |
| 12 | 2.52 | 40.3 | CH |
| 13 | 3.58 | 93.8 | CH |
| 14 | — | 134.3 | C |
| 15 | 5.03 | 136.4 | CH |
| 16 | 2.32 | 32.2 | CH |
| 17 | 1.13 | 37.4 | CH$_2$ |
| 18 | 1.29 | 37.3 | CH$_2$ |
| 19 | 1.87 | 32.9 | CH$_2$ |
| 20 | 5.24 | 135.9 | CH |
| 21 | 5.27 | 129.3 | CH |
| 22 | 2.11 | 37.3 | CH |
| 23 | 1.97 | 40.6 | CH$_2$ |
| 24 | 5.41 | 130.0 | CH |
| 25 | 5.41 | 130.0 | CH |
| 26 | 2.01 | 29.6 | CH$_2$ |
| 27 | 1.64 | 27.2 | CH$_2$ |
| 28 | 3.34 | 48.2 | CH$_2$ |
| 29 | 2.06 | 12.4 | CH$_3$ |
| 30 | 1.21 | 17.4 | CH$_3$ |
| 31 | 1.60 | 11.4 | CH$_3$ |
| 32 | 0.92 | 20.7 | CH$_3$ |
| 33 | 0.97 | 20.3 | CH$_3$ |
| 1' | — | 111.4 | C |
| 2' | — | 199.3 | C |
| 3' | 2.35 | 31.0 | CH$_2$ |
| 4' | 2.35 | 31.0 | CH$_2$ |
| 5' | — | 199.3 | C |
| 1" | 4.20 | 102.9 | CH |
| 2" | 3.27 | 74.6 | CH |
| 3" | 3.36 | 77.6 | CH |
| 4" | 3.41 | 72.9 | CH |
| 5" | 3.40 | 76.2 | CH |
| 6" | — | 176.1 | C |
| 1'" | — | 157.7 | C |
| 1"" | 3.00 | 35.8 | CH$_3$ |

Mass spectra (FIGS. 1, 2, and 3) analysis shown in Table 6 gave a mass (m/z) of 836.4, which confirmed a molecular formula of $C_{46}H_{68}N_4O_{10}$, and fragments that also confirmed structure assignment of Compound 1 including a sugar moiety.

TABLE 6

Mass Spectrometry data for Compound 1

| Figure | Ionization | Mass (m/z) | Fragment |
|---|---|---|---|
| 1 | +mode (+Q1) | 837.5 | (M + H)$^+$ |
|   |   | 823.7 | (M − CH$_3$)$^+$ |
| 2 | +mode (+EPI) | 837.3 | (M + H)$^+$ |
|   |   | 662.1 | (M − sugar)$^+$ |
|   |   | 644.1 | (M − O − sugar)$^+$ |
| 3 | mode (−Q1) | 835.3 | (M − H)$^−$ |
|   |   | 821.5 | (M − CH$_3$)$^−$ |

The UV spectrum for Compound 1 exhibited UV $λ_{max}$ at 258.77 and 362.77 nm in methanol in accordance with the methylpentaene amide of the 2-aminocyclopenta-1,3-dione tautomer.

Compound 2

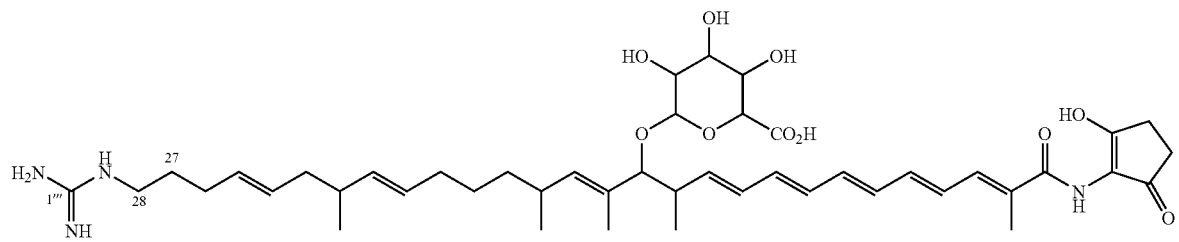

Compound 2 is named 6-{16-guanidino-1-[11-(2-hydroxy-5-oxocyclopent-1-enylcarbamoyl)-1-methyldodeca-2,4,6,8,10-pentaenyl]-2,4,10-trimethylhexadeca-2,8,12-trienyloxy}-3,4,5-trihydroxy-tetrahydro-pyran-2-carboxylic acid.

Figure 5:
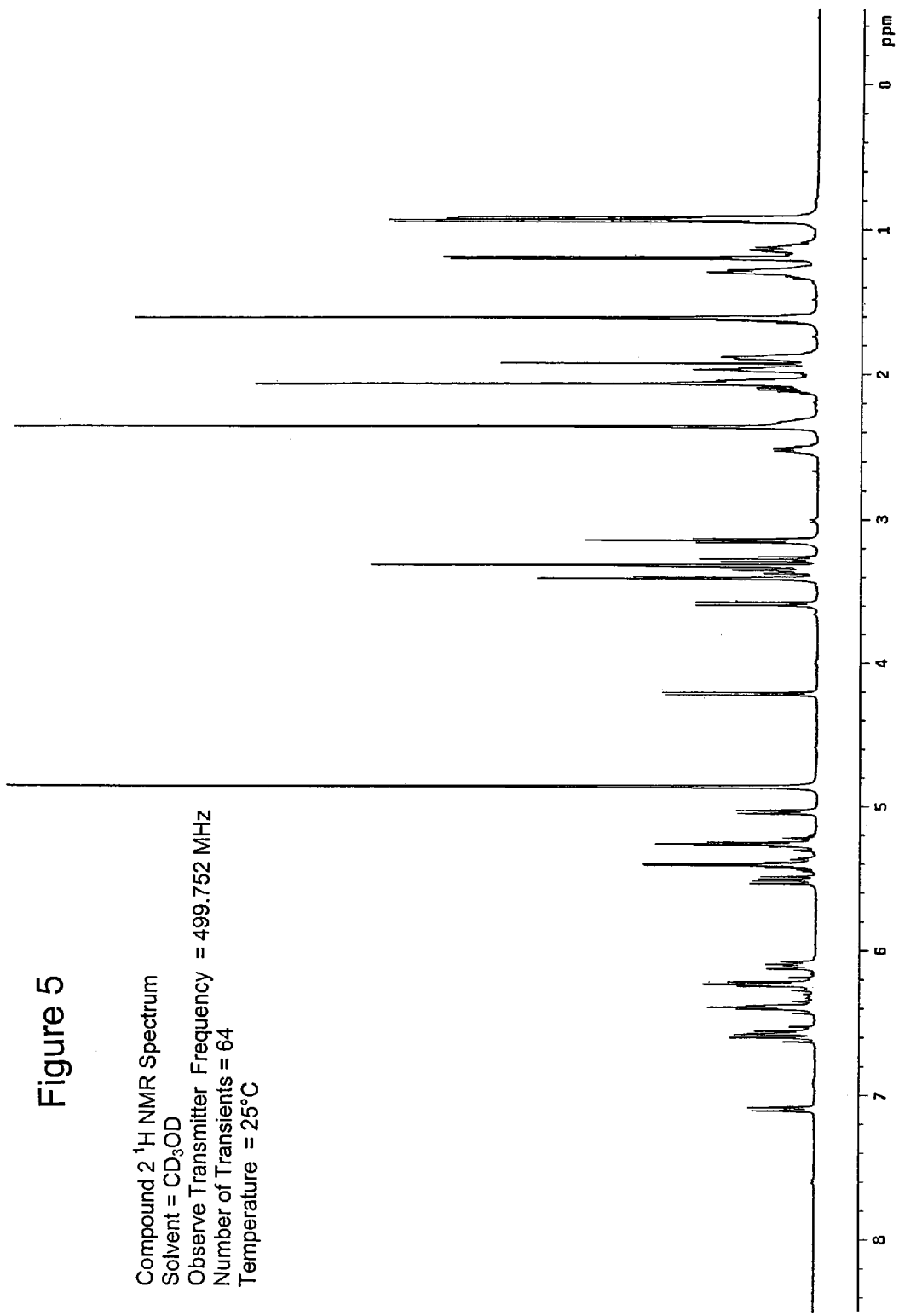
FIG. 5: 500 MHz proton nuclear magnetic resonance ($^1$H-NMR) spectrum of Compound 2 in $d_4$-MeOH.

Structure of Compound 2 was confirmed by $^1$H (FIG. 5) and $^{13}$C NMR. The signals of 1'''' carbon (35.8 ppm) and protons (singlet at 3.00 ppm) of Compound 1 (see Table 5) were absent from the spectra, which confirmed the absence of this CH$_3$ residue. Only small shifts in the guanidine area were observed in the $^{13}$C NMR of Compound 2. No further changes from the structure of Compound 1 previously described were present.

in methanol (334 μL, Fisher Chemicals) was added to Compound 1 (20 mg) in methanol (2 mL). Dimethyl sulfate (5.68 μL, Sigma) was added and the reaction stirred at room temperature for 24 hours. Additional sodium hydroxide in methanol (334 μL) and dimethyl sulfate (10 μL) were added and the reaction stirred for an additional 24 hours. A third portion of sodium hydroxide in methanol (400 μL) and dimethyl sulfate (15 μL) were added and the reaction mixture stirred for an additional 24 hours. The reaction was monitored by TLC (Merck Silica gel 60 F$_{254}$, eluting with 7% methanol in chloroform) visualized under UV. The reaction was concentrated in vacuo.

Compound 7

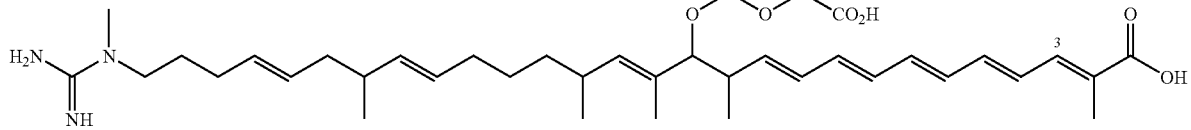

Compound 7 is named 6-[1-(11-carboxy-1-methyldodeca-2,4,5,8,10-pentaenyl)-2,4,10-trimethyl-16-(N-methylguanidino)-hexadeca-2,8,12-trienyloxy]-3,4,5-trihydroxy-tetrahydropyran-2-carboxylic acid.

Figure 10:
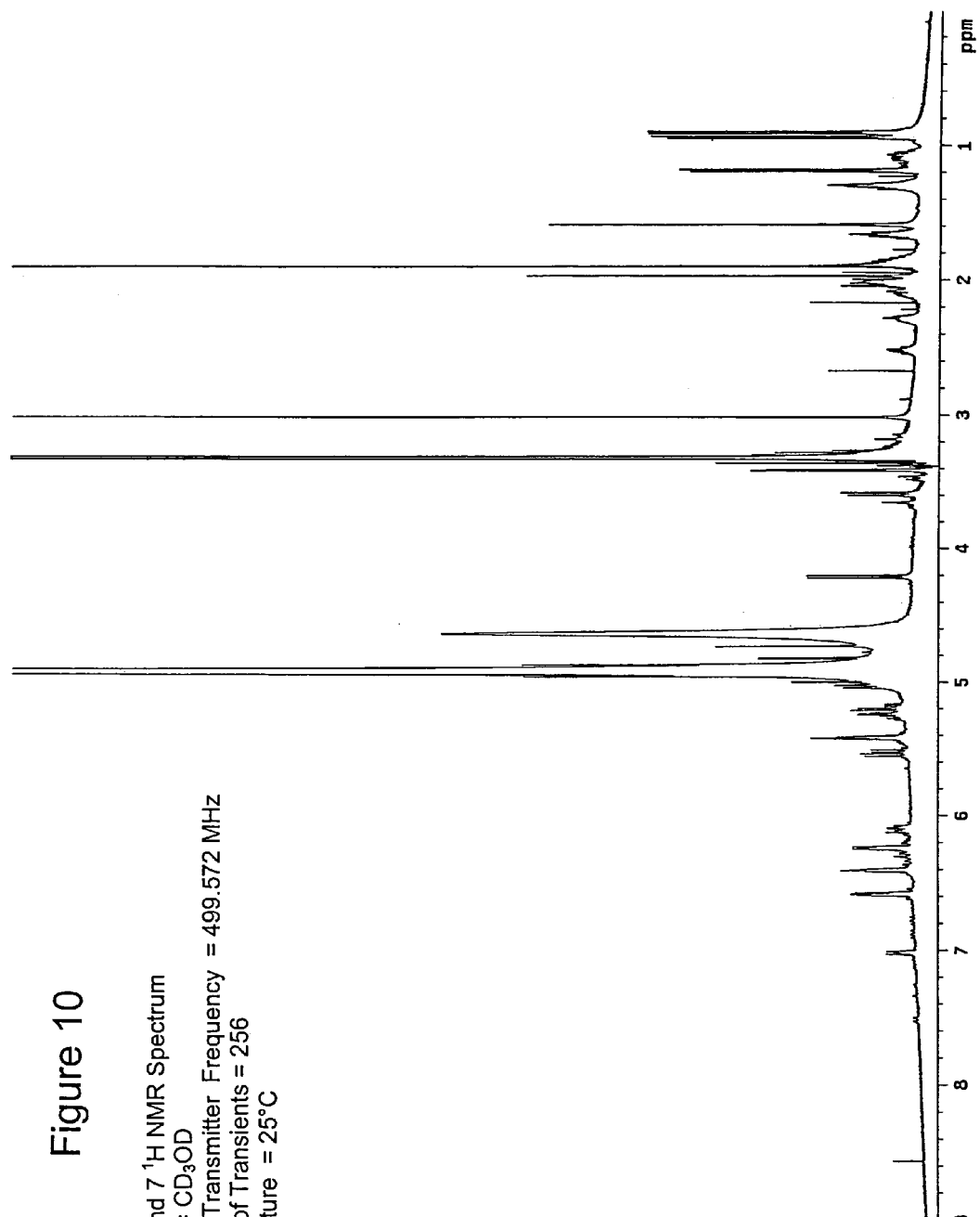
FIG. 10: 500 MHz proton nuclear magnetic resonance ($^1$H NMR) spectrum of Compound 7 in $d_4$-MeOH.

Structure analysis of Compound 7 was accomplished by spectral data analysis including $^1$H NMR (FIG. 10) and Mass spectra. The later gave a mass of 739.37 at negative ionization (ES−) and 741.53 at positive ionization (ES+), which is consistent with a molecular formula of C$_{41}$H$_{63}$N$_3$O$_9$ and a calculated mass of 741.95.

Analysis of the $^1$H NMR (FIG. 10) showed the absence of the signal at δ 2.35 ppm (Table 5) from the NMR spectrum of Compound 1. This signal was previously assigned to the two methylene groups of the cyclopentenone of Compound 1. An effect was also observed at position 3, which doublet (found at about 7.1 ppm in the case of Compound 1) has moved 0.1 ppm (to 7.0 ppm), the rest of the spectra remaining mostly the same.

The crude residue was purified by multiple injection on an HPLC Waters Auto-Purification System using a Symmetry (C-18, 5μ, 30×100 mm) column and the following eluent: A (10 mM ammonium acetate in water (10 mM NH$_4$OAc)) and B acetonitrile (MeCN), 74:26 to 50:50 A:B gradient in 20 minutes, 40 mL/min. The fractions having retention times 9.4, 11.5 and 15.5 minutes were collected to give respectively Compound 4 (0.53 mg), Compound 3 (5.36 mg) and Compound 5 (4.04 mg).

Structures of Compounds 3, 4 and 5:

Compound 3

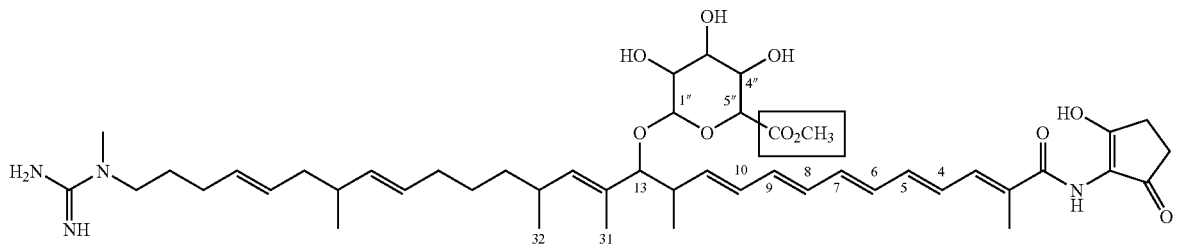

EXAMPLE 5

Preparation and Identification of Compounds 3, 4 and 5

Compounds 3, 4 and 5 were prepared according to the following procedure. A 0.1 M solution of sodium hydroxide Compound 3 is named 3,4,5-trihydroxy-6-[1-[11-(2-hydroxy-5-oxocyclopent-1-enylcarbamoyl)-1-methyldodeca-2,4,6,8,10-pentaenyl]-2,4,10-tri methyl-16-(N-methylguanidino)-hexadeca-2,8,12-trienyloxy]-tetrahydropyran-2-carboxylic acid methyl ester.

Figure 6:
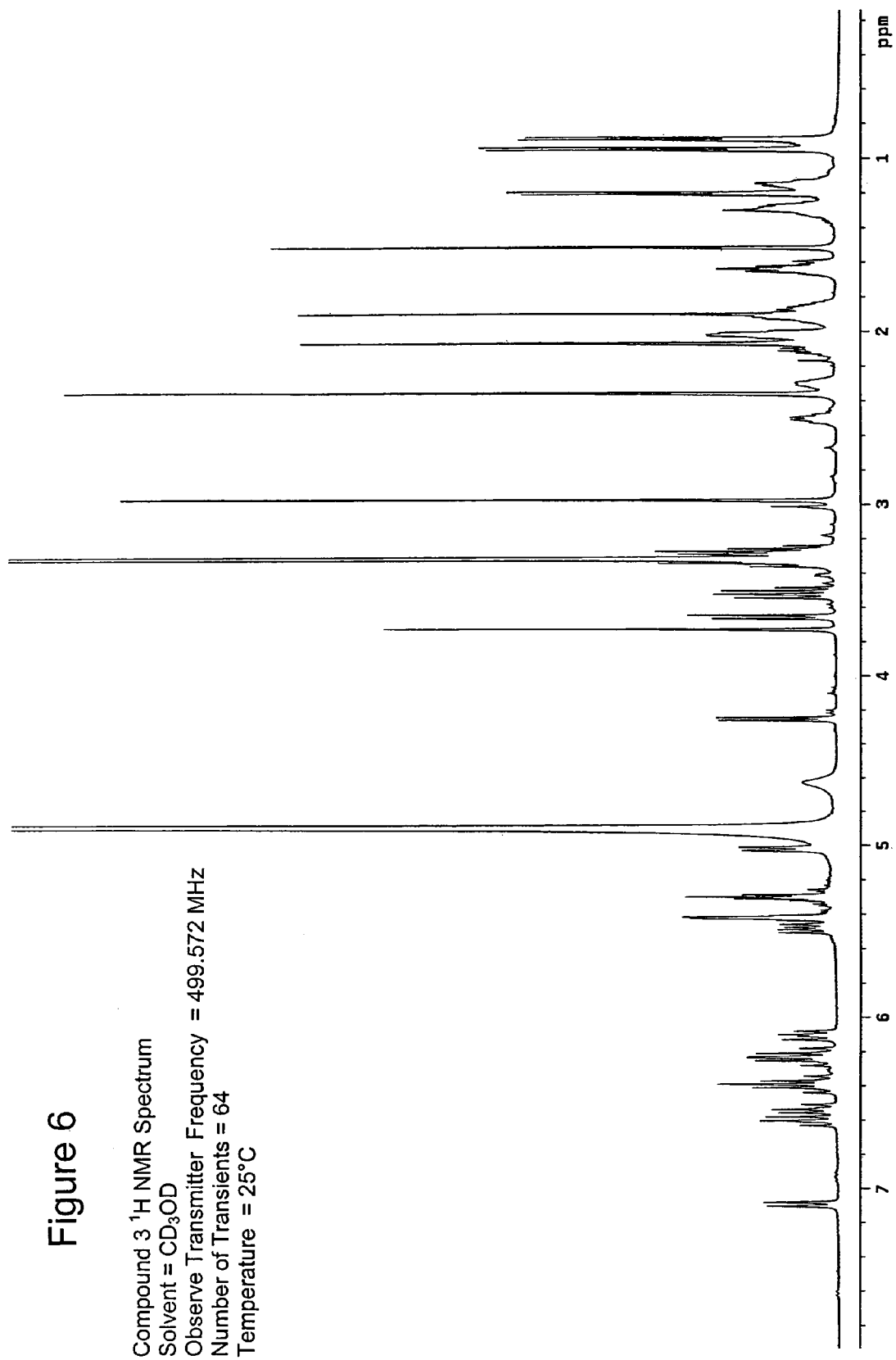
FIG. 6: 500 MHz proton nuclear magnetic resonance ($^1$H NMR) spectrum of Compound 3 in $d_4$-MeOH.

Structure determination of Compound 3 was accomplished by spectral data analysis including $^1$H NMR (FIG. 6) and $^{13}$C NMR and mass spectrometry. The molecular ion was found at mass 852.03 (M+H)$^+$ and 849.97 (M−H)$^-$, respectively for positive and negative ionization, which confirms a calculated molecular weight of 851.08, for C$_{47}$H$_{70}$N$_4$O$_{10}$ as molecular formula. The methyl group (in the squares) was easily assigned to the carboxylic ester from NMR chemical shifts, of the new methyl group (singlet at δ

3.73 ppm integrating for 3 protons) and of the surrounding proton and carbon atoms. The protons most affected were 4" and 5" (δ 3.40-3.48 ppm (Table 5) moved to δ 3.50-3.56 ppm), 1" (doublet δ 4.20 ppm (Table 5) moved to δ 4.26 ppm), 13 (doublet δ 4.58 ppm (Table 5) moved to δ 4.68 ppm) and 31 (δ 1.60 ppm (Table 5) moved to δ 1.52 ppm). Smaller effects were also observed at proton positions 4 to 10 and 32. These last effects might be due to a minor change in conformation and polarity difference between the carboxylic acid of Compound 1 and the ester of Compound 3.

confirms a calculated molecular weight of 851.08, for $C_{47}H_{70}N_4O_{10}$ as molecular formula. The $^1H$ NMR spectral analysis confirmed the presence of the methyl group (in the square) as a singlet integrating for three protons at 4.07 ppm. This methyl was also confirmed to be on the cyclopentenone as the two methylene groups were non-equivalent. In fact, in Compound 1, the two methylene groups from the cyclopentenone (positions 3' and 4') are equivalent (a 4 proton singlet at 2.35 ppm) due to the symmetry of the tautomeric forms.

Compound 4

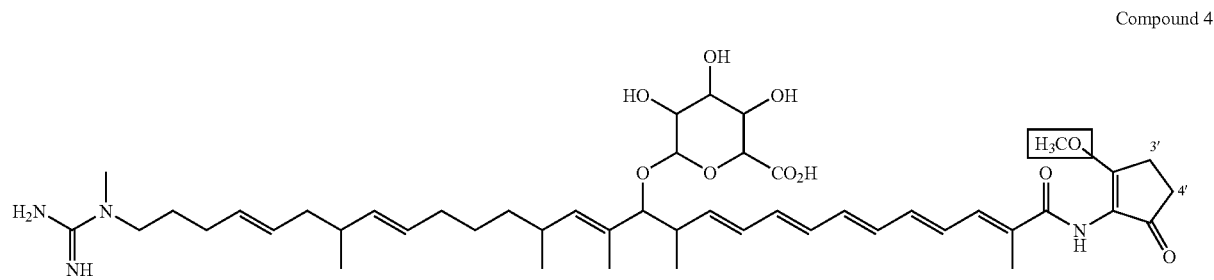

Compound 4 is named 3,4,5-trihydroxy-6-[1-[11-(2-methoxy-5-oxo-cyclopent-1-enylcarbamoyl)-1-methyl-dodeca-2,4,6,8,10-pentaenyl]-2,4,10-trimethyl-16-(N-methyl-guanidino)-hexadeca-2,8,12-trienyloxy]-tetrahydropyran-2-carboxylic acid.

Figure 7:
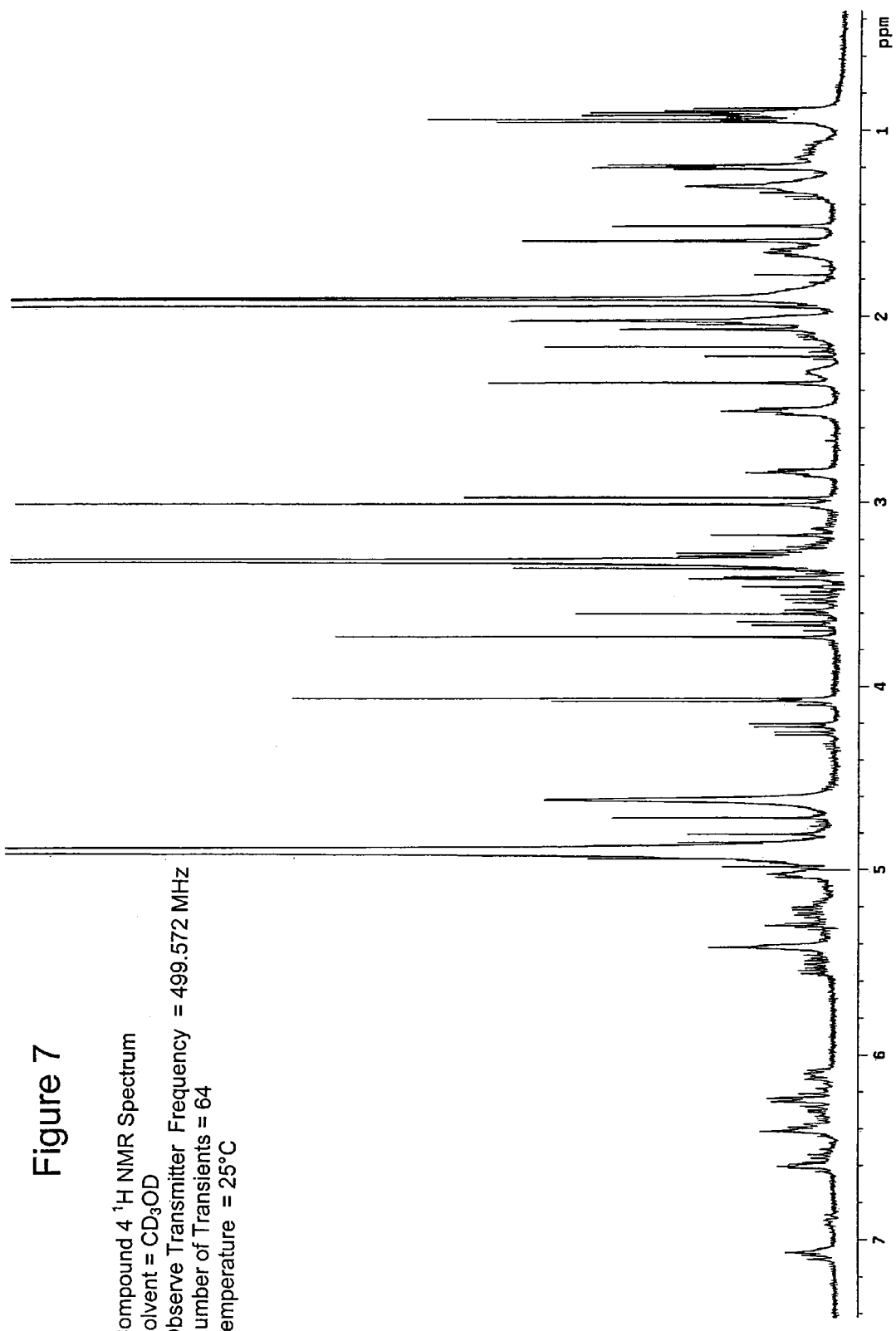
FIG. 7: 500 MHz proton nuclear magnetic resonance ($^1$H NMR) spectrum of Compound 4 in $d_4$-MeOH.

Structure determination of Compound 4 was accomplished by spectral data analysis including $^1H$ NMR (FIG. 7) and $^{13}C$ NMR and mass spectrometry. The molecular ion was found at mass 852.03 (M+H)$^+$ and 849.98 (M−H)$^-$, respectively for positive and negative ionization, which In Compound 4, the protons of these two positions appear as two separate triplets at 2.84 ppm and 2.52 ppm, integrating for two protons each.

Compound 5

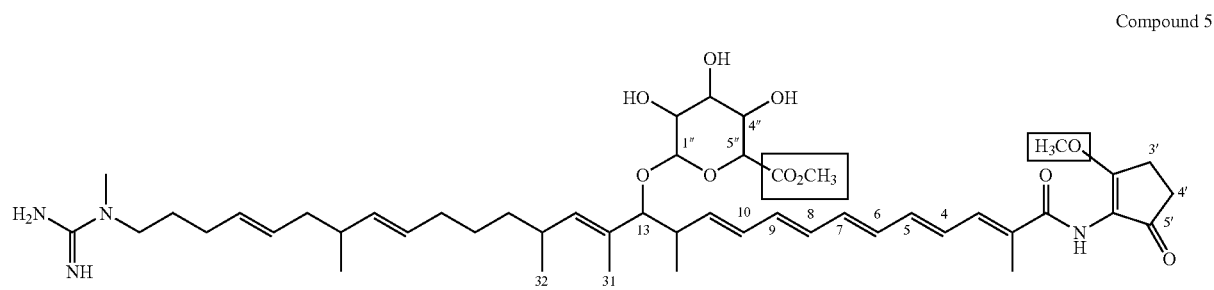

Compound 5 is named 3,4,5-trihydroxy-6-[1-[11-(2-methoxy-5-oxo-cyclopent-1-enylcarbamoyl)-1-methyl-dodeca-2,4,6,8,10-pentaenyl]-2,4,10-trimethyl-16-(N-methyl-guanidino)-hexadeca-2,8,12-trienyloxy]-tetrahydropyran-2-carboxylic acid methyl ester.

Figure 8:
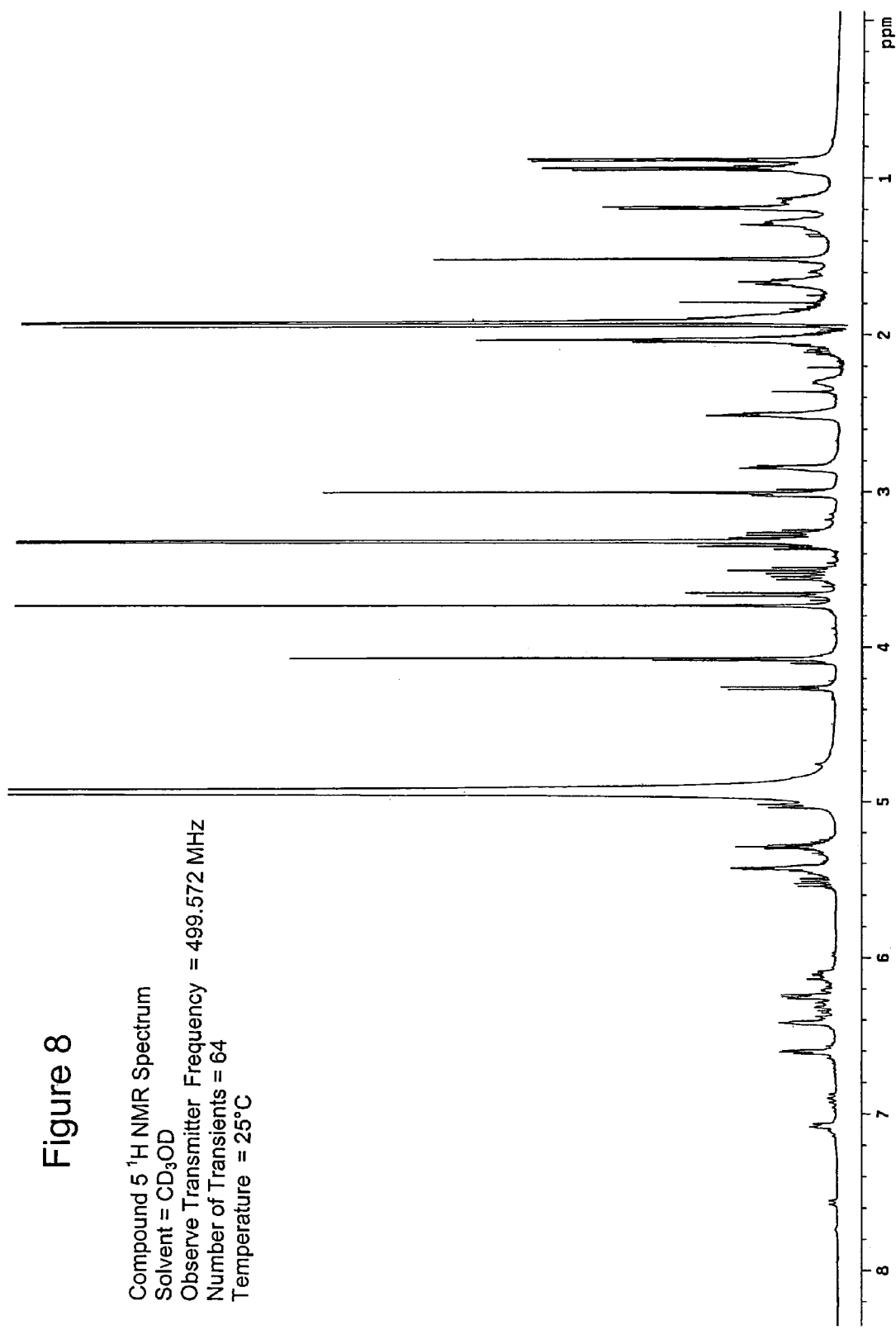
FIG. 8: 500 MHz proton nuclear magnetic resonance ($^1$H NMR) spectrum of Compound 5 in $d_4$-MeOH.

Structure determination of Compound 5 was accomplished by spectral data analysis including $^1H$ NMR (FIG. 8)

and $^{13}C$ NMR and mass spectrometry. The molecular ion was found at mass 866.06 $(M+H)^+$ and 863.89 $(M-H)^-$, respectively for positive and negative ionization, which confirms a calculated molecular weight of 865.11, for $C_{48}H_{72}N_4O_{10}$ as molecular formula. The $^1H$ NMR spectral analysis confirmed the presence of two methyl groups (in the square) as singlets integrating for three protons at 3.73 ppm and 4.07 ppm. One of the methyl (4.07 ppm) was confirmed to be on the cyclopentenone as the two methylene groups, as in Compound 4, were non-equivalent and appearing as two separate triplets at 2.84 ppm and 2.52 ppm, integrating for two protons each. The other methyl group (3.73 ppm) was confirmed as the methyl ester of the glucoronic acid (see Compound 3 determination above).

EXAMPLE 6

Preparation of Compound 3 by Esterification of Compound 1

1-methyldodeca-2,4,6,8,10-pentaenyl]-2,4,10-trimethyl hexadeca-2,8,12-trienyloxy}-3,4,5-trihydroxytetrahydropyran-2-carboxylic acid.

Compound 6 was prepared by acetylation of Compound 1 using the following procedure. Acetic anhydride (3.38 µL, Sigma) was added to a solution of Compound 1 (20 mg) in methanol (2 mL) and the reaction stirred at room temperature for 72 hours. Additional portions of acetic anhydride (20 µL) were added after 24 and 48 hours. The reaction was monitored by TLC (Merck Silica gel 60 $F_{254}$, eluting with 7% methanol in chloroform) visualized under UV. The reaction was concentrated in vacuo.

The crude residue was purified by multiple injection on an HPLC Waters Auto-Purification System using a Symmetry (C-18, 5µ, 30×100 mm) column and the following eluent: A (10 mM ammonium acetate in water (10 mM $NH_4OAc$)) adjusted to pH 5 with glacial acetic acid and B acetonitrile (MeCN), 74:26 to 50:50 A:B gradient in 20 minutes, 40

Compound 3

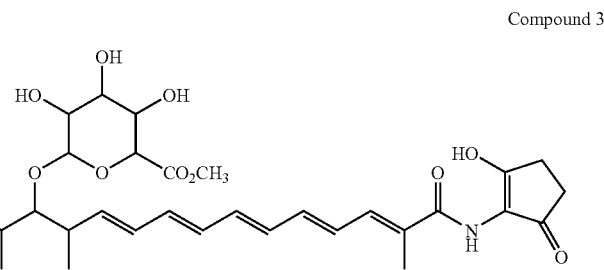

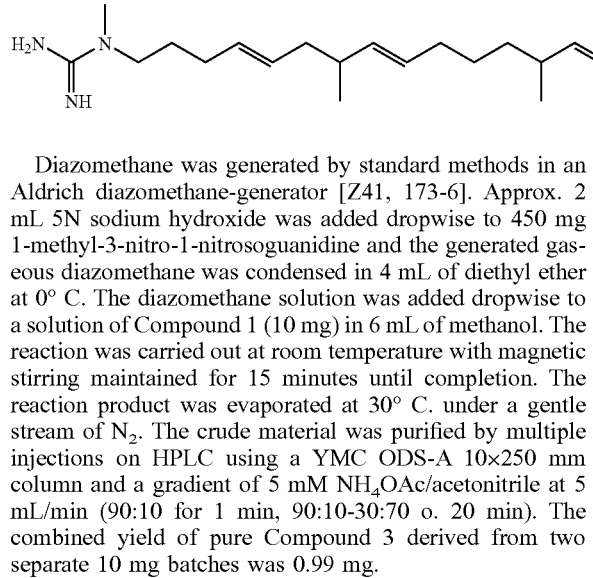

Diazomethane was generated by standard methods in an Aldrich diazomethane-generator [Z41, 173-6]. Approx. 2 mL 5N sodium hydroxide was added dropwise to 450 mg 1-methyl-3-nitro-1-nitrosoguanidine and the generated gaseous diazomethane was condensed in 4 mL of diethyl ether at 0° C. The diazomethane solution was added dropwise to a solution of Compound 1 (10 mg) in 6 mL of methanol. The reaction was carried out at room temperature with magnetic stirring maintained for 15 minutes until completion. The reaction product was evaporated at 30° C. under a gentle stream of $N_2$. The crude material was purified by multiple injections on HPLC using a YMC ODS-A 10×250 mm column and a gradient of 5 mM $NH_4OAc$/acetonitrile at 5 mL/min (90:10 for 1 min, 90:10-30:70 o. 20 min). The combined yield of pure Compound 3 derived from two separate 10 mg batches was 0.99 mg.

EXAMPLE 7

Preparation and Identification of Compound 6 mL/min. The fractions having retention times 9.4, 11.5 and 15.5 minutes were collected to give Compound 6 (6.43 mg).

Figure 9:
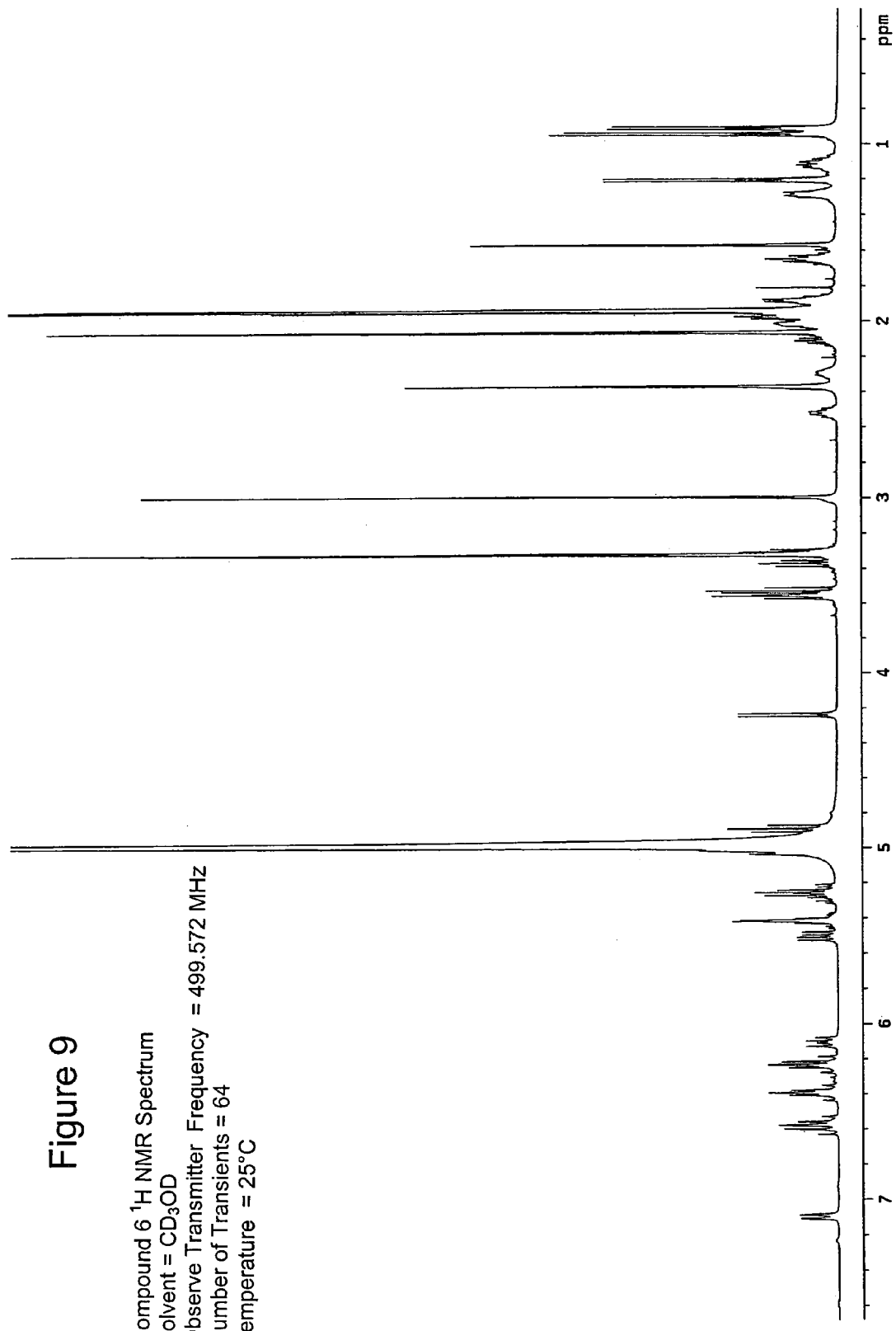
FIG. 9: 500 MHz proton nuclear magnetic resonance ($^1$H NMR) spectrum of Compound 6 in $d_4$-MeOH.

Structure determination of Compound 6 was accomplished by spectral data analysis including $^1H$ NMR (FIG. 9) and $^{13}C$ NMR and mass spectrometry. The molecular ion was found at mass 880.03 $(M+H)^+$ and 877.98 $(M-H)^-$, respectively for positive and negative ionization, which confirms a calculated molecular weight of 879.09, for $C_{48}H_{70}N_4O_{11}$ as molecular formula. Analysis of the $^1H$ NMR spectrum also confirmed the presence of an acetyl group as a singlet at 1.95 ppm integrating for 3 protons. No important changes were observed at other positions, which indicate this acetyl group is on the guanidine.

EXAMPLE 8

Anti-microbial Activity of Compounds 1 to 7

Antibacterial activity of Compounds 1 and 2 (Table 7) was measured by determining the minimal inhibitory con- Compound 6

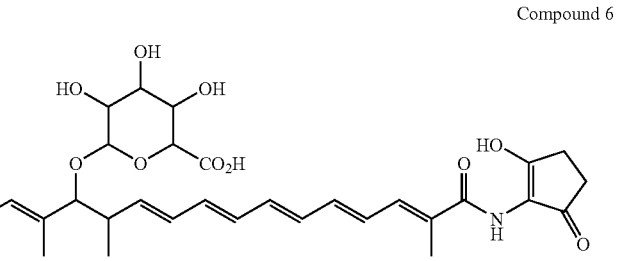

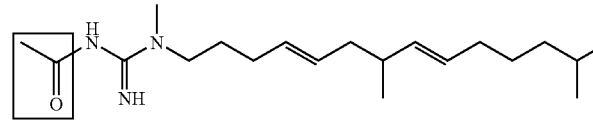

Compound 6 is named 6-{16-(N'-acetyl-N-methylguanidino)-1-[11-(2-hydroxy-5-oxocyclopent-1-enylcarbamoyl)- centration (MIC) necessary to obtain a complete inhibition of bacteria growth in eight indicator strains, namely Staphylococcus aureus (ATCC™ 6538P), Staphylococcus aureus MRS3 (ATCC™ 700699), Staphylococcus epidermidis (ATCC™ 12228), Bacillus subtilis (ATCC™ 23857), Bacillus megaterium (ATCC™ 14581), Enterococcus faecalis VRE-1 (ATCC™ 29212), Enterococcus faecalis VRE-2 (ATCC™ 51299) and Micrococcus luteus (ATCC™ 9341). Indicator strains preparation and MIC determination were performed according to the National Committee for Clinical Laboratory Standards (NCCLS) guideline M7-A5 *Methods for Dilution Antimicrobial Susceptibility Tests for Bacteria That Grow Aerobically; Approved Standard-Fifth Edition.* (NCCLS document M7-A5, ISBN 1-56238-394-9; NCCLS, 940 West Valley Road, Suite 1400, Wayne, Pa. 19087-1898 USA), the content of which is incorporated herein by reference.

Compounds 1 and 2 were prepared as 100× stock solution in DMSO, with concentrations ranging from 3.2 mg/ml to 0.003 mg/ml (a two-fold dilution series over 11 points). An aliquot of each 100× stock solution was diluted 50-fold in test medium described below to give a set of eleven (11) 2× solutions. 50 μl of each of the eleven 2× solutions was aliquoted into the corresponding well of a 12-well row, with the final well reserved for medium alone control.

Vancomycin (Sigma™) used as positive control compounds, was prepared as 2× stock solutions in Mueller-Hinton test medium ranging from 64 μg/ml to 0.06 μg/ml (a two-fold dilution series over 11 points). An aliquot of 50 μl corresponding to each concentration (at 2×) was then transferred to 96-well microplates to obtain a series of eleven two-fold dilutions.

An isolated colony of each of the eight indicator strains was used to inoculate tubes containing 2 ml of test medium. Mueller-Hinton test medium was used for *Staphylococcus aureus* (ATCC™ 6538P), *Staphylococcus aureus* MRS3 (ATCC™ 700699), *Staphylococcus epidermidis* (ATCC™ 12228), *Bacillus subtilis* (ATCC™ 23857), *Bacillus megaterium* (ATCC™ 14581) and *Micrococcus luteus* (ATCC™ 9341) indicator strains, and BHI test medium was used for *Enterococcus faecalis* VRE-1 (ATCC™ 29212) and *Enterococcus faecalis* VRE-2 (ATCC™ 51299) indicator strains. Cells were grown overnight at 28° C. with shaking. Inoculum density for each indicator strain was adjusted to $OD_{600}=0.1$ in 5 ml 0.85% saline, then further diluted 1/100 in appropriate medium. 50 μl of the final dilution (in test medium) of each indicator strain was added to each well of a 12-well row. This brings the final dilution of the test article or control compound in solution to 1×. The final inoculum is approximately $5 \times 10^5$ CFU/ml.

The indicator strains were incubated with 11 concentrations of each of Compounds 1 and 2, Vancomycin (Sigma™) control compound and one media alone control. For MIC determination, assay plates were incubated at 35° C. for 16 to 20 hours. The MIC for each indicator was assessed as the lowest concentration of compound resulting in total absence of growth and is shown below.

TABLE 7

Antibacterial activity of Compounds 1 and 2, MIC (μg/ml)

| Strain | Compound 1 | Compound 2 | Vancomycin |
|---|---|---|---|
| *S. aureus* ATCC ™ 6538P | 2 | 1 | 2 |
| *S. aureus* ATCC ™ 700699 | 4 | 2 | 4 |
| *S. epidermidis* ATCC ™ 12228 | 4 | 2 | 2 |
| *B. subtilis* ATCC ™ 23857 | 1 | 2 | 0.25 |
| *B. megaterium* ATCC ™ 14581 | 1 | 1 | 0.125 |
| *E. faecalis* ATCC ™ 29212 | 8-16 | 16 | 4 |
| *E. faecalis* ATCC ™ 51299 | 16 | 16 | 8-16 |
| *M. luteus* ATCC ™ 9341 | 4 | 1-2 | 1 |

Antibacterial activitiy of Compounds 3, 4, 5, 6 and 7 are accomplished using the same method in a panel of bacterial strains and Vancomycin as positive control.

Antibacterial efficacy of Compounds 1, 2, 3, 4, 5 and 6 on bacterial strain *Staphylococcus aureus* NRRL B-313 (ATCC™ 6538P) was determined at different pH concentrations. These results are shown in Table 8 together with the antibacterial activity of Compound 7 on the same strain.

TABLE 8

Compounds 1 to 7 Antibacterial activity on *S. Aureus* (ATCC ™ 6538P), and effect of pH (MIC (μg/ml))

| | 1 | 2 | 3 | 4 | 5 | 6 | 7 | Vancomycin |
|---|---|---|---|---|---|---|---|---|
| pH 5.0 | 0.125 | 0.0625 | 2 | 2 | 2 | 0.25 | ND* | 1 |
| pH 6.0 | 0.25 | 0.125 | 4-8 | 2 | 4 | 0.5 | ND* | 1 |
| pH 7.0 | 1 | 1 | 16 | 2 | 4 | 2 | 32-64 | 1 |

*ND: not determined

EXAMPLE 9

Preparation of Compound 10 by Oxidation of Compound 8

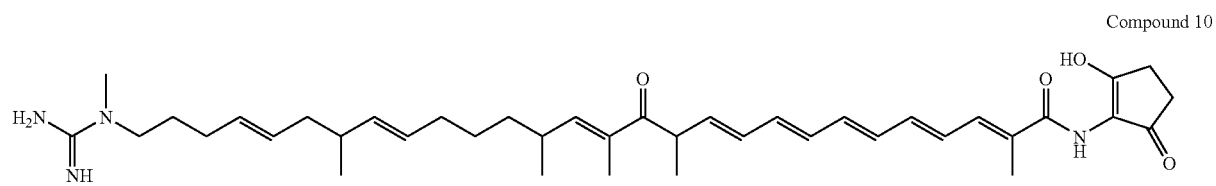

Compound 10

To a methylene choride solution of Dess-Martin periodinane (1,1,1-triacetoxy-1,1-dihydro-1,2-benziodoxol-3(1H) one, Sigma-Aldrich Co.) is added a solution of Compound 8 in methylene chloride and the reaction stirred at room temperature for 1 hour. The mixture is diluted with diethyl ether and a saturated aqueous sodium bicarbonate solution containing sodium thiosulfate. Organic layer is separated and washed with saturated aqueous sodium bicarbonate, water and brine, dried over magnesium sulfate, filtered and concentrated in vacuo. The crude residue is purified by HPLC according to the procedure described in Example 5. Pure Compound 10 is obtained by pooling and concentrating the appropriate eluate fractions.

EXAMPLE 10

Preparation of Compound 11 by Reduction of Compound 1

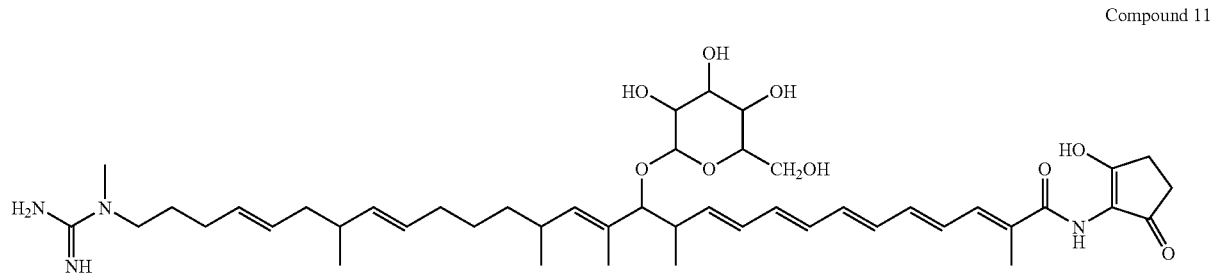

Compound 11

LAH (lithium aluminum hydride) is added to a 0° C. solution of Compound 1 in THF (tetrahydrofuran). After hydrogen gas has stopped evolving, the reaction is allowed to warm to room temperature and stirred overnight. Water is slowly added and 1M hydrochloric solution is used to acidify the solution carefully. The mixture is extracted three times with ethyl acetate. Organic layers are combined and washed with saturated aqueous sodium bicarbonate, water and brine, dried over magnesium sulfate, filtered and concentrated in vacuo. Pure Compound 11 is obtained by pooling and concentrating the appropriate fractions of HPLC purification according to Example 5.

EXAMPLE 11

Preparation of Compound 23 from Compound 1

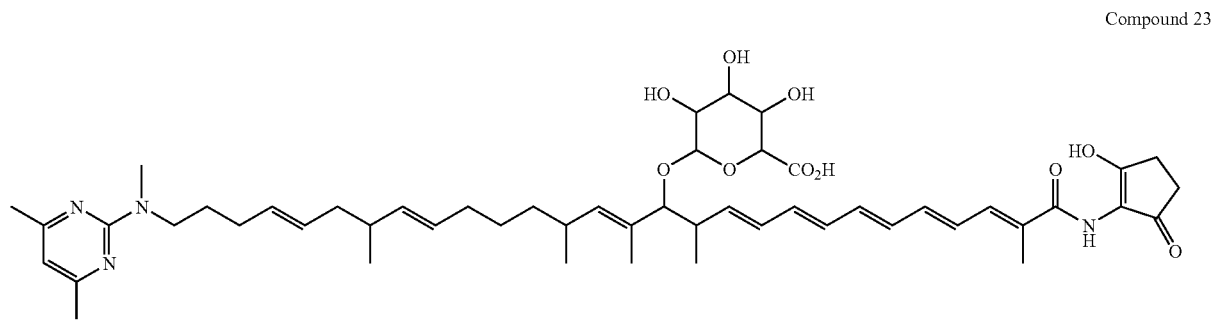

Compound 23

Compound 23 is prepared by modification of the guanidino group of Compound 1 according to the procedure described in Argoudelis et al., J. Antibiotics, Vol. XL, No. 6, June 1987, pp 750-760. A mixture of 200 mg of Compound 1 in 1.2 ml water, 1.0 ml of absolute ethanol, 1.0 ml of 2,4-pentadione and 120 mg of sodium bicarbonate is stirred at 90° C. for 3 hours. The mixture is allowed to cool to room temperature, concentrated to dryness, dissolved in 5 ml of 2N acetic acid, and purified by HPLC as described in Example 5. Pure Compound 23 is obtained by pooling and concentrating the appropriate eluate fractions.

EXAMPLE 12

Preparation of Compound 24 by Alkylation of Compound 1

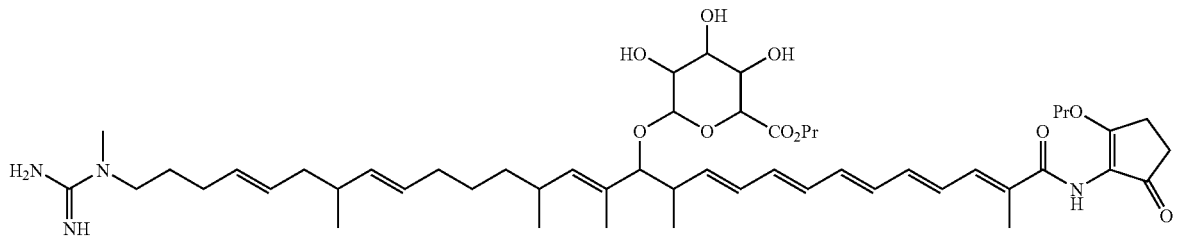

Compound 24

Compound 24 is prepared as follows. See Bartzatt et al., Biotechnol. Appl. Biochem. (2002) 36, 89-93. A Wheaton-type double-chamber device (Wheaton Co., Miliville, N.J., U.S.A.) is utilized to generate diazopropane ($CH_3CH_2CHN_2$). Approx. 5.0 mg of Compound 1 is placed into an organic solvent (ethyl acetate/diethyl ether, 1:1, v/v) and the diazopropane gas formed is allowed to dissolve in the mixture. Diazopropane is generated by mixing 0.15 ml of 5 M NaOH with 0.15 g of 3-nitro-1-nitroso-1-propylguanidine. Excess diazoalkane and the solvent are removed by nitrogen gas flow or under vacuum. The remaining residue is dissolved in methanol, and the methanol solution is purified by HPLC as described in Example 5. Pure Compound 24 is obtained by pooling and concentrating the appropriate eluate fractions.

EXAMPLE 13

Preparation of Compound 25 by Acylation of Compound 1

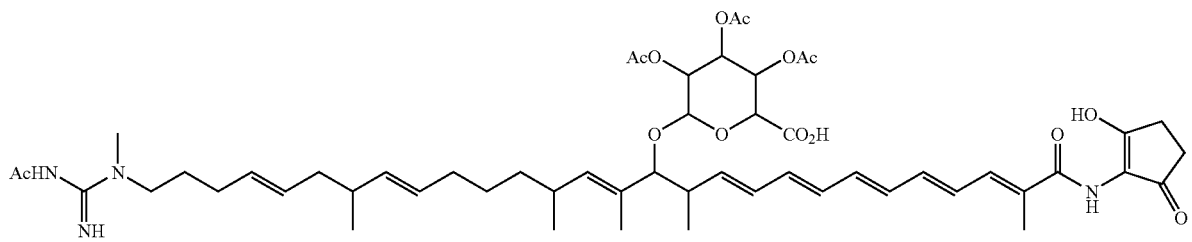

Compound 25

Compound 25 is prepared by acylation of Compound 1 as follows. Acetic anhydride (4.5 equivalents) is added dropwise to a solution of 50 mg/ml of Compound 1 and in acetonitrile and pyridine (9:1). The mixture is stirred under reflux and monitored by TLC (see example 5). The solvent is removed under vacuum and the residue is dissolved in methanol. The methanol solution is purified by HPLC as described in Example 5. Pure Compound 25 is obtained by pooling and concentratin the appropriate eluate fractions.

EXAMPLE 14

Preparation of Compound 26 by Esterification of Compound 25

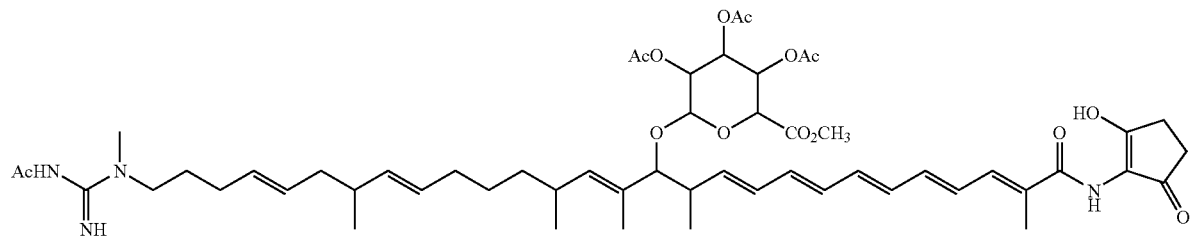

Compound 26

To a solution of Compound 25 in diethyl ether/ethyl acetate (1/1) is added 1 equivalent of diazomethane in diethyl ether. The reaction mixture is allowed to stand at room temperature overnight. Excess diazomethane and the solvent are removed by nitrogen gas flow or under vacuum. The remaining residue is dissolved in methanol, and the methanol solution is purified by HPLC as described in Example 5. Pure Compound 26 is obtained by pooling and concentrating the appropriate eluate fractions.

EXAMPLE 15

Preparation of Compound 27 by Acylation of Compound 1

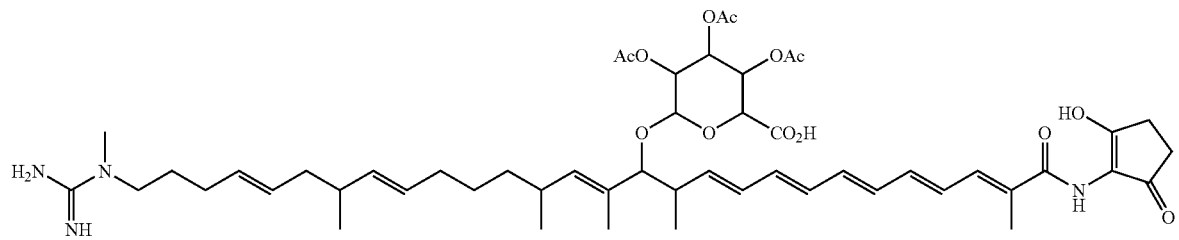

Compound 27

Compound 27 is prepared by acylation of Compound 1 as follows. Acetic anhydride (3.2 equivalents) is added dropwise to a solution of 50 mg/ml of Compound 1 in acetonitrile. The mixture is stirred under reflux and monitored by TLC (see Example 5). The solvent is removed under vacuum and the residue is dissolved in methanol. The methanol solution is purified by HPLC as described in Example 5. Pure Compound 27 is obtained by pooling and concentrating the appropriate eluate fractions.

EXAMPLE 16

Preparation of Compound 28 by Esterification of Compound 27

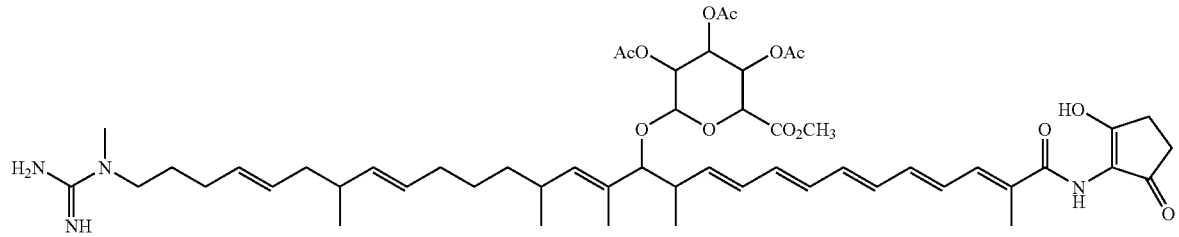

Compound 28

To a solution of Compound 27 in diethyl ether is added 1 equivalent of diazomethane in diethyl ether. The reaction mixture is allowed to stand at room temperature overnight. Excess diazomethane and the solvent is removed by nitrogen gas flow or under vacuum. The remaining residue is dissolved in methanol, and the methanol solution is purified by HPLC as described in Example 5. Pure Compound 28 is obtained by pooling and concentrating the appropriate eluate fractions.

EXAMPLE 17

Biosynthesis and Isolation of Compound 8 thiostrepton resistance producing a disruption plasmid. The plasmid is introduced into *Amycolatopsis orientalis* by either PEG-mediated protoplast transformation or RK2-mediated conjugation. Spores from individual transformants or transconjugants are cultured on non-selective plates to induce recombination. This cycle is repeated three times to enhance the opportunity for recombination. Crossovers yielding targeted gene recombinants are then selected and screened using kanamycin and thiostrepton for single crossovers and kanamycin for double crossovers. Replica plating and southern hybridization are used to confirm the double crossover inactivation in *Amycolatopsis orientalis* transfor-

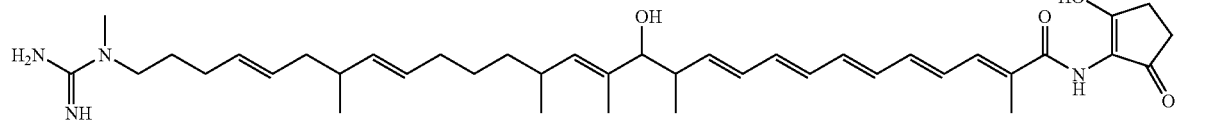

Compound 8

Figure 22:
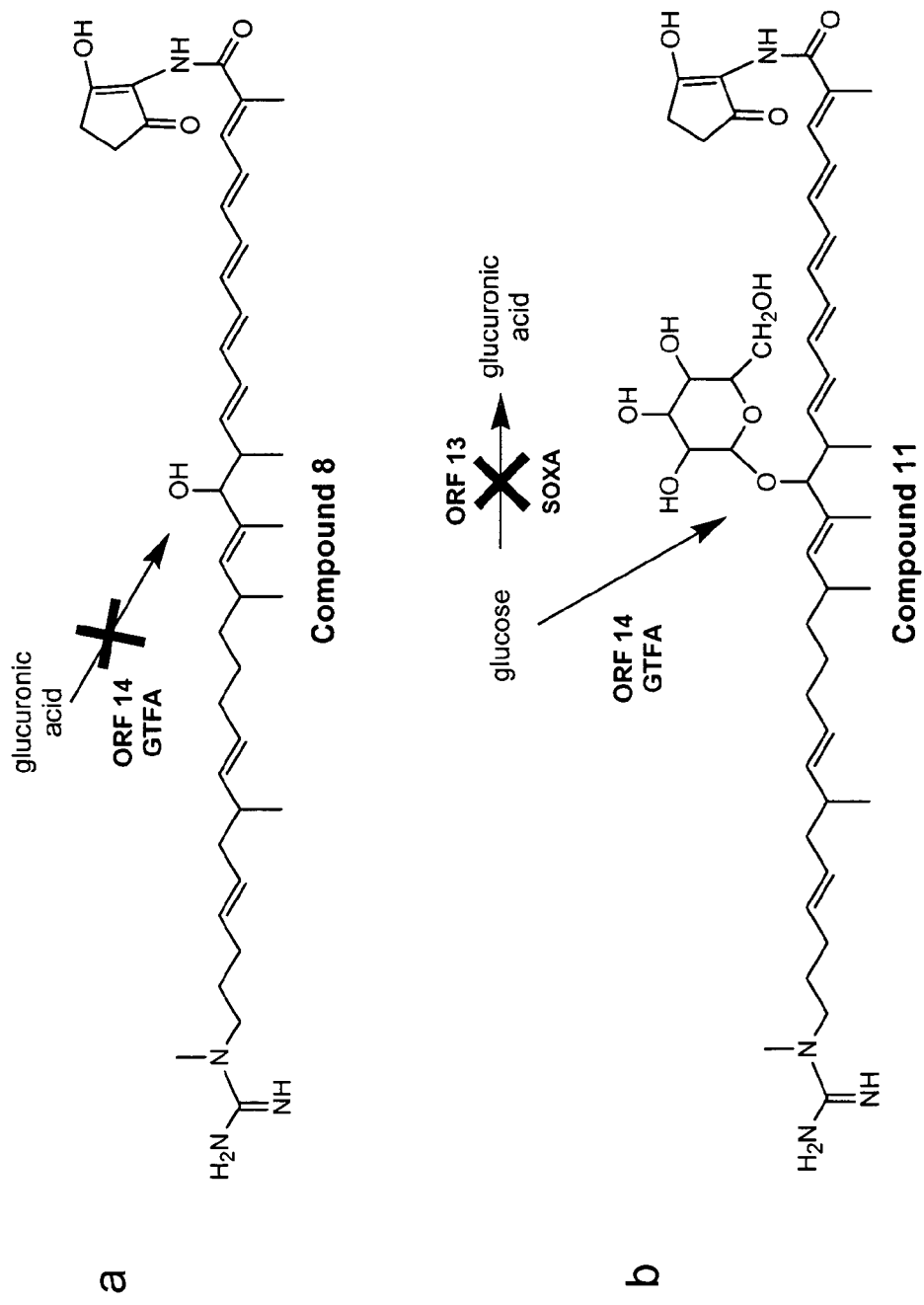
FIG. 22: inactivation of glycosyltransferase ORF 14 (SEQ ID NO: 29) and sugar oxidoreductase ORF 13 (SEQ ID NO: 27).

Compound 8 is produced by inactivation of glycosyltransferase ORF 14 (SEQ ID NO: 29) followed by fermentation as described in Example 2 and isolation of the compound as described in Example 3. Targeted inactivation of the gene product of ORF 14 (SEQ ID NO: 29) is achieved by insertional gene disruption using replicative plasmid-mediated homologous recombination. Inactivation of glycosyltransferase ORF 14 (SEQ ID NO: 29) is described in FIG. 22a. Referring to FIG. 22a, inactivation of the glycosyltransferase gene (SEQ ID NO: 30) disrupts the transfer of the sugar moiety onto the backbone of the polyketide core. The absence of the sugar moiety results in a non-glycosylated Compound 8. Insertional inactivation of glycosyltransferase genes involved in polyketide biosynthesis in *streptomyces* is known in the art. Blanco et al. (*Mol. Gen. Genet.* 262, 991-1000 (2000)), identified two genes of the mithramycin biosynthetic gene cluster as glycosyltransferases by the production of a non-glycosylated mithramycin upon inactivation of these genes. Similarly, Chen et al. (*Gene* 263, 255-64 (2001)) investigated genes responsible for glycosylation in the biosynthetic pathways encoding pikromycin, narbomycin, methymycin and neomethymycin by producing non-glycosylated analogs.

A plasmid for homologous recombination is constructed by cloning a kanamycin resistance marker between the left and right flanking regions of SEQ ID NO: 30. The construct is cloned into a delivery plasmid that is marked with mants. The *Amycolatopsis orientalis* transformant is cultured as described in Example 2 and Compound 8 is isolated using the protocol of Example 3.

EXAMPLE 18

Biosynthesis and Isolation of Compound 11

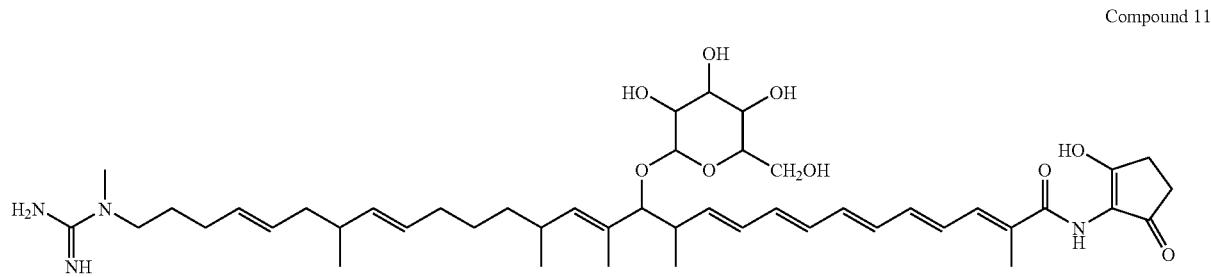

Compound 11

Compound 11 is produced by inactivation of inactivation of sugar oxidoreductase gene product of ORF 13 (SEQ ID NO: 27) followed by transfer of the glucose onto the polyketide backbone chain by the glycosyltransferase gene product of ORF 14 (SEQ ID NO: 29) as illustrated in FIG. 22b. Referring to FIG. 22b, glucuronic acid is synthesised by oxidation of glucose catalyzed by the sugar oxidoreductase gene product of ORF 13 (SEQ ID NO: 27). Inactivation of the ORF 13 (SEQ ID NO: 27) disrupts the conversion of glucose to glucuronic acid producing Compound 11 when the glucose substrate is transferred onto the polyketide backbone chain by the glycosyltransferase gene product of ORF 14 (SEQ ID NO: 29). Targeted inactivation of the sugar oxidoreductase ORF 13 (SEQ ID NO: 27) is achieved by insertional gene disruption using replicative plasmid-mediated homologous recombination.

A plasmid for homologous recombination is constructed by cloning a kanamycin resistance marker between the left and right flanking regions of SEQ ID NO: 28. The construct is cloned into a delivery plasmid that is marked with thiostrepton resistance producing a disruption plasmid. The plasmid is introduced into *Amycolatopsis orientalis* by either PEG-mediated protoplast transformation or RK2-mediated conjugation. Spores from individual transformants or transconjugants are cultured on non-selective plates to induce recombination. This cycle is repeated three times to enhance the opportunity for recombination. Crossovers yielding targeted gene recombinants are then selected and screened using kanamycin and thiostrepton for single crossovers and kanamycin for double crossovers. Replica plating and southern hybridization are used to confirm the double crossover inactivation in *Amycolatopsis orientalis* transformants. The *Amycolatopsis orientalis* transformant is cultured as described in Example 2 and Compound 11 is isolated using the protocol of Example 3.

EXAMPLE 19

Biosynthesis and Isolation of Compound 7 clopentenone. Gene disruption of ORF 15 (SEQ ID NO: 32) results in the inactivation of the adenylating/condensing synthetase gene product of ORF 15 (SEQ ID NO: 31) preventing transfer of the aminohydroxycyclopentenone unit to the polyketide chain. Compound 7 is provided by targeted inactivation of acyltransferase ORF 16 (SEQ ID NO: 33), acyl CoA ligase ORF 17 (SEQ ID NO: 35), oradenylating/condensing synthetase ORF 15 (SEQ ID NO: 31). Targeted inactivation of ORF 16, ORF 17 or ORF 14 (SEQ ID NO: 29) is achieved by insertional gene disruption using replicative plasmid-mediated homologous recombination.

A plasmid for homologous recombination is constructed by cloning a kanamycin resistance marker between the left and right flanking regions of SEQ ID NOS: 34, 36 or 32. The construct is cloned into a delivery plasmid that is marked with thiostrepton resistance producing a disruption plasmid. The plasmid is introduced into *Amycolatopsis orientalis* by either PEG-mediated protoplast transformation or RK2-mediated conjugation. Spores from individual transformants or transconjugants are cultured on non-selective plates to

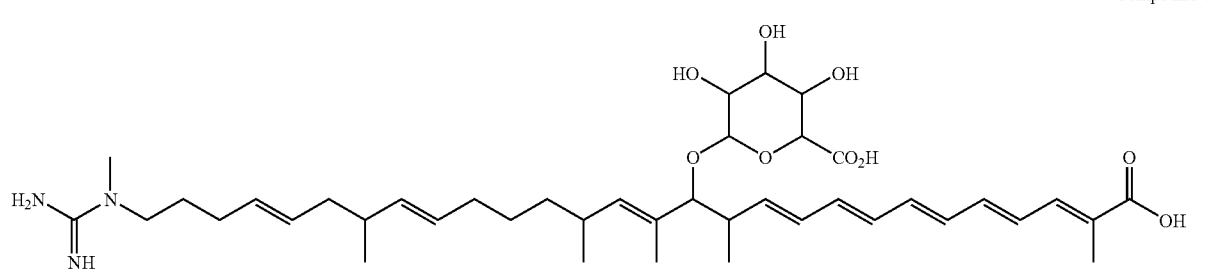

Compound 7

Figure 23:
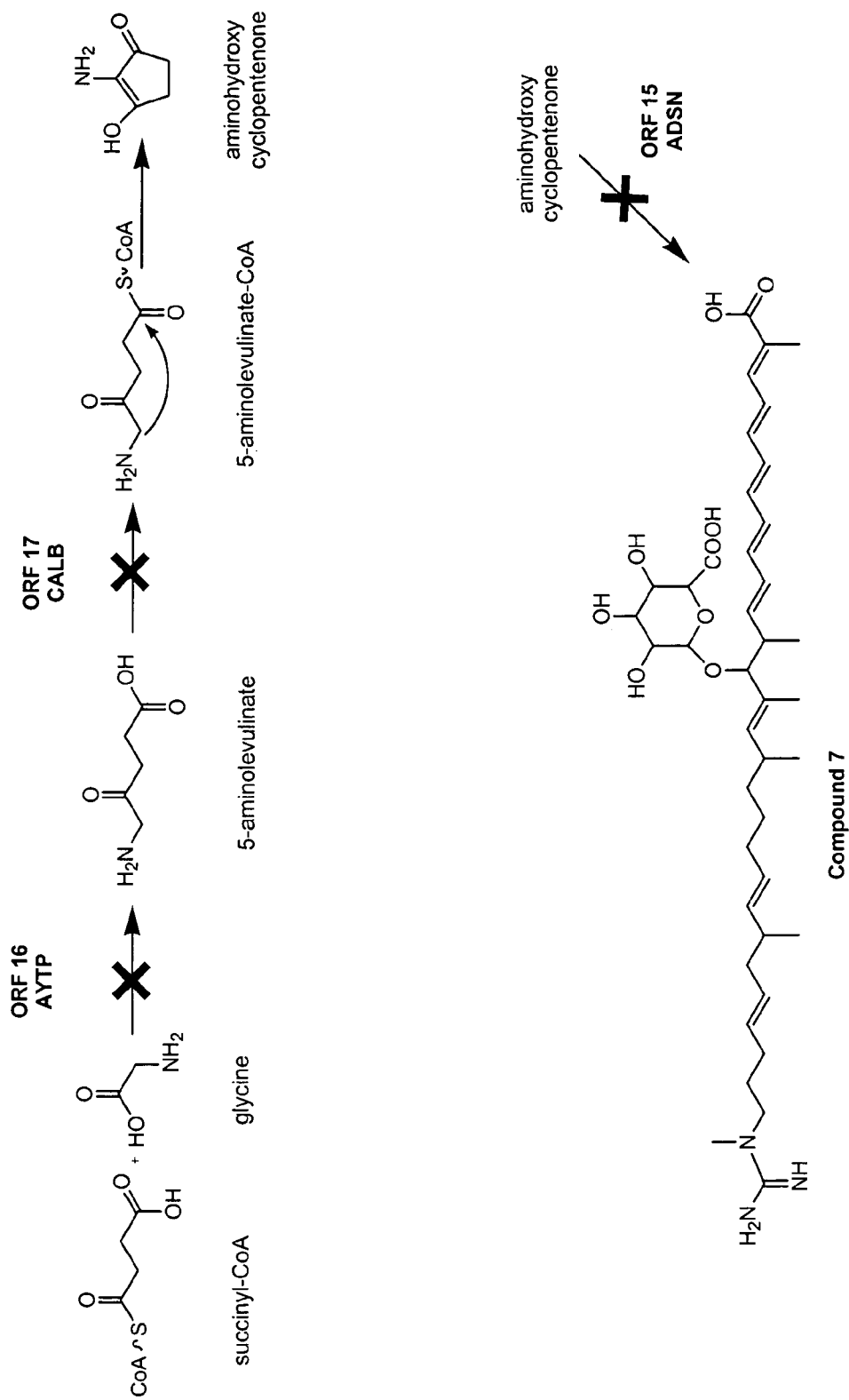
FIG. 23: inactivation of acyltransferase ORF 16 (SEQ ID NO: 33), acyl CoA ligase ORF 17 (SEQ ID NO: 35), or adenylating/condensing synthetase ORF 15 (SEQ ID NO: 31) so as to produce Compound 7.

Compound 7 is also produced by inactivation of any one of acyltransferase ORF 16 (SEQ ID NO: 33), acyl CoA ligase ORF 17 (SEQ ID NO: 35), or adenylating/condensing synthetase ORF 15 (SEQ ID NO: 31) followed by fermentation as described in Example 2 and isolation of the compound as described in Example 3. Referring to FIG. 23, gene disruption of ORF 16 (SEQ ID NO: 34) results in the inactivation of the acyltransferase gene product of ORF 16 (SEQ ID NO: 33) preventing condensation of succinyl-CoA and glycine to form 5-aminolevulinate. Gene disruption of ORF 17 (SEQ ID NO: 36) results in the inactivation of the acyl CoA ligase gene product of ORF 17 (SEQ ID NO: 35) preventing the conversion of 5-aminolevulinate to 5-aminolevulinate-CoA which cyclizes to form aminohydroxycyinduce recombination. This cycle is repeated three times to enhance the opportunity for recombination. Crossovers yielding targeted gene recombinants are then selected and screened using kanamycin and thiostrepton for single crossovers and kanamycin for double crossovers. Replica plating and southern hybridization are used to confirm the double crossover inactivation in *Amycolatopsis orientalis* transformants. The *Amycolatopsis orientalis* transformant is cultured as described in Example 2 and Compound 7 is isolated using the protocol of Example 3.

EXAMPLE 20

Biosynthesis and Isolation of Compound 9

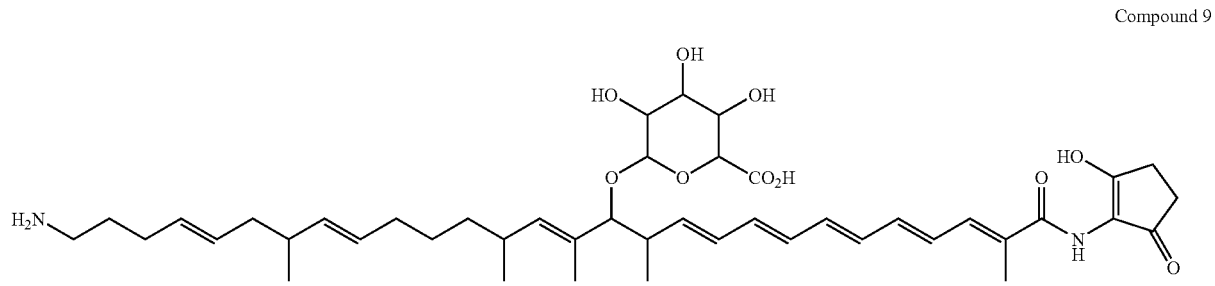

Compound 9

Figure 24:
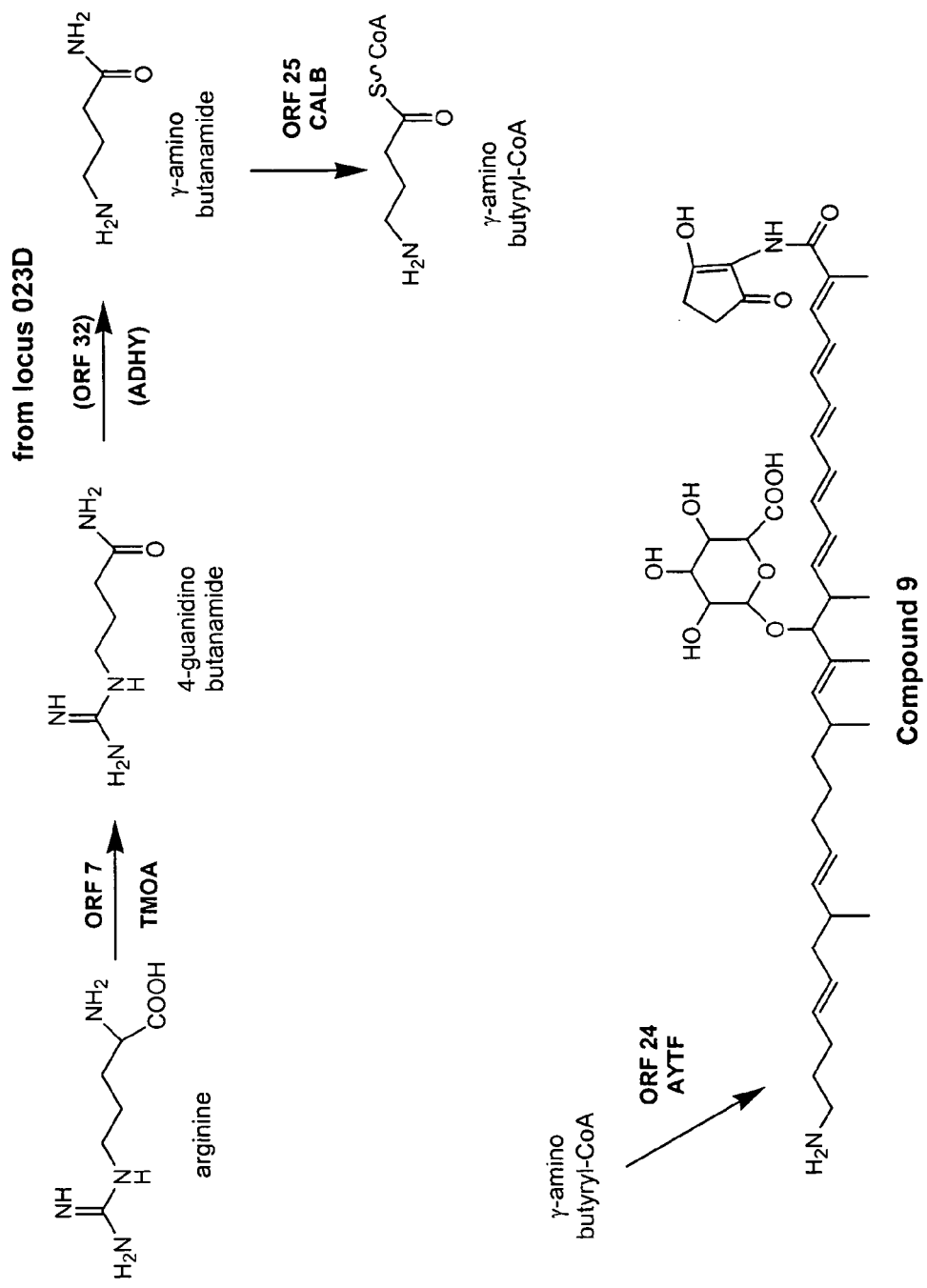
FIG. 24: incorporation of an amidino hydrolase to catalyze the conversion of 4-guanidinobutanamide to γ-amino butanamide resulting in production of Compound 9.

Compound 9 is produced by incorporation of the amidino hydrolase of SEQ ID NO: 65 of co-pending application U.S. Ser. No. 60/494,568, the contents and teachings of which are incorporated herein by reference. The amidino hydrolase catalyzes the conversion of 4-guanidinobutanamide to γ-amino butanamide. The supplementation of SEQ ID NO: 65 of co-pending application U.S. Ser. No. 60/494,568 effects synthesis of γ-amino butanamide from 4-guanidino butanamide, as described in FIG. 24. To promote catalytic activity of the amidinohydrolase enzyme, the N-methyltransferase of ORF 5 (SEQ ID NO: 10) is inactivated by insertional mutagenesis to prevent methylation of the guanidino group and thus avoid interference with the enzymatic activity of the amidino hydrolase SEQ ID NO: 65 of co-pending application U.S. Ser. No. 60/494,568. Referring to FIG. 24, the γ-amino butanamide is converted by acyl CoA ligase ORF 25 (SEQ ID NO: 52) to form γ-aminobutyryl-CoA which is then tethered onto the ACP domain of module 0 of ORF 18 (SEQ ID NOS: 37) of the polyketide synthase enzyme through the action of acyltransferase ORF 24 (SEQ ID NO: 50).

To supplement amidinohydrolase activity, SEQ IS NO: 65 of co-pending application U.S. Ser. No. 60/494,568, i.e ORF 32 of a biosynthetic locus for the production of a polyketide in *Streptomyces aizunensis*, is cloned into vector pBW160 as described in Hussain and Ward (*Appl. Environ. Microbiol.* 69, 373-382 (2003)) and the vector transferred into *Amycolatopsis orientalis*. The vector contains inducible promoter elements placed upstream of the cloned amidinohydrolase gene. Transfer of the expression vector to *Amycolatopsis* host strain is achieved by direct transformation of mycelia and electroporation. Development of cloning vectors and transformation methods for *amycolatopsis* are described in Dhingra et al. (*J. Ind. Microbiol. Biotechnol.* 30,195-204 (2003)). The *Amycolatopsis orientalis* transformant is cultured as described in Example 2 and Compound 9 is isolated using the protocol of Example 3.

All patents, patent applications, and published references cited herein are hereby incorporated by reference in their entirety. While this invention has been particularly shown and described with reference to preferred embodiments thereof, it will be understood by those skilled in the art that various changes in form and details may be made therein without departing from the scope of the invention encompassed by the appended claims.

The invention claimed is:

1. An isolated compound of Formula I, or a pharmaceutically acceptable salt thereof:

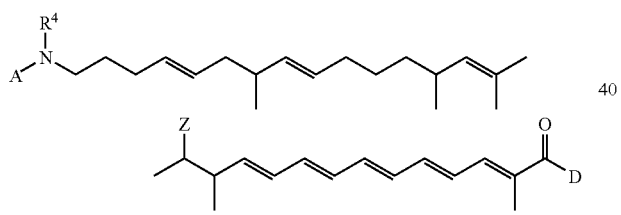

Formula I wherein,

A is selected from —C(NH)NHR¹, CH₃, H and

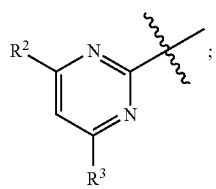

R¹ is selected from H, C$_{1-6}$alkyl, C$_{6-10}$aryl, C(O)C$_{1-6}$alkyl and C(O)C$_{6-10}$aryl;

R² and R³ are each independently selected from H, C$_{1-6}$ alkyl, C$_{2-7}$ alkene and C$_{6-10}$aryl;

R⁴ is selected from H and CH₃;

Z is OH or O when taken with adjacent carbon atom to form a carbonyl; or Z may be a tetrahydropyranoxy of formula:

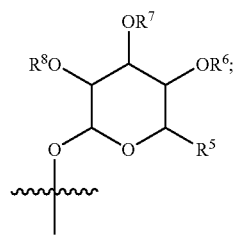

R⁵ is selected from H, COOH, C$_{1-6}$ alkyl and C(O)OC$_{1-6}$ alkyl;

R⁶, R⁷ and R⁸ are each independently selected from H, C$_{1-6}$ alkyl and C(O)C$_{1-6}$ alkyl; or R⁶, R⁷ and R⁸ may each independently be absent when the adjacent oxygen and carbon atoms are taken together to form a carbonyl; or R⁶, R⁷ and R⁸ may each independently be a bond when any of two neighboring R⁶, R⁷ and R⁸ are taken together with attached oxygen and carbon atoms to form a 1,3-dioxolane ring of formula:

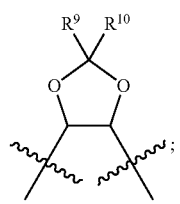

R⁹ and R¹⁰ are each independently selected from H, C$_{1-6}$ alkyl, C$_{2-7}$ alkene and C$_{6-10}$ aryl; or R⁹ and R¹⁰ are taken together with adjacent carbon atom to form a ring having from 5 to 7 carbons;

D is selected from OH, NH$_2$, NH(C$_{1-3}$alkyl), N(C$_{1-3}$alkyl)$_2$, OC$_{1-3}$alkyl and

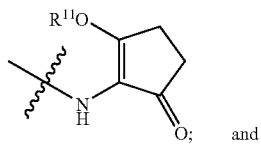

R$^{11}$ is selected from H and C$_{1-3}$ alkyl.

2. An isolated compound of Formula II, or a pharmaceutically acceptable salt thereof:

Formula II

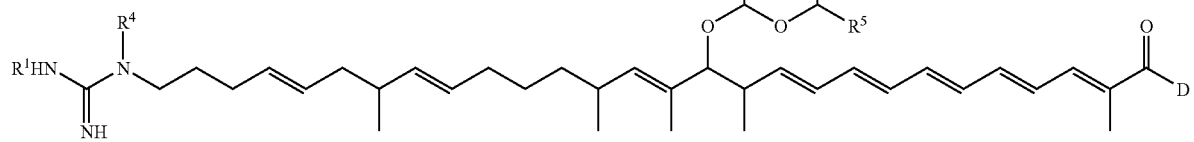

wherein,
R$^1$ is selected from H and C(O)C$_{1-3}$alkyl;
R$^4$ is selected from H and CH$_3$;
R$^5$ is selected from C(O)OH and C(O)OC$_{1-3}$alkyl;
D is selected from OH or the cyclopentenone of the formula:

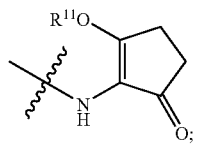

wherein R$^{11}$ is selected from H and C$_{1-3}$alkyl.

3. The isolated compound of claim 2 wherein D is

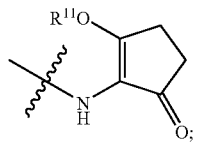

R$^1$ and R$^{11}$ are H; R$^4$ is CH$_3$; and R$^5$ is C(O)OH, or a pharmaceutically acceptable salt thereof.

4. The isolated compound of claim 2 wherein D is

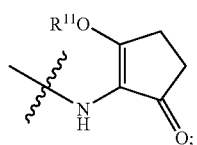

R$^1$, R$^4$ and R$^{11}$ are H and R$^5$ is C(O)OH, or a pharmaceutically acceptable salt thereof.

5. The isolated compound of claim 2 wherein D is

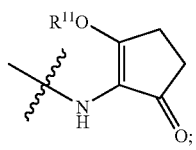

R$^1$ and R$^{11}$ are H, R$^4$ is CH$_3$ and R$^5$ is C(O)OCH$_3$, or a pharmaceutically acceptable salt thereof.

6. The isolated compound of claim 2 wherein D is

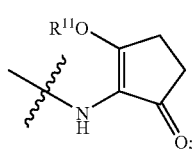

R$^1$ is H; R$^4$ and R$^{11}$ are CH$_3$; and R$^5$ is C(O)OH; or a pharmaceutically acceptable salt thereof.

7. The isolated compound of claim 2 wherein D is

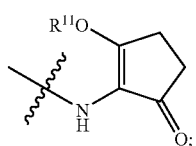

R$^1$ is H; R$^4$ and R$^{11}$ are CH$_3$; and R$^5$ is C(O)OCH$_3$; or a pharmaceutically acceptable salt thereof.

8. The isolated compound of claim 2 wherein D is

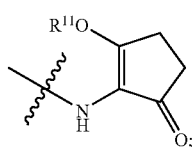

R$^1$ is C(O)CH$_3$; R$^4$ is CH$_3$; R$^5$ is C(O)OH; and R$^{11}$ is H; or a pharmaceutically acceptable salt thereof.

9. The compound of claim 2, wherein D is OH, $R^1$ is H, $R^4$ is $CH_3$, $R^5$ is C(O)OH or a pharmaceutically acceptable salt thereof.
10. An isolated compound or a pharmaceutically acceptable salt thereof, wherein said compound is selected from the group consisting of:
Compound 1
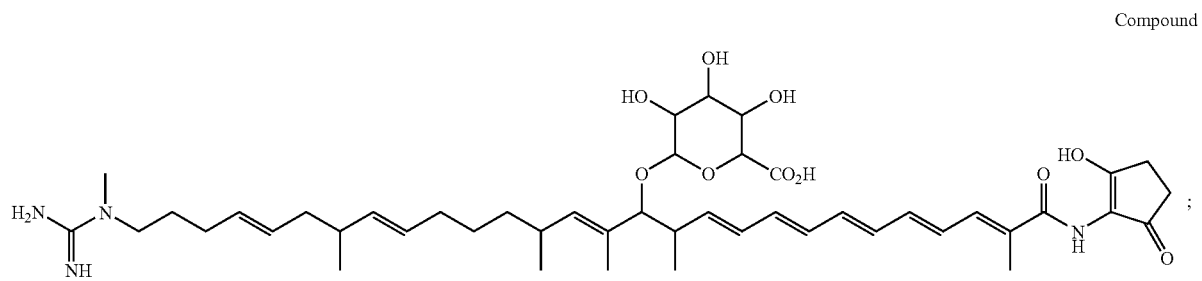
Compound 2
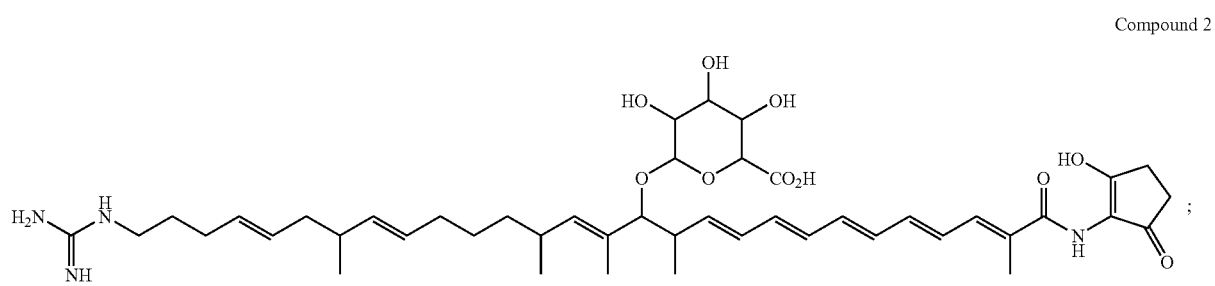
Compound 3
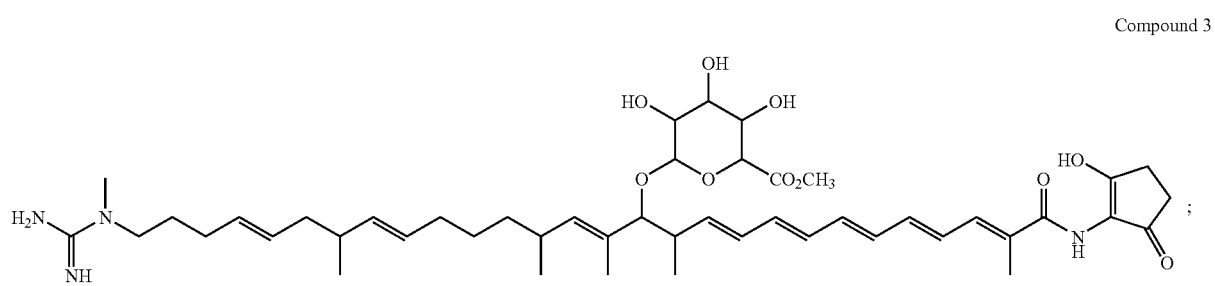
Compound 4
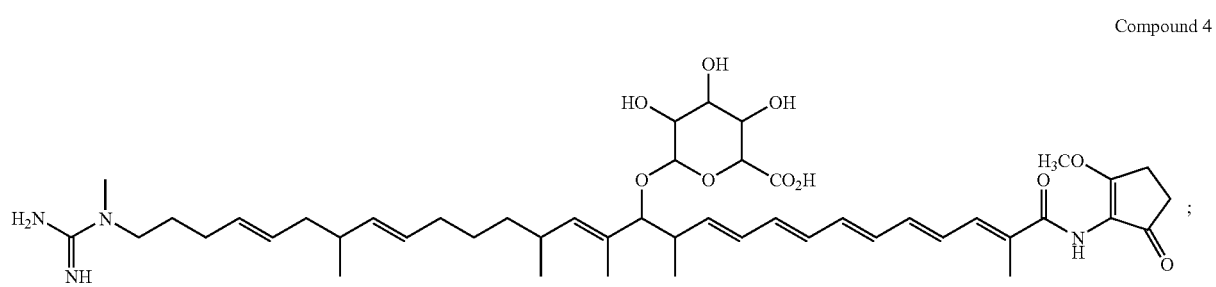
Compound 5
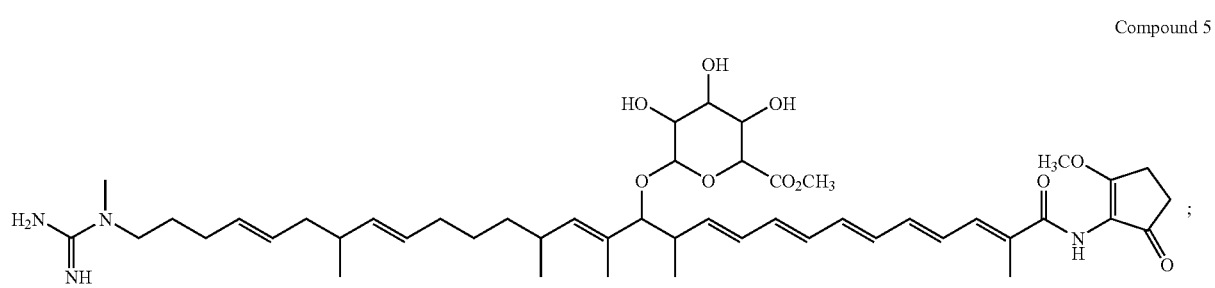

Compound 6
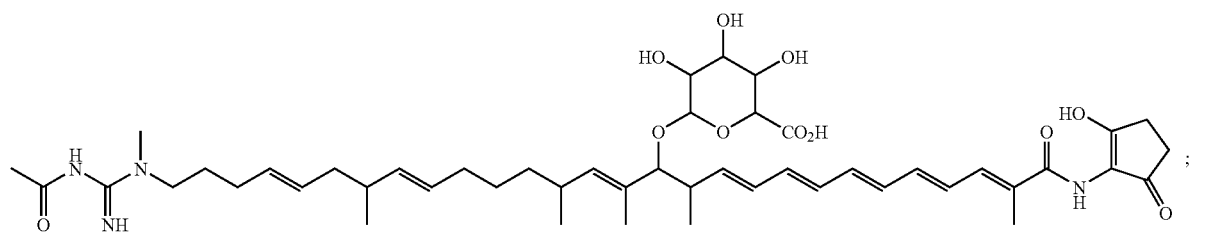
Compound 7
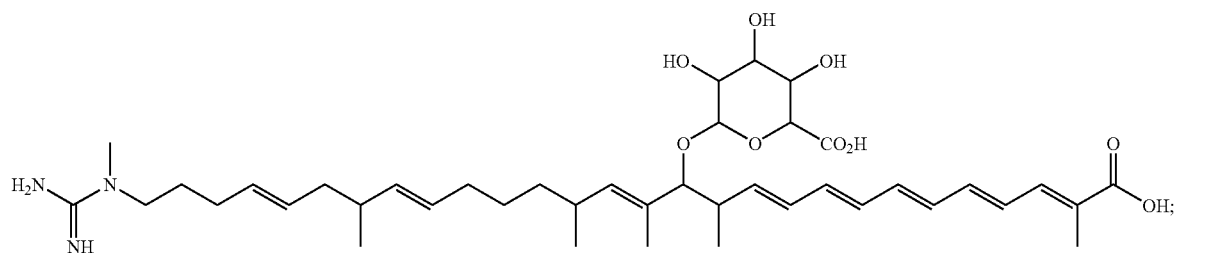
Compound 8
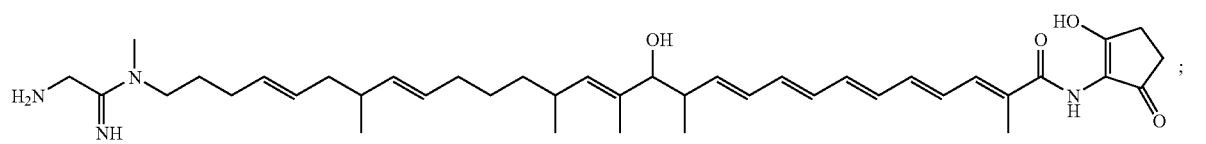
Compound 9
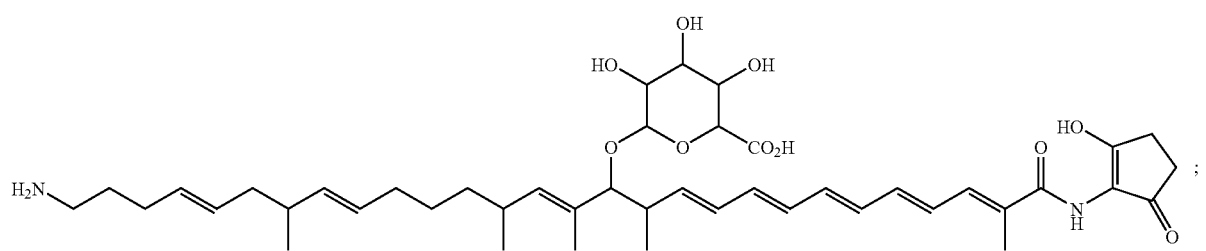
Compound 10
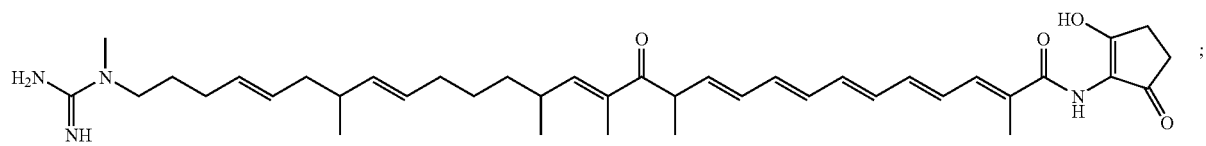
Compound 11
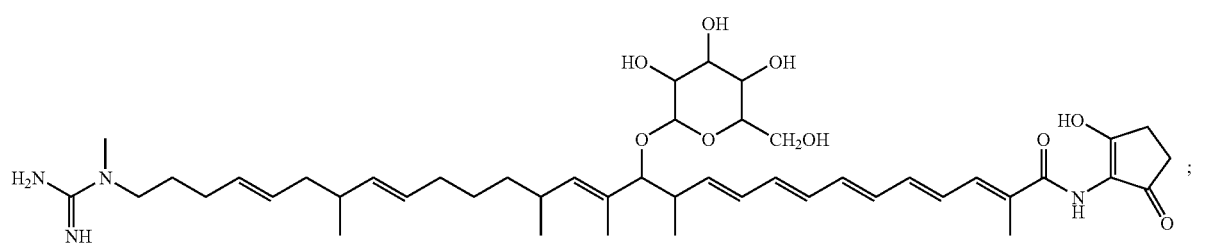
Compound 12
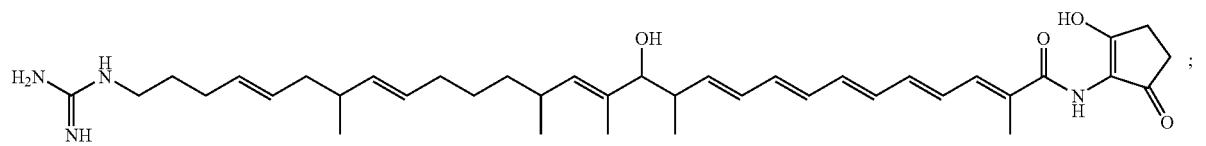

-continued
Compound 13
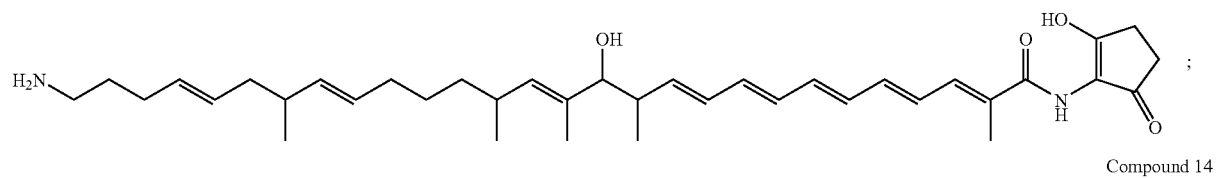
Compound 14
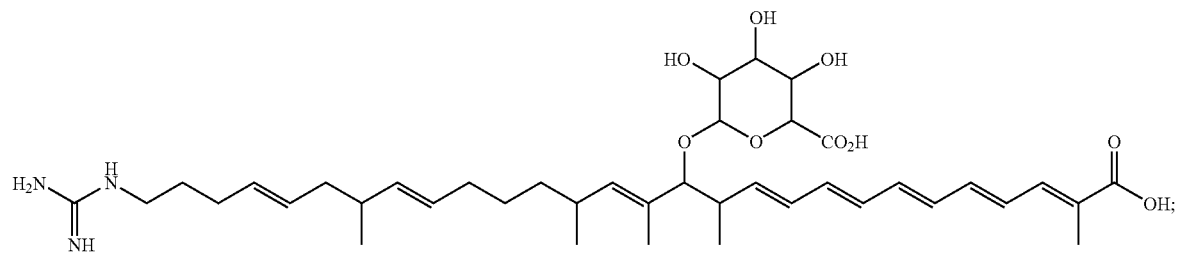
Compound 15
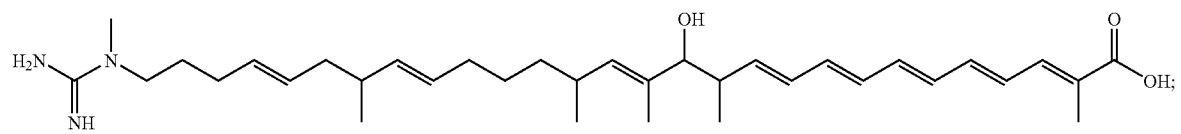
Compound 16
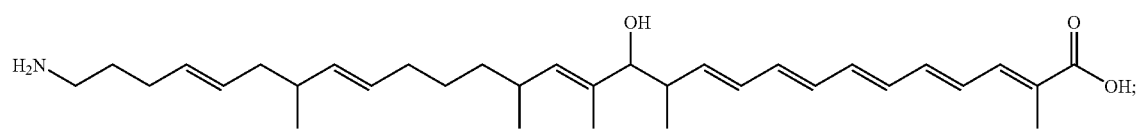
Compound 17
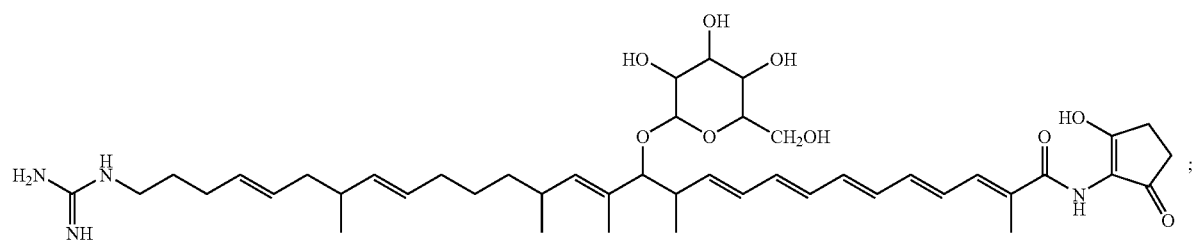
Compound 18
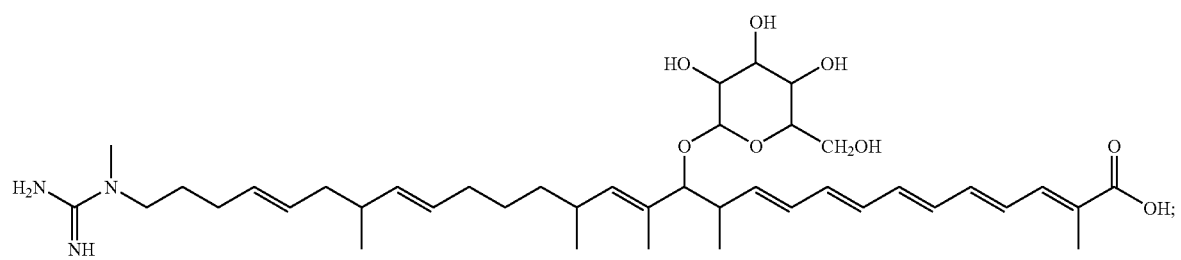
Compound 19
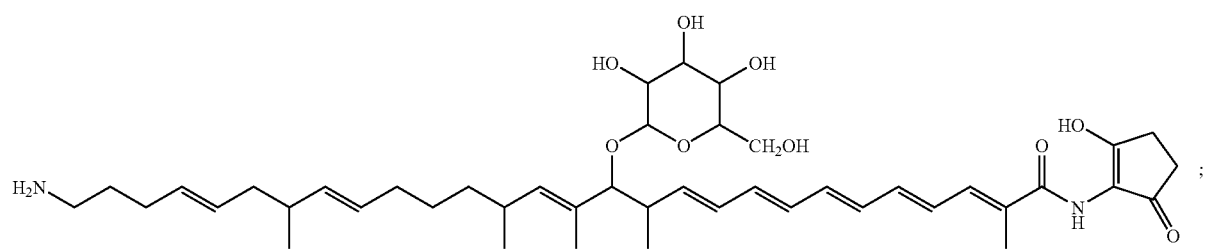

-continued
Compound 20
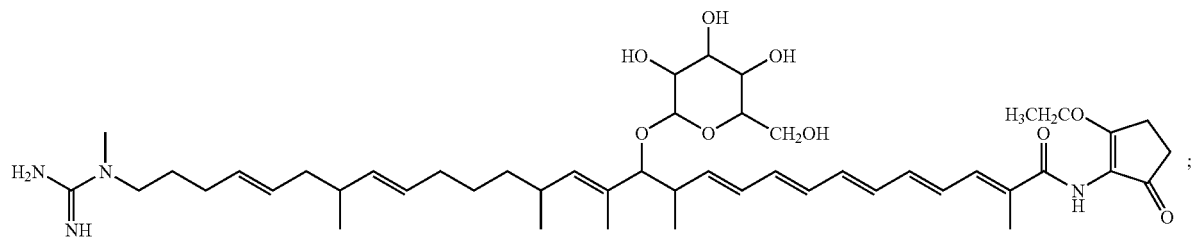
Compound 21
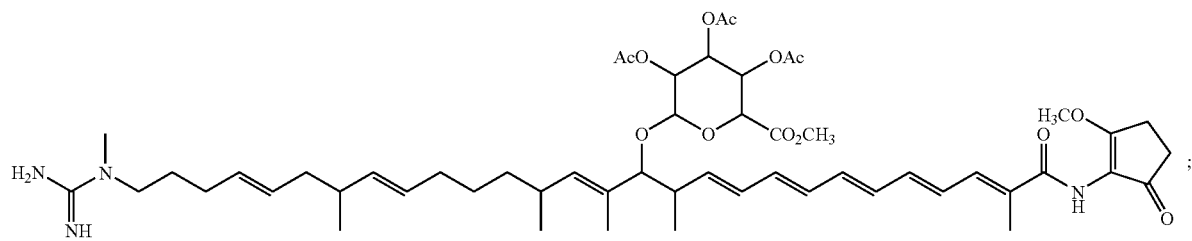
Compound 22
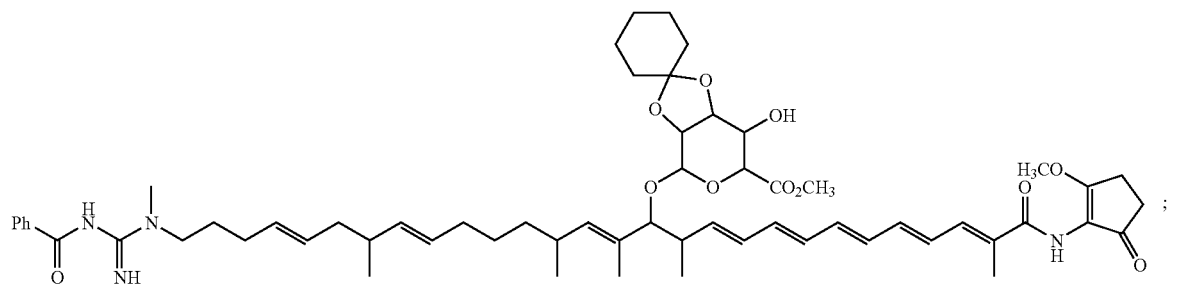
Compound 23
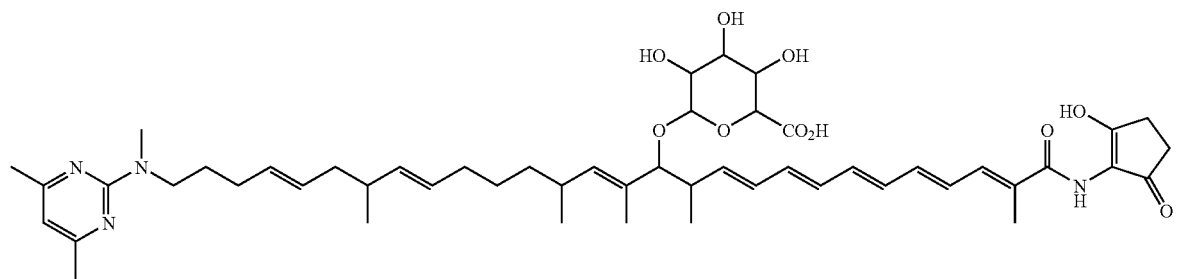
Compound 24
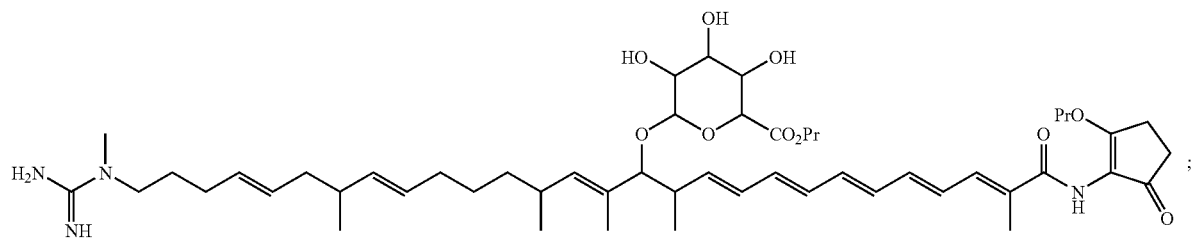

Compound 25
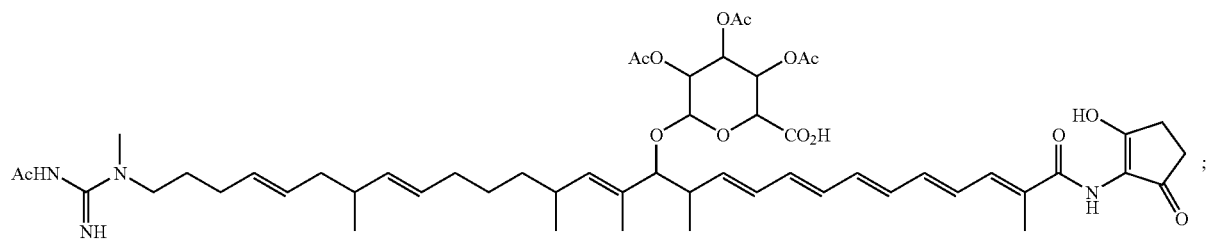
Compound 26
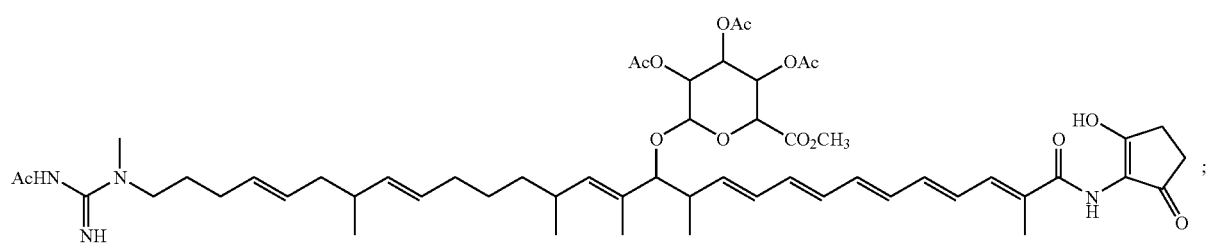
Compound 27
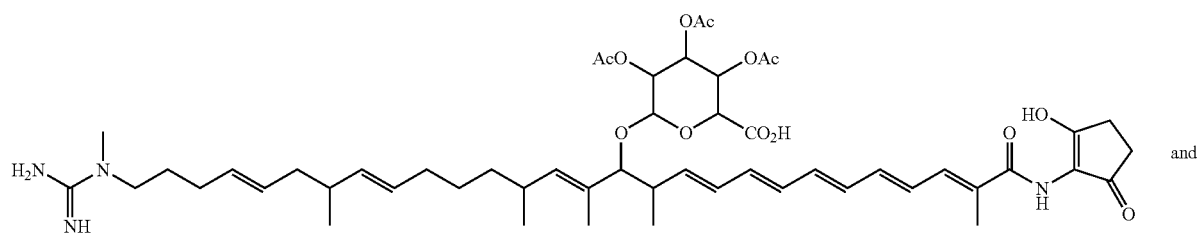
and
Compound 28
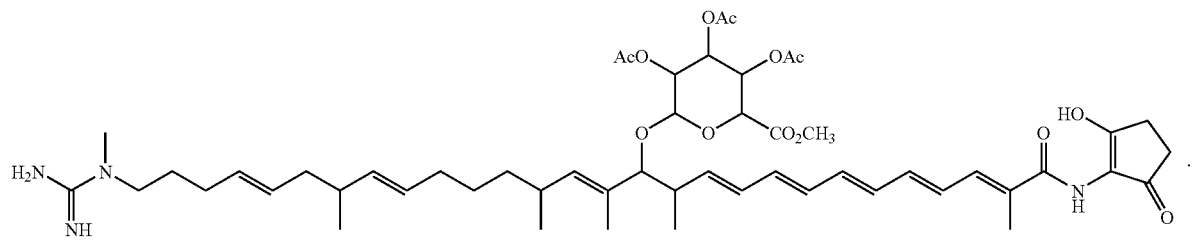
11. An isolated compound or a pharmaceutically acceptable salt thereof, wherein said compound is selected from the group consisting of:
Compound 1
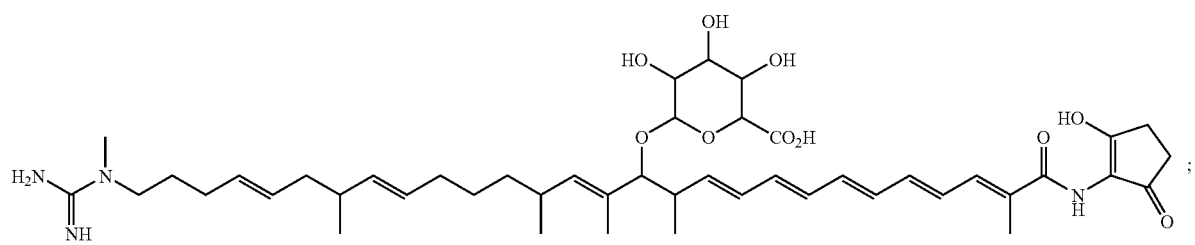

-continued
Compound 2
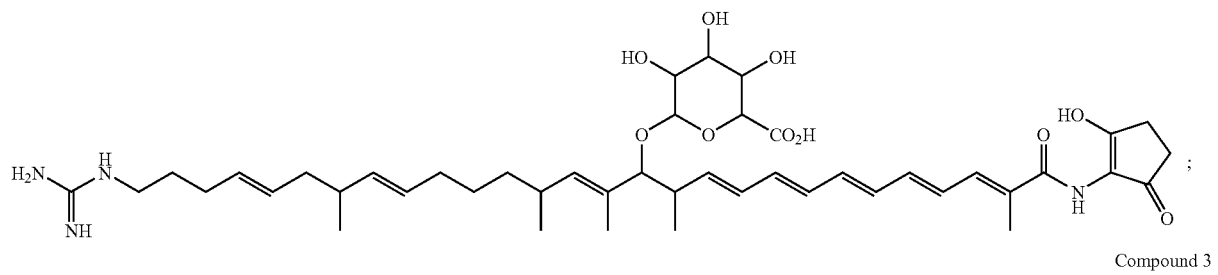
Compound 3
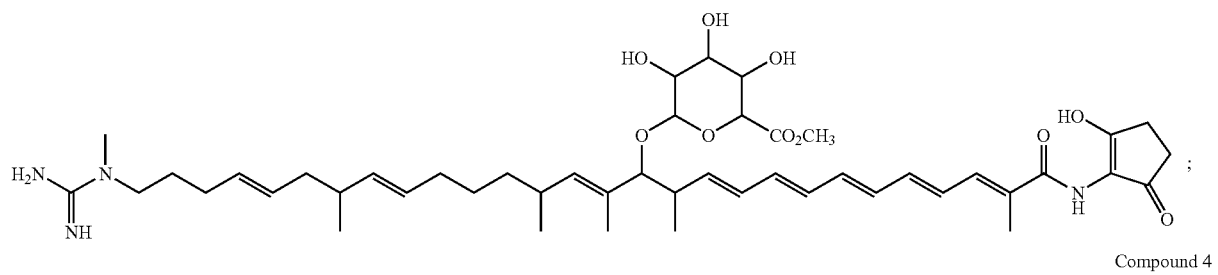
Compound 4
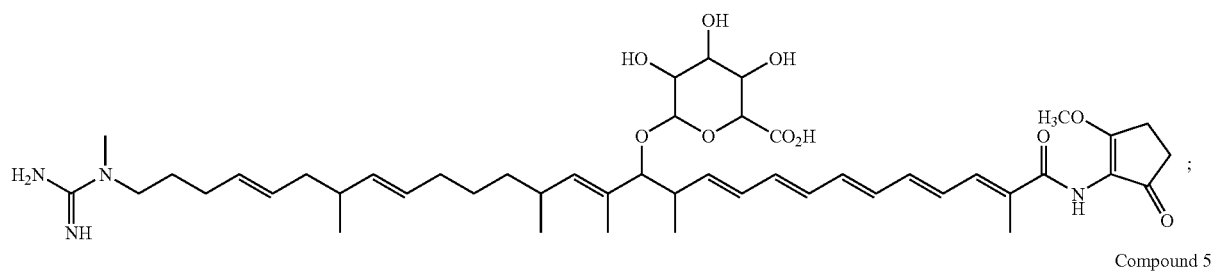
Compound 5
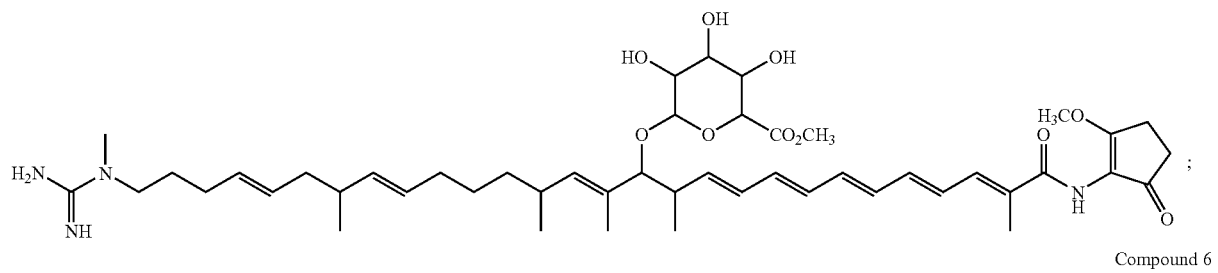
Compound 6
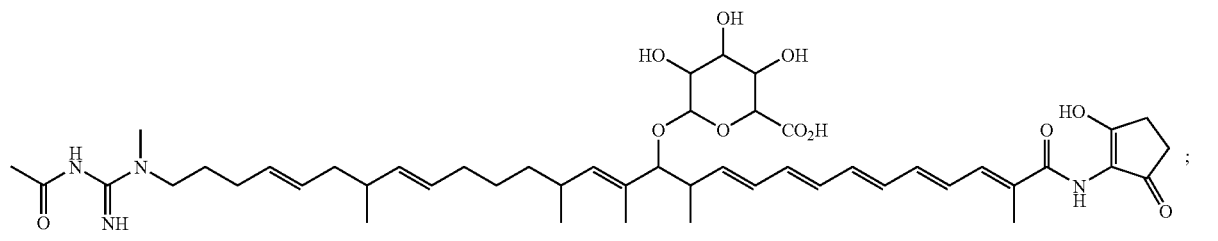
Compound 7
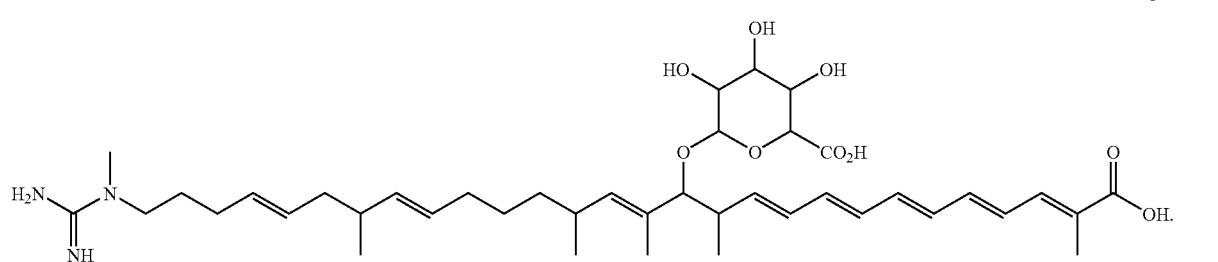

12. A pharmaceutical composition comprising a compound of claim 1 or a pharmaceutically acceptable salt thereof, together with a pharmaceutically acceptable carrier.

13. A pharmaceutical composition comprising a compound of claim 2 or a pharmaceutically acceptable salt thereof, together with a pharmaceutically acceptable carrier.

14. A pharmaceutical composition comprising a compound of claim 10 or a pharmaceutically acceptable salt thereof, together with a pharmaceutically acceptable carrier.

15. A pharmaceutical composition comprising a compound of claim 11 or a pharmaceutically acceptable salt thereof, together with a pharmaceutically acceptable carrier.

16. A process for making a compound of claim 1, comprising:
(a) cultivating a *Amycolatopsis orientalis* ATCC 43491 or *Amycolatopsis orientalis* IDAC 220604-01, in a nutrient medium comprising at least one source of carbon atoms and at least one source of nitrogen atoms; and
(b) isolating said compound.

17. The process of claim 16, wherein the cultivating occurs under aerobic conditions.

18. The process of claim 16, wherein said carbon atom and said nitrogen atom sources are chosen from the components shown in Table 1.

19. The process of claim 16, wherein said cultivation is carried out at a temperature ranging from 18° C. to 40° C.

20. The process of claim 16, wherein said cultivation is carried out at a pH ranging from 6 to 9.

21. A method of treating a bacterial infection in a mammal, comprising administering a therapeutically effective amount of a compound of claim 1, or a pharmaceutically acceptable salt thereof, to a mammal having a bacterial infection, such that said bacterial infection is treated.

22. A method of treating a bacterial infection in a mammal, comprising administering a therapeutically effective amount of a compound of claim 2, or a pharmaceutically acceptable salt thereof, to a mammal having a bacterial infection, such that said bacterial infection is treated.

23. A method of treating a bacterial infection in a mammal, comprising administering a therapeutically effective amount of a compound of claim 10, or a pharmaceutically acceptable salt thereof, to a mammal having a bacterial infection, such that said bacterial infection is treated.

24. A method of treating a bacterial infection in a mammal, comprising administering a therapeutically effective amount of a pharmaceutical composition of claim 12 to said mammal having a bacterial infection, such that said bacterial infection is treated.

25. A method of treating a bacterial infection in a mammal, comprising administering a therapeutically effective amount of a pharmaceutical composition of claim 13 to said mammal having a bacterial infection, such that said bacterial infection is treated.

26. A method of treating a bacterial infection in a mammal, comprising administering a therapeutically effective amount of a pharmaceutical composition of claim 14 to said mammal having a bacterial infection, such that said bacterial infection is treated.

* * * * *